(12) United States Patent
Beyer et al.

(10) Patent No.: US 8,710,188 B2
(45) Date of Patent: Apr. 29, 2014

(54) FACTOR IXA CRYSTALS, RELATED COMPLEXES AND METHODS

(75) Inventors: Brian M. Beyer, Lincroft, NJ (US); Alan W. Hruza, Hakettstown, NJ (US); Richard N. Ingram, Scotch Plains, NJ (US); Vincent S. Madison, Ukiah, CA (US); Andrew J. Prongay, Billerica, MA (US); Paul Reichert, Montville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 492 days.

(21) Appl. No.: 13/149,011

(22) Filed: May 31, 2011

(65) Prior Publication Data

US 2013/0157281 A1    Jun. 20, 2013

Related U.S. Application Data

(62) Division of application No. 12/437,116, filed on May 7, 2009, now Pat. No. 7,968,683.

(60) Provisional application No. 61/051,128, filed on May 7, 2008.

(51) Int. Cl.
| | | |
|---|---|---|
| *A61K 35/14* | (2006.01) | |
| *A61K 38/48* | (2006.01) | |
| *C07K 1/00* | (2006.01) | |
| *C07K 14/00* | (2006.01) | |
| *C07K 17/00* | (2006.01) | |
| *G01N 31/00* | (2006.01) | |

(52) U.S. Cl.
USPC .............................. 530/384; 436/4

(58) Field of Classification Search
None
See application file for complete search history.

(56) References Cited

PUBLICATIONS

McKean, M.L. & Adelman, S.J., Expert Opin Investig Drugs 7:687-690 (1998).
Weitz J.I. & Bates S.M.J. Thromb. Haemost. 3:1843-1853 (2005).
Weber, Advances in Protein Chemistry 41:1-36 (1991).
Giegé, et al., Acta Crystallogr. D50: 339-350 (1994).
McPherson, Eur. J. Biochem. 189: 1-23 (1990).
McPherson, J. Biol. Chem. 251: 6300-6303 (1976).
Schmidt et al., Trends Cardiovasc Med 13(1):39-45 (2003).
Perera et al., Thromb Haemost 85:596-603 (2001).
Howard et al., Arterioscler Thromb Vasc Biol 27:722-727 (2007).
Lattman, Meth. Enzymol., 115: 55-77 (1985).
Bricogne, G.,"The Bayesian Statistical Viewpoint on Structure Determination: Basic Concepts and Examples", in Methods in Enzymology, 276A, 361-423, C.W. Carter & R.M. Sweet, Eds. (1997).
Roversi et al., "Modelling prior distributions of atoms for Macromolecular Refinement and Completion", Acta Cryst., D56, 1313-1323 (2000).
Hopfner et al., EMBO, 16, 6626-6635 (1997).

*Primary Examiner* — Suzanne M Noakes

(57) ABSTRACT

The present invention relates to factor IXa complexes and crystals thereof as well as methods for identifying inhibitors of factor IXa.

5 Claims, 8 Drawing Sheets

US 8,710,188 B2

FACTOR IXA CRYSTALS, RELATED COMPLEXES AND METHODS

The present application is a divisional of co-pending U.S. application Ser. No. 12/437,116 filed May 7, 2009, which claims the benefit of U.S. provisional patent application No. 61/051,128, filed May 7, 2008, which is herein incorporated by reference in its entirety.

FIELD OF THE INVENTION

The present application relates to crystals of engineered human factor IXa-inhibitor complexes, methods for crystallizing the same, methods for preparing the same using recombinant technology, and uses therefor. The present application also relates to methods of using human factor IXa structure coordinates to solve the structure of homologous proteins or protein complexes. In addition, this invention relates to methods of using factor IXa structure coordinates for screening, identifying, and designing compounds, including inhibitory compounds, that bind to factor IXa, or complexes thereof.

BACKGROUND OF THE INVENTION

Human coagulation factor IXa (fIXa) plays a key role in maintaining internal homeostasis in the intrinsic pathway of the clotting cascade. The importance of fIXa in homeostasis is indicated by the frequency of hemophilia, which afflicts 1 in 30,000 males.

Human coagulation factor IX (fIX) is a 415 residue single chain molecule circulating in the plasma. Factor IX is converted to activated factor IX (fIXa) through the cleavage of two bonds by either factor VIIa or factor XIa, releasing a 35 residue activation peptide. After release of the peptide, factor IXa consists of an N-terminal light chain and a C-terminal heavy chain held together by a disulfide bond. fIXa assembles with factor VIIIa on the surface of endothelial cells or activated platelets forming the intrinsic Xase, a potent activator of factor X.

FIX is a multi-domain protein consisting of an N-terminal γ-carboxyl glutamic acid domain followed by two epidermal growth factor-like repeats, an activation peptide and a C-terminal protease domain with a trypsin-like active site. This multi-domain structure defines the fIX gene family of clotting factors, which also includes fVII, fX and protein C. Within this family, fIXa has unique proteolytic properties. Complex formation of fIXa with fVIIIa on a phospholipid surface increases reactivity against the natural substrate IX $10^6$-fold while virtually no cleavage of peptides with the corresponding fX sequences was observed.

Inhibition of fIXa presents an alternative and viable way of treating thrombosis arising from both venous as well as arterial vascular injuries. It is believed that inhibiting fIXa selectively limits thrombosis at sites with low tissue factor presence, but does not inhibit clotting in high tissue factor environments such as vascular injuries of surgical wounds (McKean, M. L. & Adelman, S. J., *Expert Opin Investig Drugs* (1998) 7:687; Weitz J. I. & Bates S. M. J. *Thromb. Haemost.* (2005) 3:1843). Factor IXa-specific inhibitors could provide a choice of anti-coagulants with improved therapeutic index compared to existing therapies which target thrombin.

The provision of factor IXa crystals bound to inhibitor compounds provides, e.g., valuable insight into the requirements for compounds that effectively bind to and inhibit factor IXa, and, thus, factor IXa-dependent clotting events. Such crystals also provide useful tools of the generation of novel factor IXa complexes.

SUMMARY OF THE INVENTION

The present invention provides, in part, factor IXa (e.g., human factor IXa) and factor IXa-inhibitor complex crystals that are useful for the determination of the three dimensional structure of factor IXa and the design of factor IXa inhibitors. Assay methods for identifying inhibitors of factor IXa are also provided.

For example, the present invention provides a complex comprising a factor IXa polypeptide complexed with a molecule selected from the group consisting of

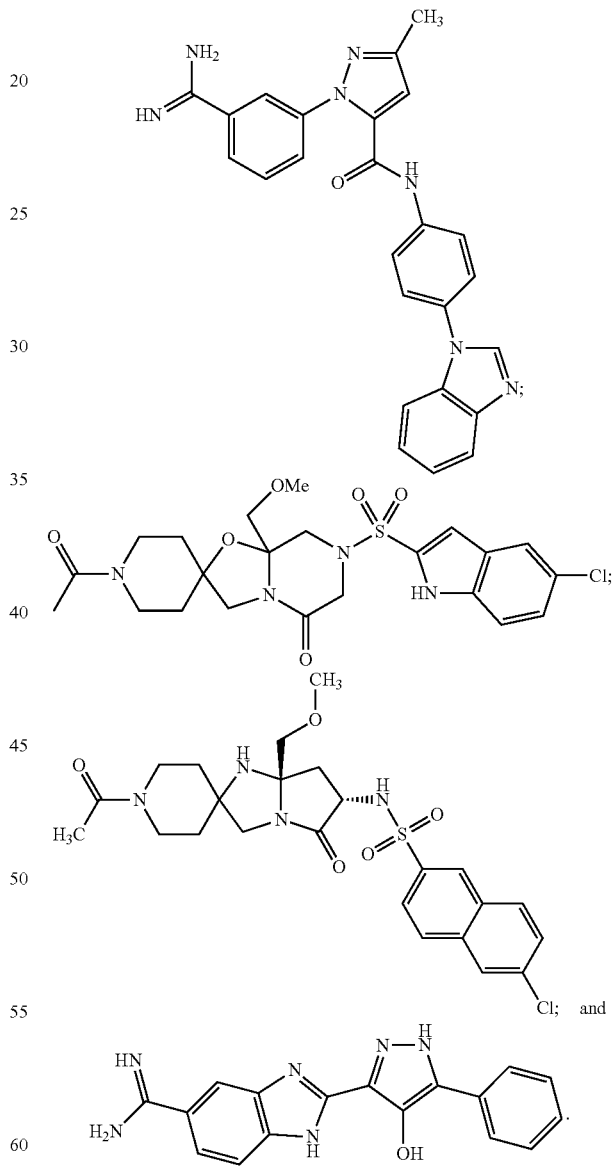

For example, the present invention includes embodiments wherein the complex has a three dimensional structure characterized by structural coordinates comprising a root mean square deviation of conserved residue backbone atoms or of alpha carbon atoms of less than about 1.5 Å when superimposed on backbone atoms described in Table 2, 3, 4, 5 or 6 (e.g., wherein the complex has a three dimensional structure characterized by structural coordinates described in Table 2, 3, 4, 5 or 6). In an embodiment of the invention, the complex is crystalline.

The present invention includes a crystalline complex comprising a polypeptide complex comprising a polypeptide which comprises the amino acid sequence: DVTCNIKNGRCEQFCKNSADNKVVCSCTEGYRLAENQKSCEPAVPFPCGRVSVSQTSKLTR (SEQ ID NO: 13); bound to a polypeptide comprising the amino acid sequence: VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGRSALVLQYLRVPLVDRATCLRSTKFTIYNNMFCAGFHEGGRDSCQGD SGGPHVTEVEGTSFLTGIISWGEECAMKGKYGIYTKVSRYVNWIKEKTKLT (SEQ ID NO: 14) or VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGASALVLQYLRVPLVDRATCLRSTKFTIYNNMFCAGFHEGGRDSCQGD SGGPHVIEVEGTSFLTGIISWGEECAMKGKYGIYTKVSRYVNWIKEKTKLT (SEQ ID NO: 18); bound to a molecule represented by the following structural formula:

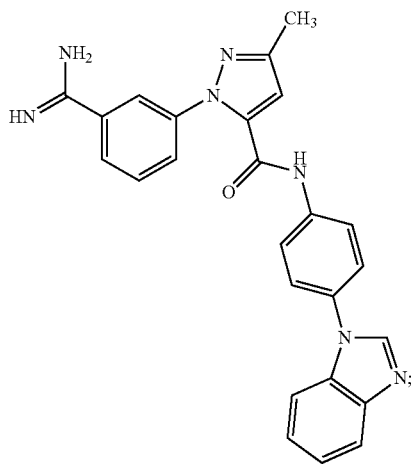 [SMILES: Cc1cc(C(=O)Nc2ccc(-n3cnc4ccccc43)cc2)n(-c2cccc(C(=N)N)c2)n1]

(i) comprising unit cell dimensions: a=48.1 Å, b=69.8 Å, c=92.1 Å, α=β=γ=90°; and in space group: P2₁2₁2₁; or (ii) comprising unit cell dimensions: a=100.4 Å, b=100.4 Å, c=97.3 Å, α=β=γ=90°; and in space group: P4₃2₁2 (e.g., wherein the complex is characterized by structural coordinates comprising a root mean square deviation of conserved residue backbone atoms or of alpha carbon atoms of less than about 1.5 Å when superimposed on backbone atoms described in Table 2 or 4). In an embodiment of the invention, the crystalline complex can diffract X-rays for structural determination of said complex to a resolution of about 1.64 angstroms to about 2.10 angstroms (e.g., 1.64 angstroms or 2.10 angstroms) or a lower number.

The present invention includes a crystalline complex comprising a polypeptide complex comprising a polypeptide which comprises the amino acid sequence: DVTCNIKNGRCEQFCKNSADNKVVCSCTEGYRLAENQKSCEPAVPFPCGRVSVSQTSKLTR (SEQ ID NO: 13); bound to a polypeptide comprising the amino acid sequence: VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGRSALVLQYLRVPLVDRATCLRSTKFTIYNNMFCAGFHEGGRDSCQGD SGGPHVTEVEGTSFLTGIISWGEECAMKGKYGIYTKVSRYVNWIKEKTKLT (SEQ ID NO: 14) or VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGASALVLQYLRVPLVDRATCLRSTKFTIYNNMFCAGFHEGGRDSCQGD SGGPHVTEVEGTSFLTGIISWGEECAMKGKYGIYTKVSRYVNWIKEKTKLT (SEQ ID NO: 18); bound to a molecule represented by the following structural formula:

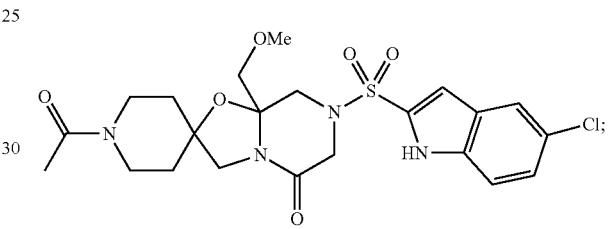

comprising unit cell dimensions: a=100.6 Å, b=100.6 Å, c=98.1 Å, α=β=γ=90°; and in space group P4₃2₁2 (e.g., wherein the complex is characterized by structural coordinates comprising a root mean square deviation of conserved residue backbone atoms or of alpha carbon atoms of less than about 1.5 Å when superimposed on backbone atoms described in Table 3). In an embodiment of the invention, the crystalline complex can diffract X-rays for structural determination of said complex to a resolution of about 2.45 angstroms or a lower number The present invention includes a crystalline complex comprising a polypeptide complex comprising a polypeptide which comprises the amino acid sequence: DVTCNIKNGRCEQFCKNSADNKVVCSCTEGYRLAENQKSCEPAVPFPCGRVSVSQTSKLTR (SEQ ID NO: 13); bound to a polypeptide comprising the amino acid sequence: VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGRSALVLQYLRVPLVDRATCLRSTKFTIYNNMFCAGFHEGGRDSCQGD SGGPHVTEVEGTSFLTGIISWGEECAMKGKYGIYTKVSRYVNWIKEKTKLT (SEQ ID NO: 14) or VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGASALVLQYLRVPLVDRATCLRSTKFTIYNNMFCAGFHEGGRDSCQGD SGGPHVTEVEGTSFLTGIISWGEECAMKGKYGIYTKVSRYVNWIKEKTKLT (SEQ ID NO: 18); bound to a molecule represented by the following structural formula:

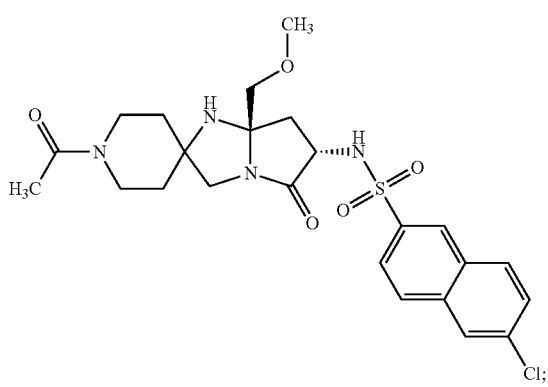 [SMILES: COC[C@@]12C[C@H](NS(=O)(=O)c3ccc4cc(Cl)ccc4c3)C(=O)N1CC1(CCN(C(C)=O)CC1)N2]

comprising unit cell dimensions: a=99.2 Å, b=99.2 Å, c=97.3 Å, α=β=γ=90°; and in space group: P4₃2₁2 (e.g., wherein the complex is characterized by structural coordinates comprising a root mean square deviation of conserved residue backbone atoms or of alpha carbon atoms of less than about 1.5 Å when superimposed on backbone atoms described in Table 5). In an embodiment of the invention, the crystalline complex can diffract X-rays for structural determination of said complex to a resolution of about 2.30 angstroms or a lower number.

The present invention includes a crystalline complex comprising a polypeptide complex comprising a polypeptide which comprises the amino acid sequence: DVTCNIKNGRCEQFCKNSADNKVVCSCTEGYRLAENQKSCEPAVPFPCGRVSVSQTSKLTR (SEQ ID NO: 13); bound to a polypeptide comprising the amino acid sequence: VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGRSALVLQYLRVPLVDRATCLRSTKFTIYNNMFCAGFHEGGRDSCQGD SGGPHVTEVEGTSFLTGIISWGEECAMKGKYGIYTKVSRYVNWIKEKTKLT (SEQ ID NO: 14) or VVGGEDAKPGQFPWQVVLNGKVDAFCGGSIVNEKWIVTAAHCVETGVKITVVAGEHNIEE TEHTEQKRNVIRIIPHHNYNAAINKYNHDIALLELDEPLVLNSYVTPICIADKEYTNIFLKFGSG YVSGWGRVFHKGASALVLQYLRVPLVDRATCLRSTKFTIYNNMFCAGFHEGGRDSCQGD SGGPHVIEVEGTSFLTGIISWGEECAMKGKYGIYTKVSRYVNWIKEKTKLT (SEQ ID NO: 18); bound to a molecule represented by the following structural formula:

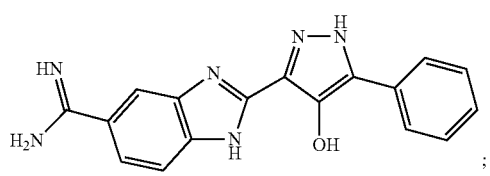 [SMILES: N=C(N)c1ccc2[nH]c(-c3n[nH]c(-c4ccccc4)c3O)nc2c1]

comprising unit cell dimensions: a=100.5 Å, b=100.5 Å, c=98.4 Å, α=β=γ=90°; and in space group: P4₃2₁2 (e.g., wherein the complex is characterized by structural coordinates comprising a root mean square deviation of conserved residue backbone atoms or of alpha carbon atoms of less than about 1.5 Å when superimposed on backbone atoms described in Table 6). In an embodiment of the invention, the crystalline complex can diffract X-rays for structural determination of said complex to a resolution of about 2.50 angstroms or a lower number.

The present invention further provides a method for determining the structure of a complex comprising a compound bound to factor IXa protein, said method comprising: (a) mixing the factor IXa protein with the compound; (b) crystallizing a factor IXa protein-compound complex; and (c) determining the structure of the complex by employing the data of any one of Tables 2-6 optionally varied by a root mean square deviation of conserved residue backbone atoms or of alpha carbon atoms of less than about 1.5 Å when superimposed on backbone atoms described in Table 2, 3, 4, 5 or 6.

The scope of the present invention also encompasses a method for identifying a substance which inhibits blood clotting comprising (a) mixing the factor IXa protein with the substance; (b) crystallizing a factor IXa protein-substance complex; and (c) determining the structure of the complex by employing the data of any one of Tables 2-6 optionally varied by a root mean square deviation of conserved residue backbone atoms or of alpha carbon atoms of less than about 1.5 Å when superimposed on backbone atoms described in Table 2, 3, 4, 5 or 6; and, if said substance is observed to complex with factor IXa; determining if the substance selectively inhibits factor IXa proteolytic activity but not factor Xa proteolytic activity; wherein the substance is identified as a blot clotting inhibitor if said selection inhibition is observed (e.g., wherein said proteolytic activity is determined by measuring proteolysis of Methylsulfonyl-D-cyclohexylglycyl-glycyl-arginine-paranitroanilide).

The present invention also provides a method for determining the structure of a complex comprising a second compound bound to factor IXa protein, said method comprising: (a) providing a crystal of factor IXa protein complexed with a first compound; (b) soaking the crystal comprising the first compound with a second compound to form a complex between said factor IXa protein and said second compound; and (c) determining the structure of the complex comprising the second compound by employing the data of any one of Tables 2-6 optionally varied by a root mean square deviation of conserved residue backbone atoms or of alpha carbon atoms of less than about 1.5 Å when superimposed on backbone atoms described in Table 2, 3, 4, 5 or 6.

In addition, the present invention provides a method for identifying a substance which inhibits blood clotting comprising (a) providing a crystal of factor IXa protein complexed with a first substance; (b) soaking the crystal comprising the first substance with a second substance to form a complex between said factor IXa protein and said second substance; and (c) determining the structure of the complex comprising the second substance by employing the data of any one of Tables 2-6 optionally varied by a root mean square deviation of conserved residue backbone atoms or of alpha carbon atoms of less than about 1.5 Å when superimposed on backbone atoms described in Table 2, 3, 4, 5 or 6; and, if said substance is observed to complex with factor IXa; determining if the substance selectively inhibits factor IXa proteolytic activity but not factor Xa proteolytic activity; wherein the substance is identified as a blot clotting inhibitor if said selection inhibition is observed (e.g., wherein said proteolytic activity is determined by measuring proteolysis of Methylsulfonyl-D-cyclohexylglycyl-glycyl-arginine-paranitroanilide).

The present invention provides a method for producing a crystal of factor IXa complexed with a compound represented by structural formula A:

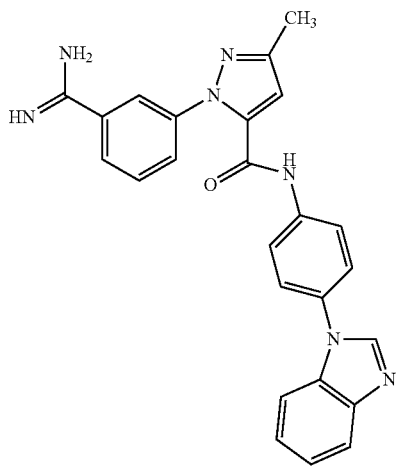 [SMILES: Cc1cc(C(=O)Nc2ccc(-n3cnc4ccccc43)cc2)n(-c2cccc(C(=N)N)c2)n1]

comprising mixing about 0.5 µl of a solution comprising about 6 mg/ml of the factor IXa/compound A complex in a buffer, e.g., a pH 8 buffer such as 25 mM Tris, pH 8.0 and a salt such as sodium chloride (e.g., 0.15 M NaCl) with about 0.5 µl of precipitant solution comprising about 20% of a precipitant such as PEG, for example, PEG-6000 (v/v), 0.1 M citric acid, pH 5.9 and incubating the mixture in the presence of about 0.08 mL of the precipitant solution, at about 4° C., e.g., in a sealed container.

The present invention also provides a method for producing a crystal of factor IXa complexed with a compound represented by structural formula B:

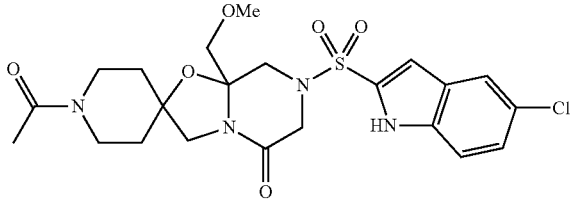 [SMILES: COCC12CN(S(=O)(=O)c3cc4cc(Cl)ccc4[nH]3)CC(=O)N1CC1(CCN(C(C)=O)CC1)O2]

comprising mixing about 0.5 µl of a solution comprising about 15 mg/ml of the complex in a pH 8 buffer such as 25 mM Tris, pH 8.0, a salts such as sodium chloride (e.g., 0.15 M), with about 0.5 µl of a precipitant solution comprising 16% of a precipitant such as PEG-6000 (v/v), 0.1 M citric acid, pH 5.9 and incubating the mixture in the presence of about 0.08 mL of the precipitant solution, at about 4° C., e.g., in a sealed container.

The present invention also provides a method for producing a crystal of factor IXa complexed with a compound represented by structural formula A:

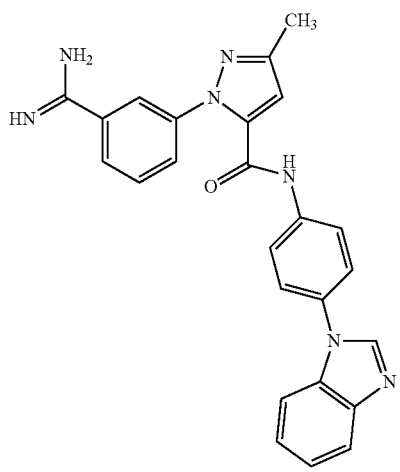 [SMILES: Cc1cc(C(=O)Nc2ccc(-n3cnc4ccccc43)cc2)n(-c2cccc(C(=N)N)c2)n1]

comprising incubating a crystal comprising a factor IXa polypeptide complexed with a compound represented by structural formula B:

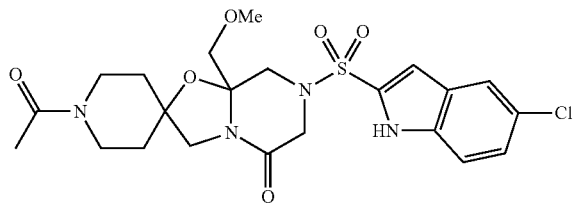 [SMILES: COCC12CN(S(=O)(=O)c3cc4cc(Cl)ccc4[nH]3)CC(=O)N1CC1(CCN(C(C)=O)CC1)O2]

in a drop comprising about 1 mM of the compound represented by structural formula A, 1% DMSO, 16% of a precipitant such as PEG 6000 (v/v), 0.1 M citric acid, pH 5.9 at about 4° C.

The scope of the present invention also encompasses a method for producing a crystal of factor IXa complexed with a compound represented by structural formula C:

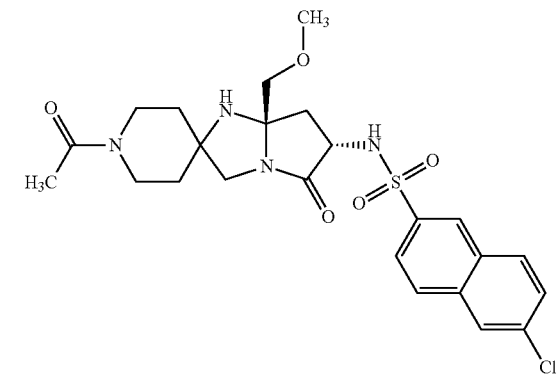 [SMILES: COC[C@@]12C[C@H](NS(=O)(=O)c3ccc4cc(Cl)ccc4c3)C(=O)N1CC1(CCN(C(C)=O)CC1)N2]

comprising mixing about 0.5 µl of a solution comprising about 10 mg/ml of the complex in a pH 8 buffer such as 25 mM Tris, pH 8.0, and a salt such as NaCl, e.g., 0.15 M sodium chloride, 1% DMSO buffer with about 0.5 µl of precipitant solution comprising 14% of a precipitant such as PEG, e.g., PEG 6000 (v/v), 0.1 M citric acid, pH 5.67 and incubating the mixture in the presence of about 0.08 mL of the precipitant solution at about 4° C.

Further, the present invention provides a method for producing a crystal of factor IXa complexed with a compound represented by structural formula D:

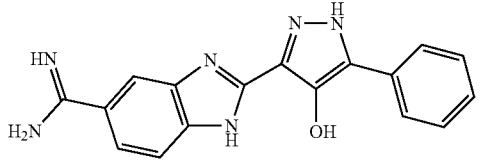 [SMILES: N=C(N)c1ccc2[nH]c(-c3n[nH]c(-c4ccccc4)c3O)nc2c1]

comprising incubating a crystal comprising a factor IXa polypeptide complexed with a compound represented by structural formula C:

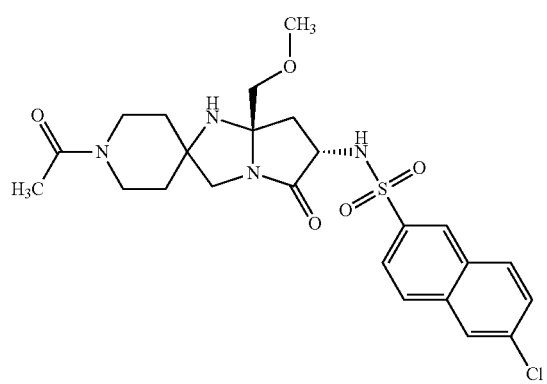 [SMILES: COC[C@@]12C[C@H](NS(=O)(=O)c3ccc4cc(Cl)ccc4c3)C(=O)N1CC1(CCN(C(C)=O)CC1)N2]

in a drop comprising about 1 mM of said compound represented by structural formula D, 1% DMSO, 14% of a precipitant such as PEG, e.g., PEG 6000 (v/v), 0.1 M citric acid, pH 5.67 solution at about 4° C.

The present invention further provides a method, e.g., a computer assisted drug design method, for identifying a substance which binds to factor IXa or inhibits blood clotting comprising: determining the structure of a complex comprising a compound represented by structural formula A, B, C or D by employing the data of any one of Tables 2-6 optionally varied by a root mean square deviation of conserved residue backbone atoms or of alpha carbon atoms of less than about 1.5 Å when superimposed on backbone atoms or alpha carbon atoms described in Table 2, 3, 4, 5 or 6; and, employing a computational means, e.g., using known computer software platforms, to dock a candidate substance with the factor IXa serine protease domain, or any other relevant factor IXa domain, e.g., as discussed herein, to determine if said candidate substance binds to said serine protease domain; and, optionally, synthesizing said candidate substance; and, optionally, determining if said candidate substance binds to factor IXa or inhibits factor IXa proteolytic activity.

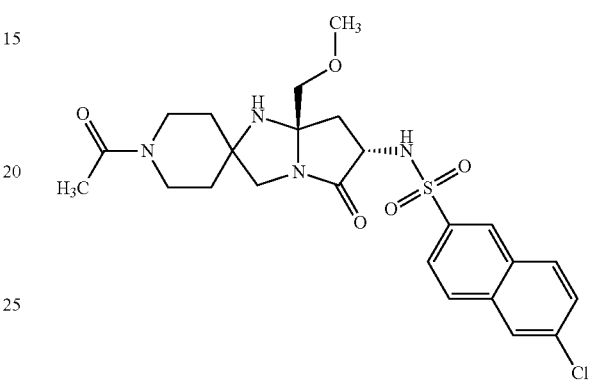

complex. SDS PAGE analysis showed no visible signs of complex degradation four days post setup.

Lane 1: Bio-Rad low molecular weight standards standard
Lanes 2-6: Factor IXa

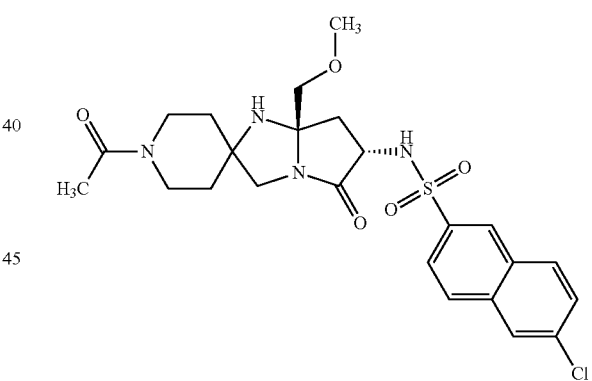

complex; 4 days post setup (10, 5, 2.5, 1.25 and 0.625 ug load, respectively)

Figure 7:
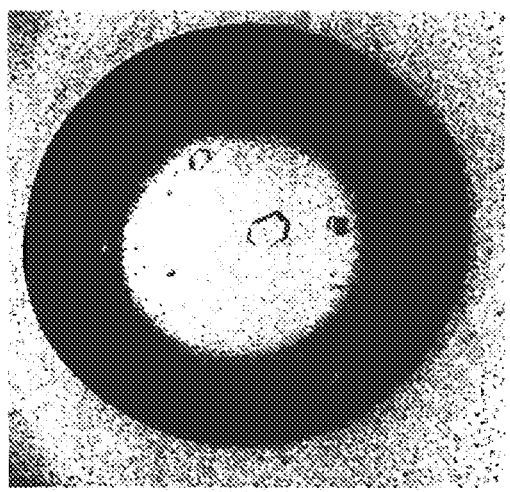

FIG. 7. Photomicrograph of human wild type factor IXa-Compound C complex crystals at 70× magnification. The crystals were prepared with precipitant solution containing 14% PEG 6000 (v/v), 0.1M citric acid, pH 5.67 and were grown at 4° C. for 8 days.

Figure 8:
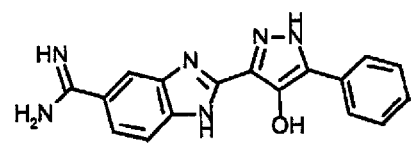

FIG. 8. Molecular structure of Compound D.

DETAILED DESCRIPTION OF THE INVENTION

The present invention relates to the production of crystalline fIXa and fIXa-inhibitor complexes, the structures of fIXa and fIXa-inhibitor complexes as determined by X-ray crystallography, the use of those structures to solve the structure of fIXa homologues and other crystal forms of fIXa and co-complexes of fIXa to design inhibitors of fIXa. In an embodiment of the invention, iterative structure-assisted drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, fIXa and fIXa-inhibitor complex crystals provided by this invention may be soaked in the presence of a compound or compounds, such as a fIXa inhibitor, substrates, or other ligands to provide novel fIXa/compound crystal complexes.

The term "soaked" includes a process in which the crystal is transferred to a solution containing the compound of interest.

Factor IXa

The present invention comprises factor IXa and fragments and mutants thereof which are optionally complexed with any other molecule, for example any substrate or ligand molecule or any inhibitor molecule such as Compound A, B, C, or D (see, e.g., FIGS. 1, 3, 5, and 8).

Compound A:

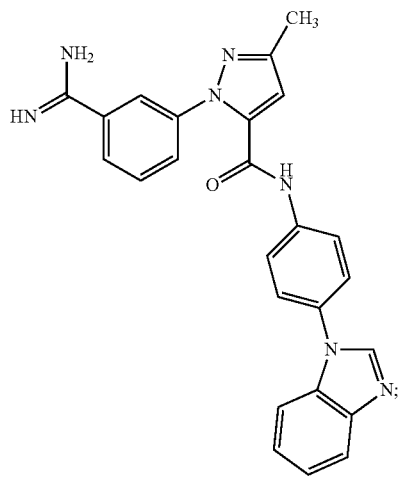

Compound B:

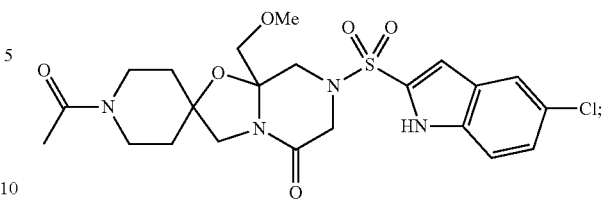

Compound C:

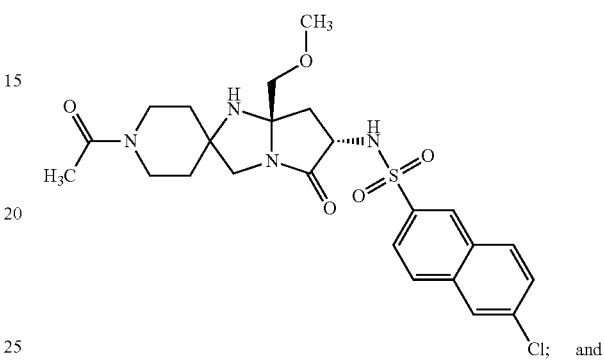

and

Compound D:

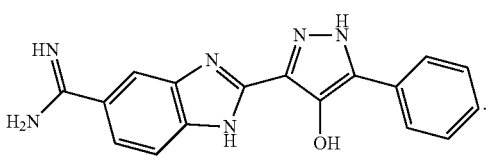

The term "factor IXa" or "fIXa" includes any form or type of factor IXa from any species (e.g., human). Factor IXa is produced by activation of Factor IX through the cleavage of two bonds, releasing a 35 residue activation peptide. The FIXa thus formed comprises a light chain and a heavy chain held together by a disulfide bond. In an embodiment of the invention, full length human factor IX (lacking the signal sequence) comprises the amino acid sequence:

(SEQ ID NO: 1)
<u>YNSGKLEEFVQGNLERECMEEKCSFEEAREVFENTERTTEFWKQYVDGDQCESNPCLNGGSCKDDIN</u>

<u>SYECWCPFGFEGKNCELDVTCNIKNGRCEQFCKNSADNKVVCSCTEGYRLAENQKSCEPAVPFPCGR</u>

<u>VSVSQTSKLTR</u>AETVFPDVDYVNSTEAETILDNITQTQSFNDFTR*VVGGEDAKPGQFPWQVVLNGK*

*VDAFCGGSIVNEKWIVTAAHCVETGVKITVVAGEHNIEETEHTEQKRNVIRIIPHHNYNAAINKYNH*

*DIALLELDEPLVLNSYVTPICIADKEYTNIFLKFGSGYVSGWGRVFHKGRSALVLQYLRVPLVDRAT*

*CLRSTKFTIYNNMFCAGFHEGGRDSCQGDSGGPHVTEVEGTSFLTGIISWGEECAMKGKYGIYTKVS*

*RYVNWIKEKTKLT*.
(Activation peptide is shown in bold; light chain is underscored; heavy chain is italicized).

In an embodiment of the invention, the full length factor IXa comprises the amino acid sequence:

```
                            (SEQ ID NO: 15; signal peptide underscored)
MQRVNMIMAE SPGLITICLL GYLLSAECTV FLDHENANKI LNRPKRYNSG KLEEFVQGNL

ERECMEEKCS FEEAREVFEN TERTTEFWKQ YVDGDQCESN PCLNGGSCKD DINSYECWCP

FGFEGKNCEL DVTCNIKNGR CEQFCKNSAD NKVVCSCTEG YRLAENQKSC EPAVPFPCGR

VSVSQTSKLT RAETVFPDVD YVNSTEAETI LDNITQSTQS FNDFTRVVGG EDAKPGQFPW

QVVLNGKVDA FCGGSIVNEK WIVTAAHCVE TGVKITVVAG EHNIEETEHT EQKRNVIRII

PHHNYNAAIN KYNHDIALLE LDEPLVLNSY VTPICIADKE YTNIFLKFGS GYVSGWGRVF

HKGRSALVLQ YLRVPLVDRA TCLRSTKFTI YNNMFCAGFH EGGRDSCQGD SGGPHVTEVE

GTSFLTGIIS WGEECAMKGK YGIYTKVSRY VNWIKEKTKL T
```

The light chain of human fIXa comprises a γ-carboxyglutamic acid (Gla) domain (CTVFLDHENANKILNRPKRYNSGKLEEFVQGNLERECMEEKCSFEEAREVFENTERTTEF WKQYV; residues 28-92 of SEQ ID NO: 15, or, alternatively, YNSGKLEEFVQGNLERECMEEKCSFEEAREVFENTERTTEFWKQYV; residues 47-92 of SEQ ID NO: 15) and two epidermal growth factor (EGF)-like domains: EGF1 (DGDQCESNPCLNGGSCKDDINSYECWCPFGFEGKNCE; residues 93-129 of SEQ ID NO: 15) and EGF2 (LDVTCNIKNGRCEQFCKNSADNKWCSCTEGYRLAENQKSCE; residues 130-171 of SEQ ID NO: 15). In an embodiment of the invention, the light chain of human factor IXa comprises the amino acid sequence:

```
                                                  (SEQ ID NO: 2)
YNSGKLEEPV QGNLERECME EKCSFEEARE VFENTERTTE FWKQYVDGDQ CESNPCLNGG

SCKDDINSYE CWCPFGFEGK NCELDVTCNI KNGRCEQFCK NSADNKVVCS CTEGYPLAEN

QKSCEPAVPF PCGRVSVSQT SKLTR.
(Gla domain shown in italics, EGF1 and EGF2 domains shown in bold)
```

The heavy chain of human fIXa comprises a serine protease domain with catalytic residues Ser365, His221, and Asp289 and helix 330 (residues 330-338 of SEQ ID NO: 1; LVDRATCLR). In an embodiment of the invention, the heavy chain of human factor IXa comprises the amino acid sequence:

```
                                                  (SEQ ID NO: 3)
VVGGEDAKPG QFPWQVVLNG KVDAFCGGSI VNEKWIVTAA HCVETGVKIT VVAGEHNIEE

TEHTEQKRNV IRIIPHHNYN AAINKYNHDI ALLELDEPLV LNSYVTPICI ADKEYTNIFL

KFGSGYVSGW GRVFHKGRSA LVLQYLRVPL VDRATCLRST KFTIYNNMFC AGFHEGGRDS

CQGDSGGPHV TEVEGTSFLT GIISWGEECA MKGKYGIYTK VSRYVNWIKE KTK
(Catalytic residues in bold, helix 330-338 shown in italic)
```

In one embodiment of the invention, the human factor IX used is a recombinant human factor IX. Recombinant human factor IX may comprise, for example, the EGF2 domain, the activation peptide, and the catalytic domain of the factor IX protein. In an embodiment of the invention, recombinant human factor IX comprises the amino acid sequence from D85 to T415 of factor IX as follows:

(SEQ ID NO: 4)
DVTCNIKNGRCEQFCKNSADNKVVCSCTEGYRLAENQKSCEPAVPFPCGRVSVSQTSKLTRETVFP

DVDYVNSTEAETILDNITQSTQSFNDFTRVVGGEDAKPGQFPWQVVLNGKVDAFCGGSIVNEKWIVT

AAHCVETGVKITVVAGEHNIEETEHTEQKRNVIRIIPHHNYNAAINKYNHDIALLELDEPLVLNSYV

TPICIADKEYTNIFLKFGSGYVSGWGRVFHKGRSALVLQYLRVPLVDRATCLRSTKFTIYNNMFCAG

FHEGGRDSCQGDSGGPHVTEVEGTSFLTGIISWGEECAMKGKYGIYTKVSRYVNWIKEKTKLT.
(Activation peptide is shown in bold; light chain is underscored; heavy chain is italicized).

In an embodiment of the invention, the light chain of recombinant human fIXa comprises the EGF2 domain (residues 88-127). In an embodiment of the invention, the light chain of recombinant human factor IXa comprises the amino acid sequence: DVTCNIKNGRCEQFCKNSADNKVVC-SCTEGYRLAEN QKSCEPAVPFPCGRVSVSQT SKLTR (SEQ ID NO: 5). (EGF2 domain shown in bold as amino acid residues 4-43 of SEQ ID NO: 5)

As set forth herein, the scope of the present invention comprises crystalline proteins comprising factor IXa, e.g., human factor IXa, e.g., recombinant human factor IXa.

An "enzymatically active" factor IXa comprises any of the activities that characterize factor IXa, including but not limited to binding to factor VIIIa, activation of factor X, and promotion of coagulation at any activity level whatsoever. A substance inhibits factor IXa when, for example, it reduces the ability of factor IXa to bind to factor VIIIa, to activate factor X, to promote coagulation, or to perform any other function to any degree.

The terms "mutant" and "mutation" refer to any detectable change in genetic material or amino acid sequence. This includes gene mutations, in which the structure (e.g., DNA sequence) of a gene is altered, any gene or DNA arising from any mutation process, and any expression product (e.g., RNA or protein) expressed by a modified gene or DNA sequence. The term "variant" may also be used to indicate a modified or altered gene, DNA sequence, polypeptide or enzyme, etc., i.e., any kind of mutant. Sequence- and function-conservative variants of factor IXa (e.g., comprising a heavy chain of SEQ ID NO: 3 and a light chain of SEQ ID NO: 5) or enzymatically active fragments thereof are contemplated for use in the present invention and the present invention includes any crystal comprising any factor IXa variant. A natural allelic variant is one of several alternate naturally occurring forms of a gene occupying a given locus on a chromosome of an organism (Genes II, Lewin, B., ed., John Wiley & Sons, New York (1985)). "Function-conservative variants" of factor IXa (e.g., comprising a heavy chain of SEQ ID NO: 3 and a light chain of SEQ ID NO: 5) or fragments or mutants thereof are those in which a given amino acid residue in a factor IXa heavy chain or light chain polypeptide has been changed without significantly altering the overall conformation and/or function of the factor IXa protein, including, but not limited to, replacement of an amino acid with one having similar properties (such as, for example, polarity, hydrogen bonding potential, acidic, basic, hydrophobic, aromatic (see infra)). A sequence conservative variant is a variant wherein the DNA sequence encoding a polypeptide is changed or mutated in a manner wherein the encoded amino acid sequence is unchanged.

Protein or polypeptide sequence homology, or sequence identity, is determined by optimizing residue matches, if necessary, by introducing gaps as required. See, e.g., Needleham, et al. *J. Mol. Biol.* 48:443-453 (1970); Sankoff et al., "Time Warps, String Edits, and Macromolecules: The Theory and Practice of Sequence Comparison", Ch. 1, Addison-Wesley, Reading, Mass. (1983); and software packages from Intelli-Genetics, Mountain View, Calif. and the University of Wisconsin Genetics Computer Group (GCG), Madison, Wis.

The present invention includes any factor IXa crystal wherein the crystal comprises a factor IXa protein comprising a light chain and a heavy chain that comprise less than 100% similarity or identity to, for example, SEQ ID NO: 3 and SEQ ID NO: 5, respectively (e.g., natural allelic variations or homologues). In an embodiment of the invention, a factor IXa protein comprising a light chain or heavy chain that is less than 100% similar or identical to the amino acid sequence of SEQ ID NO: 3 or SEQ ID NO: 5, respectively, is enzymatically active. Sequence "identity" refers to exact matches between the amino acids of two sequences which are being compared. Sequence "similarity" refers to both exact matches between the amino acids of two polypeptides which are being compared in addition to matches between nonidentical, biochemically related amino acids. For example, biochemically related amino acids which share similar properties can fall, in an embodiment of the invention, within the following groups: polar/hydrophilic amino acids including asparagine, glutamine, serine, cysteine, threonine, lysine, arginine, histidine, aspartic acid and glutamic acid; nonpolar/hydrophobic amino acids including glycine, alanine, valine, leucine, isoleucine, proline, tyrosine, phenylalanine, tryptophan and methionine; acidic amino acids including aspartic acid and glutamic acid and basic amino acids including histidine, lysine and arginine. Typical factor IXa proteins and homologues thereof which are used in this invention will comprise a light chain and a heavy chain exhibiting from 50-100% similarity or identity, to 60-100% similarity or identity, e.g., with a light chain comprising the amino acid sequence of SEQ ID NO: 3 and a heavy chain comprising the amino acid sequence of SEQ ID NO: 5, respectively. The present invention includes crystals comprising factor IXa light chain and heavy chain polypeptides or homologues thereof comprising at least about 70% similarity or identity, generally at least 76% similarity or identity, more generally at least 81% similarity or identity, often at least 85% similarity or identity, more often at least 88% similarity or identity, typically at least 90% similarity or identity, more typically at least 92% similarity or identity, usually at least 94% similarity or identity, more usually at least 95% similarity or identity, preferably at least 96% similarity or identity, and more preferably at least 97% similarity or identity, and in particularly preferred embodiments, at least 98% or more (e.g., 99%) similarity or identity to the amino acid sequence of SEQ ID NO: 3 and the amino acid sequence of SEQ ID NO: 5, respectively.

The terms "express" and "expression" mean, in an embodiment of the invention, allowing or causing the information in a gene or DNA sequence to become manifest, e.g., producing a protein by activating the cellular functions involved in transcription and, optionally, translation of a corresponding gene or DNA sequence. A DNA sequence can be expressed using in vitro translation systems (e.g., rabbit reticulocyte lysate-based systems) or in or by a cell (e.g., an insect cell or bacterial cell such as *E. coli*) to form an "expression product" such as an mRNA or a protein. The expression product, e.g. the resulting protein, may also be referred to as "expressed".

An insect cell used in this invention includes any cell derived from an organism of the class Insecta. In an embodiment of the invention, the insect is *Spodoptera fruigiperda* (e.g., Sf9 or Sf21) or *Trichoplusia ni* (e.g., High Five™ cells; Invitrogen; Carlsbad, Calif.)). Other examples of insect expression systems that can be used with the present invention, for example to produce a polypeptide, include Bac-To-Bac (Invitrogen Corporation, Carlsbad, Calif.) or Gateway (Invitrogen Corporation, Carlsbad, Calif.).

A factor IXa heavy and/or light chain polypeptide can also be produced by any conventional method, including synthetic methods and recombinant DNA methods.

It may also be desirable to add amino adds at the amino- or carboxy-terminus of a factor IXa light chain and/or heavy chain polypeptide, e.g., to prepare a fusion protein. In one embodiment of the invention, the addition is a polyhistidine tag of 5-20 amino acids (e.g., 6 amino acids) in length. A histidine tag for aiding in purification of a factor IXa heavy chain and/or light chain polypeptide can be located at the carboxy-terminus. Other tags include glutathione-S-transferase, myc, FLAG (i.e., DYKDDDDK; SEQ ID NO: 13), calmodulin-binding peptide (CBP), maltose binding protein (MBP); hemagglutinin influenza virus (HAI); green fluorescent protein (GFP); thioredoxin; streptococcal protein G and streptococcal protein A.

In an embodiment of the invention, a protease cleavage site is located between any tag appended to a polypeptide of the present invention (e.g., a factor IXa heavy chain and/or light chain polypeptide) and said polypeptide. For example any of the following cleavage sites can, in an embodiment of the invention be incorporated into a polypeptide of the invention: enterokinase (DDDDK*) (SEQ ID NO: 6); factor Xa (IDGR*) (SEQ ID NO: 7); thrombin (LVPR*GS) (SEQ ID NO: 8); preScission (LEVLFQ*GP) (SEQ ID NO: 9); TEV protease (ENLYFQ*G) (SEQ ID NO: 10); 3C protease (ETLFQ*GP) (SEQ ID NO: 11); sortase A (LPET*G) (SEQ ID NO: 12) or granzyme B (D*X, N*X, M*N, S*X); wherein * indicates the protease cleavage point (see e.g., Arnau et al., (2006) Protein Expression and Purification 48, 1-13).

Crystals

The present invention comprises a factor IXa protein or a factor IXa-inhibitor complex as set forth herein in a crystalline or crystallizable composition or solution. A factor IXa (e.g., comprising a heavy chain of SEQ ID NO: 3 and a light chain of SEQ ID NO: 5) or factor IXa-inhibitor preparation can contain one or more members selected from the group consisting of a precipitant, a protein stabilizing agent, a salt, a buffering agent and a reducing agent or oxygen scavenger. Examples of reducing agents are dithiothreitol (DTT), dithioerythritol (DTE), β-mercaptoethanol (BME) and Tris(2-carboxyethyl)phosphine (TCEP). A "precipitant" is a compound that decreases the solubility of a protein in a concentrated solution. Alternatively, the term "precipitant" can be used to refer to a change in physical or chemical parameters which decreases protein solubility, including temperature, pH and salt concentrations. Precipitants induce crystallization by forming an energetically unfavorable precipitant-depleted layer around the protein molecules. To minimize the relative amount of this depletion layer, the proteins form associations and, ultimately, crystals. This process is explained in Weber, *Advances in Protein Chemistry* 41:1-36 (1991) which is incorporated by reference. In addition to precipitants, other materials are sometimes added to the protein crystallization solution. These include buffers, such as Tris or Hepes, to adjust the pH of the solution (and hence surface charge on the peptide) and salts, such as sodium chloride, lithium chloride and sodium citrate, to reduce the solubility of the protein. Other additives include glycerol and ethylene glycol, and detergents, such as n-octyl-β-D-glucopyranoside. Various precipitants are known in the art and include the following: ammonium sulfate, ethanol, isopropanol, 3-methyl-2,4 pentanediol; and many of the polyglycols, such as polyethylene glycol (e.g., PEG 400).

Crystallization may be accomplished by using known methods in the art (Giegé, et al., (1994) *Acta Crystallogr.* D50: 339-350; McPherson, (1990) *Eur. J. Biochem.* 189: 1-23). Such techniques include hanging drop vapor diffusion, sitting drop vapor diffusion, microbatch and dialysis. In an embodiment of the invention, hanging-drop vapor diffusion (see e.g., McPherson, (1976) *J. Biol. Chem.* 251: 6300-6303) is used. Both hanging drop and sitting drop vapor diffusion entail a droplet containing purified protein, buffer, and precipitant being allowed to equilibrate with a larger reservoir containing similar buffers and precipitants in higher concentrations. Initially, the droplet of protein solution contains an insufficient concentration of precipitant for crystallization, but as water and other volatile organic components vaporize from the drop and transfers to the reservoir, the precipitant concentration increases to a level optimal for crystallization. This may occur prior to or after reaching equilibrium. Once the system is in equilibrium, these optimum conditions are maintained until the crystallization is complete. The hanging drop method differs from the sitting drop method in the vertical orientation of the protein solution drop within the system. In the microbatch method, protein is mixed with precipitants to achieve supersaturation, the vessel is sealed and set aside until crystals appear. In the dialysis method, protein is retained in a sealed dialysis membrane which is placed into a solution containing precipitant. Equilibration across the membrane increases the precipitant concentration thereby causing the protein to reach supersaturation levels. It is desirable to use a factor IXa protein preparation having a concentration of at least about 1 mg/mL; for example, about 5 mg/mL to about 20 mg/mL (e.g., 6, 10, or 15 mg/mL).

The crystals of the present invention have a wide range of uses. For example, high quality crystals are suitable for X-ray or neutron diffraction analysis to determine the three dimensional structure of factor IXa or factor IXa-inhibitor complexes. Knowledge of these structures and solvent accessible residues allow structure-based design and construction of inhibitors and antagonists for factor IXa.

In addition, crystallization itself can be used as a purification method. In some instances, a polypeptide or protein crystallizes from a heterogeneous mixture into crystals. Isolation of such crystals by filtration and/or centrifugation, followed by redissolving the protein affords a purified solution suitable for use in growing high-quality crystals which are preferred for diffraction analysis.

Once a crystal of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of a factor IXa protein or a factor IXa-inhibitor complex. The present invention includes crystals which effectively diffract X-rays for the determination of the atomic coordinates of factor IXa or a factor IXa-inhibitor complex to a resolution of greater than about 5.0 Ångströms (e.g., about 4.5 Å, about 4.0 Å, about 3 Å, about 2.5 Å, about 2 Å, about 1 Å, about 0.5 Å), preferably greater than about 4.0 Ångströms (e.g., about 3 Å, about 2.5 Å, about 2 Å, about 1 Å, about 0.5 Å), more preferably greater than about 2.8 Ångströms (e.g., about 2.5 Å, about 2 Å, about 1 Å, about 0.5 Å) and most preferably greater than about 2.0 Ångströms (e.g., about 1.5 Å, about 1.0 Å, about 0.5 Å).

The present invention includes factor IXa or factor IXa-inhibitor complex crystals whose three-dimensional structure is described by the structure coordinates set forth in any of Tables 2-6. The scope of the present invention also includes crystals which possess structural coordinates which are similar to those set forth in any of Tables 2-6. In an embodiment of the invention, the crystals include a protein which comprises factor IXa or an enzymatically active fragment thereof. In another embodiment of the invention, the crystals include a protein which comprises factor IXa or an enzymatically active fragment thereof, and a substrate, ligand, or inhibitor of factor IXa, Structural similarity between crystals is discussed in detail below.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates, for an enzyme or an enzyme-complex or a portion thereof, is a relative set of points that define a shape in three dimensions.

The present invention includes crystals exhibiting structural coordinates which are similar to those set forth in any of Tables 2-6 but for crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Tables 2-6, the resulting three-dimensional shape is considered to be the same and, accordingly, the modified crystal is considered to be within the scope of the present invention.

Various computational analyses may be necessary to determine whether a crystal is sufficiently similar to the crystals whose structural coordinates are set forth in Tables 2-6 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is, in general, divided into four steps: 1) input the structures to be compared; 2) define the atom equivalences in these structures; 3) perform a fitting operation; and 4) analyze the results.

Generally, each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, C$\alpha$, C and O) or alpha carbon atoms (C$\alpha$) only for all conserved residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Ångströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

For the purpose of this invention, any set of structure coordinates of a molecule that has a RMSD of conserved residue backbone atoms (N, C$\alpha$, C, O) or alpha carbon atoms (C$\alpha$) only of less than about 1.5 Å when superimposed—using backbone atoms or alpha carbon atoms—on the relevant structure coordinates of Table 2-6 are considered identical and the crystals which they characterize are both within the scope of the present invention. In an embodiment of the invention, the root mean square deviation is less than about 1.0 Å, e.g., less than about 0.5 Å, e.g., less than about 0.1 Å.

The term "least squares" refers to a method based on the principle that the best estimate of a value is that in which the sum of the squares of the deviations of observed values is a minimum.

Computers

In accordance with the present invention, the structure coordinates of a factor IXa protein or a factor IXa-inhibitor complex may be stored in a machine-readable storage medium. Such data may be used for a variety of purposes, such as drug discovery and X-ray crystallographic analysis of a protein crystal. Accordingly, one aspect of this invention provides a machine-readable data storage medium comprising a data storage material encoded with the structure coordinates set forth in at least one of Tables 2-6. The machine-readable data storage medium may also include any set of structure coordinates of a molecule that has a root mean square deviation of conserved residue backbone atoms (N, C$\alpha$, C, O) of less than about 1.5 Å, preferably, less than about 1.0 Å, more preferably less than about 0.5 Å and even more preferably less than about 0.1 Å when superimposed—using backbone atoms—on the relevant structure coordinates of any one of Tables 2-6.

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages will be known to those skilled in the art.

Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of factor IXa or a factor IXa-inhibitor complex using a program such as INSIGHT (Molecular Simulations Inc., San Diego, Calif.) or QUANTA as described herein. Output hardware might also include a printer, so that hard copy output may be produced, or a disk drive, to store system output for later use. In an embodiment of the invention, the computer possesses a display that is displaying a three dimensional representation of factor IXa or a factor IXa-inhibitor complex.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which preferably is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

"Structure factors" are mathematical expressions derived from three-dimensional structure coordinates of a molecule. These mathematical expressions include, for example, amplitude and phase information. The term "structure factors" is known to those of ordinary skill in the art.

The present invention permits the use of structure-assisted drug design techniques to design, select, and synthesize chemical entities, including inhibitory compounds that are capable of binding to a factor IXa protein (e.g., comprising a heavy chain of SEQ ID NO: 3 and a light chain of SEQ ID NO: 5). Also, de novo and iterative drug design methods can be used to develop drugs from the structure of the factor IXa and factor IXa-inhibitor complex crystals of this invention.

The present method comprises a method by which the three-dimensional structure of any factor IXa or factor IXa-inhibitor crystal of the invention (e.g., factor IXa-Compound A complex; factor IXa-Compound B complex; factor IXa-Compound C complex; or factor IXa-Compound D complex crystal, or a crystal formed by soaking any of the above crystals with any one of Compounds A-D) can be used to identify a factor IXa antagonist or inhibitor or a substance that binds to factor IXa. For example, the present invention comprises a method for identifying a factor IXa inhibitor comprising the steps of: a) crystallizing factor IXa (e.g., comprising a heavy chain of SEQ ID NO: 3 and a light chain of SEQ ID NO: 5) to form at least one crystal; b) irradiating the crystal produced by step (a) to obtain a diffraction pattern of said crystal; c) determining the atomic coordinates of the three-dimensional structure of the factor IXa from the diffraction pattern; d) using the atomic coordinates and one or more molecular modeling techniques to identify a substance that interacts with the factor IXa or a binding pocket thereof; and, optionally, e) determining if the substance inhibits the ability of factor IXa to bind to factor VIIIa, activate factor X, or promote coagulation; wherein the substance is selected if it inhibits the binding of factor IXa to factor VIIIa, the activation of factor X, or promotion of coagulation. The ability of factor IXa to bind to factor VIIIa, activate factor X, or promote coagulation can be determined by, for example, any of the assays set forth in the "Assays" section herein. Another optional step comprises generating a crystalline complex between the substance and the protein and examining the three-dimensional structure of the complex. For example, the crystalline complex is, in an embodiment of the invention, generated by soaking a crystal of factor IXa or factor IXa-inhibitor complex with a solution containing the substance. Soaking is performed by either adding the substance directly to a droplet the crystals grew in, or by transferring the uncomplexed crystals into a solution containing the substance; cryoprotection of the crystals e.g., by adding ethylene glycol to the crystal then subjecting the suspension to a liquid nitrogen bath or stream to freeze; followed by irradiating the crystal to obtain a diffraction pattern of the crystal from which the atomic coordinates of the three-dimensional structure of the complex is obtained. These data confirm the existence of the complex, provide valuable data regarding the design of future inhibitors and provide insight as to the mechanism of inhibition by the substance.

One particularly useful drug design technique enabled by this invention is structure-assisted drug design. Structure-assisted drug design is a method for optimizing associations between a protein and a compound by determining and evaluating the three-dimensional structures of successive sets of protein/compound complexes.

Numerous computer programs are available and suitable for structure-assisted drug design and the processes of computer modeling, model building, and computationally identifying, selecting and evaluating potential inhibitors in the methods described herein. These include, for example, GOLD (available from CCDC, Cambridge, UK), Glide (available from SCHRODINGER, Portland, Oreg.), AUTODOCK (available from Art Olson at The Scripps Research Institute, La Jolla, Calif.), FlexX (available from Tripos, St. Louis. Mo.), DOCK (available from University of California, San Francisco, Calif.), ICM (available from MolSoft, San Diego, Calif.), GRID (available form Oxford University, UK), Fred (available from OpenEye Scientific Software, Santa Fe, N. Mex.), Slide (available from L. Kuhn, MSU, East Lansing, Mich.), Surflex (available from Discovery Partners International, San Diego, Calif.) and QXP (available from C. McMartin, Conn.), and 3D database systems such as MACCS-3D (available from MDL Information Systems, San Leandro, Calif.), UNITY (available from Tripos), and CATALYST (available from Accelrys, San Diego, Calif.), CoMFA (available from Tripos), Phase (available from SCHRODINGER).

Potential inhibitors may also be computationally designed "de novo" using such software packages as Cerius2/LUDI and AutoLudi (available from Accelrys), LeapFrog (Tripos), SPROUT (available from SimBioSys Inc. Canada), ALLEGROW (available from Regine S. Bohacek, Boston De Novo Design, Mass.), BOMB (available from W. Jorgensen, Yale University, New Haven, Conn.) and CombiSMoG (available from Concurrent Pharmaceuticals, MA). Compound deformation energy and electrostatic repulsion, may be evaluated using the programs based on QM/Semiempirical methods, such as: GAUSSIAN 98 (available from Gaussian, Inc.), Jaguar (available from SCHRODINGER), or based on Forcefield methods, such as: AMBER, QUANTA/CHARMM, INSIGHT II/DISCOVER, MacroModel, and Sybyl. These computer evaluation and modeling techniques may be performed on any suitable hardware including for example, workstations available from Silicon Graphics, Sun Microsystems, PC or IBM Linux workstations and the like. These techniques, methods, hardware and software packages are representative and are not intended to be comprehensive listing. Other modeling techniques known in the art may also be employed in accordance with this invention. See for example, N. C. Cohen, Molecular Modeling in Drug Design, Academic Press (1996) (and references therein).

Those skilled in the art will appreciate that association of natural ligands or substrates with the binding pockets of their corresponding receptors or enzymes is the basis of many biological mechanisms of action. The terms "binding pocket" or "binding site," as used herein, include any region or domain of a molecule or molecular complex that, as a result of its shape, favorably associates with another chemical entity or compound. The Gla, EGF1, EGF2, and serine protease domains of factor IXa, e.g., may all be defined as binding pockets. Binding pockets of factor IXa may be as described in, e.g., Schmidt et al., *Trends Cardiovasc Med* 13(1):39-45 (2003); Perera et al., Thromb Haemost 85:596-603 (2001); and Howard et al., *Arterioscler Thromb Vase Biol* 27:722-727 (2007), all of which are incorporated herein by reference in their entireties. Drugs may exert their biological effects through association with the binding pockets. Such association may occur with all or any part of the binding pockets. An understanding of such associations will help lead to the design of drugs having more favorable associations with the target enzyme, and thus, improved biological effects. Therefore, this information is valuable in designing potential enzyme inhibitors, such as inhibitors of factor IXa. An embodiment of the present invention includes methods wherein, using computer assisted drug design software, a candidate substance is docked into a binding pocket of factor IXa (e.g., the serine protease domain), in order to determine if the candidate is an effective binder. Evaluation of the binding properties of a candidate during this process can depend on several parameters including the deformation energy of the candidate as well as the interaction energies of the inhibitor and protein. Other effective parameters include the subjective evaluation of the technician performing the computer-assisted docking operation.

In general, computer assisted drug design can include conformational analysis which includes the exploration of energetically favorable spatial arrangements (shapes) of a molecule (conformations) using molecular mechanics, molecular dynamics, quantum chemical calculations or analysis of experimentally-determined structural data, e.g., NMR or crystal structures. Molecular mechanics and quantum chemical methods can be employed to compute conformational energies, whereas systematic and random searches, Monte Carlo, molecular dynamics, and distance geometry are methods (often combined with energy minimization procedures) used to explore the conformational space.

In iterative structure-assisted drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of a new protein, solving the three-dimensional structure of the protein, and comparing the associations between the new protein and previously solved protein. By observing how changes in the compound affected the protein/compound associations, these associations may be optimized.

In some cases, iterative structure-assisted drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. In an embodiment of the invention, factor IXa or factor IXa-inhibitor complex crystals provided by this invention may be soaked in the presence of a compound or compounds, such as a factor IXa inhibitor (e.g., Compound A, B, C, or D), to provide novel factor IXa/compound crystal complexes. As used herein, the term "soaked" includes a process in which the crystal is transferred to a solution containing the compound of interest. The term "factor IXa-inhibitor complex crystal" also encompasses crystals prepared by soaking a factor IXa-inhibitor complex crystal in the presence of a factor IXa inhibitor (e.g., Compound A, B, C, or D).

The structure coordinates set forth in any of Tables 2-6 can also be used to aid in obtaining structural information about another crystallized molecule or molecular complex. This may be achieved by any of a number of well-known techniques, including molecular replacement.

The structure coordinates set forth in any of Tables 2-6 can also be used for determining at least a portion of the three-dimensional structure of molecules or molecular complexes which contain at least some structurally similar features to factor IXa or factor IXa-inhibitor complexes. In particular, structural information about another crystallized molecule or molecular complex may be obtained by well-known techniques, including molecular replacement.

Therefore, another aspect of this invention provides a method of utilizing molecular replacement to obtain structural information about a crystallized molecule or molecular complex, whose structure is unknown, comprising the steps of generating an X-ray diffraction pattern from said crystallized molecule or molecular complex and applying crystallographic phases derived from at least a portion of the structure coordinates set forth in any one of Tables 2-6 to the X-ray diffraction pattern to generate a three-dimensional electron density map of the molecule or molecular complex whose structure is unknown. Once the structure coordinates of a protein crystal have been determined, they are useful in solving the structures of other crystals. For example, proteins may be crystallized and their structure elucidated by for example, difference Fourier techniques and molecular replacement.

By using molecular replacement, all or part of the structure coordinates of, for example, the factor IXa protein or factor IXa-inhibitor complex provided by this invention (and set forth in any one of Tables 2-6) can be used to determine the previously unknown structure of a crystallized molecule or molecular complex more quickly and efficiently than attempting to determine such information ab initio.

Molecular replacement provides an accurate estimation of the phases for an unknown structure. Phases are a factor in equations used to solve crystal structures that cannot be measured experimentally. Obtaining accurate values for the phases, by methods other than molecular replacement, is a time-consuming process. However, when the crystal structure of a protein containing a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of factor IXa crystal or factor IXa-inhibitor complex crystal according to any one of Tables 2-6 within the unit cell of the crystal of the unknown molecule or molecular complex so as best to account for the observed X-ray diffraction pattern amplitudes to generate an election density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in *Meth. Enzymol.*, 115: 55-77 (1985); Rossman, ed., "The Molecular Replacement Method", *Int. Sci. Rev. Ser.*, No. 13, Gordon & Breach, New York (1972)).

Phase information from the structure coordinates of the present invention may be used to elucidate the structure of other crystals. For example, the structure of factor IXa in complex with other atoms or molecules may be elucidated. Such complexes include, for example, those containing atoms soaked into or co-crystallized within the crystal lattice. Other structures which can be elucidated using the phase information of the present invention include for example other kinases or homologues or mutants thereof having sufficient three-dimensional structure similarity to factor IXa complex as to be solved using molecular replacement. Also, these protein molecules in a complex with a small molecule substrate(s), inhibitor(s), transition state analog(s), product(s) or analog(s) of any of these may also be solved using the phase information of the present invention.

The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

Factor IXa or factor IXa-inhibitor crystals may be studied using well-known X-ray diffraction techniques and may be refined versus X-ray data to 3 Å resolution or better to an $R_{free}$ value of about 0.40 or less using computer software such as X-PLOR (Yale University, 1992, distributed by Molecular Simulations, Inc.; see e.g., Blundell & Johnson, supra; *Meth, Enzymol.*, vol. 114 & 115, H. W. Wyckoff et al., eds., Academic Press (1985)) and BUSTER (Bricogne, G. (1993). Acta Cryst. D49, 37-60, "Direct Phase Determination by Entropy Maximisation and Likelihood Ranking: Status Report and Perspectives"; Bricogne, G. (1997) "The Bayesian Statistical Viewpoint on Structure Determination: Basic Concepts and Examples", in Methods in Enzymology, 276A, 361-423, C. W. Carter & R. M. Sweet, eds.; and Roversi et al., (2000), "Modelling prior distributions of atoms for Macromolecular Refinement and Completion", Acta Cryst., D56, 1313-1323). This information may be used to optimize known factor IXa inhibitors and to design new factor IXa inhibitors.

Assays

One use for factor IXa or factor IXa-inhibitor complexes is for the identification of novel factor IXa inhibitors, which may be, e.g., antibodies, aptamers, or chemical compounds. Factor IXa inhibitors are useful, for example, as anti-coagulation agents. A factor IXa inhibitor identified using an assay of the present invention can be administered to a subject to treat or prevent coagulation-related disorders, e.g., thrombosis arising from venous and/or arterial vascular injuries, myocardial infarction, and ischemic stroke. A factor IXa inhibitor identified using an assay of the present invention can also be administered to prevent coagulation during procedures such as cardiac valve replacement, hemodialysis, and coronary intervention. In an embodiment of the invention, substances which selectively inhibit factor IXa, but not factor Xa are selected as optimal anti-coagulation agents.

In an embodiment of the invention, factor IXa or Xa activity is measured in vitro using an assay whereby a factor IXa substrate is added to factor IXa and proteolytic cleavage of the substrate by the factor IXa is detected. For example, in an embodiment of the invention, the substrate is methylsulfonyl-D-cyclohexylglycyl-glycyl-arginine-paranitroanilide, e.g., the monoacetate salt thereof; wherein cleavage by factor IXa liberates the paranitroanalide chromophore which can be detected fluorescently (e.g., absorbance 360 nm; emission 440 nm). In an embodiment of the invention, a candidate inhibitor of factor IXa or Xa is incubated with the factor IXa or Xa assay and activity is measured and compared to that of an assay in the absence of the candidate inhibitor. Inhibition of cleavage of the substrate in the presence of the candidate inhibitor, relative to that of the assay performed in the absence of the candidate inhibitor indicates that the candidate inhibitor is a factor IXa or Xa inhibitor.

The present invention provides methods for determining the structure of a complex comprising a compound bound to factor IXa protein. Such methods may be used to determine whether the compound is a suitable factor IXa inhibitor. For example, observation of the compound bound to factor IXa would indicate that the compound is a factor IXa inhibitor. In an embodiment of the invention, said method includes (a) mixing the factor IXa protein with the compound; (b) crystallizing a factor IXa protein-compound complex; and (c) determining the structure of the complex, for example, by employing the data of any one of Tables 2-6 optionally varied by a root mean square deviation of conserved residue backbone atoms or of alpha carbon atoms of less than about 1.5 Å when superimposed on backbone atoms described in Table 2, 3, 4, 5 or 6. The present invention also provides a soaking method for determining the structure of a complex comprising a second compound bound to factor IXa protein including: (a) providing a crystal of factor IXa protein complexed with a first compound; (b) soaking the crystal comprising the first compound with a second compound to form a complex between said factor IXa protein and said second compound; and (c) determining the structure of the complex comprising the second compound by employing the data of any one of Tables 2-6 optionally varied by a root mean square deviation of conserved residue backbone atoms or of alpha carbon atoms of less than about 1.5 Å when superimposed on backbone atoms described in Table 2, 3, 4, 5 or 6. For example, if the second compound is shown to displace the first compound and form a complex with factor IXa, then this indicates that the second compound is a factor IXa inhibitor.

In an embodiment of the invention, such methods can be supplemented by directly testing whether the compound selectively inhibits factor IXa and not factor Xa, for example, by the protease assay methods discussed above. In an embodiment of the invention, the compound is selected if it is observed to bind to factor IXa and to selectively inhibit factor IXa protease activity over factor Xa activity, to any degree.

In an embodiment of the invention, selective inhibition of factor IXa over factor Xa by a compound comprises any detectably greater inhibition of factor IXa over factor Xa, whatsoever. In another embodiment, selective inhibition comprises, e.g., 1%, greater, 5% greater, 10% greater inhibition, 25% greater inhibition, 50% greater inhibition, 75% greater inhibition, 100% greater inhibition, 200% greater inhibition, 500% greater inhibition or 1000% greater inhibition.

Rates of blood coagulation, e.g., following administration of an anti-clotting agent identified using a method or composition of the present invention, can be determined using one or more assays selected from the group consisting of activated partial thromboplastin time (aPTT) assays, prothrombin time (PT) assays, thrombin time (TCT) assays, clot formation and lysis global (CIQFAL) assays, and chromogenic assays.

EXAMPLES

The following Examples are intended for exemplification of the present invention only and should not be construed to limit the scope of the invention. Any composition (e.g., crystals as defined by amino acid sequence, space group and/or unit cell dimensions) or method or product of such method disclosed in the Examples section forms part of the present invention.

Example 1

Cloning of Recombinant Human Factor IX

Recombinant factor IX (fIX) was cloned to encode the EGF2 domain, the activation peptide, and the catalytic domain corresponding to residues D85 to T415 as previously described (Hopfner et al., EMBO, 16, 6626-6635 (1997)). The DNA was amplified using the pCMVC-XL4 vector containing the insert for factor IX (accession #NM_000133.2). The PCR primers added CACCATG (SEQ ID NO:19) to the 5' and a stop codon to the 3' ends. The PCR product was then inserted into the shuttle vector, pENTR/SD/D-TOPO (Invitrogen), according to the manufacturer's instructions. The expression vector was made by the Gateway LR reaction between the shuttle and pDest14 vector. All vectors were sequence confirmed.

Example 2

Expression of Recombinant Human Factor IX

A colony from freshly transformed cells was grown in 10 ml terrific broth with 100 µg/ml ampicillin for 3 hours at 37° C. Terrific broth is prepared by adding the following to 800 ml distilled H2O:

12 g Tryptone 24 g Yeast extract, and 4 ml Glycerol

Next, the volume is adjusted to 900 ml with distilled $H_2O$. The broth is sterilized by autoclaving; cooled to room temperature. The volume adjusted to 1000 ml with 100 ml of a filter sterilized solution of 0.17M $KH_2PO_4$ and 0.72M $K_2HPO_4$. The 10 ml of culture was then used to initiate a 1.0 L culture with the same medium, and it was grown to an OD of approximately 1.0 at 37° C. and stored at 4° C. overnight for inoculation of a 10 L tank (terrific broth containing 100 µg/ml ampicillin). The 10 L culture was grown to an OD of 0.8-1.0 at 37° C., and was induced with 0.5 mM IPTG. The cells were harvested by centrifugation at 5000 g after 4-6 hours and stored at −20° C.

Example 3

Purification of Recombinant Human Factor IX

The purification and refolding of f IX was performed essentially as described by Hopfner et al. (supra). The pellet from the 6 L fermentation was re-suspended in 150 ml of 50 mM Tris pH 7.3 and lysed by 2 passes through a microfluidizer. DNA was digested by the addition of 2 mM $MgCl_2$ and 1000 U Benzonase and incubated at room temperature for 30 minutes. The mixture was made with 2% Triton X-100, 0.5 M NaCl and 20 mM EDTA and was incubated for an additional 30 minutes. Inclusion bodies were isolated by centrifugation at 25,000 g for 30 minutes. The inclusion bodies were solubilized in 6 M guanidine HCl, 100 mM Tris-HCl, 20 mM EDTA, 150 mM oxidized glutathione/15 mM reduced glutathione, pH 8.2 at a concentration of 5.0 mg/ml and incubated for 3 hours at room temperature. After adjusting the pH to 5.0 the protein was dialyzed, at 4° C., against several changes of 6 M guanidine HCl, 100 mM Tris-HCl, 20 mM EDTA, pH 5.0. The dialyzed protein was recovered and refolding was initiated by diluting 100-fold into 50 mM Tris, 0.5 M arginine, 1 mM EDTA, 20 mM $CaCl_2$, 0.5 mM cysteine, pH 8.5 and incubated with gentle stirring for at least 3 days at 4° C.

The refolding solution was concentrated to a minimum volume using an Amicon pellicon device fitted with a 10 k filter, clarified by centrifugation at 5000 g for 15 minutes and dialyzed overnight against several changes of 50 mM Tris-HCl pH 8.0, 0.05 M NaCl. The dialyzed protein was applied to a 10 ml Q-Sepharose FF column equilibrated with 50 mM Tris-HCl pH 8.0, 50 mM NaCl and the refolded rFIX was eluted with a 50-500 mM NaCl gradient. The protein containing fractions were pooled, adjusted to 1 mg/ml, and stored at −80° C.

Example 4

Activation and Preparation of Factor IXa Complexes (General)

Aliquots of purified fIX were defrosted as needed and were activated by incubating overnight at 37° C. with 20 μg/ml of Russell's Viper venom (RVV) (Sigma V2501). The activated protein was desalted into 50 mM Tris-HCl pH 8.0, 50 mM NaCl, using a HiPrep desalting column, and applied to a HiTrap 5 ml QHP column. The flow-through containing the purified fIXa was collected, concentrated to and applied to a Superdex S-200 column equilibrated with 25 mM Tris-HCl pH 8.0, 0.15 M NaCl. The monomer fractions were pooled and inhibitor was added to 100 μM. The protein was concentrated to 10 mg/ml (330 μM) and additional inhibitor was added to 660-1000 μM.

Following activation, the activation polypeptide was removed to create two separate polypeptides: DVTCNIKN-GRCEQFCKNSADNKVVCSCTEGYRLAEN-QKSCEPAVPFPCGRVSVSQTSKLTR (SEQ ID NO: 13); and VVGGEDAKPGQFPWQVVLNGKVDAFCGGSI-VNEKWIVTAAHCVETGVKITVVAGEHNIEETEHTE-OKIINVIRIIPHH NYNAAINKYWHDIALLELDEPLV-LNSYVTPICIADKEYTNIFLKFGSGYNTSGWGRVF-HKGRSALVLQYLRVPINDRA TCLRSTKFTIYNNMF-CAGFHEGGRDSCQGDSGGPHITTEVEGTSFLTGI-ISWGEECAMKGKYGIYTKVSRYVNWIKEK TKLT (SEQ ID NO: 14); which were joined by disulfide bridges. This activated dimeric molecule is factor IXa and was used for further crystallization studies.

Example 5

Preparation of Specific Factor IXa-Compound A Complex

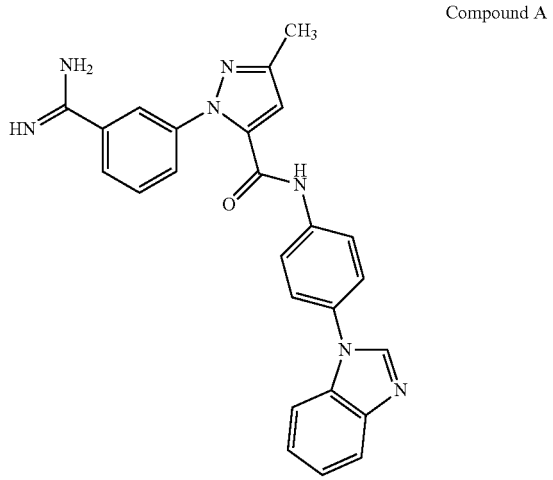 [SMILES: Cc1cc(C(=O)Nc2ccc(-n3cnc4ccccc43)cc2)n(-c2cccc(C(=N)N)c2)n1]

Compound A

Compound A was added to a final concentration of 1 mM into 22.5 μL of fIXa at 0.23 mg/mL (6.4 μM). The final DMSO concentration was 1%. The complex was rotated on a nutator for 2-18 hours at 2° C. The sample was clarified by low speed centrifugation followed by a 52 fold concentration step using centrifugation with a 5000 Molecular Weight Cut Off Millipore Ultrafree micro concentrator to 10-12 mg/ml. Dynamic light scattering was used to measure the aggregation state of the concentrated fIXa-Compound A complex. A single component was observed-consistent with a monodisperse monomer (33000 MW) in solution. SDS PAGE analysis showed no visible signs of degradation four days post setup. Dynamic light scattering and SDS PAGE results were consistent with a stable monodisperse fIXa complex suitable for crystallization screening.

Example 6

Crystallization of Factor IXa-Compound A Complex

Figure 1:
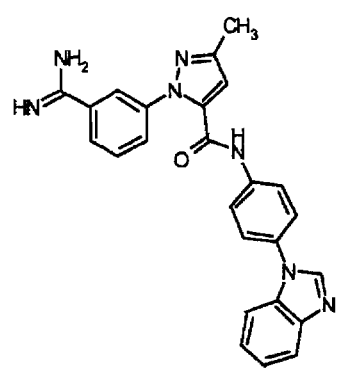
FIG. 1. Molecular structure of Compound A.
Figure 2:
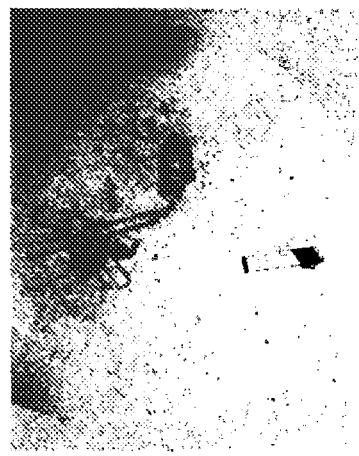
FIG. 2. Photomicrograph of human wild type factor IXa-Compound A complex crystals at 70× magnification. The crystals were prepared with precipitant solution containing 20% PEG 6000 (v/v), 0.1 M citric acid, pH 6.0 and were grown at 4° C. for 3 days.
Figure 3:
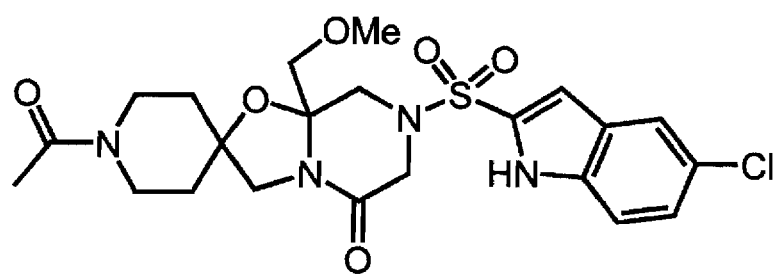
FIG. 3. Molecular structure of Compound B.

The factor IXa-Compound A complex from Example 5 was crystallized using a hanging-drop vapor diffusion method. The protein (0.5 μl; 6 mg/ml) in 25 mM Tris, pH 8.0, 0.15 M sodium chloride, buffer was mixed with an equal volume of precipitant solution containing 20% PEG 6000 (v/v), 0.1 M citric acid, pH 5.9 placed on the underside of a siliconized Teflon coverslip and sealed in close proximity to 0.08 mL of the precipitant solution. Crystallization plates were incubated at 4° C.; orthorhombic crystals (0.01×0.05 mm) grew over 1-9 days. FIG. 2 shows a photomicrograph of the factor IXa-Compound A complex crystals grown for 3 days, at 70× magnification.

Example 7

Crystallographic Analysis of Factor IXa-Compound A Complex

Prior to data collection, crystals were harvested at 4° C. and transferred into the crystallization solution with 25% glycerol added. After a 5-10 minute exposure to this cryoprotectant, the crystals were frozen in liquid nitrogen. The frozen crystals were then mounted onto the X-Ray detector in a nitrogen cooled stream. X-ray diffraction was collected at the Schering Plough Research Institute using a Rigaku FRE superbright X-ray generator equipped with a Rigaku HTC image plate detector. Data were integrated and scaled using the HKL package.

| Data Collection Statistics | |
| --- | --- |
| Resolution | 30.0-1.64 Å |
| No. of collected reflections | 446523 |
| No. of unique reflections (F >= 0) | 38787 |
| R-sym | 6.0% |
| Percent of theoretical (I/s >= 1) | 88.5% |
| Unit Cell | a = 48.1 Å, b = 69.8 Å, c = 92.1 Å, $\alpha = \beta = \gamma = 90°$ |
| Space Group | $P2_12_12_1$ |
| Asymmetric unit | 1 molecule |

Example 8

Factor IXa-Compound A Complex Structure Determination

The crystal structure was solved using molecular replacement (CCP4) using the search model 1RFN. Refinement was done using the program AUTOBUSTER (Global Phasing Limited).

| | |
|---|---|
| Number of reflections | 34185 |
| Resolution limits | 28.3-1.64 Å |
| Completeness for range | 88.1% |
| FREE R TEST SET COUNT & SIZE | 1727 (5.1%) |
| Number of protein atoms | 2381 |
| Number of solvent atoms | 163 |
| R-factor | 0.223 |
| R-free | 0.253 |
| RMSD bond length | 0.011 Å |
| RMSD bond angles | 1.26° |

The following table contains one line for each atom in one Factor IXa monomer. The columns are: 1) residue number, 2) 1-letter amino acid code, 3) atom name, 4) x-coordinate, 5) y-coordinate, 6) z-coordinate, 7) B-factor, 8) Chain ID. (Amino Acid Code X are Calcium or Citrate, Z is Compound A and O for water) The numbering scheme is based on chymotrypsin. Note: B fractors greater than 100 appear as 0 in column 7.

TABLE 2

Atomic Coordinates of Factor IXa co-crystal Compound A complex

| Res# | AA | Atom | x | y | z | B | Chain |
|---|---|---|---|---|---|---|---|
| 16 | V | N | -20.4 | -9.2 | -25.5 | 9 | A |
| 16 | V | CA | -19.6 | -10.3 | -25.0 | 10 | A |
| 16 | V | C | -20.2 | -11.5 | -25.6 | 10 | A |
| 16 | V | O | -21.4 | -11.8 | -25.3 | 10 | A |
| 16 | V | CB | -19.7 | -10.3 | -23.4 | 14 | A |
| 16 | V | CG1 | -18.8 | -11.5 | -22.9 | 13 | A |
| 16 | V | CG2 | -19.2 | -9.0 | -22.8 | 14 | A |
| 17 | V | N | -19.4 | -12.3 | -26.3 | 11 | A |
| 17 | V | CA | -19.8 | -13.5 | -26.9 | 11 | A |
| 17 | V | C | -19.3 | -14.6 | -25.9 | 12 | A |
| 17 | V | O | -18.2 | -14.6 | -25.4 | 12 | A |
| 17 | V | CB | -19.1 | -13.8 | -28.3 | 14 | A |
| 17 | V | CG1 | -19.5 | -15.1 | -28.8 | 16 | A |
| 17 | V | CG2 | -19.5 | -12.7 | -29.3 | 14 | A |
| 18 | G | N | -20.1 | -15.6 | -25.6 | 12 | A |
| 18 | G | CA | -19.8 | -16.7 | -24.7 | 14 | A |
| 18 | G | C | -19.5 | -16.4 | -23.3 | 16 | A |
| 18 | G | O | -18.8 | -17.1 | -22.6 | 15 | A |
| 19 | G | N | -20.2 | -15.3 | -22.8 | 14 | A |
| 19 | G | CA | -20.1 | -14.9 | -21.4 | 16 | A |
| 19 | G | C | -21.3 | -15.4 | -20.6 | 17 | A |
| 19 | G | O | -22.2 | -16.3 | -21.0 | 15 | A |
| 20 | E | N | -21.4 | -14.8 | -19.5 | 13 | A |
| 20 | E | CA | -22.6 | -15.1 | -18.6 | 16 | A |
| 20 | E | C | -23.2 | -13.8 | -18.1 | 17 | A |
| 20 | E | O | -22.6 | -12.8 | -18.0 | 16 | A |
| 20 | E | CB | -22.1 | -15.9 | -17.4 | 18 | A |
| 20 | E | CG | -21.2 | -17.1 | -17.8 | 28 | A |
| 20 | E | CD | -20.5 | -17.7 | -16.6 | 48 | A |
| 20 | E | OE1 | -19.3 | -17.3 | -16.3 | 27 | A |
| 20 | E | OE2 | -21.1 | -18.4 | -15.8 | 37 | A |
| 21 | D | N | -24.5 | -13.9 | -17.6 | 14 | A |
| 21 | D | CA | -25.2 | -12.8 | -17.0 | 15 | A |
| 21 | D | C | -24.5 | -12.4 | -15.7 | 18 | A |
| 21 | D | O | -24.4 | -13.2 | -14.8 | 16 | A |
| 21 | D | CB | -26.6 | -13.2 | -16.6 | 17 | A |
| 21 | D | CG | -27.5 | -13.5 | -17.8 | 22 | A |
| 21 | D | OD1 | -28.7 | -13.9 | -17.5 | 24 | A |
| 21 | D | OD2 | -27.1 | -13.4 | -19.0 | 19 | A |
| 22 | A | N | -24.2 | -11.1 | -15.6 | 15 | A |
| 22 | A | CA | -23.7 | -10.5 | -14.4 | 13 | A |
| 22 | A | C | -24.9 | -10.5 | -13.4 | 17 | A |
| 22 | A | O | -26.0 | -10.3 | -13.8 | 18 | A |
| 22 | A | CB | -23.2 | -9.1 | -14.6 | 14 | A |
| 23 | K | N | -24.6 | -10.6 | -12.1 | 15 | A |
| 23 | K | CA | -25.7 | -10.4 | -11.1 | 14 | A |
| 23 | K | C | -25.7 | -8.9 | -10.8 | 19 | A |
| 23 | K | O | -24.8 | -8.2 | -10.9 | 17 | A |
| 23 | K | CB | -25.3 | -11.1 | -9.8 | 18 | A |
| 23 | K | CG | -25.3 | -12.6 | -9.9 | 24 | A |
| 23 | K | CD | -26.7 | -13.2 | -9.7 | 47 | A |

TABLE 2-continued

Atomic Coordinates of Factor IXa co-crystal Compound A complex

| Res# | AA | Atom | x | y | z | B | Chain |
|---|---|---|---|---|---|---|---|
| 23 | K | CE | -26.6 | -14.8 | -9.9 | 68 | A |
| 23 | K | NZ | -27.9 | -15.3 | -10.5 | 72 | A |
| 24 | P | N | -26.9 | -8.4 | -10.2 | 16 | A |
| 24 | P | CA | -27.0 | -7.0 | -9.8 | 15 | A |
| 24 | P | C | -25.8 | -6.6 | -8.9 | 18 | A |
| 24 | P | O | -25.4 | -7.4 | -8.0 | 18 | A |
| 24 | P | CB | -28.3 | -7.0 | -9.1 | 16 | A |
| 24 | P | CG | -29.1 | -8.0 | -9.7 | 21 | A |
| 24 | P | CD | -28.1 | -9.2 | -9.9 | 17 | A |
| 25 | G | N | -25.1 | -5.5 | -9.2 | 16 | A |
| 25 | G | CA | -24.0 | -5.0 | -8.5 | 15 | A |
| 25 | G | C | -22.7 | -5.8 | -8.6 | 15 | A |
| 25 | G | O | -21.7 | -5.6 | -7.8 | 13 | A |
| 26 | Q | N | -22.6 | -6.8 | -9.5 | 12 | A |
| 26 | Q | CA | -21.4 | -7.6 | -9.6 | 11 | A |
| 26 | Q | C | -20.2 | -6.8 | -10.2 | 13 | A |
| 26 | Q | O | -19.0 | -7.1 | -9.9 | 15 | A |
| 26 | Q | CB | -21.6 | -8.8 | -10.5 | 13 | A |
| 26 | Q | CG | -20.5 | -9.8 | -10.4 | 15 | A |
| 26 | Q | CD | -20.7 | -11.1 | -11.2 | 18 | A |
| 26 | Q | OE1 | -21.9 | -11.4 | -11.6 | 17 | A |
| 26 | Q | NE2 | -19.7 | -11.8 | -11.5 | 20 | A |
| 27 | F | N | -20.5 | -5.8 | -11.0 | 12 | A |
| 27 | F | CA | -19.5 | -4.9 | -11.7 | 11 | A |
| 27 | F | C | -20.0 | -3.5 | -11.5 | 12 | A |
| 27 | F | O | -20.4 | -2.8 | -12.5 | 12 | A |
| 27 | F | CB | -19.3 | -5.3 | -13.1 | 13 | A |
| 27 | F | CG | -18.9 | -6.7 | -13.3 | 13 | A |
| 27 | F | CD1 | -19.9 | -7.7 | -13.5 | 15 | A |
| 27 | F | CD2 | -17.6 | -7.1 | -13.2 | 14 | A |
| 27 | F | CE1 | -19.5 | -9.0 | -13.7 | 14 | A |
| 27 | F | CE2 | -17.2 | -8.4 | -13.3 | 16 | A |
| 27 | F | CZ | -18.2 | -9.4 | -13.6 | 13 | A |
| 28 | P | N | -20.0 | -3.0 | -10.3 | 12 | A |
| 28 | P | CA | -20.6 | -1.7 | -10.0 | 10 | A |
| 28 | P | C | -19.8 | -0.5 | -10.6 | 12 | A |
| 28 | P | O | -20.4 | 0.6 | -10.5 | 12 | A |
| 28 | P | CB | -20.6 | -1.6 | -8.4 | 11 | A |
| 28 | P | CG | -19.4 | -2.5 | -8.1 | 15 | A |
| 28 | P | CD | -19.4 | -3.6 | -9.1 | 14 | A |
| 29 | W | N | -18.7 | -0.7 | -11.2 | 12 | A |
| 29 | W | CA | -17.9 | 0.3 | -11.8 | 12 | A |
| 29 | W | C | -18.4 | 0.5 | -13.3 | 13 | A |
| 29 | W | O | -18.0 | 1.4 | -14.0 | 12 | A |
| 29 | W | CB | -16.4 | 0.1 | -11.8 | 11 | A |
| 29 | W | CG | -16.1 | -1.3 | -12.0 | 12 | A |
| 29 | W | CD1 | -15.9 | -2.0 | -13.2 | 14 | A |
| 29 | W | CD2 | -15.9 | -2.3 | -11.0 | 12 | A |
| 29 | W | NE1 | -15.6 | -3.3 | -13.0 | 14 | A |
| 29 | W | CE2 | -15.7 | -3.5 | -11.6 | 15 | A |
| 29 | W | CE3 | -16.0 | -2.2 | -9.6 | 13 | A |
| 29 | W | CZ2 | -15.5 | -4.7 | -10.9 | 15 | A |
| 29 | W | CZ3 | -15.9 | -3.4 | -8.9 | 15 | A |
| 29 | W | CH2 | -15.6 | -4.6 | -9.5 | 16 | A |
| 30 | Q | N | -19.1 | -0.5 | -13.8 | 8 | A |
| 30 | Q | CA | -19.5 | -0.5 | -15.2 | 9 | A |
| 30 | Q | C | -20.6 | 0.5 | -15.5 | 13 | A |
| 30 | Q | O | -21.6 | 0.6 | -14.8 | 14 | A |
| 30 | Q | CB | -20.1 | -1.9 | -15.6 | 9 | A |
| 30 | Q | CG | -20.7 | -2.0 | -17.0 | 10 | A |
| 30 | Q | CD | -19.7 | -2.2 | -18.1 | 13 | A |
| 30 | Q | OE1 | -19.8 | -1.4 | -19.1 | 14 | A |
| 30 | Q | NE2 | -18.9 | -3.2 | -18.0 | 9 | A |
| 31 | V | N | -20.4 | 1.3 | -16.6 | 11 | A |
| 31 | V | CA | -21.5 | 2.2 | -17.1 | 10 | A |
| 31 | V | C | -21.8 | 1.9 | -18.6 | 11 | A |
| 31 | V | O | -21.0 | 1.3 | -19.2 | 11 | A |
| 31 | V | CB | -21.1 | 3.7 | -16.9 | 14 | A |
| 31 | V | CG1 | -20.7 | 4.0 | -15.5 | 15 | A |
| 31 | V | CG2 | -19.9 | 4.1 | -17.9 | 15 | A |
| 32 | V | N | -22.9 | 2.3 | -19.1 | 10 | A |
| 32 | V | CA | -23.3 | 2.2 | -20.5 | 10 | A |
| 32 | V | C | -23.4 | 3.6 | -21.0 | 11 | A |
| 32 | V | O | -23.8 | 4.5 | -20.3 | 11 | A |
| 32 | V | CB | -24.6 | 1.3 | -20.7 | 12 | A |
| 32 | V | CG1 | -25.8 | 2.1 | -20.0 | 12 | A |
| 32 | V | CG2 | -24.9 | 1.2 | -22.1 | 11 | A |

TABLE 2-continued

Atomic Coordinates of Factor IXa co-crystal Compound A complex

| | | | | | | | |
|---|---|---|---|---|---|---|---|
| 33 | L | N | −23.0 | 3.8 | −22.3 | 10 | A |
| 33 | L | CA | −23.2 | 5.1 | −23.0 | 10 | A |
| 33 | L | C | −24.3 | 5.0 | −24.0 | 15 | A |
| 33 | L | O | −24.4 | 4.0 | −24.7 | 12 | A |
| 33 | L | CB | −21.9 | 5.4 | −23.7 | 11 | A |
| 33 | L | CG | −20.6 | 5.3 | −22.9 | 14 | A |
| 33 | L | CD1 | −19.4 | 5.9 | −23.7 | 14 | A |
| 33 | L | CD2 | −20.7 | 6.1 | −21.5 | 16 | A |
| 34 | N | N | −25.1 | 6.0 | −24.0 | 12 | A |
| 34 | N | CA | −26.3 | 6.1 | −24.9 | 13 | A |
| 34 | N | C | −26.1 | 7.4 | −25.8 | 18 | A |
| 34 | N | O | −25.7 | 8.4 | −25.3 | 16 | A |
| 34 | N | CB | −27.6 | 6.2 | −24.2 | 15 | A |
| 34 | N | CG | −27.9 | 4.9 | −23.4 | 17 | A |
| 34 | N | OD1 | −27.5 | 3.9 | −23.8 | 19 | A |
| 34 | N | ND2 | −28.5 | 5.1 | −22.2 | 23 | A |
| 35 | G | N | −26.5 | 7.3 | −27.1 | 20 | A |
| 35 | G | CA | −26.5 | 8.4 | −28.0 | 21 | A |
| 35 | G | C | −27.8 | 8.3 | −28.9 | 27 | A |
| 35 | G | O | −28.8 | 7.9 | −28.4 | 27 | A |
| 36 | K | N | −27.6 | 8.6 | −30.2 | 27 | A |
| 36 | K | CA | −28.7 | 8.5 | −31.1 | 28 | A |
| 36 | K | C | −29.0 | 7.0 | −31.1 | 28 | A |
| 36 | K | O | −30.1 | 6.6 | −31.4 | 27 | A |
| 36 | K | CB | −28.2 | 8.9 | −32.5 | 33 | A |
| 36 | K | CG | −26.8 | 9.4 | −32.6 | 69 | A |
| 36 | K | CD | −26.4 | 10.0 | −34.0 | 87 | A |
| 36 | K | CE | −25.7 | 11.3 | −33.9 | 97 | A |
| 36 | K | NZ | −24.9 | 11.6 | −35.1 | 0 | A |
| 39 | V | N | −28.0 | 6.2 | −30.8 | 24 | A |
| 39 | V | CA | −28.1 | 4.7 | −30.7 | 23 | A |
| 39 | V | C | −27.8 | 4.4 | −29.2 | 22 | A |
| 39 | V | O | −26.9 | 4.9 | −28.6 | 20 | A |
| 39 | V | CB | −26.9 | 4.0 | −31.6 | 27 | A |
| 39 | V | CG1 | −26.8 | 2.5 | −31.3 | 26 | A |
| 39 | V | CG2 | −27.1 | 4.4 | −33.1 | 28 | A |
| 40 | D | N | −28.7 | 3.6 | −28.6 | 20 | A |
| 40 | D | CA | −28.5 | 3.3 | −27.2 | 20 | A |
| 40 | D | C | −27.5 | 2.2 | −27.0 | 20 | A |
| 40 | D | O | −27.3 | 1.3 | −27.9 | 21 | A |
| 40 | D | CB | −29.8 | 2.8 | −26.5 | 22 | A |
| 40 | D | CG | −30.8 | 4.0 | −26.3 | 35 | A |
| 40 | D | OD1 | −30.4 | 5.1 | −26.1 | 32 | A |
| 40 | D | OD2 | −32.0 | 3.7 | −26.5 | 48 | A |
| 41 | A | N | −26.8 | 2.2 | −25.8 | 15 | A |
| 41 | A | CA | −25.9 | 1.1 | −25.5 | 16 | A |
| 41 | A | C | −24.8 | 0.8 | −26.6 | 17 | A |
| 41 | A | O | −24.5 | −0.3 | −26.9 | 15 | A |
| 41 | A | CB | −26.7 | −0.2 | −25.2 | 18 | A |
| 42 | F | N | −24.3 | 1.9 | −27.1 | 12 | A |
| 42 | F | CA | −23.3 | 1.8 | −28.2 | 13 | A |
| 42 | F | C | −21.9 | 1.5 | −27.8 | 15 | A |
| 42 | F | O | −21.0 | 1.1 | −28.6 | 15 | A |
| 42 | F | CB | −23.4 | 3.0 | −29.2 | 14 | A |
| 42 | F | CG | −22.8 | 4.2 | −28.6 | 15 | A |
| 42 | F | CD1 | −23.5 | 5.1 | −27.8 | 17 | A |
| 42 | F | CD2 | −21.4 | 4.5 | −28.7 | 18 | A |
| 42 | F | CE1 | −22.9 | 6.3 | −27.3 | 17 | A |
| 42 | F | CE2 | −20.8 | 5.6 | −28.2 | 19 | A |
| 42 | F | CZ | −21.6 | 6.5 | −27.5 | 17 | A |
| 43 | C | N | −21.6 | 1.8 | −26.5 | 12 | A |
| 43 | C | CA | −20.3 | 1.5 | −25.9 | 11 | A |
| 43 | C | C | −20.5 | 1.4 | −24.4 | 10 | A |
| 43 | C | O | −21.5 | 1.8 | −23.9 | 9 | A |
| 43 | C | CB | −19.3 | 2.7 | −26.2 | 11 | A |
| 43 | C | SG | −18.5 | 2.7 | −27.8 | 15 | A |
| 44 | G | N | −19.4 | 1.1 | −23.7 | 9 | A |
| 44 | G | CA | −19.4 | 1.1 | −22.3 | 8 | A |
| 44 | G | C | −18.8 | 2.1 | −21.8 | 12 | A |
| 44 | G | O | −17.6 | 2.8 | −22.5 | 11 | A |
| 45 | G | N | −18.2 | 2.1 | −20.4 | 10 | A |
| 45 | G | CA | −17.2 | 2.9 | −19.7 | 7 | A |
| 45 | G | C | −17.0 | 2.4 | −18.3 | 13 | A |
| 45 | G | O | −17.7 | 1.4 | −17.9 | 11 | A |
| 46 | S | N | −16.1 | 3.0 | −17.5 | 10 | A |
| 46 | S | CA | −15.9 | 2.6 | −16.2 | 11 | A |
| 46 | S | C | −15.9 | 3.9 | −15.3 | 12 | A |
| 46 | S | O | −15.4 | 4.9 | −15.7 | 12 | A |
| 46 | S | CB | −14.5 | 2.0 | −16.0 | 13 | A |
| 46 | S | OG | −14.4 | 0.8 | −16.8 | 15 | A |
| 47 | I | N | −16.5 | 3.8 | −14.1 | 10 | A |
| 47 | I | CA | −16.4 | 4.9 | −13.2 | 9 | A |
| 47 | I | C | −15.0 | 5.1 | −12.6 | 13 | A |
| 47 | I | O | −14.5 | 4.2 | −11.9 | 13 | A |
| 47 | I | CB | −17.4 | 4.6 | −12.0 | 11 | A |
| 47 | I | CG1 | −18.9 | 4.5 | −12.6 | 11 | A |
| 47 | I | CG2 | −17.4 | 5.8 | −11.0 | 14 | A |
| 47 | I | CD1 | −19.9 | 4.1 | −11.6 | 12 | A |
| 48 | V | N | −14.4 | 6.2 | −12.8 | 9 | A |
| 48 | V | CA | −13.2 | 6.6 | −12.1 | 10 | A |
| 48 | V | C | −13.5 | 7.2 | −10.8 | 14 | A |
| 48 | V | O | −12.9 | 6.8 | −9.7 | 12 | A |
| 48 | V | CB | −12.4 | 7.6 | −13.0 | 12 | A |
| 48 | V | CG1 | −11.2 | 8.1 | −12.3 | 13 | A |
| 48 | V | CG2 | −12.1 | 7.0 | −14.4 | 10 | A |
| 49 | N | N | −14.5 | 8.1 | −10.7 | 11 | A |
| 49 | N | CA | −15.0 | 8.7 | −9.5 | 12 | A |
| 49 | N | C | −16.4 | 9.2 | −9.7 | 17 | A |
| 49 | N | O | −16.9 | 9.1 | −10.8 | 16 | A |
| 49 | N | CB | −14.0 | 9.7 | −8.9 | 15 | A |
| 49 | N | CG | −13.7 | 10.8 | −9.8 | 13 | A |
| 49 | N | OD1 | −14.5 | 11.3 | −10.6 | 14 | A |
| 49 | N | ND2 | −12.5 | 11.3 | −9.7 | 14 | A |
| 50 | E | N | −16.9 | 9.9 | −8.7 | 14 | A |
| 50 | E | CA | −18.3 | 10.4 | −8.9 | 14 | A |
| 50 | E | C | −18.5 | 11.3 | −10.1 | 15 | A |
| 50 | E | O | −19.7 | 11.5 | −10.5 | 16 | A |
| 50 | E | CB | −18.7 | 11.2 | −7.6 | 16 | A |
| 50 | E | CG | −18.4 | 10.6 | −6.3 | 36 | A |
| 50 | E | CD | −17.8 | 11.6 | −5.3 | 59 | A |
| 50 | E | OE1 | −18.1 | 12.8 | −5.5 | 38 | A |
| 50 | E | OE2 | −17.1 | 11.2 | −4.3 | 42 | A |
| 51 | K | N | −17.5 | 12.0 | −10.6 | 13 | A |
| 51 | K | CA | −17.6 | 12.9 | −11.7 | 15 | A |
| 51 | K | C | −17.0 | 12.6 | −13.0 | 16 | A |
| 51 | K | O | −17.2 | 13.3 | −14.0 | 12 | A |
| 51 | K | CB | −16.9 | 14.2 | −11.3 | 20 | A |
| 51 | K | CG | −17.8 | 15.4 | −10.9 | 37 | A |
| 51 | K | CD | −18.3 | 16.1 | −12.1 | 38 | A |
| 51 | K | CE | −17.8 | 17.6 | −11.8 | 35 | A |
| 51 | K | NZ | −19.0 | 18.3 | −13.0 | 39 | A |
| 52 | W | N | −16.3 | 11.4 | −13.1 | 11 | A |
| 52 | W | CA | −15.6 | 11.0 | −14.2 | 11 | A |
| 52 | W | C | −15.7 | 9.6 | −14.7 | 15 | A |
| 52 | W | O | −15.6 | 8.6 | −13.9 | 15 | A |
| 52 | W | CB | −14.1 | 11.3 | −14.0 | 11 | A |
| 52 | W | CG | −13.7 | 12.8 | −13.9 | 13 | A |
| 52 | W | CD1 | −13.7 | 13.5 | −12.7 | 16 | A |
| 52 | W | CD2 | −13.5 | 13.7 | −14.9 | 13 | A |
| 52 | W | NE1 | −13.5 | 14.9 | −13.0 | 16 | A |
| 52 | W | CE2 | −13.3 | 15.0 | −14.4 | 16 | A |
| 52 | W | CE3 | −13.3 | 13.5 | −16.3 | 14 | A |
| 52 | W | CZ2 | −12.9 | 16.1 | −15.2 | 17 | A |
| 52 | W | CZ3 | −12.9 | 14.6 | −17.1 | 16 | A |
| 52 | W | CH2 | −12.7 | 15.9 | −16.5 | 17 | A |
| 53 | I | N | −15.8 | 9.4 | −16.0 | 11 | A |
| 53 | I | CA | −15.9 | 8.1 | −16.6 | 10 | A |
| 53 | I | C | −14.6 | 7.9 | −17.5 | 14 | A |
| 53 | I | O | −14.3 | 8.8 | −18.2 | 13 | A |
| 53 | I | CB | −17.1 | 7.9 | −17.4 | 11 | A |
| 53 | I | CG1 | −18.4 | 8.1 | −16.6 | 11 | A |
| 53 | I | CG2 | −17.2 | 6.5 | −18.2 | 11 | A |
| 53 | I | CD1 | −18.6 | 7.2 | −15.4 | 11 | A |
| 54 | V | N | −14.1 | 6.7 | −17.6 | 9 | A |
| 54 | V | CA | −13.0 | 6.4 | −18.6 | 9 | A |
| 54 | V | C | −13.7 | 5.5 | −19.6 | 10 | A |
| 54 | V | O | −14.4 | 4.5 | −19.3 | 9 | A |
| 54 | V | CB | −11.7 | 5.9 | −18.0 | 12 | A |
| 54 | V | CG1 | −10.5 | 5.9 | −19.0 | 12 | A |
| 54 | V | CG2 | −11.8 | 4.5 | −17.3 | 13 | A |
| 55 | T | N | −13.3 | 5.8 | −20.9 | 11 | A |
| 55 | T | CA | −13.9 | 5.0 | −22.0 | 10 | A |
| 55 | T | C | −12.9 | 5.0 | −23.2 | 10 | A |
| 55 | T | O | −11.7 | 5.4 | −23.0 | 12 | A |

TABLE 2-continued

Atomic Coordinates of Factor IXa co-crystal Compound A complex

| | | | | | | | |
|---|---|---|---|---|---|---|---|
| 55 | T | CB | −15.3 | 5.6 | −22.5 | 12 | A |
| 55 | T | OG1 | −15.9 | 4.7 | −23.4 | 11 | A |
| 55 | T | CG2 | −15.0 | 6.9 | −23.1 | 10 | A |
| 56 | A | N | −13.3 | 4.4 | −24.3 | 8 | A |
| 56 | A | CA | −12.4 | 4.4 | −25.5 | 9 | A |
| 56 | A | C | −12.6 | 5.7 | −26.3 | 13 | A |
| 56 | A | O | −13.8 | 6.2 | −26.5 | 12 | A |
| 56 | A | CB | −12.8 | 3.2 | −26.5 | 10 | A |
| 57 | A | N | −11.6 | 6.3 | −26.8 | 14 | A |
| 57 | A | CA | −11.7 | 7.5 | −27.6 | 13 | A |
| 57 | A | C | −12.6 | 7.4 | −28.9 | 15 | A |
| 57 | A | O | −13.3 | 8.3 | −29.3 | 14 | A |
| 57 | A | CB | −10.3 | 8.2 | −27.9 | 14 | A |
| 58 | H | N | −12.5 | 6.2 | −29.5 | 13 | A |
| 58 | H | CA | −13.3 | 6.0 | −30.7 | 13 | A |
| 58 | H | C | −14.8 | 6.0 | −30.5 | 16 | A |
| 58 | H | O | −15.6 | 6.2 | −31.4 | 17 | A |
| 58 | H | CB | −12.8 | 4.8 | −31.5 | 14 | A |
| 58 | H | CG | −13.4 | 3.5 | −31.0 | 14 | A |
| 58 | H | ND1 | −12.7 | 2.6 | −30.2 | 14 | A |
| 58 | H | CD2 | −14.7 | 3.0 | −31.2 | 15 | A |
| 58 | H | CE1 | −13.5 | 1.6 | −30.0 | 14 | A |
| 58 | H | NE2 | −14.7 | 1.8 | −30.5 | 14 | A |
| 59 | C | N | −15.2 | 5.8 | −29.3 | 13 | A |
| 59 | C | CA | −16.7 | 5.8 | −28.9 | 12 | A |
| 59 | C | C | −17.3 | 7.2 | −28.9 | 15 | A |
| 59 | C | O | −18.5 | 7.4 | −28.9 | 15 | A |
| 59 | C | CB | −16.8 | 5.2 | −27.5 | 12 | A |
| 59 | C | SG | −16.6 | 3.4 | −27.5 | 15 | A |
| 60 | V | N | −16.4 | 8.2 | −28.6 | 14 | A |
| 60 | V | CA | −16.9 | 9.5 | −28.2 | 15 | A |
| 60 | V | C | −16.2 | 10.6 | −29.1 | 27 | A |
| 60 | V | O | −15.2 | 10.4 | −29.6 | 30 | A |
| 60 | V | CB | −16.7 | 9.8 | −26.7 | 15 | A |
| 60 | V | CG1 | −17.6 | 8.8 | −25.9 | 14 | A |
| 60 | V | CG2 | −15.2 | 9.6 | −26.3 | 15 | A |
| 60 | E | N | −16.9 | 11.7 | −29.2 | 31 | A |
| 60 | E | CA | −16.4 | 12.7 | −30.1 | 33 | A |
| 60 | E | C | −17.0 | 14.0 | −29.7 | 38 | A |
| 60 | E | O | −18.2 | 14.1 | −29.4 | 37 | A |
| 60 | E | CB | −16.7 | 12.4 | −31.6 | 34 | A |
| 60 | E | CG | −15.9 | 11.3 | −32.2 | 48 | A |
| 60 | E | CD | −14.4 | 11.5 | −32.0 | 83 | A |
| 60 | E | OE1 | −13.6 | 11.3 | −33.0 | 81 | A |
| 60 | E | OE2 | −14.0 | 11.8 | −30.8 | 83 | A |
| 60A | T | N | −16.2 | 15.0 | −29.6 | 37 | A |
| 60A | T | CA | −16.6 | 16.3 | −29.1 | 37 | A |
| 60A | T | C | −17.7 | 16.8 | −30.1 | 37 | A |
| 60A | T | O | −17.6 | 16.6 | −31.3 | 35 | A |
| 60A | T | CB | −15.5 | 17.3 | −29.0 | 58 | A |
| 60A | T | OG1 | −14.5 | 16.8 | −28.1 | 62 | A |
| 60A | T | CG2 | −16.0 | 18.6 | −28.5 | 59 | A |
| 61 | G | N | −18.8 | 17.3 | −29.6 | 34 | A |
| 61 | G | CA | −19.9 | 17.8 | −30.4 | 33 | A |
| 61 | G | C | −21.0 | 16.7 | −30.6 | 36 | A |
| 61 | G | O | −22.1 | 17.1 | −31.1 | 35 | A |
| 62 | V | N | −20.8 | 15.5 | −30.1 | 29 | A |
| 62 | V | CA | −21.8 | 14.5 | −30.2 | 27 | A |
| 62 | V | C | −22.3 | 14.1 | −28.9 | 27 | A |
| 62 | V | O | −21.5 | 13.7 | −28.0 | 23 | A |
| 62 | V | CB | −21.2 | 13.2 | −30.9 | 33 | A |
| 62 | V | CG1 | −22.3 | 12.1 | −30.9 | 33 | A |
| 62 | V | CG2 | −20.8 | 13.6 | −32.4 | 34 | A |
| 63 | K | N | −23.6 | 14.4 | −28.6 | 22 | A |
| 63 | K | CA | −24.2 | 14.2 | −27.3 | 21 | A |
| 63 | K | C | −24.2 | 12.7 | −26.8 | 24 | A |
| 63 | K | O | −24.6 | 11.9 | −27.5 | 26 | A |
| 63 | K | CB | −25.6 | 14.8 | −27.2 | 23 | A |
| 63 | K | CG | −26.0 | 14.9 | −25.8 | 24 | A |
| 63 | K | CD | −27.5 | 14.8 | −25.6 | 30 | A |
| 63 | K | CE | −27.9 | 14.4 | −24.2 | 43 | A |
| 63 | K | NZ | −28.7 | 15.5 | −23.5 | 65 | A |
| 64 | I | N | −23.8 | 12.6 | −25.5 | 18 | A |
| 64 | I | CA | −23.7 | 11.3 | −24.9 | 18 | A |
| 64 | I | C | −24.4 | 11.4 | −23.5 | 18 | A |
| 64 | I | O | −24.2 | 12.4 | −22.8 | 15 | A |
| 64 | I | CB | −22.2 | 10.9 | −24.5 | 21 | A |
| 64 | I | CG1 | −21.3 | 10.9 | −25.7 | 23 | A |
| 64 | I | CG2 | −22.1 | 9.6 | −23.7 | 20 | A |
| 64 | I | CD1 | −21.6 | 9.6 | −26.6 | 26 | A |
| 65 | T | N | −25.0 | 10.3 | −23.1 | 15 | A |
| 65 | T | CA | −25.6 | 10.1 | −21.7 | 13 | A |
| 65 | T | C | −25.0 | 8.9 | −21.1 | 14 | A |
| 65 | T | O | −24.7 | 7.9 | −21.9 | 14 | A |
| 65 | T | CB | −27.1 | 10.2 | −21.6 | 19 | A |
| 65 | T | OG1 | −27.6 | 9.0 | −22.1 | 21 | A |
| 65 | T | CG2 | −27.6 | 11.4 | −22.4 | 18 | A |
| 66 | V | N | −24.7 | 8.9 | −19.9 | 11 | A |
| 66 | V | CA | −24.1 | 7.8 | −19.1 | 11 | A |
| 66 | V | C | −25.1 | 7.3 | −18.2 | 13 | A |
| 66 | V | O | −25.8 | 8.0 | −17.6 | 13 | A |
| 66 | V | CB | −22.8 | 8.4 | −18.3 | 14 | A |
| 66 | V | CG1 | −22.4 | 7.4 | −17.2 | 14 | A |
| 66 | V | CG2 | −21.7 | 8.7 | −19.3 | 13 | A |
| 67 | V | N | −25.1 | 6.0 | −18.0 | 10 | A |
| 67 | V | CA | −26.0 | 5.4 | −17.0 | 11 | A |
| 67 | V | C | −25.2 | 4.4 | −16.2 | 11 | A |
| 67 | V | O | −24.7 | 3.4 | −16.7 | 12 | A |
| 67 | V | CB | −27.3 | 4.7 | −17.6 | 15 | A |
| 67 | V | CG1 | −28.2 | 4.2 | −16.5 | 15 | A |
| 67 | V | CG2 | −28.0 | 5.7 | −18.6 | 14 | A |
| 68 | A | N | −25.1 | 4.7 | −14.9 | 9 | A |
| 68 | A | CA | −24.4 | 3.8 | −13.9 | 12 | A |
| 68 | A | C | −25.5 | 3.0 | −13.2 | 13 | A |
| 68 | A | O | −26.7 | 3.4 | −13.3 | 12 | A |
| 68 | A | CB | −23.7 | 4.7 | −12.9 | 13 | A |
| 69 | G | N | −25.1 | 2.0 | −12.5 | 12 | A |
| 69 | G | CA | −26.1 | 1.2 | −11.7 | 13 | A |
| 69 | G | C | −27.0 | 0.4 | −12.6 | 17 | A |
| 69 | G | O | −28.1 | −0.1 | −12.2 | 17 | A |
| 70 | E | N | −26.6 | 0.2 | −13.9 | 14 | A |
| 70 | E | CA | −27.5 | −0.6 | −14.8 | 15 | A |
| 70 | E | C | −27.2 | −2.1 | −14.7 | 18 | A |
| 70 | E | O | −26.1 | −2.5 | −14.5 | 18 | A |
| 70 | E | CB | −27.2 | −0.2 | −16.3 | 18 | A |
| 70 | E | CG | −28.2 | 0.8 | −16.8 | 34 | A |
| 70 | E | CD | −29.6 | 0.1 | −17.1 | 29 | A |
| 70 | E | OE1 | −29.9 | −0.9 | −16.4 | 25 | A |
| 70 | E | OE2 | −30.3 | 0.7 | −17.9 | 29 | A |
| 71 | H | N | −28.2 | −2.9 | −15.0 | 16 | A |
| 71 | H | CA | −28.1 | −4.3 | −14.9 | 15 | A |
| 71 | H | C | −28.8 | −4.9 | −16.2 | 18 | A |
| 71 | H | O | −28.2 | −5.3 | −17.1 | 14 | A |
| 71 | H | CB | −28.7 | −4.9 | −13.6 | 15 | A |
| 71 | H | CG | −28.8 | −6.4 | −13.6 | 18 | A |
| 71 | H | ND1 | −27.7 | −7.2 | −13.6 | 20 | A |
| 71 | H | CD2 | −29.8 | −7.2 | −13.5 | 19 | A |
| 71 | H | CE1 | −28.1 | −8.5 | −13.6 | 19 | A |
| 71 | H | NE2 | −29.4 | −8.5 | −13.5 | 21 | A |
| 72 | N | N | −30.1 | −4.7 | −16.2 | 17 | A |
| 72 | N | CA | −30.9 | −5.1 | −17.4 | 16 | A |
| 72 | N | C | −31.4 | −3.8 | −18.1 | 19 | A |
| 72 | N | O | −32.2 | −3.1 | −17.5 | 20 | A |
| 72 | N | CB | −32.1 | −6.1 | −17.0 | 18 | A |
| 72 | N | CG | −32.9 | −6.5 | −18.3 | 17 | A |
| 72 | N | OD1 | −33.0 | −5.7 | −19.2 | 25 | A |
| 72 | N | ND2 | −33.3 | −7.7 | −18.3 | 27 | A |
| 73 | I | N | −30.8 | −3.5 | −19.3 | 19 | A |
| 73 | I | CA | −31.1 | −2.3 | −19.9 | 22 | A |
| 73 | I | C | −32.6 | −2.1 | −20.4 | 35 | A |
| 73 | I | O | −33.0 | −1.0 | −20.7 | 36 | A |
| 73 | I | CB | −30.1 | −2.0 | −21.1 | 26 | A |
| 73 | I | CG1 | −30.0 | −3.1 | −22.1 | 27 | A |
| 73 | I | CG2 | −28.7 | −1.6 | −20.6 | 27 | A |
| 73 | I | CD1 | −29.6 | −2.7 | −23.5 | 35 | A |
| 74 | E | N | −33.4 | −3.2 | −20.3 | 32 | A |
| 74 | E | CA | −34.8 | −3.1 | −20.7 | 35 | A |
| 74 | E | C | −35.7 | −2.9 | −19.5 | 39 | A |
| 74 | E | O | −36.8 | −2.4 | −19.8 | 39 | A |
| 74 | E | CB | −35.1 | −4.4 | −21.4 | 37 | A |
| 74 | E | CG | −36.2 | −4.3 | −22.5 | 55 | A |
| 74 | E | CD | −35.7 | −4.1 | −23.9 | 88 | A |
| 74 | E | OE1 | −35.3 | −3.0 | −24.3 | 90 | A |
| 74 | E | OE2 | −35.7 | −5.1 | −24.6 | 84 | A |

TABLE 2-continued

Atomic Coordinates of Factor IXa co-crystal Compound A complex

| | | | | | | | |
|---|---|---|---|---|---|---|---|
| 75 | E | N | −35.3 | −3.2 | −18.3 | 33 | A |
| 75 | E | CA | −36.1 | −3.0 | −17.1 | 34 | A |
| 75 | E | C | −35.6 | −1.9 | −16.2 | 38 | A |
| 75 | E | O | −34.4 | −1.5 | −16.3 | 37 | A |
| 75 | E | CB | −36.1 | −4.3 | −16.3 | 36 | A |
| 75 | E | CG | −37.3 | −5.2 | −16.4 | 58 | A |
| 75 | E | CD | −37.7 | −5.6 | −17.8 | 88 | A |
| 75 | E | OE1 | −37.0 | −6.5 | −18.4 | 86 | A |
| 75 | E | OE2 | −38.6 | −4.9 | −18.4 | 83 | A |
| 76 | T | N | −36.5 | −1.3 | −15.4 | 35 | A |
| 76 | T | CA | −36.2 | −0.3 | −14.4 | 33 | A |
| 76 | T | C | −35.9 | −1.0 | −13.1 | 34 | A |
| 76 | T | O | −36.9 | −1.5 | −12.5 | 33 | A |
| 76 | T | CB | −37.3 | 0.8 | −14.3 | 48 | A |
| 76 | T | OG1 | −37.4 | 1.4 | −15.6 | 46 | A |
| 76 | T | CG2 | −36.9 | 1.8 | −13.3 | 49 | A |
| 77 | E | N | −34.7 | −1.0 | −12.6 | 27 | A |
| 77 | E | CA | −34.3 | −1.7 | −11.4 | 26 | A |
| 77 | S | C | −34.1 | −0.8 | −10.1 | 27 | A |
| 77 | E | O | −33.7 | −1.3 | −9.0 | 26 | A |
| 77 | E | CB | −33.2 | −2.7 | −11.6 | 28 | A |
| 77 | E | CG | −33.5 | −3.8 | −12.6 | 31 | A |
| 77 | E | CD | −32.3 | −4.3 | −13.3 | 49 | A |
| 77 | E | OE1 | −31.7 | −3.5 | −14.1 | 22 | A |
| 77 | E | OE2 | −32.0 | −5.5 | −13.2 | 31 | A |
| 78 | H | N | −34.4 | 0.5 | −10.3 | 22 | A |
| 78 | H | CA | −34.3 | 1.5 | −9.2 | 23 | A |
| 78 | H | C | −32.8 | 1.9 | −8.8 | 27 | A |
| 78 | H | O | −32.6 | 2.8 | −8.0 | 30 | A |
| 78 | H | CB | −35.0 | 1.0 | −7.9 | 25 | A |
| 78 | H | CG | −36.4 | 0.6 | −8.2 | 29 | A |
| 78 | H | ND1 | −37.4 | 1.6 | −8.6 | 32 | A |
| 78 | H | CD2 | −37.1 | −0.5 | −8.1 | 31 | A |
| 78 | H | CE1 | −38.5 | 1.0 | −8.7 | 30 | A |
| 78 | H | NE2 | −38.4 | −0.3 | −8.5 | 30 | A |
| 79 | T | N | −31.9 | 1.2 | −9.4 | 19 | A |
| 79 | T | CA | −30.5 | 1.5 | −9.1 | 16 | A |
| 79 | T | C | −29.8 | 2.4 | −10.1 | 20 | A |
| 79 | T | O | −28.6 | 2.8 | −9.9 | 17 | A |
| 79 | T | CB | −29.8 | 0.1 | −9.0 | 16 | A |
| 79 | T | OG1 | −29.9 | −0.6 | −10.3 | 16 | A |
| 79 | T | CG2 | −30.3 | −0.8 | −7.8 | 19 | A |
| 80 | E | N | −30.4 | 2.6 | −11.2 | 16 | A |
| 80 | E | CA | −29.8 | 3.4 | −12.3 | 16 | A |
| 80 | E | C | −29.6 | 4.9 | −11.9 | 18 | A |
| 80 | E | O | −30.5 | 5.6 | −11.3 | 17 | A |
| 80 | E | CB | −30.7 | 3.3 | −13.6 | 17 | A |
| 80 | E | CG | −30.9 | 1.9 | −14.0 | 18 | A |
| 80 | E | CD | −32.1 | 1.2 | −13.3 | 33 | A |
| 80 | E | OE1 | −32.7 | 1.9 | −12.4 | 25 | A |
| 80 | E | OE2 | −32.4 | 0.1 | −13.7 | 33 | A |
| 81 | Q | N | −28.5 | 5.5 | −12.4 | 12 | A |
| 81 | Q | CA | −28.2 | 6.9 | −12.2 | 11 | A |
| 81 | Q | C | −27.8 | 7.4 | −13.6 | 16 | A |
| 81 | Q | O | −26.8 | 7.0 | −14.1 | 14 | A |
| 81 | Q | CB | −27.2 | 7.2 | −11.2 | 14 | A |
| 81 | Q | CG | −27.6 | 6.9 | −9.7 | 14 | A |
| 81 | Q | CD | −26.5 | 7.2 | −8.7 | 15 | A |
| 81 | Q | OE1 | −25.7 | 8.1 | −9.0 | 18 | A |
| 81 | Q | NE2 | −26.3 | 6.3 | −7.7 | 15 | A |
| 82 | K | N | −28.7 | 8.2 | −14.2 | 13 | A |
| 82 | K | CA | −28.4 | 8.8 | −15.6 | 12 | A |
| 82 | K | C | −27.7 | 10.1 | −15.5 | 15 | A |
| 82 | K | O | −28.1 | 11.0 | −14.6 | 15 | A |
| 82 | K | CB | −29.7 | 8.9 | −16.4 | 15 | A |
| 82 | K | CG | −29.5 | 9.4 | −17.8 | 25 | A |
| 82 | K | CD | −30.9 | 9.8 | −18.4 | 27 | A |
| 82 | K | CE | −30.7 | 10.2 | −19.9 | 37 | A |
| 82 | K | NZ | −31.8 | 9.7 | −20.8 | 39 | A |
| 83 | R | N | −26.7 | 10.4 | −16.2 | 12 | A |
| 83 | R | CA | −26.0 | 11.7 | −16.2 | 13 | A |
| 83 | R | C | −25.7 | 12.2 | −17.6 | 15 | A |
| 83 | R | O | −25.5 | 11.4 | −18.5 | 12 | A |
| 83 | R | CB | −24.7 | 11.6 | −15.5 | 13 | A |
| 83 | R | CG | −24.8 | 11.2 | −14.0 | 13 | A |
| 83 | R | CD | −25.5 | 12.4 | −13.2 | 12 | A |
| 83 | R | NE | −25.5 | 12.2 | −11.8 | 15 | A |
| 83 | R | CZ | −26.5 | 11.5 | −11.1 | 15 | A |
| 83 | R | NH1 | −27.5 | 10.9 | −11.7 | 15 | A |
| 83 | R | NH2 | −26.4 | 11.4 | −9.8 | 16 | A |
| 84 | N | N | −25.5 | 13.5 | −17.7 | 12 | A |
| 84 | N | CA | −25.1 | 14.1 | −19.0 | 10 | A |
| 84 | N | C | −23.6 | 14.2 | −19.0 | 14 | A |
| 84 | N | O | −23.0 | 14.2 | −17.9 | 15 | A |
| 84 | N | CB | −25.7 | 15.5 | −19.1 | 12 | A |
| 84 | W | CG | −27.1 | 15.6 | −19.2 | 20 | A |
| 84 | N | OD1 | −27.7 | 14.8 | −20.0 | 15 | A |
| 84 | N | ND2 | −27.8 | 16.3 | −18.3 | 14 | A |
| 85 | V | N | −23.0 | 14.2 | −20.2 | 14 | A |
| 85 | V | CA | −21.6 | 14.4 | −20.3 | 12 | A |
| 85 | V | C | −21.3 | 15.8 | −20.7 | 16 | A |
| 85 | V | O | −21.8 | 16.3 | −21.8 | 14 | A |
| 85 | V | CB | −21.1 | 13.5 | −21.5 | 16 | A |
| 85 | V | CG1 | −19.6 | 13.7 | −21.7 | 16 | A |
| 85 | V | CG2 | −21.2 | 12.0 | −21.1 | 16 | A |
| 86 | I | N | −20.6 | 16.6 | −19.9 | 12 | A |
| 86 | I | CA | −20.3 | 18.0 | −20.2 | 14 | A |
| 86 | I | C | −18.9 | 18.2 | −20.8 | 19 | A |
| 86 | I | O | −18.7 | 19.3 | −21.4 | 18 | A |
| 86 | I | CB | −20.5 | 18.8 | −18.9 | 15 | A |
| 86 | I | CG1 | −19.4 | 18.6 | −17.9 | 13 | A |
| 86 | I | CG2 | −21.9 | 18.6 | −18.3 | 16 | A |
| 86 | I | CD1 | −19.4 | 19.5 | −16.7 | 15 | A |
| 87 | R | N | −18.0 | 17.3 | −20.8 | 14 | A |
| 87 | R | CA | −16.7 | 17.4 | −21.4 | 13 | A |
| 87 | R | C | −16.2 | 16.1 | −21.8 | 16 | A |
| 87 | R | O | −16.3 | 15.1 | −21.0 | 16 | A |
| 87 | R | CB | −15.8 | 18.1 | −20.5 | 13 | A |
| 87 | R | CG | −14.5 | 18.5 | −21.1 | 20 | A |
| 87 | R | CD | −13.6 | 19.3 | −20.2 | 19 | A |
| 87 | R | NE | −12.3 | 19.6 | −20.7 | 35 | A |
| 87 | R | CZ | −11.2 | 19.7 | −20.0 | 50 | A |
| 87 | R | NH1 | −11.3 | 19.6 | −18.6 | 36 | A |
| 87 | R | NH2 | −10.1 | 19.9 | −20.5 | 39 | A |
| 88 | I | N | −15.5 | 16.0 | −23.0 | 15 | A |
| 88 | I | CA | −14.8 | 14.8 | −23.4 | 13 | A |
| 88 | I | C | −13.4 | 15.1 | −23.6 | 17 | A |
| 88 | I | O | −13.0 | 16.1 | −24.3 | 19 | A |
| 88 | I | CB | −15.4 | 14.3 | −24.8 | 16 | A |
| 88 | I | CG1 | −16.9 | 14.0 | −24.6 | 18 | A |
| 88 | I | CG2 | −14.6 | 13.1 | −25.3 | 16 | A |
| 88 | I | CD1 | −17.6 | 13.7 | −26.0 | 21 | A |
| 89 | I | N | −12.5 | 14.3 | −22.9 | 14 | A |
| 89 | I | CA | −11.1 | 14.5 | −23.1 | 14 | A |
| 89 | I | C | −10.4 | 13.3 | −23.6 | 17 | A |
| 89 | I | O | −10.1 | 12.3 | −22.9 | 16 | A |
| 89 | I | CB | −10.4 | 14.9 | −21.7 | 16 | A |
| 89 | I | CG1 | −11.2 | 16.0 | −21.0 | 17 | A |
| 89 | I | CG2 | −8.9 | 15.3 | −22.0 | 14 | A |
| 89 | I | CD1 | −10.5 | 16.4 | −19.6 | 20 | A |
| 90 | P | N | −10.2 | 13.3 | −24.9 | 16 | A |
| 90 | P | CA | −9.5 | 12.1 | −25.5 | 16 | A |
| 90 | P | C | −8.0 | 12.3 | −25.1 | 17 | A |
| 90 | P | O | −7.5 | 13.5 | −25.0 | 17 | A |
| 90 | P | CB | −9.7 | 12.3 | −27.0 | 18 | A |
| 90 | P | CG | −10.0 | 13.8 | −27.2 | 23 | A |
| 90 | P | CD | −10.7 | 14.2 | −26.0 | 17 | A |
| 91 | H | N | −7.2 | 11.3 | −25.0 | 18 | A |
| 91 | H | CA | −5.8 | 11.4 | −24.7 | 18 | A |
| 91 | H | C | −5.2 | 12.3 | −25.8 | 18 | A |
| 91 | H | O | −5.5 | 12.1 | −27.0 | 19 | A |
| 91 | H | CB | −5.1 | 10.1 | −24.6 | 17 | A |
| 91 | H | CG | −3.7 | 10.2 | −24.2 | 21 | A |
| 91 | H | ND1 | −3.3 | 10.3 | −22.9 | 24 | A |
| 91 | H | CD2 | −2.5 | 10.3 | −24.9 | 22 | A |
| 91 | H | CE1 | −2.0 | 10.4 | −22.8 | 22 | A |
| 91 | H | NE2 | −1.5 | 10.4 | −24.0 | 23 | A |
| 92 | H | N | −4.2 | 13.1 | −25.4 | 16 | A |
| 92 | H | CA | −3.6 | 14.0 | −26.4 | 18 | A |
| 92 | H | C | −2.9 | 13.3 | −27.6 | 20 | A |
| 92 | H | O | −2.7 | 13.8 | −28.6 | 21 | A |
| 92 | H | CB | −2.6 | 15.0 | −25.7 | 19 | A |
| 92 | H | CG | −1.4 | 14.3 | −25.1 | 24 | A |
| 92 | H | ND1 | −0.2 | 14.1 | −25.8 | 27 | A |

TABLE 2-continued

Atomic Coordinates of Factor IXa co-crystal Compound A complex

| | | | | | | | |
|---|---|---|---|---|---|---|---|
| 92 | H | CD2 | −1.3 | 13.7 | −23.9 | 27 | A |
| 92 | H | CE1 | 0.6 | 13.4 | −25.0 | 27 | A |
| 92 | H | NE2 | −0.0 | 13.1 | −23.9 | 27 | A |
| 93 | N | N | −2.5 | 12.0 | −27.4 | 17 | A |
| 93 | N | CA | −1.9 | 11.2 | −28.5 | 19 | A |
| 93 | N | C | −2.9 | 10.7 | −29.4 | 22 | A |
| 93 | N | O | −2.6 | 10.1 | −30.5 | 22 | A |
| 93 | N | CB | −1.0 | 10.1 | −27.9 | 22 | A |
| 93 | N | CG | 0.3 | 10.6 | −27.4 | 42 | A |
| 93 | N | OD1 | 0.9 | 9.9 | −26.5 | 35 | A |
| 93 | N | ND2 | 0.8 | 11.6 | −28.0 | 25 | A |
| 94 | Y | N | −4.2 | 10.7 | −29.1 | 17 | A |
| 94 | Y | CA | −5.2 | 10.2 | −29.9 | 16 | A |
| 94 | Y | C | −5.4 | 11.1 | −31.1 | 22 | A |
| 94 | Y | O | −5.6 | 12.3 | −31.0 | 22 | A |
| 94 | Y | CB | −6.6 | 10.0 | −29.2 | 16 | A |
| 94 | Y | CG | −7.6 | 9.3 | −30.0 | 16 | A |
| 94 | Y | CD1 | −7.5 | 8.0 | −30.3 | 18 | A |
| 94 | Y | CD2 | −8.7 | 10.1 | −30.6 | 16 | A |
| 94 | Y | CE1 | −8.5 | 7.3 | −31.0 | 15 | A |
| 94 | Y | CE2 | −9.7 | 9.4 | −31.3 | 18 | A |
| 94 | Y | CZ | −9.6 | 8.1 | −31.6 | 16 | A |
| 94 | Y | OH | −10.6 | 7.4 | −32.3 | 18 | A |
| 95 | N | N | −5.4 | 10.5 | −32.3 | 18 | A |
| 95 | N | CA | −5.6 | 11.2 | −33.6 | 19 | A |
| 95 | N | C | −6.4 | 10.4 | −34.5 | 22 | A |
| 95 | N | O | −5.8 | 9.6 | −35.3 | 21 | A |
| 95 | N | CB | −4.2 | 11.5 | −34.2 | 18 | A |
| 95 | N | CG | −4.3 | 12.4 | −35.4 | 38 | A |
| 95 | N | OD1 | −5.3 | 12.5 | −36.0 | 28 | A |
| 95 | N | ND2 | −3.1 | 13.1 | −35.7 | 32 | A |
| 96 | A | N | −7.7 | 10.6 | −34.6 | 21 | A |
| 96 | A | CA | −8.6 | 9.9 | −35.4 | 22 | A |
| 96 | A | C | −8.2 | 10.0 | −36.9 | 28 | A |
| 96 | A | O | −8.5 | 9.1 | −37.7 | 26 | A |
| 96 | A | CB | −10.0 | 10.4 | −35.2 | 23 | A |
| 97 | A | N | −7.5 | 11.1 | −37.3 | 27 | A |
| 97 | A | CA | −7.0 | 11.3 | −38.6 | 28 | A |
| 97 | A | C | −6.0 | 10.2 | −39.1 | 31 | A |
| 97 | A | O | −5.9 | 9.8 | −40.2 | 33 | A |
| 97 | A | CB | −6.5 | 12.7 | −38.9 | 29 | A |
| 95 | I | N | −5.2 | 9.7 | −38.1 | 24 | A |
| 95 | I | CA | −4.2 | 8.7 | −38.4 | 24 | A |
| 95 | I | C | −4.6 | 7.3 | −38.1 | 26 | A |
| 95 | I | O | −4.3 | 6.4 | −38.9 | 26 | A |
| 95 | I | CB | −2.8 | 9.0 | −37.8 | 27 | A |
| 95 | I | CG1 | −2.3 | 10.4 | −38.4 | 27 | A |
| 95 | I | CG2 | −1.8 | 7.9 | −38.1 | 28 | A |
| 95 | I | CD1 | −1.5 | 11.2 | −37.4 | 39 | A |
| 95 | N | N | −5.3 | 7.1 | −37.0 | 22 | A |
| 95 | N | CA | −5.7 | 5.8 | −36.6 | 19 | A |
| 95 | N | C | −6.7 | 5.9 | −35.5 | 22 | A |
| 95 | N | O | −6.4 | 6.3 | −34.4 | 20 | A |
| 95 | N | CB | −4.5 | 5.0 | −36.1 | 19 | A |
| 95 | N | CG | −4.8 | 3.5 | −35.8 | 35 | A |
| 95 | N | OD1 | −5.9 | 3.2 | −35.4 | 22 | A |
| 95 | N | ND2 | −3.9 | 2.6 | −36.0 | 27 | A |
| 96 | K | N | −8.0 | 5.6 | −35.8 | 20 | A |
| 96 | K | CA | −9.1 | 5.7 | −34.9 | 17 | A |
| 96 | K | C | −9.0 | 4.8 | −33.6 | 20 | A |
| 96 | K | O | −9.7 | 5.0 | −32.7 | 17 | A |
| 96 | K | CB | −10.4 | 5.5 | −35.5 | 20 | A |
| 96 | K | CG | −10.8 | 6.7 | −36.4 | 34 | A |
| 96 | K | CD | −12.3 | 6.6 | −36.8 | 35 | A |
| 96 | K | CE | −12.5 | 7.3 | −38.1 | 37 | A |
| 96 | K | NZ | −13.9 | 7.2 | −38.7 | 31 | A |
| 97 | Y | K | −8.0 | 3.9 | −33.7 | 15 | A |
| 97 | Y | CA | −7.9 | 2.8 | −32.6 | 16 | A |
| 97 | Y | C | −6.6 | 2.8 | −31.9 | 20 | A |
| 97 | Y | O | −6.3 | 1.9 | −31.1 | 19 | A |
| 97 | Y | CB | −8.2 | 1.5 | −33.3 | 16 | A |
| 97 | Y | CG | −9.6 | 1.4 | −33.9 | 15 | A |
| 97 | Y | CD1 | −10.7 | 1.3 | −33.1 | 17 | A |
| 97 | Y | CD2 | −9.8 | 1.8 | −35.2 | 17 | A |
| 97 | Y | CE1 | −11.9 | 1.4 | −33.6 | 19 | A |
| 97 | Y | CE2 | −11.0 | 1.9 | −35.7 | 17 | A |
| 97 | Y | CZ | −12.1 | 1.7 | −34.9 | 23 | A |
| 97 | Y | OH | −13.4 | 1.8 | −35.4 | 26 | A |
| 98 | N | N | −5.7 | 3.7 | −32.2 | 17 | A |
| 98 | N | CA | −4.4 | 3.8 | −31.5 | 14 | A |
| 98 | N | C | −4.5 | 4.9 | −30.3 | 16 | A |
| 98 | N | O | −5.1 | 6.0 | −30.5 | 17 | A |
| 98 | N | CB | −3.3 | 4.2 | −32.5 | 16 | A |
| 98 | N | CG | −1.9 | 3.9 | −31.9 | 28 | A |
| 98 | N | OD1 | −0.9 | 4.4 | −32.4 | 28 | A |
| 98 | N | ND2 | −1.9 | 3.1 | −30.9 | 18 | A |
| 99 | H | N | −4.0 | 4.6 | −29.2 | 16 | A |
| 99 | H | CA | −4.1 | 5.5 | −28.0 | 16 | A |
| 99 | H | C | −5.6 | 5.8 | −27.7 | 15 | A |
| 99 | H | O | −6.0 | 6.9 | −27.5 | 16 | A |
| 99 | H | CB | −3.4 | 6.8 | −28.3 | 19 | A |
| 99 | H | CG | −1.9 | 6.7 | −28.6 | 25 | A |
| 99 | H | ND1 | −1.4 | 6.8 | −29.9 | 28 | A |
| 99 | H | CD2 | −0.9 | 6.4 | −27.8 | 28 | A |
| 99 | H | CE1 | −0.1 | 6.6 | −29.8 | 28 | A |
| 99 | H | NE2 | 0.2 | 6.3 | −28.6 | 28 | A |
| 100 | D | N | −6.3 | 4.7 | −27.8 | 13 | A |
| 100 | D | CA | −7.8 | 4.7 | −27.8 | 14 | A |
| 100 | D | C | −8.4 | 4.9 | −26.4 | 17 | A |
| 100 | D | O | −9.1 | 4.0 | −25.9 | 16 | A |
| 100 | D | CB | −8.2 | 3.5 | −28.5 | 16 | A |
| 100 | D | CG | −9.7 | 3.6 | −29.0 | 15 | A |
| 100 | D | OD1 | −10.3 | 4.6 | −28.8 | 18 | A |
| 100 | D | OD2 | −10.2 | 2.5 | −29.4 | 19 | A |
| 101 | I | N | −8.2 | 6.0 | −25.8 | 15 | A |
| 101 | I | CA | −8.7 | 6.3 | −24.5 | 12 | A |
| 101 | I | C | −9.2 | 7.7 | −24.3 | 15 | A |
| 101 | I | O | −8.6 | 8.7 | −24.9 | 15 | A |
| 101 | I | CB | −7.6 | 5.9 | −23.4 | 14 | A |
| 101 | I | CG1 | −8.3 | 5.8 | −22.0 | 15 | A |
| 101 | I | CG2 | −6.4 | 6.8 | −23.5 | 14 | A |
| 101 | I | CD1 | −7.3 | 5.2 | −20.9 | 13 | A |
| 102 | A | N | −10.3 | 7.9 | −23.5 | 12 | A |
| 102 | A | CA | −10.9 | 9.2 | −23.3 | 12 | A |
| 102 | A | C | −11.5 | 9.2 | −21.9 | 16 | A |
| 102 | A | O | −12.0 | 8.2 | −21.4 | 14 | A |
| 102 | A | CB | −11.9 | 9.5 | −24.4 | 13 | A |
| 103 | L | N | −11.7 | 10.5 | −21.4 | 13 | A |
| 103 | L | CA | −12.3 | 10.7 | −20.1 | 12 | A |
| 103 | L | C | −13.6 | 11.5 | −20.4 | 14 | A |
| 103 | L | O | −13.7 | 12.4 | −21.3 | 13 | A |
| 103 | L | CB | −11.4 | 11.6 | −19.2 | 13 | A |
| 103 | L | CG | −10.2 | 10.8 | −18.8 | 17 | A |
| 103 | L | CD1 | −9.2 | 11.8 | −18.1 | 18 | A |
| 103 | L | CD2 | −10.7 | 9.7 | −17.9 | 17 | A |
| 104 | L | N | −14.7 | 11.2 | −19.7 | 11 | A |
| 104 | L | CA | −16.0 | 11.9 | −19.8 | 11 | A |
| 104 | L | C | −16.2 | 12.6 | −18.4 | 15 | A |
| 104 | L | O | −16.2 | 11.9 | −17.4 | 14 | A |
| 104 | L | CB | −17.1 | 10.9 | −20.0 | 11 | A |
| 104 | L | CG | −17.0 | 9.9 | −21.2 | 14 | A |
| 104 | L | CD1 | −18.1 | 9.0 | −21.4 | 13 | A |
| 104 | L | CD2 | −16.5 | 10.6 | −22.5 | 17 | A |
| 105 | E | N | −16.5 | 13.9 | −18.4 | 14 | A |
| 105 | E | CA | −16.9 | 14.6 | −17.2 | 12 | A |
| 105 | E | C | −18.4 | 14.6 | −17.2 | 15 | A |
| 105 | E | O | −19.1 | 15.0 | −18.2 | 15 | A |
| 105 | E | CB | −16.4 | 16.0 | −17.2 | 14 | A |
| 105 | E | CG | −16.6 | 16.7 | −15.9 | 20 | A |
| 105 | E | CD | −16.0 | 18.1 | −15.9 | 18 | A |
| 105 | E | OE1 | −15.4 | 18.6 | −16.9 | 19 | A |
| 105 | E | OE2 | −16.1 | 18.8 | −14.8 | 24 | A |
| 106 | L | N | −19.0 | 14.3 | −16.1 | 12 | A |
| 106 | L | CA | −20.4 | 14.2 | −15.8 | 11 | A |
| 106 | L | C | −21.0 | 15.6 | −15.3 | 16 | A |
| 106 | L | O | −20.2 | 16.4 | −14.7 | 16 | A |
| 106 | L | CB | −20.7 | 13.2 | −14.7 | 11 | A |
| 106 | L | CG | −20.2 | 11.8 | −15.0 | 14 | A |
| 106 | L | CD1 | −20.7 | 10.8 | −14.0 | 14 | A |
| 106 | L | CD2 | −20.7 | 11.5 | −16.5 | 15 | A |
| 107 | D | N | −22.2 | 15.9 | −15.7 | 13 | A |
| 107 | D | CA | −22.8 | 17.2 | −15.2 | 12 | A |
| 107 | D | C | −22.9 | 17.2 | −13.7 | 17 | A |
| 107 | D | O | −22.5 | 18.2 | −13.1 | 19 | A |

TABLE 2-continued

Atomic Coordinates of Factor IXa co-crystal Compound A complex

| | | | | | | |
|---|---|---|---|---|---|---|
| 107 | D | CB | −24.1 | 17.5 | −15.9 | 12 A |
| 107 | D | CG | −25.2 | 16.4 | −15.7 | 17 A |
| 107 | D | OD1 | −25.0 | 15.2 | −15.5 | 15 A |
| 107 | D | OD2 | −26.4 | 16.8 | −15.8 | 19 A |
| 108 | E | N | −23.6 | 16.2 | −13.2 | 16 A |
| 108 | E | CA | −23.8 | 16.1 | −11.7 | 17 A |
| 108 | E | C | −23.2 | 14.9 | −11.2 | 19 A |
| 108 | E | O | −23.1 | 13.8 | −11.8 | 15 A |
| 108 | E | CB | −25.3 | 16.1 | −11.5 | 21 A |
| 108 | E | CG | −26.2 | 15.2 | −12.3 | 39 A |
| 108 | E | CD | −27.6 | 15.0 | −11.7 | 58 A |
| 108 | E | OE1 | −27.9 | 15.7 | −10.7 | 58 A |
| 108 | E | OE2 | −28.3 | 14.1 | −12.2 | 36 A |
| 109 | P | N | −22.5 | 15.0 | −10.0 | 16 A |
| 109 | P | CA | −21.8 | 13.8 | −9.4 | 16 A |
| 109 | P | C | −22.8 | 12.6 | −9.3 | 18 A |
| 109 | P | O | −23.9 | 12.8 | −8.9 | 17 A |
| 109 | P | CB | −21.4 | 14.3 | −8.1 | 18 A |
| 109 | P | CG | −21.2 | 15.8 | −8.2 | 24 A |
| 109 | P | CB | −22.3 | 16.2 | −9.2 | 19 A |
| 110 | L | N | −22.2 | 11.5 | −9.5 | 14 A |
| 110 | L | CA | −22.9 | 10.2 | −9.2 | 15 A |
| 110 | L | C | −23.0 | 10.1 | −7.7 | 17 A |
| 110 | L | O | −22.1 | 10.6 | −6.9 | 18 A |
| 110 | L | CB | −22.1 | 9.0 | −9.7 | 14 A |
| 110 | L | CG | −22.0 | 9.0 | −11.3 | 15 A |
| 110 | L | CD1 | −20.9 | 7.9 | −11.7 | 16 A |
| 110 | L | CD2 | −23.3 | 8.5 | −11.8 | 18 A |
| 111 | V | N | −23.9 | 9.4 | −7.2 | 16 A |
| 111 | V | CA | −24.0 | 9.1 | −5.7 | 18 A |
| 111 | V | C | −23.5 | 7.7 | −5.6 | 17 A |
| 111 | V | O | −24.1 | 6.7 | −6.0 | 17 A |
| 111 | V | CB | −25.4 | 9.2 | −5.2 | 19 A |
| 111 | V | CG1 | −25.5 | 8.8 | −3.7 | 20 A |
| 111 | V | CG2 | −25.9 | 10.7 | −5.3 | 18 A |
| 112 | L | N | −22.3 | 7.5 | −4.9 | 16 A |
| 112 | L | CA | −21.7 | 6.2 | −4.8 | 15 A |
| 112 | L | C | −22.5 | 5.4 | −3.8 | 19 A |
| 112 | L | O | −23.0 | 5.8 | −2.8 | 19 A |
| 112 | L | CB | −20.3 | 6.3 | −4.3 | 15 A |
| 112 | L | CG | −19.4 | 7.1 | −5.2 | 18 A |
| 112 | L | CD1 | −18.0 | 6.9 | −4.7 | 19 A |
| 112 | L | CD2 | −19.5 | 6.7 | −6.7 | 17 A |
| 113 | N | N | −22.7 | 4.1 | −4.2 | 14 A |
| 113 | N | CA | −23.4 | 3.1 | −3.4 | 14 A |
| 113 | N | C | −23.0 | 1.7 | −3.8 | 16 A |
| 113 | N | O | −22.1 | 1.5 | −4.7 | 16 A |
| 113 | N | CB | −24.9 | 3.4 | −3.4 | 18 A |
| 113 | N | CG | −25.5 | 3.2 | −4.8 | 22 A |
| 113 | N | OD1 | −25.1 | 2.4 | −5.6 | 20 A |
| 113 | N | ND2 | −26.5 | 4.0 | −5.1 | 18 A |
| 114 | S | N | −23.7 | 0.7 | −3.3 | 15 A |
| 114 | S | CA | −23.3 | −0.6 | −3.7 | 16 A |
| 114 | S | C | −23.5 | −0.9 | −5.2 | 17 A |
| 114 | S | O | −22.9 | −1.9 | −5.7 | 18 A |
| 114 | S | CB | −24.0 | −1.7 | −2.9 | 21 A |
| 114 | S | OG | −23.7 | −1.6 | −1.5 | 28 A |
| 115 | Y | N | −24.3 | −0.2 | −6.0 | 14 A |
| 115 | Y | CA | −24.5 | −0.5 | −7.4 | 13 A |
| 115 | Y | C | −23.7 | 0.5 | −8.3 | 16 A |
| 115 | Y | O | −23.6 | 0.3 | −9.5 | 15 A |
| 115 | Y | CB | −25.9 | −0.3 | −7.8 | 15 A |
| 115 | Y | CG | −26.8 | −1.2 | −7.0 | 16 A |
| 115 | Y | CD1 | −27.0 | −0.5 | −7.5 | 16 A |
| 115 | Y | CD2 | −27.4 | −0.9 | −5.8 | 17 A |
| 115 | Y | CE1 | −27.8 | −3.5 | −6.8 | 20 A |
| 115 | Y | CE2 | −28.1 | −1.8 | −5.1 | 18 A |
| 115 | Y | CZ | −28.3 | −3.1 | −5.6 | 26 A |
| 115 | Y | OH | −29.1 | −4.1 | −4.9 | 29 A |
| 116 | V | N | −23.1 | 1.6 | −7.7 | 13 A |
| 116 | V | CA | −22.4 | 2.6 | −8.5 | 11 A |
| 116 | V | C | −21.1 | 2.8 | −7.6 | 15 A |
| 116 | V | O | −21.1 | 3.5 | −6.7 | 15 A |
| 116 | V | CB | −23.3 | 3.9 | −8.4 | 13 A |
| 116 | V | CG1 | −22.6 | 5.1 | −9.0 | 14 A |
| 116 | V | CG2 | −24.6 | 3.6 | −9.1 | 14 A |
| 117 | T | N | −20.0 | 2.1 | −8.0 | 12 A |
| 117 | T | CA | −18.8 | 2.2 | −7.3 | 12 A |
| 117 | T | C | −17.6 | 2.4 | −8.2 | 14 A |
| 117 | T | O | −17.6 | 1.6 | −9.2 | 12 A |
| 117 | T | CB | −18.6 | 0.9 | −6.5 | 16 A |
| 117 | T | OG1 | −19.7 | 0.6 | −5.6 | 16 A |
| 117 | T | CG2 | −17.3 | 0.9 | −5.6 | 15 A |
| 118 | P | N | −16.6 | 3.2 | −7.9 | 11 A |
| 118 | P | CA | −15.5 | 3.3 | −8.9 | 11 A |
| 118 | P | C | −14.7 | 2.1 | −8.9 | 12 A |
| 118 | P | O | −14.7 | 1.2 | −8.0 | 13 A |
| 118 | P | CB | −14.6 | 4.5 | −8.2 | 14 A |
| 118 | P | CG | −15.5 | 5.2 | −7.3 | 16 A |
| 118 | P | CD | −16.5 | 4.1 | −6.8 | 12 A |
| 119 | I | N | −13.9 | 2.0 | −10.0 | 10 A |
| 119 | I | CA | −12.9 | 0.9 | −10.2 | 10 A |
| 119 | I | C | −11.6 | 1.5 | −9.7 | 15 A |
| 119 | I | O | −11.4 | 2.7 | −9.8 | 14 A |
| 119 | I | CB | −12.8 | 0.5 | −11.7 | 13 A |
| 119 | I | CG1 | −11.8 | −0.7 | −11.8 | 14 A |
| 119 | I | CG2 | −12.2 | 1.7 | −12.5 | 13 A |
| 119 | I | CD1 | −12.3 | −1.9 | −11.1 | 11 A |
| 120 | C | N | −10.8 | 0.7 | −9.1 | 12 A |
| 120 | C | CA | −9.6 | 1.2 | −8.5 | 11 A |
| 120 | C | C | −8.6 | 1.4 | −9.6 | 11 A |
| 120 | C | O | −8.5 | 0.6 | −10.6 | 12 A |
| 120 | C | CB | −8.9 | 0.3 | −7.5 | 10 A |
| 120 | C | SG | −9.9 | −0.0 | −6.0 | 15 A |
| 121 | I | N | −7.7 | 2.4 | −9.5 | 12 A |
| 121 | I | CA | −6.6 | 2.6 | −10.5 | 12 A |
| 121 | I | C | −5.3 | 2.7 | −9.8 | 14 A |
| 121 | I | O | −5.1 | 3.7 | −9.0 | 14 A |
| 121 | I | CB | −6.9 | 3.7 | −11.4 | 15 A |
| 121 | I | CG1 | −8.2 | 3.5 | −12.2 | 15 A |
| 121 | I | CG2 | −5.8 | 3.8 | −12.5 | 16 A |
| 121 | I | CD1 | −8.6 | 4.7 | −12.9 | 14 A |
| 122 | A | N | −4.4 | 1.8 | −10.0 | 14 A |
| 122 | A | CA | −3.1 | 1.8 | −9.4 | 13 A |
| 122 | A | C | −2.1 | 2.6 | −10.2 | 17 A |
| 122 | A | O | −2.4 | 3.2 | −11.2 | 16 A |
| 122 | A | CB | −2.5 | 0.4 | −9.4 | 13 A |
| 123 | D | N | −0.9 | 2.8 | −9.7 | 14 A |
| 123 | D | CA | 0.1 | 3.5 | −10.4 | 14 A |
| 123 | D | C | 0.6 | 2.7 | −11.7 | 17 A |
| 123 | D | O | 0.2 | 1.6 | −11.9 | 17 A |
| 123 | D | CB | 1.3 | 4.0 | −9.5 | 15 A |
| 123 | D | CG | 2.3 | 2.8 | −9.2 | 20 A |
| 123 | D | OD1 | 2.1 | 1.7 | −9.6 | 18 A |
| 123 | D | OD2 | 3.1 | 3.1 | −8.2 | 22 A |
| 124 | K | N | 1.4 | 3.4 | −12.5 | 15 A |
| 124 | K | CA | 1.8 | 2.7 | −13.7 | 16 A |
| 124 | K | C | 2.4 | 1.4 | −13.5 | 21 A |
| 124 | K | O | 2.1 | 0.4 | −14.2 | 20 A |
| 124 | K | CB | 2.7 | 3.7 | −14.5 | 20 A |
| 124 | K | CG | 3.3 | 3.0 | −15.8 | 27 A |
| 124 | K | CD | 4.4 | 3.8 | −16.4 | 34 A |
| 124 | K | CE | 5.5 | 2.9 | −17.1 | 51 A |
| 124 | K | NZ | 6.0 | 3.5 | −18.4 | 66 A |
| 125 | E | N | 3.4 | 1.3 | −12.5 | 17 A |
| 125 | E | CA | 4.0 | 0.0 | −12.3 | 17 A |
| 125 | E | C | 3.1 | −1.1 | −11.9 | 18 A |
| 125 | E | O | 3.2 | −2.2 | −12.4 | 17 A |
| 125 | E | CB | 5.1 | 0.3 | −11.2 | 18 A |
| 125 | E | CG | 5.8 | −1.0 | −10.7 | 20 A |
| 125 | E | CD | 6.8 | −0.8 | −9.6 | 27 A |
| 125 | E | OE1 | 7.6 | −1.7 | −9.4 | 28 A |
| 125 | E | OE2 | 6.7 | 0.3 | −8.9 | 26 A |
| 126 | Y | N | 2.3 | −0.8 | −10.9 | 15 A |
| 126 | Y | CA | 1.3 | −1.8 | −10.4 | 14 A |
| 126 | Y | C | 0.2 | −2.2 | −11.4 | 15 A |
| 126 | Y | O | −0.1 | −3.3 | −11.5 | 15 A |
| 126 | Y | CB | 0.8 | −1.5 | −9.0 | 14 A |
| 126 | Y | CG | 1.7 | −1.9 | −7.9 | 16 A |
| 126 | Y | CD1 | 2.7 | −1.1 | −7.4 | 18 A |
| 126 | Y | CD2 | 1.7 | −3.2 | −7.5 | 17 A |
| 126 | Y | CE1 | 3.6 | −1.5 | −6.4 | 19 A |
| 126 | Y | CE2 | 2.6 | −3.7 | −6.5 | 18 A |
| 126 | Y | CZ | 3.6 | −2.8 | −6.0 | 24 A |

TABLE 2-continued

Atomic Coordinates of Factor IXa co-crystal Compound A complex

| | | | | | | |
|---|---|---|---|---|---|---|
| 126 | Y | OH | 4.5 | −3.3 | −5.1 | 22 A |
| 127 | T | N | −0.2 | −1.2 | −12.1 | 13 A |
| 127 | T | CA | −1.2 | −1.5 | −13.2 | 13 A |
| 127 | T | C | −0.6 | −2.6 | −14.1 | 17 A |
| 127 | T | O | −1.3 | −3.6 | −14.5 | 15 A |
| 127 | T | CB | −1.6 | −0.3 | −13.9 | 13 A |
| 127 | T | OG1 | −2.3 | 0.6 | −13.0 | 12 A |
| 127 | T | CG2 | −2.7 | −0.7 | −15.1 | 14 A |
| 127A | N | N | 0.6 | −2.4 | −14.5 | 17 A |
| 127A | N | CA | 1.3 | −3.4 | −15.4 | 17 A |
| 127A | N | C | 1.5 | −4.7 | −14.7 | 19 A |
| 127A | N | O | 1.3 | −5.8 | −15.3 | 17 A |
| 127A | N | CB | 2.6 | −2.8 | −15.9 | 18 A |
| 127A | N | CG | 3.3 | −3.7 | −16.9 | 24 A |
| 127A | N | OD1 | 2.7 | −4.0 | −17.9 | 20 A |
| 127A | N | ND2 | 4.5 | −4.1 | −16.6 | 25 A |
| 127B | I | N | 1.9 | −4.6 | −13.4 | 16 A |
| 127B | I | CA | 2.1 | −5.8 | −12.6 | 16 A |
| 127B | I | C | 0.8 | −6.6 | −12.6 | 18 A |
| 127B | I | O | 0.8 | −7.8 | −12.8 | 17 A |
| 127B | I | CB | 2.6 | −5.5 | −11.2 | 18 A |
| 127B | I | CG1 | 4.1 | −5.2 | −11.2 | 18 A |
| 127B | I | CG2 | 2.3 | −6.7 | −10.3 | 17 A |
| 127B | I | CD1 | 4.5 | −4.3 | −10.0 | 20 A |
| 128 | F | N | −0.3 | −5.9 | −12.4 | 15 A |
| 128 | F | CA | −1.6 | −6.6 | −12.3 | 14 A |
| 128 | F | C | −2.0 | −7.1 | −13.6 | 18 A |
| 128 | F | O | −2.6 | −8.2 | −13.7 | 18 A |
| 128 | F | CB | −2.7 | −5.6 | −11.7 | 16 A |
| 128 | F | CG | −2.4 | −5.2 | −10.3 | 15 A |
| 128 | F | CD1 | −1.5 | −5.9 | −9.5 | 17 A |
| 128 | F | CD2 | −3.1 | −4.1 | −9.8 | 17 A |
| 128 | F | CE1 | −1.3 | −5.4 | −8.2 | 17 A |
| 128 | F | CE2 | −2.8 | −3.6 | −8.5 | 19 A |
| 128 | F | CZ | −2.0 | −4.3 | −7.7 | 16 A |
| 129 | L | N | −1.8 | −6.4 | −14.7 | 16 A |
| 129 | L | CA | −2.1 | −7.0 | −16.1 | 16 A |
| 129 | L | C | −1.4 | −8.3 | −16.2 | 20 A |
| 129 | L | O | −1.9 | −9.2 | −16.8 | 18 A |
| 129 | L | CB | −1.7 | −6.0 | −17.2 | 15 A |
| 129 | L | CG | −1.9 | −6.5 | −18.6 | 19 A |
| 129 | L | CD1 | −1.2 | −5.6 | −19.6 | 21 A |
| 129 | L | CD2 | −3.4 | −6.6 | −19.0 | 21 A |
| 129 | K | N | −0.1 | −8.3 | −15.8 | 19 A |
| 129 | K | CA | 0.7 | −9.4 | −16.0 | 19 A |
| 129 | K | C | 0.3 | −10.7 | −15.1 | 24 A |
| 129 | K | O | 0.8 | −11.8 | −15.4 | 23 A |
| 129 | K | CB | 2.2 | −9.1 | −15.8 | 23 A |
| 129 | K | CG | 2.7 | −8.1 | −16.8 | 27 A |
| 129 | K | CD | 4.2 | −8.3 | −17.1 | 47 A |
| 129 | K | CE | 4.8 | −7.1 | −18.0 | 64 A |
| 129 | K | NZ | 6.3 | −7.0 | −17.8 | 75 A |
| 129 | F | N | −0.6 | −10.5 | −14.2 | 19 A |
| 129 | F | CA | −1.1 | −11.7 | −13.5 | 20 A |
| 129 | F | C | −1.7 | −12.7 | −14.5 | 23 A |
| 129 | F | O | −1.9 | −13.9 | −14.2 | 23 A |
| 129 | F | CB | −2.2 | −11.4 | −12.5 | 23 A |
| 129 | F | CG | −1.8 | −10.7 | −11.2 | 26 A |
| 129 | F | CD1 | −0.4 | −10.4 | −11.0 | 30 A |
| 129 | F | CD2 | −2.7 | −10.3 | −10.2 | 28 A |
| 129 | F | CE1 | −0.0 | −9.8 | −9.9 | 32 A |
| 129 | F | CE2 | −2.3 | −9.7 | −9.1 | 31 A |
| 129 | F | CZ | −1.0 | −9.4 | −8.9 | 29 A |
| 130 | G | N | −2.1 | −12.1 | −15.6 | 21 A |
| 130 | G | CA | −2.6 | −12.8 | −16.8 | 20 A |
| 130 | G | C | −4.1 | −13.2 | −16.9 | 21 A |
| 130 | G | O | −4.4 | −13.9 | −17.8 | 19 A |
| 131 | S | N | −4.9 | −12.7 | −16.0 | 16 A |
| 131 | S | CA | −6.3 | −13.1 | −16.0 | 16 A |
| 131 | S | C | −7.2 | −11.9 | −15.6 | 19 A |
| 131 | S | O | −7.2 | −11.5 | −14.5 | 20 A |
| 131 | S | CB | −6.6 | −14.3 | −15.2 | 19 A |
| 131 | S | OG | −8.0 | −14.7 | −15.4 | 27 A |
| 132 | G | N | −8.0 | −11.4 | −16.6 | 17 A |
| 132 | G | CA | −8.9 | −10.2 | −16.3 | 16 A |
| 132 | G | C | −10.3 | −10.5 | −16.7 | 17 A |
| 132 | G | O | −10.6 | −11.4 | −17.4 | 17 A |
| 133 | Y | N | −11.2 | −9.7 | −16.1 | 15 A |
| 133 | Y | CA | −12.6 | −9.8 | −16.4 | 13 A |
| 133 | Y | C | −13.1 | −8.6 | −17.3 | 12 A |
| 133 | Y | O | −12.8 | −7.5 | −17.0 | 13 A |
| 133 | Y | CB | −13.5 | −9.8 | −15.2 | 16 A |
| 133 | Y | CG | −13.4 | −11.1 | −14.5 | 19 A |
| 133 | Y | CD1 | −12.4 | −11.4 | −13.6 | 23 A |
| 133 | Y | CD2 | −14.4 | −12.1 | −14.7 | 21 A |
| 133 | Y | CE1 | −12.3 | −12.6 | −13.0 | 25 A |
| 133 | Y | CE2 | −14.3 | −13.3 | −14.1 | 22 A |
| 133 | Y | CZ | −13.3 | −13.6 | −13.3 | 31 A |
| 133 | Y | OH | −13.3 | −14.8 | −12.7 | 38 A |
| 134 | V | N | −13.8 | −8.9 | −18.4 | 11 A |
| 134 | V | CA | −14.4 | −7.9 | −19.2 | 10 A |
| 134 | V | C | −15.9 | −7.9 | −19.1 | 13 A |
| 134 | V | O | −16.5 | −9.0 | −18.7 | 13 A |
| 134 | V | CB | −14.0 | −8.0 | −20.7 | 12 A |
| 134 | V | CG1 | −12.4 | −7.8 | −20.9 | 14 A |
| 134 | V | CG2 | −14.4 | −9.4 | −21.3 | 12 A |
| 135 | S | N | −16.6 | −6.8 | −19.3 | 10 A |
| 135 | S | CA | −18.0 | −6.9 | −19.1 | 9 A |
| 135 | S | C | −18.7 | −5.8 | −20.0 | 12 A |
| 135 | S | O | −18.0 | −4.9 | −20.4 | 10 A |
| 135 | S | CB | −18.4 | −6.6 | −17.7 | 12 A |
| 135 | S | OG | −17.7 | −5.4 | −17.1 | 14 A |
| 136 | G | N | −20.0 | −6.0 | −20.3 | 10 A |
| 136 | G | CA | −20.6 | −5.0 | −21.2 | 10 A |
| 136 | G | C | −21.9 | −5.5 | −21.8 | 13 A |
| 136 | G | O | −22.2 | −6.7 | −21.7 | 12 A |
| 137 | W | N | −22.7 | −4.6 | −22.4 | 10 A |
| 137 | W | CA | −23.9 | −4.9 | −23.1 | 11 A |
| 137 | W | C | −23.8 | −5.1 | −24.6 | 14 A |
| 137 | W | O | −24.7 | −4.9 | −25.4 | 13 A |
| 137 | W | CB | −24.9 | −3.8 | −22.8 | 11 A |
| 137 | W | CG | −25.4 | −3.8 | −21.4 | 11 A |
| 137 | W | CD1 | −26.4 | −4.6 | −20.9 | 14 A |
| 137 | W | CD2 | −24.9 | −3.1 | −20.3 | 11 A |
| 137 | W | NE1 | −26.7 | −4.3 | −19.5 | 14 A |
| 137 | W | CE2 | −25.7 | −3.4 | −19.2 | 14 A |
| 137 | W | CE3 | −23.8 | −2.2 | −20.2 | 11 A |
| 137 | W | CZ2 | −25.4 | −2.8 | −17.9 | 12 A |
| 137 | W | CZ3 | −23.6 | −1.6 | −18.9 | 12 A |
| 137 | W | CH2 | −24.4 | −1.9 | −17.8 | 13 A |
| 138 | G | N | −22.6 | −5.5 | −25.0 | 12 A |
| 138 | G | CA | −22.2 | −5.7 | −26.4 | 12 A |
| 138 | G | C | −22.9 | −6.9 | −27.0 | 16 A |
| 138 | G | O | −23.6 | −7.7 | −26.3 | 13 A |
| 139 | R | N | −22.6 | −7.1 | −28.3 | 12 A |
| 139 | R | CA | −23.2 | −8.2 | −29.0 | 12 A |
| 139 | R | C | −22.8 | −9.6 | −28.4 | 11 A |
| 139 | R | O | −21.6 | −9.8 | −28.0 | 13 A |
| 139 | R | CB | −22.7 | −8.2 | −30.5 | 13 A |
| 139 | R | CG | −23.3 | −7.0 | −31.3 | 18 A |
| 139 | R | CD | −22.6 | −7.0 | −32.7 | 20 A |
| 139 | R | NB | −23.1 | −5.8 | −33.4 | 25 A |
| 139 | R | CZ | −23.0 | −5.7 | −34.7 | 32 A |
| 139 | R | NH1 | −22.3 | −6.6 | −35.4 | 25 A |
| 139 | R | NH2 | −23.4 | −4.6 | −35.3 | 25 A |
| 140 | V | N | −23.8 | −10.5 | −28.5 | 10 A |
| 140 | V | CA | −23.6 | −11.9 | −28.1 | 11 A |
| 140 | V | C | −23.2 | −12.8 | −29.2 | 15 A |
| 140 | V | O | −22.9 | −13.9 | −29.0 | 14 A |
| 140 | V | CB | −24.7 | −12.4 | −27.2 | 13 A |
| 140 | V | CG1 | −25.0 | −11.4 | −26.1 | 12 A |
| 140 | V | CG2 | −26.0 | −12.5 | −28.1 | 13 A |
| 141 | F | N | −23.1 | −12.2 | −30.4 | 15 A |
| 141 | F | CA | −22.7 | −13.0 | −31.6 | 16 A |
| 141 | F | C | −22.1 | −11.8 | −32.5 | 19 A |
| 141 | F | O | −22.8 | −10.8 | −32.6 | 17 A |
| 141 | F | CB | −23.8 | −13.7 | −32.3 | 19 A |
| 141 | F | CG | −23.5 | −14.3 | −33.6 | 23 A |
| 141 | F | CD1 | −22.3 | −13.8 | −33.8 | 27 A |
| 141 | F | CD2 | −24.2 | −14.0 | −34.8 | 28 A |
| 141 | F | CE1 | −22.0 | −15.7 | −35.0 | 29 A |
| 141 | F | CE2 | −23.9 | −14.6 | −36.0 | 31 A |
| 141 | F | CZ | −22.7 | −15.4 | −36.1 | 29 A |
| 143 | H | N | −21.0 | −12.0 | −33.2 | 19 A |

TABLE 2-continued

Atomic Coordinates of Factor IXa co-crystal Compound A complex

| | | | | | | | |
|---|---|---|---|---|---|---|---|
| 143 | H | CA | −20.5 | −10.9 | −34.0 | 19 | A |
| 143 | H | C | −21.4 | −10.2 | −35.0 | 24 | A |
| 143 | H | O | −21.3 | −9.0 | −35.3 | 21 | A |
| 143 | H | CB | −19.1 | −11.2 | −34.6 | 21 | A |
| 143 | H | CG | −19.1 | −12.1 | −35.8 | 25 | A |
| 143 | H | ND1 | −19.0 | −11.6 | −37.1 | 27 | A |
| 143 | H | CD2 | −19.3 | −13.4 | −35.9 | 28 | A |
| 143 | H | CE1 | −19.1 | −12.6 | −37.9 | 27 | A |
| 143 | H | NE2 | −19.3 | −13.7 | −37.2 | 28 | A |
| 144 | K | N | −22.4 | −11.0 | −35.5 | 22 | A |
| 144 | K | CA | −23.3 | −10.4 | −36.5 | 23 | A |
| 144 | K | C | −24.7 | −10.4 | −35.9 | 29 | A |
| 144 | K | O | −25.6 | −10.1 | −36.7 | 28 | A |
| 144 | K | CB | −23.3 | −11.3 | −37.8 | 25 | A |
| 144 | K | CG | −21.9 | −11.3 | −38.5 | 45 | A |
| 144 | K | CD | −22.1 | −10.9 | −40.0 | 62 | A |
| 144 | K | CE | −21.4 | −9.6 | −40.2 | 80 | A |
| 144 | K | NZ | −20.4 | −9.6 | −41.3 | 89 | A |
| 145 | G | N | −24.8 | −10.5 | −34.6 | 26 | A |
| 145 | G | CA | −26.1 | −10.6 | −34.0 | 25 | A |
| 145 | G | C | −26.4 | −9.5 | −33.0 | 26 | A |
| 145 | G | O | −25.9 | −8.4 | −33.0 | 27 | A |
| 147 | R | N | −27.4 | −9.9 | −32.2 | 20 | A |
| 147 | R | CA | −27.9 | −8.9 | −31.2 | 18 | A |
| 147 | R | C | −27.1 | −8.6 | −30.0 | 22 | A |
| 147 | R | O | −26.2 | −9.4 | −29.6 | 22 | A |
| 147 | R | CB | −29.3 | −9.3 | −30.8 | 19 | A |
| 147 | R | CG | −29.4 | −10.5 | −29.8 | 28 | A |
| 147 | R | CD | −30.9 | −10.5 | −29.3 | 30 | A |
| 147 | R | NE | −31.1 | −11.7 | −28.4 | 23 | A |
| 147 | R | CZ | −31.5 | −12.9 | −28.9 | 41 | A |
| 147 | R | NH1 | −31.6 | −13.1 | −30.2 | 32 | A |
| 147 | R | NH2 | −31.7 | −13.9 | −28.0 | 22 | A |
| 148 | S | N | −27.3 | −7.5 | −29.4 | 18 | A |
| 148 | S | CA | −26.6 | −7.0 | −28.2 | 18 | A |
| 148 | S | C | −27.4 | −7.6 | −26.9 | 24 | A |
| 148 | S | O | −28.5 | −8.0 | −27.0 | 22 | A |
| 148 | S | CB | −26.6 | −5.5 | −28.1 | 23 | A |
| 148 | S | OG | −27.8 | −5.0 | −28.5 | 35 | A |
| 149 | A | N | −26.7 | −7.5 | −25.8 | 19 | A |
| 149 | A | CA | −27.3 | −8.1 | −24.6 | 17 | A |
| 149 | A | C | −28.2 | −7.1 | −23.9 | 19 | A |
| 149 | A | O | −28.0 | −5.9 | −23.9 | 20 | A |
| 149 | A | CB | −26.2 | −8.5 | −23.6 | 17 | A |
| 150 | L | N | −29.3 | −7.7 | −23.3 | 15 | A |
| 150 | L | CA | −30.2 | −6.9 | −22.4 | 17 | A |
| 150 | L | C | −29.5 | −6.9 | −21.0 | 17 | A |
| 150 | L | O | −29.5 | −5.8 | −20.3 | 19 | A |
| 150 | L | CB | −31.6 | −7.5 | −22.3 | 18 | A |
| 150 | L | CG | −32.3 | −7.5 | −23.6 | 25 | A |
| 150 | L | CD1 | −33.8 | −7.9 | −23.3 | 26 | A |
| 150 | L | CD2 | −32.2 | −6.2 | −24.3 | 27 | A |
| 151 | V | N | −29.1 | −8.0 | −20.5 | 15 | A |
| 151 | V | CA | −28.5 | −8.2 | −19.2 | 14 | A |
| 151 | V | C | −27.0 | −8.1 | −19.3 | 15 | A |
| 151 | V | O | −26.4 | −8.6 | −20.2 | 14 | A |
| 151 | V | CB | −28.8 | −9.6 | −18.5 | 16 | A |
| 151 | V | CG1 | −28.2 | −9.7 | −17.1 | 16 | A |
| 151 | V | CG2 | −30.4 | −9.8 | −18.4 | 16 | A |
| 152 | L | N | −26.3 | −7.3 | −18.4 | 13 | A |
| 152 | L | CA | −24.9 | −7.1 | −18.5 | 14 | A |
| 152 | L | C | −24.2 | −8.5 | −18.5 | 16 | A |
| 152 | L | O | −24.6 | −9.4 | −17.7 | 14 | A |
| 152 | L | CB | −24.4 | −6.4 | −17.2 | 13 | A |
| 152 | L | CG | −22.9 | −6.1 | −17.0 | 14 | A |
| 152 | L | CD1 | −22.4 | −5.2 | −18.2 | 11 | A |
| 152 | L | CD2 | −22.7 | −5.4 | −15.7 | 12 | A |
| 153 | Q | N | −23.3 | −8.6 | −19.4 | 12 | A |
| 153 | Q | CA | −22.5 | −9.9 | −19.6 | 11 | A |
| 153 | Q | C | −21.1 | −9.7 | −19.0 | 15 | A |
| 153 | Q | O | −20.5 | −8.6 | −19.0 | 13 | A |
| 153 | Q | CB | −22.4 | −10.3 | −21.1 | 13 | A |
| 153 | Q | CG | −23.7 | −10.5 | −21.7 | 14 | A |
| 153 | Q | CD | −24.5 | −11.7 | −21.1 | 15 | A |
| 153 | Q | OE1 | −25.5 | −11.5 | −20.4 | 17 | A |
| 153 | Q | NE2 | −24.0 | −12.9 | −21.3 | 11 | A |
| 154 | Y | N | −20.5 | −10.8 | −18.6 | 10 | A |
| 154 | Y | CA | −19.1 | −10.8 | −18.2 | 12 | A |
| 154 | Y | C | −18.3 | −12.0 | −18.6 | 16 | A |
| 154 | Y | O | −18.9 | −13.1 | −18.9 | 17 | A |
| 154 | Y | CB | −18.9 | −10.5 | −16.7 | 14 | A |
| 154 | Y | CG | −19.2 | −11.8 | −15.9 | 16 | A |
| 154 | Y | CD1 | −18.2 | −12.7 | −15.5 | 17 | A |
| 154 | Y | CD2 | −20.5 | −12.1 | −15.5 | 18 | A |
| 154 | Y | CE1 | −18.5 | −13.8 | −14.7 | 15 | A |
| 154 | Y | CE2 | −20.8 | −13.2 | −14.7 | 19 | A |
| 154 | Y | CZ | −19.8 | −14.1 | −14.3 | 20 | A |
| 154 | Y | OH | −20.1 | −15.2 | −13.5 | 20 | A |
| 155 | L | N | −17.0 | −11.9 | −18.7 | 12 | A |
| 155 | L | CA | −16.1 | −12.9 | −19.2 | 11 | A |
| 155 | L | C | −14.8 | −12.8 | −18.7 | 16 | A |
| 155 | L | O | −14.2 | −11.7 | −18.7 | 14 | A |
| 155 | L | CB | −16.1 | −12.9 | −20.7 | 10 | A |
| 155 | L | CG | −15.2 | −13.9 | −21.4 | 16 | A |
| 155 | L | CD1 | −15.7 | −15.3 | −21.3 | 17 | A |
| 155 | L | CD2 | −15.1 | −13.5 | −22.9 | 16 | A |
| 156 | R | N | −14.2 | −13.9 | −18.2 | 13 | A |
| 156 | R | CA | −12.8 | −13.9 | −17.8 | 13 | A |
| 156 | R | C | −11.9 | −14.2 | −19.1 | 16 | A |
| 156 | R | O | −12.3 | −15.1 | −19.8 | 16 | A |
| 156 | R | CB | −12.5 | −14.9 | −16.8 | 15 | A |
| 156 | R | CG | −11.1 | −15.1 | −16.4 | 21 | A |
| 156 | R | CD | −10.9 | −16.3 | −15.4 | 24 | A |
| 156 | R | NE | −11.3 | −15.8 | −14.1 | 52 | A |
| 156 | R | CZ | −10.9 | −16.3 | −13.0 | 79 | A |
| 156 | R | NH1 | −10.1 | −17.3 | −12.9 | 77 | A |
| 156 | R | NH2 | −11.3 | −15.7 | −11.8 | 60 | A |
| 157 | V | N | −11.0 | −13.4 | −19.4 | 15 | A |
| 157 | V | CA | −10.1 | −13.6 | −20.5 | 15 | A |
| 157 | V | C | −8.6 | −13.6 | −20.2 | 19 | A |
| 157 | V | O | −8.2 | −12.8 | −19.4 | 16 | A |
| 157 | V | CB | −10.3 | −12.5 | −21.6 | 17 | A |
| 157 | V | CG1 | −11.8 | −12.6 | −22.2 | 16 | A |
| 157 | V | CG2 | −10.0 | −11.1 | −21.0 | 17 | A |
| 158 | P | N | −7.9 | −14.6 | −20.7 | 17 | A |
| 158 | P | CA | −6.5 | −14.7 | −20.3 | 17 | A |
| 158 | P | C | −5.6 | −13.8 | −21.2 | 19 | A |
| 158 | P | O | −5.9 | −13.7 | −22.4 | 18 | A |
| 158 | P | CB | −6.1 | −16.2 | −20.7 | 18 | A |
| 158 | P | CG | −7.2 | −16.6 | −21.7 | 23 | A |
| 158 | P | CD | −8.4 | −15.9 | −21.3 | 18 | A |
| 159 | L | N | −4.5 | −13.3 | −20.6 | 15 | A |
| 159 | L | CA | −3.6 | −12.5 | −21.4 | 16 | A |
| 159 | L | C | −2.9 | −13.3 | −22.4 | 21 | A |
| 159 | L | O | −2.5 | −14.4 | −22.1 | 20 | A |
| 159 | L | CB | −2.6 | −11.8 | −20.4 | 16 | A |
| 159 | L | CG | −1.6 | −10.9 | −21.1 | 19 | A |
| 159 | L | CD1 | −2.3 | −9.7 | −21.7 | 20 | A |
| 159 | L | CD2 | −0.6 | −10.4 | −20.0 | 24 | A |
| 160 | V | N | −2.8 | −12.8 | −23.6 | 19 | A |
| 160 | V | CA | −2.1 | −13.5 | −24.7 | 19 | A |
| 160 | V | C | −0.7 | −12.9 | −24.9 | 25 | A |
| 160 | V | O | −0.5 | −11.7 | −25.1 | 24 | A |
| 160 | V | CB | −3.0 | −13.3 | −26.0 | 21 | A |
| 160 | V | CG1 | −2.2 | −13.8 | −27.2 | 21 | A |
| 160 | V | CG2 | −4.3 | −14.1 | −25.8 | 21 | A |
| 161 | D | N | 0.3 | −13.8 | −25.0 | 25 | A |
| 161 | D | CA | 1.7 | −13.4 | −25.2 | 26 | A |
| 161 | D | C | 1.8 | −12.4 | −26.4 | 26 | A |
| 161 | D | O | 1.2 | −12.7 | −27.4 | 23 | A |
| 161 | D | CB | 2.5 | −12.7 | −25.5 | 29 | A |
| 161 | D | CG | 3.7 | −14.4 | −26.4 | 48 | A |
| 161 | D | OD1 | 4.8 | −14.0 | −25.8 | 53 | A |
| 161 | D | OD2 | 3.6 | −14.6 | −27.6 | 54 | A |
| 162 | R | N | 2.5 | −11.4 | −26.2 | 24 | A |
| 162 | R | CA | 2.6 | −10.4 | −27.3 | 24 | A |
| 162 | R | C | 3.0 | −10.9 | −28.7 | 28 | A |
| 162 | R | O | 2.4 | −10.5 | −29.7 | 26 | A |
| 162 | R | CB | 3.4 | −9.1 | −26.9 | 28 | A |
| 162 | R | CG | 3.7 | −8.2 | −28.0 | 37 | A |
| 162 | R | CD | 4.2 | −6.8 | −27.5 | 57 | A |
| 162 | R | NE | 5.1 | −6.2 | −28.5 | 80 | A |
| 162 | R | CZ | 5.9 | −5.2 | −28.2 | 0 | A |
| 162 | R | NH1 | 5.9 | −4.6 | −27.0 | 93 | A |

TABLE 2-continued

Atomic Coordinates of Factor IXa co-crystal Compound A complex

| | | | | | | | |
|---|---|---|---|---|---|---|---|
| 162 | R | NH2 | 6.7 | −4.7 | −29.1 | 93 | A |
| 163 | A | N | 4.0 | −11.7 | −28.8 | 26 | A |
| 163 | A | CA | 4.4 | −12.2 | −30.1 | 26 | A |
| 163 | A | C | 3.3 | −13.0 | −30.7 | 25 | A |
| 163 | A | O | 3.1 | −12.9 | −31.9 | 22 | A |
| 163 | A | CB | 5.8 | −13.0 | −30.0 | 27 | A |
| 164 | T | N | 2.6 | −13.8 | −29.9 | 24 | A |
| 164 | T | CA | 1.5 | −14.6 | −30.4 | 24 | A |
| 164 | T | C | 0.4 | −13.7 | −31.1 | 30 | A |
| 164 | T | O | −0.1 | −14.0 | −32.1 | 27 | A |
| 164 | T | CB | 0.8 | −15.5 | −29.3 | 33 | A |
| 164 | T | OG1 | 1.7 | −16.4 | −28.8 | 33 | A |
| 164 | T | CG2 | −0.4 | −16.2 | −29.8 | 31 | A |
| 165 | C | N | 0.1 | −12.6 | −30.4 | 27 | A |
| 165 | C | CA | −0.9 | −11.7 | −30.9 | 28 | A |
| 165 | C | C | −0.4 | −11.0 | −32.2 | 30 | A |
| 165 | C | O | −1.2 | −10.9 | −33.1 | 28 | A |
| 165 | C | CB | −1.2 | −10.6 | −29.9 | 28 | A |
| 165 | C | SG | −2.7 | −9.8 | −30.3 | 32 | A |
| 166 | L | N | 0.8 | −10.5 | −32.2 | 27 | A |
| 166 | L | CA | 1.3 | −9.8 | −33.4 | 27 | A |
| 166 | L | C | 1.2 | −10.7 | −34.7 | 30 | A |
| 166 | L | O | 0.9 | −10.2 | −35.8 | 30 | A |
| 166 | L | CB | 2.7 | −9.4 | −33.2 | 27 | A |
| 166 | L | CG | 3.0 | −7.9 | −32.9 | 34 | A |
| 166 | L | CD1 | 2.1 | −7.5 | −31.7 | 35 | A |
| 166 | L | CD2 | 4.5 | −7.7 | −32.6 | 34 | A |
| 167 | R | N | 1.4 | −12.0 | −34.5 | 28 | A |
| 167 | R | CA | 1.3 | −12.9 | −35.6 | 29 | A |
| 167 | R | C | −0.1 | −13.2 | −36.0 | 33 | A |
| 167 | R | O | −0.4 | −13.9 | −37.0 | 31 | A |
| 167 | R | CB | 2.1 | −14.2 | −35.3 | 35 | A |
| 167 | R | CG | 2.0 | −15.3 | −36.4 | 54 | A |
| 167 | R | CD | 1.8 | −16.7 | −35.8 | 75 | A |
| 167 | R | NE | 1.9 | −17.7 | −36.8 | 92 | A |
| 167 | R | CZ | 1.9 | −19.0 | −36.6 | 0 | A |
| 167 | R | NH1 | 2.0 | −19.5 | −35.4 | 96 | A |
| 167 | R | NH2 | 2.0 | −19.8 | −37.7 | 96 | A |
| 168 | S | N | −1.0 | −12.9 | −35.1 | 27 | A |
| 168 | S | CA | −2.4 | −13.3 | −35.3 | 26 | A |
| 168 | S | C | −3.2 | −12.4 | −36.3 | 27 | A |
| 168 | S | O | −4.3 | −12.6 | −36.7 | 26 | A |
| 168 | S | CB | −3.2 | −13.3 | −34.0 | 29 | A |
| 168 | S | OG | −3.5 | −11.9 | −33.6 | 29 | A |
| 169 | T | N | −2.6 | −11.2 | −36.6 | 24 | A |
| 169 | T | CA | −3.2 | −10.2 | −37.4 | 23 | A |
| 169 | T | C | −2.3 | −9.4 | −38.3 | 26 | A |
| 169 | T | O | −1.1 | 9.3 | −37.9 | 25 | A |
| 169 | T | CB | −3.9 | −9.2 | −36.4 | 22 | A |
| 169 | T | OG1 | −4.6 | −8.2 | −37.1 | 26 | A |
| 169 | T | CG2 | −2.9 | −8.5 | −35.5 | 24 | A |
| 170 | K | N | −2.8 | −8.8 | −39.3 | 21 | A |
| 170 | K | CA | −2.1 | −7.9 | −40.2 | 22 | A |
| 170 | K | C | −2.1 | −6.4 | −39.8 | 26 | A |
| 170 | K | O | 1.3 | −5.7 | −40.2 | 29 | A |
| 170 | K | CB | −2.4 | −8.2 | −41.7 | 25 | A |
| 170 | K | CG | −2.1 | −9.6 | −42.1 | 39 | A |
| 170 | K | CD | −0.6 | −9.9 | −42.0 | 60 | A |
| 170 | K | CE | −0.3 | −11.2 | −42.6 | 78 | A |
| 170 | K | NZ | 1.2 | −11.4 | −43.0 | 84 | A |
| 171 | F | N | −3.1 | −6.1 | −39.0 | 19 | A |
| 171 | F | CA | −3.1 | −4.7 | −38.4 | 17 | A |
| 171 | F | C | −1.9 | −4.6 | −37.5 | 22 | A |
| 171 | F | O | −1.3 | −5.6 | −37.0 | 24 | A |
| 171 | F | CB | −4.4 | −4.5 | −37.6 | 17 | A |
| 171 | F | CG | −5.6 | −4.3 | −38.4 | 17 | A |
| 171 | F | CD1 | −5.9 | −3.1 | −39.0 | 18 | A |
| 171 | F | CD2 | −6.5 | −5.4 | −38.5 | 19 | A |
| 171 | F | CE1 | −7.1 | −2.9 | −39.8 | 18 | A |
| 171 | F | CE2 | −7.7 | −5.2 | −39.2 | 18 | A |
| 171 | F | CZ | −8.0 | −4.0 | −39.9 | 16 | A |
| 172 | T | N | −1.5 | −3.4 | −37.3 | 19 | A |
| 172 | T | CA | −0.4 | −3.1 | −36.4 | 20 | A |
| 172 | T | C | −0.9 | −3.1 | −34.9 | 22 | A |
| 172 | T | O | −1.8 | −2.4 | −34.6 | 23 | A |
| 172 | T | CB | 0.3 | −1.8 | −36.7 | 33 | A |
| 172 | T | OG1 | 0.6 | −1.7 | −38.1 | 36 | A |
| 172 | T | CG2 | 1.5 | −1.6 | −35.8 | 31 | A |
| 173 | I | N | −0.2 | −3.9 | −34.1 | 21 | A |
| 173 | I | CA | −0.5 | −3.9 | −32.6 | 20 | A |
| 173 | I | C | 0.6 | −3.0 | −32.0 | 24 | A |
| 173 | I | O | 1.7 | −3.5 | −31.9 | 23 | A |
| 173 | I | CB | −0.6 | −5.3 | −32.0 | 24 | A |
| 173 | I | CG1 | −1.6 | −6.2 | −32.8 | 24 | A |
| 173 | I | CG2 | −0.9 | −5.3 | −30.5 | 25 | A |
| 173 | I | CD1 | −3.1 | −5.6 | −32.8 | 23 | A |
| 174 | Y | N | 0.2 | −1.8 | −31.6 | 19 | A |
| 174 | Y | CA | 1.1 | −0.9 | −30.9 | 20 | A |
| 174 | Y | C | 1.3 | −1.2 | −29.4 | 21 | A |
| 174 | Y | O | 0.6 | −2.1 | −28.8 | 20 | A |
| 174 | Y | CB | 0.6 | 0.5 | −31.1 | 22 | A |
| 174 | Y | CG | 0.6 | 1.0 | −32.5 | 25 | A |
| 174 | Y | CD1 | −0.6 | 0.8 | −33.3 | 26 | A |
| 174 | Y | CD2 | 1.7 | 1.6 | −33.1 | 27 | A |
| 174 | Y | CE1 | −0.6 | 1.2 | −34.6 | 26 | A |
| 174 | Y | CE2 | 1.7 | 2.0 | −34.4 | 28 | A |
| 174 | Y | CZ | 0.6 | 1.8 | −35.2 | 34 | A |
| 174 | Y | OH | 0.6 | 2.2 | −36.5 | 32 | A |
| 175 | N | N | 2.4 | −0.6 | −28.8 | 20 | A |
| 175 | N | CA | 2.8 | −0.9 | −27.4 | 20 | A |
| 175 | N | C | 1.8 | −0.6 | −26.4 | 21 | A |
| 175 | N | O | 1.8 | −1.2 | −25.3 | 23 | A |
| 175 | N | CB | 4.1 | −0.3 | −27.1 | 21 | A |
| 175 | N | CG | 5.2 | −0.9 | −28.0 | 43 | A |
| 175 | N | OD1 | 5.3 | −2.1 | −28.2 | 36 | A |
| 175 | N | ND2 | 6.1 | 0.0 | −28.4 | 46 | A |
| 176 | N | N | 0.9 | 0.3 | −26.7 | 20 | A |
| 176 | N | CA | −0.2 | 0.7 | −25.8 | 19 | A |
| 176 | N | C | −1.4 | −0.2 | −25.9 | 21 | A |
| 176 | N | O | −2.5 | 0.1 | −25.4 | 22 | A |
| 176 | N | CB | −0.7 | 2.2 | −26.1 | 19 | A |
| 176 | N | CG | −1.2 | 2.4 | −27.5 | 31 | A |
| 176 | N | OD1 | −2.4 | 2.3 | −27.7 | 21 | A |
| 176 | N | ND2 | −0.3 | 2.7 | −28.4 | 29 | A |
| 177 | M | N | −1.3 | −1.3 | −26.7 | 14 | A |
| 177 | M | CA | −2.4 | −2.2 | −26.9 | 14 | A |
| 177 | M | C | −2.0 | −3.5 | −26.3 | 19 | A |
| 177 | M | O | −0.8 | −3.9 | −26.3 | 17 | A |
| 177 | M | CB | −2.7 | −2.4 | −28.4 | 13 | A |
| 177 | M | CG | −3.2 | −2.1 | −29.1 | 16 | A |
| 177 | M | SD | −3.3 | −1.6 | −30.9 | 19 | A |
| 177 | M | CE | −3.7 | −0.1 | −31.5 | 17 | A |
| 178 | F | N | −2.9 | −4.3 | −25.9 | 15 | A |
| 178 | F | CA | −2.6 | −5.5 | −25.5 | 14 | A |
| 178 | F | C | −3.7 | −6.6 | −26.0 | 19 | A |
| 178 | F | O | −4.8 | −6.2 | −26.4 | 18 | A |
| 178 | F | CB | −2.4 | −5.8 | −24.0 | 16 | A |
| 178 | F | CG | −3.6 | −5.7 | −23.2 | 16 | A |
| 178 | F | CD1 | −4.4 | −6.8 | −22.9 | 16 | A |
| 178 | F | CD2 | −3.9 | −4.5 | −22.5 | 15 | A |
| 178 | F | CE1 | −5.5 | −6.7 | −22.0 | 16 | A |
| 178 | F | CE2 | −5.0 | −4.4 | −21.6 | 14 | A |
| 178 | F | CZ | −5.8 | −5.5 | −21.4 | 13 | A |
| 179 | C | N | −3.4 | −7.9 | −26.0 | 17 | A |
| 179 | C | CA | −4.4 | −8.9 | −26.4 | 20 | A |
| 179 | C | C | −4.8 | −9.9 | −25.4 | 18 | A |
| 179 | C | O | −4.0 | −10.2 | −24.5 | 15 | A |
| 179 | C | CB | −3.8 | −9.6 | −27.6 | 24 | A |
| 179 | C | SG | −2.9 | −8.6 | −28.7 | 31 | A |
| 180 | A | N | −6.0 | −10.3 | −25.5 | 15 | A |
| 180 | A | CA | −6.6 | −11.2 | −24.5 | 15 | A |
| 180 | A | C | −7.7 | −12.0 | −25.2 | 19 | A |
| 180 | A | O | −8.3 | −11.5 | −26.1 | 16 | A |
| 180 | A | CB | −7.2 | −10.5 | −23.2 | 18 | A |
| 181 | G | N | −7.8 | −13.2 | −24.8 | 18 | A |
| 181 | G | CA | −8.8 | −14.1 | −25.4 | 17 | A |
| 181 | G | C | −8.3 | −15.5 | −25.5 | 21 | A |
| 181 | G | O | −7.3 | −15.9 | −24.9 | 18 | A |
| 181A | F | N | −9.1 | −16.3 | −26.2 | 17 | A |
| 181A | F | CA | −8.9 | −17.7 | −26.3 | 19 | A |
| 181A | F | C | −8.4 | −18.2 | −27.7 | 28 | A |
| 181A | F | O | −8.9 | −17.8 | −28.7 | 28 | A |
| 181A | F | CB | −10.2 | −18.5 | −26.0 | 19 | A |
| 181A | F | CG | −10.6 | −18.2 | −24.6 | 20 | A |

TABLE 2-continued

Atomic Coordinates of Factor IXa co-crystal Compound A complex

| | | | | | | | |
|---|---|---|---|---|---|---|---|
| 181A | F | CD1 | −11.4 | −17.1 | −24.3 | 21 | A |
| 181A | F | CD2 | −10.2 | −19.0 | −23.5 | 22 | A |
| 181A | F | CE1 | −11.8 | −16.8 | −23.0 | 21 | A |
| 181A | F | CE2 | −10.6 | −18.7 | −22.2 | 25 | A |
| 181A | F | CZ | −11.4 | −17.6 | −21.9 | 22 | A |
| 182 | H | N | −7.4 | −19.1 | −27.7 | 30 | A |
| 182 | H | CA | −6.8 | −19.7 | −28.9 | 33 | A |
| 182 | H | C | −7.9 | −20.4 | −29.8 | 34 | A |
| 182 | H | O | −7.8 | −20.3 | −31.0 | 34 | A |
| 182 | H | CB | −5.8 | −20.8 | −28.4 | 35 | A |
| 182 | H | CG | −5.1 | −21.5 | −29.5 | 41 | A |
| 182 | H | ND1 | −5.7 | −22.6 | −30.1 | 44 | A |
| 182 | H | CD2 | −3.9 | −21.5 | −30.0 | 45 | A |
| 182 | H | CE1 | −4.9 | −23.1 | −31.0 | 44 | A |
| 182 | H | NE2 | −3.7 | −22.5 | −30.9 | 45 | A |
| 183 | E | N | −8.9 | −21.0 | −29.1 | 28 | A |
| 183 | E | CA | −10.0 | −21.6 | −29.9 | 27 | A |
| 183 | E | C | −11.2 | −20.7 | −30.3 | 31 | A |
| 183 | E | O | −12.1 | −21.2 | −30.9 | 30 | A |
| 183 | E | CB | −10.5 | −22.8 | −29.2 | 29 | A |
| 183 | E | CG | −9.5 | −23.6 | −28.4 | 45 | A |
| 183 | E | CD | −8.5 | −24.3 | −29.3 | 75 | A |
| 183 | E | OE1 | −8.6 | −24.2 | −30.6 | 69 | A |
| 183 | E | OE2 | −7.6 | −25.0 | −28.8 | 78 | A |
| 184 | G | N | −11.2 | −19.5 | −29.8 | 28 | A |
| 184 | G | CA | −12.3 | −18.6 | −30.0 | 27 | A |
| 184 | G | C | −13.6 | −19.0 | −29.3 | 27 | A |
| 184 | G | O | −13.5 | −19.8 | −28.3 | 25 | A |
| 184 | G | N | −14.8 | −18.5 | −29.7 | 17 | A |
| 184 | G | CA | −16.0 | −18.8 | −29.0 | 16 | A |
| 184 | G | C | −16.3 | −17.9 | −27.8 | 17 | A |
| 184 | G | O | −17.4 | −17.9 | −27.3 | 15 | A |
| 184A | R | N | −15.3 | −17.2 | −27.3 | 13 | A |
| 184A | R | CA | −15.6 | −16.3 | −26.1 | 14 | A |
| 184A | R | C | −14.8 | −15.0 | −26.4 | 15 | A |
| 184A | R | O | −13.6 | −15.1 | −26.7 | 15 | A |
| 184A | R | CB | −15.0 | −17.0 | −24.9 | 16 | A |
| 184A | R | CG | −16.0 | −18.2 | −24.4 | 19 | A |
| 184A | R | CD | −15.3 | −19.0 | −23.4 | 31 | A |
| 184A | R | NE | −14.3 | −19.9 | −23.9 | 44 | A |
| 184A | R | CZ | −13.4 | −20.6 | −23.2 | 55 | A |
| 184A | R | NH1 | −13.5 | −20.6 | −21.8 | 30 | A |
| 184A | R | NH2 | −12.5 | −21.3 | −23.7 | 41 | A |
| 185 | D | N | −15.4 | −13.9 | −26.2 | 13 | A |
| 185 | D | CA | −14.7 | −12.6 | −26.5 | 13 | A |
| 185 | D | C | −15.6 | −11.5 | −26.2 | 11 | A |
| 185 | D | O | −16.8 | −11.6 | −26.0 | 12 | A |
| 185 | D | CB | −14.5 | −12.6 | −28.0 | 13 | A |
| 185 | D | CG | −13.4 | −11.6 | −28.5 | 13 | A |
| 185 | D | OD1 | −12.7 | −10.9 | −27.7 | 14 | A |
| 185 | D | OD2 | −13.1 | −11.6 | −29.7 | 15 | A |
| 186 | S | N | −15.0 | −10.3 | −26.1 | 12 | A |
| 186 | S | CA | −15.8 | −9.1 | −26.0 | 11 | A |
| 186 | S | C | −16.2 | −8.7 | −27.5 | 14 | A |
| 186 | S | O | −15.7 | −9.4 | −28.4 | 16 | A |
| 186 | S | CB | −15.0 | −7.9 | −25.3 | 12 | A |
| 186 | S | OG | −13.7 | −7.8 | −25.9 | 21 | A |
| 187 | C | N | −17.1 | −7.8 | −27.7 | 11 | A |
| 187 | C | CA | −17.5 | −7.5 | −29.0 | 12 | A |
| 187 | C | C | −18.1 | −6.1 | −29.1 | 17 | A |
| 187 | C | O | −18.2 | −5.4 | −28.1 | 16 | A |
| 187 | C | CB | −18.6 | −8.6 | −29.4 | 12 | A |
| 187 | C | SG | −18.9 | −8.8 | −31.2 | 14 | A |
| 188 | Q | N | −18.5 | −5.7 | −30.4 | 14 | A |
| 188 | Q | CA | −19.1 | −4.4 | −30.6 | 14 | A |
| 188 | Q | C | −20.2 | −4.1 | −29.5 | 15 | A |
| 188 | Q | O | −21.0 | −5.0 | −29.2 | 14 | A |
| 188 | Q | CB | −19.8 | −4.3 | −32.0 | 14 | A |
| 188 | Q | CG | −20.0 | −2.9 | −32.4 | 16 | A |
| 188 | Q | CD | −20.6 | −2.8 | −33.7 | 26 | A |
| 188 | Q | OE1 | −20.2 | −3.4 | −34.7 | 31 | A |
| 188 | Q | NE2 | −21.6 | −1.8 | −33.8 | 23 | A |
| 188 | G | N | −20.1 | −2.9 | −29.0 | 13 | A |
| 188 | G | CA | −21.0 | −2.5 | −27.9 | 10 | A |
| 188 | G | C | −20.3 | −2.6 | −26.5 | 12 | A |
| 188 | G | O | −20.7 | −1.9 | −25.6 | 12 | A |
| 189 | D | N | −19.3 | −3.5 | −26.4 | 9 | A |
| 189 | D | CA | −18.6 | −3.6 | −25.2 | 10 | A |
| 189 | D | C | −17.5 | −2.5 | −25.1 | 10 | A |
| 189 | D | O | −16.9 | −2.2 | −24.1 | 11 | A |
| 189 | D | CB | −17.9 | −5.0 | −25.1 | 10 | A |
| 189 | D | CG | −19.0 | −6.1 | −25.0 | 10 | A |
| 189 | D | OD1 | −19.9 | −5.9 | −24.2 | 12 | A |
| 189 | D | OD2 | −18.7 | −7.2 | −25.5 | 13 | A |
| 190 | S | N | −17.1 | −2.1 | −26.3 | 9 | A |
| 190 | S | CA | −16.0 | −1.1 | −26.4 | 11 | A |
| 190 | S | C | −16.1 | 0.0 | −25.5 | 11 | A |
| 190 | S | O | −17.2 | 0.5 | −25.3 | 10 | A |
| 190 | S | CB | −15.9 | −0.5 | −27.9 | 18 | A |
| 190 | S | OG | −15.8 | −1.6 | −28.8 | 22 | A |
| 191 | G | N | −14.9 | 0.5 | −24.9 | 10 | A |
| 191 | G | CA | −14.9 | 1.5 | −23.9 | 10 | A |
| 191 | G | C | −15.1 | 1.0 | −22.5 | 11 | A |
| 191 | G | O | −14.8 | 1.7 | −21.5 | 10 | A |
| 192 | G | N | −15.6 | −0.2 | −22.4 | 10 | A |
| 192 | G | CA | −15.8 | −0.9 | −21.1 | 9 | A |
| 192 | G | C | −14.5 | −1.3 | −20.4 | 12 | A |
| 192 | G | O | −13.4 | −1.2 | −21.0 | 10 | A |
| 193 | P | N | −14.7 | −1.9 | −19.3 | 11 | A |
| 193 | P | CA | −13.6 | −2.3 | −18.4 | 12 | A |
| 193 | P | C | −13.0 | −3.6 | −18.7 | 13 | A |
| 193 | P | O | −13.7 | −4.6 | −19.0 | 12 | A |
| 193 | P | CB | −14.2 | −2.4 | −17.0 | 12 | A |
| 193 | P | CG | −15.6 | −2.7 | −17.2 | 14 | A |
| 193 | P | CD | −16.0 | −1.9 | −18.5 | 10 | A |
| 194 | H | N | −11.7 | −3.7 | −18.5 | 12 | A |
| 194 | H | CA | −10.9 | −5.0 | −18.4 | 12 | A |
| 194 | H | C | −10.3 | −4.9 | −17.0 | 12 | A |
| 194 | H | O | −9.6 | −3.9 | −16.7 | 12 | A |
| 194 | H | CB | −9.8 | −5.1 | −19.4 | 13 | A |
| 194 | H | CG | −8.9 | −6.3 | −19.2 | 14 | A |
| 194 | H | ND1 | −7.9 | −6.3 | −18.2 | 14 | A |
| 194 | H | CD2 | −8.8 | −7.5 | −19.9 | 14 | A |
| 194 | H | CE1 | −7.3 | −7.5 | −18.3 | 14 | A |
| 194 | H | NE2 | −7.7 | −8.2 | −19.3 | 13 | A |
| 195 | V | N | −10.7 | −5.7 | −16.0 | 10 | A |
| 195 | V | CA | −10.2 | −5.5 | −14.6 | 10 | A |
| 195 | V | C | −9.5 | −6.7 | −14.1 | 14 | A |
| 195 | V | O | −9.8 | −7.9 | −14.5 | 14 | A |
| 195 | V | CB | −11.4 | −5.1 | −13.6 | 13 | A |
| 195 | V | CG1 | −12.2 | −3.9 | −14.1 | 11 | A |
| 195 | V | CG2 | −12.3 | −6.2 | −13.3 | 14 | A |
| 196 | T | N | −8.6 | −6.5 | −13.1 | 11 | A |
| 196 | T | CA | −7.9 | −7.6 | −12.5 | 11 | A |
| 196 | T | C | −8.2 | −7.5 | −11.0 | 15 | A |
| 196 | T | O | −8.0 | −6.5 | −10.3 | 15 | A |
| 196 | T | CB | −6.4 | −7.4 | −12.8 | 12 | A |
| 196 | T | OG1 | −6.2 | −7.6 | −14.2 | 14 | A |
| 196 | T | CG2 | −5.5 | −8.5 | −12.0 | 16 | A |
| 197 | E | N | −8.5 | −8.7 | −10.4 | 14 | A |
| 197 | E | CA | −8.8 | −8.8 | −9.0 | 16 | A |
| 197 | E | C | −7.5 | −9.1 | −8.2 | 20 | A |
| 197 | E | O | −6.8 | −10.0 | −8.5 | 22 | A |
| 197 | E | CB | −9.8 | −9.9 | −8.7 | 19 | A |
| 197 | E | CG | −11.0 | −9.9 | −9.7 | 27 | A |
| 197 | E | CD | −12.1 | −10.9 | −9.4 | 47 | A |
| 197 | E | OE1 | −11.7 | −12.1 | −9.1 | 32 | A |
| 197 | E | OE2 | −13.2 | −10.6 | −9.5 | 26 | A |
| 198 | V | N | −7.3 | −8.3 | −7.2 | 18 | A |
| 198 | V | CA | −6.1 | −8.4 | −6.3 | 18 | A |
| 198 | V | C | −6.6 | −8.5 | −4.9 | 22 | A |
| 198 | V | O | −7.1 | −7.5 | −4.3 | 20 | A |
| 198 | V | CB | −5.2 | −7.1 | −6.5 | 21 | A |
| 198 | V | CG1 | −3.9 | −7.3 | −5.7 | 22 | A |
| 198 | V | CG2 | −4.9 | −6.9 | −8.0 | 21 | A |
| 199 | E | N | −6.6 | −9.6 | −4.4 | 23 | A |
| 199 | E | CA | −7.2 | −10.0 | −3.0 | 24 | A |
| 199 | E | C | −8.6 | −9.4 | −2.8 | 29 | A |
| 199 | E | O | −8.8 | −8.8 | −1.7 | 32 | A |
| 199 | E | CB | −6.2 | −9.4 | −2.0 | 25 | A |
| 199 | E | CG | −4.7 | −9.7 | −2.3 | 37 | A |
| 199 | E | CD | −4.1 | −10.7 | −1.3 | 65 | A |
| 199 | E | OE1 | −3.5 | −10.2 | −0.4 | 35 | A |
| 199 | S | OE2 | −4.3 | −11.9 | −1.5 | 70 | A |

TABLE 2-continued

Atomic Coordinates of Factor IXa co-crystal Compound A complex

| | | | | | | | |
|---|---|---|---|---|---|---|---|
| 200 | G | N | −9.4 | −9.5 | −3.7 | 22 | A |
| 200 | G | CA | −10.8 | −9.0 | −3.5 | 22 | A |
| 200 | G | C | −11.0 | −7.6 | −3.9 | 26 | A |
| 200 | G | O | −12.1 | −7.0 | −3.6 | 26 | A |
| 201 | T | N | −10.0 | −6.9 | −4.5 | 22 | A |
| 201 | T | CA | −10.2 | −5.5 | −4.9 | 21 | A |
| 201 | T | C | −9.8 | −5.5 | −6.3 | 20 | A |
| 201 | T | O | −8.7 | −5.9 | −6.8 | 19 | A |
| 201 | T | CB | −9.2 | −4.6 | −4.1 | 25 | A |
| 201 | T | OG1 | −9.4 | −4.7 | −2.7 | 23 | A |
| 201 | T | CG2 | −9.4 | −3.1 | −4.6 | 26 | A |
| 202 | S | N | −10.7 | −5.0 | −7.2 | 16 | A |
| 202 | S | CA | −10.5 | −5.0 | −8.6 | 14 | A |
| 202 | S | C | −9.8 | −3.6 | −9.0 | 14 | A |
| 202 | S | O | −10.2 | −2.6 | −8.5 | 14 | A |
| 202 | S | CB | −11.8 | −5.1 | −9.4 | 13 | A |
| 202 | S | OG | −12.4 | −6.4 | −9.1 | 17 | A |
| 203 | F | N | −9.0 | −3.8 | −10.0 | 13 | A |
| 203 | F | CA | −8.2 | −2.7 | −10.5 | 13 | A |
| 203 | F | C | −8.4 | −2.7 | −12.0 | 14 | A |
| 203 | F | O | −8.4 | −3.7 | −12.7 | 12 | A |
| 203 | F | CB | −6.7 | −2.9 | −10.2 | 14 | A |
| 203 | F | CG | −6.3 | −2.5 | −8.8 | 13 | A |
| 203 | F | CD1 | −6.5 | −3.5 | −7.7 | 14 | A |
| 203 | F | CD2 | −5.9 | −1.3 | −8.4 | 14 | A |
| 203 | F | CE1 | −6.2 | −3.2 | −6.4 | 16 | A |
| 203 | F | CE2 | −5.6 | −0.9 | −7.1 | 17 | A |
| 203 | F | CZ | −5.8 | −1.9 | −6.1 | 16 | A |
| 204 | L | N | −8.4 | −1.5 | −12.6 | 9 | A |
| 204 | L | CA | −8.5 | −1.4 | −14.1 | 8 | A |
| 204 | L | C | −7.2 | −1.6 | −14.8 | 12 | A |
| 204 | L | O | −6.2 | −0.9 | −14.5 | 13 | A |
| 204 | L | CB | −9.0 | 0.1 | −14.4 | 10 | A |
| 204 | L | CG | −9.5 | 0.3 | −15.9 | 13 | A |
| 204 | L | CD1 | −10.7 | −0.5 | −16.2 | 14 | A |
| 204 | L | CD2 | −9.7 | 1.8 | −16.1 | 14 | A |
| 205 | T | N | −7.2 | −2.6 | −15.6 | 10 | A |
| 205 | T | CA | −5.9 | −3.0 | −16.3 | 10 | A |
| 205 | T | C | −6.0 | −2.7 | −17.8 | 14 | A |
| 205 | T | O | −5.0 | −2.6 | −18.5 | 15 | A |
| 205 | T | CB | −5.5 | −4.4 | −16.0 | 11 | A |
| 205 | T | OG1 | −6.6 | −5.3 | −16.0 | 12 | A |
| 205 | T | CG2 | −4.8 | −4.5 | −14.6 | 13 | A |
| 206 | G | N | −7.3 | −2.6 | −18.4 | 11 | A |
| 206 | G | CA | −7.4 | −2.3 | −19.8 | 10 | A |
| 206 | G | C | −8.8 | −1.7 | −20.2 | 14 | A |
| 206 | G | O | −9.7 | −1.7 | −19.3 | 12 | A |
| 207 | I | N | −8.8 | −1.1 | −21.4 | 11 | A |
| 207 | I | CA | −10.1 | −0.6 | −21.9 | 10 | A |
| 207 | I | C | −10.4 | −1.6 | −23.0 | 12 | A |
| 207 | I | O | −9.6 | −1.9 | −23.9 | 12 | A |
| 207 | I | CB | −9.9 | 0.8 | −22.5 | 13 | A |
| 207 | I | CG1 | −9.3 | 1.7 | −21.5 | 14 | A |
| 207 | I | CG2 | −11.3 | 1.2 | −23.0 | 12 | A |
| 207 | I | CD1 | −10.1 | 1.9 | −20.2 | 12 | A |
| 208 | I | N | −11.7 | −2.1 | −23.1 | 10 | A |
| 208 | I | CA | −12.1 | −2.9 | −24.2 | 9 | A |
| 208 | I | C | −12.0 | −2.0 | −25.5 | 13 | A |
| 208 | I | O | −12.6 | −0.9 | −25.6 | 13 | A |
| 208 | I | CB | −13.5 | −3.4 | −24.0 | 12 | A |
| 208 | I | CG1 | −13.6 | −4.3 | −22.7 | 12 | A |
| 208 | I | CG2 | −14.0 | −4.2 | −25.2 | 16 | A |
| 208 | I | CD1 | −15.0 | −4.5 | −22.3 | 14 | A |
| 209 | S | N | −11.2 | −2.5 | −26.5 | 11 | A |
| 209 | S | CA | −11.0 | −1.6 | −27.7 | 12 | A |
| 209 | S | C | −11.5 | −2.1 | −29.0 | 14 | A |
| 209 | S | O | −12.4 | −1.4 | −29.6 | 14 | A |
| 209 | S | CB | −9.5 | −1.3 | −27.8 | 12 | A |
| 209 | S | OG | −9.3 | −0.2 | −28.6 | 14 | A |
| 210 | W | N | −11.0 | −3.1 | −29.6 | 13 | A |
| 210 | W | CA | −11.4 | −3.6 | −30.9 | 12 | A |
| 210 | W | C | −11.0 | −5.1 | −31.1 | 15 | A |
| 210 | W | O | −10.3 | −5.7 | −30.2 | 12 | A |
| 210 | W | CB | −10.9 | −2.8 | −32.0 | 12 | A |
| 210 | W | CG | −9.4 | −2.7 | −32.1 | 12 | A |
| 210 | W | CD1 | −8.5 | −1.9 | −31.3 | 15 | A |
| 210 | W | CD2 | −8.5 | −3.4 | −33.0 | 13 | A |
| 210 | W | NE1 | −7.2 | −2.2 | −31.6 | 15 | A |
| 210 | W | CE2 | −7.1 | −3.0 | −32.7 | 18 | A |
| 210 | W | CE3 | −8.7 | −4.3 | −34.0 | 14 | A |
| 210 | W | CZ2 | −6.0 | −3.6 | −33.3 | 18 | A |
| 210 | W | CZ3 | −7.6 | −4.9 | −34.6 | 15 | A |
| 210 | W | CH2 | −6.3 | −4.5 | −34.3 | 16 | A |
| 211 | G | N | −11.4 | −5.6 | −32.2 | 13 | A |
| 211 | G | CA | −11.0 | −6.9 | −32.7 | 13 | A |
| 211 | G | C | −11.5 | −7.1 | −34.1 | 17 | A |
| 211 | G | O | −12.4 | −6.3 | −34.6 | 16 | A |
| 212 | E | N | −11.0 | −8.1 | −34.8 | 16 | A |
| 212 | E | CA | −11.5 | −8.4 | −36.2 | 16 | A |
| 212 | E | C | −12.7 | −9.3 | −36.0 | 18 | A |
| 212 | E | O | −12.5 | −10.5 | −35.8 | 16 | A |
| 212 | E | CB | −10.3 | −9.0 | −37.0 | 17 | A |
| 212 | E | CG | −9.3 | −7.9 | −37.2 | 24 | A |
| 212 | E | CD | −8.0 | −8.5 | −37.8 | 33 | A |
| 212 | E | OE1 | −7.1 | −8.9 | −37.0 | 25 | A |
| 212 | E | OE2 | −7.9 | −8.6 | −39.0 | 22 | A |
| 214 | E | N | −13.9 | −8.7 | −36.0 | 15 | A |
| 214 | E | CA | −15.1 | −9.4 | −35.7 | 15 | A |
| 214 | E | C | −15.0 | −9.9 | −34.2 | 17 | A |
| 214 | E | O | −14.3 | −9.2 | −33.4 | 17 | A |
| 214 | E | CB | −15.4 | −10.6 | −36.7 | 16 | A |
| 214 | E | CG | −15.9 | −10.0 | −38.0 | 27 | A |
| 214 | E | CD | −17.0 | −8.9 | −37.9 | 46 | A |
| 214 | E | OE1 | −16.7 | −7.7 | −38.2 | 48 | A |
| 214 | E | OE2 | −18.2 | −9.2 | −37.7 | 22 | A |
| 215 | C | N | −15.6 | −11.0 | −33.8 | 14 | A |
| 215 | C | CA | −15.6 | −11.4 | −32.4 | 14 | A |
| 215 | C | C | −15.5 | −12.9 | −32.3 | 19 | A |
| 215 | C | O | −16.2 | −13.6 | −33.0 | 18 | A |
| 215 | C | CB | −16.8 | −10.9 | −31.7 | 14 | A |
| 215 | C | SG | −17.1 | −9.1 | −32.0 | 16 | A |
| 216 | A | N | −14.8 | −13.4 | −31.3 | 15 | A |
| 216 | A | CA | −14.7 | −14.8 | −31.0 | 15 | A |
| 216 | A | C | −14.3 | −15.7 | −32.1 | 19 | A |
| 216 | A | O | −14.6 | −16.9 | −32.1 | 19 | A |
| 216 | A | CB | −16.1 | −15.2 | −30.4 | 15 | A |
| 216A | M | N | −13.6 | −15.2 | −33.1 | 18 | A |
| 216A | M | CA | −13.1 | −16.0 | −34.3 | 19 | A |
| 216A | M | C | −11.9 | −16.8 | −33.8 | 23 | A |
| 216A | M | O | −10.9 | −16.2 | −33.3 | 23 | A |
| 216A | M | CB | −12.8 | −15.1 | −35.5 | 22 | A |
| 216A | M | CG | −13.9 | −14.4 | −36.1 | 28 | A |
| 216A | M | SD | −15.3 | −15.4 | −36.5 | 36 | A |
| 216A | M | CE | −16.5 | −14.3 | −35.8 | 34 | A |
| 217 | K | N | −11.8 | −18.0 | −34.2 | 21 | A |
| 217 | K | CA | −10.7 | −18.8 | −33.8 | 22 | A |
| 217 | K | C | −9.4 | −18.2 | −34.5 | 25 | A |
| 217 | K | O | −9.5 | −17.8 | −35.7 | 26 | A |
| 217 | K | CB | −10.8 | −20.3 | −34.2 | 26 | A |
| 217 | K | CG | −9.6 | −21.1 | −33.8 | 27 | A |
| 217 | K | CD | −9.8 | −22.6 | −34.1 | 35 | A |
| 217 | K | CE | −8.5 | −23.3 | −34.1 | 50 | A |
| 217 | K | NZ | −8.6 | −24.8 | −34.0 | 60 | A |
| 219 | G | N | −8.3 | −18.1 | −33.8 | 21 | A |
| 219 | G | CA | −7.1 | −17.5 | −34.4 | 19 | A |
| 219 | G | C | −7.0 | −16.0 | −34.2 | 25 | A |
| 219 | G | O | −6.0 | −15.4 | −34.5 | 24 | A |
| 220 | K | N | −8.1 | −15.4 | −33.7 | 22 | A |
| 220 | K | CA | −8.1 | −13.9 | −33.4 | 20 | A |
| 220 | K | C | −8.2 | −13.7 | −32.0 | 20 | A |
| 220 | K | O | −8.7 | −14.5 | −31.2 | 20 | A |
| 220 | K | CB | −9.2 | −13.2 | −34.2 | 22 | A |
| 220 | K | CG | −9.1 | −13.2 | −35.7 | 23 | A |
| 220 | K | CD | −8.0 | −12.3 | −36.2 | 24 | A |
| 220 | K | CE | −7.8 | −12.4 | −37.6 | 22 | A |
| 220 | K | NZ | −6.6 | −11.6 | −38.0 | 22 | A |
| 221 | Y | N | −7.8 | −12.5 | −31.5 | 17 | A |
| 221 | Y | CA | −7.9 | −12.1 | −30.1 | 16 | A |
| 221 | Y | C | −8.6 | −10.8 | −29.9 | 20 | A |
| 221 | Y | O | −8.6 | −9.9 | −30.8 | 19 | A |
| 221 | Y | CB | −6.5 | −12.1 | −29.4 | 18 | A |
| 221 | Y | CG | −5.9 | −13.5 | −29.5 | 19 | A |
| 221 | Y | CD1 | −6.3 | −14.5 | −28.6 | 22 | A |
| 221 | Y | CD2 | −4.8 | −13.7 | −30.4 | 20 | A |

TABLE 2-continued

Atomic Coordinates of Factor IXa co-crystal Compound A complex

| 221 | Y | CE1 | -5.7 | -15.7 | -28.7 | 23 | A |
| 221 | Y | CE2 | -4.2 | -14.9 | -30.5 | 20 | A |
| 221 | Y | CZ | -4.6 | -15.9 | -29.6 | 29 | A |
| 221 | Y | OH | -4.0 | -17.2 | -29.7 | 32 | A |
| 221 | G | N | -9.0 | -10.5 | -28.7 | 15 | A |
| 221 | G | CA | -9.5 | -9.2 | -28.4 | 14 | A |
| 221 | G | C | -8.4 | -8.3 | -28.2 | 16 | A |
| 221 | G | O | -7.3 | -8.6 | -27.6 | 15 | A |
| 222 | I | N | -8.5 | -7.0 | -28.6 | 14 | A |
| 222 | I | CA | -7.4 | -6.0 | -28.5 | 12 | A |
| 222 | I | C | -7.9 | -5.0 | -27.5 | 16 | A |
| 222 | I | O | -9.1 | -4.5 | -27.6 | 14 | A |
| 222 | I | CB | -7.1 | -5.3 | -29.8 | 15 | A |
| 222 | I | CG1 | -7.0 | -6.3 | -31.0 | 15 | A |
| 222 | I | CG2 | -5.7 | -4.6 | -29.7 | 15 | A |
| 222 | I | CD1 | -5.9 | -7.4 | -30.7 | 18 | A |
| 223 | Y | N | -7.1 | -4.6 | -26.5 | 12 | A |
| 223 | Y | CA | -7.4 | -3.8 | -25.4 | 11 | A |
| 223 | Y | C | -6.4 | -2.7 | -25.3 | 16 | A |
| 223 | Y | O | -5.2 | -2.9 | -25.6 | 14 | A |
| 223 | Y | CB | -7.3 | -4.6 | -24.1 | 12 | A |
| 223 | Y | CG | -8.4 | -5.7 | -24.1 | 11 | A |
| 223 | Y | CD1 | -8.2 | -6.9 | -24.8 | 13 | A |
| 223 | Y | CD2 | -9.6 | -5.5 | -23.5 | 11 | A |
| 223 | Y | CE1 | -9.2 | -7.9 | -24.8 | 13 | A |
| 223 | Y | CE2 | -10.6 | -6.5 | -23.6 | 10 | A |
| 223 | Y | CZ | -10.4 | -7.7 | -24.2 | 15 | A |
| 223 | Y | OH | -11.5 | -8.6 | -24.3 | 16 | A |
| 224 | T | N | -6.8 | -1.5 | -24.7 | 13 | A |
| 224 | T | CA | -5.9 | -0.5 | -24.4 | 11 | A |
| 224 | T | C | -5.2 | -0.7 | -23.0 | 16 | A |
| 224 | T | O | -5.9 | -1.0 | -22.1 | 15 | A |
| 224 | T | CB | -6.6 | 0.9 | -24.4 | 15 | A |
| 224 | T | OG1 | -7.2 | 1.2 | -25.6 | 15 | A |
| 224 | T | CG2 | -5.6 | 2.0 | -24.0 | 12 | A |
| 225 | K | N | -3.9 | -0.7 | -23.0 | 16 | A |
| 225 | K | CA | -3.1 | -0.8 | -21.8 | 15 | A |
| 225 | K | C | -3.3 | 0.4 | -20.9 | 17 | A |
| 225 | K | O | -2.7 | 1.5 | -21.2 | 19 | A |
| 225 | K | CB | -1.6 | -1.0 | -22.1 | 18 | A |
| 225 | K | CG | -1.2 | -2.3 | -22.4 | 22 | A |
| 225 | K | CD | 0.4 | -2.3 | -22.4 | 21 | A |
| 225 | K | CE | 0.9 | -3.5 | -23.2 | 24 | A |
| 225 | K | NZ | 2.4 | -3.4 | -23.2 | 26 | A |
| 226 | V | N | -4.1 | 0.2 | -19.8 | 13 | A |
| 226 | V | CA | -4.3 | 1.3 | -18.9 | 14 | A |
| 226 | V | C | -3.0 | 1.9 | -18.2 | 14 | A |
| 226 | V | O | -2.9 | 3.1 | -17.9 | 16 | A |
| 226 | V | CB | -5.5 | 1.0 | -17.9 | 17 | A |
| 226 | V | CG1 | -5.5 | 1.9 | -16.7 | 16 | A |
| 226 | V | CG2 | -6.8 | 1.0 | -18.7 | 17 | A |
| 227 | S | N | -2.1 | 1.0 | -18.0 | 12 | A |
| 227 | S | CA | -0.8 | 1.4 | -17.3 | 13 | A |
| 227 | S | C | -0.2 | 2.6 | -18.0 | 17 | A |
| 227 | S | O | 0.4 | 3.5 | -17.3 | 19 | A |
| 227 | S | CB | 0.2 | 0.2 | -17.3 | 15 | A |
| 227 | S | OG | 0.6 | -0.2 | -18.6 | 16 | A |
| 228 | R | N | -0.3 | 2.7 | -19.3 | 16 | A |
| 228 | R | CA | 0.3 | 3.8 | -20.1 | 16 | A |
| 228 | R | C | -0.4 | 5.2 | -19.8 | 20 | A |
| 228 | R | O | 0.2 | 6.2 | -20.1 | 21 | A |
| 228 | R | CB | 0.2 | 3.5 | -21.5 | 18 | A |
| 228 | R | CG | 1.2 | 2.4 | -22.0 | 30 | A |
| 228 | R | CD | 2.5 | 3.0 | -22.0 | 50 | A |
| 228 | R | NE | 2.4 | 4.5 | -22.0 | 72 | A |
| 228 | R | CZ | 2.2 | 5.2 | -23.1 | 90 | A |
| 228 | R | NH1 | 2.2 | 4.6 | -24.3 | 79 | A |
| 228 | R | NH2 | 2.0 | 6.5 | -23.0 | 73 | A |
| 229 | Y | N | -1.6 | 5.2 | -19.3 | 14 | A |
| 229 | Y | CA | -2.4 | 6.4 | -19.1 | 14 | A |
| 229 | Y | C | -2.7 | 6.8 | -17.7 | 17 | A |
| 229 | Y | O | -3.4 | 7.7 | -17.5 | 15 | A |
| 229 | Y | CB | -3.6 | 6.3 | -20.0 | 15 | A |
| 229 | Y | CG | -3.3 | 6.0 | -21.4 | 16 | A |
| 229 | Y | GD1 | -2.8 | 7.0 | -22.3 | 16 | A |
| 229 | Y | CD2 | -3.4 | 4.7 | -21.9 | 15 | A |
| 229 | Y | CE1 | -2.5 | 6.7 | -23.6 | 17 | A |
| 229 | Y | CE2 | -3.0 | 4.4 | -23.1 | 17 | A |
| 229 | Y | CZ | -2.6 | 5.3 | -24.0 | 20 | A |
| 229 | Y | OH | -2.3 | 5.0 | -25.3 | 19 | A |
| 230 | V | N | -2.3 | 6.0 | -16.7 | 14 | A |
| 230 | V | CA | -2.7 | 6.2 | -15.3 | 15 | A |
| 230 | V | C | -2.4 | 7.7 | -14.8 | 17 | A |
| 230 | V | O | -3.2 | 8.3 | -14.2 | 17 | A |
| 230 | V | CB | -2.0 | 5.2 | -14.4 | 21 | A |
| 230 | V | CG1 | -2.0 | 5.6 | -12.9 | 22 | A |
| 230 | V | CG2 | -2.7 | 3.8 | -14.6 | 20 | A |
| 231 | N | N | -1.2 | 8.2 | -15.1 | 16 | A |
| 231 | N | CA | -0.8 | 9.5 | -14.6 | 15 | A |
| 231 | N | C | -1.8 | 10.5 | -15.1 | 19 | A |
| 231 | N | O | -2.4 | 11.4 | -14.3 | 18 | A |
| 231 | N | CB | 0.6 | 9.9 | -15.0 | 17 | A |
| 231 | N | CG | 1.6 | 9.2 | -14.2 | 48 | A |
| 231 | N | OD1 | 1.4 | 8.3 | -13.4 | 33 | A |
| 231 | N | ND2 | 2.9 | 9.7 | -14.3 | 51 | A |
| 232 | W | N | -2.1 | 10.4 | -16.4 | 17 | A |
| 232 | W | CA | -3.1 | 11.3 | -17.1 | 19 | A |
| 232 | W | C | -4.5 | 11.1 | -16.5 | 20 | A |
| 232 | W | O | -5.1 | 12.1 | -16.2 | 19 | A |
| 232 | W | CB | -3.0 | 10.9 | -18.6 | 19 | A |
| 232 | W | CG | -4.1 | 11.6 | -19.4 | 20 | A |
| 232 | W | CD1 | -4.1 | 12.9 | -19.9 | 24 | A |
| 232 | W | CD2 | -5.3 | 11.0 | -20.0 | 19 | A |
| 232 | W | NE1 | -5.3 | 13.1 | -20.6 | 24 | A |
| 232 | W | CE2 | -6.0 | 12.0 | -20.7 | 23 | A |
| 232 | W | CE3 | -5.8 | 9.7 | -19.9 | 19 | A |
| 232 | W | CZ2 | -7.2 | 11.7 | -21.3 | 21 | A |
| 232 | W | CZ3 | -7.0 | 9.4 | -20.5 | 20 | A |
| 232 | W | CH2 | -7.7 | 10.4 | -21.2 | 20 | A |
| 233 | I | N | -4.9 | 9.9 | -16.3 | 15 | A |
| 233 | I | CA | -6.2 | 9.7 | -15.7 | 13 | A |
| 233 | I | C | -6.3 | 10.4 | -14.3 | 20 | A |
| 233 | I | O | -7.3 | 11.1 | -14.0 | 18 | A |
| 233 | I | CB | -6.6 | 8.2 | -15.5 | 14 | A |
| 233 | I | CG1 | -6.8 | 7.6 | -16.9 | 15 | A |
| 233 | I | CG2 | -7.8 | 8.0 | -14.7 | 16 | A |
| 233 | I | CD1 | -6.8 | 6.0 | -16.9 | 16 | A |
| 234 | K | N | -5.3 | 10.1 | -13.5 | 17 | A |
| 234 | K | CA | -5.3 | 10.6 | -12.1 | 19 | A |
| 234 | K | C | -5.2 | 12.1 | -12.1 | 21 | A |
| 234 | K | O | -5.9 | 12.8 | -11.3 | 21 | A |
| 234 | K | CB | -4.1 | 10.0 | -11.3 | 22 | A |
| 234 | K | CG | -4.6 | 9.1 | -10.1 | 41 | A |
| 234 | K | CD | -5.1 | 7.8 | -10.6 | 40 | A |
| 234 | K | CE | -4.9 | 6.6 | -9.6 | 22 | A |
| 234 | K | NZ | -6.1 | 6.4 | -8.6 | 19 | A |
| 235 | E | N | -4.5 | 12.7 | -13.0 | 19 | A |
| 235 | E | CA | -4.4 | 14.2 | -13.0 | 21 | A |
| 235 | E | C | -5.7 | 14.9 | -13.4 | 26 | A |
| 235 | E | O | -6.2 | 15.7 | -12.7 | 27 | A |
| 235 | E | CB | -3.3 | 14.6 | -14.0 | 24 | A |
| 235 | E | CG | -3.6 | 16.0 | -14.6 | 39 | A |
| 235 | E | CD | -2.5 | 16.5 | -15.5 | 67 | A |
| 235 | E | OE1 | -2.3 | 15.9 | -16.6 | 69 | A |
| 235 | E | OE2 | -1.8 | 17.4 | -15.2 | 71 | A |
| 236 | K | N | -6.2 | 14.5 | -14.6 | 20 | A |
| 236 | K | CA | -7.5 | 15.1 | -15.1 | 19 | A |
| 236 | K | C | -8.8 | 14.9 | -14.2 | 21 | A |
| 236 | K | O | -9.7 | 15.7 | -14.3 | 23 | A |
| 236 | K | CB | -7.7 | 14.6 | -16.5 | 19 | A |
| 236 | K | CG | -6.6 | 14.9 | -17.5 | 30 | A |
| 236 | K | CD | -6.3 | 16.4 | -17.7 | 41 | A |
| 236 | K | CE | -5.3 | 16.6 | -18.8 | 50 | A |
| 236 | K | NZ | -5.8 | 16.5 | -20.2 | 59 | A |
| 237 | T | N | -8.9 | 13.8 | -13.5 | 17 | A |
| 237 | T | CA | -10.1 | 13.4 | -12.8 | 15 | A |
| 237 | T | C | -10.0 | 13.8 | -11.3 | 19 | A |
| 237 | T | O | -11.0 | 13.6 | -10.6 | 19 | A |
| 237 | T | CB | -10.4 | 11.9 | -12.9 | 15 | A |
| 237 | T | OG1 | -9.4 | 11.1 | -12.3 | 15 | A |
| 237 | T | CG2 | -10.5 | 11.5 | -14.4 | 15 | A |
| 238 | K | N | -8.9 | 14.3 | -10.9 | 21 | A |
| 238 | K | CA | -8.7 | 14.6 | -9.5 | 22 | A |
| 238 | K | C | -9.8 | 15.5 | -9.0 | 25 | A |

TABLE 2-continued

Atomic Coordinates of Factor IXa co-crystal Compound A complex

| | | | | | | | |
|---|---|---|---|---|---|---|---|
| 238 | K | O | −10.1 | 16.5 | −9.6 | 25 | A |
| 238 | K | CB | −7.3 | 15.2 | −9.2 | 27 | A |
| 238 | K | CG | −6.9 | 14.9 | −7.8 | 51 | A |
| 238 | K | CD | −5.4 | 15.2 | −7.6 | 65 | A |
| 238 | K | CE | −5.1 | 16.4 | −6.8 | 84 | A |
| 238 | K | NZ | −5.9 | 16.4 | −5.5 | 97 | A |
| 239 | L | N | −10.4 | 15.2 | −7.8 | 24 | A |
| 239 | L | CA | −11.5 | 16.0 | −7.3 | 27 | A |
| 239 | L | C | −10.9 | 17.0 | −6.3 | 35 | A |
| 239 | L | O | −10.0 | 16.7 | −5.5 | 36 | A |
| 239 | L | CB | −12.5 | 15.1 | −6.6 | 27 | A |
| 239 | L | CG | −13.1 | 14.0 | −7.5 | 31 | A |
| 239 | L | CD1 | −13.8 | 13.0 | −6.6 | 31 | A |
| 239 | L | CD2 | −14.1 | 14.7 | −8.5 | 30 | A |
| 88 | C | N | 10.6 | −5.9 | −1.5 | 31 | B |
| 88 | C | CA | 9.4 | −5.8 | −2.4 | 29 | B |
| 88 | C | C | 9.5 | −6.8 | −3.5 | 37 | B |
| 88 | C | O | 8.5 | −7.2 | −4.0 | 36 | B |
| 88 | C | CB | 9.2 | −4.4 | −3.0 | 27 | B |
| 88 | C | SG | 8.8 | −3.1 | −1.7 | 29 | B |
| 89 | N | N | 10.7 | −7.2 | −4.0 | 35 | B |
| 89 | N | CA | 10.8 | −8.1 | −5.1 | 36 | B |
| 89 | N | C | 10.5 | −9.6 | −4.7 | 40 | B |
| 89 | N | O | 10.4 | −10.4 | −5.6 | 38 | B |
| 89 | N | CB | 12.0 | −8.0 | −6.0 | 40 | B |
| 89 | N | CG | 13.3 | −8.0 | −5.2 | 76 | B |
| 89 | N | OD1 | 13.4 | −8.8 | −4.2 | 79 | B |
| 89 | N | ND2 | 14.3 | −7.3 | −5.7 | 69 | B |
| 90 | I | N | 10.3 | −9.8 | −3.4 | 38 | B |
| 90 | I | CA | 9.9 | −11.2 | −2.9 | 38 | B |
| 90 | I | C | 8.5 | −11.1 | −2.4 | 40 | B |
| 90 | I | O | 8.3 | −10.5 | −1.3 | 40 | B |
| 90 | I | CB | 10.9 | −11.8 | −1.9 | 42 | B |
| 90 | I | CG1 | 12.3 | −11.8 | −2.5 | 43 | B |
| 90 | I | CG2 | 10.4 | −13.2 | −1.6 | 43 | B |
| 90 | I | CD1 | 12.5 | −12.9 | −3.6 | 55 | B |
| 91 | K | N | 7.5 | −11.7 | −3.1 | 36 | B |
| 91 | K | CA | 6.1 | −11.7 | −2.7 | 36 | B |
| 91 | K | C | 5.6 | −10.4 | −2.3 | 36 | B |
| 91 | K | O | 4.8 | −10.3 | −1.4 | 33 | B |
| 91 | K | CB | 6.0 | −12.7 | −1.5 | 40 | B |
| 91 | K | CG | 4.7 | −13.5 | −1.6 | 69 | B |
| 91 | K | CD | 4.6 | −14.5 | −0.4 | 86 | B |
| 91 | K | CE | 3.1 | −14.8 | −0.1 | 97 | B |
| 91 | K | NZ | 3.0 | −15.7 | 1.1 | 0 | B |
| 92 | N | N | 6.1 | −9.4 | −3.0 | 31 | B |
| 92 | N | CA | 5.6 | −8.0 | −2.9 | 30 | B |
| 92 | N | C | 5.7 | −7.5 | −1.4 | 32 | B |
| 92 | N | O | 4.9 | −6.7 | −0.9 | 28 | B |
| 92 | N | CB | 4.1 | −7.8 | −3.3 | 30 | B |
| 92 | N | CG | 3.7 | −6.4 | −3.6 | 24 | B |
| 92 | N | OD1 | 2.6 | −6.0 | −3.2 | 28 | B |
| 92 | N | ND2 | 4.6 | −5.7 | −4.3 | 22 | B |
| 93 | G | N | 6.8 | −7.9 | −0.7 | 29 | B |
| 93 | G | CA | 7.1 | −7.6 | 0.6 | 30 | B |
| 93 | G | C | 6.0 | −7.9 | 1.6 | 31 | B |
| 93 | G | O | 5.9 | −7.3 | 2.7 | 31 | B |
| 94 | R | N | 5.1 | −8.8 | 1.3 | 28 | B |
| 94 | R | CA | 3.9 | −9.2 | 2.0 | 27 | B |
| 94 | R | C | 2.8 | −8.1 | 2.0 | 30 | B |
| 94 | R | O | 1.8 | −8.3 | 2.7 | 28 | B |
| 94 | R | CB | 4.3 | −9.6 | 3.5 | 31 | B |
| 94 | R | CG | 5.4 | −10.6 | 3.5 | 44 | B |
| 94 | R | CD | 5.0 | −12.0 | 2.9 | 61 | B |
| 94 | R | NE | 6.1 | −12.9 | 3.0 | 77 | B |
| 94 | R | CZ | 6.0 | −14.3 | 2.8 | 95 | B |
| 94 | R | NH1 | 4.8 | −14.8 | 2.6 | 84 | B |
| 94 | R | NH2 | 7.1 | −15.1 | 2.9 | 81 | B |
| 95 | C | N | 3.0 | −7.1 | 1.2 | 25 | B |
| 95 | C | CA | 2.0 | −6.1 | 1.1 | 24 | B |
| 95 | C | C | 0.8 | −6.5 | 0.2 | 27 | B |
| 95 | C | O | 0.9 | −7.1 | −0.8 | 24 | B |
| 95 | C | CB | 2.6 | −4.8 | 0.4 | 22 | B |
| 95 | C | SG | 4.1 | −4.2 | 1.3 | 25 | B |
| 96 | E | N | −0.4 | −6.3 | 0.8 | 22 | B |
| 96 | E | CA | −1.6 | −6.7 | 0.0 | 22 | B |
| 96 | E | C | −1.7 | −6.0 | −1.3 | 24 | B |
| 96 | E | O | −2.1 | −6.6 | −2.3 | 24 | B |
| 96 | E | CB | −2.9 | −6.4 | 0.9 | 23 | B |
| 96 | E | CG | −4.2 | −6.9 | 0.2 | 26 | B |
| 96 | E | CD | −5.4 | −6.5 | 1.1 | 37 | B |
| 96 | E | OE1 | −5.3 | −6.5 | 2.3 | 26 | B |
| 96 | E | OE2 | −6.5 | −6.2 | 0.5 | 27 | B |
| 97 | Q | N | −1.4 | −4.7 | −1.3 | 20 | B |
| 97 | Q | CA | −1.5 | −3.9 | −2.5 | 19 | B |
| 97 | Q | C | −0.1 | −3.4 | −3.0 | 23 | B |
| 97 | Q | O | 0.5 | −4.1 | −3.9 | 23 | B |
| 97 | Q | CB | −2.5 | −2.8 | −2.4 | 20 | B |
| 97 | Q | CG | −3.9 | −3.3 | −2.6 | 20 | B |
| 97 | Q | CD | −5.0 | −2.3 | −2.3 | 17 | B |
| 97 | Q | OE1 | −4.7 | −1.1 | −2.3 | 17 | B |
| 97 | Q | NE2 | −6.2 | −2.8 | −2.2 | 20 | B |
| 98 | F | N | 0.4 | −2.3 | −2.5 | 18 | B |
| 98 | F | CA | 1.6 | −1.7 | −2.9 | 16 | B |
| 98 | F | C | 2.8 | −1.8 | −1.9 | 22 | B |
| 98 | F | O | 2.6 | −1.7 | −0.7 | 24 | B |
| 98 | F | CB | 1.4 | −0.3 | −3.3 | 17 | B |
| 98 | F | CG | 0.1 | −0.0 | −4.1 | 17 | B |
| 98 | F | CD1 | −0.2 | −0.9 | −5.1 | 17 | B |
| 98 | F | CD2 | −0.7 | 1.0 | −3.8 | 17 | B |
| 98 | F | CE1 | −1.5 | −0.7 | −5.8 | 16 | B |
| 98 | F | CE2 | −1.9 | 1.2 | −4.5 | 18 | B |
| 98 | F | CZ | −2.3 | 0.3 | −5.5 | 17 | B |
| 99 | C | N | 4.0 | −2.0 | −2.4 | 18 | B |
| 99 | C | CA | 5.2 | −2.1 | −1.6 | 21 | B |
| 99 | C | C | 6.3 | −1.1 | −2.1 | 25 | B |
| 99 | C | O | 6.5 | −0.9 | −3.2 | 24 | B |
| 99 | C | CB | 5.8 | −3.5 | −1.9 | 23 | B |
| 99 | C | SG | 7.2 | −3.9 | −0.8 | 28 | B |
| 100 | K | N | 7.0 | −0.5 | −1.1 | 22 | B |
| 100 | K | CA | 8.0 | 0.5 | −1.3 | 24 | B |
| 100 | K | C | 9.2 | 0.4 | −0.4 | 30 | B |
| 100 | K | O | 9.1 | −0.3 | 0.6 | 28 | B |
| 100 | K | CB | 7.4 | 1.9 | −1.3 | 27 | B |
| 100 | K | CG | 7.5 | 2.7 | −2.6 | 40 | B |
| 100 | K | CD | 6.5 | 3.8 | −2.6 | 54 | B |
| 100 | K | CE | 7.0 | 5.0 | −3.5 | 74 | B |
| 100 | K | NZ | 6.0 | 6.1 | −3.4 | 86 | B |
| 107 | V | N | 10.7 | −2.4 | 4.3 | 33 | B |
| 107 | V | CA | 9.5 | −2.4 | 3.4 | 33 | B |
| 107 | V | C | 8.3 | −1.5 | 4.0 | 35 | B |
| 107 | V | O | 8.1 | −1.6 | 5.2 | 35 | B |
| 107 | V | CB | 9.0 | −3.8 | 3.2 | 37 | B |
| 107 | V | CG1 | 7.5 | −3.9 | 3.2 | 36 | B |
| 107 | V | CG2 | 9.7 | −4.4 | 1.9 | 36 | B |
| 108 | V | N | 7.7 | −0.7 | 3.1 | 29 | B |
| 108 | V | CA | 6.6 | 0.1 | 3.6 | 27 | B |
| 108 | V | C | 5.4 | −0.2 | 2.6 | 27 | B |
| 108 | V | O | 5.5 | −0.0 | 1.4 | 27 | B |
| 108 | V | CB | 6.9 | 1.6 | 3.5 | 30 | B |
| 108 | V | CG1 | 5.6 | 2.5 | 3.6 | 30 | B |
| 108 | V | CG2 | 7.9 | 2.0 | 4.7 | 31 | B |
| 109 | C | N | 4.3 | −0.7 | 3.2 | 24 | B |
| 109 | C | CA | 3.1 | −1.1 | 2.4 | 22 | B |
| 109 | C | C | 2.2 | 0.1 | 2.3 | 23 | B |
| 109 | C | O | 2.3 | 1.0 | 3.1 | 21 | B |
| 109 | C | CB | 2.4 | −2.3 | 3.0 | 22 | B |
| 109 | C | SG | 3.3 | −3.8 | 3.2 | 25 | B |
| 110 | S | N | 1.4 | 0.1 | 1.3 | 18 | B |
| 110 | S | CA | 0.4 | 1.2 | 1.1 | 17 | B |
| 110 | S | C | −0.7 | 0.6 | 0.3 | 19 | B |
| 110 | S | O | −0.6 | −0.5 | −0.2 | 16 | B |
| 110 | S | CB | 1.1 | 2.4 | 0.4 | 17 | B |
| 110 | S | OG | 1.7 | 1.9 | −0.8 | 21 | B |
| 111 | C | N | −1.8 | 1.4 | 0.2 | 19 | B |
| 111 | C | CA | −3.0 | 0.9 | −0.4 | 19 | B |
| 111 | C | C | −3.6 | 2.1 | −1.3 | 19 | B |
| 111 | C | O | −3.1 | 3.2 | −1.1 | 19 | B |
| 111 | C | CB | −4.1 | 0.7 | 0.7 | 20 | B |
| 111 | C | SG | −3.5 | −0.4 | 2.0 | 24 | B |
| 112 | T | N | −4.5 | 1.7 | −2.1 | 16 | B |
| 112 | T | CA | −5.1 | 2.7 | −3.0 | 13 | B |
| 112 | T | C | −6.0 | 3.7 | −2.3 | 14 | B |
| 112 | T | O | −6.5 | 3.4 | −1.2 | 17 | B |

TABLE 2-continued

Atomic Coordinates of Factor IXa co-crystal Compound A complex

| | | | | | | |
|---|---|---|---|---|---|---|
| 112 | T | CB | −5.8 | 2.0 | −4.2 | 16 | B |
| 112 | T | OG1 | −6.0 | 2.9 | −5.3 | 17 | B |
| 112 | T | CG2 | −7.1 | 1.3 | −3.8 | 15 | B |
| 113 | E | N | −6.4 | 4.7 | −2.9 | 17 | B |
| 113 | E | CA | −7.3 | 5.7 | −2.4 | 19 | B |
| 113 | E | C | −8.6 | 5.0 | −1.9 | 21 | B |
| 113 | E | O | −9.2 | 4.2 | −2.6 | 20 | B |
| 113 | E | CB | −7.5 | 6.8 | −3.4 | 22 | B |
| 113 | E | CG | −6.2 | 7.4 | −4.0 | 37 | B |
| 113 | E | CD | −6.5 | 8.0 | −5.4 | 61 | B |
| 113 | E | OE1 | −5.6 | 7.8 | −6.3 | 34 | B |
| 113 | E | OE2 | −7.5 | 8.7 | −5.6 | 52 | B |
| 114 | G | N | −9.1 | 5.4 | −0.8 | 19 | B |
| 114 | G | CA | −10.3 | 4.8 | −0.2 | 17 | B |
| 114 | G | C | −10.0 | 3.7 | 0.7 | 21 | B |
| 114 | G | O | −10.9 | 3.2 | 1.4 | 19 | B |
| 115 | Y | N | −8.7 | 3.3 | 0.8 | 19 | B |
| 115 | Y | CA | −8.3 | 2.2 | 1.7 | 17 | B |
| 115 | Y | C | −7.3 | 2.8 | 2.7 | 23 | B |
| 115 | Y | O | −6.6 | 3.8 | 2.3 | 24 | B |
| 115 | Y | CB | −7.7 | 1.0 | 0.9 | 18 | B |
| 115 | Y | CG | −8.7 | 0.2 | 0.1 | 16 | B |
| 115 | Y | CD1 | −9.2 | −0.9 | 0.6 | 17 | B |
| 115 | Y | CD2 | −9.1 | 0.7 | −1.1 | 15 | B |
| 115 | Y | CE1 | −10.2 | −1.7 | −0.1 | 17 | B |
| 115 | Y | CE2 | −10.1 | 0.0 | −1.9 | 16 | B |
| 115 | Y | CZ | −10.6 | −1.2 | −1.4 | 20 | B |
| 115 | Y | OH | −11.6 | −1.9 | −2.1 | 17 | B |
| 116 | R | N | −7.1 | 2.1 | 3.8 | 21 | B |
| 116 | R | CA | −6.1 | 2.5 | 4.8 | 19 | B |
| 116 | R | C | −5.3 | 1.3 | 5.1 | 23 | B |
| 116 | R | O | −5.8 | 0.1 | 5.0 | 21 | B |
| 116 | R | CB | −6.6 | 3.1 | 6.1 | 22 | B |
| 116 | R | CG | −7.3 | 2.1 | 7.0 | 26 | B |
| 116 | R | CD | −7.6 | 2.6 | 8.4 | 21 | B |
| 116 | R | NE | −8.3 | 1.6 | 9.2 | 31 | B |
| 116 | R | CZ | −7.8 | 1.0 | 10.3 | 44 | B |
| 116 | R | NH1 | −6.7 | 1.5 | 10.8 | 24 | B |
| 116 | R | NH2 | −8.5 | 0.1 | 10.9 | 39 | B |
| 117 | L | N | −4.0 | 1.5 | 5.4 | 21 | B |
| 117 | L | CA | −3.2 | 0.3 | 5.8 | 20 | B |
| 117 | L | C | −3.6 | −0.1 | 7.2 | 24 | B |
| 117 | L | O | −3.8 | 0.7 | 8.1 | 22 | B |
| 117 | L | CB | −1.7 | 0.8 | 5.9 | 20 | B |
| 117 | L | CG | −0.7 | −0.4 | 6.0 | 22 | B |
| 117 | L | CD1 | −0.7 | −1.2 | 4.7 | 21 | B |
| 117 | L | CD2 | 0.7 | 0.2 | 6.3 | 23 | B |
| 118 | A | N | −3.9 | −1.4 | 7.3 | 19 | B |
| 118 | A | CA | −4.4 | −2.0 | 8.6 | 19 | B |
| 118 | A | C | −3.4 | −1.9 | 9.7 | 25 | B |
| 118 | A | O | −2.2 | −1.5 | 9.5 | 23 | B |
| 118 | A | CB | −4.8 | −3.5 | 8.3 | 20 | B |
| 119 | E | N | −3.8 | −2.3 | 10.9 | 21 | B |
| 119 | E | CA | −2.9 | −2.3 | 12.1 | 22 | B |
| 119 | E | C | −1.7 | −3.2 | 11.9 | 27 | B |
| 119 | E | O | −0.6 | −2.9 | 12.4 | 28 | B |
| 119 | E | CB | −3.6 | −2.7 | 13.3 | 23 | B |
| 119 | E | CG | −4.7 | −1.7 | 13.8 | 28 | B |
| 119 | E | CD | −5.9 | −1.7 | 12.9 | 60 | B |
| 119 | E | OE1 | −6.2 | −2.6 | 12.2 | 34 | B |
| 119 | E | OE2 | −6.6 | −0.7 | 13.0 | 72 | B |
| 120 | N | N | −1.8 | −4.3 | 11.1 | 23 | B |
| 120 | N | CA | −0.7 | −5.2 | 10.8 | 21 | B |
| 120 | N | C | 0.3 | −4.6 | 9.7 | 26 | B |
| 120 | N | O | 1.3 | −5.3 | 9.4 | 25 | B |
| 120 | N | CB | −1.2 | −6.6 | 10.3 | 18 | B |
| 120 | N | CG | −1.8 | −6.6 | 8.9 | 33 | B |
| 120 | N | OD1 | −1.8 | −5.6 | 8.2 | 22 | B |
| 120 | N | ND2 | −2.4 | −7.7 | 8.6 | 28 | B |
| 121 | Q | N | 0.0 | −3.4 | 9.3 | 23 | B |
| 121 | Q | CA | 1.0 | −2.7 | 8.3 | 21 | B |
| 121 | Q | C | 1.2 | −3.4 | 7.0 | 23 | B |
| 121 | Q | O | 2.1 | −3.0 | 6.2 | 22 | B |
| 121 | Q | CB | 2.3 | −2.5 | 9.0 | 23 | B |
| 121 | Q | CG | 2.2 | −1.6 | 10.2 | 33 | B |
| 121 | Q | CD | 1.5 | −0.3 | 10.0 | 65 | B |
| 121 | Q | OE1 | 2.0 | 0.7 | 9.5 | 66 | B |
| 121 | Q | NE2 | 0.2 | −0.4 | 10.4 | 61 | B |
| 122 | K | N | 0.3 | −4.3 | 6.6 | 21 | B |
| 122 | K | CA | 0.4 | −5.0 | 5.4 | 21 | B |
| 122 | K | C | −0.9 | −5.0 | 4.6 | 24 | B |
| 122 | K | O | −0.9 | −4.9 | 3.4 | 23 | B |
| 122 | K | CB | 0.8 | −6.5 | 5.6 | 23 | B |
| 122 | K | CG | 2.2 | −6.7 | 6.2 | 36 | B |
| 122 | K | CD | 3.3 | −6.0 | 5.4 | 44 | B |
| 122 | K | CE | 4.7 | −6.3 | 6.0 | 59 | B |
| 122 | K | NZ | 5.6 | −5.1 | 5.8 | 64 | B |
| 123 | S | N | −2.0 | −5.2 | 5.3 | 19 | B |
| 123 | S | CA | −3.3 | −5.4 | 4.7 | 18 | B |
| 123 | S | C | −4.0 | −4.1 | 4.4 | 24 | B |
| 123 | S | O | −3.6 | −3.0 | 5.0 | 22 | B |
| 123 | S | CB | −4.3 | −6.2 | 5.6 | 23 | B |
| 123 | S | OG | −3.7 | −7.5 | 5.7 | 31 | B |
| 124 | C | N | −5.0 | −4.1 | 3.5 | 22 | B |
| 124 | C | CA | −5.7 | −2.8 | 3.1 | 21 | B |
| 124 | C | C | −7.1 | −3.0 | 3.5 | 25 | B |
| 124 | C | O | −7.7 | −4.0 | 3.2 | 26 | B |
| 124 | C | CB | −5.5 | −2.6 | 1.6 | 22 | B |
| 124 | C | SG | −3.8 | −2.2 | 1.2 | 25 | B |
| 125 | E | N | −7.6 | −2.0 | 4.3 | 25 | B |
| 125 | E | CA | −8.9 | −2.0 | 4.8 | 26 | B |
| 125 | E | C | −9.7 | −0.8 | 4.3 | 27 | B |
| 125 | E | O | −9.1 | 0.3 | 4.1 | 23 | B |
| 125 | E | CB | −8.7 | −1.8 | 6.4 | 28 | B |
| 125 | E | CG | −10.0 | −1.8 | 7.2 | 48 | B |
| 125 | E | CD | −10.0 | −3.0 | 8.1 | 60 | B |
| 125 | E | OE1 | −8.9 | −3.5 | 8.4 | 50 | B |
| 125 | E | OE2 | −11.1 | −3.4 | 8.5 | 58 | B |
| 126 | P | N | −11.0 | −1.0 | 4.0 | 25 | B |
| 126 | P | CA | −11.6 | 0.2 | 3.5 | 22 | B |
| 126 | P | C | −11.7 | 1.4 | 4.5 | 25 | B |
| 126 | P | O | −11.8 | 1.1 | 5.7 | 25 | B |
| 126 | P | CB | −13.1 | −0.3 | 3.1 | 24 | B |
| 126 | P | CG | −12.9 | −1.8 | 2.9 | 30 | B |
| 126 | P | CD | −11.6 | −2.2 | 3.4 | 26 | B |
| 127 | A | N | −11.6 | 2.6 | 4.0 | 21 | B |
| 127 | A | CA | −11.7 | 3.8 | 4.9 | 21 | B |
| 127 | A | C | −12.9 | 4.6 | 4.6 | 24 | B |
| 127 | A | O | −13.1 | 5.6 | 5.2 | 24 | B |
| 127 | A | CB | −10.4 | 4.6 | 4.8 | 22 | B |
| 128 | V | N | −13.6 | 4.2 | 3.5 | 20 | B |
| 128 | V | CA | −14.8 | 4.9 | 3.1 | 18 | B |
| 128 | V | C | −15.9 | 3.9 | 2.9 | 18 | B |
| 128 | V | O | −15.6 | 2.7 | 2.9 | 18 | B |
| 128 | V | CB | −14.6 | 5.6 | 1.7 | 22 | B |
| 128 | V | CG1 | −13.7 | 6.8 | 1.8 | 23 | B |
| 128 | V | CG2 | −14.1 | 4.6 | 0.6 | 21 | B |
| 129 | P | N | −17.1 | 4.3 | 2.9 | 17 | B |
| 129 | P | CA | −18.3 | 3.4 | 2.9 | 16 | B |
| 129 | P | C | −18.4 | 2.6 | 1.6 | 20 | B |
| 129 | P | O | −18.8 | 1.5 | 1.6 | 20 | B |
| 129 | P | CB | −19.5 | 4.4 | 3.0 | 18 | B |
| 129 | P | CG | −18.9 | 5.7 | 3.6 | 21 | B |
| 129 | P | CD | −17.5 | 5.7 | 3.1 | 17 | B |
| 130 | F | N | −17.9 | 3.3 | 0.5 | 16 | B |
| 130 | F | CA | −17.9 | 2.6 | −0.9 | 16 | B |
| 130 | F | C | −16.6 | 2.7 | −1.6 | 21 | B |
| 130 | F | O | −16.4 | 3.4 | −2.5 | 20 | B |
| 130 | F | CB | −19.1 | 3.2 | −1.7 | 16 | B |
| 130 | F | CG | −20.4 | 3.0 | −1.1 | 15 | B |
| 130 | F | CD1 | −21.1 | 4.0 | −0.4 | 18 | B |
| 130 | F | CD2 | −20.9 | 1.7 | −1.1 | 17 | B |
| 130 | F | CE1 | −22.3 | 3.7 | 0.2 | 18 | B |
| 130 | F | CE2 | −22.1 | 1.4 | −0.5 | 20 | B |
| 130 | F | CZ | −22.8 | 2.4 | 0.2 | 17 | B |
| 131 | P | N | −15.7 | 1.9 | −1.1 | 19 | B |
| 131 | P | CA | −14.3 | 1.9 | −1.7 | 18 | B |
| 131 | P | C | −14.3 | 1.3 | −3.1 | 21 | B |
| 131 | P | O | −15.1 | 0.4 | −3.4 | 18 | B |
| 131 | P | CB | −13.5 | 1.0 | −0.8 | 19 | B |
| 131 | P | CG | −14.5 | 0.1 | −0.2 | 23 | B |
| 131 | P | CD | −15.8 | 0.8 | −0.1 | 19 | B |
| 132 | C | N | −13.4 | 1.9 | −3.9 | 17 | B |
| 132 | C | CA | −13.3 | 1.4 | −5.3 | 15 | B |

TABLE 2-continued

Atomic Coordinates of Factor IXa co-crystal Compound A complex

| 132 | C | C | -13.0 | -0.2 | -5.3 | 18 | B |
|---|---|---|---|---|---|---|---|
| 132 | C | O | -12.4 | -0.8 | -4.5 | 17 | B |
| 132 | C | CB | -12.2 | 2.1 | -6.0 | 15 | B |
| 132 | C | SG | -10.5 | 1.8 | -5.3 | 18 | B |
| 133 | G | N | -13.5 | -0.7 | -6.5 | 15 | B |
| 133 | G | CA | -13.2 | -2.1 | -6.8 | 13 | B |
| 133 | G | C | -13.7 | -3.2 | -5.9 | 19 | B |
| 133 | G | O | -13.2 | -4.3 | -6.0 | 19 | B |
| 134 | R | N | -14.7 | -2.9 | -5.1 | 18 | B |
| 134 | R | CA | -15.2 | -3.9 | -4.2 | 19 | B |
| 134 | R | C | -16.7 | -4.1 | -4.5 | 19 | B |
| 134 | R | O | -17.4 | -3.2 | -4.7 | 17 | B |
| 134 | R | CB | -15.0 | -3.5 | -2.8 | 28 | B |
| 134 | R | CG | -13.6 | -3.8 | -2.3 | 46 | B |
| 134 | R | CD | -13.5 | -4.6 | -1.0 | 60 | B |
| 134 | R | NE | -12.3 | -5.3 | -0.8 | 75 | B |
| 134 | R | CZ | -11.5 | -5.2 | 0.2 | 98 | B |
| 134 | R | NH1 | -11.9 | -4.5 | 1.3 | 91 | B |
| 134 | R | NH2 | -10.4 | -5.9 | 0.3 | 84 | B |
| 135 | V | N | -17.1 | -5.4 | -4.4 | 18 | B |
| 135 | V | CA | -18.5 | -5.8 | -4.7 | 18 | B |
| 135 | V | C | -19.1 | -5.9 | -3.3 | 22 | B |
| 135 | V | O | -18.6 | -6.5 | -2.4 | 22 | B |
| 135 | V | CB | -18.5 | -7.2 | -5.3 | 21 | B |
| 135 | V | CG1 | -19.9 | -7.7 | -5.4 | 21 | B |
| 135 | V | CG2 | -17.9 | -7.0 | -6.7 | 22 | B |
| 136 | S | N | -20.2 | -5.1 | -3.1 | 20 | B |
| 136 | S | CA | -20.9 | -5.0 | -1.8 | 19 | B |
| 136 | S | C | -22.4 | -5.5 | -1.9 | 27 | B |
| 136 | S | O | -22.9 | -5.7 | -0.8 | 28 | B |
| 136 | S | CB | -20.7 | -3.7 | -1.2 | 21 | B |
| 136 | S | OG | -21.2 | -2.6 | -2.0 | 26 | B |
| 137 | V | N | -23.0 | -5.6 | -3.0 | 25 | B |
| 137 | V | CA | -24.3 | -6.1 | -3.1 | 25 | B |
| 137 | V | C | -24.2 | -7.6 | -3.0 | 32 | B |
| 137 | V | O | -23.3 | -8.3 | -3.5 | 31 | B |
| 137 | V | CB | -25.0 | -5.8 | -4.5 | 27 | B |
| 137 | V | CG1 | -26.4 | -6.5 | -4.6 | 28 | B |
| 137 | V | CG2 | -25.1 | -4.3 | -4.7 | 27 | B |
| 138 | S | N | -25.1 | -8.3 | -2.2 | 31 | B |
| 138 | S | CA | -25.0 | -9.7 | -2.0 | 32 | B |
| 138 | S | C | -25.1 | -10.4 | -3.3 | 37 | B |
| 138 | S | O | -26.0 | -10.0 | -4.2 | 36 | B |
| 138 | S | CB | -26.0 | -10.3 | -1.0 | 35 | B |
| 138 | S | OG | -25.8 | -11.7 | -0.8 | 42 | B |
| 139 | Q | N | -24.3 | -11.4 | -3.5 | 35 | B |
| 139 | Q | CA | -24.4 | -12.2 | -4.7 | 35 | B |
| 139 | Q | C | -24.9 | -13.6 | -4.4 | 42 | B |
| 139 | Q | O | -24.6 | -14.6 | -4.9 | 44 | B |
| 139 | Q | CB | -23.0 | -12.3 | -5.3 | 36 | B |
| 139 | Q | CG | -22.3 | -10.9 | -5.3 | 26 | B |
| 139 | Q | CD | -22.7 | -10.1 | -6.6 | 39 | B |
| 139 | Q | OE1 | -23.2 | -9.0 | -6.4 | 30 | B |
| 139 | Q | NE2 | -22.5 | -10.7 | -7.7 | 25 | B |
| 500 | X | CA | -32.3 | -1.5 | -15.8 | 37 | Q |
| 1 | Z | N1 | -12.7 | -8.1 | -28.6 | 15 | S |
| 1 | Z | C2 | -13.3 | -7.9 | -29.8 | 14 | S |
| 1 | Z | N3 | -13.3 | -9.0 | -30.7 | 15 | S |
| 1 | Z | C4 | -14.0 | -6.7 | -30.1 | 12 | S |
| 1 | Z | C5 | -14.2 | -5.6 | -29.2 | 10 | S |
| 1 | Z | C6 | -14.8 | -4.4 | -29.6 | 14 | S |
| 1 | Z | C7 | -15.4 | -4.3 | -30.9 | 14 | S |
| 1 | Z | C8 | -15.3 | -5.3 | -31.7 | 14 | S |
| 1 | Z | C9 | -14.6 | -6.5 | -31.4 | 15 | S |
| 1 | Z | N14 | -15.9 | -5.4 | -33.0 | 14 | S |
| 1 | Z | C15 | -15.5 | -4.9 | -34.2 | 15 | S |
| 1 | Z | C16 | -16.4 | -5.4 | -35.1 | 14 | S |
| 1 | Z | C17 | -17.4 | -6.3 | -34.5 | 13 | S |
| 1 | Z | N18 | -17.1 | -6.1 | -33.2 | 13 | S |
| 1 | Z | C19 | -18.6 | -6.7 | -35.0 | 12 | S |
| 1 | Z | C23 | -14.3 | -4.1 | -34.4 | 17 | S |
| 1 | Z | N24 | -13.8 | -4.0 | -35.6 | 18 | S |
| 1 | Z | C25 | -12.6 | -3.4 | -36.0 | 17 | S |
| 1 | Z | O26 | -13.6 | -3.7 | -33.4 | 13 | S |
| 1 | Z | C27 | -11.7 | -4.0 | -36.9 | 18 | S |
| 1 | Z | C28 | -10.4 | -3.4 | -37.1 | 18 | S |
| 1 | Z | C29 | -10.1 | -2.2 | -36.5 | 19 | S |
| 1 | Z | C30 | -11.0 | -1.6 | -35.6 | 16 | S |
| 1 | Z | C31 | -12.2 | -2.2 | -35.3 | 17 | S |
| 1 | Z | N36 | -8.8 | -1.6 | -36.6 | 19 | S |
| 1 | Z | C37 | -8.5 | -0.6 | -37.6 | 22 | S |
| 1 | Z | C38 | -7.2 | -0.2 | -37.3 | 24 | S |
| 1 | Z | N39 | -6.7 | -0.9 | -36.2 | 21 | S |
| 1 | Z | C40 | -7.7 | -1.7 | -35.9 | 19 | S |
| 1 | Z | C41 | -9.2 | 0.0 | -38.6 | 25 | S |
| 1 | Z | C42 | -8.6 | 1.0 | -39.4 | 25 | S |
| 1 | Z | C43 | -7.3 | 1.4 | -39.1 | 25 | S |
| 1 | Z | C44 | -6.6 | 0.8 | -38.1 | 23 | S |
| 1 | O | O | -18.5 | -2.5 | -21.7 | 11 | W |
| 2 | O | O | -22.7 | -8.4 | -23.8 | 11 | W |
| 3 | O | O | -21.2 | -2.2 | -22.8 | 11 | W |
| 4 | O | O | -11.0 | -10.9 | -25.5 | 16 | W |
| 5 | O | O | -4.9 | -0.1 | -12.2 | 14 | W |
| 6 | O | O | -22.7 | -15.8 | -26.9 | 13 | W |
| 7 | O | O | -13.4 | 1.6 | -19.1 | 14 | W |
| 8 | O | O | -5.1 | 1.8 | -27.6 | 13 | W |
| 9 | O | O | -10.7 | 5.3 | -9.5 | 15 | W |
| 10 | O | O | -2.3 | -1.9 | -18.3 | 14 | W |
| 11 | O | O | -11.4 | -6.0 | -27.0 | 14 | W |
| 12 | O | O | -6.6 | -0.0 | -29.4 | 17 | W |
| 13 | O | O | -6.3 | -10.6 | -19.8 | 16 | W |
| 14 | O | O | -22.9 | -17.4 | -23.5 | 17 | W |
| 15 | O | O | -11.6 | 7.3 | 7.0 | 18 | W |
| 16 | O | O | -22.5 | 1.0 | -12.3 | 17 | W |
| 17 | O | O | -4.8 | 7.7 | -32.6 | 21 | W |
| 18 | O | O | -8.4 | 6.8 | -10.2 | 19 | W |
| 19 | O | O | -24.3 | 0.9 | -15.6 | 13 | W |
| 20 | O | O | 0.3 | -2.8 | -18.7 | 15 | W |
| 21 | O | O | -22.8 | -4.5 | -12.1 | 14 | W |
| 22 | O | O | -16.6 | -8.5 | -10.0 | 17 | W |
| 23 | O | O | -23.9 | 19.6 | -21.3 | 16 | W |
| 24 | O | O | -22.8 | 15.2 | -24.4 | 19 | W |
| 25 | O | O | -22.4 | -13.6 | -23.4 | 14 | W |
| 26 | O | O | 0.2 | 2.0 | -7.0 | 22 | W |
| 27 | O | O | -7.8 | 3.9 | -7.1 | 18 | W |
| 28 | O | O | -4.4 | -9.9 | -17.8 | 17 | W |
| 29 | O | O | -6.9 | 11.4 | -9.0 | 25 | W |
| 30 | O | O | -19.6 | -1.6 | -3.9 | 17 | W |
| 31 | O | O | -24.4 | -2.1 | -10.6 | 16 | W |
| 32 | O | O | -25.1 | 14.9 | -22.4 | 19 | W |
| 33 | O | O | -6.1 | -11.0 | -33.2 | 22 | W |
| 34 | O | O | -19.4 | 11.5 | -28.3 | 20 | W |
| 35 | O | O | -0.4 | -3.2 | 1.0 | 22 | W |
| 36 | O | O | 2.8 | -9.9 | -12.4 | 24 | W |
| 37 | O | O | -21.5 | -4.2 | -5.4 | 19 | W |
| 38 | O | O | -26.5 | -3.7 | -11.0 | 18 | W |
| 39 | O | O | -12.6 | -12.4 | -33.5 | 17 | W |
| 40 | O | O | -8.8 | 9.7 | -10.0 | 19 | W |
| 41 | O | O | -15.6 | -16.3 | -17.6 | 17 | W |
| 43 | O | O | -9.2 | -9.7 | -33.4 | 20 | W |
| 44 | O | O | -6.6 | 13.9 | -29.2 | 26 | W |
| 45 | O | O | -17.5 | -0.6 | -2.3 | 23 | W |
| 46 | O | O | -0.7 | -9.0 | -25.4 | 21 | W |
| 48 | O | O | -18.6 | -0.7 | -29.2 | 21 | W |
| 49 | O | O | -14.2 | -7.9 | -10.7 | 18 | W |
| 50 | O | O | -4.6 | -9.7 | -15.2 | 22 | W |
| 51 | O | O | -5.5 | -9.4 | -40.0 | 27 | W |
| 52 | O | O | -23.6 | -1.9 | -13.4 | 18 | W |
| 53 | O | O | -6.7 | -5.6 | -2.1 | 23 | W |
| 54 | O | O | -0.4 | 8.8 | -18.2 | 23 | W |
| 55 | O | O | -0.1 | 10.2 | -20.7 | 37 | W |
| 56 | O | O | -11.1 | -12.1 | -31.4 | 22 | W |
| 57 | O | O | -8.7 | -11.1 | -12.1 | 24 | W |
| 58 | O | O | -11.7 | 4.2 | -3.3 | 26 | W |
| 59 | O | O | -27.6 | 9.3 | -0.6 | 53 | W |
| 60 | O | O | -17.5 | 6.0 | -0.1 | 26 | W |
| 61 | O | O | -29.4 | 13.2 | -16.2 | 24 | W |
| 62 | O | O | -25.0 | 5.9 | -1.0 | 28 | W |
| 63 | O | O | -19.1 | -14.0 | -32.6 | 23 | W |
| 64 | O | O | -16.7 | 0.1 | 3.8 | 30 | W |
| 65 | O | O | -1.8 | 3.8 | 2.0 | 25 | W |
| 66 | O | O | -10.5 | 10.2 | -7.8 | 23 | W |
| 67 | O | O | -13.2 | 22.7 | -16.8 | 36 | W |
| 68 | O | O | -25.8 | 0.9 | -1.3 | 29 | W |

TABLE 2-continued

Atomic Coordinates of Factor IXa co-crystal Compound A complex

| | | | | | | |
|---|---|---|---|---|---|---|
| 69 | O | O | −15.1 | −7.5 | −4.1 | 30 | W |
| 71 | O | O | −25.4 | −4.9 | −13.1 | 21 | W |
| 72 | O | O | −13.3 | 17.2 | −11.3 | 23 | W |
| 73 | O | O | −21.2 | 9.8 | −3.2 | 22 | W |
| 74 | O | O | −28.5 | 1.1 | −3.1 | 36 | W |
| 75 | O | O | −0.9 | 12.0 | −12.2 | 24 | W |
| 77 | O | O | −5.0 | 14.9 | −23.2 | 34 | W |
| 78 | O | O | −31.4 | 7.7 | −10.0 | 36 | W |
| 79 | O | O | 7.2 | −9.3 | −5.7 | 33 | W |
| 81 | O | O | −24.4 | −17.7 | −20.2 | 21 | W |
| 82 | O | O | −8.9 | 13.8 | −30.5 | 32 | W |
| 83 | O | O | −28.9 | 6.3 | −35.4 | 38 | W |
| 84 | O | O | −6.8 | −8.5 | −34.4 | 23 | W |
| 85 | O | O | −30.2 | 17.0 | −26.0 | 26 | W |
| 86 | O | O | −22.6 | −13.9 | −11.7 | 30 | W |
| 87 | O | O | −28.3 | 4.1 | −7.6 | 16 | W |
| 88 | O | O | −29.3 | −3.3 | −10.5 | 19 | W |
| 89 | O | O | −25.5 | −16.7 | −17.7 | 23 | W |
| 90 | O | O | −9.3 | −8.3 | −41.0 | 27 | W |
| 91 | O | O | −3.0 | −16.9 | −23.2 | 27 | W |
| 92 | O | O | −28.9 | 1.7 | −22.6 | 24 | W |
| 93 | O | O | −2.9 | −0.8 | −38.4 | 28 | W |
| 94 | O | O | −29.2 | −10.6 | −22.3 | 28 | W |
| 96 | O | O | 2.1 | 4.5 | −31.1 | 35 | W |
| 97 | O | O | −29.7 | 13.3 | −18.8 | 30 | W |
| 98 | O | O | −9.8 | 5.5 | −6.8 | 33 | W |
| 99 | O | O | −15.5 | −16.7 | −14.6 | 27 | W |
| 100 | O | O | −5.7 | −20.1 | −32.6 | 34 | W |
| 102 | O | O | −11.0 | −14.8 | −27.8 | 27 | W |
| 103 | O | O | −28.6 | −12.5 | −32.3 | 34 | W |
| 104 | O | O | −21.2 | 20.7 | −22.0 | 25 | W |
| 106 | O | O | −12.6 | 11.0 | −28.7 | 24 | W |
| 107 | O | O | −21.7 | 12.2 | −4.8 | 25 | W |
| 108 | O | O | −39.4 | −1.0 | −17.8 | 42 | W |
| 109 | O | O | −35.8 | −7.9 | −20.7 | 41 | W |
| 110 | O | O | −22.9 | 8.2 | −30.4 | 38 | W |
| 111 | O | O | −11.2 | −15.1 | −30.4 | 28 | W |
| 112 | O | O | −29.3 | −8.5 | −6.2 | 29 | W |
| 113 | O | O | −6.5 | −20.3 | −24.5 | 42 | W |
| 114 | O | O | −9.2 | −13.3 | −10.5 | 33 | W |
| 116 | O | O | −6.0 | −9.2 | −43.1 | 36 | W |
| 117 | O | O | −14.0 | −1.3 | −31.9 | 16 | W |
| 118 | O | O | −11.0 | 4.0 | −39.4 | 38 | W |
| 119 | O | O | 5.5 | −12.2 | −32.9 | 30 | W |
| 120 | O | O | −32.1 | 12.3 | −15.9 | 40 | W |
| 121 | O | O | −22.3 | −11.9 | −1.5 | 48 | W |
| 123 | O | O | −0.9 | 5.6 | −35.1 | 28 | W |
| 131 | O | O | −9.7 | 1.5 | −26.4 | 19 | W |
| 132 | O | O | −22.2 | −0.3 | −30.8 | 19 | W |
| 133 | O | O | −19.4 | −3.2 | −37.0 | 21 | W |
| 134 | O | O | −14.4 | −6.2 | −37.6 | 14 | W |
| 141 | O | O | 2.0 | 6.1 | −11.9 | 23 | W |
| 142 | O | O | −3.8 | 3.8 | −6.5 | 21 | W |
| 143 | O | O | −17.8 | −2.4 | −0.1 | 33 | W |
| 144 | O | O | −3.3 | 4.5 | 5.5 | 25 | W |
| 145 | O | O | −29.4 | 2.4 | −20.4 | 24 | W |
| 146 | O | O | −15.4 | −5.4 | −15.4 | 18 | W |
| 151 | O | O | −25.7 | −15.0 | −20.9 | 25 | W |
| 152 | O | O | −18.4 | −15.8 | −18.1 | 21 | W |
| 153 | O | O | −26.8 | −9.4 | −6.6 | 28 | W |
| 154 | O | O | −30.0 | −6.2 | −6.2 | 31 | W |
| 155 | O | O | −31.0 | −4.8 | −9.1 | 33 | W |
| 156 | O | O | −2.3 | 7.9 | −34.1 | 29 | W |
| 157 | O | O | −28.3 | 15.0 | −15.0 | 29 | W |
| 158 | O | O | −31.0 | 9.5 | −12.9 | 26 | W |
| 159 | O | O | −22.2 | 7.7 | −1.3 | 29 | W |
| 160 | O | O | 5.6 | 2.1 | −8.2 | 44 | W |
| 161 | O | O | 4.8 | 3.7 | −11.2 | 24 | W |
| 162 | O | O | 3.1 | 1.1 | −18.8 | 33 | W |
| 163 | O | O | −24.4 | −3.0 | −27.5 | 26 | W |
| 164 | O | O | −1.5 | 3.9 | −37.1 | 31 | W |
| 165 | O | O | −4.0 | −0.5 | −35.9 | 23 | W |
| 166 | O | O | 1.4 | −10.3 | −38.7 | 40 | W |
| 167 | O | O | 0.8 | −7.4 | −36.4 | 33 | W |
| 168 | O | O | −8.2 | −17.3 | −31.1 | 33 | W |
| 169 | O | O | 4.2 | 1.4 | −0.3 | 28 | W |
| 170 | O | O | −11.0 | 0.6 | 8.1 | 23 | W |
| 171 | O | O | −0.4 | 3.4 | 8.5 | 38 | W |
| 173 | O | O | −24.0 | −2.5 | −29.9 | 33 | W |
| 174 | O | O | −13.3 | −7.1 | −6.7 | 28 | W |
| 175 | O | O | −20.4 | 9.1 | −29.7 | 20 | W |
| 181 | O | O | −11.4 | 12.7 | −30.6 | 33 | W |
| 182 | O | O | −8.6 | 13.0 | −33.3 | 32 | W |
| 183 | O | O | −11.8 | 18.5 | −24.1 | 38 | W |
| 184 | O | O | −20.6 | 15.0 | −25.8 | 29 | W |
| 185 | O | O | −21.2 | 18.1 | −23.7 | 34 | W |
| 186 | O | O | −29.5 | 7.4 | −21.3 | 35 | W |
| 187 | O | O | −30.6 | 12.1 | −12.7 | 44 | W |
| 188 | O | O | −29.7 | 10.0 | −10.0 | 25 | W |
| 189 | O | O | 0.5 | 7.1 | −25.5 | 34 | W |
| 190 | O | O | −8.6 | 5.0 | −38.4 | 37 | W |
| 191 | O | O | −1.2 | 4.2 | −6.4 | 28 | W |
| 192 | O | O | −30.0 | −10.2 | −26.1 | 37 | W |
| 193 | O | O | −31.0 | −6.8 | −27.9 | 30 | W |
| 194 | O | O | 1.8 | −5.0 | −27.1 | 29 | W |
| 195 | O | O | 4.3 | −1.3 | 5.8 | 23 | W |
| 196 | O | O | −15.9 | 9.9 | −6.3 | 30 | W |

Example 9

Preparation of Specific Factor IXa-Compound B Complex

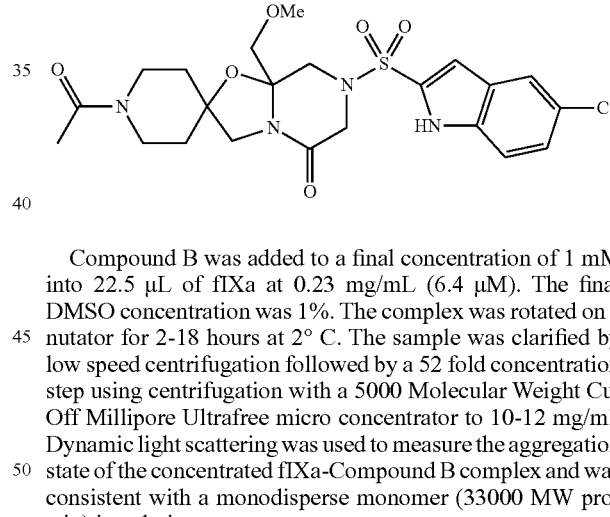

Compound B

Compound B was added to a final concentration of 1 mM into 22.5 μL of fIXa at 0.23 mg/mL (6.4 μM). The final DMSO concentration was 1%. The complex was rotated on a nutator for 2-18 hours at 2° C. The sample was clarified by low speed centrifugation followed by a 52 fold concentration step using centrifugation with a 5000 Molecular Weight Cut Off Millipore Ultrafree micro concentrator to 10-12 mg/ml. Dynamic light scattering was used to measure the aggregation state of the concentrated fIXa-Compound B complex and was consistent with a monodisperse monomer (33000 MW protein) in solution.

Example 10

Crystallization of Factor IXa-Compound B Complex

Figure 4:
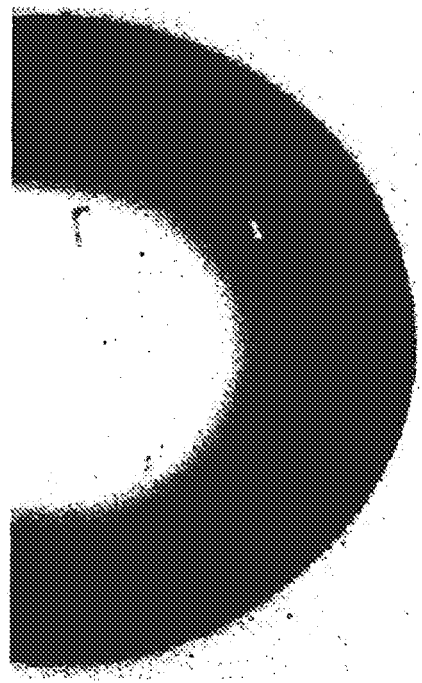
FIG. 4. Photomicrograph of human wild type factor IXa-Compound B complex crystals at 70× magnification. The crystals were prepared with precipitant solution containing 16% PEG 6000 (v/v), 0.1 M citric acid, pH 5.9 and were grown at 4° C. for 9 days.
Figure 5:
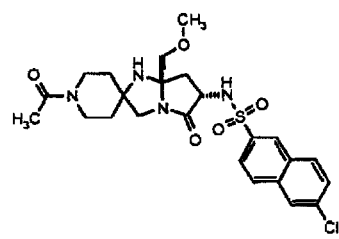
FIG. 5. Molecular structure of Compound C.

The Factor IXa-Compound B complex from Example 9 was crystallized using a hanging-drop vapor diffusion method. The protein (0.5 μl; 15 mg/ml) in 25 mM Tris, pH 8.0, 0.15 M sodium chloride, buffer was mixed with an equal volume of precipitant solution containing 16% PEG 6000 (v/v), 0.1 M citric acid, pH 5.9 placed on the underside of a siliconized Teflon coverslip and sealed in close proximity to 0.08 mL of the precipitant solution. Crystallization plates were incubated at 4° C.; orthorhombic crystals (0.01×0.05 mm) grew over 1-9 days. FIG. 4 shows a photomicrograph of the factor IXa-Compound B complex crystals grown over 9 days, at 70× magnification.

Example 11

Crystallographic Analysis of Factor IXa-Compound B Complex Crystals

Prior to data collection crystals were harvested and cryo-protected for 5-10 minutes in the crystallization solution containing 25% glycerol. The crystals were then frozen directly into liquid nitrogen. X-ray diffraction was collected using a Rigaku generator equipped with a Raxis 4 detector. Data were integrated and scaled using the HKL package.

| Data Collection Statistics | |
|---|---|
| Resolution | 40.0-2.45 Å |
| No. of collected reflections | 493003 |
| No. of unique reflections (F >= 0) | 19092 |
| R-sym | 8.7% |
| Percent of theoretical (I/s >= 1) | 100.0% |
| Unit Cell | a = 100.6 Å, b = 100.6, c = 98.1 Å, α = β = γ = 90° |
| Space Group | P4₃2₁2 |
| Asymmetric unit | 1 molecule |

Example 12

Structure Determination of Factor IXa-Compound B Complex

The crystal structure was solved using Rigid Body refinement with the starting model 1RFN. Refinement was done using the program AUTOBUSTER (Global Phasing Limited.).

| | |
|---|---|
| Number of reflections | 19020 |
| Resolution limits | 35.6-2.45 Å |
| Completeness for range | 99.6% |
| FREE R TEST SET COUNT & SIZE | 912 (4.8%) |
| Number of protein atoms | 2215 |
| Number of solvent atoms | 74 |
| R-factor | 0.209 |
| R-free | 0.252 |
| RMSD bond length | 0.011 Å |
| RMSD bond angles | 1.28° |

Table 3. Coordinates of Factor IXa Co-Crystal Compound B Complex

The following table contains one line for each atom in one Factor IXa monomer. The columns are: 1) residue number, 2) 1-letter amino acid code, 3) atom name, 4) x-coordinate, 5) y-coordinate, 6) z-coordinate, 7) B-factor, 8) Chain ID. (Amino Acid Code X are Calcium or Citrate, Z is Compound B and O for water) The numbering scheme is based on chymotrypsin. Note: B tractors greater than 100 appear as 0 in column 7.

TABLE 3

Coordinates of Factor IXa co-crystal Compound B complex

| 16 | V | N | −18.7 | −28.1 | −26.8 | 32 | A |
|---|---|---|---|---|---|---|---|
| 16 | V | CA | −18.9 | −29.5 | −27.2 | 30 | A |
| 16 | V | C | −19.6 | −29.5 | −28.6 | 35 | A |
| 16 | V | O | −20.8 | −29.1 | −28.6 | 35 | A |
| 16 | V | CB | −19.5 | −30.4 | −26.1 | 33 | A |
| 16 | V | CG1 | −20.0 | −31.8 | −26.6 | 32 | A |
| 16 | V | CG2 | −18.6 | −30.5 | −24.9 | 30 | A |
| 17 | V | N | −18.9 | −30.0 | −29.6 | 31 | A |
| 17 | V | CA | −19.6 | −30.2 | −30.9 | 31 | A |
| 17 | V | C | −20.2 | −31.6 | −31.0 | 36 | A |
| 17 | V | O | −19.6 | −32.6 | −30.5 | 36 | A |
| 17 | V | CB | −18.6 | −30.1 | −32.1 | 36 | A |
| 17 | V | CG1 | −19.3 | −30.4 | −33.4 | 35 | A |
| 17 | V | CG2 | −18.0 | −28.7 | −32.0 | 35 | A |
| 18 | G | N | −21.5 | −31.6 | −31.5 | 34 | A |
| 18 | G | CA | −22.2 | −32.9 | −31.6 | 33 | A |
| 18 | G | C | −22.6 | −33.7 | −30.3 | 40 | A |
| 18 | G | O | −22.8 | −34.9 | −30.4 | 39 | A |
| 19 | G | N | −22.8 | −32.9 | −29.2 | 38 | A |
| 19 | G | CA | −23.1 | −33.5 | −27.9 | 37 | A |
| 19 | G | C | −24.6 | −33.3 | −27.6 | 41 | A |
| 19 | G | O | −25.4 | −33.1 | −28.5 | 40 | A |
| 20 | E | N | −24.9 | −33.4 | −26.3 | 35 | A |
| 20 | E | CA | −26.3 | −33.4 | −25.9 | 35 | A |
| 20 | E | C | −26.3 | −32.5 | −24.6 | 40 | A |
| 20 | E | O | −25.3 | −32.3 | −23.9 | 39 | A |
| 20 | E | CB | −26.8 | −34.7 | −25.5 | 36 | A |
| 20 | E | CG | −27.5 | −35.5 | −26.5 | 47 | A |
| 20 | E | CD | −27.6 | −37.0 | −26.2 | 84 | A |
| 20 | E | OE1 | −26.7 | −37.6 | −25.5 | 67 | A |
| 20 | E | OE2 | −28.6 | −37.6 | −26.6 | 95 | A |
| 21 | D | N | −27.5 | −31.9 | −24.4 | 38 | A |
| 21 | D | CA | −27.8 | −31.1 | −23.2 | 39 | A |
| 21 | D | C | −27.8 | −32.0 | −22.0 | 44 | A |
| 21 | D | O | −28.4 | −33.1 | −22.0 | 43 | A |
| 21 | D | CB | −29.2 | −30.5 | −23.2 | 40 | A |
| 21 | D | CG | −29.4 | −29.4 | −24.2 | 48 | A |
| 21 | D | OD1 | −30.4 | −28.8 | −24.2 | 52 | A |
| 21 | D | OD2 | −28.4 | −29.1 | −25.0 | 46 | A |
| 22 | A | N | −27.1 | −31.6 | −20.9 | 39 | A |
| 22 | A | CA | −27.0 | −32.3 | −19.7 | 38 | A |
| 22 | A | C | −28.3 | −31.9 | −19.0 | 41 | A |
| 22 | A | O | −28.8 | −30.8 | −19.1 | 42 | A |
| 22 | A | CB | −25.8 | −31.9 | −18.9 | 38 | A |
| 23 | K | N | −28.8 | −32.9 | −18.2 | 38 | A |
| 23 | K | CA | −29.9 | −32.6 | −17.3 | 37 | A |
| 23 | K | C | −29.3 | −32.0 | −16.0 | 42 | A |
| 23 | K | O | −28.1 | −32.1 | −15.7 | 40 | A |
| 23 | K | CB | −30.6 | −33.9 | −16.9 | 40 | A |
| 23 | K | CG | −31.4 | −34.5 | −18.0 | 47 | A |
| 23 | K | CD | −31.8 | −35.9 | −17.7 | 63 | A |
| 23 | K | CE | −32.5 | −36.6 | −18.9 | 75 | A |
| 23 | K | NZ | −33.0 | −38.0 | −18.6 | 82 | A |
| 24 | P | N | −30.2 | −31.3 | −15.2 | 41 | A |
| 24 | P | CA | −29.6 | −30.7 | −14.0 | 39 | A |
| 24 | P | C | −29.0 | −31.7 | −13.0 | 43 | A |
| 24 | P | O | −29.6 | −32.8 | −12.9 | 41 | A |
| 24 | P | CB | −30.8 | −29.9 | −13.4 | 40 | A |
| 24 | P | CG | −31.7 | −29.6 | −14.5 | 44 | A |
| 24 | P | CD | −31.4 | −30.6 | −15.6 | 41 | A |
| 25 | G | N | −27.8 | −31.5 | −12.4 | 39 | A |
| 25 | G | CA | −27.2 | −32.3 | −11.5 | 37 | A |
| 25 | G | C | −26.6 | −33.6 | −12.2 | 39 | A |
| 25 | G | O | −26.2 | −34.5 | −11.5 | 37 | A |
| 26 | Q | N | −26.5 | −33.5 | −13.5 | 35 | A |
| 26 | Q | CA | −26.0 | −34.7 | −14.2 | 36 | A |
| 26 | Q | C | −24.5 | −34.9 | −14.2 | 38 | A |
| 26 | Q | O | −24.0 | −36.0 | −14.3 | 38 | A |
| 26 | Q | CB | −26.5 | −34.7 | −15.7 | 38 | A |
| 26 | Q | CG | −26.3 | −36.1 | −16.3 | 29 | A |
| 26 | Q | CD | −26.7 | −36.1 | −17.8 | 40 | A |
| 26 | Q | OE1 | −27.4 | −35.2 | −18.3 | 34 | A |
| 26 | Q | NE2 | −26.3 | −37.2 | −18.5 | 32 | A |
| 27 | F | N | −23.7 | −33.7 | −14.1 | 32 | A |
| 27 | F | CA | −22.3 | −33.6 | −14.0 | 30 | A |
| 27 | F | C | −22.0 | −32.6 | −12.9 | 31 | A |
| 27 | F | O | −21.4 | −31.5 | −13.1 | 32 | A |
| 27 | F | CB | −21.6 | −33.2 | −15.3 | 31 | A |

TABLE 3-continued

Coordinates of Factor IXa co-crystal Compound B complex

| | | | | | | |
|---|---|---|---|---|---|---|
| 27 | F | CG | −22.0 | −34.1 | −16.4 | 33 | A |
| 27 | F | CD1 | −23.1 | −33.8 | −17.3 | 34 | A |
| 27 | F | CD2 | −21.3 | −35.3 | −16.6 | 33 | A |
| 27 | F | CE1 | −23.5 | −34.8 | −18.2 | 34 | A |
| 27 | F | CE2 | −21.6 | −36.2 | −17.6 | 34 | A |
| 27 | F | CZ | −22.8 | −36.0 | −18.4 | 32 | A |
| 28 | P | N | −22.3 | −32.9 | −11.6 | 26 | A |
| 28 | P | CA | −22.2 | −31.9 | −10.5 | 25 | A |
| 28 | P | C | −20.8 | −31.5 | −10.2 | 31 | A |
| 28 | P | O | −20.6 | −30.6 | −9.3 | 29 | A |
| 28 | P | CB | −22.9 | −32.7 | −9.4 | 26 | A |
| 28 | P | CG | −22.8 | −34.1 | −9.7 | 31 | A |
| 28 | P | CD | −22.9 | −34.2 | −11.2 | 27 | A |
| 29 | W | N | −19.8 | −32.2 | −10.7 | 29 | A |
| 29 | W | CA | −18.4 | −31.9 | −10.4 | 28 | A |
| 29 | W | C | −17.9 | −30.8 | −11.4 | 33 | A |
| 29 | W | O | −16.9 | −30.3 | −11.2 | 35 | A |
| 29 | W | CB | −17.5 | −33.1 | −10.5 | 26 | A |
| 29 | W | CG | −17.9 | −33.9 | −11.7 | 26 | A |
| 29 | W | CD1 | −17.5 | −33.7 | −13.0 | 29 | A |
| 29 | W | CD2 | −18.7 | −35.1 | −11.8 | 26 | A |
| 29 | W | NE1 | −18.0 | −34.6 | −13.9 | 28 | A |
| 29 | W | CE2 | −18.8 | −35.5 | −13.1 | 30 | A |
| 29 | W | CE3 | −19.4 | −35.8 | −10.8 | 27 | A |
| 29 | W | CZ2 | −19.6 | −36.5 | −13.6 | 29 | A |
| 29 | W | CZ3 | −20.2 | −36.9 | −11.2 | 29 | A |
| 29 | W | CH2 | −20.3 | −37.2 | −12.6 | 29 | A |
| 30 | Q | N | −18.7 | −30.5 | −12.4 | 29 | A |
| 30 | Q | CA | −18.4 | −29.5 | −13.4 | 29 | A |
| 30 | Q | C | −18.4 | −28.1 | −13.0 | 33 | A |
| 30 | Q | O | −19.4 | −27.7 | −12.2 | 32 | A |
| 30 | Q | CB | −19.5 | −29.7 | −14.6 | 29 | A |
| 30 | Q | CG | −19.3 | −28.7 | −15.8 | 28 | A |
| 30 | Q | CD | −18.0 | −29.0 | −16.7 | 41 | A |
| 30 | Q | OE1 | −17.2 | −28.2 | −16.9 | 36 | A |
| 30 | Q | NE2 | −18.1 | −30.2 | −17.3 | 33 | A |
| 31 | V | N | −17.4 | −27.3 | −13.4 | 27 | A |
| 31 | V | CA | −17.4 | −25.9 | −13.1 | 26 | A |
| 31 | V | C | −17.1 | −25.1 | −14.4 | 33 | A |
| 31 | V | O | −16.6 | −25.7 | −15.4 | 32 | A |
| 31 | V | CB | −16.6 | −25.5 | −11.9 | 28 | A |
| 31 | V | CG1 | −16.9 | −26.3 | −10.6 | 27 | A |
| 31 | V | CG2 | −15.1 | −25.4 | −12.2 | 27 | A |
| 32 | V | N | −17.4 | −23.8 | −14.4 | 31 | A |
| 32 | V | CA | −17.0 | −22.9 | −15.5 | 30 | A |
| 32 | V | C | −16.2 | −21.8 | −14.8 | 30 | A |
| 32 | V | O | −16.5 | −21.4 | −13.7 | 28 | A |
| 32 | V | CB | −18.3 | −22.3 | −16.2 | 34 | A |
| 32 | V | CG1 | −19.2 | −21.4 | −15.3 | 32 | A |
| 32 | V | CG2 | −17.9 | −21.6 | −17.5 | 33 | A |
| 33 | L | N | −15.2 | −21.3 | −15.6 | 31 | A |
| 33 | L | CA | −14.3 | −20.2 | −15.2 | 32 | A |
| 33 | L | C | −14.8 | −19.0 | −16.0 | 40 | A |
| 33 | L | O | −15.1 | −19.1 | −17.2 | 39 | A |
| 33 | L | CB | −12.9 | −20.5 | −15.5 | 31 | A |
| 33 | L | CG | −12.3 | −21.9 | −15.0 | 35 | A |
| 33 | L | CD1 | −10.9 | −21.9 | −14.9 | 33 | A |
| 33 | L | CD2 | −12.9 | −22.2 | −13.6 | 37 | A |
| 34 | N | N | −14.8 | −17.8 | −15.3 | 39 | A |
| 34 | N | CA | −15.1 | −16.5 | −15.9 | 39 | A |
| 34 | N | C | −14.0 | −15.6 | −15.5 | 43 | A |
| 34 | N | O | −13.5 | −15.7 | −14.4 | 44 | A |
| 34 | N | CB | −16.4 | −15.9 | −15.2 | 34 | A |
| 34 | N | CG | −17.6 | −16.8 | −15.4 | 45 | A |
| 34 | N | OD1 | −17.9 | −17.2 | −16.5 | 40 | A |
| 34 | N | ND2 | −18.1 | −17.1 | −14.3 | 43 | A |
| 35 | G | N | −13.5 | −14.8 | −16.5 | 42 | A |
| 35 | G | CA | −12.4 | −13.9 | −16.3 | 44 | A |
| 35 | G | C | −12.7 | −12.7 | −17.2 | 54 | A |
| 35 | G | O | −13.8 | −12.2 | −17.3 | 52 | A |
| 36 | K | N | −11.7 | −12.3 | −18.0 | 57 | A |
| 36 | K | CA | −11.8 | −11.3 | −19.0 | 59 | A |
| 36 | K | C | −13.1 | −11.6 | −19.9 | 63 | A |
| 36 | K | O | −14.0 | −10.8 | −20.0 | 63 | A |
| 36 | K | CB | −10.6 | −11.1 | −20.0 | 63 | A |
| 36 | K | CG | −9.3 | −11.6 | −19.3 | 83 | A |
| 36 | K | CD | −8.1 | −11.2 | −20.2 | 94 | A |
| 36 | K | CE | −7.0 | −10.5 | −19.4 | 99 | A |
| 36 | K | NZ | −6.0 | −9.8 | −20.3 | 98 | A |
| 38 | V | N | −13.1 | −12.9 | −20.3 | 57 | A |
| 38 | V | CA | −14.2 | −13.4 | −21.1 | 54 | A |
| 38 | V | C | −14.9 | −14.4 | −20.1 | 54 | A |
| 38 | V | O | −14.3 | −15.0 | −19.2 | 53 | A |
| 38 | V | CB | −13.8 | −14.1 | −22.4 | 56 | A |
| 38 | V | CG1 | −15.0 | −14.9 | −23.0 | 55 | A |
| 38 | V | CG2 | −13.3 | −13.1 | −23.4 | 56 | A |
| 39 | D | N | −16.3 | −14.4 | −20.2 | 48 | A |
| 39 | D | CA | −17.0 | −15.3 | −19.3 | 47 | A |
| 39 | D | C | −17.0 | −16.7 | −20.0 | 48 | A |
| 39 | D | O | −16.9 | −16.8 | −21.3 | 47 | A |
| 39 | D | CB | −18.5 | −14.8 | −19.2 | 49 | A |
| 39 | D | CG | −18.7 | −14.0 | −17.9 | 63 | A |
| 39 | D | OD1 | −17.7 | −13.3 | −17.5 | 65 | A |
| 39 | D | OD2 | −19.8 | −14.1 | −17.4 | 68 | A |
| 40 | A | N | −17.1 | −17.7 | −19.2 | 43 | A |
| 40 | A | CA | −17.2 | −19.1 | −19.7 | 42 | A |
| 40 | A | C | −16.0 | −19.4 | −20.7 | 45 | A |
| 40 | A | O | −16.2 | −19.9 | −21.8 | 45 | A |
| 40 | A | CB | −18.6 | −19.4 | −20.4 | 43 | A |
| 41 | F | N | −14.8 | −18.9 | −20.3 | 39 | A |
| 41 | F | CA | −13.7 | −19.1 | −21.2 | 38 | A |
| 41 | F | C | −13.0 | −20.5 | −21.1 | 42 | A |
| 41 | F | O | −12.3 | −20.9 | −22.0 | 44 | A |
| 41 | F | CB | −12.7 | −18.0 | −21.0 | 38 | A |
| 41 | F | CG | −11.9 | −18.1 | −19.7 | 38 | A |
| 41 | F | CD1 | −12.4 | −17.6 | −18.5 | 37 | A |
| 41 | F | CD2 | −10.6 | −18.7 | −19.8 | 36 | A |
| 41 | F | CE1 | −11.6 | −17.7 | −17.4 | 36 | A |
| 41 | F | CE2 | −9.9 | −18.8 | −18.6 | 38 | A |
| 41 | F | CZ | −10.4 | −18.4 | −17.4 | 34 | A |
| 42 | C | N | −13.2 | −21.2 | −20.0 | 37 | A |
| 42 | C | CA | −12.6 | −22.5 | −19.8 | 36 | A |
| 42 | C | C | −13.5 | −23.3 | −18.8 | 35 | A |
| 42 | C | O | −14.3 | −22.7 | −18.1 | 32 | A |
| 42 | C | CB | −11.2 | −22.4 | −19.2 | 38 | A |
| 42 | C | SG | −9.9 | −22.5 | −20.5 | 44 | A |
| 43 | G | N | −13.3 | −24.6 | −18.6 | 30 | A |
| 43 | G | CA | −14.0 | −25.4 | −17.7 | 28 | A |
| 43 | G | C | −13.1 | −25.9 | −16.6 | 28 | A |
| 43 | G | O | −11.9 | −25.6 | −16.6 | 29 | A |
| 44 | G | N | −13.6 | −26.6 | −15.6 | 24 | A |
| 44 | G | CA | −12.9 | −27.1 | −14.5 | 23 | A |
| 44 | G | C | −13.7 | −28.2 | −13.8 | 26 | A |
| 44 | G | O | −14.8 | −28.4 | −14.2 | 25 | A |
| 45 | S | N | −13.1 | −28.9 | −12.8 | 25 | A |
| 45 | S | CA | −13.7 | −29.9 | −11.9 | 25 | A |
| 45 | S | C | −13.5 | −29.7 | −10.6 | 29 | A |
| 45 | S | O | −12.4 | −29.2 | −10.2 | 26 | A |
| 45 | S | CB | −13.1 | −31.3 | −12.4 | 27 | A |
| 45 | S | OG | −13.1 | −31.6 | −13.7 | 45 | A |
| 46 | I | N | −14.5 | −30.1 | −9.8 | 29 | A |
| 46 | I | CA | −14.3 | −29.9 | −8.3 | 28 | A |
| 46 | I | C | −13.5 | −31.1 | −7.7 | 31 | A |
| 46 | I | O | −13.9 | −32.3 | −7.9 | 29 | A |
| 46 | I | CB | −15.8 | −29.9 | −7.7 | 31 | A |
| 46 | I | CG1 | −16.5 | −28.7 | −8.2 | 31 | A |
| 46 | I | CG2 | −15.7 | −29.9 | −6.2 | 32 | A |
| 46 | I | CD1 | −18.0 | −28.7 | −7.7 | 33 | A |
| 47 | V | N | −12.5 | −30.8 | −7.0 | 25 | A |
| 47 | V | CA | −11.7 | −31.8 | −6.4 | 24 | A |
| 47 | V | C | −12.2 | −31.9 | −4.9 | 33 | A |
| 47 | V | O | −12.4 | −33.0 | −4.4 | 33 | A |
| 47 | V | CB | −10.2 | −31.4 | −6.4 | 25 | A |
| 47 | V | CG1 | −9.4 | −32.3 | −5.4 | 24 | A |
| 47 | V | CG2 | −9.6 | −31.3 | −7.8 | 24 | A |
| 48 | N | N | −12.5 | −30.8 | −4.3 | 30 | A |
| 48 | N | CA | −13.1 | −30.7 | −3.0 | 30 | A |
| 48 | N | C | −13.7 | −29.3 | −2.8 | 36 | A |
| 48 | N | O | −13.8 | −28.6 | −3.8 | 34 | A |
| 48 | N | CB | −12.2 | −31.2 | −1.9 | 27 | A |
| 48 | N | CG | −11.0 | −30.3 | −1.7 | 38 | A |
| 48 | N | OD1 | −11.1 | −29.1 | −1.7 | 30 | A |
| 48 | N | ND2 | −9.8 | −30.9 | −1.4 | 30 | A |
| 49 | E | N | −14.2 | −29.0 | −1.7 | 33 | A |
| 49 | E | CA | −14.9 | −27.7 | −1.5 | 32 | A |
| 49 | E | C | −14.1 | −26.4 | −1.7 | 33 | A |

TABLE 3-continued

Coordinates of Factor IXa co-crystal Compound B complex

| | | | | | | |
|---|---|---|---|---|---|---|
| 49 | E | O | −14.6 | −25.4 | −1.9 | 33 A |
| 49 | E | CB | −15.7 | −27.6 | −0.1 | 33 A |
| 49 | E | CG | −16.3 | −28.9 | 0.3 | 53 A |
| 49 | E | CD | −15.6 | −29.5 | 1.4 | 88 A |
| 49 | E | OE1 | −15.7 | −28.9 | 2.6 | 74 A |
| 49 | E | OE2 | −14.9 | −30.5 | 1.2 | 76 A |
| 50 | K | N | −12.8 | −26.6 | −1.5 | 28 A |
| 50 | K | CA | −11.9 | −25.4 | −1.7 | 27 A |
| 50 | K | C | −11.1 | −25.5 | −3.0 | 30 A |
| 50 | K | O | −10.4 | −24.5 | −3.3 | 32 A |
| 50 | K | CB | −11.0 | −25.3 | −0.4 | 31 A |
| 50 | K | CG | −11.6 | −24.7 | 0.8 | 39 A |
| 50 | K | CD | −11.6 | −23.1 | 0.7 | 44 A |
| 50 | K | CE | −10.3 | −22.5 | 1.2 | 41 A |
| 50 | K | NZ | −10.3 | −21.0 | 1.1 | 50 A |
| 51 | W | N | −11.1 | −26.6 | −3.7 | 27 A |
| 51 | W | CA | −10.2 | −26.8 | −4.9 | 26 A |
| 51 | W | C | −10.8 | −27.2 | −6.2 | 29 A |
| 51 | W | O | −11.6 | −28.2 | −6.2 | 30 A |
| 51 | W | CB | −9.1 | −27.7 | −4.5 | 25 A |
| 51 | W | CG | −8.2 | −27.2 | −3.4 | 25 A |
| 51 | W | CD1 | −8.3 | −27.3 | −2.1 | 27 A |
| 51 | W | CD2 | −7.0 | −26.4 | −3.6 | 25 A |
| 51 | W | NE1 | −7.3 | −26.7 | −1.4 | 26 A |
| 51 | W | CE2 | −6.5 | −26.1 | −2.4 | 27 A |
| 51 | W | CE3 | −6.3 | −26.0 | −4.8 | 25 A |
| 51 | W | CZ2 | −5.4 | −25.3 | −2.2 | 26 A |
| 51 | W | CZ3 | −5.2 | −25.2 | −4.6 | 26 A |
| 51 | W | CH2 | −4.7 | −24.8 | −3.3 | 27 A |
| 52 | I | N | −10.4 | −26.6 | −7.3 | 25 A |
| 52 | I | CA | −10.8 | −26.9 | −8.6 | 24 A |
| 52 | I | C | −9.6 | −27.3 | −9.3 | 29 A |
| 52 | I | O | −8.5 | −26.8 | −9.1 | 29 A |
| 52 | I | CB | −11.4 | −25.6 | −9.3 | 28 A |
| 52 | I | CG1 | −12.7 | −25.1 | −8.5 | 26 A |
| 52 | I | CG2 | −11.7 | −25.8 | −10.8 | 28 A |
| 52 | I | CD1 | −13.8 | −26.1 | −8.2 | 30 A |
| 53 | V | N | −9.7 | −28.3 | −10.3 | 25 A |
| 53 | V | CA | −8.6 | −28.7 | −11.1 | 24 A |
| 53 | V | C | −9.0 | −28.3 | −12.6 | 30 A |
| 53 | V | O | −10.1 | −28.5 | −13.0 | 29 A |
| 53 | V | CB | −8.1 | −30.1 | −11.0 | 27 A |
| 53 | V | CG1 | −6.8 | −30.3 | −11.8 | 25 A |
| 53 | V | CG2 | −9.2 | −31.1 | −11.5 | 27 A |
| 54 | T | N | −8.0 | −27.7 | −13.2 | 25 A |
| 54 | T | CA | −8.3 | −27.2 | −14.6 | 25 A |
| 54 | T | C | −7.0 | −27.4 | −15.4 | 28 A |
| 54 | T | O | −6.0 | −28.0 | −14.9 | 25 A |
| 54 | T | CB | −8.7 | −25.7 | −14.5 | 33 A |
| 54 | T | OG1 | −9.1 | −25.2 | −15.8 | 34 A |
| 54 | T | CG2 | −7.6 | −24.8 | −13.8 | 26 A |
| 55 | A | N | −7.0 | −26.8 | −16.6 | 25 A |
| 55 | A | CA | −5.8 | −26.8 | −17.5 | 25 A |
| 55 | A | C | −4.9 | −25.5 | −17.2 | 31 A |
| 55 | A | O | −5.5 | −24.5 | −16.9 | 31 A |
| 55 | A | CB | −6.3 | −26.7 | −18.9 | 25 A |
| 56 | A | N | −3.6 | −25.7 | −17.1 | 28 A |
| 56 | A | CA | −2.7 | −24.6 | −16.8 | 27 A |
| 56 | A | C | −2.8 | −23.5 | −17.9 | 34 A |
| 56 | A | O | −2.7 | −22.3 | −17.5 | 34 A |
| 56 | A | CB | −1.3 | −25.1 | −16.6 | 27 A |
| 57 | H | N | −3.0 | −23.8 | −19.2 | 32 A |
| 57 | H | CA | −3.0 | −22.7 | −20.2 | 31 A |
| 57 | H | C | −4.2 | −21.8 | −20.1 | 36 A |
| 57 | H | O | −4.3 | −20.8 | −20.7 | 36 A |
| 57 | H | CB | −2.9 | −23.4 | −21.6 | 31 A |
| 57 | H | CG | −4.1 | −24.0 | −22.1 | 34 A |
| 57 | H | ND1 | −4.4 | −25.3 | −22.1 | 36 A |
| 57 | H | CD2 | −5.3 | −23.4 | −22.6 | 35 A |
| 57 | H | CE1 | −5.6 | −25.6 | −22.5 | 34 A |
| 57 | H | NE2 | −6.2 | −24.4 | −22.9 | 35 A |
| 58 | C | N | −5.2 | −22.2 | −19.2 | 37 A |
| 58 | C | CA | −6.4 | −21.4 | −19.1 | 38 A |
| 58 | C | C | −6.2 | −20.3 | −18.0 | 44 A |
| 58 | C | O | −7.1 | −19.4 | −17.9 | 44 A |
| 58 | C | CB | −7.5 | −22.3 | −18.5 | 39 A |
| 58 | C | SG | −8.2 | −23.4 | −19.7 | 44 A |
| 59 | V | N | −5.2 | −20.5 | −17.2 | 41 A |
| 59 | V | CA | −5.0 | −19.6 | −16.1 | 41 A |
| 59 | V | C | −3.6 | −19.0 | −16.0 | 54 A |
| 59 | V | O | −2.9 | −19.1 | −16.9 | 55 A |
| 59 | V | CB | −5.5 | −20.2 | −14.8 | 42 A |
| 59 | V | CG1 | −7.0 | −20.5 | −14.8 | 40 A |
| 59 | V | CG2 | −4.8 | −21.5 | −14.5 | 41 A |
| 60 | E | N | −3.4 | −18.2 | −14.9 | 57 A |
| 60 | E | CA | −2.2 | −17.5 | −14.7 | 61 A |
| 60 | E | C | −2.4 | −16.5 | −13.6 | 69 A |
| 60 | E | O | −3.3 | −15.7 | −13.6 | 67 A |
| 60 | E | CB | −1.7 | −16.8 | −16.0 | 63 A |
| 60 | E | CG | −2.3 | −15.4 | −16.2 | 75 A |
| 60 | E | CD | −2.0 | −14.9 | −17.6 | 0 A |
| 60 | E | OE1 | −0.9 | −14.3 | −17.8 | 95 A |
| 60 | E | OE2 | −2.8 | −15.1 | −18.5 | 99 A |
| 60A | T | N | −1.5 | −16.6 | −12.5 | 69 A |
| 60A | T | CA | −1.5 | −15.7 | −11.4 | 70 A |
| 60A | T | C | −1.5 | −14.3 | −11.9 | 75 A |
| 60A | T | O | −0.9 | −14.0 | −13.0 | 76 A |
| 60A | T | CB | −0.3 | −16.1 | −10.4 | 79 A |
| 60A | T | OG1 | −0.4 | −17.4 | −9.8 | 72 A |
| 60A | T | CG2 | −0.1 | −15.0 | −9.3 | 78 A |
| 61 | G | N | −2.3 | −13.4 | −11.3 | 69 A |
| 61 | G | CA | −2.4 | −12.1 | −11.8 | 68 A |
| 61 | G | C | −3.7 | −11.7 | −12.4 | 69 A |
| 61 | G | O | −4.2 | −10.6 | −12.2 | 70 A |
| 62 | V | N | −4.2 | −12.7 | −13.2 | 62 A |
| 62 | V | CA | −5.5 | −12.5 | −13.9 | 58 A |
| 62 | V | C | −6.6 | −13.0 | −13.0 | 57 A |
| 62 | V | O | −6.7 | −14.2 | −12.7 | 55 A |
| 62 | V | CB | −5.5 | −13.3 | −15.3 | 61 A |
| 62 | V | CG1 | −6.7 | −12.9 | −16.1 | 59 A |
| 62 | V | CG2 | −4.2 | −13.2 | −16.0 | 60 A |
| 63 | K | N | −7.5 | −12.1 | −12.6 | 52 A |
| 63 | K | CA | −8.6 | −12.4 | −11.6 | 51 A |
| 63 | K | C | −9.7 | −13.3 | −12.2 | 51 A |
| 63 | K | O | −10.3 | −13.0 | −13.2 | 50 A |
| 63 | K | CB | −9.1 | −11.1 | −11.1 | 54 A |
| 63 | K | CG | −10.1 | −11.3 | −9.9 | 78 A |
| 63 | K | CD | −11.4 | −10.6 | −10.1 | 93 A |
| 63 | K | CE | −12.6 | −11.5 | −10.1 | 99 A |
| 63 | K | NZ | −13.5 | −11.4 | −8.9 | 0 A |
| 64 | I | N | −9.8 | −14.5 | −11.6 | 45 A |
| 64 | I | CA | −10.8 | −15.5 | −12.0 | 43 A |
| 64 | I | C | −11.9 | −15.8 | −11.0 | 41 A |
| 64 | I | O | −11.7 | −15.9 | −9.8 | 39 A |
| 64 | I | CB | −10.0 | −16.8 | −12.4 | 47 A |
| 64 | I | CG1 | −9.2 | −16.5 | −13.7 | 48 A |
| 64 | I | CG2 | −10.9 | −18.0 | −12.6 | 49 A |
| 64 | I | CD1 | −10.1 | −15.8 | −14.7 | 47 A |
| 65 | T | N | −13.1 | −16.1 | −11.6 | 36 A |
| 65 | T | CA | −14.2 | −16.6 | −10.7 | 35 A |
| 65 | T | C | −14.6 | −18.0 | −11.2 | 38 A |
| 65 | T | O | −14.5 | −18.3 | −12.4 | 35 A |
| 65 | T | CB | −15.4 | −15.7 | −10.6 | 46 A |
| 65 | T | OG1 | −16.0 | −15.5 | −11.8 | 46 A |
| 65 | T | CG2 | −14.9 | −14.3 | −10.0 | 39 A |
| 66 | V | N | −15.1 | −18.8 | −10.4 | 34 A |
| 66 | V | CA | −15.6 | −20.2 | −10.6 | 33 A |
| 66 | V | C | −17.1 | −20.3 | −10.3 | 36 A |
| 66 | V | O | −17.5 | −19.8 | −9.3 | 37 A |
| 66 | V | CB | −14.8 | −21.2 | −9.8 | 36 A |
| 66 | V | CG1 | −15.4 | −22.6 | −9.8 | 37 A |
| 66 | V | CG2 | −13.3 | −21.2 | −10.2 | 36 A |
| 67 | V | N | −17.9 | −21.0 | −11.2 | 32 A |
| 67 | V | CA | −19.3 | −21.2 | −10.9 | 30 A |
| 67 | V | C | −19.6 | −22.7 | −10.9 | 34 A |
| 67 | V | O | −19.6 | −23.4 | −12.0 | 33 A |
| 67 | V | CB | −20.2 | −20.4 | −11.9 | 33 A |
| 67 | V | CG1 | −21.7 | −20.5 | −11.4 | 31 A |
| 67 | V | CG2 | −19.8 | −18.9 | −12.0 | 33 A |
| 68 | A | N | −19.9 | −23.2 | −9.7 | 32 A |
| 68 | A | CA | −20.3 | −24.6 | −9.5 | 32 A |
| 68 | A | C | −21.9 | −24.6 | −9.6 | 38 A |
| 68 | A | O | −22.5 | −23.6 | −9.4 | 39 A |
| 68 | A | CB | −19.8 | −25.1 | −8.2 | 32 A |
| 69 | G | N | −22.5 | −25.8 | −9.9 | 34 A |
| 69 | G | CA | −23.9 | −25.9 | −9.9 | 33 A |

TABLE 3-continued

Coordinates of Factor IXa co-crystal Compound B complex

| | | | | | | |
|---|---|---|---|---|---|---|
| 69 | G | C | −24.6 | −25.2 | −11.1 | 39 | A |
| 69 | G | O | −25.8 | −25.0 | −11.1 | 41 | A |
| 70 | E | N | −23.8 | −24.9 | −12.1 | 34 | A |
| 70 | E | CA | −24.3 | −24.3 | −13.3 | 33 | A |
| 70 | E | C | −24.9 | −25.3 | −14.3 | 41 | A |
| 70 | E | O | −24.5 | −26.4 | −14.4 | 42 | A |
| 70 | E | CB | −23.2 | −23.5 | −13.9 | 33 | A |
| 70 | E | CG | −23.6 | −22.6 | −15.1 | 37 | A |
| 70 | E | CD | −24.7 | −21.6 | −14.7 | 58 | A |
| 70 | E | OE1 | −25.8 | −22.1 | −14.6 | 57 | A |
| 70 | E | OE2 | −24.4 | −20.4 | −14.4 | 45 | A |
| 71 | H | N | −26.0 | −24.9 | −14.9 | 39 | A |
| 71 | H | CA | −26.7 | −25.7 | −15.9 | 39 | A |
| 71 | H | C | −27.0 | −24.9 | −17.2 | 44 | A |
| 71 | H | O | −26.3 | −25.1 | −18.2 | 44 | A |
| 71 | H | CB | −28.1 | −26.2 | −15.3 | 40 | A |
| 71 | H | CG | −28.9 | −26.9 | −16.3 | 45 | A |
| 71 | H | ND1 | −28.5 | −28.0 | −17.1 | 47 | A |
| 71 | H | CD2 | −30.2 | −26.6 | −16.8 | 46 | A |
| 71 | H | CE1 | −29.5 | −28.4 | −17.9 | 47 | A |
| 71 | H | NE2 | −30.5 | −27.6 | −17.7 | 47 | A |
| 72 | N | N | −27.8 | −23.9 | −17.1 | 42 | A |
| 72 | N | CA | −28.1 | −22.9 | −18.2 | 42 | A |
| 72 | N | C | −27.4 | −21.6 | −17.8 | 49 | A |
| 72 | N | O | −27.8 | −21.0 | −16.8 | 48 | A |
| 72 | N | CB | −29.6 | −22.7 | −18.3 | 43 | A |
| 72 | N | CG | −29.9 | −21.9 | −19.5 | 54 | A |
| 72 | N | OD1 | −29.1 | −21.1 | −20.1 | 42 | A |
| 72 | N | ND2 | −31.2 | −22.1 | −20.0 | 44 | A |
| 73 | I | N | −26.4 | −21.2 | −18.5 | 49 | A |
| 73 | I | CA | −25.6 | −20.0 | −18.3 | 51 | A |
| 73 | I | C | −26.4 | −18.7 | −18.3 | 59 | A |
| 73 | I | O | −26.0 | −17.6 | −17.9 | 60 | A |
| 73 | I | CB | −24.4 | −19.9 | −19.2 | 55 | A |
| 73 | I | CG1 | −23.3 | −20.9 | −18.8 | 55 | A |
| 73 | I | CG2 | −23.7 | −18.6 | −19.1 | 59 | A |
| 73 | I | CD1 | −22.0 | −20.6 | −19.4 | 59 | A |
| 74 | E | N | −27.7 | −18.8 | −18.8 | 57 | A |
| 74 | E | CA | −28.5 | −17.6 | −19.0 | 57 | A |
| 74 | E | C | −29.8 | −17.6 | −18.2 | 61 | A |
| 74 | E | O | −30.7 | −16.9 | −18.6 | 62 | A |
| 74 | E | CB | −28.6 | −17.2 | −20.4 | 58 | A |
| 74 | E | CG | −29.9 | −17.8 | −21.1 | 71 | A |
| 74 | E | CD | −30.2 | −17.0 | −22.4 | 93 | A |
| 74 | E | OE1 | −29.4 | −16.1 | −22.8 | 0 | A |
| 74 | E | OE2 | −31.2 | −17.4 | −23.0 | 66 | A |
| 75 | E | N | −29.9 | −18.3 | −17.2 | 55 | A |
| 75 | E | CA | −31.1 | −18.4 | −16.4 | 54 | A |
| 75 | E | C | −30.9 | −18.9 | −15.0 | 58 | A |
| 75 | E | O | −30.5 | −20.1 | −14.8 | 59 | A |
| 75 | E | CB | −32.1 | −19.4 | −17.2 | 56 | A |
| 75 | E | CG | −33.5 | −19.2 | −16.7 | 72 | A |
| 75 | E | CD | −34.4 | −20.5 | −16.9 | 0 | A |
| 75 | E | OE1 | −34.7 | −20.9 | −18.0 | 0 | A |
| 75 | E | OE2 | −34.7 | −21.1 | −15.8 | 90 | A |
| 76 | T | N | −31.0 | −18.0 | −14.1 | 55 | A |
| 76 | T | CA | −30.7 | −18.4 | −12.7 | 54 | A |
| 76 | T | C | −31.6 | −19.5 | −12.2 | 57 | A |
| 76 | T | O | −32.8 | −19.5 | −12.3 | 58 | A |
| 76 | T | CB | −31.0 | −17.2 | −11.8 | 62 | A |
| 76 | T | OG1 | −30.0 | −16.2 | −12.1 | 61 | A |
| 76 | T | CG2 | −30.9 | −17.6 | −10.3 | 62 | A |
| 77 | E | N | −31.0 | −20.6 | −11.8 | 50 | A |
| 77 | E | CA | −31.8 | −21.8 | −11.3 | 48 | A |
| 77 | E | C | −31.6 | −22.1 | −9.9 | 48 | A |
| 77 | E | O | −32.2 | −23.1 | −9.4 | 46 | A |
| 77 | E | CB | −31.5 | −23.0 | −12.2 | 48 | A |
| 77 | E | CG | −31.5 | −22.6 | −13.7 | 55 | A |
| 77 | E | CD | −30.5 | −23.4 | −14.5 | 70 | A |
| 77 | E | OE1 | −29.3 | −23.0 | −14.6 | 52 | A |
| 77 | E | OE2 | −30.9 | −24.4 | −15.2 | 50 | A |
| 78 | H | N | −31.0 | −21.2 | −9.1 | 45 | A |
| 78 | H | CA | −30.9 | −21.3 | −7.7 | 48 | A |
| 78 | H | C | −30.0 | −22.5 | −7.2 | 49 | A |
| 78 | H | O | −30.1 | −23.0 | −6.1 | 50 | A |
| 78 | H | CB | −32.2 | −21.3 | −7.0 | 50 | A |
| 78 | H | CG | −33.0 | −20.1 | −7.5 | 56 | A |
| 78 | H | ND1 | −32.7 | −18.8 | −7.1 | 59 | A |
| 78 | H | CD2 | −34.0 | −20.0 | −8.4 | 59 | A |
| 78 | H | CE1 | −33.5 | −17.9 | −7.8 | 59 | A |
| 78 | H | NE2 | −34.3 | −18.6 | −8.6 | 60 | A |
| 79 | T | N | −29.2 | −23.0 | −8.1 | 43 | A |
| 79 | T | CA | −28.4 | −24.2 | −7.7 | 41 | A |
| 79 | T | C | −26.9 | −23.7 | −7.8 | 38 | A |
| 79 | T | O | −26.1 | −24.4 | −7.2 | 35 | A |
| 79 | T | CB | −28.6 | −25.4 | −8.7 | 45 | A |
| 79 | T | OG1 | −28.5 | −24.9 | −10.0 | 44 | A |
| 79 | T | CG2 | −30.0 | −25.9 | −8.4 | 41 | A |
| 80 | E | N | −26.6 | −22.6 | −8.4 | 33 | A |
| 80 | E | CA | −25.3 | −22.1 | −8.6 | 32 | A |
| 80 | E | C | −24.5 | −21.6 | −7.4 | 38 | A |
| 80 | E | O | −25.1 | −20.9 | −6.6 | 41 | A |
| 80 | E | CB | −25.2 | −21.1 | −9.7 | 33 | A |
| 80 | E | CG | −26.0 | −21.3 | −11.0 | 48 | A |
| 80 | E | CD | −27.6 | −21.1 | −10.8 | 67 | A |
| 80 | E | OE1 | −28.0 | −20.9 | −9.7 | 62 | A |
| 80 | E | OE2 | −28.3 | −21.1 | −11.9 | 57 | A |
| 81 | Q | N | −23.2 | −21.8 | −7.4 | 31 | A |
| 81 | Q | CA | −22.4 | −21.2 | −6.4 | 29 | A |
| 81 | Q | C | −21.2 | −20.6 | −7.1 | 33 | A |
| 81 | Q | O | −20.4 | −21.3 | −7.7 | 31 | A |
| 81 | Q | CB | −22.0 | −22.3 | −5.4 | 30 | A |
| 81 | Q | CG | −23.1 | −22.8 | −4.6 | 30 | A |
| 81 | Q | CD | −22.7 | −23.9 | −3.7 | 37 | A |
| 81 | Q | OE1 | −21.7 | −23.9 | −3.0 | 32 | A |
| 81 | Q | NE2 | −23.6 | −25.0 | −3.6 | 33 | A |
| 82 | K | N | −21.0 | −19.3 | −6.9 | 28 | A |
| 82 | K | CA | −19.9 | −18.6 | −7.5 | 27 | A |
| 82 | K | C | −18.9 | −18.3 | −6.4 | 35 | A |
| 82 | K | O | −19.2 | −18.1 | −5.2 | 33 | A |
| 82 | K | CB | −20.4 | −17.3 | −8.1 | 25 | A |
| 82 | K | CG | −19.4 | −16.6 | −9.0 | 37 | A |
| 82 | K | CD | −19.9 | −15.3 | −9.4 | 46 | A |
| 82 | K | CE | −19.2 | −14.1 | −8.7 | 69 | A |
| 82 | K | NZ | −19.5 | −12.8 | −9.4 | 88 | A |
| 83 | R | N | −17.6 | −18.3 | −6.8 | 32 | A |
| 83 | R | CA | −16.5 | −18.1 | −5.8 | 30 | A |
| 83 | R | C | −15.3 | −17.4 | −6.5 | 34 | A |
| 83 | R | O | −15.1 | −17.6 | −7.7 | 36 | A |
| 83 | R | CB | −16.1 | −19.5 | −5.3 | 29 | A |
| 83 | R | CG | −17.2 | −20.2 | −4.5 | 33 | A |
| 83 | R | CD | −17.2 | −19.6 | −3.1 | 31 | A |
| 83 | R | NE | −18.1 | −20.4 | −2.2 | 33 | A |
| 83 | R | CZ | −19.4 | −20.4 | −2.3 | 36 | A |
| 83 | R | NH1 | −20.0 | −19.7 | −3.2 | 27 | A |
| 83 | R | NH2 | −20.2 | −21.1 | −1.5 | 29 | A |
| 84 | N | N | −14.5 | −16.7 | −5.8 | 30 | A |
| 84 | N | CA | −13.4 | −16.1 | −6.3 | 30 | A |
| 84 | N | C | −12.2 | −17.0 | −6.1 | 38 | A |
| 84 | N | O | −12.1 | −17.7 | −5.1 | 40 | A |
| 84 | N | CB | −13.1 | −14.8 | −5.5 | 30 | A |
| 84 | N | CG | −14.0 | −13.7 | −5.8 | 49 | A |
| 84 | N | OD1 | −15.0 | −13.7 | −6.6 | 39 | A |
| 84 | N | ND2 | −13.8 | −12.6 | −5.1 | 40 | A |
| 85 | V | N | −11.3 | −17.0 | −7.1 | 33 | A |
| 85 | V | CA | −10.1 | −17.8 | −7.0 | 33 | A |
| 85 | V | C | −9.0 | −17.0 | −6.3 | 39 | A |
| 85 | V | O | −8.7 | −15.9 | −6.7 | 40 | A |
| 85 | V | CB | −9.6 | −18.3 | −8.5 | 35 | A |
| 85 | V | CG1 | −8.2 | −18.7 | −8.5 | 34 | A |
| 85 | V | CG2 | −10.6 | −19.4 | −9.0 | 34 | A |
| 86 | I | N | −8.5 | −17.5 | −5.1 | 37 | A |
| 86 | I | CA | −7.6 | −16.7 | −4.4 | 37 | A |
| 86 | I | C | −6.1 | −17.1 | −4.6 | 45 | A |
| 86 | I | O | −5.2 | −16.5 | −4.2 | 45 | A |
| 86 | I | CB | −7.9 | −16.7 | −2.8 | 39 | A |
| 86 | I | CG1 | −7.6 | −18.1 | −2.3 | 37 | A |
| 86 | I | CG2 | −9.3 | −16.1 | −2.5 | 39 | A |
| 86 | I | CD1 | −7.9 | −18.2 | −0.9 | 32 | A |
| 87 | R | N | −6.0 | −18.3 | −5.2 | 41 | A |
| 87 | R | CA | −4.6 | −18.8 | −5.5 | 40 | A |
| 87 | R | C | −4.7 | −19.8 | −6.7 | 40 | A |
| 87 | R | O | −5.6 | −20.6 | −6.8 | 39 | A |
| 87 | R | CB | −4.1 | −19.5 | −4.2 | 43 | A |
| 87 | R | CG | −2.7 | −20.1 | −4.4 | 54 | A |
| 87 | R | CD | −2.0 | −20.1 | −3.0 | 61 | A |

TABLE 3-continued

Coordinates of Factor IXa co-crystal Compound B complex

| | | | | | | |
|---|---|---|---|---|---|---|
| 87 | R | NE | -1.3 | -21.3 | -2.8 | 76 A |
| 87 | R | CZ | -1.6 | -22.3 | -1.9 | 90 A |
| 87 | R | NH1 | -2.8 | -22.2 | -1.3 | 74 A |
| 87 | R | NH2 | -0.8 | -23.3 | -1.8 | 80 A |
| 88 | I | N | -3.7 | -19.6 | -7.6 | 34 A |
| 88 | I | CA | -3.6 | -20.5 | -8.7 | 33 A |
| 88 | I | C | -2.3 | -21.3 | -8.6 | 36 A |
| 88 | I | O | -1.2 | -20.7 | -8.3 | 38 A |
| 88 | I | CB | -3.6 | -19.7 | -10.0 | 36 A |
| 88 | I | CG1 | -4.9 | -19.0 | -10.2 | 36 A |
| 88 | I | CG2 | -3.3 | -20.6 | -11.2 | 36 A |
| 88 | I | CD1 | -5.0 | -18.2 | -11.5 | 31 A |
| 89 | I | N | -2.4 | -22.6 | -8.7 | 29 A |
| 89 | I | CA | -1.1 | -23.5 | -8.7 | 28 A |
| 89 | I | C | -0.9 | -24.2 | -10.0 | 30 A |
| 89 | I | O | -1.5 | -25.3 | -10.2 | 27 A |
| 89 | I | CB | -1.1 | -24.4 | -7.5 | 31 A |
| 89 | I | CG1 | -1.3 | -23.7 | -6.2 | 32 A |
| 89 | I | CG2 | 0.3 | -25.2 | -7.4 | 28 A |
| 89 | I | CD1 | -1.2 | -24.5 | -4.9 | 32 A |
| 90 | P | N | -0.1 | -23.7 | -10.9 | 30 A |
| 90 | P | CA | 0.1 | -24.6 | -12.1 | 30 A |
| 90 | P | C | 1.1 | -25.6 | -11.7 | 33 A |
| 90 | P | O | 1.9 | -25.4 | -10.8 | 33 A |
| 90 | P | CB | 0.7 | -23.6 | -13.1 | 30 A |
| 90 | P | CG | 1.3 | -22.5 | -12.3 | 33 A |
| 90 | P | CD | 0.5 | -22.4 | -11.0 | 30 A |
| 91 | H | N | 1.1 | -26.8 | -12.3 | 31 A |
| 91 | H | CA | 2.1 | -27.8 | -12.0 | 30 A |
| 91 | H | C | 3.4 | -27.2 | -12.2 | 33 A |
| 91 | H | O | 3.7 | -26.4 | -13.1 | 34 A |
| 91 | H | CB | 1.8 | -29.1 | -12.8 | 29 A |
| 91 | H | CG | 2.8 | -30.2 | -12.5 | 31 A |
| 91 | H | ND1 | 2.5 | -31.2 | -11.6 | 33 A |
| 91 | H | CD2 | 4.0 | -30.5 | -12.9 | 31 A |
| 91 | H | CE1 | 3.5 | -32.0 | -11.5 | 31 A |
| 91 | H | NE2 | 4.5 | -31.6 | -12.3 | 30 A |
| 92 | H | N | 4.4 | -27.5 | -11.3 | 28 A |
| 92 | H | CA | 5.7 | -27.0 | -11.4 | 28 A |
| 92 | H | C | 6.5 | -27.2 | -12.7 | 33 A |
| 92 | H | O | 7.4 | -26.5 | -13.0 | 34 A |
| 92 | H | CB | 6.5 | -27.3 | -10.2 | 28 A |
| 92 | H | CG | 6.8 | -28.8 | -10.0 | 32 A |
| 92 | H | ND1 | 8.0 | -29.3 | -10.5 | 34 A |
| 92 | H | CD2 | 6.1 | -29.8 | -9.5 | 33 A |
| 92 | H | CE1 | 7.9 | -30.6 | -10.3 | 33 A |
| 92 | H | NE2 | 6.8 | -30.9 | -9.6 | 33 A |
| 93 | N | N | 6.1 | -28.3 | -13.5 | 28 A |
| 93 | N | CA | 6.8 | -28.5 | -14.7 | 29 A |
| 93 | N | C | 6.1 | -27.8 | -15.9 | 38 A |
| 93 | N | O | 6.5 | -27.9 | -17.1 | 37 A |
| 93 | N | CB | 6.8 | -30.0 | -15.1 | 25 A |
| 93 | N | CG | 7.6 | -30.9 | -14.2 | 35 A |
| 93 | N | OD1 | 7.2 | -32.0 | -13.9 | 37 A |
| 93 | N | ND2 | 8.7 | -30.4 | -13.7 | 35 A |
| 94 | Y | N | 5.1 | -27.0 | -15.6 | 34 A |
| 94 | Y | CA | 4.4 | -26.2 | -16.6 | 32 A |
| 94 | Y | C | 5.2 | -25.0 | -16.9 | 37 A |
| 94 | Y | O | 5.5 | -24.2 | -16.1 | 35 A |
| 94 | Y | CB | 3.0 | -25.8 | -16.2 | 31 A |
| 94 | Y | CG | 2.3 | -25.1 | -17.3 | 29 A |
| 94 | Y | CD1 | 1.9 | -25.8 | -18.4 | 30 A |
| 94 | Y | CD2 | 2.1 | -23.7 | -17.3 | 28 A |
| 94 | Y | CE1 | 1.2 | -25.2 | -19.4 | 28 A |
| 94 | Y | CE2 | 1.5 | -23.0 | -18.3 | 28 A |
| 94 | Y | CZ | 1.1 | -23.8 | -19.4 | 34 A |
| 94 | Y | OH | 0.4 | -23.2 | -20.5 | 36 A |
| 95 | N | N | 5.4 | -24.7 | -18.2 | 36 A |
| 95 | N | CA | 6.1 | -23.5 | -18.7 | 36 A |
| 95 | N | C | 5.6 | -23.2 | -20.1 | 41 A |
| 95 | N | O | 6.0 | -23.8 | -21.0 | 39 A |
| 95 | N | CB | 7.6 | -23.7 | -18.6 | 35 A |
| 95 | N | CG | 8.4 | -22.4 | -19.0 | 52 A |
| 95 | N | OD1 | 7.9 | -21.5 | -19.6 | 42 A |
| 95 | N | ND2 | 9.7 | -22.4 | -18.6 | 48 A |
| 95A | A | N | 4.7 | -22.2 | -20.1 | 41 A |
| 95A | A | CA | 4.1 | -21.7 | -21.4 | 41 A |
| 95A | A | C | 5.1 | -21.2 | -22.5 | 48 A |
| 95A | A | O | 4.8 | -21.3 | -23.6 | 52 A |
| 95A | A | CB | 3.1 | -20.7 | -21.1 | 41 A |
| 95B | A | N | 6.2 | -20.7 | -22.1 | 45 A |
| 95B | A | CA | 7.2 | -20.2 | -23.0 | 46 A |
| 95B | A | C | 7.9 | -21.3 | -23.7 | 51 A |
| 95B | A | O | 8.3 | -21.1 | -24.9 | 55 A |
| 95B | A | CB | 8.2 | -19.3 | -22.3 | 47 A |
| 96 | I | N | 8.0 | -22.5 | -23.1 | 44 A |
| 96 | I | CA | 8.6 | -23.6 | -23.7 | 41 A |
| 96 | I | C | 7.5 | -24.2 | -24.5 | 46 A |
| 96 | I | O | 7.7 | -24.9 | -25.6 | 46 A |
| 96 | I | CB | 9.3 | -24.5 | -22.7 | 44 A |
| 96 | I | CG1 | 10.4 | -23.8 | -22.0 | 44 A |
| 96 | I | CG2 | 9.7 | -25.8 | -23.3 | 43 A |
| 96 | I | CD1 | 10.9 | -24.4 | -20.7 | 44 A |
| 97 | N | N | 6.4 | -24.7 | -23.8 | 40 A |
| 97 | N | CA | 5.3 | -25.5 | -24.4 | 38 A |
| 97 | N | C | 4.0 | -25.2 | -23.7 | 40 A |
| 97 | N | O | 3.8 | -25.5 | -22.5 | 41 A |
| 97 | N | CB | 5.6 | -27.0 | -24.3 | 33 A |
| 97 | N | CG | 4.8 | -27.9 | -25.2 | 41 A |
| 97 | N | OD1 | 3.6 | -27.6 | -25.4 | 42 A |
| 97 | N | ND2 | 5.4 | -28.8 | -25.9 | 37 A |
| 98 | K | N | 3.0 | -24.6 | -24.4 | 32 A |
| 98 | K | CA | 1.8 | -24.2 | -23.8 | 31 A |
| 98 | K | C | 0.9 | -25.4 | -23.3 | 35 A |
| 98 | K | O | 0.0 | -25.1 | -22.5 | 34 A |
| 98 | K | CB | 1.0 | -23.4 | -24.9 | 32 A |
| 98 | K | CG | -0.3 | -22.8 | -24.4 | 40 A |
| 98 | K | CD | -1.0 | -22.2 | -25.5 | 42 A |
| 98 | K | CE | -2.2 | -21.4 | -24.9 | 62 A |
| 98 | K | NZ | -1.9 | -20.9 | -23.5 | 84 A |
| 99 | Y | N | 1.1 | -26.5 | -23.9 | 28 A |
| 99 | Y | CA | 0.2 | -27.6 | -23.6 | 27 A |
| 99 | Y | C | 0.8 | -28.9 | -23.0 | 31 A |
| 99 | Y | O | 0.2 | -29.9 | -22.9 | 33 A |
| 99 | Y | CB | -0.6 | -28.0 | -24.9 | 29 A |
| 99 | Y | CG | -1.4 | -26.9 | -25.5 | 30 A |
| 99 | Y | CD1 | -2.6 | -26.6 | -25.0 | 31 A |
| 99 | Y | CD2 | -0.9 | -26.2 | -26.5 | 32 A |
| 99 | Y | CE1 | -3.3 | -25.5 | -25.5 | 31 A |
| 99 | Y | CE2 | -1.6 | -25.2 | -27.1 | 33 A |
| 99 | Y | CZ | -2.9 | -24.8 | -26.6 | 38 A |
| 99 | Y | OH | -3.6 | -23.8 | -27.1 | 41 A |
| 100 | N | N | 2.1 | -28.7 | -22.6 | 28 A |
| 100 | N | CA | 2.7 | -29.9 | -21.9 | 28 A |
| 100 | N | C | 2.6 | -29.6 | -20.3 | 33 A |
| 100 | N | O | 2.6 | -28.4 | -19.9 | 30 A |
| 100 | N | CB | 4.2 | -30.0 | -22.3 | 22 A |
| 100 | N | CG | 4.7 | -31.4 | -22.0 | 42 A |
| 100 | N | OD1 | 5.9 | -31.6 | -22.3 | 35 A |
| 100 | N | ND2 | 3.9 | -32.3 | -21.5 | 27 A |
| 101 | H | N | 2.4 | -30.6 | -19.6 | 30 A |
| 101 | H | CA | 2.2 | -30.5 | -18.1 | 31 A |
| 101 | H | C | 1.1 | -29.5 | -17.8 | 33 A |
| 101 | H | O | 1.3 | -28.6 | -17.0 | 32 A |
| 101 | H | CB | 3.5 | -30.1 | -17.4 | 32 A |
| 101 | H | CG | 4.7 | -31.1 | -17.7 | 34 A |
| 101 | H | ND1 | 5.8 | -30.6 | -18.5 | 35 A |
| 101 | H | CD2 | 5.0 | -32.3 | -17.4 | 34 A |
| 101 | H | CE1 | 6.6 | -31.6 | -18.6 | 33 A |
| 101 | H | NE2 | 6.2 | -32.7 | -17.9 | 33 A |
| 102 | D | N | 0.1 | -29.5 | -18.6 | 28 A |
| 102 | D | CA | -1.0 | -28.6 | -18.7 | 26 A |
| 102 | D | C | -2.1 | -28.8 | -17.6 | 31 A |
| 102 | D | O | -3.2 | -29.3 | -17.9 | 30 A |
| 102 | D | CB | -1.7 | -28.7 | -20.1 | 26 A |
| 102 | D | CG | -2.5 | -27.4 | -20.4 | 29 A |
| 102 | D | OD1 | -2.3 | -26.5 | -19.5 | 32 A |
| 102 | D | OD2 | -3.1 | -27.3 | -21.4 | 33 A |
| 103 | I | N | -1.8 | -28.5 | -16.4 | 29 A |
| 103 | I | CA | -2.8 | -28.8 | -15.3 | 27 A |
| 103 | I | C | -2.5 | -27.8 | -14.2 | 31 A |
| 103 | I | O | -1.3 | -27.5 | -13.9 | 30 A |
| 103 | I | CB | -2.7 | -30.3 | -14.8 | 29 A |
| 103 | I | CG1 | -3.9 | -30.7 | -14.0 | 27 A |
| 103 | I | CG2 | -1.2 | -30.7 | -14.4 | 26 A |
| 103 | I | CD1 | -3.8 | -32.2 | -13.6 | 23 A |

TABLE 3-continued

Coordinates of Factor IXa co-crystal Compound B complex

| | | | | | | |
|---|---|---|---|---|---|---|
| 104 | A | N | -3.6 | -27.3 | -13.6 | 25 | A |
| 104 | A | CA | -3.4 | -26.3 | -12.6 | 23 | A |
| 104 | A | C | -4.5 | -26.5 | -11.5 | 30 | A |
| 104 | A | O | -5.6 | -27.0 | -11.9 | 30 | A |
| 104 | A | CB | -3.5 | -24.9 | -13.2 | 23 | A |
| 105 | L | N | -4.3 | -26.0 | -10.3 | 28 | A |
| 105 | L | CA | -5.3 | -26.1 | -9.3 | 27 | A |
| 105 | L | C | -5.7 | -24.7 | -8.9 | 32 | A |
| 105 | L | O | -4.8 | -23.8 | -8.8 | 30 | A |
| 105 | L | CB | -4.6 | -26.8 | -8.1 | 26 | A |
| 105 | L | CG | -4.3 | -28.3 | -8.3 | 28 | A |
| 105 | L | CD1 | -3.3 | -28.9 | -7.3 | 28 | A |
| 105 | L | CD2 | -5.6 | -29.2 | -8.3 | 23 | A |
| 106 | L | N | -7.0 | -24.5 | -8.6 | 30 | A |
| 106 | L | CA | -7.5 | -23.2 | -8.2 | 30 | A |
| 106 | L | C | -8.1 | -23.3 | -6.8 | 34 | A |
| 106 | L | O | -8.9 | -24.2 | -6.5 | 35 | A |
| 106 | L | CB | -8.7 | -22.8 | -9.1 | 30 | A |
| 106 | L | CG | -8.5 | -22.9 | -10.6 | 32 | A |
| 106 | L | CD1 | -9.7 | -22.4 | -11.3 | 31 | A |
| 106 | L | CD2 | -7.2 | -22.1 | -11.1 | 32 | A |
| 107 | E | N | -7.6 | -22.5 | -5.8 | 31 | A |
| 107 | E | CA | -8.2 | -22.4 | -4.5 | 29 | A |
| 107 | E | C | -9.3 | -21.4 | -4.4 | 31 | A |
| 107 | E | O | -9.1 | -20.3 | -4.9 | 30 | A |
| 107 | E | CB | -7.1 | -22.1 | -3.4 | 30 | A |
| 107 | E | CG | -7.6 | -22.1 | -2.0 | 35 | A |
| 107 | E | CD | -6.6 | -22.0 | -1.0 | 47 | A |
| 107 | E | OE1 | -5.5 | -21.4 | -1.3 | 45 | A |
| 107 | E | OE2 | -6.8 | -22.6 | 0.2 | 42 | A |
| 108 | L | N | -10.4 | -21.8 | -3.8 | 31 | A |
| 108 | L | CA | -11.6 | -20.9 | -3.7 | 31 | A |
| 108 | L | C | -11.5 | -20.1 | -2.4 | 34 | A |
| 108 | L | O | -11.0 | -20.5 | -1.4 | 33 | A |
| 108 | L | CB | -12.8 | -21.8 | -3.6 | 30 | A |
| 108 | L | CG | -13.0 | -22.7 | -4.9 | 33 | A |
| 108 | L | CD1 | -14.3 | -23.5 | -4.8 | 32 | A |
| 108 | L | CD2 | -12.8 | -21.9 | -6.2 | 32 | A |
| 109 | D | N | -12.1 | -18.8 | -2.4 | 31 | A |
| 109 | D | CA | -12.1 | -18.0 | -1.2 | 31 | A |
| 109 | D | C | -12.8 | -18.5 | -0.1 | 37 | A |
| 109 | D | O | -12.5 | -18.3 | 1.1 | 37 | A |
| 109 | D | CB | -12.5 | -16.6 | -1.5 | 33 | A |
| 109 | D | CG | -13.9 | -16.5 | -2.2 | 45 | A |
| 109 | D | OD1 | -14.4 | -17.6 | -2.7 | 46 | A |
| 109 | D | OD2 | -14.4 | -15.4 | -2.5 | 45 | A |
| 110 | E | N | -13.9 | -19.2 | -0.4 | 33 | A |
| 110 | E | CA | -14.8 | -19.8 | 0.7 | 33 | A |
| 110 | E | C | -15.3 | -21.1 | 0.1 | 38 | A |
| 110 | E | O | -15.6 | -21.2 | -1.1 | 40 | A |
| 110 | E | CB | -16.0 | -18.8 | 0.8 | 34 | A |
| 110 | E | CG | -16.4 | -18.4 | 2.1 | 46 | A |
| 110 | E | CD | -15.3 | -17.7 | 3.0 | 44 | A |
| 110 | E | OE1 | -15.2 | -16.5 | 2.9 | 39 | A |
| 110 | E | OE2 | -15.0 | -18.3 | 4.0 | 38 | A |
| 111 | P | N | -15.4 | -22.1 | 1.0 | 34 | A |
| 111 | P | CA | -15.8 | -23.5 | 0.6 | 33 | A |
| 111 | P | C | -17.1 | -23.5 | -0.2 | 37 | A |
| 111 | P | O | -18.0 | -22.7 | 0.1 | 35 | A |
| 111 | P | CB | -16.1 | -24.2 | 1.9 | 34 | A |
| 111 | P | CG | -15.3 | -23.5 | 2.9 | 37 | A |
| 111 | P | CD | -15.2 | -22.1 | 2.5 | 33 | A |
| 112 | L | N | -17.2 | -24.5 | -1.1 | 34 | A |
| 112 | L | CA | -18.5 | -24.7 | -1.8 | 32 | A |
| 112 | L | C | -19.3 | -25.5 | -0.8 | 35 | A |
| 112 | L | O | -18.7 | -26.1 | 0.2 | 32 | A |
| 112 | L | CB | -18.3 | -25.5 | -3.0 | 31 | A |
| 112 | L | CG | -17.5 | -24.9 | -4.2 | 33 | A |
| 112 | L | CD1 | -16.9 | -26.0 | -5.1 | 34 | A |
| 112 | L | CD2 | -18.4 | -23.9 | -4.9 | 24 | A |
| 113 | V | N | -20.6 | -25.6 | -1.0 | 31 | A |
| 113 | V | CA | -21.4 | -26.4 | -0.1 | 30 | A |
| 113 | V | C | -21.9 | -27.6 | -1.0 | 35 | A |
| 113 | V | O | -22.6 | -27.4 | -1.9 | 35 | A |
| 113 | V | CB | -22.6 | -25.5 | 0.4 | 31 | A |
| 113 | V | CG1 | -23.7 | -26.4 | 1.1 | 27 | A |
| 113 | V | CG2 | -22.1 | -24.4 | 1.3 | 31 | A |
| 114 | L | N | -21.4 | -28.8 | -0.6 | 33 | A |
| 114 | L | CA | -21.8 | -30.0 | -1.4 | 33 | A |
| 114 | L | C | -23.3 | -30.2 | -1.3 | 39 | A |
| 114 | L | O | -23.9 | -30.1 | -0.2 | 40 | A |
| 114 | L | CB | -21.0 | -31.2 | -0.9 | 32 | A |
| 114 | L | CG | -19.4 | -30.9 | -0.9 | 36 | A |
| 114 | L | CD1 | -18.6 | -32.1 | -0.6 | 35 | A |
| 114 | L | CD2 | -19.0 | -30.3 | -2.3 | 38 | A |
| 115 | N | N | -23.8 | -30.6 | -2.4 | 36 | A |
| 115 | N | CA | -25.2 | -30.9 | -2.5 | 35 | A |
| 115 | N | C | -25.4 | -31.7 | -3.8 | 41 | A |
| 115 | N | O | -24.4 | -32.0 | -4.5 | 42 | A |
| 115 | N | CB | -26.1 | -29.6 | -2.4 | 29 | A |
| 115 | N | CG | -25.9 | -28.6 | -3.6 | 47 | A |
| 115 | N | OD1 | -25.8 | -29.0 | -4.7 | 44 | A |
| 115 | N | ND2 | -26.0 | -27.3 | -3.3 | 36 | A |
| 116 | S | N | -26.6 | -32.0 | -4.2 | 37 | A |
| 116 | S | CA | -26.8 | -32.8 | -5.4 | 36 | A |
| 116 | S | C | -26.3 | -32.1 | -6.7 | 40 | A |
| 116 | S | O | -26.1 | -32.7 | -7.8 | 40 | A |
| 116 | S | CB | -28.3 | -33.3 | -5.6 | 38 | A |
| 116 | S | OG | -28.7 | -34.1 | -4.8 | 44 | A |
| 117 | Y | N | -26.1 | -30.8 | -6.7 | 34 | A |
| 117 | Y | CA | -25.7 | -30.0 | -7.8 | 34 | A |
| 117 | Y | C | -24.2 | -29.6 | -7.8 | 35 | A |
| 117 | Y | O | -23.7 | -29.2 | -8.9 | 34 | A |
| 117 | Y | CB | -26.5 | -28.7 | -8.0 | 36 | A |
| 117 | Y | CG | -28.0 | -29.0 | -8.1 | 38 | A |
| 117 | Y | CD1 | -28.6 | -29.4 | -9.3 | 39 | A |
| 117 | Y | CD2 | -28.8 | -28.9 | -6.9 | 40 | A |
| 117 | Y | CE1 | -29.9 | -29.7 | -9.3 | 40 | A |
| 117 | Y | CE2 | -30.2 | -29.3 | -7.0 | 40 | A |
| 117 | Y | CZ | -30.7 | -29.6 | -8.2 | 45 | A |
| 117 | Y | OH | -32.1 | -29.9 | -8.3 | 44 | A |
| 118 | V | N | -23.6 | -29.8 | -6.7 | 31 | A |
| 118 | V | CA | -22.2 | -29.5 | -6.4 | 29 | A |
| 118 | V | C | -21.6 | -30.6 | -5.6 | 35 | A |
| 118 | V | O | -21.8 | -30.8 | -4.4 | 34 | A |
| 118 | V | CB | -22.1 | -28.1 | -5.6 | 32 | A |
| 118 | V | CG1 | -20.6 | -27.7 | -5.4 | 30 | A |
| 118 | V | CG2 | -22.9 | -27.0 | -6.3 | 31 | A |
| 119 | T | N | -20.9 | -31.5 | -6.4 | 34 | A |
| 119 | T | CA | -20.3 | -32.7 | -5.8 | 34 | A |
| 119 | T | C | -18.9 | -32.9 | -6.4 | 34 | A |
| 119 | T | O | -18.8 | -32.6 | -7.6 | 34 | A |
| 119 | T | CB | -21.3 | -33.9 | -6.3 | 42 | A |
| 119 | T | OG1 | -22.6 | -33.7 | -5.7 | 45 | A |
| 119 | T | CG2 | -20.7 | -35.3 | -5.8 | 36 | A |
| 120 | P | N | -17.9 | -33.3 | -5.7 | 29 | A |
| 120 | P | CA | -16.6 | -33.5 | -6.2 | 27 | A |
| 120 | P | C | -16.5 | -34.8 | -7.2 | 31 | A |
| 120 | P | O | -17.4 | -35.7 | -7.1 | 29 | A |
| 120 | P | CB | -15.7 | -33.8 | -5.0 | 27 | A |
| 120 | P | CG | -16.6 | -33.3 | -3.8 | 31 | A |
| 120 | P | CD | -18.0 | -33.6 | -4.2 | 28 | A |
| 121 | I | N | -15.5 | -34.7 | -8.1 | 28 | A |
| 121 | I | CA | -15.2 | -35.9 | -8.9 | 28 | A |
| 121 | I | C | -14.3 | -36.8 | -8.1 | 33 | A |
| 121 | I | O | -13.5 | -36.3 | -7.3 | 34 | A |
| 121 | I | CB | -14.6 | -35.5 | -10.3 | 30 | A |
| 121 | I | CG1 | -14.4 | -36.6 | -11.2 | 28 | A |
| 121 | I | CG2 | -13.2 | -34.8 | -10.1 | 27 | A |
| 121 | I | CD1 | -15.7 | -37.2 | -11.7 | 20 | A |
| 122 | C | N | -14.4 | -38.1 | -8.3 | 29 | A |
| 122 | C | CA | -13.5 | -39.0 | -7.6 | 31 | A |
| 122 | C | C | -12.2 | -39.0 | -8.3 | 33 | A |
| 122 | C | O | -12.1 | -38.9 | -9.5 | 30 | A |
| 122 | C | CB | -14.0 | -40.4 | -7.3 | 33 | A |
| 122 | C | SG | -15.7 | -40.5 | -6.7 | 38 | A |
| 123 | I | N | -11.1 | -39.2 | -7.5 | 31 | A |
| 123 | I | CA | -9.8 | -39.3 | -8.1 | 30 | A |
| 123 | I | C | -9.1 | -40.5 | -7.5 | 33 | A |
| 123 | I | O | -8.8 | -40.5 | -6.3 | 32 | A |
| 123 | I | CB | -9.0 | -38.1 | -8.0 | 31 | A |
| 123 | I | CG1 | -9.7 | -36.9 | -8.5 | 31 | A |
| 123 | I | CG2 | -7.6 | -38.3 | -8.7 | 32 | A |
| 123 | I | CD1 | -8.9 | -35.5 | -8.5 | 20 | A |
| 124 | A | N | -8.8 | -41.5 | -8.3 | 31 | A |
| 124 | A | CA | -8.1 | -42.7 | -7.7 | 27 | A |

TABLE 3-continued

Coordinates of Factor IXa co-crystal Compound B complex

| | | | | | | |
|---|---|---|---|---|---|---|
| 124 | A | C | −6.6 | −42.5 | −7.7 | 33 | A |
| 124 | A | O | −6.2 | −41.4 | −8.1 | 34 | A |
| 124 | A | CB | −8.5 | −43.9 | −8.6 | 27 | A |
| 125 | D | N | −5.9 | −43.6 | −7.3 | 28 | A |
| 125 | D | CA | −4.4 | −43.5 | −7.4 | 27 | A |
| 125 | D | C | −4.0 | −43.7 | −8.8 | 31 | A |
| 125 | D | O | −4.8 | −44.0 | −9.7 | 34 | A |
| 125 | D | CB | −3.8 | −44.6 | −6.4 | 29 | A |
| 125 | D | CG | −3.9 | −46.0 | −6.9 | 42 | A |
| 125 | D | OD1 | −4.6 | −46.3 | −7.9 | 42 | A |
| 125 | D | OD2 | −3.3 | −46.9 | −6.3 | 54 | A |
| 126 | K | N | −2.7 | −43.4 | −9.1 | 26 | A |
| 126 | K | CA | −2.1 | −43.5 | −10.4 | 26 | A |
| 126 | K | C | −2.5 | −44.7 | −11.2 | 33 | A |
| 126 | K | O | −2.9 | −44.6 | −12.3 | 34 | A |
| 126 | K | CB | −0.6 | −43.4 | −10.2 | 29 | A |
| 126 | K | CG | 0.3 | −43.6 | −11.4 | 39 | A |
| 126 | K | CD | 1.8 | −43.3 | −11.2 | 36 | A |
| 126 | K | CE | 2.6 | −43.5 | −12.4 | 40 | A |
| 126 | K | NZ | 4.1 | −43.3 | −12.2 | 51 | A |
| 127 | E | N | −2.2 | −45.9 | −10.6 | 30 | A |
| 127 | E | CA | −2.5 | −47.2 | −11.2 | 29 | A |
| 127 | E | C | −4.0 | −47.3 | −11.7 | 32 | A |
| 127 | E | O | −4.2 | −47.8 | −12.8 | 34 | A |
| 127 | E | CB | −2.2 | −48.3 | −10.3 | 31 | A |
| 127 | E | CG | −2.8 | −49.7 | −10.7 | 43 | A |
| 127 | E | CD | −2.5 | −50.8 | −9.7 | 65 | A |
| 127 | E | OE1 | −2.3 | −51.9 | −10.1 | 53 | A |
| 127 | E | OE2 | −2.6 | −50.6 | −8.4 | 63 | A |
| 128 | Y | N | −4.9 | −47.1 | −10.8 | 28 | A |
| 128 | Y | CA | −6.3 | −47.3 | −11.1 | 28 | A |
| 128 | Y | C | −6.9 | −46.2 | −12.1 | 32 | A |
| 128 | Y | O | −7.7 | −46.4 | −12.9 | 33 | A |
| 128 | Y | CB | −7.2 | −47.4 | −9.9 | 30 | A |
| 128 | Y | CG | −7.4 | −48.8 | −9.4 | 32 | A |
| 128 | Y | CD1 | −6.6 | −49.3 | −8.4 | 35 | A |
| 128 | Y | CD2 | −8.3 | −49.6 | −10.1 | 32 | A |
| 128 | Y | CE1 | −6.8 | −50.6 | −7.9 | 35 | A |
| 128 | Y | CE2 | −8.4 | −50.9 | −9.6 | 34 | A |
| 128 | Y | CZ | −7.7 | −51.4 | −8.6 | 42 | A |
| 128 | Y | OH | −7.8 | −52.7 | −8.2 | 45 | A |
| 129 | T | N | −6.4 | −45.0 | −12.0 | 28 | A |
| 129 | T | CA | −6.8 | −43.9 | −12.8 | 27 | A |
| 129 | T | C | −6.4 | −44.3 | −14.3 | 32 | A |
| 129 | T | O | −7.1 | −44.2 | −15.2 | 33 | A |
| 129 | T | CB | −6.1 | −42.6 | −12.4 | 34 | A |
| 129 | T | OG1 | −6.7 | −42.1 | −11.2 | 34 | A |
| 129 | T | CG2 | −6.3 | −41.5 | −13.4 | 34 | A |
| 129A | N | N | −5.2 | −44.9 | −14.4 | 28 | A |
| 129A | N | CA | −4.7 | −45.4 | −15.6 | 29 | A |
| 129A | N | C | −5.5 | −46.6 | −16.2 | 32 | A |
| 129A | N | O | −5.9 | −46.6 | −17.4 | 32 | A |
| 129A | N | CB | −3.2 | −45.7 | −15.6 | 27 | A |
| 129A | N | CG | −2.7 | −46.2 | −17.0 | 38 | A |
| 129A | N | OD1 | −3.2 | −45.6 | −18.0 | 38 | A |
| 129A | N | ND2 | −2.0 | −47.3 | −17.0 | 29 | A |
| 129B | I | N | −5.9 | −47.5 | −15.3 | 27 | A |
| 129B | I | CA | −6.7 | −48.7 | −15.6 | 28 | A |
| 129B | I | C | −8.1 | −48.2 | −16.1 | 32 | A |
| 129B | I | O | −8.6 | −48.7 | −17.1 | 35 | A |
| 129B | I | CB | −6.9 | −49.6 | −14.3 | 32 | A |
| 129B | I | CG1 | −5.7 | −50.5 | −14.1 | 32 | A |
| 129B | I | CG2 | −8.2 | −50.4 | −14.4 | 32 | A |
| 129B | I | CD1 | −5.6 | −51.2 | −12.8 | 39 | A |
| 130 | F | N | −8.7 | −47.1 | −15.4 | 27 | A |
| 130 | F | CA | −10.0 | −46.6 | −15.8 | 26 | A |
| 130 | F | C | −9.9 | −45.9 | −17.2 | 29 | A |
| 130 | F | O | −10.8 | −46.1 | −18.1 | 29 | A |
| 130 | F | CB | −10.5 | −45.6 | −14.8 | 28 | A |
| 130 | F | CG | −10.8 | −46.2 | −13.4 | 30 | A |
| 130 | F | CD1 | −11.0 | −47.6 | −13.3 | 33 | A |
| 130 | F | CD2 | −10.9 | −45.4 | −12.3 | 33 | A |
| 130 | F | CE1 | −11.3 | −48.1 | −12.0 | 33 | A |
| 130 | F | CE2 | −11.2 | −45.9 | −11.0 | 35 | A |
| 130 | F | CZ | −11.4 | −47.3 | −10.9 | 32 | A |
| 131 | L | N | −8.8 | −45.1 | −17.4 | 25 | A |
| 131 | L | CA | −8.7 | −44.5 | −18.8 | 24 | A |
| 131 | L | C | −8.7 | −45.6 | −19.8 | 31 | A |
| 131 | L | O | −9.3 | −45.4 | −20.9 | 32 | A |
| 131 | L | CB | −7.3 | −43.9 | −18.9 | 23 | A |
| 131 | L | CG | −7.1 | −43.2 | −20.2 | 27 | A |
| 131 | L | CD1 | −5.6 | −42.7 | −20.4 | 25 | A |
| 131 | L | CD2 | −8.1 | −42.0 | −20.4 | 26 | A |
| 132 | K | N | −8.1 | −46.7 | −19.5 | 29 | A |
| 132 | K | CA | −8.0 | −47.9 | −20.5 | 28 | A |
| 132 | K | C | −9.3 | −48.6 | −20.7 | 32 | A |
| 132 | K | O | −9.3 | −49.4 | −21.7 | 32 | A |
| 132 | K | CB | −6.8 | −48.8 | −20.2 | 29 | A |
| 132 | K | CG | −5.4 | −48.1 | −20.2 | 33 | A |
| 132 | K | CD | −4.3 | −49.1 | −20.3 | 45 | A |
| 132 | K | CE | −3.2 | −49.0 | −19.3 | 65 | A |
| 132 | K | NZ | −1.8 | −49.4 | −19.7 | 64 | A |
| 133 | F | N | −10.4 | −48.4 | −20.0 | 29 | A |
| 133 | F | CA | −11.7 | −49.0 | −20.2 | 26 | A |
| 133 | F | C | −12.1 | −48.5 | −21.6 | 33 | A |
| 133 | F | O | −12.9 | −49.1 | −22.3 | 35 | A |
| 133 | F | CB | −12.7 | −48.5 | −19.2 | 28 | A |
| 133 | F | CG | −12.6 | −49.2 | −17.8 | 29 | A |
| 133 | F | CD1 | −11.7 | −50.2 | −17.6 | 32 | A |
| 133 | F | CD2 | −13.5 | −48.8 | −16.8 | 31 | A |
| 133 | F | CE1 | −11.6 | −50.8 | −16.3 | 31 | A |
| 133 | F | CE2 | −13.4 | −49.4 | −15.5 | 33 | A |
| 133 | F | CZ | −12.4 | −50.4 | −15.3 | 30 | A |
| 134 | G | N | −11.6 | −47.3 | −21.9 | 30 | A |
| 134 | G | CA | −11.7 | −46.7 | −23.3 | 28 | A |
| 134 | G | C | −12.9 | −45.7 | −23.7 | 29 | A |
| 134 | G | O | −13.2 | −45.7 | −24.9 | 29 | A |
| 135 | S | N | −13.7 | −45.5 | −22.7 | 26 | A |
| 135 | S | CA | −14.9 | −44.7 | −23.0 | 25 | A |
| 135 | S | C | −15.1 | −43.6 | −21.9 | 31 | A |
| 135 | S | O | −15.3 | −44.0 | −20.7 | 31 | A |
| 135 | S | CB | −16.1 | −45.6 | −23.1 | 25 | A |
| 135 | S | OG | −17.3 | −44.8 | −23.2 | 43 | A |
| 136 | G | N | −14.9 | −42.4 | −22.2 | 27 | A |
| 136 | G | CA | −15.1 | −41.4 | −21.1 | 27 | A |
| 136 | G | C | −16.2 | −40.4 | −21.5 | 31 | A |
| 136 | G | O | −16.6 | −40.4 | −22.7 | 29 | A |
| 137 | Y | N | −16.5 | −39.5 | −20.6 | 29 | A |
| 137 | Y | CA | −17.5 | −38.5 | −20.9 | 30 | A |
| 137 | Y | C | −16.8 | −37.1 | −20.7 | 32 | A |
| 137 | Y | O | −16.1 | −36.9 | −19.7 | 30 | A |
| 137 | Y | CB | −18.7 | −38.5 | −19.9 | 32 | A |
| 137 | Y | CG | −19.6 | −39.6 | −20.3 | 36 | A |
| 137 | Y | CD1 | −19.4 | −41.0 | −19.9 | 37 | A |
| 137 | Y | CD2 | −20.7 | −39.4 | −21.2 | 38 | A |
| 137 | Y | CE1 | −20.3 | −42.0 | −20.3 | 38 | A |
| 137 | Y | CE2 | −21.5 | −40.4 | −21.6 | 40 | A |
| 137 | Y | CZ | −21.3 | −41.7 | −21.2 | 52 | A |
| 137 | Y | OH | −22.2 | −42.7 | −21.6 | 55 | A |
| 138 | V | N | −17.0 | −36.2 | −21.6 | 28 | A |
| 138 | V | CA | −16.5 | −34.8 | −21.5 | 26 | A |
| 138 | V | C | −17.8 | −34.0 | −21.4 | 30 | A |
| 138 | V | O | −18.8 | −34.4 | −21.7 | 30 | A |
| 138 | V | CB | −15.5 | −34.4 | −22.6 | 30 | A |
| 138 | V | CG1 | −14.3 | −35.3 | −22.6 | 29 | A |
| 138 | V | CG2 | −16.2 | −34.6 | −24.0 | 29 | A |
| 139 | S | N | −17.6 | −32.8 | −20.8 | 29 | A |
| 139 | S | CA | −18.7 | −31.9 | −20.6 | 28 | A |
| 139 | S | C | −18.2 | −30.4 | −20.6 | 31 | A |
| 139 | S | O | −17.0 | −30.2 | −20.4 | 27 | A |
| 139 | S | CB | −19.4 | −32.2 | −19.3 | 30 | A |
| 139 | S | OG | −18.5 | −32.4 | −18.2 | 32 | A |
| 140 | G | N | −19.0 | −29.5 | −21.0 | 32 | A |
| 140 | G | CA | −18.6 | −28.1 | −21.0 | 32 | A |
| 140 | G | C | −19.6 | −27.1 | −21.7 | 38 | A |
| 140 | G | O | −20.5 | −27.6 | −22.3 | 39 | A |
| 141 | W | N | −19.3 | −25.9 | −21.5 | 35 | A |
| 141 | W | CA | −20.1 | −24.8 | −22.2 | 34 | A |
| 141 | W | C | −19.3 | −24.2 | −23.3 | 37 | A |
| 141 | W | O | −19.5 | −23.1 | −23.7 | 38 | A |
| 141 | W | CB | −20.5 | −23.7 | −21.2 | 32 | A |
| 141 | W | CG | −21.6 | −24.1 | −20.1 | 33 | A |
| 141 | W | CD1 | −22.9 | −24.0 | −20.3 | 36 | A |
| 141 | W | CD2 | −21.3 | −24.6 | −18.8 | 33 | A |
| 141 | W | NE1 | −23.5 | −24.4 | −19.1 | 35 | A |
| 141 | W | CE2 | −22.6 | −24.8 | −18.2 | 37 | A |

TABLE 3-continued

Coordinates of Factor IXa co-crystal Compound B complex

| | | | | | | |
|---|---|---|---|---|---|---|
| 141 | W | CE3 | −20.2 | −25.0 | −18.1 | 33 A |
| 141 | W | CZ2 | −22.7 | −25.3 | −16.9 | 36 A |
| 141 | W | CZ3 | −20.3 | −25.4 | −16.8 | 34 A |
| 141 | W | CH2 | −21.5 | −25.5 | −16.2 | 34 A |
| 142 | G | N | −18.4 | −25.0 | −24.0 | 33 A |
| 142 | G | CA | −17.7 | −24.5 | −25.1 | 33 A |
| 142 | G | C | −18.5 | −24.4 | −26.4 | 36 A |
| 142 | G | O | −19.7 | −24.6 | −26.4 | 35 A |
| 143 | R | N | −17.9 | −24.0 | −27.5 | 34 A |
| 143 | R | CA | −18.6 | −23.9 | −28.7 | 35 A |
| 143 | R | C | −19.1 | −25.2 | −29.2 | 43 A |
| 143 | R | O | −18.5 | −26.2 | −29.0 | 44 A |
| 143 | R | CB | −17.7 | −23.4 | −29.9 | 30 A |
| 143 | R | CG | −16.8 | −22.3 | −29.5 | 38 A |
| 143 | R | CD | −16.0 | −21.9 | −30.7 | 51 A |
| 143 | R | NE | −16.0 | −20.5 | −30.8 | 67 A |
| 143 | R | CZ | −14.9 | −19.8 | −31.2 | 76 A |
| 143 | R | NH1 | −13.8 | −20.4 | −31.6 | 80 A |
| 143 | R | NH2 | −15.0 | −18.5 | −31.2 | 49 A |
| 144 | V | N | −20.3 | −25.1 | −29.8 | 41 A |
| 144 | V | CA | −21.0 | −26.3 | −30.4 | 42 A |
| 144 | V | C | −20.7 | −26.5 | −31.8 | 49 A |
| 144 | V | O | −21.2 | −27.5 | −32.5 | 49 A |
| 144 | V | CB | −22.5 | −26.3 | −30.0 | 44 A |
| 144 | V | CG1 | −22.7 | −26.2 | −28.5 | 42 A |
| 144 | V | CG2 | −23.1 | −25.1 | −30.7 | 44 A |
| 145 | F | N | −19.9 | −25.6 | −32.4 | 47 A |
| 145 | F | CA | −19.5 | −25.7 | −33.8 | 47 A |
| 145 | F | C | −18.1 | −25.1 | −33.9 | 52 A |
| 145 | F | O | −17.8 | −24.2 | −33.1 | 51 A |
| 145 | F | CB | −20.5 | −24.9 | −34.7 | 49 A |
| 145 | F | CG | −21.7 | −25.7 | −35.0 | 50 A |
| 145 | F | CD1 | −22.9 | −25.2 | −34.5 | 52 A |
| 145 | F | CD2 | −21.8 | −26.9 | −35.7 | 54 A |
| 145 | F | CE1 | −24.1 | −25.9 | −34.6 | 53 A |
| 145 | F | CE2 | −23.0 | −27.5 | −35.9 | 56 A |
| 145 | F | CZ | −24.1 | −27.0 | −35.3 | 53 A |
| 147 | H | N | −17.3 | −25.6 | −34.8 | 50 A |
| 147 | H | CA | −15.9 | −25.1 | −34.9 | 51 A |
| 147 | H | C | −15.7 | −23.6 | −34.7 | 60 A |
| 147 | H | O | −14.8 | −23.2 | −33.8 | 62 A |
| 147 | H | CB | −15.2 | −25.7 | −36.2 | 52 A |
| 147 | H | CG | −13.9 | −25.0 | −36.5 | 55 A |
| 147 | H | ND1 | −13.0 | −24.8 | −35.5 | 58 A |
| 147 | H | CD2 | −13.4 | −24.5 | −37.6 | 57 A |
| 147 | H | CE1 | −11.9 | −24.2 | −36.0 | 57 A |
| 147 | H | NE2 | −12.1 | −24.0 | −37.3 | 57 A |
| 148 | K | N | −16.4 | −22.8 | −35.4 | 56 A |
| 148 | K | CA | −16.1 | −21.3 | −35.2 | 56 A |
| 148 | K | C | −17.4 | −20.7 | −34.8 | 58 A |
| 148 | K | O | −17.7 | −19.5 | −35.1 | 58 A |
| 148 | K | CB | −15.5 | −20.7 | −36.4 | 57 A |
| 148 | K | CG | −14.0 | −20.6 | −36.4 | 59 A |
| 148 | K | CD | −13.4 | −21.1 | −37.7 | 73 A |
| 148 | K | CE | −12.7 | −20.0 | −38.5 | 93 A |
| 148 | K | NZ | −11.2 | −20.3 | −38.7 | 0 A |
| 149 | G | N | −18.3 | −21.5 | −34.1 | 50 A |
| 149 | G | CA | −19.6 | −21.1 | −33.8 | 47 A |
| 149 | G | C | −20.0 | −20.7 | −32.4 | 48 A |
| 149 | G | O | −19.1 | −20.4 | −31.6 | 46 A |
| 150 | R | N | −21.3 | −20.7 | −32.1 | 46 A |
| 150 | R | CA | −21.8 | −20.3 | −30.8 | 46 A |
| 150 | R | C | −21.5 | −21.2 | −29.7 | 48 A |
| 150 | R | O | −21.5 | −22.4 | −29.8 | 47 A |
| 150 | R | CB | −23.3 | −20.1 | −31.0 | 48 A |
| 150 | R | CG | −24.0 | −21.4 | −31.2 | 60 A |
| 150 | R | CD | −25.5 | −21.2 | −31.3 | 61 A |
| 150 | R | NE | −26.3 | −22.4 | −30.8 | 68 A |
| 150 | R | CZ | −26.5 | −23.5 | −31.6 | 93 A |
| 150 | R | NH1 | −25.9 | −23.6 | −32.8 | 85 A |
| 150 | R | NH2 | −27.1 | −24.5 | −31.1 | 77 A |
| 151 | S | N | −21.2 | −20.6 | −28.5 | 44 A |
| 151 | S | CA | −21.0 | −21.2 | −27.3 | 43 A |
| 151 | S | C | −22.3 | −21.8 | −26.8 | 49 A |
| 151 | S | O | −23.4 | −21.2 | −27.1 | 50 A |
| 151 | S | CB | −20.4 | −20.3 | −26.3 | 44 A |
| 151 | S | OG | −19.2 | −19.9 | −26.7 | 53 A |
| 152 | A | N | −22.3 | −22.8 | −25.9 | 44 A |
| 152 | A | CA | −23.5 | −23.4 | −25.4 | 42 A |
| 152 | A | C | −24.0 | −22.6 | −24.2 | 46 A |
| 152 | A | O | −23.2 | −21.9 | −23.5 | 47 A |
| 152 | A | CB | −23.3 | −24.9 | −25.0 | 42 A |
| 153 | L | N | −25.3 | −22.6 | −24.0 | 44 A |
| 153 | L | CA | −26.0 | −22.0 | −22.9 | 44 A |
| 153 | L | C | −26.3 | −23.0 | −21.9 | 43 A |
| 153 | L | O | −26.1 | −22.9 | −20.7 | 44 A |
| 153 | L | CB | −27.3 | −21.3 | −23.3 | 45 A |
| 153 | L | CG | −27.1 | −20.0 | −24.2 | 50 A |
| 153 | L | CD1 | −28.3 | −19.3 | −24.4 | 50 A |
| 153 | L | CD2 | −26.0 | −19.1 | −23.5 | 50 A |
| 154 | V | N | −26.7 | −24.2 | −22.4 | 35 A |
| 154 | V | CA | −26.9 | −25.4 | −21.6 | 34 A |
| 154 | V | C | −25.7 | −26.3 | −21.6 | 36 A |
| 154 | V | O | −25.1 | −26.4 | −22.7 | 35 A |
| 154 | V | CB | −28.2 | −26.2 | −22.0 | 36 A |
| 154 | V | CG1 | −28.4 | −27.4 | −21.1 | 35 A |
| 154 | V | CG2 | −29.4 | −25.3 | −22.0 | 36 A |
| 155 | L | N | −25.3 | −26.8 | −20.5 | 31 A |
| 155 | L | CA | −24.2 | −27.7 | −20.4 | 30 A |
| 155 | L | C | −24.3 | −28.9 | −21.4 | 33 A |
| 155 | L | O | −25.4 | −29.5 | −21.5 | 31 A |
| 155 | L | CB | −24.1 | −28.2 | −19.0 | 29 A |
| 155 | L | CG | −22.9 | −29.1 | −18.6 | 31 A |
| 155 | L | CD1 | −21.6 | −28.3 | −18.8 | 30 A |
| 155 | L | CD2 | −22.9 | −29.6 | −17.1 | 32 A |
| 156 | Q | N | −23.3 | −29.1 | −22.1 | 31 A |
| 156 | Q | CA | −23.3 | −30.2 | −23.1 | 31 A |
| 156 | Q | C | −22.4 | −31.3 | −22.6 | 34 A |
| 156 | Q | O | −21.4 | −31.1 | −23.1 | 31 A |
| 156 | Q | CB | −22.7 | −29.8 | −24.4 | 33 A |
| 156 | Q | CG | −23.3 | −28.6 | −25.1 | 28 A |
| 156 | Q | CD | −24.8 | −28.9 | −25.5 | 43 A |
| 156 | Q | OE1 | −25.7 | −28.3 | −24.9 | 41 A |
| 156 | Q | NE2 | −25.0 | −29.7 | −26.5 | 23 A |
| 157 | Y | N | −22.7 | −32.6 | −22.9 | 33 A |
| 157 | Y | CA | −21.9 | −33.7 | −22.6 | 32 A |
| 157 | Y | C | −21.7 | −34.6 | −23.8 | 36 A |
| 157 | Y | O | −22.6 | −34.6 | −24.7 | 34 A |
| 157 | Y | CB | −22.5 | −34.5 | −21.4 | 32 A |
| 157 | Y | CG | −23.7 | −35.3 | −21.7 | 32 A |
| 157 | Y | CD1 | −23.6 | −36.7 | −22.0 | 33 A |
| 157 | Y | CD2 | −24.9 | −34.8 | −21.6 | 33 A |
| 157 | Y | CE1 | −24.7 | −37.4 | −22.3 | 30 A |
| 157 | Y | CE2 | −26.1 | −35.5 | −21.8 | 33 A |
| 157 | Y | CZ | −26.0 | −36.9 | −22.1 | 38 A |
| 157 | Y | OH | −27.1 | −37.6 | −22.4 | 42 A |
| 158 | L | N | −20.6 | −35.4 | −23.8 | 33 A |
| 158 | L | CA | −20.3 | −36.3 | −24.9 | 30 A |
| 158 | L | C | −19.5 | −37.5 | −24.5 | 33 A |
| 158 | L | O | −18.5 | −37.3 | −23.8 | 33 A |
| 158 | L | CB | −19.6 | −35.5 | −26.0 | 29 A |
| 158 | L | CG | −19.1 | −36.2 | −27.2 | 30 A |
| 158 | L | CD1 | −20.2 | −36.6 | −28.2 | 28 A |
| 158 | L | CD2 | −18.1 | −35.3 | −27.9 | 28 A |
| 159 | R | N | −19.8 | −38.7 | −24.9 | 29 A |
| 159 | R | CA | −19.0 | −39.9 | −24.7 | 28 A |
| 159 | R | C | −18.0 | −40.0 | −25.8 | 31 A |
| 159 | R | O | −18.4 | −39.9 | −27.0 | 31 A |
| 159 | R | CB | −19.9 | −41.1 | −24.8 | 25 A |
| 159 | R | CG | −19.3 | −42.4 | −24.2 | 35 A |
| 159 | R | CD | −20.0 | −43.6 | −24.7 | 36 A |
| 159 | R | NE | −19.7 | −43.8 | −26.2 | 50 A |
| 159 | R | CZ | −18.6 | −44.4 | −26.7 | 57 A |
| 159 | R | NH1 | −17.6 | −44.8 | −25.9 | 25 A |
| 159 | R | NH2 | −18.5 | −44.5 | −28.0 | 38 A |
| 160 | V | N | −16.7 | −40.1 | −25.5 | 26 A |
| 160 | V | CA | −15.7 | −40.1 | −26.5 | 25 A |
| 160 | V | C | −14.9 | −41.4 | −26.2 | 28 A |
| 160 | V | O | −14.4 | −41.6 | −25.1 | 28 A |
| 160 | V | CB | −14.8 | −38.9 | −26.5 | 27 A |
| 160 | V | CG1 | −15.6 | −37.6 | −27.0 | 26 A |
| 160 | V | CG2 | −14.2 | −38.7 | −25.2 | 26 A |
| 161 | P | N | −14.5 | −42.1 | −27.3 | 23 A |
| 161 | P | CA | −13.7 | −43.3 | −27.2 | 23 A |
| 161 | P | C | −12.2 | −42.9 | −27.2 | 30 A |
| 161 | P | O | −11.8 | −41.9 | −27.8 | 32 A |

TABLE 3-continued

Coordinates of Factor IXa co-crystal Compound B complex

| | | | | | | |
|---|---|---|---|---|---|---|
| 161 | P | CB | −14.0 | −44.0 | −28.6 | 24 | A |
| 161 | P | CG | −14.7 | −43.1 | −29.4 | 29 | A |
| 161 | P | CD | −15.3 | −42.0 | −28.6 | 25 | A |
| 162 | L | N | −11.4 | −43.8 | −26.6 | 28 | A |
| 162 | L | CA | −10.0 | −43.6 | −26.5 | 26 | A |
| 162 | L | C | −9.5 | −44.1 | −27.9 | 30 | A |
| 162 | L | O | −10.0 | −45.1 | −28.4 | 29 | A |
| 162 | L | CB | −9.4 | −44.5 | −25.4 | 25 | A |
| 162 | L | CG | −7.9 | −44.4 | −25.1 | 25 | A |
| 162 | L | CD1 | −7.6 | −43.1 | −24.5 | 23 | A |
| 162 | L | CD2 | −7.6 | −45.5 | −24.1 | 23 | A |
| 163 | V | N | −8.5 | −43.4 | −28.4 | 28 | A |
| 163 | V | CA | −7.9 | −43.6 | −29.7 | 27 | A |
| 163 | V | C | −6.5 | −44.1 | −29.4 | 35 | A |
| 163 | V | O | −5.7 | −43.6 | −28.6 | 38 | A |
| 163 | V | CB | −7.9 | −42.3 | −30.5 | 29 | A |
| 163 | V | CG1 | −7.0 | −42.4 | −31.8 | 27 | A |
| 163 | V | CG2 | −9.3 | −41.9 | −30.9 | 29 | A |
| 164 | D | N | −6.1 | −45.2 | −30.1 | 31 | A |
| 164 | D | CA | −4.8 | −45.8 | −29.9 | 32 | A |
| 164 | D | C | −3.7 | −44.8 | −30.2 | 34 | A |
| 164 | D | O | −3.9 | −43.9 | −31.0 | 32 | A |
| 164 | D | CB | −4.6 | −47.1 | −30.7 | 37 | A |
| 164 | D | CG | −4.3 | −46.8 | −32.2 | 61 | A |
| 164 | D | OD1 | −3.1 | −46.5 | −32.5 | 68 | A |
| 164 | D | OD2 | −5.2 | −47.0 | −33.0 | 63 | A |
| 165 | R | N | −2.6 | −44.9 | −29.5 | 32 | A |
| 165 | R | CA | −1.5 | −44.0 | −29.6 | 32 | A |
| 165 | R | C | −1.0 | −43.9 | −31.1 | 37 | A |
| 165 | R | O | −0.8 | −42.8 | −31.6 | 38 | A |
| 165 | R | CB | −0.4 | −44.2 | −28.6 | 30 | A |
| 165 | R | CG | 0.8 | −43.4 | −28.9 | 39 | A |
| 165 | R | CD | 1.8 | −43.4 | −27.8 | 33 | A |
| 165 | R | NE | 2.1 | −42.0 | −27.4 | 50 | A |
| 165 | R | CZ | 3.2 | −41.4 | −27.6 | 56 | A |
| 165 | R | NH1 | 4.2 | −42.0 | −28.2 | 56 | A |
| 165 | R | NH2 | 3.3 | −40.1 | −27.3 | 43 | A |
| 166 | A | N | −0.8 | −45.1 | −31.7 | 32 | A |
| 166 | A | CA | −0.3 | −45.1 | −33.1 | 31 | A |
| 166 | A | C | −1.2 | −44.3 | −34.1 | 34 | A |
| 166 | A | O | −0.7 | −43.4 | −34.8 | 34 | A |
| 166 | A | CB | −0.2 | −46.6 | −33.7 | 31 | A |
| 167 | T | N | −2.5 | −44.5 | −34.0 | 31 | A |
| 167 | T | CA | −3.4 | −43.6 | −34.8 | 31 | A |
| 167 | T | C | −3.3 | −42.2 | −34.4 | 42 | A |
| 167 | T | O | −3.3 | −41.3 | −35.3 | 46 | A |
| 167 | T | CB | −4.8 | −44.1 | −34.5 | 34 | A |
| 167 | T | OG1 | −4.9 | −45.4 | −35.1 | 36 | A |
| 167 | T | CG2 | −5.8 | −43.2 | −35.2 | 21 | A |
| 168 | C | N | −3.3 | −41.9 | −33.1 | 39 | A |
| 168 | C | CA | −3.2 | −40.5 | −32.7 | 40 | A |
| 168 | C | C | −1.9 | −39.9 | −33.2 | 37 | A |
| 168 | C | O | −1.9 | −38.7 | −33.7 | 35 | A |
| 168 | C | CB | −3.2 | −40.5 | −31.1 | 43 | A |
| 168 | C | SG | −3.0 | −38.9 | −30.4 | 49 | A |
| 169 | L | N | −0.8 | −40.6 | −33.1 | 33 | A |
| 169 | L | CA | 0.5 | −40.0 | −33.6 | 33 | A |
| 169 | L | C | 0.5 | −39.7 | −35.1 | 39 | A |
| 169 | L | O | 1.0 | −38.7 | −35.5 | 41 | A |
| 169 | L | CB | 1.6 | −41.0 | −33.3 | 33 | A |
| 169 | L | CG | 2.5 | −40.6 | −32.1 | 38 | A |
| 169 | L | CD1 | 1.7 | −39.9 | −31.0 | 36 | A |
| 169 | L | CD2 | 3.3 | −41.8 | −31.6 | 45 | A |
| 170 | R | N | −0.2 | −40.5 | −35.9 | 35 | A |
| 170 | R | CA | −0.2 | −40.3 | −37.4 | 36 | A |
| 170 | R | C | −1.1 | −39.2 | −37.7 | 41 | A |
| 170 | R | O | −1.2 | −38.7 | −38.9 | 40 | A |
| 170 | R | CB | −0.7 | −41.6 | −38.1 | 31 | A |
| 170 | R | CG | 0.2 | −42.8 | −38.2 | 33 | A |
| 170 | R | CD | −0.4 | −43.9 | −39.0 | 42 | A |
| 170 | R | NE | −1.6 | −44.5 | −38.5 | 50 | A |
| 170 | R | CZ | −1.8 | −45.6 | −37.8 | 58 | A |
| 170 | R | NH1 | −0.7 | −46.3 | −37.5 | 53 | A |
| 170 | R | NH2 | −2.9 | −46.1 | −37.4 | 40 | A |
| 171 | S | N | −2.0 | −38.8 | −36.8 | 36 | A |
| 171 | S | CA | −3.0 | −37.8 | −37.0 | 34 | A |
| 171 | S | C | −2.5 | −36.4 | −37.0 | 35 | A |
| 171 | S | O | −3.3 | −35.4 | −37.4 | 35 | A |
| 171 | S | CB | −4.1 | −38.0 | −35.9 | 35 | A |
| 171 | S | OG | −3.9 | −37.2 | −34.8 | 32 | A |
| 172 | T | N | −1.3 | −36.1 | −36.5 | 31 | A |
| 172 | T | CA | −0.9 | −34.8 | −36.3 | 31 | A |
| 172 | T | C | 0.6 | −34.6 | −36.5 | 38 | A |
| 172 | T | O | 1.4 | −35.6 | −36.5 | 38 | A |
| 172 | T | CB | −1.3 | −34.3 | −34.9 | 34 | A |
| 172 | T | OG1 | −0.9 | −32.9 | −34.7 | 34 | A |
| 172 | T | CG2 | −0.7 | −35.1 | −33.7 | 30 | A |
| 173 | K | N | 1.0 | −33.4 | −36.8 | 38 | A |
| 173 | K | CA | 2.4 | −33.1 | −37.0 | 39 | A |
| 173 | K | C | 3.0 | −32.7 | −35.6 | 41 | A |
| 173 | K | O | 4.2 | −32.6 | −35.4 | 43 | A |
| 173 | K | CB | 2.5 | −31.8 | −37.9 | 41 | A |
| 173 | K | CG | 1.9 | −30.6 | −37.3 | 66 | A |
| 173 | K | CD | 2.0 | −29.3 | −38.1 | 76 | A |
| 173 | K | CE | 1.5 | −28.1 | −37.3 | 82 | A |
| 173 | K | NZ | 0.5 | −27.3 | −38.0 | 85 | A |
| 174 | F | N | 2.1 | −32.4 | −34.7 | 36 | A |
| 174 | F | CA | 2.5 | −32.0 | −33.3 | 33 | A |
| 174 | F | C | 2.9 | −33.2 | −32.6 | 35 | A |
| 174 | F | O | 2.6 | −34.3 | −32.9 | 35 | A |
| 174 | F | CB | 1.3 | −31.4 | −32.6 | 34 | A |
| 174 | F | CG | 1.0 | −30.0 | −33.1 | 34 | A |
| 174 | F | CD1 | 1.9 | −29.0 | −32.9 | 36 | A |
| 174 | F | CD2 | −0.2 | −29.7 | −33.7 | 33 | A |
| 174 | F | CE1 | 1.7 | −27.7 | −33.4 | 36 | A |
| 174 | F | CE2 | −0.5 | −28.4 | −34.1 | 36 | A |
| 174 | F | CZ | 0.4 | −27.4 | −34.0 | 34 | A |
| 175 | T | N | 3.7 | −33.0 | −31.5 | 34 | A |
| 175 | T | CA | 4.2 | −34.1 | −30.7 | 33 | A |
| 175 | T | C | 3.1 | −34.4 | −29.6 | 37 | A |
| 175 | T | O | 2.6 | −33.5 | −29.0 | 38 | A |
| 175 | T | CB | 5.5 | −33.7 | −30.0 | 38 | A |
| 175 | T | OG1 | 6.4 | −33.4 | −31.1 | 43 | A |
| 175 | T | CG2 | 6.1 | −34.9 | −29.2 | 35 | A |
| 176 | I | N | 2.8 | −35.7 | −29.4 | 34 | A |
| 176 | I | CA | 1.9 | −36.2 | −28.5 | 33 | A |
| 176 | I | C | 2.8 | −36.9 | −27.5 | 35 | A |
| 176 | I | O | 3.4 | −37.8 | −27.8 | 32 | A |
| 176 | I | CB | 0.8 | −37.1 | −29.1 | 36 | A |
| 176 | I | CG1 | 0.0 | −36.4 | −30.2 | 35 | A |
| 176 | I | CG2 | −0.3 | −37.5 | −28.0 | 34 | A |
| 176 | I | CD1 | −0.6 | −35.0 | −29.9 | 32 | A |
| 177 | Y | N | 2.9 | −36.3 | −26.3 | 31 | A |
| 177 | Y | CA | 3.8 | −36.9 | −25.2 | 28 | A |
| 177 | Y | C | 3.0 | −38.1 | −24.6 | 30 | A |
| 177 | Y | O | 1.8 | −38.2 | −24.8 | 33 | A |
| 177 | Y | CB | 4.1 | −35.9 | −24.2 | 29 | A |
| 177 | Y | CG | 5.0 | −34.8 | −24.7 | 31 | A |
| 177 | Y | CD1 | 4.5 | −33.5 | −24.9 | 32 | A |
| 177 | Y | CD2 | 6.2 | −35.1 | −25.2 | 33 | A |
| 177 | Y | CE1 | 5.3 | −32.5 | −25.5 | 33 | A |
| 177 | Y | CE2 | 7.0 | −34.1 | −25.8 | 34 | A |
| 177 | Y | CZ | 6.6 | −32.8 | −25.9 | 46 | A |
| 177 | Y | OH | 7.4 | −31.8 | −26.4 | 56 | A |
| 178 | N | N | 3.7 | −39.0 | −24.0 | 27 | A |
| 178 | N | CA | 3.1 | −40.2 | −23.4 | 26 | A |
| 178 | N | C | 2.1 | −40.0 | −22.4 | 29 | A |
| 178 | N | O | 1.2 | −40.9 | −22.1 | 26 | A |
| 178 | N | CB | 4.2 | −41.1 | −22.9 | 30 | A |
| 178 | N | CG | 5.0 | −41.7 | −24.1 | 40 | A |
| 178 | N | OD1 | 4.6 | −42.6 | −24.8 | 35 | A |
| 178 | N | ND2 | 6.1 | −41.0 | −24.3 | 33 | A |
| 179 | N | N | 2.1 | −38.9 | −21.7 | 27 | A |
| 179 | N | CA | 1.1 | −38.5 | −20.7 | 28 | A |
| 179 | N | C | −0.1 | −37.7 | −21.2 | 28 | A |
| 179 | N | O | −0.8 | −37.1 | −20.4 | 24 | A |
| 179 | N | CB | 1.7 | −38.1 | −19.3 | 28 | A |
| 179 | N | CG | 2.2 | −39.3 | −18.5 | 34 | A |
| 179 | N | OD1 | 1.5 | −40.2 | −18.3 | 30 | A |
| 179 | N | ND2 | 3.5 | −39.3 | −18.3 | 23 | A |
| 180A | M | N | −0.2 | −37.6 | −22.5 | 26 | A |
| 180B | M | N | −0.2 | −37.6 | −22.5 | 26 | A |
| 180A | M | CA | −1.3 | −37.0 | −23.2 | 25 | A |
| 180B | M | CA | −1.4 | −37.0 | −23.1 | 25 | A |
| 180A | M | C | −2.0 | −38.2 | −23.9 | 31 | A |
| 180B | M | C | −2.1 | −38.2 | −23.7 | 31 | A |

TABLE 3-continued

Coordinates of Factor IXa co-crystal Compound B complex

| | | | | | | |
|---|---|---|---|---|---|---|
| 180A | M | O | −1.4 | −39.2 | −24.3 | 31 | A |
| 180B | M | O | −1.5 | −39.3 | −23.8 | 31 | A |
| 180A | M | CB | −0.8 | −36.0 | −24.3 | 27 | A |
| 180B | M | CB | −1.1 | −36.1 | −24.3 | 27 | A |
| 180A | M | CG | −0.1 | −34.8 | −23.9 | 31 | A |
| 180B | M | CG | −0.1 | −35.0 | −24.0 | 31 | A |
| 180A | M | SD | 0.7 | −33.8 | −25.3 | 35 | A |
| 180B | M | SD | −0.5 | −33.7 | −22.9 | 35 | A |
| 180A | M | CE | 0.5 | −32.1 | −24.6 | 30 | A |
| 180B | M | CE | −1.8 | −32.6 | −23.8 | 30 | A |
| 181 | F | N | −3.3 | −38.1 | −24.2 | 28 | A |
| 181 | F | CA | −4.0 | −39.1 | −24.8 | 26 | A |
| 181 | F | C | −5.0 | −38.5 | −25.8 | 33 | A |
| 181 | F | O | −5.3 | −37.3 | −25.7 | 30 | A |
| 181 | F | CB | −4.7 | −40.1 | −23.8 | 26 | A |
| 181 | F | CG | −5.9 | −39.5 | −23.1 | 23 | A |
| 181 | F | CD1 | −7.2 | −39.6 | −23.7 | 24 | A |
| 181 | F | CD2 | −5.8 | −39.0 | −21.8 | 20 | A |
| 181 | F | CE1 | −8.3 | −39.1 | −23.0 | 24 | A |
| 181 | F | CE2 | −6.9 | −38.6 | −21.1 | 21 | A |
| 181 | F | CZ | −8.2 | −38.7 | −21.7 | 20 | A |
| 182 | C | N | −5.4 | −39.3 | −26.8 | 36 | A |
| 182 | C | CA | −6.3 | −38.9 | −27.8 | 38 | A |
| 182 | C | C | −7.6 | −39.5 | −27.6 | 33 | A |
| 182 | C | O | −7.7 | −40.7 | −27.2 | 31 | A |
| 182 | C | CB | −5.8 | −39.4 | −29.2 | 42 | A |
| 182 | C | SG | −4.9 | −38.2 | −30.2 | 49 | A |
| 183 | A | N | −8.7 | −38.8 | −27.9 | 25 | A |
| 183 | A | CA | −10.0 | −39.4 | −27.8 | 23 | A |
| 183 | A | C | −10.9 | −38.7 | −28.8 | 28 | A |
| 183 | A | O | −10.7 | −37.6 | −29.1 | 26 | A |
| 183 | A | CB | −10.6 | −39.2 | −26.3 | 23 | A |
| 184 | G | N | −11.9 | −39.4 | −29.3 | 28 | A |
| 184 | G | CA | −12.8 | −38.8 | −30.3 | 26 | A |
| 184 | G | C | −13.2 | −39.9 | −31.4 | 32 | A |
| 184 | G | O | −12.9 | −41.1 | −31.2 | 32 | A |
| 184A | F | N | −13.7 | −39.4 | −32.5 | 28 | A |
| 184A | F | CA | −14.2 | −40.3 | −33.6 | 27 | A |
| 184A | F | C | −13.5 | −40.2 | −34.9 | 31 | A |
| 184A | F | O | −13.2 | −39.1 | −35.4 | 32 | A |
| 184A | F | CB | −15.7 | −39.9 | −33.8 | 29 | A |
| 184A | F | CG | −16.6 | −40.2 | −32.6 | 29 | A |
| 184A | F | CD1 | −16.7 | −39.3 | −31.6 | 31 | A |
| 184A | F | CD2 | −17.2 | −41.5 | −32.4 | 28 | A |
| 184A | F | CE1 | −17.5 | −39.6 | −30.5 | 31 | A |
| 184A | F | CE2 | −18.0 | −41.8 | −31.4 | 31 | A |
| 184A | F | CZ | −18.1 | −40.8 | −30.3 | 31 | A |
| 185 | H | N | −13.3 | −41.3 | −35.6 | 28 | A |
| 185 | H | CA | −12.7 | −41.4 | −36.9 | 28 | A |
| 185 | H | C | −13.2 | −40.4 | −37.9 | 33 | A |
| 185 | H | O | −12.5 | −39.8 | −38.6 | 35 | A |
| 185 | H | CB | −12.9 | −42.8 | −37.5 | 27 | A |
| 185 | H | CG | −12.1 | −43.1 | −38.7 | 29 | A |
| 185 | H | ND1 | −12.4 | −42.7 | −39.9 | 30 | A |
| 185 | H | CD2 | −11.0 | −43.9 | −38.8 | 27 | A |
| 185 | H | CE1 | −11.5 | −43.2 | −40.8 | 28 | A |
| 185 | H | NE2 | −10.6 | −43.9 | −40.1 | 28 | A |
| 186 | E | N | −14.5 | −40.2 | −38.0 | 29 | A |
| 186 | E | CA | −15.2 | −39.3 | −38.9 | 29 | A |
| 186 | E | C | −15.4 | −37.9 | −38.4 | 35 | A |
| 186 | E | O | −16.0 | −37.1 | −39.0 | 36 | A |
| 186 | E | CB | −16.5 | −39.9 | −39.4 | 30 | A |
| 186 | E | CG | −16.3 | −41.2 | −40.2 | 36 | A |
| 186 | E | CD | −15.5 | −41.0 | −41.5 | 48 | A |
| 186 | E | OE1 | −14.3 | −41.2 | −41.4 | 40 | A |
| 186 | E | OE2 | −16.2 | −40.6 | −42.5 | 51 | A |
| 187 | G | N | −14.9 | −37.6 | −37.1 | 34 | A |
| 187 | G | CA | −15.1 | −36.3 | −36.6 | 34 | A |
| 187 | G | C | −16.6 | −36.1 | −36.3 | 34 | A |
| 187 | G | O | −17.3 | −37.0 | −36.0 | 34 | A |
| 188 | G | N | −17.0 | −34.8 | −36.2 | 31 | A |
| 188 | G | CA | −18.4 | −34.5 | −36.0 | 30 | A |
| 188 | G | C | −18.8 | −34.4 | −34.5 | 36 | A |
| 188 | G | O | −19.9 | −33.8 | −34.2 | 37 | A |
| 188A | R | N | −18.0 | −35.0 | −33.6 | 32 | A |
| 188A | R | CA | −18.3 | −35.0 | −32.2 | 32 | A |
| 188A | R | C | −17.0 | −34.8 | −31.5 | 36 | A |
| 188A | R | O | −16.0 | −35.5 | −31.8 | 34 | A |
| 188A | R | CB | −18.9 | −36.3 | −31.7 | 30 | A |
| 188A | R | CG | −20.2 | −36.7 | −32.4 | 31 | A |
| 188A | R | CD | −20.6 | −38.1 | −31.8 | 41 | A |
| 188A | R | NE | −21.8 | −38.6 | −32.5 | 45 | A |
| 188A | R | CZ | −22.2 | −39.8 | −32.3 | 53 | A |
| 188A | R | NH1 | −21.7 | −40.6 | −31.4 | 31 | A |
| 188A | R | NH2 | −23.3 | −40.3 | −32.9 | 45 | A |
| 189 | D | N | −16.8 | −33.7 | −30.7 | 34 | A |
| 189 | D | CA | −15.5 | −33.4 | −30.1 | 33 | A |
| 189 | D | C | −15.7 | −32.3 | −29.0 | 35 | A |
| 189 | D | O | −16.8 | −31.8 | −28.8 | 33 | A |
| 189 | D | CB | −14.7 | −32.7 | −31.2 | 34 | A |
| 189 | D | CG | −13.2 | −32.8 | −30.9 | 42 | A |
| 189 | D | OD1 | −12.8 | −33.4 | −29.9 | 40 | A |
| 189 | D | OD2 | −12.4 | −32.4 | −31.8 | 43 | A |
| 190 | S | N | −14.7 | −32.1 | −28.3 | 34 | A |
| 190 | S | CA | −14.6 | −31.0 | −27.3 | 34 | A |
| 190 | S | C | −14.3 | −29.7 | −28.2 | 39 | A |
| 190 | S | O | −13.9 | −29.9 | −29.3 | 36 | A |
| 190 | S | CB | −13.4 | −31.2 | −26.3 | 35 | A |
| 190 | S | OG | −13.8 | −32.1 | −25.3 | 39 | A |
| 191 | C | N | −14.4 | −28.5 | −27.6 | 39 | A |
| 191 | C | CA | −14.1 | −27.4 | −28.4 | 40 | A |
| 191 | C | C | −13.6 | −26.2 | −27.6 | 40 | A |
| 191 | C | O | −13.3 | −26.3 | −26.4 | 38 | A |
| 191 | C | CB | −15.3 | −27.0 | −29.3 | 42 | A |
| 191 | C | SG | −15.0 | −26.0 | −30.8 | 48 | A |
| 192 | Q | N | −13.4 | −25.0 | −28.2 | 39 | A |
| 192 | Q | CA | −13.0 | −23.9 | −27.5 | 37 | A |
| 192 | Q | C | −14.0 | −23.5 | −26.3 | 37 | A |
| 192 | Q | O | −15.2 | −23.5 | −26.5 | 37 | A |
| 192 | Q | CB | −12.9 | −22.7 | −28.4 | 39 | A |
| 192 | Q | CG | −12.2 | −21.5 | −27.8 | 46 | A |
| 192 | Q | CD | −11.8 | −20.5 | −28.8 | 62 | A |
| 192 | Q | OE1 | −12.5 | −20.3 | −29.8 | 58 | A |
| 192 | Q | NE2 | −10.7 | −19.8 | −28.5 | 65 | A |
| 193 | G | N | −13.4 | −23.3 | −25.2 | 32 | A |
| 193 | G | CA | −14.2 | −23.1 | −24.0 | 31 | A |
| 193 | G | C | −14.3 | −24.3 | −23.1 | 35 | A |
| 193 | G | O | −14.6 | −24.1 | −21.9 | 36 | A |
| 194 | D | N | −14.2 | −25.5 | −23.6 | 30 | A |
| 194 | D | CA | −14.2 | −26.7 | −22.8 | 29 | A |
| 194 | D | C | −12.9 | −27.1 | −22.1 | 32 | A |
| 194 | D | O | −12.9 | −27.8 | −21.1 | 31 | A |
| 194 | D | CB | −14.6 | −27.9 | −23.7 | 29 | A |
| 194 | D | CG | −16.0 | −27.7 | −24.4 | 34 | A |
| 194 | D | OD1 | −16.9 | −27.2 | −23.7 | 36 | A |
| 194 | D | OD2 | −16.2 | −28.1 | −25.5 | 37 | A |
| 195 | S | N | −11.8 | −26.5 | −22.7 | 27 | A |
| 195 | S | CA | −10.5 | −26.8 | −22.1 | 29 | A |
| 195 | S | C | −10.4 | −26.6 | −20.6 | 31 | A |
| 195 | S | O | −11.1 | −25.7 | −20.1 | 29 | A |
| 195 | S | CB | −9.4 | −25.9 | −22.8 | 32 | A |
| 195 | S | OG | −9.5 | −26.1 | −24.2 | 52 | A |
| 196 | G | N | −9.7 | −27.5 | −20.0 | 26 | A |
| 196 | G | CA | −9.6 | −27.4 | −18.5 | 26 | A |
| 196 | G | C | −10.7 | −28.2 | −17.9 | 28 | A |
| 196 | G | O | −10.7 | −28.5 | −16.7 | 30 | A |
| 197 | G | N | −11.7 | −28.6 | −18.6 | 24 | A |
| 197 | G | CA | −12.8 | −29.3 | −18.1 | 25 | A |
| 197 | G | C | −12.5 | −30.8 | −18.0 | 31 | A |
| 197 | G | O | −11.4 | −31.3 | −18.3 | 29 | A |
| 198 | P | N | −13.5 | −31.6 | −17.5 | 30 | A |
| 198 | P | CA | −13.3 | −33.0 | −17.1 | 28 | A |
| 198 | P | C | −13.5 | −34.0 | −18.3 | 31 | A |
| 198 | P | O | −14.4 | −33.9 | −19.1 | 30 | A |
| 198 | P | CB | −14.5 | −33.2 | −16.1 | 29 | A |
| 198 | P | CG | −15.5 | −32.2 | −16.5 | 33 | A |
| 198 | P | CD | −14.8 | −31.0 | −17.0 | 29 | A |
| 199 | H | N | −12.7 | −35.0 | −18.2 | 28 | A |
| 199 | H | CA | −12.9 | −36.3 | −19.0 | 26 | A |
| 199 | H | C | −13.1 | −37.3 | −17.9 | 27 | A |
| 199 | H | O | −12.2 | −37.4 | −17.0 | 23 | A |
| 199 | H | CB | −11.7 | −36.6 | −19.9 | 25 | A |
| 199 | H | CG | −11.8 | −37.9 | −20.5 | 28 | A |
| 199 | H | ND1 | −11.4 | −39.1 | −19.9 | 29 | A |
| 199 | H | CD2 | −12.0 | −38.3 | −21.8 | 31 | A |
| 199 | H | CE1 | −11.6 | −40.1 | −20.7 | 29 | A |

TABLE 3-continued

Coordinates of Factor IXa co-crystal Compound B complex

| | | | | | | |
|---|---|---|---|---|---|---|
| 199 | H | NE2 | −11.9 | −39.7 | −21.9 | 30 | A |
| 200 | V | N | −14.2 | −37.9 | −17.7 | 27 | A |
| 200 | V | CA | −14.4 | −38.8 | −16.6 | 27 | A |
| 200 | V | C | −14.8 | −40.2 | −17.0 | 32 | A |
| 200 | V | O | −15.4 | −40.4 | −18.1 | 30 | A |
| 200 | V | CB | −15.4 | −38.3 | −15.6 | 30 | A |
| 200 | V | CG1 | −15.1 | −36.8 | −15.2 | 29 | A |
| 200 | V | CG2 | −16.9 | −38.4 | −16.1 | 29 | A |
| 201 | T | N | −14.5 | −41.2 | −16.2 | 28 | A |
| 201 | T | CA | −14.8 | −42.6 | −16.5 | 27 | A |
| 201 | T | C | −15.8 | −43.2 | −15.4 | 30 | A |
| 201 | T | O | −15.5 | −43.0 | −14.3 | 29 | A |
| 201 | T | CB | −13.5 | −43.4 | −16.7 | 30 | A |
| 201 | T | OG1 | −12.7 | −42.9 | −17.8 | 26 | A |
| 201 | T | CG2 | −13.8 | −44.9 | −16.9 | 23 | A |
| 202 | E | N | −16.9 | −43.7 | −15.9 | 30 | A |
| 202 | E | CA | −17.9 | −44.3 | −14.9 | 31 | A |
| 202 | E | C | −17.5 | −45.7 | −14.5 | 35 | A |
| 202 | E | O | −17.4 | −46.6 | −15.4 | 36 | A |
| 202 | E | CB | −19.3 | −44.3 | −15.5 | 32 | A |
| 202 | E | CG | −19.8 | −42.9 | −15.9 | 53 | A |
| 202 | E | CD | −21.2 | −43.1 | −16.7 | 80 | A |
| 202 | E | OE1 | −21.5 | −44.2 | −17.2 | 74 | A |
| 202 | E | OE2 | −21.9 | −42.1 | −16.8 | 70 | A |
| 203 | V | N | −17.2 | −45.9 | −13.3 | 32 | A |
| 203 | V | CA | −16.8 | −47.2 | −12.8 | 32 | A |
| 203 | V | C | −18.0 | −47.7 | −11.9 | 39 | A |
| 203 | V | O | −18.1 | −47.3 | −10.7 | 40 | A |
| 203 | V | CB | −15.6 | −47.1 | −12.0 | 35 | A |
| 203 | V | CG1 | −15.1 | −48.5 | −11.5 | 34 | A |
| 203 | V | CG2 | −14.5 | −46.4 | −12.8 | 35 | A |
| 204 | E | N | −18.9 | −48.6 | −12.4 | 37 | A |
| 204 | E | CA | −20.0 | −49.1 | −11.7 | 38 | A |
| 204 | E | C | −20.8 | −48.0 | −11.0 | 44 | A |
| 204 | E | O | −21.1 | −48.2 | −9.8 | 45 | A |
| 204 | E | CB | −19.5 | −50.1 | −10.6 | 40 | A |
| 204 | E | CG | −19.0 | −51.4 | −11.2 | 54 | A |
| 204 | E | CD | −20.1 | −52.4 | −11.3 | 89 | A |
| 204 | E | OE1 | −19.9 | −53.5 | −10.6 | 0 | A |
| 204 | E | OE2 | −21.1 | −52.2 | −11.9 | 84 | A |
| 205 | G | N | −21.2 | −47.0 | −11.7 | 41 | A |
| 205 | G | CA | −22.0 | −45.9 | −11.0 | 40 | A |
| 205 | G | C | −21.3 | −44.8 | −10.4 | 44 | A |
| 205 | G | O | −21.9 | −43.8 | −10.0 | 46 | A |
| 206 | T | N | −19.9 | −44.9 | −10.3 | 36 | A |
| 206 | T | CA | −19.1 | −43.8 | −9.8 | 35 | A |
| 206 | T | C | −18.1 | −43.2 | −10.8 | 37 | A |
| 206 | T | O | −17.4 | −44.0 | −11.4 | 36 | A |
| 206 | T | CB | −18.3 | −44.3 | −8.5 | 31 | A |
| 206 | T | OG1 | −19.2 | −44.9 | −7.6 | 39 | A |
| 206 | T | CG2 | −17.6 | −43.2 | −7.8 | 27 | A |
| 207 | S | N | −18.1 | −41.9 | −11.0 | 32 | A |
| 207 | S | CA | −17.3 | −41.3 | −12.0 | 30 | A |
| 207 | S | C | −15.9 | −41.0 | −11.4 | 32 | A |
| 207 | S | O | −15.9 | −40.5 | −10.2 | 31 | A |
| 207 | S | CB | −17.9 | −40.1 | −12.6 | 32 | A |
| 207 | S | OG | −19.1 | −40.6 | −13.3 | 38 | A |
| 208 | F | N | −14.9 | −41.2 | −12.1 | 26 | A |
| 208 | F | CA | −13.5 | −40.9 | −11.7 | 24 | A |
| 208 | F | C | −12.9 | −39.9 | −12.8 | 27 | A |
| 208 | F | O | −13.2 | −40.1 | −14.0 | 28 | A |
| 208 | F | CB | −12.7 | −42.1 | −11.6 | 25 | A |
| 208 | F | CG | −12.9 | −42.9 | −10.3 | 26 | A |
| 208 | F | CD1 | −14.0 | −43.8 | −10.3 | 28 | A |
| 208 | F | CD2 | −12.1 | −42.7 | −9.2 | 27 | A |
| 208 | F | CE1 | −14.2 | −44.5 | −9.1 | 29 | A |
| 208 | F | CE2 | −12.4 | −43.4 | −8.0 | 28 | A |
| 208 | F | CZ | −13.4 | −44.3 | −8.0 | 27 | A |
| 209 | L | N | −12.1 | −39.0 | −12.3 | 25 | A |
| 209 | L | CA | −11.4 | −38.1 | −13.3 | 25 | A |
| 209 | L | C | −10.3 | −38.8 | −14.0 | 31 | A |
| 209 | L | O | −9.3 | −39.2 | −13.3 | 32 | A |
| 209 | L | CB | −10.8 | −36.9 | −12.5 | 24 | A |
| 209 | L | CG | −10.4 | −35.7 | −13.3 | 28 | A |
| 209 | L | CD1 | −11.6 | −35.1 | −14.0 | 27 | A |
| 209 | L | CD2 | −9.7 | −34.7 | −12.5 | 23 | A |
| 210 | T | N | −10.4 | −39.0 | −15.3 | 27 | A |
| 210 | T | CA | −9.4 | −39.6 | −16.1 | 26 | A |
| 210 | T | C | −8.6 | −38.7 | −17.0 | 30 | A |
| 210 | T | O | −7.4 | −39.0 | −17.3 | 29 | A |
| 210 | T | CB | −9.9 | −41.0 | −16.8 | 28 | A |
| 210 | T | OG1 | −11.1 | −40.7 | −17.5 | 27 | A |
| 210 | T | CG2 | −10.1 | −42.0 | −15.8 | 19 | A |
| 211 | G | N | −9.1 | −37.5 | −17.3 | 27 | A |
| 211 | G | CA | −8.3 | −36.6 | −18.1 | 26 | A |
| 211 | G | C | −8.7 | −35.1 | −17.9 | 30 | A |
| 211 | G | O | −9.8 | −34.8 | −17.4 | 29 | A |
| 212 | I | N | −7.9 | −34.3 | −18.4 | 28 | A |
| 212 | I | CA | −8.2 | −32.8 | −18.5 | 27 | A |
| 212 | I | C | −8.3 | −32.5 | −20.0 | 31 | A |
| 212 | I | O | −7.4 | −32.7 | −20.7 | 32 | A |
| 212 | I | CB | −7.1 | −32.0 | −17.8 | 27 | A |
| 212 | I | CG1 | −6.7 | −32.5 | −16.4 | 25 | A |
| 212 | I | CG2 | −7.6 | −30.5 | −17.7 | 28 | A |
| 212 | I | CD1 | −7.7 | −32.4 | −15.2 | 24 | A |
| 213 | I | N | −9.4 | −31.9 | −20.4 | 27 | A |
| 213 | I | CA | −9.6 | −31.5 | −21.7 | 26 | A |
| 213 | I | C | −8.5 | −30.5 | −22.0 | 31 | A |
| 213 | I | O | −8.3 | −29.5 | −21.3 | 31 | A |
| 213 | I | CB | −11.0 | −30.8 | −21.9 | 29 | A |
| 213 | I | CG1 | −12.1 | −31.8 | −21.5 | 29 | A |
| 213 | I | CG2 | −11.2 | −30.4 | −23.4 | 31 | A |
| 213 | I | CD1 | −13.5 | −31.2 | −21.6 | 34 | A |
| 214 | S | N | −7.7 | −30.8 | −23.1 | 29 | A |
| 214 | S | CA | −6.6 | −29.9 | −23.3 | 29 | A |
| 214 | S | C | −6.6 | −29.1 | −24.6 | 33 | A |
| 214 | S | O | −6.7 | −27.9 | −24.6 | 32 | A |
| 214 | S | CB | −5.3 | −30.7 | −23.2 | 29 | A |
| 214 | S | OG | −4.1 | −29.8 | −23.1 | 44 | A |
| 215 | W | N | −6.6 | −29.7 | −25.8 | 29 | A |
| 215 | W | CA | −6.5 | −29.0 | −27.1 | 29 | A |
| 215 | W | C | −6.8 | −29.9 | −28.3 | 37 | A |
| 215 | W | O | −6.8 | −31.1 | −28.2 | 36 | A |
| 215 | W | CB | −5.2 | −28.4 | −27.2 | 27 | A |
| 215 | W | CG | −4.0 | −29.4 | −27.4 | 28 | A |
| 215 | W | CD1 | −3.2 | −29.8 | −26.3 | 30 | A |
| 215 | W | CD2 | −3.4 | −29.9 | −28.6 | 28 | A |
| 215 | W | NE1 | −2.2 | −30.6 | −26.8 | 30 | A |
| 215 | W | CE2 | −2.3 | −30.6 | −28.2 | 33 | A |
| 215 | W | CE3 | −3.7 | −29.7 | −29.9 | 30 | A |
| 215 | W | CZ2 | −1.5 | −31.3 | −29.1 | 33 | A |
| 215 | W | CZ3 | −3.0 | −30.4 | −30.9 | 31 | A |
| 215 | W | CH2 | −1.9 | −31.2 | −30.5 | 33 | A |
| 216 | G | N | −6.9 | −29.2 | −29.4 | 36 | A |
| 216 | G | CA | −7.1 | −29.9 | −30.7 | 35 | A |
| 216 | G | C | −6.8 | −28.9 | −31.8 | 39 | A |
| 216 | G | O | −6.7 | −27.7 | −31.6 | 40 | A |
| 217 | E | N | −6.8 | −29.4 | −33.1 | 35 | A |
| 217 | E | CA | −6.5 | −28.6 | −34.3 | 33 | A |
| 217 | E | C | −7.9 | −28.4 | −34.8 | 41 | A |
| 217 | E | O | −8.5 | −29.3 | −35.5 | 42 | A |
| 217 | E | CB | −5.6 | −29.4 | −35.2 | 33 | A |
| 217 | E | CG | −4.2 | −29.5 | −34.6 | 39 | A |
| 217 | E | CD | −3.3 | −30.5 | −35.4 | 63 | A |
| 217 | E | OE1 | −3.0 | −31.6 | −34.9 | 45 | A |
| 217 | E | OE2 | −2.9 | −30.1 | −36.6 | 48 | A |
| 219 | E | N | −8.6 | −27.3 | −34.5 | 41 | A |
| 219 | E | CA | −9.9 | −27.0 | −34.9 | 42 | A |
| 219 | E | C | −10.8 | −27.8 | −33.9 | 46 | A |
| 219 | E | O | −10.4 | −28.1 | −32.8 | 45 | A |
| 219 | E | CB | −10.3 | −27.2 | −36.3 | 43 | A |
| 219 | E | CG | −9.4 | −26.3 | −37.3 | 52 | A |
| 219 | E | CD | −9.6 | −26.7 | −38.8 | 67 | A |
| 219 | E | OE1 | −9.5 | −27.9 | −39.1 | 76 | A |
| 219 | E | OE2 | −9.9 | −25.8 | −39.5 | 54 | A |
| 220 | C | N | −12.0 | −28.2 | −34.4 | 44 | A |
| 220 | C | CA | −12.9 | −29.0 | −33.6 | 43 | A |
| 220 | C | C | −13.6 | −29.9 | −34.5 | 42 | A |
| 220 | C | O | −14.1 | −29.5 | −35.6 | 41 | A |
| 220 | C | CB | −14.0 | −28.1 | −32.9 | 44 | A |
| 220 | C | SG | −13.4 | −26.8 | −31.8 | 49 | A |
| 221 | A | N | −13.8 | −31.2 | −34.0 | 36 | A |
| 221 | A | CA | −14.6 | −32.1 | −34.7 | 35 | A |
| 221 | A | C | −14.3 | −32.5 | −36.2 | 38 | A |
| 221 | A | O | −15.2 | −33.0 | −36.9 | 36 | A |
| 221 | A | CB | −16.1 | −31.8 | −34.5 | 35 | A |

TABLE 3-continued

Coordinates of Factor IXa co-crystal Compound B complex

| | | | | | | |
|---|---|---|---|---|---|---|
| 221A | M | N | −13.1 | −32.3 | −36.6 | 34 | A |
| 221A | M | CA | −12.7 | −32.6 | −38.0 | 34 | A |
| 221A | M | C | −12.3 | −34.0 | −38.2 | 37 | A |
| 221A | M | O | −11.5 | −34.5 | −37.5 | 40 | A |
| 221A | M | CB | −11.5 | −31.7 | −38.5 | 36 | A |
| 221A | M | CG | −11.8 | −30.2 | −38.4 | 41 | A |
| 221A | M | SD | −13.1 | −29.6 | −39.5 | 46 | A |
| 221A | M | CE | −14.0 | −28.5 | −38.4 | 42 | A |
| 222 | K | N | −12.8 | −34.6 | −39.2 | 32 | A |
| 222 | K | CA | −12.5 | −36.0 | −39.3 | 31 | A |
| 222 | K | C | −11.0 | −36.1 | −39.7 | 36 | A |
| 222 | K | O | −10.4 | −35.2 | −40.4 | 36 | A |
| 222 | K | CB | −13.1 | −36.4 | −40.9 | 32 | A |
| 222 | K | CG | −12.3 | −37.3 | −41.7 | 23 | A |
| 222 | K | CD | −13.0 | −38.1 | −42.9 | 22 | A |
| 222 | K | CE | −12.3 | −39.4 | −43.1 | 29 | A |
| 222 | K | NZ | −12.8 | −40.1 | −44.3 | 52 | A |
| 223 | G | N | −10.3 | −37.0 | −39.1 | 32 | A |
| 223 | G | CA | −8.9 | −37.2 | −39.1 | 30 | A |
| 223 | G | C | −8.2 | −36.5 | −37.9 | 34 | A |
| 223 | G | O | −7.0 | −36.7 | −37.7 | 32 | A |
| 224 | K | N | −8.9 | −35.7 | −37.2 | 33 | A |
| 224 | K | CA | −8.3 | −35.1 | −36.0 | 34 | A |
| 224 | K | C | −9.0 | −35.6 | −34.8 | 37 | A |
| 224 | K | O | −10.1 | −36.1 | −34.8 | 37 | A |
| 224 | K | CB | −8.5 | −33.5 | −36.1 | 34 | A |
| 224 | K | CG | −7.7 | −32.8 | −37.1 | 28 | A |
| 224 | K | CD | −6.2 | −33.1 | −36.9 | 38 | A |
| 224 | K | CE | −5.4 | −32.8 | −38.1 | 46 | A |
| 224 | K | NZ | −3.9 | −32.7 | −37.8 | 51 | A |
| 225 | Y | N | −8.2 | −35.6 | −33.6 | 33 | A |
| 225 | Y | CA | −8.8 | −36.0 | −32.4 | 31 | A |
| 225 | Y | C | −8.6 | −35.0 | −31.3 | 35 | A |
| 225 | Y | O | −7.8 | −34.0 | −31.6 | 34 | A |
| 225 | Y | CB | −8.1 | −37.3 | −31.9 | 30 | A |
| 225 | Y | CG | −8.4 | −38.4 | −32.9 | 29 | A |
| 225 | Y | CD1 | −9.6 | −39.1 | −32.9 | 28 | A |
| 225 | Y | CD2 | −7.4 | −38.8 | −33.9 | 30 | A |
| 225 | Y | CE1 | −9.8 | −40.1 | −33.8 | 26 | A |
| 225 | Y | CE2 | −7.7 | −39.8 | −34.9 | 30 | A |
| 225 | Y | CZ | −9.0 | −40.4 | −34.8 | 32 | A |
| 225 | Y | OH | −9.2 | −41.4 | −35.7 | 30 | A |
| 226 | G | N | −9.2 | −35.1 | −30.2 | 34 | A |
| 226 | G | CA | −9.0 | −34.2 | −29.1 | 33 | A |
| 226 | G | C | −7.9 | −34.7 | −28.3 | 31 | A |
| 226 | G | O | −7.7 | −36.0 | −28.2 | 29 | A |
| 227 | I | N | −7.0 | −33.8 | −27.7 | 26 | A |
| 227 | I | CA | −5.9 | −34.1 | −26.9 | 25 | A |
| 227 | I | C | −6.2 | −33.7 | −25.4 | 30 | A |
| 227 | I | O | −6.7 | −32.6 | −25.1 | 29 | A |
| 227 | I | CB | −4.6 | −33.5 | −27.4 | 28 | A |
| 227 | I | CG1 | −4.5 | −33.5 | −29.0 | 29 | A |
| 227 | I | CG2 | −3.4 | −34.2 | −26.8 | 24 | A |
| 227 | I | CD1 | −4.5 | −34.9 | −29.6 | 26 | A |
| 228 | Y | N | −6.0 | −34.7 | −24.6 | 27 | A |
| 228 | Y | CA | −6.3 | −34.6 | −23.2 | 23 | A |
| 228 | Y | C | −5.1 | −34.9 | −22.4 | 26 | A |
| 228 | Y | O | −4.2 | −35.7 | −22.8 | 25 | A |
| 228 | Y | CB | −7.3 | −35.7 | −22.8 | 23 | A |
| 228 | Y | CG | −8.6 | −35.5 | −23.6 | 23 | A |
| 228 | Y | CD1 | −8.8 | −36.0 | −24.9 | 23 | A |
| 228 | Y | CD2 | −9.7 | −34.9 | −23.0 | 24 | A |
| 228 | Y | CE1 | −10.0 | −35.8 | −25.6 | 21 | A |
| 228 | Y | CE2 | −10.9 | −34.7 | −23.7 | 24 | A |
| 228 | Y | CZ | −11.0 | −35.1 | −25.0 | 30 | A |
| 228 | Y | OH | −12.2 | −34.9 | −25.7 | 28 | A |
| 229 | T | N | −5.0 | −34.4 | −21.2 | 24 | A |
| 229 | T | CA | −3.9 | −34.7 | −20.2 | 25 | A |
| 229 | T | C | −4.3 | −35.9 | −19.4 | 27 | A |
| 229 | T | O | −5.4 | −36.0 | −18.9 | 25 | A |
| 229 | T | CB | −3.7 | −33.5 | −19.3 | 29 | A |
| 229 | T | OG1 | −3.3 | −32.4 | −20.2 | 29 | A |
| 229 | T | CG2 | −2.6 | −33.8 | −18.3 | 22 | A |
| 230 | K | N | −3.3 | −36.8 | −19.2 | 23 | A |
| 230 | K | CA | −3.6 | −38.0 | −18.3 | 23 | A |
| 230 | K | C | −3.5 | −37.5 | −16.9 | 26 | A |
| 230 | K | O | −2.5 | −37.0 | −16.4 | 27 | A |
| 230 | K | CB | −2.6 | −39.1 | −18.6 | 24 | A |
| 230 | K | CG | −2.9 | −39.9 | −19.9 | 22 | A |
| 230 | K | CD | −1.9 | −41.1 | −20.0 | 18 | A |
| 230 | K | CE | −1.8 | −41.6 | −21.4 | 21 | A |
| 230 | K | NZ | −0.9 | −42.8 | −21.5 | 21 | A |
| 231 | V | N | −4.6 | −37.7 | −16.2 | 23 | A |
| 231 | V | CA | −4.7 | −37.3 | −14.8 | 23 | A |
| 231 | V | C | −3.8 | −38.3 | −13.9 | 27 | A |
| 231 | V | O | −3.2 | −37.9 | −12.9 | 28 | A |
| 231 | V | CB | −6.2 | −37.2 | −14.3 | 27 | A |
| 231 | V | CG1 | −6.3 | −37.3 | −12.8 | 26 | A |
| 231 | V | CG2 | −6.8 | −35.9 | −15.0 | 26 | A |
| 232 | S | N | −3.7 | −39.5 | −14.3 | 25 | A |
| 232 | S | CA | −2.8 | −40.5 | −13.6 | 26 | A |
| 232 | S | C | −1.5 | −40.0 | −13.4 | 28 | A |
| 232 | S | O | −0.8 | −40.3 | −12.4 | 27 | A |
| 232 | S | CB | −2.7 | −41.8 | −14.4 | 30 | A |
| 232 | S | OG | −2.2 | −41.7 | −15.7 | 34 | A |
| 233 | R | N | −1.0 | −39.2 | −14.3 | 25 | A |
| 233 | R | CA | 0.4 | −38.6 | −14.2 | 23 | A |
| 233 | R | C | 0.6 | −37.6 | −13.0 | 30 | A |
| 233 | R | O | 1.7 | −37.3 | −12.6 | 29 | A |
| 233 | R | CB | 0.8 | −38.1 | −15.5 | 18 | A |
| 233 | R | CG | 1.9 | −37.0 | −15.5 | 24 | A |
| 233 | R | CD | 3.2 | −37.6 | −15.2 | 16 | A |
| 233 | R | NE | 4.3 | −36.5 | −15.3 | 29 | A |
| 233 | R | CZ | 4.6 | −35.7 | −14.3 | 41 | A |
| 233 | R | NH1 | 3.9 | −35.7 | −13.2 | 26 | A |
| 233 | R | NH2 | 5.5 | −34.8 | −14.6 | 24 | A |
| 234 | Y | N | −0.6 | −37.1 | −12.5 | 26 | A |
| 234 | Y | CA | −0.6 | −36.0 | −11.5 | 25 | A |
| 234 | Y | C | −1.3 | −36.2 | −10.2 | 34 | A |
| 234 | Y | O | −1.5 | −35.3 | −9.4 | 35 | A |
| 234 | Y | CB | −1.4 | −34.8 | −12.2 | 24 | A |
| 234 | Y | CG | −0.6 | −34.3 | −13.5 | 23 | A |
| 234 | Y | CD1 | 0.6 | −33.8 | −13.3 | 24 | A |
| 234 | Y | CD2 | −1.0 | −34.6 | −14.8 | 24 | A |
| 234 | Y | CE1 | 1.4 | −33.4 | −14.4 | 28 | A |
| 234 | Y | CE2 | −0.3 | −34.2 | −15.9 | 25 | A |
| 234 | Y | CZ | 1.0 | −33.7 | −15.7 | 30 | A |
| 234 | Y | OH | 1.8 | −33.3 | −16.8 | 33 | A |
| 235 | V | N | −1.8 | −37.5 | −10.0 | 31 | A |
| 235 | V | CA | −2.5 | −37.8 | −8.8 | 31 | A |
| 235 | V | C | −1.9 | −37.4 | −7.5 | 33 | A |
| 235 | V | O | −2.5 | −36.8 | −6.6 | 33 | A |
| 235 | V | CB | −3.2 | −39.3 | −8.9 | 35 | A |
| 235 | V | CG1 | −3.8 | −39.6 | −7.6 | 37 | A |
| 235 | V | CG2 | −4.2 | −39.4 | −10.0 | 32 | A |
| 236 | N | N | −0.6 | −37.8 | −7.3 | 32 | A |
| 236 | N | CA | 0.1 | −37.4 | −6.0 | 32 | A |
| 236 | N | C | 0.1 | −35.9 | −5.8 | 36 | A |
| 236 | N | O | −0.2 | −35.5 | −4.7 | 39 | A |
| 236 | N | CB | 1.5 | −38.0 | −5.9 | 22 | A |
| 236 | N | CG | 2.4 | −37.4 | −4.7 | 49 | A |
| 236 | N | OD1 | 2.7 | −36.2 | −4.7 | 43 | A |
| 236 | N | ND2 | 2.6 | −38.2 | −3.6 | 35 | A |
| 237 | W | N | 0.4 | −35.1 | −6.8 | 30 | A |
| 237 | W | CA | 0.4 | −33.7 | −6.7 | 28 | A |
| 237 | W | C | −1.0 | −33.1 | −6.4 | 32 | A |
| 237 | W | O | −1.2 | −32.2 | −5.5 | 32 | A |
| 237 | W | CB | 1.0 | −33.1 | −8.0 | 26 | A |
| 237 | W | CG | 0.9 | −31.6 | −8.2 | 26 | A |
| 237 | W | CD1 | 1.8 | −30.7 | −7.8 | 29 | A |
| 237 | W | CD2 | −0.1 | −30.9 | −9.0 | 23 | A |
| 237 | W | NE1 | 1.4 | −29.4 | −8.2 | 27 | A |
| 237 | W | CE2 | 0.3 | −29.5 | −9.0 | 27 | A |
| 237 | W | CE3 | −1.2 | −31.3 | −9.7 | 23 | A |
| 237 | W | CZ2 | −0.4 | −28.5 | −9.6 | 26 | A |
| 237 | W | CZ3 | −1.9 | −30.3 | −10.4 | 25 | A |
| 237 | W | CH2 | −1.5 | −29.0 | −10.3 | 26 | A |
| 238 | I | N | −2.1 | −33.6 | −7.1 | 28 | A |
| 238 | I | CA | −3.4 | −33.1 | −6.8 | 27 | A |
| 238 | I | C | −3.8 | −33.4 | −5.3 | 33 | A |
| 238 | I | O | −4.3 | −34.5 | −4.5 | 30 | A |
| 238 | I | CB | −4.5 | −33.8 | −7.7 | 28 | A |
| 238 | I | CG1 | −4.2 | −33.4 | −9.2 | 28 | A |
| 238 | I | CG2 | −5.9 | −33.4 | −7.3 | 24 | A |
| 238 | I | CD1 | −5.1 | −34.2 | −10.2 | 22 | A |
| 239 | K | N | −3.7 | −34.7 | −4.9 | 31 | A |

TABLE 3-continued

Coordinates of Factor IXa co-crystal Compound B complex

| | | | | | | |
|---|---|---|---|---|---|---|
| 239 | K | CA | −4.0 | −35.1 | −3.6 | 30 | A |
| 239 | K | C | −3.2 | −34.3 | −2.5 | 35 | A |
| 239 | K | O | −3.8 | −33.9 | −1.4 | 37 | A |
| 239 | K | CB | −4.0 | −36.6 | −3.4 | 31 | A |
| 239 | K | CG | −5.4 | −37.2 | −3.8 | 37 | A |
| 239 | K | CD | −5.3 | −38.5 | −4.6 | 53 | A |
| 239 | K | CE | −6.5 | −39.4 | −4.4 | 50 | A |
| 239 | K | NZ | −7.8 | −38.6 | −4.5 | 53 | A |
| 240 | E | N | −2.0 | −33.9 | −2.8 | 29 | A |
| 240 | E | CA | −1.1 | −33.2 | −1.9 | 27 | A |
| 240 | E | C | −1.4 | −31.7 | −1.8 | 36 | A |
| 240 | E | O | −1.2 | −31.1 | −0.7 | 38 | A |
| 240 | E | CB | 0.3 | −33.5 | −2.3 | 28 | A |
| 240 | E | CG | 1.3 | −32.5 | −1.7 | 33 | A |
| 240 | E | CD | 1.5 | −32.8 | −0.3 | 57 | A |
| 240 | E | OE1 | 1.2 | −33.9 | 0.2 | 63 | A |
| 240 | E | OE2 | 2.0 | −31.8 | 0.4 | 52 | A |
| 241 | K | N | −1.7 | −31.0 | −2.9 | 32 | A |
| 241 | K | CA | −1.9 | −29.6 | −2.8 | 30 | A |
| 241 | K | C | −3.3 | −29.3 | −2.4 | 33 | A |
| 241 | K | O | −3.6 | −28.2 | −1.9 | 34 | A |
| 241 | K | CB | −1.7 | −28.9 | −4.2 | 30 | A |
| 241 | K | CG | −0.3 | −29.2 | −4.8 | 35 | A |
| 241 | K | CD | 0.8 | −28.5 | −4.0 | 42 | A |
| 241 | K | CE | 2.2 | −29.2 | −4.2 | 48 | A |
| 241 | K | NZ | 3.3 | −28.3 | −3.9 | 52 | A |
| 242 | T | N | −4.3 | −30.2 | −2.5 | 31 | A |
| 242 | T | CA | −5.7 | −29.9 | −2.2 | 30 | A |
| 242 | T | C | −6.1 | −30.5 | −0.8 | 37 | A |
| 242 | T | O | −7.3 | −30.5 | −0.5 | 36 | A |
| 242 | T | CB | −6.6 | −30.5 | −3.3 | 28 | A |
| 242 | T | OG1 | −6.5 | −31.9 | −3.3 | 30 | A |
| 242 | T | CG2 | −6.3 | −29.9 | −4.6 | 23 | A |
| 243 | K | N | −5.1 | −31.0 | −0.1 | 38 | A |
| 243 | K | CA | −5.3 | −31.6 | 1.3 | 38 | A |
| 243 | K | C | −6.1 | −30.6 | 2.1 | 43 | A |
| 243 | K | O | −5.7 | −29.4 | 2.2 | 41 | A |
| 243 | K | CB | −3.9 | −31.9 | 1.9 | 37 | A |
| 243 | K | CG | −3.7 | −33.4 | 2.2 | 43 | A |
| 243 | K | CD | −2.1 | −33.6 | 2.1 | 45 | A |
| 243 | K | CE | −1.8 | −35.0 | 2.7 | 60 | A |
| 243 | K | NZ | −2.0 | −36.1 | 1.7 | 72 | A |
| 244 | L | N | −7.2 | −31.0 | 2.8 | 42 | A |
| 244 | L | CA | −8.0 | −30.1 | 3.6 | 43 | A |
| 244 | L | C | −7.7 | −30.2 | 5.1 | 50 | A |
| 244 | L | O | −7.6 | −31.3 | 5.7 | 50 | A |
| 244 | L | CB | −9.5 | −30.3 | 3.3 | 42 | A |
| 244 | L | CG | −9.8 | −29.6 | 2.1 | 45 | A |
| 244 | L | CD1 | −11.3 | −29.6 | 1.8 | 43 | A |
| 244 | L | CD2 | −9.3 | −28.2 | 2.1 | 47 | A |
| 86 | M | N | −10.5 | −64.2 | −5.5 | 79 | B |
| 86 | M | CA | −9.2 | −64.9 | −5.6 | 79 | B |
| 86 | M | C | −8.0 | −64.0 | −5.9 | 78 | B |
| 86 | M | O | −7.2 | −63.7 | −4.9 | 77 | B |
| 86 | M | CB | −9.2 | −66.1 | −6.6 | 83 | B |
| 86 | M | CG | −9.0 | −67.5 | −5.9 | 88 | B |
| 86 | M | SD | −8.6 | −68.8 | −7.2 | 95 | B |
| 86 | M | CE | −7.2 | −69.6 | −6.3 | 91 | B |
| 87 | T | N | −7.9 | −63.5 | −7.1 | 71 | B |
| 87 | T | CA | −6.8 | −62.6 | −7.4 | 69 | B |
| 87 | T | C | −7.2 | −61.2 | −8.1 | 67 | B |
| 87 | T | O | −8.2 | −61.1 | −8.8 | 66 | B |
| 87 | T | CB | −5.6 | −63.2 | −8.2 | 73 | B |
| 87 | T | OG1 | −4.5 | −62.4 | −8.2 | 70 | B |
| 87 | T | CG2 | −6.0 | −63.5 | −9.7 | 70 | B |
| 88 | C | N | −6.4 | −60.2 | −7.8 | 59 | B |
| 88 | C | CA | −6.8 | −58.8 | −8.4 | 57 | B |
| 88 | C | C | −6.7 | −58.8 | −9.9 | 61 | B |
| 88 | C | O | −7.6 | −58.1 | −10.5 | 60 | B |
| 88 | C | CB | −5.9 | −57.7 | −7.7 | 55 | B |
| 88 | C | SG | −6.3 | −57.4 | −6.0 | 58 | B |
| 89 | N | N | −5.7 | −59.4 | −10.5 | 59 | B |
| 89 | N | CA | −5.6 | −59.4 | −11.9 | 60 | B |
| 89 | N | C | −6.6 | −60.3 | −12.7 | 64 | B |
| 89 | N | O | −6.4 | −60.5 | −13.9 | 63 | B |
| 89 | N | CB | −4.2 | −59.7 | −12.4 | 66 | B |
| 89 | N | C | −3.6 | −61.0 | −11.8 | 0 | B |
| 89 | N | OD1 | −3.9 | −62.1 | −12.3 | 0 | B |
| 89 | N | ND2 | −2.8 | −60.8 | −10.8 | 96 | B |
| 90 | I | N | −7.6 | −60.8 | −12.0 | 61 | B |
| 90 | I | CA | −8.7 | −61.5 | −12.6 | 60 | B |
| 90 | I | C | −10.0 | −60.9 | −12.2 | 60 | B |
| 90 | I | O | −10.4 | −61.1 | −11.0 | 59 | B |
| 90 | I | CB | −8.6 | −63.1 | −12.2 | 64 | B |
| 90 | I | CG1 | −7.3 | −63.7 | −12.7 | 64 | B |
| 90 | I | CG2 | −9.8 | −63.9 | −12.8 | 64 | B |
| 90 | I | CD1 | −7.0 | −63.4 | −14.2 | 66 | B |
| 91 | K | N | −10.5 | −60.1 | −13.1 | 55 | B |
| 91 | K | CA | −11.8 | −59.4 | −12.8 | 53 | B |
| 91 | K | C | −11.8 | −58.5 | −11.6 | 55 | B |
| 91 | K | O | −12.8 | −58.3 | −11.0 | 54 | B |
| 91 | K | CB | −13.0 | −60.3 | −12.9 | 55 | B |
| 91 | K | CG | −13.6 | −60.4 | −14.2 | 73 | B |
| 91 | K | CD | −15.1 | −61.0 | −14.2 | 88 | B |
| 91 | K | CE | −16.1 | −59.9 | −13.9 | 0 | B |
| 91 | K | NZ | −16.9 | −60.2 | −12.7 | 0 | B |
| 92 | N | N | −10.6 | −57.9 | −11.3 | 51 | B |
| 92 | N | CA | −10.4 | −57.0 | −10.2 | 51 | B |
| 92 | N | C | −10.6 | −57.6 | −8.8 | 55 | B |
| 92 | N | O | −10.8 | −56.9 | −7.8 | 53 | B |
| 92 | N | CB | −11.1 | −55.7 | −10.4 | 48 | B |
| 92 | N | CG | −10.6 | −54.5 | −9.6 | 52 | B |
| 92 | N | OD1 | −11.3 | −53.8 | −9.0 | 35 | B |
| 92 | N | ND2 | −9.3 | −54.4 | −9.6 | 37 | B |
| 93 | G | N | −10.5 | −58.9 | −8.7 | 52 | B |
| 93 | G | CA | −10.7 | −59.6 | −7.4 | 51 | B |
| 93 | G | C | −12.2 | −59.5 | −7.0 | 55 | B |
| 93 | G | O | −12.6 | −59.8 | −5.9 | 55 | B |
| 94 | R | N | −13.0 | −59.2 | −8.0 | 53 | B |
| 94 | R | CA | −14.4 | −59.0 | −7.8 | 53 | B |
| 94 | R | C | −14.8 | −57.7 | −7.1 | 54 | B |
| 94 | R | O | −15.9 | −57.3 | −6.9 | 52 | B |
| 94 | R | CB | −15.1 | −60.2 | −7.1 | 57 | B |
| 94 | R | CG | −15.6 | −61.3 | −8.0 | 69 | B |
| 94 | R | CD | −15.2 | −61.1 | −9.4 | 87 | B |
| 94 | R | NE | −14.6 | −62.3 | −10.0 | 0 | B |
| 94 | R | CZ | −15.1 | −62.9 | −11.1 | 0 | B |
| 94 | R | NH1 | −16.2 | −62.4 | −11.7 | 0 | B |
| 94 | R | NH2 | −14.5 | −64.0 | −11.5 | 94 | B |
| 95 | C | N | −13.7 | −56.9 | −6.8 | 49 | B |
| 95 | C | CA | −13.9 | −55.6 | −6.2 | 48 | B |
| 95 | C | C | −14.5 | −54.5 | −7.1 | 49 | B |
| 95 | C | O | −14.1 | −54.3 | −8.2 | 48 | B |
| 95 | C | CB | −12.5 | −55.1 | −5.6 | 50 | B |
| 95 | C | SG | −11.7 | −56.4 | −4.6 | 54 | B |
| 96 | E | N | −15.6 | −53.9 | −6.5 | 45 | B |
| 96 | E | CA | −16.2 | −52.8 | −7.3 | 44 | B |
| 96 | E | C | −15.3 | −51.7 | −7.7 | 45 | B |
| 96 | E | O | −15.3 | −51.3 | −8.9 | 46 | B |
| 96 | E | CB | −17.4 | −52.3 | −6.5 | 44 | B |
| 96 | E | CG | −18.3 | −51.3 | −7.3 | 43 | B |
| 96 | E | CD | −19.4 | −50.7 | −6.5 | 57 | B |
| 96 | E | OE1 | −20.1 | −51.4 | −5.8 | 65 | B |
| 96 | E | OE2 | −19.5 | −49.4 | −6.5 | 68 | B |
| 97 | Q | N | −14.4 | −51.3 | −6.8 | 37 | B |
| 97 | Q | CA | −13.5 | −50.3 | −7.0 | 34 | B |
| 97 | Q | C | −12.1 | −50.8 | −7.0 | 37 | B |
| 97 | Q | O | −11.5 | −51.1 | −8.0 | 38 | B |
| 97 | Q | CB | −13.7 | −49.1 | −6.0 | 35 | B |
| 97 | Q | CG | −14.6 | −48.0 | −6.5 | 37 | B |
| 97 | Q | CD | −15.1 | −47.0 | −5.4 | 43 | B |
| 97 | Q | OE1 | −14.4 | −46.6 | −4.5 | 38 | B |
| 97 | Q | NE2 | −16.3 | −46.5 | −5.6 | 35 | B |
| 98 | F | N | −11.4 | −50.8 | −5.8 | 35 | B |
| 98 | F | CA | −10.0 | −51.2 | −5.7 | 36 | B |
| 98 | F | C | −9.8 | −52.6 | −5.0 | 48 | B |
| 98 | F | O | −10.5 | −53.0 | −4.1 | 47 | B |
| 98 | F | CB | −9.2 | −50.1 | −5.0 | 35 | B |
| 98 | F | CG | −9.6 | −48.7 | −5.4 | 33 | B |
| 98 | F | CD1 | −9.8 | −48.3 | −6.7 | 34 | B |
| 98 | F | CD2 | −9.8 | −47.8 | −4.4 | 32 | B |
| 98 | F | CE1 | −10.1 | −47.0 | −7.0 | 34 | B |
| 98 | F | CE2 | −10.2 | −46.4 | −4.7 | 35 | B |
| 98 | F | CZ | −10.3 | −46.0 | −6.0 | 31 | B |
| 99 | C | N | −8.7 | −53.2 | −5.5 | 49 | B |
| 99 | C | CA | −8.4 | −54.5 | −5.0 | 51 | B |

TABLE 3-continued

Coordinates of Factor IXa co-crystal Compound B complex

| | | | | | | |
|---|---|---|---|---|---|---|
| 99 | C | C | −6.9 | −54.6 | −4.7 | 57 | B |
| 99 | C | O | −6.1 | −54.1 | −5.5 | 57 | B |
| 99 | C | CB | −8.7 | −55.5 | −6.1 | 53 | B |
| 99 | C | SG | −8.3 | −57.3 | −5.8 | 57 | B |
| 100 | K | N | −6.5 | −55.2 | −3.6 | 56 | B |
| 100 | K | CA | −5.2 | −55.4 | −3.2 | 57 | B |
| 100 | K | C | −5.0 | −56.9 | −2.9 | 59 | B |
| 100 | K | O | −6.0 | −57.5 | −2.4 | 60 | B |
| 100 | K | CB | −4.9 | −54.6 | −1.9 | 60 | B |
| 100 | K | CG | −3.8 | −53.5 | −2.0 | 86 | B |
| 100 | K | CD | −3.9 | −52.5 | −0.8 | 99 | B |
| 100 | K | CE | −3.4 | −51.1 | −1.1 | 0 | B |
| 100 | K | NZ | −3.1 | −50.3 | 0.1 | 0 | B |
| 101 | N | N | −3.9 | −57.5 | −3.2 | 55 | B |
| 101 | N | CA | −3.7 | −59.0 | −3.0 | 56 | B |
| 101 | N | C | −3.3 | −59.2 | −1.5 | 61 | B |
| 101 | N | O | −2.4 | −58.5 | −1.0 | 61 | B |
| 101 | N | CB | −2.7 | −59.6 | −3.9 | 53 | B |
| 101 | N | CG | −3.4 | −60.0 | −5.3 | 59 | B |
| 101 | N | OD1 | −4.6 | −60.2 | −5.3 | 50 | B |
| 101 | N | ND2 | −2.5 | −60.0 | −6.3 | 49 | B |
| 107 | V | N | −7.3 | −61.6 | −1.3 | 52 | B |
| 107 | V | CA | −7.8 | −60.3 | −1.9 | 53 | B |
| 107 | V | C | −8.6 | −59.5 | −0.9 | 59 | B |
| 107 | V | O | −9.5 | −59.9 | −0.2 | 59 | B |
| 107 | V | CB | −8.6 | −60.6 | −3.2 | 56 | B |
| 107 | V | CG1 | −9.7 | −59.6 | −3.3 | 55 | B |
| 107 | V | CG2 | −7.6 | −60.5 | −4.4 | 56 | B |
| 108 | V | N | −8.1 | −58.2 | −0.8 | 54 | B |
| 108 | V | CA | −8.8 | −57.2 | 0.0 | 53 | B |
| 108 | V | C | −9.4 | −56.1 | −0.8 | 57 | B |
| 108 | V | O | −8.6 | −55.4 | −1.5 | 58 | B |
| 108 | V | CB | −7.8 | −56.6 | 1.1 | 56 | B |
| 108 | V | CG1 | −8.6 | −55.7 | 2.0 | 55 | B |
| 108 | V | CG2 | −7.0 | −57.6 | 1.8 | 56 | B |
| 109 | C | N | −10.7 | −55.9 | −0.8 | 54 | B |
| 109 | C | CA | −11.3 | −54.8 | −1.6 | 52 | B |
| 109 | C | C | −11.3 | −53.5 | −0.8 | 55 | B |
| 109 | C | O | −11.3 | −53.6 | 0.4 | 54 | B |
| 109 | C | CB | −12.8 | −55.2 | −2.0 | 51 | B |
| 109 | C | SG | −13.0 | −56.6 | −3.0 | 55 | B |
| 110 | S | N | −11.3 | −52.4 | −1.5 | 50 | B |
| 110 | S | CA | −11.3 | −51.0 | −0.9 | 48 | B |
| 110 | S | C | −12.1 | −50.1 | −1.8 | 53 | B |
| 110 | S | O | −12.4 | −50.5 | −3.0 | 52 | B |
| 110 | S | CB | −9.9 | −50.5 | −0.5 | 49 | B |
| 110 | S | OG | −9.0 | −50.5 | −1.6 | 49 | B |
| 111 | C | N | −12.3 | −48.9 | −1.3 | 49 | B |
| 111 | C | CA | −13.2 | −47.9 | −2.0 | 49 | B |
| 111 | C | C | −12.5 | −46.5 | −1.9 | 47 | B |
| 111 | C | O | −11.7 | −46.3 | −1.0 | 45 | B |
| 111 | C | CB | −14.5 | −47.8 | −1.3 | 51 | B |
| 111 | C | SG | −15.6 | −49.3 | −1.2 | 56 | B |
| 112 | T | N | −13.0 | −45.6 | −2.7 | 42 | B |
| 112 | T | CA | −12.5 | −44.2 | −2.7 | 40 | B |
| 112 | T | C | −13.2 | −43.5 | −1.5 | 45 | B |
| 112 | T | O | −14.3 | −43.9 | −1.2 | 46 | B |
| 112 | T | CB | −12.8 | −43.5 | −4.0 | 42 | B |
| 112 | T | OG1 | −12.0 | −42.3 | −4.1 | 43 | B |
| 112 | T | CG2 | −14.3 | −43.2 | −4.3 | 30 | B |
| 113 | E | N | −12.5 | −42.5 | −1.0 | 42 | B |
| 113 | E | CA | −13.1 | −41.7 | 0.1 | 43 | B |
| 113 | E | C | −14.5 | −41.3 | −0.1 | 46 | B |
| 113 | E | O | −14.9 | −40.9 | −1.2 | 46 | B |
| 113 | E | CB | −12.2 | −40.4 | 0.2 | 45 | B |
| 113 | E | CG | −12.5 | −39.6 | 1.4 | 63 | B |
| 113 | E | CD | −11.3 | −39.4 | 2.4 | 96 | B |
| 113 | E | OE1 | −11.2 | −40.2 | 3.3 | 0 | B |
| 113 | E | OE2 | −10.4 | −38.6 | 2.1 | 91 | B |
| 114 | G | N | −15.3 | −41.3 | 1.0 | 40 | B |
| 114 | G | CA | −16.7 | −41.0 | 1.0 | 39 | B |
| 114 | G | C | −17.5 | −42.3 | 0.9 | 46 | B |
| 114 | G | O | −18.7 | −42.3 | 0.9 | 46 | B |
| 115 | Y | N | −16.8 | −43.4 | 0.6 | 41 | B |
| 115 | Y | CA | −17.4 | −44.7 | 0.4 | 41 | B |
| 115 | Y | C | −16.9 | −45.7 | 1.4 | 45 | B |
| 115 | Y | O | −15.8 | −45.6 | 2.0 | 42 | B |
| 115 | Y | CB | −17.1 | −45.2 | −1.0 | 41 | B |
| 115 | Y | CG | −17.8 | −44.5 | −2.1 | 42 | B |
| 115 | Y | CD1 | −19.0 | −44.9 | −2.5 | 43 | B |
| 115 | Y | CD2 | −17.2 | −43.3 | −2.6 | 42 | B |
| 115 | Y | CE1 | −19.7 | −44.1 | −3.5 | 44 | B |
| 115 | Y | CE2 | −17.8 | −42.6 | −3.6 | 41 | B |
| 115 | Y | CZ | −19.0 | −43.0 | −4.1 | 43 | B |
| 115 | Y | OH | −19.6 | −42.2 | −5.1 | 43 | B |
| 116 | R | N | −17.7 | −46.7 | 1.6 | 45 | B |
| 116 | R | CA | −17.3 | −47.8 | 2.6 | 46 | B |
| 116 | R | C | −17.6 | −49.1 | 2.0 | 52 | B |
| 116 | R | O | −18.6 | −49.2 | 1.2 | 51 | B |
| 116 | R | CB | −18.0 | −47.5 | 4.0 | 44 | B |
| 116 | R | CG | −19.3 | −48.2 | 4.1 | 52 | B |
| 116 | R | CD | −20.0 | −47.9 | 5.4 | 55 | B |
| 116 | R | NE | −21.4 | −47.5 | 5.1 | 63 | B |
| 116 | R | CZ | −22.0 | −46.4 | 5.7 | 77 | B |
| 116 | R | NH1 | −21.3 | −45.7 | 6.6 | 57 | B |
| 116 | R | NH2 | −23.2 | −46.1 | 5.4 | 64 | B |
| 117 | L | N | −16.8 | −50.1 | 2.3 | 52 | B |
| 117 | L | CA | −17.0 | −51.4 | 1.8 | 54 | B |
| 117 | L | C | −18.3 | −52.0 | 2.3 | 62 | B |
| 117 | L | O | −18.5 | −52.1 | 3.5 | 64 | B |
| 117 | L | CB | −15.8 | −52.3 | 2.2 | 54 | B |
| 117 | L | CG | −15.5 | −53.5 | 1.2 | 58 | B |
| 117 | L | CD1 | −15.1 | −53.0 | −0.2 | 57 | B |
| 117 | L | CD2 | −14.5 | −54.4 | 1.8 | 62 | B |
| 118 | A | N | −19.2 | −52.4 | 1.4 | 60 | B |
| 118 | A | CA | −20.5 | −53.0 | 1.8 | 61 | B |
| 118 | A | C | −20.3 | −54.3 | 2.5 | 72 | B |
| 118 | A | O | −19.2 | −54.9 | 2.7 | 72 | B |
| 118 | A | CB | −21.3 | −53.2 | 0.5 | 62 | B |
| 119 | E | N | −21.4 | −54.8 | 3.1 | 72 | B |
| 119 | E | CA | −21.4 | −56.1 | 3.8 | 72 | B |
| 119 | E | C | −20.8 | −57.2 | 3.0 | 73 | B |
| 119 | E | O | −20.1 | −58.0 | 3.6 | 72 | B |
| 119 | E | CB | −22.8 | −56.4 | 4.4 | 74 | B |
| 119 | E | CG | −23.2 | −55.5 | 5.5 | 91 | B |
| 119 | E | CD | −23.4 | −54.0 | 5.1 | 0 | B |
| 119 | E | OE1 | −23.8 | −53.8 | 3.9 | 0 | B |
| 119 | E | OE2 | −23.3 | −53.1 | 5.9 | 0 | B |
| 120 | N | N | −21.1 | −57.3 | 1.7 | 68 | B |
| 120 | N | CA | −20.6 | −58.4 | 0.9 | 66 | B |
| 120 | N | C | −19.1 | −58.3 | 0.7 | 68 | B |
| 120 | N | O | −18.5 | −59.2 | 0.0 | 66 | B |
| 120 | N | CB | −21.3 | −58.4 | −0.5 | 65 | B |
| 120 | N | CG | −20.9 | −57.3 | −1.4 | 78 | B |
| 120 | N | OD1 | −20.0 | −56.5 | −1.1 | 72 | B |
| 120 | N | ND2 | −21.5 | −57.3 | −2.6 | 63 | B |
| 121 | Q | N | −18.5 | −57.3 | 1.3 | 63 | B |
| 121 | Q | CA | −17.0 | −57.2 | 1.3 | 62 | B |
| 121 | Q | C | −16.4 | −56.8 | −0.1 | 65 | B |
| 121 | Q | O | −15.2 | −56.8 | −0.3 | 64 | B |
| 121 | Q | CB | −16.4 | −58.5 | 1.9 | 62 | B |
| 121 | Q | CG | −16.4 | −58.5 | 3.4 | 68 | B |
| 121 | Q | CD | −16.3 | −57.2 | 4.1 | 86 | B |
| 121 | Q | OE1 | −15.2 | −56.6 | 4.3 | 77 | B |
| 121 | Q | NE2 | −17.5 | −56.6 | 4.5 | 81 | B |
| 122 | K | N | −17.3 | −56.6 | −1.1 | 60 | B |
| 122 | K | CA | −16.8 | −56.3 | −2.4 | 61 | B |
| 122 | K | C | −17.3 | −55.0 | −2.9 | 62 | B |
| 122 | K | O | −16.5 | −54.2 | −3.4 | 60 | B |
| 122 | K | CB | −17.3 | −57.4 | −3.4 | 64 | B |
| 122 | K | CG | −16.7 | −58.8 | −3.1 | 76 | B |
| 122 | K | CD | −15.8 | −59.3 | −4.2 | 84 | B |
| 122 | K | CE | −14.7 | −60.1 | −3.7 | 97 | B |
| 122 | K | NZ | −14.8 | −61.5 | −4.3 | 0 | B |
| 123 | S | N | −18.6 | −54.7 | −2.8 | 55 | B |
| 123 | S | CA | −19.3 | −53.5 | −3.3 | 52 | B |
| 123 | S | C | −19.0 | −52.3 | −2.4 | 55 | B |
| 123 | S | O | −18.7 | −52.4 | −1.2 | 54 | B |
| 123 | S | CB | −20.8 | −53.8 | −3.3 | 51 | B |
| 123 | S | OG | −21.1 | −54.6 | −4.5 | 48 | B |
| 124 | C | N | −19.2 | −51.1 | −3.0 | 53 | B |
| 124 | C | CA | −18.9 | −49.9 | −2.3 | 53 | B |
| 124 | C | C | −20.2 | −49.0 | −2.1 | 57 | B |
| 124 | C | O | −21.1 | −48.9 | −2.9 | 57 | B |
| 124 | C | CB | −17.9 | −49.0 | −3.2 | 53 | B |
| 124 | C | SG | −16.3 | −49.6 | −3.1 | 56 | B |

TABLE 3-continued

Coordinates of Factor IXa co-crystal Compound B complex

| | | | | | | |
|---|---|---|---|---|---|---|
| 125 | E | N | −20.3 | −48.5 | −0.9 | 53 | B |
| 125 | E | CA | −21.4 | −47.7 | −0.6 | 54 | B |
| 125 | E | C | −21.1 | −46.4 | 0.1 | 57 | B |
| 125 | E | O | −20.0 | −46.3 | 0.7 | 56 | B |
| 125 | E | CB | −22.4 | −48.6 | 0.3 | 56 | B |
| 125 | E | CG | −22.3 | −48.2 | 1.8 | 72 | B |
| 125 | E | CD | −23.2 | −49.2 | 2.7 | 0 | B |
| 125 | E | OE1 | −23.0 | −50.4 | 2.5 | 80 | B |
| 125 | E | OE2 | −24.0 | −48.7 | 3.5 | 0 | B |
| 126 | P | N | −22.0 | −45.4 | −0.1 | 51 | B |
| 126 | P | CA | −21.8 | −44.1 | 0.4 | 51 | B |
| 126 | P | C | −21.8 | −44.0 | 2.0 | 55 | B |
| 126 | P | O | −22.6 | −44.6 | 2.6 | 57 | B |
| 126 | P | CB | −23.1 | −43.4 | −0.1 | 52 | B |
| 126 | P | CG | −23.4 | −44.1 | −1.3 | 55 | B |
| 126 | P | CD | −23.0 | −45.5 | −1.1 | 51 | B |
| 127 | A | N | −20.7 | −43.4 | 2.5 | 50 | B |
| 127 | A | CA | −20.5 | −43.3 | 3.9 | 50 | B |
| 127 | A | C | −20.7 | −41.8 | 4.3 | 55 | B |
| 127 | A | O | −20.4 | −41.4 | 5.4 | 55 | B |
| 127 | A | CB | −19.0 | −43.6 | 4.2 | 51 | B |
| 128 | V | N | −21.2 | −41.0 | 3.3 | 48 | B |
| 128 | V | CA | −21.4 | −39.5 | 3.5 | 45 | B |
| 128 | V | C | −22.6 | −39.0 | 2.7 | 47 | B |
| 128 | V | O | −23.1 | −39.7 | 1.9 | 47 | B |
| 128 | V | CB | −20.1 | −38.7 | 3.2 | 49 | B |
| 128 | V | CG1 | −18.9 | −39.3 | 4.0 | 48 | B |
| 128 | V | CG2 | −19.8 | −38.8 | 1.7 | 48 | B |
| 129 | P | N | −23.1 | −37.9 | 3.1 | 43 | B |
| 129 | P | CA | −24.3 | −37.4 | 2.3 | 42 | B |
| 129 | P | C | −24.0 | −37.2 | 0.8 | 46 | B |
| 129 | P | O | −24.8 | −37.6 | 0.0 | 45 | B |
| 129 | P | CB | −24.6 | −36.1 | 3.0 | 43 | B |
| 129 | P | CG | −23.8 | −36.0 | 4.3 | 48 | B |
| 129 | P | CD | −22.6 | −36.9 | 4.1 | 44 | B |
| 130 | F | N | −22.9 | −36.6 | 0.5 | 41 | B |
| 130 | F | CA | −22.6 | −36.4 | −1.0 | 39 | B |
| 130 | F | C | −21.3 | −36.9 | −1.4 | 41 | B |
| 130 | F | O | −20.4 | −36.1 | −1.6 | 39 | B |
| 130 | F | CB | −22.8 | −34.9 | −1.3 | 39 | B |
| 130 | F | CG | −24.2 | −34.4 | −1.1 | 38 | B |
| 130 | F | CD1 | −24.5 | −33.8 | 0.2 | 39 | B |
| 130 | F | CD2 | −25.2 | −34.7 | −2.0 | 37 | B |
| 130 | F | CE1 | −25.8 | −33.4 | 0.5 | 37 | B |
| 130 | F | CE2 | −26.6 | −34.3 | −1.7 | 40 | B |
| 130 | F | CZ | −26.9 | −33.7 | −0.5 | 36 | B |
| 131 | P | N | −21.1 | −38.2 | −1.6 | 38 | B |
| 131 | P | CA | −19.9 | −38.8 | −2.0 | 36 | B |
| 131 | P | C | −19.5 | −38.4 | −3.5 | 39 | B |
| 131 | P | O | −20.3 | −38.2 | −4.3 | 33 | B |
| 131 | P | CB | −20.1 | −40.3 | −1.9 | 37 | B |
| 131 | P | CG | −21.6 | −40.5 | −2.1 | 40 | B |
| 131 | P | CD | −22.2 | −39.3 | −1.5 | 37 | B |
| 132 | C | N | −18.2 | −38.3 | −3.7 | 38 | B |
| 132 | C | CA | −17.7 | −37.9 | −5.0 | 37 | B |
| 132 | C | C | −18.2 | −38.8 | −6.1 | 39 | B |
| 132 | C | O | −18.5 | −39.9 | −5.8 | 40 | B |
| 132 | C | CB | −16.1 | −37.9 | −5.0 | 37 | B |
| 132 | C | SG | −15.5 | −39.6 | −4.9 | 40 | B |
| 133 | G | N | −18.3 | −38.2 | −7.3 | 34 | B |
| 133 | G | CA | −18.6 | −39.0 | −8.5 | 33 | B |
| 133 | G | C | −20.0 | −39.6 | −8.6 | 40 | B |
| 133 | G | O | −20.2 | −40.5 | −9.5 | 41 | B |
| 134 | R | N | −21.0 | −39.2 | −7.8 | 39 | B |
| 134 | R | CA | −22.3 | −39.8 | −8.0 | 39 | B |
| 134 | R | C | −23.3 | −38.7 | −8.3 | 40 | B |
| 134 | R | O | −23.3 | −37.6 | −7.8 | 41 | B |
| 134 | R | CB | −22.8 | −40.5 | −6.7 | 43 | B |
| 134 | R | CG | −22.0 | −41.7 | −6.3 | 68 | B |
| 134 | R | CD | −22.5 | −42.9 | −7.1 | 83 | B |
| 134 | R | NE | −22.1 | −44.2 | −6.4 | 0 | B |
| 134 | R | CZ | −22.7 | −44.7 | −5.4 | 0 | B |
| 134 | R | NH1 | −23.8 | −44.1 | −4.9 | 0 | B |
| 134 | R | NH2 | −22.3 | −45.8 | −4.8 | 0 | B |
| 135 | V | N | −24.2 | −39.1 | −9.2 | 35 | B |
| 135 | V | CA | −25.4 | −38.2 | −9.6 | 35 | B |
| 135 | V | C | −26.4 | −38.6 | −8.6 | 45 | B |
| 135 | V | O | −26.8 | −39.7 | −8.4 | 47 | B |
| 135 | V | CB | −25.8 | −38.6 | −11.1 | 36 | B |
| 135 | V | CG1 | −27.2 | −37.9 | −11.4 | 35 | B |
| 135 | V | CG2 | −24.7 | −38.2 | −12.0 | 34 | B |
| 136 | S | N | −26.9 | −37.5 | −7.9 | 43 | B |
| 136 | S | CA | −27.9 | −37.8 | −6.8 | 44 | B |
| 136 | S | C | −29.2 | −37.1 | −7.0 | 54 | B |
| 136 | S | O | −30.1 | −37.1 | −6.1 | 54 | B |
| 136 | S | CB | −27.3 | −37.4 | −5.4 | 42 | B |
| 136 | S | OG | −27.0 | −36.0 | −5.4 | 43 | B |
| 137 | V | N | −29.4 | −36.4 | −8.1 | 54 | B |
| 137 | V | CA | −30.6 | −35.7 | −8.5 | 55 | B |
| 137 | V | C | −31.4 | −36.5 | −9.5 | 66 | B |
| 137 | V | O | −30.8 | −37.1 | −10.4 | 67 | B |
| 137 | V | CB | −30.2 | −34.3 | −9.2 | 59 | B |
| 137 | V | CG1 | −31.3 | −33.9 | −10.1 | 59 | B |
| 137 | V | CG2 | −29.9 | −33.3 | −8.2 | 60 | B |
| 138 | S | N | −32.7 | −36.6 | −9.3 | 67 | B |
| 138 | S | CA | −33.6 | −37.4 | −10.2 | 67 | B |
| 138 | S | C | −33.2 | −37.1 | −11.7 | 72 | B |
| 138 | S | O | −33.1 | −36.0 | −12.2 | 72 | B |
| 138 | S | CB | −35.0 | −37.0 | −10.0 | 70 | B |
| 138 | S | OG | −35.8 | −37.2 | −11.1 | 78 | B |
| 139 | Q | N | −32.9 | −38.2 | −12.4 | 70 | B |
| 139 | Q | CA | −32.6 | −38.1 | −13.8 | 69 | B |
| 139 | Q | C | −33.8 | −38.5 | −14.7 | 75 | B |
| 139 | Q | O | −33.9 | −37.9 | −15.8 | 76 | B |
| 139 | Q | CB | −31.4 | −39.0 | −14.2 | 70 | B |
| 139 | Q | CG | −30.0 | −38.4 | −13.8 | 66 | B |
| 139 | Q | CD | −29.7 | −37.1 | −14.4 | 74 | B |
| 139 | Q | OE1 | −29.7 | −36.1 | −13.6 | 62 | B |
| 139 | Q | NE2 | −29.5 | −37.0 | −15.7 | 68 | B |
| 500 | X | CA | −27.7 | −20.4 | −14.4 | 87 | Q |
| 501 | X | C1 | 6.2 | −36.1 | −18.3 | 28 | Q |
| 501 | X | O1 | 5.4 | −37.2 | −18.0 | 28 | Q |
| 501 | X | O2 | 6.3 | −35.2 | −17.3 | 32 | Q |
| 501 | X | C2 | 6.8 | −35.9 | −19.6 | 26 | Q |
| 501 | X | C3 | 6.8 | −37.1 | −20.6 | 28 | Q |
| 501 | X | O7 | 7.6 | −38.1 | −20.1 | 29 | Q |
| 501 | X | C4 | 7.4 | −36.7 | −22.0 | 31 | Q |
| 501 | X | C5 | 7.5 | −37.8 | −23.0 | 39 | Q |
| 501 | X | O3 | 6.4 | −38.4 | −23.5 | 38 | Q |
| 501 | X | O4 | 8.7 | −38.0 | −23.3 | 45 | Q |
| 501 | X | C6 | 5.4 | −37.8 | −20.7 | 27 | Q |
| 501 | X | O5 | 5.6 | −39.0 | −20.4 | 27 | Q |
| 501 | X | O6 | 4.4 | −37.1 | −21.2 | 30 | Q |
| 502 | X | C1 | 9.4 | −41.2 | −18.4 | 49 | Q |
| 502 | X | O1 | 9.9 | −40.9 | −19.6 | 51 | Q |
| 502 | X | O2 | 10.0 | −40.6 | −17.4 | 53 | Q |
| 502 | X | C2 | 8.2 | −41.9 | −18.3 | 40 | Q |
| 502 | X | C3 | 7.0 | −41.4 | −19.2 | 36 | Q |
| 502 | X | O7 | 6.9 | −40.0 | −18.9 | 29 | Q |
| 502 | X | C4 | 5.7 | −42.1 | −19.0 | 35 | Q |
| 502 | X | C5 | 5.2 | −42.3 | −17.6 | 41 | Q |
| 502 | X | O3 | 4.7 | −41.3 | −17.0 | 43 | Q |
| 502 | X | O4 | 5.3 | −43.5 | −17.1 | 43 | Q |
| 502 | X | C6 | 7.3 | −41.4 | −20.7 | 37 | Q |
| 502 | X | O5 | 7.3 | −40.1 | −21.0 | 34 | Q |
| 502 | X | O6 | 7.6 | −42.4 | −21.3 | 41 | Q |
| 503 | X | C1 | 4.7 | −33.7 | −7.7 | 37 | Q |
| 503 | X | O1 | 5.3 | −32.9 | −8.6 | 35 | Q |
| 503 | X | O2 | 4.4 | −33.2 | −6.5 | 42 | Q |
| 503 | X | C2 | 4.3 | −35.1 | −8.1 | 31 | Q |
| 503 | X | C3 | 4.3 | −35.5 | −9.6 | 31 | Q |
| 503 | X | O7 | 3.3 | −34.6 | −10.2 | 33 | Q |
| 503 | X | C4 | 4.0 | −36.9 | −9.8 | 27 | Q |
| 503 | X | C5 | 2.6 | −37.3 | −9.4 | 35 | Q |
| 503 | X | O3 | 1.7 | −36.3 | −9.3 | 35 | Q |
| 503 | X | O4 | 2.3 | −38.4 | −9.1 | 37 | Q |
| 503 | X | C6 | 5.7 | −35.2 | −10.3 | 33 | Q |
| 503 | X | O5 | 5.6 | −34.4 | −11.4 | 35 | Q |
| 503 | X | O6 | 6.8 | −35.7 | −9.9 | 35 | Q |
| 1 | Z | CL7 | −10.0 | −31.9 | −26.4 | 37 | S |
| 1 | Z | N1 | −10.5 | −27.4 | −30.0 | 36 | S |
| 1 | Z | C2 | −10.1 | −26.4 | −29.2 | 43 | S |
| 1 | Z | C3 | −10.0 | −28.3 | −28.0 | 35 | S |
| 1 | Z | C4 | −9.8 | −26.9 | −27.9 | 34 | S |
| 1 | Z | C6 | −10.5 | −28.6 | −29.3 | 34 | S |
| 1 | Z | C8 | −10.7 | −29.9 | −29.7 | 33 | S |

TABLE 3-continued

Coordinates of Factor IXa co-crystal Compound B complex

| | | | | | | |
|---|---|---|---|---|---|---|
| 1 | Z | C9 | −9.9 | −29.3 | −27.0 | 38 | S |
| 1 | Z | C10 | −10.6 | −30.9 | −28.8 | 36 | S |
| 1 | Z | C11 | −10.2 | −30.6 | −27.5 | 38 | S |
| 1 | Z | S12 | −10.1 | −24.8 | −29.8 | 51 | S |
| 1 | Z | O13 | −11.0 | −24.6 | −30.8 | 50 | S |
| 1 | Z | O14 | −10.1 | −23.9 | −28.6 | 56 | S |
| 1 | Z | C15 | −7.1 | −24.8 | −32.6 | 41 | S |
| 1 | Z | O16 | −6.9 | −25.2 | −33.8 | 42 | S |
| 1 | Z | C17 | −8.4 | −25.1 | −31.9 | 40 | S |
| 1 | Z | N18 | −8.5 | −24.5 | −30.6 | 48 | S |
| 1 | Z | C19 | −6.3 | −23.7 | −30.6 | 45 | S |
| 1 | Z | C20 | −6.6 | −22.2 | −30.5 | 48 | S |
| 1 | Z | O21 | −6.9 | −22.0 | −29.1 | 55 | S |
| 1 | Z | C22 | −7.3 | −20.7 | −28.8 | 56 | S |
| 1 | Z | C23 | −7.3 | −24.6 | −29.8 | 46 | S |
| 1 | Z | N24 | −6.1 | −24.2 | −32.0 | 45 | S |
| 1 | Z | C25 | −4.7 | −24.1 | −32.4 | 41 | S |
| 1 | Z | N27 | −1.5 | −25.7 | −31.2 | 41 | S |
| 1 | Z | C28 | −0.4 | −26.3 | −30.6 | 47 | S |
| 1 | Z | O1 | 0.6 | −25.7 | −30.4 | 54 | S |
| 1 | Z | C30 | −2.8 | −26.5 | −31.5 | 40 | S |
| 1 | Z | C31 | −0.5 | −27.8 | −30.2 | 43 | S |
| 1 | Z | C32 | −1.5 | −24.3 | −31.6 | 36 | S |
| 1 | Z | C33 | −4.0 | −24.3 | −31.0 | 40 | S |
| 1 | Z | O34 | −5.0 | −23.8 | −30.1 | 44 | S |
| 1 | Z | C35 | −3.9 | −25.8 | −30.7 | 39 | S |
| 1 | Z | C38 | −2.7 | −23.6 | −30.9 | 38 | S |
| 1 | O | O | −23.1 | −30.2 | −28.4 | 35 | W |
| 2 | O | O | −23.0 | −29.3 | −32.4 | 48 | W |
| 3 | O | O | −32.3 | −33.3 | −13.5 | 52 | W |
| 4 | O | O | −26.6 | −35.2 | −9.1 | 32 | W |
| 5 | O | O | −17.8 | −34.8 | −17.1 | 28 | W |
| 6 | O | O | −15.4 | −28.0 | −19.9 | 29 | W |
| 7 | O | O | −21.1 | −25.4 | −13.0 | 37 | W |
| 9 | O | O | −26.0 | −25.2 | −4.9 | 32 | W |
| 10 | O | O | 4.5 | −20.5 | −17.7 | 42 | W |
| 11 | O | O | 4.6 | −26.5 | −20.1 | 32 | W |
| 12 | O | O | −18.7 | −27.1 | 2.8 | 37 | W |
| 13 | O | O | −11.9 | −35.6 | −5.4 | 30 | W |
| 14 | O | O | −0.7 | −46.3 | −7.8 | 37 | W |
| 15 | O | O | −16.7 | −25.4 | −19.9 | 34 | W |
| 17 | O | O | −4.4 | −42.0 | −27.0 | 28 | W |
| 18 | O | O | −0.7 | −31.2 | −37.8 | 42 | W |
| 19 | O | O | 3.3 | −30.3 | −29.1 | 47 | W |
| 20 | O | O | 2.5 | −36.8 | −33.7 | 44 | W |
| 21 | O | O | −10.9 | −38.0 | −36.7 | 33 | W |
| 22 | O | O | −13.8 | −36.5 | −32.8 | 40 | W |
| 23 | O | O | −18.7 | −39.3 | −36.4 | 39 | W |
| 24 | O | O | −12.5 | −35.4 | −28.2 | 31 | W |
| 25 | O | O | −9.7 | −23.2 | −24.7 | 45 | W |
| 27 | O | O | −12.4 | −44.7 | −20.2 | 30 | W |
| 28 | O | O | −17.3 | −44.0 | −18.9 | 26 | W |
| 29 | O | O | −7.9 | −34.1 | −2.7 | 38 | W |
| 31 | O | O | −9.2 | −41.2 | −11.1 | 27 | W |
| 32 | O | O | −11.1 | −30.7 | −14.7 | 24 | W |
| 33 | O | O | −6.2 | −34.9 | −0.9 | 45 | W |
| 34 | O | O | −9.9 | −33.8 | −0.6 | 47 | W |
| 35 | O | O | −20.7 | −26.9 | −25.2 | 33 | W |
| 36 | O | O | −22.9 | −38.5 | −15.3 | 34 | W |
| 41 | O | O | −9.9 | −32.5 | −32.7 | 49 | W |
| 42 | O | O | −12.5 | −34.7 | −34.2 | 35 | W |
| 43 | O | O | −10.5 | −31.5 | −35.3 | 36 | W |
| 44 | O | O | −5.3 | −35.2 | −33.8 | 26 | W |
| 45 | O | O | −4.6 | −32.8 | −32.9 | 38 | W |
| 46 | O | O | −24.4 | −37.0 | −28.9 | 38 | W |
| 47 | O | O | −21.3 | −41.3 | −12.3 | 46 | W |
| 48 | O | O | −20.4 | −39.2 | −15.7 | 43 | W |
| 49 | O | O | −25.0 | −29.5 | −11.3 | 32 | W |
| 50 | O | O | −27.2 | −28.6 | −12.6 | 38 | W |
| 51 | O | O | −21.1 | −28.2 | −10.5 | 29 | W |
| 52 | O | O | −20.5 | −29.1 | 2.1 | 40 | W |
| 54 | O | O | −1.0 | −19.4 | −19.0 | 62 | W |
| 57 | O | O | −22.5 | −19.6 | −2.5 | 33 | W |
| 58 | O | O | −24.9 | −19.7 | −4.0 | 40 | W |
| 59 | O | O | 8.3 | −33.8 | −12.0 | 22 | W |
| 60 | O | O | 3.0 | −34.6 | −21.0 | 36 | W |
| 63 | O | O | −9.4 | −42.7 | −4.4 | 34 | W |
| 64 | O | O | −5.2 | −40.8 | −16.6 | 23 | W |
| 65 | O | O | −3.7 | −42.8 | −17.5 | 31 | W |
| 66 | O | O | −8.2 | −51.2 | −18.0 | 36 | W |
| 67 | O | O | −11.0 | −43.5 | −22.2 | 23 | W |
| 68 | O | O | −11.9 | −41.7 | −23.8 | 28 | W |
| 69 | O | O | −20.8 | −40.1 | −28.4 | 39 | W |
| 70 | O | O | −1.0 | −47.9 | −30.8 | 43 | W |
| 71 | O | O | −5.1 | −46.7 | −39.9 | 41 | W |
| 72 | O | O | −10.2 | −43.7 | −34.7 | 32 | W |
| 73 | O | O | −14.7 | −33.2 | −40.8 | 46 | W |
| 81 | O | O | −10.6 | −14.5 | −19.8 | 62 | W |
| 83 | O | O | −22.6 | −39.2 | −26.2 | 35 | W |
| 84 | O | O | −29.5 | −26.5 | −12.2 | 51 | W |
| 85 | O | O | −24.5 | −30.8 | −13.8 | 47 | W |
| 86 | O | O | −23.8 | −36.9 | −26.2 | 41 | W |
| 87 | O | O | −26.9 | −40.1 | −24.1 | 59 | W |
| 88 | O | O | −7.9 | −34.2 | −40.7 | 41 | W |
| 89 | O | O | −24.0 | −36.3 | −33.0 | 58 | W |
| 90 | O | O | −22.3 | −40.2 | −36.1 | 48 | W |
| 92 | O | O | −1.9 | −17.3 | −7.2 | 40 | W |
| 93 | O | O | −15.0 | −51.9 | −18.3 | 46 | W |
| 94 | O | O | 0.2 | −40.1 | −9.9 | 51 | W |
| 95 | O | O | −21.3 | −43.0 | −28.8 | 52 | W |
| 97 | O | O | −24.5 | −42.7 | −31.5 | 47 | W |

Example 13

Generation of Factor IXa-Compound A Complex Crystals by Soaking

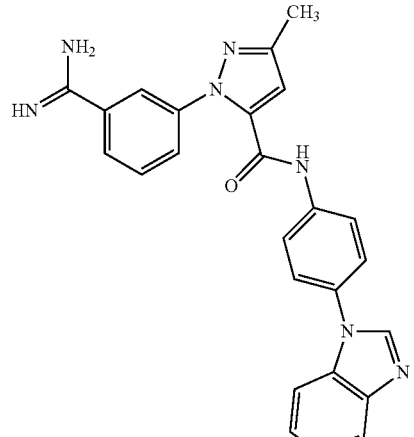

Compound A

A factor IXa-Compound B crystal as described in example 12 was transferred to a 1 μl hanging drop containing 1 mM Compound A, 1% DMSO, 16% PEG 6000 (v/v), 0.1 M citric acid, pH 5.9 solution. The drop was subsequently incubated at 4° C. for 1-20 days.

Example 14

Crystallographic Analysis of Soaked Factor IXa-Complex A Crystals

Prior to data collection crystals were harvested and cryo-protected for 5-10 minutes in the crystallization solution containing 25% glycerol. The crystals were then frozen directly into liquid nitrogen. X-ray diffraction was collected at the Cornell High Energy Synchrotron Source on the A1 beam line. This beam fine was equipped with an ADSC Quantum 210 CCD detector. Data were integrated and scaled using the HKL package.

| Data Collection Statistics | |
|---|---|
| Resolution | 50.0-2.1 Å |
| No. of collected reflections | 793469 |
| No. of unique reflections (F >= 0) | 29730 |
| R-sym | 5.5% |
| Percent of theoretical (I/s >= 1) | 99.4% |
| Unit Cell | a = 100.4 Å, b = 100.4 Å, c = 97.3 Å, α = β = γ = 90° |
| Space Group | P4$_3$2$_1$2 |
| Asymmetric unit | 1 molecule |

Example 15

Structure Determination of Soaked Factor IXa-Compound A Complex Crystals

The crystal structure was solved using Rigid Body refinement with the starting model 1RFN Refinement was done using the program AUTOBUSTER (Global Phasing Limited).

| | |
|---|---|
| Number of reflections | 28909 |
| Resolution limits | 13.9-2.10 Å |
| Completeness for range | 97.9% |
| FREE R TEST SET COUNT & SIZE | 1373 (4.8%) |
| Number of protein atoms | 2207 |
| Number of solvent atoms | 120 |
| R-factor | 0.211 |
| R-free | 0.251 |
| RMSD bond length | 0.010 Å |
| RMSD bond angles | 1.24° |

The following table contains one line for each atom in one Factor IXa monomer. The columns are: 1) residue number, 2) 1-letter amino acid code, 3) atom name, 4) x-coordinate, 5) y-coordinate, 6) z-coordinate, 7) B-factor, 8) Chain ID. (Amino Acid Code X are Calcium or Citrate, Z is Compound A and O for water) The numbering scheme is based on chymotrypsin. Note: B tractors greater than 100 appear as 0 in column 7.

TABLE 4

Coordinates of Soaked Factor IXa-Compound A Complex

| 16 | V | N | −18.6 | −28.2 | −26.7 | 38 | A |
|---|---|---|---|---|---|---|---|
| 16 | V | CA | −18.9 | −29.5 | −27.2 | 37 | A |
| 16 | V | C | −19.7 | −29.5 | −28.5 | 41 | A |
| 16 | V | O | −20.8 | −29.1 | −28.5 | 42 | A |
| 16 | V | CB | −19.6 | −30.4 | −26.2 | 41 | A |
| 16 | V | CG1 | −19.7 | −31.9 | −26.7 | 41 | A |
| 16 | V | CG2 | −18.9 | −30.3 | −24.8 | 39 | A |
| 17 | V | N | −19.1 | −30.0 | −29.6 | 38 | A |
| 17 | V | CA | −19.8 | −30.2 | −30.9 | 38 | A |
| 17 | V | C | −20.4 | −31.6 | −30.9 | 42 | A |
| 17 | V | O | −19.8 | −32.6 | −30.6 | 40 | A |
| 17 | V | CB | −18.7 | −30.0 | −32.0 | 41 | A |
| 17 | V | CG1 | −19.5 | −30.2 | −33.4 | 40 | A |
| 17 | V | CG2 | −18.0 | −28.7 | −32.0 | 40 | A |
| 18 | G | N | −21.7 | −31.6 | −31.3 | 38 | A |
| 18 | G | CA | −22.4 | −32.9 | −31.5 | 38 | A |
| 18 | G | C | −22.7 | −33.6 | −30.2 | 44 | A |
| 18 | G | O | −22.8 | −34.9 | −30.2 | 43 | A |
| 19 | G | N | −22.9 | −32.9 | −29.1 | 42 | A |
| 19 | G | CA | −23.2 | −33.6 | −27.8 | 42 | A |
| 19 | G | C | −24.6 | −33.3 | −27.5 | 45 | A |
| 19 | G | O | −25.4 | −33.0 | −28.4 | 43 | A |
| 20 | E | N | −25.0 | −33.5 | −26.3 | 40 | A |
| 20 | E | CA | −26.4 | −33.3 | −25.9 | 41 | A |
| 20 | E | C | −26.4 | −32.4 | −24.7 | 46 | A |
| 20 | E | O | −25.4 | −32.2 | −24.0 | 44 | A |
| 20 | E | CB | −27.1 | −34.6 | −25.5 | 43 | A |
| 20 | E | CG | −27.1 | −35.7 | −26.5 | 57 | A |
| 20 | E | CD | −27.4 | −37.0 | −25.9 | 91 | A |
| 20 | E | OE1 | −26.4 | −37.8 | −25.6 | 77 | A |
| 20 | E | OE2 | −28.6 | −37.4 | −25.8 | 99 | A |
| 21 | D | N | −27.6 | −31.8 | −24.4 | 45 | A |
| 21 | D | CA | −27.9 | −31.0 | −23.2 | 46 | A |
| 21 | D | C | −27.8 | −32.0 | −22.0 | 50 | A |
| 21 | D | O | −28.4 | −33.1 | −22.0 | 52 | A |
| 21 | D | CB | −29.4 | −30.5 | −23.2 | 48 | A |
| 21 | D | CG | −29.6 | −29.3 | −24.2 | 59 | A |
| 21 | D | OD1 | −30.6 | −28.7 | −24.0 | 64 | A |
| 21 | D | OD2 | −28.7 | −29.0 | −25.0 | 54 | A |
| 22 | A | N | −27.1 | −31.5 | −21.0 | 44 | A |
| 22 | A | CA | −27.0 | −32.3 | −19.8 | 43 | A |
| 22 | A | C | −28.3 | −32.0 | −19.0 | 48 | A |
| 22 | A | O | −28.8 | −30.9 | −19.2 | 46 | A |
| 22 | A | CB | −25.8 | −31.8 | −18.9 | 42 | A |
| 23 | K | N | −28.8 | −32.9 | −18.2 | 44 | A |
| 23 | K | CA | −29.9 | −32.6 | −17.3 | 44 | A |
| 23 | K | C | −29.3 | −31.9 | −16.0 | 50 | A |
| 23 | K | O | −28.2 | −32.0 | −15.7 | 49 | A |
| 23 | K | CB | −30.6 | −33.9 | −16.9 | 45 | A |
| 23 | K | CG | −31.5 | −34.4 | −18.0 | 55 | A |
| 23 | K | CD | −31.9 | −35.9 | −17.6 | 70 | A |
| 23 | K | CE | −32.7 | −36.5 | −18.8 | 80 | A |
| 23 | K | NZ | −33.0 | −37.9 | −18.5 | 89 | A |
| 24 | P | N | −30.2 | −31.2 | −15.3 | 48 | A |
| 24 | P | CA | −29.7 | −30.5 | −14.0 | 46 | A |
| 24 | P | C | −29.1 | −31.6 | −13.1 | 48 | A |
| 24 | P | O | −29.7 | −32.7 | −12.9 | 48 | A |
| 24 | P | CB | −30.9 | −29.9 | −13.4 | 47 | A |
| 24 | P | CG | −31.8 | −29.6 | −14.6 | 51 | A |
| 24 | P | CD | −31.5 | −30.6 | −15.7 | 47 | A |
| 25 | G | N | −27.9 | −31.3 | −12.5 | 43 | A |
| 25 | G | CA | −27.3 | −32.3 | −11.6 | 40 | A |
| 25 | G | C | −26.7 | −33.5 | −12.3 | 41 | A |
| 25 | G | O | −26.3 | −34.4 | −11.6 | 40 | A |
| 26 | Q | N | −26.7 | −33.5 | −13.6 | 38 | A |
| 26 | Q | CA | −26.1 | −34.7 | −14.3 | 40 | A |
| 26 | Q | C | −24.6 | −34.8 | −14.2 | 43 | A |
| 26 | Q | O | −24.0 | −35.9 | −14.3 | 43 | A |
| 26 | Q | CB | −26.6 | −34.8 | −15.8 | 40 | A |
| 26 | Q | CG | −26.2 | −36.1 | −16.4 | 40 | A |
| 26 | Q | CD | −26.7 | −36.2 | −17.9 | 44 | A |
| 26 | Q | OE1 | −27.5 | −35.3 | −18.3 | 41 | A |
| 26 | Q | NE2 | −26.2 | −37.2 | −18.6 | 36 | A |
| 27 | F | N | −23.9 | −33.6 | −14.1 | 36 | A |
| 27 | F | CA | −22.4 | −33.6 | −14.0 | 35 | A |
| 27 | F | C | −22.1 | −32.6 | −12.9 | 39 | A |
| 27 | F | O | −21.6 | −31.5 | −13.2 | 39 | A |
| 27 | F | CB | −21.8 | −33.1 | −15.4 | 36 | A |
| 27 | F | CG | −22.1 | −34.1 | −16.5 | 38 | A |
| 27 | F | CD1 | −23.2 | −33.9 | −17.3 | 38 | A |
| 27 | F | CD2 | −21.3 | −35.3 | −16.7 | 40 | A |
| 27 | F | CE1 | −23.5 | −34.8 | −18.3 | 39 | A |
| 27 | F | CE2 | −21.6 | −36.2 | −17.7 | 40 | A |
| 27 | F | CZ | −22.7 | −36.0 | −18.5 | 37 | A |
| 28 | P | N | −22.4 | −32.9 | −11.7 | 36 | A |
| 28 | P | CA | −22.3 | −31.9 | −10.6 | 35 | A |
| 28 | P | C | −20.9 | −31.6 | −10.2 | 36 | A |
| 28 | P | O | −20.7 | −30.6 | −9.4 | 33 | A |
| 28 | P | CB | −23.1 | −32.6 | −9.4 | 35 | A |
| 28 | P | CG | −22.9 | −34.1 | −9.7 | 41 | A |
| 28 | P | CD | −22.9 | −34.2 | −11.2 | 38 | A |
| 29 | W | N | −19.9 | −32.2 | −10.8 | 32 | A |
| 29 | W | CA | −18.5 | −31.8 | −10.5 | 31 | A |
| 29 | W | C | −18.0 | −30.8 | −11.5 | 34 | A |
| 29 | W | O | −16.9 | −30.2 | −11.3 | 36 | A |
| 29 | W | CB | −17.6 | −33.0 | −10.6 | 30 | A |
| 29 | W | CG | −18.0 | −33.9 | −11.8 | 30 | A |

TABLE 4-continued

Coordinates of Soaked Factor IXa-Compound A Complex

| 29 | W | CD1 | −17.6 | −33.7 | −13.1 | 32 | A |
| 29 | W | CD2 | −18.8 | −35.0 | −11.8 | 30 | A |
| 29 | W | NE1 | −18.1 | −34.7 | −13.9 | 31 | A |
| 29 | W | CE2 | −18.9 | −35.5 | −13.1 | 34 | A |
| 29 | W | CE3 | −19.5 | −35.7 | −10.8 | 33 | A |
| 29 | W | CZ2 | −19.7 | −36.6 | −13.5 | 34 | A |
| 29 | W | CZ3 | −20.3 | −36.8 | −11.2 | 35 | A |
| 29 | W | CH2 | −20.4 | −37.3 | −12.5 | 35 | A |
| 30 | Q | N | −18.8 | −30.5 | −12.5 | 31 | A |
| 30 | Q | CA | −18.4 | −29.6 | −13.5 | 31 | A |
| 30 | Q | C | −18.5 | −28.1 | −13.0 | 39 | A |
| 30 | Q | O | −19.5 | −27.8 | −12.3 | 39 | A |
| 30 | Q | CB | −19.4 | −29.7 | −14.7 | 32 | A |
| 30 | Q | CG | −19.2 | −28.6 | −15.8 | 32 | A |
| 30 | Q | CD | −18.1 | −28.9 | −16.8 | 40 | A |
| 30 | Q | OE1 | −17.3 | −28.0 | −17.1 | 40 | A |
| 30 | Q | NE2 | −18.1 | −30.1 | −17.3 | 30 | A |
| 31 | V | N | −17.6 | −27.3 | −13.3 | 34 | A |
| 31 | V | CA | −17.6 | −25.8 | −13.0 | 32 | A |
| 31 | V | C | −17.3 | −25.1 | −14.3 | 37 | A |
| 31 | V | O | −16.7 | −25.7 | −15.3 | 36 | A |
| 31 | V | CB | −16.7 | −25.4 | −11.8 | 35 | A |
| 31 | V | CG1 | −17.0 | −26.2 | −10.6 | 35 | A |
| 31 | V | CG2 | −15.2 | −25.3 | −12.2 | 34 | A |
| 32 | V | N | −17.7 | −23.8 | −14.4 | 34 | A |
| 32 | V | CA | −17.3 | −23.0 | −15.5 | 34 | A |
| 32 | V | C | −16.5 | −21.9 | −14.9 | 37 | A |
| 32 | V | O | −16.7 | −21.5 | −13.8 | 36 | A |
| 32 | V | CB | −18.6 | −22.4 | −16.2 | 38 | A |
| 32 | V | CG1 | −19.5 | −21.6 | −15.3 | 37 | A |
| 32 | V | CG2 | −18.2 | −21.6 | −17.4 | 38 | A |
| 33 | L | N | −15.5 | −21.4 | −15.7 | 35 | A |
| 33 | L | CA | −14.6 | −20.3 | −15.3 | 36 | A |
| 33 | L | C | −15.0 | −19.0 | −16.0 | 43 | A |
| 33 | L | O | −15.2 | −19.1 | −17.2 | 41 | A |
| 33 | L | CB | −13.1 | −20.6 | −15.6 | 36 | A |
| 33 | L | CG | −12.5 | −21.9 | −15.0 | 41 | A |
| 33 | L | CD1 | −11.0 | −21.7 | −15.1 | 40 | A |
| 33 | L | CD2 | −12.9 | −22.3 | −13.6 | 42 | A |
| 34 | N | N | −15.0 | −17.9 | −15.3 | 42 | A |
| 34 | N | CA | −15.3 | −16.6 | −15.9 | 43 | A |
| 34 | N | C | −14.2 | −15.6 | −15.6 | 47 | A |
| 34 | N | O | −13.7 | −15.6 | −14.5 | 47 | A |
| 34 | N | CB | −16.6 | −16.0 | −15.3 | 43 | A |
| 34 | N | CG | −17.8 | −16.9 | −15.5 | 42 | A |
| 34 | N | OD1 | −18.1 | −17.3 | −16.6 | 43 | A |
| 34 | N | ND2 | −18.6 | −17.1 | −14.4 | 49 | A |
| 35 | G | N | −13.8 | −14.8 | −16.5 | 48 | A |
| 35 | G | CA | −12.8 | −13.8 | −16.4 | 51 | A |
| 35 | G | C | −13.1 | −12.6 | −17.3 | 60 | A |
| 35 | G | O | −14.2 | −12.1 | −17.3 | 59 | A |
| 36 | K | N | −12.1 | −12.2 | −18.1 | 61 | A |
| 36 | K | CA | −12.3 | −11.1 | −19.1 | 62 | A |
| 36 | K | C | −13.6 | −11.5 | −19.9 | 66 | A |
| 36 | K | O | −14.5 | −10.7 | −20.1 | 66 | A |
| 36 | K | CB | −11.1 | −11.0 | −20.0 | 67 | A |
| 36 | K | CG | −9.8 | −11.5 | −19.4 | 89 | A |
| 36 | K | CD | −8.6 | −11.0 | −20.4 | 97 | A |
| 36 | K | CE | −7.4 | −10.5 | −19.6 | 0 | A |
| 36 | K | NZ | −6.5 | −9.7 | −20.4 | 0 | A |
| 38 | V | N | −13.6 | −12.7 | −20.3 | 61 | A |
| 38 | V | CA | −14.7 | −13.3 | −21.0 | 58 | A |
| 38 | V | C | −15.4 | −14.3 | −20.0 | 58 | A |
| 38 | V | O | −14.7 | −14.9 | −19.2 | 57 | A |
| 38 | V | CB | −14.2 | −14.1 | −22.3 | 63 | A |
| 38 | V | CG1 | −15.3 | −14.7 | −23.1 | 62 | A |
| 38 | V | CG2 | −13.3 | −13.2 | −23.1 | 63 | A |
| 39 | D | N | −16.7 | −14.4 | −20.1 | 51 | A |
| 39 | D | CA | −17.4 | −15.4 | −19.2 | 50 | A |
| 39 | D | C | −17.3 | −16.7 | −19.9 | 50 | A |
| 39 | D | O | −17.3 | −16.9 | −21.1 | 46 | A |
| 39 | D | CB | −18.8 | −15.0 | −19.1 | 53 | A |
| 39 | D | CG | −19.1 | −14.0 | −17.9 | 71 | A |
| 39 | D | OD1 | −18.1 | −13.3 | −17.5 | 73 | A |
| 39 | D | OD2 | −20.2 | −14.1 | −17.4 | 80 | A |
| 40 | A | N | −17.3 | −17.8 | −19.1 | 46 | A |
| 40 | A | CA | −17.3 | −19.2 | −19.6 | 45 | A |
| 40 | A | C | −16.2 | −19.4 | −20.6 | 45 | A |
| 40 | A | O | −16.5 | −19.9 | −21.7 | 48 | A |
| 40 | A | CB | −18.7 | −19.5 | −20.2 | 46 | A |
| 41 | F | N | −15.0 | −19.0 | −20.4 | 40 | A |
| 41 | F | CA | −13.9 | −19.2 | −21.3 | 38 | A |
| 41 | F | C | −13.3 | −20.5 | −21.1 | 42 | A |
| 41 | F | O | −12.5 | −21.0 | −22.0 | 42 | A |
| 41 | F | CB | −12.9 | −18.0 | −21.1 | 38 | A |
| 41 | F | CG | −12.2 | −18.1 | −19.8 | 40 | A |
| 41 | F | CD1 | −12.7 | −17.6 | −18.6 | 41 | A |
| 41 | F | CD2 | −10.9 | −18.7 | −19.7 | 40 | A |
| 41 | F | CE1 | −12.0 | −17.6 | −17.4 | 40 | A |
| 41 | F | CE2 | −10.2 | −18.8 | −18.5 | 41 | A |
| 41 | F | CZ | −10.8 | −18.2 | −17.4 | 39 | A |
| 42 | C | N | −13.6 | −21.3 | −20.0 | 39 | A |
| 42 | C | CA | −12.9 | −22.6 | −19.8 | 37 | A |
| 42 | C | C | −13.7 | −23.3 | −18.7 | 39 | A |
| 42 | C | O | −14.5 | −22.7 | −18.0 | 37 | A |
| 42 | C | CB | −11.5 | −22.4 | −19.2 | 38 | A |
| 42 | C | SG | −10.1 | −22.4 | −20.5 | 43 | A |
| 43 | G | N | −13.5 | −24.6 | −18.6 | 34 | A |
| 43 | G | CA | −14.2 | −25.4 | −17.7 | 32 | A |
| 43 | G | C | −13.3 | −25.8 | −16.6 | 32 | A |
| 43 | G | O | −12.1 | −25.5 | −16.6 | 32 | A |
| 44 | G | N | −13.7 | −26.6 | −15.6 | 29 | A |
| 44 | G | CA | −12.9 | −27.1 | −14.5 | 29 | A |
| 44 | G | C | −13.7 | −28.2 | −13.8 | 32 | A |
| 44 | G | O | −14.9 | −28.4 | −14.1 | 30 | A |
| 45 | S | N | −13.2 | −28.9 | −12.8 | 32 | A |
| 45 | S | CA | −13.9 | −29.9 | −12.1 | 31 | A |
| 45 | S | C | −13.6 | −29.7 | −10.6 | 34 | A |
| 45 | S | O | −12.5 | −29.4 | −10.2 | 30 | A |
| 45 | S | CB | −13.3 | −31.3 | −12.4 | 31 | A |
| 45 | S | OG | −13.4 | −31.6 | −13.8 | 41 | A |
| 46 | I | N | −14.6 | −30.0 | −9.8 | 34 | A |
| 46 | I | CA | −14.5 | −29.9 | −8.4 | 32 | A |
| 46 | I | C | −13.6 | −31.1 | −7.8 | 34 | A |
| 46 | I | O | −14.1 | −32.1 | −7.9 | 33 | A |
| 46 | I | CB | −15.9 | −29.9 | −7.7 | 34 | A |
| 46 | I | CG1 | −16.7 | −28.7 | −8.2 | 35 | A |
| 46 | I | CG2 | −15.7 | −29.9 | −6.1 | 34 | A |
| 46 | I | CD1 | −18.2 | −28.8 | −7.8 | 38 | A |
| 47 | V | N | −12.5 | −30.8 | −7.2 | 30 | A |
| 47 | V | CA | −11.7 | −31.8 | −6.4 | 30 | A |
| 47 | V | C | −12.3 | −31.9 | −5.0 | 37 | A |
| 47 | V | O | −12.5 | −33.0 | −4.5 | 36 | A |
| 47 | V | CB | −10.2 | −31.4 | −6.4 | 31 | A |
| 47 | V | CG1 | −9.4 | −32.3 | −5.5 | 29 | A |
| 47 | V | CG2 | −9.6 | −31.3 | −7.8 | 29 | A |
| 48 | N | N | −12.6 | −30.8 | −4.4 | 36 | A |
| 48 | N | CA | −13.3 | −30.8 | −3.1 | 35 | A |
| 48 | N | C | −13.8 | −29.4 | −2.9 | 41 | A |
| 48 | N | O | −13.8 | −28.6 | −3.8 | 37 | A |
| 48 | N | CB | −12.3 | −31.3 | −2.0 | 32 | A |
| 48 | N | CG | −11.2 | −30.3 | −1.8 | 39 | A |
| 48 | N | OD1 | −11.3 | −29.2 | −2.0 | 34 | A |
| 48 | N | ND2 | −10.0 | −30.9 | −1.4 | 38 | A |
| 49 | E | N | −14.4 | −29.1 | −1.7 | 39 | A |
| 49 | E | CA | −15.1 | −27.9 | −1.4 | 39 | A |
| 49 | E | C | −14.3 | −26.6 | −1.7 | 39 | A |
| 49 | E | O | −14.8 | −25.5 | −1.9 | 38 | A |
| 49 | E | CB | −15.8 | −27.8 | −0.0 | 41 | A |
| 49 | E | CG | −15.0 | −28.5 | 1.1 | 57 | A |
| 49 | E | CD | −15.4 | −30.0 | 1.2 | 86 | A |
| 49 | E | OE1 | −15.0 | −30.8 | 0.3 | 53 | A |
| 49 | E | OE2 | −16.2 | −30.4 | 2.1 | 76 | A |
| 50 | K | N | −13.0 | −26.7 | −1.6 | 34 | A |
| 50 | K | CA | −12.1 | −25.5 | −1.8 | 34 | A |
| 50 | K | C | −11.2 | −25.5 | −3.0 | 37 | A |
| 50 | K | O | −10.5 | −24.6 | −3.2 | 35 | A |
| 50 | K | CB | −11.2 | −25.4 | −0.6 | 36 | A |
| 50 | K | CG | −11.8 | −24.8 | 0.7 | 47 | A |
| 50 | K | CD | −11.8 | −23.2 | 0.6 | 53 | A |
| 50 | K | CE | −10.5 | −22.1 | 1.1 | 55 | A |
| 50 | K | NZ | −10.4 | −21.2 | 0.9 | 55 | A |
| 51 | W | N | −11.3 | −26.6 | −3.8 | 34 | A |
| 51 | W | CA | −10.3 | −26.7 | −4.9 | 33 | A |
| 51 | W | C | −10.9 | −27.2 | −6.2 | 35 | A |
| 51 | W | O | −11.7 | −28.1 | −6.2 | 33 | A |

TABLE 4-continued

Coordinates of Soaked Factor IXa-Compound A Complex

| | | | | | | |
|---|---|---|---|---|---|---|
| 51 | W | CB | −9.2 | −27.7 | −4.5 | 32 A |
| 51 | W | CG | −8.3 | −27.1 | −3.5 | 32 A |
| 51 | W | CD1 | −8.4 | −27.3 | −2.1 | 35 A |
| 51 | W | CD2 | −7.1 | −26.4 | −3.7 | 32 A |
| 51 | W | NE1 | −7.3 | −26.7 | −1.5 | 33 A |
| 51 | W | CE2 | −6.6 | −26.1 | −2.4 | 35 A |
| 51 | W | CE3 | −6.5 | −25.9 | −4.9 | 33 A |
| 51 | W | CZ2 | −5.4 | −25.3 | −2.3 | 36 A |
| 51 | W | CZ3 | −5.3 | −25.2 | −4.7 | 34 A |
| 51 | W | CH2 | −4.8 | −24.9 | −3.4 | 35 A |
| 52 | I | N | −10.5 | −26.6 | −7.3 | 31 A |
| 52 | I | CA | −11.0 | −26.9 | −8.7 | 31 A |
| 52 | I | C | −9.7 | −27.3 | −9.4 | 34 A |
| 52 | I | O | −8.7 | −26.8 | −9.2 | 33 A |
| 52 | I | CB | −11.6 | −25.6 | −9.4 | 33 A |
| 52 | I | CG1 | −12.8 | −25.0 | −8.7 | 31 A |
| 52 | I | CG2 | −11.9 | −25.9 | −10.9 | 31 A |
| 52 | I | CD1 | −13.8 | −26.1 | −8.2 | 28 A |
| 53 | V | N | −9.9 | −28.3 | −10.4 | 31 A |
| 53 | V | CA | −8.7 | −28.6 | −11.2 | 29 A |
| 53 | V | C | −9.1 | −28.2 | −12.6 | 32 A |
| 53 | V | O | −10.2 | −28.4 | −13.1 | 33 A |
| 53 | V | CB | −8.3 | −30.1 | −11.1 | 32 A |
| 53 | V | CG1 | −7.0 | −30.4 | −11.9 | 31 A |
| 53 | V | CG2 | −9.5 | −31.1 | −11.6 | 32 A |
| 54 | T | N | −8.2 | −27.6 | −13.3 | 29 A |
| 54 | T | CA | −8.4 | −27.2 | −14.6 | 30 A |
| 54 | T | C | −7.1 | −27.3 | −15.5 | 32 A |
| 54 | T | O | −6.1 | −27.9 | −15.0 | 31 A |
| 54 | T | CB | −9.0 | −25.7 | −14.6 | 36 A |
| 54 | T | OG1 | −9.4 | −25.3 | −15.9 | 38 A |
| 54 | T | CG2 | −7.9 | −24.7 | −14.1 | 31 A |
| 55 | A | N | −7.2 | −26.7 | −16.7 | 30 A |
| 55 | A | CA | −6.0 | −26.7 | −17.6 | 30 A |
| 55 | A | C | −5.1 | −25.5 | −17.2 | 34 A |
| 55 | A | O | −5.7 | −24.4 | −17.0 | 33 A |
| 55 | A | CB | −6.4 | −26.6 | −19.0 | 30 A |
| 56 | A | N | −3.8 | −25.6 | −17.1 | 32 A |
| 56 | A | CA | −2.9 | −24.5 | −16.8 | 32 A |
| 56 | A | C | −3.1 | −23.4 | −17.8 | 40 A |
| 56 | A | O | −3.0 | −22.2 | −17.5 | 37 A |
| 56 | A | CB | −1.5 | −24.9 | −16.7 | 32 A |
| 57 | H | N | −3.2 | −23.8 | −19.1 | 36 A |
| 57 | H | CA | −3.2 | −22.7 | −20.2 | 36 A |
| 57 | H | C | −4.4 | −21.8 | −20.0 | 42 A |
| 57 | H | O | −4.5 | −20.8 | −20.7 | 40 A |
| 57 | H | CB | −3.1 | −23.3 | −21.6 | 35 A |
| 57 | H | CG | −4.4 | −23.8 | −22.1 | 38 A |
| 57 | H | ND1 | −4.8 | −25.2 | −22.2 | 39 A |
| 57 | H | CD2 | −5.4 | −23.2 | −22.8 | 39 A |
| 57 | H | CE1 | −5.9 | −25.3 | −22.8 | 37 A |
| 57 | H | NE2 | −6.4 | −24.1 | −23.1 | 38 A |
| 58 | C | N | −5.4 | −22.2 | −19.2 | 39 A |
| 58 | C | CA | −6.7 | −21.4 | −19.1 | 39 A |
| 58 | C | C | −6.5 | −20.3 | −18.1 | 44 A |
| 58 | C | O | −7.3 | −19.4 | −18.0 | 44 A |
| 58 | C | CB | −7.8 | −22.3 | −18.5 | 38 A |
| 58 | C | SG | −8.5 | −23.4 | −19.7 | 42 A |
| 59 | V | N | −5.5 | −20.4 | −17.2 | 39 A |
| 59 | V | CA | −5.4 | −19.5 | −16.1 | 40 A |
| 59 | V | C | −4.0 | −19.0 | −15.9 | 54 A |
| 59 | V | O | −3.1 | −19.3 | −16.7 | 53 A |
| 59 | V | CB | −5.8 | −20.3 | −14.7 | 41 A |
| 59 | V | CG1 | −7.3 | −20.6 | −14.8 | 41 A |
| 59 | V | CG2 | −5.0 | −21.6 | −14.5 | 40 A |
| 60 | E | N | −3.8 | −18.1 | −15.0 | 60 A |
| 60 | E | CA | −2.5 | −17.4 | −14.8 | 65 A |
| 60 | E | C | −2.6 | −16.4 | −13.6 | 73 A |
| 60 | E | O | −3.4 | −15.5 | −13.6 | 71 A |
| 60 | E | CB | −2.0 | −16.7 | −16.1 | 67 A |
| 60 | E | CG | −2.3 | −15.2 | −16.1 | 80 A |
| 60 | E | CD | −2.4 | −14.7 | −17.5 | 0 A |
| 60 | E | OE1 | −1.4 | −14.2 | −18.0 | 94 A |
| 60 | E | OE2 | −3.5 | −14.8 | −18.1 | 87 A |
| 60A | T | N | −1.7 | −16.6 | −12.6 | 74 A |
| 60A | T | CA | −1.6 | −15.8 | −11.4 | 75 A |
| 60A | T | C | −1.6 | −14.3 | −11.9 | 80 A |
| 60A | T | O | −0.8 | −13.9 | −12.7 | 81 A |
| 60A | T | CB | −0.4 | −16.2 | −10.5 | 84 A |
| 60A | T | OG1 | −0.6 | −17.5 | −10.0 | 79 A |
| 60A | T | CG2 | −0.3 | −15.2 | −9.4 | 85 A |
| 61 | G | N | −2.5 | −13.5 | −11.4 | 75 A |
| 61 | G | CA | −2.6 | −12.1 | −11.7 | 74 A |
| 61 | G | C | −3.9 | −11.8 | −12.5 | 75 A |
| 61 | G | O | −4.3 | −10.6 | −12.4 | 75 A |
| 62 | V | N | −4.4 | −12.7 | −13.3 | 67 A |
| 62 | V | CA | −5.7 | −12.5 | −14.0 | 64 A |
| 62 | V | C | −6.8 | −13.1 | −13.1 | 63 A |
| 62 | V | O | −6.9 | −14.3 | −12.8 | 60 A |
| 62 | V | CB | −5.6 | −13.2 | −15.4 | 69 A |
| 62 | V | CG1 | −6.9 | −12.7 | −16.2 | 68 A |
| 62 | V | CG2 | −4.4 | −12.8 | −16.1 | 69 A |
| 63 | K | N | −7.6 | −12.2 | −12.6 | 56 A |
| 63 | K | CA | −8.7 | −12.5 | −11.7 | 55 A |
| 63 | K | C | −9.8 | −13.3 | −12.4 | 55 A |
| 63 | K | O | −10.3 | −12.9 | −13.4 | 56 A |
| 63 | K | CB | −9.3 | −11.2 | −11.2 | 59 A |
| 63 | K | CG | −10.1 | −11.1 | −9.8 | 84 A |
| 63 | K | CD | −11.3 | −10.5 | −9.8 | 97 A |
| 63 | K | CE | −12.6 | −11.3 | −10.1 | 98 A |
| 63 | K | NZ | −13.6 | −11.2 | −9.1 | 93 A |
| 64 | I | N | −10.2 | −14.4 | −11.8 | 49 A |
| 64 | I | CA | −11.3 | −15.2 | −12.4 | 47 A |
| 64 | I | C | −12.2 | −15.7 | −11.3 | 46 A |
| 64 | I | O | −11.9 | −15.8 | −10.1 | 44 A |
| 64 | I | CB | −10.8 | −16.5 | −13.2 | 51 A |
| 64 | I | CG1 | −9.8 | −17.3 | −12.3 | 52 A |
| 64 | I | CG2 | −10.0 | −16.1 | −14.5 | 50 A |
| 64 | I | CD1 | −9.6 | −18.7 | −12.9 | 56 A |
| 65 | T | N | −13.4 | −16.1 | −11.7 | 43 A |
| 65 | T | CA | −14.3 | −16.7 | −10.7 | 42 A |
| 65 | T | C | −14.7 | −18.0 | −11.3 | 41 A |
| 65 | T | O | −14.6 | −18.3 | −12.4 | 37 A |
| 65 | T | CB | −15.5 | −15.7 | −10.4 | 48 A |
| 65 | T | OG1 | −16.2 | −15.5 | −11.6 | 47 A |
| 65 | T | CG2 | −15.1 | −14.4 | −9.8 | 41 A |
| 66 | V | N | −15.3 | −18.8 | −10.4 | 37 A |
| 66 | V | CA | −15.7 | −20.2 | −10.7 | 36 A |
| 66 | V | C | −17.2 | −20.3 | −10.3 | 41 A |
| 66 | V | O | −17.6 | −19.8 | −9.2 | 39 A |
| 66 | V | CB | −14.9 | −21.2 | −9.7 | 39 A |
| 66 | V | CG1 | −15.6 | −22.5 | −9.6 | 39 A |
| 66 | V | CG2 | −13.4 | −21.3 | −10.1 | 39 A |
| 67 | V | N | −18.0 | −20.9 | −11.2 | 38 A |
| 67 | V | CA | −19.4 | −21.2 | −10.8 | 37 A |
| 67 | V | C | −19.6 | −22.7 | −10.8 | 40 A |
| 67 | V | O | −19.5 | −23.3 | −11.9 | 37 A |
| 67 | V | CB | −20.4 | −20.4 | −11.8 | 42 A |
| 67 | V | CG1 | −21.8 | −20.5 | −11.1 | 41 A |
| 67 | V | CG2 | −20.0 | −18.9 | −12.0 | 42 A |
| 68 | A | N | −20.0 | −23.2 | −9.7 | 38 A |
| 68 | A | CA | −20.5 | −24.6 | −9.5 | 37 A |
| 68 | A | C | −22.0 | −24.6 | −9.6 | 44 A |
| 68 | A | O | −22.6 | −23.5 | −9.4 | 43 A |
| 68 | A | CB | −20.0 | −25.1 | −8.2 | 36 A |
| 69 | G | N | −22.6 | −25.8 | −9.8 | 42 A |
| 69 | G | CA | −24.0 | −25.9 | −9.8 | 41 A |
| 69 | G | C | −24.7 | −25.2 | −11.0 | 44 A |
| 69 | G | O | −25.9 | −25.0 | −11.0 | 45 A |
| 70 | E | N | −23.9 | −26.9 | −12.0 | 39 A |
| 70 | E | CA | −24.4 | −24.3 | −13.2 | 38 A |
| 70 | E | C | −25.0 | −25.3 | −14.2 | 48 A |
| 70 | E | O | −24.6 | −26.5 | −14.2 | 47 A |
| 70 | E | CB | −23.2 | −23.5 | −13.8 | 39 A |
| 70 | E | CG | −23.6 | −22.6 | −15.0 | 45 A |
| 70 | E | CD | −24.7 | −21.6 | −14.7 | 63 A |
| 70 | E | OE1 | −25.9 | −22.1 | −14.6 | 52 A |
| 70 | E | OE2 | −24.5 | −20.4 | −14.4 | 51 A |
| 71 | H | N | −26.0 | −24.9 | −14.9 | 45 A |
| 71 | H | CA | −26.8 | −25.7 | −15.9 | 46 A |
| 71 | H | C | −27.0 | −24.8 | −17.2 | 50 A |
| 71 | H | O | −26.2 | −24.9 | −18.1 | 48 A |
| 71 | H | CB | −28.1 | −26.2 | −15.4 | 48 A |
| 71 | H | CG | −28.9 | −26.9 | −16.4 | 53 A |
| 71 | H | ND1 | −28.5 | −28.1 | −16.9 | 55 A |
| 71 | H | CD2 | −30.1 | −26.6 | −16.9 | 54 A |

TABLE 4-continued

Coordinates of Soaked Factor IXa-Compound A Complex

| | | | | | | |
|---|---|---|---|---|---|---|
| 71 | H | CE1 | −29.4 | −28.5 | −17.8 | 53 | A |
| 71 | H | NE2 | −30.4 | −27.7 | −17.8 | 54 | A |
| 72 | N | N | −27.9 | −23.9 | −17.1 | 49 | A |
| 72 | N | CA | −28.2 | −23.0 | −18.2 | 50 | A |
| 72 | N | C | −27.5 | −21.7 | −17.8 | 56 | A |
| 72 | N | O | −27.9 | −21.0 | −16.9 | 55 | A |
| 72 | N | CB | −29.7 | −22.7 | −18.4 | 52 | A |
| 72 | N | CG | −30.0 | −21.8 | −19.6 | 65 | A |
| 72 | N | OD1 | −29.2 | −21.0 | −20.0 | 51 | A |
| 72 | N | ND2 | −31.1 | −22.0 | −20.2 | 61 | A |
| 73 | I | N | −26.4 | −21.3 | −18.5 | 55 | A |
| 73 | I | CA | −25.6 | −20.1 | −18.2 | 59 | A |
| 73 | I | C | −26.4 | −18.8 | −18.3 | 68 | A |
| 73 | I | O | −25.9 | −17.8 | −17.8 | 68 | A |
| 73 | I | CB | −24.4 | −20.0 | −19.1 | 63 | A |
| 73 | I | CG1 | −23.3 | −21.1 | −18.8 | 64 | A |
| 73 | I | CG2 | −23.7 | −18.7 | −19.0 | 66 | A |
| 73 | I | CD1 | −22.2 | −21.1 | −19.9 | 78 | A |
| 74 | E | N | −27.6 | −18.8 | −18.9 | 66 | A |
| 74 | E | CA | −28.3 | −17.5 | −19.1 | 67 | A |
| 74 | E | C | −29.6 | −17.5 | −18.3 | 72 | A |
| 74 | E | O | −30.5 | −16.7 | −18.6 | 74 | A |
| 74 | E | CB | −28.6 | −17.1 | −20.5 | 68 | A |
| 74 | E | CG | −27.3 | −16.6 | −21.2 | 78 | A |
| 74 | E | CD | −27.6 | −15.8 | −22.5 | 0 | A |
| 74 | E | OE1 | −28.7 | −16.0 | −23.1 | 0 | A |
| 74 | E | OE2 | −26.7 | −15.1 | −22.9 | 99 | A |
| 75 | E | N | −29.7 | −18.3 | −17.2 | 68 | A |
| 75 | E | CA | −31.0 | −18.4 | −16.5 | 68 | A |
| 75 | E | C | −30.7 | −18.9 | −15.1 | 72 | A |
| 75 | E | O | −30.5 | −20.0 | −14.8 | 72 | A |
| 75 | E | CB | −31.9 | −19.4 | −17.2 | 70 | A |
| 75 | E | CG | −33.4 | −19.4 | −16.6 | 88 | A |
| 75 | E | CD | −34.2 | −20.5 | −17.2 | 0 | A |
| 75 | E | OE1 | −34.2 | −20.7 | −18.5 | 0 | A |
| 75 | E | OE2 | −34.8 | −21.3 | −16.4 | 0 | A |
| 76 | T | N | −30.8 | −17.9 | −14.1 | 67 | A |
| 76 | T | CA | −30.7 | −18.3 | −12.7 | 66 | A |
| 76 | T | C | −31.5 | −19.5 | −12.3 | 69 | A |
| 76 | T | O | −32.7 | −19.4 | −12.5 | 68 | A |
| 76 | T | CB | −31.0 | −17.1 | −11.8 | 71 | A |
| 76 | T | OG1 | −30.1 | −16.0 | −12.0 | 67 | A |
| 76 | T | CG2 | −30.9 | −17.5 | −10.3 | 70 | A |
| 77 | E | N | −30.9 | −20.6 | −11.8 | 63 | A |
| 77 | E | CA | −31.7 | −21.7 | −11.5 | 60 | A |
| 77 | E | C | −31.7 | −22.0 | −10.0 | 60 | A |
| 77 | E | O | −32.2 | −23.0 | −9.5 | 58 | A |
| 77 | E | CB | −31.3 | −23.0 | −12.3 | 62 | A |
| 77 | E | CG | −31.5 | −22.8 | −13.8 | 71 | A |
| 77 | E | CD | −30.5 | −23.5 | −14.6 | 79 | A |
| 77 | E | OE1 | −29.3 | −23.0 | −14.7 | 59 | A |
| 77 | E | OE2 | −30.9 | −24.5 | −15.3 | 62 | A |
| 78 | H | N | −31.0 | −21.1 | −9.3 | 59 | A |
| 78 | H | CA | −30.9 | −21.3 | −7.8 | 60 | A |
| 78 | H | C | −30.1 | −22.5 | −7.3 | 60 | A |
| 78 | H | O | −30.3 | −22.9 | −6.2 | 59 | A |
| 78 | H | CB | −32.3 | −21.2 | −7.2 | 63 | A |
| 78 | H | CG | −33.0 | −20.0 | −7.6 | 69 | A |
| 78 | H | ND1 | −33.9 | −20.0 | −8.7 | 72 | A |
| 78 | H | CD2 | −32.9 | −18.7 | −7.3 | 72 | A |
| 78 | H | CE1 | −34.3 | −18.8 | −8.9 | 72 | A |
| 78 | H | NE2 | −33.7 | −18.0 | −8.1 | 72 | A |
| 79 | T | N | −29.2 | −23.0 | −8.2 | 52 | A |
| 79 | T | CA | −28.4 | −24.2 | −7.8 | 50 | A |
| 79 | T | C | −26.9 | −23.7 | −7.9 | 48 | A |
| 79 | T | O | −26.0 | −24.4 | −7.3 | 46 | A |
| 79 | T | CB | −28.6 | −25.4 | −8.8 | 50 | A |
| 79 | T | OG1 | −26.4 | −24.9 | −10.1 | 48 | A |
| 79 | T | CG2 | −30.0 | −25.9 | −8.6 | 51 | A |
| 80 | E | N | −26.7 | −22.6 | −8.5 | 43 | A |
| 80 | E | CA | −25.3 | −22.0 | −8.7 | 43 | A |
| 80 | E | C | −24.7 | −21.5 | −7.4 | 48 | A |
| 80 | E | O | −25.3 | −21.0 | −6.5 | 50 | A |
| 80 | E | CB | −25.4 | −20.9 | −9.7 | 44 | A |
| 80 | E | CG | −26.2 | −21.2 | −11.0 | 56 | A |
| 80 | E | CD | −27.7 | −21.0 | −10.8 | 73 | A |
| 80 | E | OE1 | −28.2 | −20.6 | −9.7 | 64 | A |
| 80 | E | OE2 | −28.5 | −21.2 | −11.8 | 62 | A |
| 81 | Q | N | −23.4 | −21.7 | −7.4 | 42 | A |
| 81 | Q | CA | −22.5 | −21.2 | −6.3 | 40 | A |
| 81 | Q | C | −21.3 | −20.6 | −7.0 | 44 | A |
| 81 | Q | O | −20.5 | −21.3 | −7.7 | 41 | A |
| 81 | Q | CB | −22.1 | −22.3 | −5.4 | 41 | A |
| 81 | Q | CG | −23.2 | −22.9 | −4.7 | 37 | A |
| 81 | Q | CD | −22.8 | −24.0 | −3.7 | 43 | A |
| 81 | Q | OE1 | −21.8 | −23.9 | −3.0 | 43 | A |
| 81 | Q | NE2 | −23.6 | −25.1 | −3.6 | 38 | A |
| 82 | K | N | −21.1 | −19.3 | −6.9 | 40 | A |
| 82 | K | CA | −20.0 | −18.5 | −7.4 | 39 | A |
| 82 | K | C | −18.9 | −18.3 | −6.4 | 42 | A |
| 82 | K | O | −19.3 | −18.0 | −5.2 | 40 | A |
| 82 | K | CB | −20.6 | −17.3 | −8.0 | 41 | A |
| 82 | K | CG | −19.8 | −16.8 | −9.2 | 58 | A |
| 82 | K | CD | −19.0 | −15.6 | −8.9 | 72 | A |
| 82 | K | CE | −19.9 | −14.3 | −8.9 | 72 | A |
| 82 | K | NZ | −19.3 | −13.4 | −7.9 | 69 | A |
| 83 | R | N | −17.7 | −18.4 | −6.8 | 38 | A |
| 83 | R | CA | −16.6 | −18.2 | −5.8 | 37 | A |
| 83 | R | C | −15.5 | −17.4 | −6.5 | 40 | A |
| 83 | R | O | −15.3 | −17.6 | −7.7 | 42 | A |
| 83 | R | CB | −16.1 | −19.5 | −5.3 | 36 | A |
| 83 | R | CG | −17.2 | −20.2 | −4.5 | 37 | A |
| 83 | R | CD | −17.3 | −19.6 | −3.0 | 34 | A |
| 83 | R | NE | −18.2 | −20.4 | −2.1 | 36 | A |
| 83 | R | CZ | −19.5 | −20.5 | −2.3 | 37 | A |
| 83 | R | NH1 | −20.1 | −19.8 | −3.2 | 31 | A |
| 83 | R | NH2 | −20.1 | −21.3 | −1.4 | 40 | A |
| 84 | N | N | −14.7 | −16.7 | −5.8 | 36 | A |
| 84 | N | CA | −13.5 | −16.0 | −6.3 | 36 | A |
| 84 | N | C | −12.4 | −17.0 | −6.2 | 42 | A |
| 84 | N | O | −12.3 | −17.7 | −5.2 | 41 | A |
| 84 | N | CB | −13.1 | −14.8 | −5.5 | 39 | A |
| 84 | N | CG | −14.1 | −13.6 | −5.6 | 59 | A |
| 84 | N | OD1 | −15.0 | −13.7 | −6.4 | 48 | A |
| 84 | N | ND2 | −13.9 | −12.6 | −4.8 | 49 | A |
| 85 | V | N | −11.4 | −17.0 | −7.1 | 41 | A |
| 85 | V | CA | −10.2 | −17.8 | −7.0 | 39 | A |
| 85 | V | C | −9.2 | −17.0 | −6.3 | 41 | A |
| 85 | V | O | −8.9 | −15.9 | −6.7 | 42 | A |
| 85 | V | CB | −9.8 | −18.2 | −8.5 | 39 | A |
| 85 | V | CG1 | −8.4 | −18.8 | −8.4 | 39 | A |
| 85 | V | CG2 | −10.8 | −19.2 | −9.1 | 39 | A |
| 86 | I | N | −8.7 | −17.5 | −5.2 | 39 | A |
| 86 | I | CA | −7.7 | −16.7 | −4.4 | 39 | A |
| 86 | I | C | −6.2 | −17.2 | −4.6 | 44 | A |
| 86 | I | O | −5.3 | −16.6 | −4.2 | 43 | A |
| 86 | I | CB | −7.9 | −16.8 | −2.9 | 42 | A |
| 86 | I | CG1 | −7.6 | −18.2 | −2.4 | 40 | A |
| 86 | I | CG2 | −9.3 | −16.2 | −2.6 | 44 | A |
| 86 | I | CD1 | −8.0 | −16.5 | −0.9 | 43 | A |
| 87 | R | N | −6.1 | −18.4 | −5.3 | 40 | A |
| 87 | R | CA | −4.8 | −19.0 | −5.5 | 39 | A |
| 87 | R | C | −4.8 | −19.9 | −6.8 | 41 | A |
| 87 | R | O | −5.8 | −20.6 | −6.9 | 40 | A |
| 87 | R | CB | −4.3 | −19.7 | −4.3 | 38 | A |
| 87 | R | CG | −2.8 | −20.1 | −4.4 | 46 | A |
| 87 | R | CD | −2.3 | −20.3 | −2.9 | 51 | A |
| 87 | R | NE | −1.5 | −21.5 | −2.7 | 68 | A |
| 87 | R | CZ | −1.9 | −22.5 | −1.9 | 95 | A |
| 87 | R | NH1 | −3.0 | −22.3 | −1.1 | 81 | A |
| 87 | R | NH2 | −1.1 | −23.6 | −1.7 | 88 | A |
| 88 | I | N | −3.8 | −19.8 | −7.6 | 38 | A |
| 88 | I | CA | −3.7 | −20.6 | −8.8 | 38 | A |
| 88 | I | C | −2.4 | −21.4 | −8.7 | 43 | A |
| 88 | I | O | −1.4 | −20.7 | −8.5 | 41 | A |
| 88 | I | CB | −3.7 | −19.8 | −10.1 | 42 | A |
| 88 | I | CG1 | −5.0 | −18.9 | −10.2 | 43 | A |
| 88 | I | CG2 | −3.5 | −20.7 | −11.3 | 41 | A |
| 88 | I | CD1 | −5.0 | −18.0 | −11.4 | 46 | A |
| 89 | I | N | −2.5 | −22.7 | −8.8 | 36 | A |
| 89 | I | CA | −1.2 | −23.5 | −8.7 | 35 | A |
| 89 | I | C | −1.1 | −24.3 | −10.0 | 38 | A |
| 89 | I | O | −1.7 | −25.4 | −10.2 | 34 | A |
| 89 | I | CB | −1.2 | −24.4 | −7.5 | 39 | A |
| 89 | I | CG1 | −1.5 | −23.7 | −6.2 | 39 | A |
| 89 | I | CG2 | 0.2 | −25.1 | −7.4 | 38 | A |

TABLE 4-continued

Coordinates of Soaked Factor IXa-Compound A Complex

| | | | | | | | |
|---|---|---|---|---|---|---|---|
| 89 | I | CD1 | -1.4 | -24.5 | -5.0 | 41 | A |
| 90 | P | N | -0.4 | -23.7 | -11.0 | 37 | A |
| 90 | P | CA | -0.1 | -24.5 | -12.2 | 36 | A |
| 90 | P | C | 0.9 | -25.6 | -11.8 | 37 | A |
| 90 | P | O | 1.7 | -25.4 | -10.9 | 35 | A |
| 90 | P | CB | 0.6 | -23.5 | -13.2 | 37 | A |
| 90 | P | CG | 1.0 | -22.4 | -12.4 | 42 | A |
| 90 | P | CD | 0.4 | -22.4 | -11.0 | 39 | A |
| 91 | H | N | 0.9 | -26.8 | -12.4 | 35 | A |
| 91 | H | CA | 1.9 | -27.8 | -12.1 | 34 | A |
| 91 | H | C | 3.3 | -27.2 | -12.3 | 36 | A |
| 91 | H | O | 3.5 | -26.4 | -13.2 | 34 | A |
| 91 | H | CB | 1.7 | -29.1 | -12.9 | 34 | A |
| 91 | H | CG | 2.7 | -30.2 | -12.6 | 36 | A |
| 91 | H | ND1 | 2.4 | -31.2 | -11.7 | 37 | A |
| 91 | H | CD2 | 3.9 | -30.4 | -13.1 | 36 | A |
| 91 | H | CE1 | 3.5 | -32.0 | -11.6 | 35 | A |
| 91 | H | NE2 | 4.4 | -31.5 | -12.4 | 37 | A |
| 92 | H | N | 4.2 | -27.6 | -11.4 | 34 | A |
| 92 | H | CA | 5.5 | -27.0 | -11.5 | 36 | A |
| 92 | H | C | 6.3 | -27.2 | -12.8 | 39 | A |
| 92 | H | O | 7.1 | -26.5 | -13.2 | 38 | A |
| 92 | H | CB | 6.4 | -27.4 | -10.3 | 37 | A |
| 92 | H | CG | 6.7 | -28.8 | -10.3 | 41 | A |
| 92 | H | ND1 | 7.8 | -29.4 | -10.8 | 44 | A |
| 92 | H | CD2 | 6.0 | -29.9 | -9.8 | 44 | A |
| 92 | H | CE1 | 7.9 | -30.7 | -10.6 | 43 | A |
| 92 | H | NE2 | 6.7 | -31.0 | -10.0 | 44 | A |
| 93 | N | N | 5.9 | -28.3 | -13.6 | 37 | A |
| 93 | N | CA | 6.6 | -28.6 | -14.9 | 37 | A |
| 93 | N | C | 5.8 | -27.8 | -16.0 | 42 | A |
| 93 | N | O | 6.2 | -27.8 | -17.1 | 40 | A |
| 93 | N | CB | 6.6 | -30.0 | -15.3 | 34 | A |
| 93 | N | CG | 7.5 | -30.9 | -14.4 | 41 | A |
| 93 | N | OD1 | 7.2 | -31.9 | -14.0 | 37 | A |
| 93 | N | ND2 | 8.7 | -30.3 | -14.2 | 35 | A |
| 94 | Y | N | 4.8 | -27.0 | -15.6 | 36 | A |
| 94 | Y | CA | 4.1 | -26.2 | -16.6 | 35 | A |
| 94 | Y | C | 5.0 | -25.0 | -17.0 | 40 | A |
| 94 | Y | O | 5.4 | -24.2 | -16.1 | 36 | A |
| 94 | Y | CB | 2.8 | -25.7 | -16.2 | 34 | A |
| 94 | Y | CG | 2.0 | -25.0 | -17.3 | 35 | A |
| 94 | Y | CD1 | 1.6 | -25.7 | -18.4 | 35 | A |
| 94 | Y | CD2 | 1.7 | -23.6 | -17.3 | 38 | A |
| 94 | Y | CE1 | 0.9 | -25.1 | -19.4 | 34 | A |
| 94 | Y | CE2 | 1.3 | -22.9 | -18.4 | 37 | A |
| 94 | Y | CZ | 0.8 | -23.7 | -19.4 | 37 | A |
| 94 | Y | OH | 0.1 | -23.1 | -20.5 | 36 | A |
| 95 | N | N | 5.2 | -24.7 | -18.3 | 40 | A |
| 95 | N | CA | 6.0 | -23.5 | -18.7 | 40 | A |
| 95 | N | C | 5.4 | -23.0 | -20.0 | 43 | A |
| 95 | N | O | 5.8 | -23.6 | -21.0 | 42 | A |
| 95 | N | CB | 7.4 | -23.8 | -18.7 | 42 | A |
| 95 | N | CG | 8.3 | -22.5 | -19.1 | 59 | A |
| 95 | N | OD1 | 7.7 | -21.6 | -19.6 | 53 | A |
| 95 | N | ND2 | 9.5 | -22.6 | -18.7 | 54 | A |
| 95A | A | N | 4.6 | -22.0 | -20.0 | 41 | A |
| 95A | A | CA | 3.9 | -21.5 | -21.2 | 44 | A |
| 95A | A | C | 4.9 | -20.9 | -22.2 | 50 | A |
| 95A | A | O | 4.6 | -21.0 | -23.4 | 52 | A |
| 95A | A | CB | 2.9 | -20.5 | -20.8 | 44 | A |
| 95B | A | N | 6.0 | -20.5 | -21.8 | 49 | A |
| 95B | A | CA | 7.0 | -19.9 | -22.8 | 50 | A |
| 95B | A | C | 7.7 | -21.1 | -23.6 | 57 | A |
| 95B | A | O | 8.3 | -20.8 | -24.6 | 59 | A |
| 95B | A | CB | 8.1 | -19.1 | -22.1 | 51 | A |
| 96 | I | N | 7.5 | -22.3 | -23.1 | 50 | A |
| 96 | I | CA | 8.1 | -23.4 | -23.8 | 49 | A |
| 96 | I | C | 7.1 | -24.2 | -24.6 | 52 | A |
| 96 | I | O | 7.3 | -24.6 | -25.8 | 51 | A |
| 96 | I | CB | 8.9 | -24.4 | -22.8 | 52 | A |
| 96 | I | CG1 | 10.1 | -23.7 | -22.2 | 54 | A |
| 96 | I | CG2 | 9.4 | -25.6 | -23.5 | 51 | A |
| 96 | I | CD1 | 10.7 | -24.4 | -21.0 | 61 | A |
| 97 | N | N | 5.9 | -24.5 | -24.0 | 45 | A |
| 97 | N | CA | 4.8 | -25.2 | -24.6 | 42 | A |
| 97 | N | C | 3.6 | -25.0 | -23.7 | 44 | A |
| 97 | N | O | 3.5 | -25.4 | -22.6 | 41 | A |
| 97 | N | CB | 5.1 | -26.7 | -24.7 | 37 | A |
| 97 | N | CG | 4.0 | -27.4 | -25.6 | 46 | A |
| 97 | N | OD1 | 2.9 | -26.9 | -25.6 | 42 | A |
| 97 | N | ND2 | 4.4 | -28.4 | -26.3 | 44 | A |
| 98 | K | N | 2.7 | -24.2 | -24.3 | 40 | A |
| 98 | K | CA | 1.5 | -23.8 | -23.6 | 39 | A |
| 98 | K | C | 0.6 | -25.0 | -23.3 | 39 | A |
| 98 | K | O | -0.4 | -24.9 | -22.5 | 36 | A |
| 98 | K | CB | 0.7 | -22.8 | -24.5 | 43 | A |
| 98 | K | CG | -0.5 | -22.2 | -23.9 | 60 | A |
| 98 | K | CD | -1.1 | -21.2 | -24.9 | 74 | A |
| 98 | K | CE | -2.6 | -20.8 | -24.5 | 89 | A |
| 98 | K | NZ | -2.7 | -19.9 | -23.3 | 99 | A |
| 99 | Y | N | 0.8 | -26.1 | -23.9 | 37 | A |
| 99 | Y | CA | -0.1 | -27.3 | -23.8 | 38 | A |
| 99 | Y | C | 0.5 | -28.5 | -23.3 | 40 | A |
| 99 | Y | O | -0.1 | -29.6 | -23.2 | 42 | A |
| 99 | Y | CB | -0.7 | -27.6 | -25.2 | 39 | A |
| 99 | Y | CG | -1.5 | -26.4 | -25.7 | 43 | A |
| 99 | Y | CD1 | -2.7 | -26.1 | -25.3 | 46 | A |
| 99 | Y | CD2 | -0.8 | -25.5 | -26.5 | 45 | A |
| 99 | Y | CE1 | -3.4 | -25.0 | -25.7 | 46 | A |
| 99 | Y | CE2 | -1.4 | -24.3 | -26.9 | 47 | A |
| 99 | Y | CZ | -2.7 | -24.1 | -26.5 | 55 | A |
| 99 | Y | OH | -3.4 | -22.9 | -26.9 | 55 | A |
| 100 | N | N | 1.7 | -28.4 | -22.8 | 36 | A |
| 100 | N | CA | 2.3 | -29.6 | -22.1 | 35 | A |
| 100 | N | C | 2.2 | -29.4 | -20.6 | 38 | A |
| 100 | N | O | 2.3 | -28.3 | -20.1 | 38 | A |
| 100 | N | CB | 3.8 | -29.7 | -22.6 | 30 | A |
| 100 | N | CG | 4.4 | -31.1 | -22.3 | 49 | A |
| 100 | N | OD1 | 5.6 | -31.2 | -22.3 | 48 | A |
| 100 | N | ND2 | 3.5 | -32.0 | -21.9 | 36 | A |
| 101 | H | N | 2.1 | -30.5 | -19.8 | 35 | A |
| 101 | H | CA | 1.9 | -30.4 | -18.4 | 35 | A |
| 101 | H | C | 0.8 | -29.4 | -18.1 | 35 | A |
| 101 | H | O | 0.9 | -28.5 | -17.2 | 36 | A |
| 101 | H | CB | 3.2 | -29.9 | -17.7 | 36 | A |
| 101 | H | CG | 4.4 | -30.9 | -17.9 | 38 | A |
| 101 | H | ND1 | 5.5 | -30.6 | -18.7 | 38 | A |
| 101 | H | CD2 | 4.6 | -32.2 | -17.5 | 38 | A |
| 101 | H | CE1 | 6.3 | -31.6 | -18.7 | 37 | A |
| 101 | H | NE2 | 5.8 | -32.6 | -18.0 | 37 | A |
| 102 | D | N | -0.2 | -29.5 | -18.9 | 33 | A |
| 102 | D | CA | -1.3 | -28.5 | -18.9 | 33 | A |
| 102 | D | C | -2.4 | -28.8 | -17.8 | 35 | A |
| 102 | D | O | -3.5 | -29.2 | -18.1 | 33 | A |
| 102 | D | CB | -2.0 | -28.6 | -20.3 | 33 | A |
| 102 | D | CG | -2.8 | -27.4 | -20.6 | 39 | A |
| 102 | D | OD1 | -2.8 | -26.5 | -19.8 | 41 | A |
| 102 | D | OD2 | -3.7 | -27.5 | -21.5 | 39 | A |
| 103 | I | N | -2.0 | -28.6 | -16.6 | 33 | A |
| 103 | I | CA | -3.0 | -28.8 | -15.5 | 32 | A |
| 103 | I | C | -2.7 | -27.8 | -14.4 | 34 | A |
| 103 | I | O | -1.6 | -27.4 | -14.1 | 33 | A |
| 103 | I | CB | -2.8 | -30.2 | -15.0 | 34 | A |
| 103 | I | CG1 | -4.0 | -30.6 | -14.0 | 32 | A |
| 103 | I | CG2 | -1.4 | -30.5 | -14.5 | 33 | A |
| 103 | I | CD1 | -4.0 | -32.1 | -13.7 | 27 | A |
| 104 | A | N | -3.8 | -27.3 | -13.7 | 30 | A |
| 104 | A | CA | -3.6 | -26.3 | -12.7 | 28 | A |
| 104 | A | C | -4.7 | -26.5 | -11.6 | 33 | A |
| 104 | A | O | -5.7 | -27.0 | -12.0 | 32 | A |
| 104 | A | CB | -3.8 | -24.8 | -13.3 | 26 | A |
| 105 | L | N | -4.5 | -26.0 | -10.4 | 31 | A |
| 105 | L | CA | -5.5 | -26.2 | -9.3 | 32 | A |
| 105 | L | C | -5.8 | -24.7 | -8.9 | 37 | A |
| 105 | L | O | -5.0 | -23.8 | -9.0 | 36 | A |
| 105 | L | CB | -4.8 | -26.9 | -8.2 | 31 | A |
| 105 | L | CG | -4.5 | -28.3 | -8.4 | 33 | A |
| 105 | L | CD1 | -3.6 | -28.9 | -7.3 | 32 | A |
| 105 | L | CD2 | -5.8 | -29.1 | -8.4 | 31 | A |
| 106 | L | N | -7.1 | -24.5 | -8.6 | 35 | A |
| 106 | L | CA | -7.6 | -23.2 | -8.2 | 34 | A |
| 106 | L | C | -8.2 | -23.3 | -6.8 | 36 | A |
| 106 | L | O | -9.0 | -24.1 | -6.6 | 32 | A |
| 106 | L | CB | -8.7 | -22.8 | -9.1 | 33 | A |
| 106 | L | CG | -8.5 | -22.9 | -10.7 | 36 | A |

TABLE 4-continued

Coordinates of Soaked Factor IXa-Compound A Complex

| | | | | | | |
|---|---|---|---|---|---|---|
| 106 | L | CD1 | −9.8 | −22.5 | −11.4 | 35 | A |
| 106 | L | CD2 | −7.3 | −22.0 | −11.1 | 32 | A |
| 107 | E | N | −7.7 | −22.4 | −5.9 | 35 | A |
| 107 | E | CA | −8.2 | −22.4 | −4.6 | 36 | A |
| 107 | E | C | −9.3 | −21.4 | −4.5 | 38 | A |
| 107 | E | O | −9.3 | −20.3 | −5.0 | 38 | A |
| 107 | E | CB | −7.1 | −22.1 | −3.5 | 36 | A |
| 107 | E | CG | −7.7 | −22.3 | −2.1 | 39 | A |
| 107 | E | CD | −6.6 | −22.0 | −1.1 | 44 | A |
| 107 | E | OE1 | −5.6 | −21.5 | −1.5 | 42 | A |
| 107 | E | OE2 | −6.8 | −22.4 | 0.1 | 52 | A |
| 108 | L | N | −10.4 | −21.7 | −3.8 | 37 | A |
| 108 | L | CA | −11.6 | −20.9 | −3.7 | 38 | A |
| 108 | L | C | −11.6 | −20.1 | −2.4 | 40 | A |
| 108 | L | O | −11.1 | −20.5 | −1.4 | 38 | A |
| 108 | L | CB | −12.9 | −21.8 | −3.8 | 37 | A |
| 108 | L | CG | −13.1 | −22.6 | −5.0 | 40 | A |
| 108 | L | CD1 | −14.4 | −23.4 | −5.0 | 38 | A |
| 108 | L | CD2 | −12.9 | −21.8 | −6.3 | 38 | A |
| 109 | D | N | −12.1 | −18.8 | −2.5 | 37 | A |
| 109 | D | CA | −12.1 | −18.0 | −1.3 | 36 | A |
| 109 | D | C | −13.0 | −18.5 | −0.1 | 40 | A |
| 109 | D | O | −12.6 | −18.4 | 1.0 | 41 | A |
| 109 | D | CB | −12.6 | −16.5 | −1.6 | 37 | A |
| 109 | D | CG | −14.0 | −16.5 | −2.2 | 44 | A |
| 109 | D | OD1 | −14.6 | −17.5 | −2.6 | 48 | A |
| 109 | D | OD2 | −14.6 | −15.4 | −2.3 | 46 | A |
| 110 | E | N | −14.1 | −19.1 | −0.4 | 37 | A |
| 110 | E | CA | −15.0 | −19.8 | 0.6 | 35 | A |
| 110 | E | C | −15.4 | −21.1 | 0.1 | 41 | A |
| 110 | E | O | −15.7 | −21.3 | −1.1 | 40 | A |
| 110 | E | CB | −16.2 | −19.0 | 0.9 | 36 | A |
| 110 | E | CG | −16.1 | −17.6 | 1.5 | 38 | A |
| 110 | E | CD | −15.3 | −17.6 | 2.9 | 46 | A |
| 110 | E | OE1 | −14.9 | −16.6 | 3.4 | 42 | A |
| 110 | E | OE2 | −15.3 | −18.7 | 3.4 | 40 | A |
| 111 | P | N | −15.6 | −22.1 | 1.0 | 37 | A |
| 111 | P | CA | −16.0 | −23.4 | 0.5 | 37 | A |
| 111 | P | C | −17.3 | −23.5 | −0.3 | 41 | A |
| 111 | P | O | −18.2 | −22.8 | 0.0 | 41 | A |
| 111 | P | CB | −16.0 | −24.3 | 1.8 | 39 | A |
| 111 | P | CG | −15.4 | −23.5 | 2.9 | 42 | A |
| 111 | P | CD | −15.4 | −22.1 | 2.4 | 37 | A |
| 112 | L | N | −17.3 | −24.4 | −1.2 | 37 | A |
| 112 | L | CA | −18.6 | −24.7 | −1.9 | 36 | A |
| 112 | L | C | −19.4 | −25.6 | −0.9 | 38 | A |
| 112 | L | O | −18.8 | −26.2 | 0.0 | 38 | A |
| 112 | L | CB | −18.3 | −25.6 | −3.1 | 36 | A |
| 112 | L | CG | −17.6 | −25.0 | −4.3 | 39 | A |
| 112 | L | CD1 | −17.2 | −26.0 | −5.3 | 39 | A |
| 112 | L | CD2 | −18.5 | −23.9 | −5.0 | 35 | A |
| 113 | V | N | −20.7 | −25.6 | −1.1 | 35 | A |
| 113 | V | CA | −21.5 | −26.4 | −0.2 | 35 | A |
| 113 | V | C | −21.9 | −27.6 | −1.0 | 40 | A |
| 113 | V | O | −22.6 | −27.4 | −2.0 | 38 | A |
| 113 | V | CB | −22.7 | −25.6 | 0.3 | 40 | A |
| 113 | V | CG1 | −23.7 | −26.4 | 1.1 | 38 | A |
| 113 | V | CG2 | −22.2 | −24.3 | 1.2 | 39 | A |
| 114 | L | N | −21.5 | −28.8 | −0.6 | 42 | A |
| 114 | L | CA | −21.9 | −30.0 | −1.4 | 42 | A |
| 114 | L | C | −23.3 | −30.3 | −1.4 | 47 | A |
| 114 | L | O | −23.9 | −30.3 | −0.3 | 47 | A |
| 114 | L | CB | −21.0 | −31.2 | −0.9 | 41 | A |
| 114 | L | CG | −19.5 | −30.9 | −0.9 | 44 | A |
| 114 | L | CD1 | −18.8 | −32.2 | −0.5 | 46 | A |
| 114 | L | CD2 | −19.0 | −30.4 | −2.2 | 45 | A |
| 115 | N | N | −23.9 | −30.6 | −2.5 | 43 | A |
| 115 | N | CA | −25.3 | −31.0 | −2.6 | 43 | A |
| 115 | N | C | −25.5 | −31.7 | −3.9 | 48 | A |
| 115 | N | O | −24.5 | −32.2 | −4.5 | 49 | A |
| 115 | N | CB | −26.2 | −29.7 | −2.4 | 39 | A |
| 115 | N | CG | −26.0 | −28.7 | −3.5 | 55 | A |
| 115 | N | OD1 | −25.6 | −29.0 | −4.6 | 45 | A |
| 115 | N | ND2 | −26.1 | −27.4 | −3.1 | 44 | A |
| 116 | S | N | −26.7 | −31.9 | −4.3 | 44 | A |
| 116 | S | CA | −26.9 | −32.7 | −5.6 | 44 | A |
| 116 | S | C | −26.4 | −32.0 | −6.8 | 46 | A |
| 116 | S | O | −26.3 | −32.6 | −7.9 | 45 | A |
| 116 | S | CB | −28.4 | −33.0 | −5.7 | 46 | A |
| 116 | S | OG | −28.7 | −34.1 | −4.9 | 48 | A |
| 117 | Y | N | −26.2 | −30.7 | −6.7 | 42 | A |
| 117 | Y | CA | −25.8 | −30.0 | −7.9 | 42 | A |
| 117 | Y | C | −24.3 | −29.7 | −7.9 | 41 | A |
| 117 | Y | O | −23.8 | −29.3 | −8.9 | 41 | A |
| 117 | Y | CB | −26.6 | −28.7 | −8.0 | 45 | A |
| 117 | Y | CG | −28.1 | −29.0 | −8.1 | 49 | A |
| 117 | Y | CD1 | −28.6 | −29.4 | −9.3 | 51 | A |
| 117 | Y | CD2 | −28.9 | −28.9 | −7.0 | 51 | A |
| 117 | Y | CE1 | −30.0 | −29.6 | −9.4 | 56 | A |
| 117 | Y | CE2 | −30.2 | −29.2 | −7.1 | 52 | A |
| 117 | Y | CZ | −30.8 | −29.6 | −8.3 | 60 | A |
| 117 | Y | OH | −32.1 | −29.9 | −8.3 | 61 | A |
| 118 | V | N | −23.7 | −29.9 | −6.7 | 37 | A |
| 118 | V | CA | −22.3 | −29.5 | −6.5 | 37 | A |
| 118 | V | C | −21.7 | −30.7 | −5.7 | 41 | A |
| 118 | V | O | −21.8 | −30.7 | −4.5 | 39 | A |
| 118 | V | CB | −23.3 | −28.2 | −5.7 | 40 | A |
| 118 | V | CG1 | −20.8 | −27.7 | −5.5 | 38 | A |
| 118 | V | CG2 | −23.1 | −27.1 | −6.4 | 39 | A |
| 119 | T | N | −21.0 | −31.5 | −6.5 | 39 | A |
| 119 | T | CA | −20.4 | −32.7 | −5.9 | 38 | A |
| 119 | T | C | −19.0 | −32.9 | −6.5 | 38 | A |
| 119 | T | O | −18.8 | −32.7 | −7.6 | 38 | A |
| 119 | T | CB | −21.3 | −34.0 | −6.3 | 48 | A |
| 119 | T | OG1 | −22.6 | −33.8 | −5.8 | 45 | A |
| 119 | T | CG2 | −20.7 | −35.3 | −5.8 | 41 | A |
| 120 | P | N | −18.0 | −33.3 | −5.7 | 35 | A |
| 120 | P | CA | −16.7 | −33.5 | −6.3 | 33 | A |
| 120 | P | C | −16.6 | −34.7 | −7.3 | 38 | A |
| 120 | P | O | −17.5 | −35.6 | −7.3 | 34 | A |
| 120 | P | CB | −15.8 | −33.8 | −5.1 | 35 | A |
| 120 | P | CG | −16.5 | −33.2 | −3.9 | 38 | A |
| 120 | P | CD | −18.0 | −33.5 | −4.2 | 34 | A |
| 121 | I | N | −15.6 | −34.7 | −8.1 | 33 | A |
| 121 | I | CA | −15.4 | −35.9 | −9.0 | 30 | A |
| 121 | I | C | −14.4 | −36.8 | −8.2 | 34 | A |
| 121 | I | O | −13.6 | −36.3 | −7.4 | 34 | A |
| 121 | I | CB | −14.8 | −35.5 | −10.4 | 30 | A |
| 121 | I | CG1 | −14.6 | −36.7 | −11.3 | 28 | A |
| 121 | I | CG2 | −13.5 | −34.7 | −10.1 | 26 | A |
| 121 | I | CD1 | −16.0 | −37.4 | −11.6 | 30 | A |
| 122 | C | N | −14.5 | −38.1 | −8.3 | 33 | A |
| 122 | C | CA | −13.6 | −39.0 | −7.6 | 34 | A |
| 122 | C | C | −12.3 | −39.0 | −8.3 | 35 | A |
| 122 | C | O | −12.3 | −38.8 | −9.5 | 34 | A |
| 122 | C | CB | −14.1 | −40.4 | −7.4 | 37 | A |
| 122 | C | SG | −15.7 | −40.5 | −6.7 | 42 | A |
| 123 | I | N | −11.2 | −39.2 | −7.6 | 33 | A |
| 123 | I | CA | −9.9 | −39.3 | −8.2 | 33 | A |
| 123 | I | C | −9.2 | −40.5 | −7.5 | 39 | A |
| 123 | I | O | −8.9 | −40.5 | −6.4 | 37 | A |
| 123 | I | CB | −9.1 | −38.0 | −8.0 | 35 | A |
| 123 | I | CG1 | −9.8 | −36.8 | −8.6 | 34 | A |
| 123 | I | CG2 | −7.7 | −38.2 | −8.7 | 33 | A |
| 123 | I | CD1 | −9.0 | −35.5 | −8.5 | 31 | A |
| 124 | A | N | −8.9 | −41.5 | −8.3 | 35 | A |
| 124 | A | CA | −8.3 | −42.7 | −7.9 | 34 | A |
| 124 | A | C | −6.8 | −42.6 | −7.8 | 40 | A |
| 124 | A | O | −6.3 | −41.4 | −8.1 | 38 | A |
| 124 | A | CB | −8.7 | −43.9 | −8.8 | 33 | A |
| 125 | D | N | −6.0 | −43.6 | −7.4 | 36 | A |
| 125 | D | CA | −4.5 | −43.4 | −7.4 | 34 | A |
| 125 | D | C | −4.0 | −43.5 | −8.8 | 35 | A |
| 125 | D | O | −4.8 | −43.7 | −9.7 | 36 | A |
| 125 | D | CB | −3.8 | −44.5 | −6.5 | 36 | A |
| 125 | D | CG | −4.0 | −45.9 | −7.0 | 47 | A |
| 125 | D | OD1 | −4.6 | −46.2 | −8.0 | 48 | A |
| 125 | D | OD2 | −3.6 | −46.9 | −6.2 | 51 | A |
| 126 | K | N | −2.7 | −43.4 | −9.1 | 31 | A |
| 126 | K | CA | −2.2 | −43.4 | −10.4 | 33 | A |
| 126 | K | C | −2.5 | −44.7 | −11.2 | 38 | A |
| 126 | K | O | −2.9 | −44.6 | −12.4 | 37 | A |
| 126 | K | CB | −0.6 | −43.3 | −10.3 | 34 | A |
| 126 | K | CG | 0.2 | −43.5 | −11.6 | 36 | A |
| 126 | K | CD | 1.7 | −43.1 | −11.2 | 43 | A |
| 126 | K | CE | 2.5 | −43.1 | −12.5 | 45 | A |

TABLE 4-continued

Coordinates of Soaked Factor IXa-Compound A Complex

| | | | | | | |
|---|---|---|---|---|---|---|
| 126 | K | NZ | 4.0 | −43.0 | −12.2 | 47 | A |
| 127 | E | N | −2.4 | −45.8 | −10.6 | 34 | A |
| 127 | E | CA | −2.6 | −47.1 | −11.2 | 32 | A |
| 127 | E | C | −4.0 | −47.2 | −11.7 | 33 | A |
| 127 | E | O | −4.3 | −47.7 | −12.8 | 37 | A |
| 127 | E | CB | −2.3 | −48.2 | −10.3 | 35 | A |
| 127 | E | CG | −2.9 | −49.6 | −10.8 | 47 | A |
| 127 | E | CD | −2.5 | −50.8 | −9.9 | 64 | A |
| 127 | E | OE1 | −2.4 | −51.9 | −10.5 | 57 | A |
| 127 | E | OE2 | −2.4 | −50.7 | −8.6 | 60 | A |
| 128 | Y | N | −5.0 | −47.0 | −10.8 | 30 | A |
| 128 | Y | CA | −6.4 | −47.1 | −11.2 | 31 | A |
| 128 | Y | C | −6.9 | −46.1 | −12.1 | 34 | A |
| 128 | Y | O | −7.7 | −46.3 | −13.0 | 34 | A |
| 128 | Y | CB | −7.2 | −47.2 | −9.9 | 34 | A |
| 128 | Y | CG | −7.4 | −48.7 | −9.5 | 39 | A |
| 128 | Y | CD1 | −6.7 | −49.2 | −8.4 | 41 | A |
| 128 | Y | CD2 | −8.3 | −49.5 | −10.1 | 41 | A |
| 128 | Y | CE1 | −6.8 | −50.5 | −8.0 | 44 | A |
| 128 | Y | CE2 | −8.5 | −50.8 | −9.7 | 43 | A |
| 128 | Y | CZ | −7.7 | −51.3 | −8.7 | 52 | A |
| 128 | Y | OH | −7.8 | −52.6 | −8.3 | 53 | A |
| 129 | T | N | −6.4 | −44.9 | −12.0 | 30 | A |
| 129 | T | CA | −6.8 | −43.8 | −12.9 | 30 | A |
| 129 | T | C | −6.5 | −44.3 | −14.4 | 31 | A |
| 129 | T | O | −7.2 | −44.2 | −15.3 | 33 | A |
| 129 | T | CB | −6.2 | −42.5 | −12.6 | 33 | A |
| 129 | T | OG1 | −6.6 | −42.1 | −11.3 | 29 | A |
| 129 | T | CG2 | −6.7 | −41.4 | −13.6 | 32 | A |
| 129A | N | N | −5.3 | −44.8 | −14.5 | 29 | A |
| 129A | N | CA | −4.8 | −45.4 | −15.8 | 30 | A |
| 129A | N | C | −5.7 | −46.6 | −16.2 | 36 | A |
| 129A | N | O | −6.1 | −46.7 | −17.4 | 35 | A |
| 129A | N | CB | −3.3 | −45.7 | −15.7 | 33 | A |
| 129A | N | CG | −2.8 | −46.1 | −17.0 | 48 | A |
| 129A | N | OD1 | −3.0 | −45.4 | −18.1 | 36 | A |
| 129A | N | ND2 | −2.2 | −47.3 | −17.1 | 36 | A |
| 129B | I | N | −6.0 | −47.4 | −15.3 | 32 | A |
| 129B | I | CA | −6.9 | −48.6 | −15.6 | 31 | A |
| 129B | I | C | −8.2 | −48.0 | −16.1 | 34 | A |
| 129B | I | O | −8.8 | −48.5 | −17.0 | 33 | A |
| 129B | I | CB | −7.0 | −49.5 | −14.3 | 34 | A |
| 129B | I | CG1 | −5.7 | −50.3 | −14.1 | 34 | A |
| 129B | I | CG2 | −8.3 | −50.4 | −14.5 | 34 | A |
| 129B | I | CD1 | −5.6 | −51.0 | −12.7 | 39 | A |
| 130 | F | N | −8.8 | −47.0 | −15.4 | 29 | A |
| 130 | F | CA | −10.0 | −46.5 | −15.8 | 30 | A |
| 130 | F | C | −10.0 | −45.8 | −17.2 | 32 | A |
| 130 | F | O | −10.9 | −46.0 | −18.0 | 32 | A |
| 130 | F | CB | −10.5 | −45.5 | −14.8 | 33 | A |
| 130 | F | CG | −10.8 | −46.1 | −13.4 | 35 | A |
| 130 | F | CD1 | −11.0 | −47.5 | −13.3 | 36 | A |
| 130 | F | CD2 | −10.9 | −45.4 | −12.2 | 35 | A |
| 130 | F | CE1 | −11.3 | −48.2 | −12.1 | 34 | A |
| 130 | F | CE2 | −11.1 | −46.0 | −11.0 | 38 | A |
| 130 | F | CZ | −11.3 | −47.4 | −10.9 | 35 | A |
| 131 | L | N | −8.9 | −45.1 | −17.5 | 29 | A |
| 131 | L | CA | −8.8 | −44.4 | −18.8 | 29 | A |
| 131 | L | C | −8.8 | −45.6 | −19.9 | 35 | A |
| 131 | L | O | −9.4 | −45.4 | −20.9 | 34 | A |
| 131 | L | CB | −7.4 | −43.8 | −18.9 | 28 | A |
| 131 | L | CG | −7.2 | −43.1 | −20.3 | 34 | A |
| 131 | L | CD1 | −5.8 | −42.6 | −20.5 | 34 | A |
| 131 | L | CD2 | −8.3 | −42.0 | −20.6 | 32 | A |
| 132 | K | N | −8.1 | −46.6 | −19.6 | 35 | A |
| 132 | K | CA | −8.0 | −47.8 | −20.5 | 35 | A |
| 132 | K | C | −9.3 | −48.6 | −20.7 | 39 | A |
| 132 | K | O | −9.4 | −49.3 | −21.7 | 39 | A |
| 132 | K | CB | −6.8 | −48.7 | −20.2 | 37 | A |
| 132 | K | CG | −5.5 | −48.1 | −20.3 | 44 | A |
| 132 | K | CD | −4.4 | −49.2 | −20.0 | 53 | A |
| 132 | K | CE | −3.0 | −48.7 | −20.3 | 76 | A |
| 132 | K | NZ | −1.9 | −49.5 | −19.4 | 76 | A |
| 133 | F | N | −10.4 | −48.3 | −19.9 | 35 | A |
| 133 | F | CA | −11.7 | −48.9 | −20.2 | 35 | A |
| 133 | F | C | −12.1 | −48.4 | −21.6 | 40 | A |
| 133 | F | O | −12.9 | −49.0 | −22.2 | 41 | A |
| 133 | F | CB | −12.7 | −48.5 | −19.2 | 36 | A |
| 133 | F | CG | −12.6 | −49.1 | −17.8 | 40 | A |
| 133 | F | CD1 | −11.6 | −50.1 | −17.6 | 43 | A |
| 133 | F | CD2 | −13.4 | −48.7 | −16.7 | 42 | A |
| 133 | F | CE1 | −11.5 | −50.7 | −16.3 | 46 | A |
| 133 | F | CE2 | −13.3 | −49.4 | −15.5 | 45 | A |
| 133 | F | CZ | −12.3 | −50.3 | −15.3 | 43 | A |
| 134 | G | N | −11.6 | −47.2 | −22.0 | 36 | A |
| 134 | G | CA | −11.8 | −46.7 | −23.3 | 32 | A |
| 134 | G | C | −13.0 | −45.9 | −23.7 | 34 | A |
| 134 | G | O | −13.1 | −45.6 | −24.9 | 32 | A |
| 135 | S | N | −13.8 | −45.5 | −22.7 | 34 | A |
| 135 | S | CA | −14.9 | −44.7 | −23.0 | 34 | A |
| 135 | S | C | −15.1 | −43.6 | −21.9 | 37 | A |
| 135 | S | O | −15.3 | −44.0 | −20.7 | 36 | A |
| 135 | S | CB | −16.2 | −45.6 | −23.1 | 39 | A |
| 135 | S | OG | −17.3 | −44.7 | −23.3 | 47 | A |
| 136 | G | N | −15.0 | −42.3 | −22.2 | 33 | A |
| 136 | G | CA | −15.2 | −41.4 | −21.2 | 33 | A |
| 136 | G | C | −16.2 | −40.3 | −21.6 | 38 | A |
| 136 | G | O | −16.7 | −40.3 | −22.7 | 39 | A |
| 137 | Y | N | −16.7 | −39.5 | −20.6 | 36 | A |
| 137 | Y | CA | −17.6 | −38.4 | −20.8 | 36 | A |
| 137 | Y | C | −16.9 | −37.1 | −20.6 | 36 | A |
| 137 | Y | O | −16.2 | −36.9 | −19.6 | 34 | A |
| 137 | Y | CB | −18.8 | −38.5 | −19.8 | 39 | A |
| 137 | Y | CG | −19.7 | −39.6 | −20.2 | 46 | A |
| 137 | Y | CD1 | −19.5 | −41.0 | −19.9 | 48 | A |
| 137 | Y | CD2 | −20.8 | −39.3 | −21.1 | 48 | A |
| 137 | Y | CE1 | −20.3 | −42.0 | −20.3 | 52 | A |
| 137 | Y | CE2 | −21.6 | −40.4 | −21.5 | 50 | A |
| 137 | Y | CZ | −21.4 | −41.7 | −21.1 | 62 | A |
| 137 | Y | OH | −22.2 | −42.7 | −21.5 | 67 | A |
| 138 | V | N | −17.1 | −36.2 | −21.6 | 30 | A |
| 138 | V | CA | −16.5 | −34.8 | −21.5 | 30 | A |
| 138 | V | C | −17.8 | −34.0 | −21.4 | 37 | A |
| 138 | V | O | −18.9 | −34.3 | −21.9 | 35 | A |
| 138 | V | CB | −15.6 | −34.5 | −22.7 | 34 | A |
| 138 | V | CG1 | −14.4 | −35.4 | −22.8 | 34 | A |
| 138 | V | CG2 | −16.3 | −34.5 | −24.0 | 34 | A |
| 139 | S | N | −17.7 | −32.8 | −20.8 | 35 | A |
| 139 | S | CA | −18.8 | −31.9 | −20.7 | 34 | A |
| 139 | S | C | −18.2 | −30.4 | −20.7 | 38 | A |
| 139 | S | O | −17.0 | −30.2 | −20.4 | 34 | A |
| 139 | S | CB | −19.6 | −32.2 | −19.5 | 35 | A |
| 139 | S | OG | −18.8 | −32.4 | −18.3 | 39 | A |
| 140 | G | N | −19.1 | −29.4 | −21.0 | 37 | A |
| 140 | G | CA | −18.6 | −28.0 | −21.0 | 36 | A |
| 140 | G | C | −19.6 | −27.1 | −21.7 | 41 | A |
| 140 | G | O | −20.5 | −27.6 | −22.4 | 38 | A |
| 141 | W | N | −19.4 | −25.8 | −21.6 | 40 | A |
| 141 | W | CA | −20.2 | −24.8 | −22.2 | 40 | A |
| 141 | W | C | −19.4 | −24.2 | −23.4 | 43 | A |
| 141 | W | O | −19.7 | −23.1 | −23.8 | 42 | A |
| 141 | W | CB | −20.5 | −23.7 | −21.2 | 38 | A |
| 141 | W | CG | −21.6 | −24.1 | −20.2 | 37 | A |
| 141 | W | CD1 | −22.9 | −24.0 | −20.3 | 40 | A |
| 141 | W | CD2 | −21.3 | −24.6 | −18.9 | 37 | A |
| 141 | W | NE1 | −23.5 | −24.4 | −19.2 | 39 | A |
| 141 | W | CE2 | −22.6 | −24.8 | −18.3 | 39 | A |
| 141 | W | CE3 | −20.2 | −25.0 | −18.2 | 37 | A |
| 141 | W | CZ2 | −22.7 | −25.3 | −17.0 | 38 | A |
| 141 | W | CZ3 | −20.3 | −25.4 | −16.9 | 38 | A |
| 141 | W | CH2 | −21.5 | −25.6 | −16.3 | 38 | A |
| 142 | G | N | −18.5 | −24.9 | −23.9 | 38 | A |
| 142 | G | CA | −17.7 | −24.5 | −25.1 | 39 | A |
| 142 | G | C | −18.5 | −24.4 | −26.3 | 45 | A |
| 142 | G | O | −19.7 | −24.7 | −26.3 | 42 | A |
| 143 | R | N | −17.8 | −24.1 | −27.4 | 45 | A |
| 143 | R | CA | −18.5 | −23.9 | −28.7 | 46 | A |
| 143 | R | C | −19.2 | −25.2 | −29.1 | 53 | A |
| 143 | R | O | −18.7 | −26.3 | −28.8 | 51 | A |
| 143 | R | CB | −17.5 | −23.6 | −29.8 | 48 | A |
| 143 | R | CG | −17.3 | −22.2 | −30.1 | 60 | A |
| 143 | R | CD | −16.1 | −22.0 | −31.1 | 64 | A |
| 143 | R | NE | −15.1 | −21.2 | −30.5 | 73 | A |
| 143 | R | CZ | −14.1 | −20.5 | −31.1 | 91 | A |
| 143 | R | NH1 | −14.0 | −20.7 | −32.4 | 76 | A |
| 143 | R | NH2 | −13.3 | −19.8 | −30.4 | 83 | A |

TABLE 4-continued

Coordinates of Soaked Factor IXa-Compound A Complex

| | | | | | | |
|---|---|---|---|---|---|---|
| 144 | V | N | −20.4 | −25.1 | −29.8 | 51 | A |
| 144 | V | CA | −21.2 | −26.2 | −30.3 | 51 | A |
| 144 | V | C | −21.0 | −26.3 | −31.8 | 62 | A |
| 144 | V | O | −21.6 | −27.2 | −32.4 | 60 | A |
| 144 | V | CB | −22.6 | −26.2 | −29.8 | 55 | A |
| 144 | V | CG1 | −22.8 | −26.2 | −28.3 | 52 | A |
| 144 | V | CG2 | −23.3 | −25.0 | −30.5 | 56 | A |
| 145 | F | N | −20.2 | −25.4 | −32.3 | 65 | A |
| 145 | F | CA | −19.7 | −25.4 | −33.7 | 69 | A |
| 145 | F | C | −18.3 | −24.9 | −33.8 | 78 | A |
| 145 | F | O | −18.0 | −23.9 | −33.1 | 78 | A |
| 145 | F | CB | −20.7 | −24.6 | −34.6 | 71 | A |
| 145 | F | CG | −22.0 | −25.2 | −34.7 | 73 | A |
| 145 | F | CD1 | −23.1 | −24.7 | −34.0 | 76 | A |
| 145 | F | CD2 | −22.2 | −26.4 | −35.5 | 76 | A |
| 145 | F | CE1 | −24.3 | −25.4 | −34.0 | 77 | A |
| 145 | F | CE2 | −23.5 | −27.0 | −35.6 | 79 | A |
| 145 | F | CZ | −24.5 | −26.5 | −34.8 | 77 | A |
| 147 | H | N | −17.4 | −25.6 | −34.5 | 78 | A |
| 147 | H | CA | −16.0 | −25.2 | −34.6 | 80 | A |
| 147 | H | C | −15.7 | −23.7 | −34.5 | 85 | A |
| 147 | H | O | −14.8 | −23.2 | −33.8 | 84 | A |
| 147 | H | CB | −15.3 | −25.9 | −35.7 | 82 | A |
| 147 | H | CG | −14.0 | −25.3 | −36.1 | 87 | A |
| 147 | H | ND1 | −13.0 | −25.0 | −35.2 | 89 | A |
| 147 | H | CD2 | −13.6 | −24.8 | −37.3 | 90 | A |
| 147 | H | CE1 | −12.0 | −24.4 | −35.9 | 89 | A |
| 147 | H | NE2 | −12.3 | −24.2 | −37.1 | 90 | A |
| 148 | K | N | −16.4 | −22.9 | −35.3 | 82 | A |
| 148 | K | CA | −16.2 | −21.5 | −35.4 | 82 | A |
| 148 | K | C | −17.5 | −20.7 | −35.0 | 84 | A |
| 148 | K | O | −17.7 | −19.5 | −35.4 | 84 | A |
| 148 | K | CB | −15.8 | −21.0 | −36.8 | 84 | A |
| 148 | K | CG | −14.3 | −20.6 | −36.9 | 96 | A |
| 148 | K | CD | −13.6 | −21.2 | −38.1 | 0 | A |
| 148 | K | CE | −13.1 | −20.2 | −39.1 | 0 | A |
| 148 | K | NZ | −11.8 | −20.4 | −39.6 | 0 | A |
| 149 | G | N | −18.4 | −21.4 | −34.3 | 78 | A |
| 149 | G | CA | −19.7 | −20.8 | −34.0 | 77 | A |
| 149 | G | C | −20.0 | −20.5 | −32.5 | 77 | A |
| 149 | G | O | −19.2 | −20.2 | −31.7 | 76 | A |
| 150 | R | N | −21.3 | −20.6 | −32.2 | 71 | A |
| 150 | R | CA | −21.9 | −20.3 | −31.0 | 70 | A |
| 150 | R | C | −21.5 | −21.2 | −29.8 | 68 | A |
| 150 | R | O | −21.5 | −22.4 | −29.9 | 66 | A |
| 150 | R | CB | −23.5 | −20.2 | −31.1 | 73 | A |
| 150 | R | CG | −24.2 | −21.6 | −30.9 | 90 | A |
| 150 | R | CD | −25.3 | −21.8 | −31.9 | 0 | A |
| 150 | R | NE | −25.6 | −23.2 | −32.1 | 0 | A |
| 150 | R | CZ | −26.7 | −23.7 | −32.7 | 0 | A |
| 150 | R | NH1 | −27.6 | −22.9 | −33.2 | 0 | A |
| 150 | R | NH2 | −26.8 | −25.0 | −32.8 | 0 | A |
| 151 | S | N | −21.2 | −20.6 | −28.7 | 61 | A |
| 151 | S | CA | −20.9 | −21.3 | −27.4 | 61 | A |
| 151 | S | C | −22.2 | −21.7 | −26.8 | 64 | A |
| 151 | S | O | −23.3 | −21.2 | −27.1 | 65 | A |
| 151 | S | CB | −20.0 | −20.4 | −26.6 | 62 | A |
| 151 | S | OG | −20.7 | −20.0 | −25.4 | 71 | A |
| 152 | A | N | −22.1 | −22.7 | −25.9 | 57 | A |
| 152 | A | CA | −23.3 | −23.3 | −25.3 | 54 | A |
| 152 | A | C | −23.9 | −22.5 | −24.2 | 55 | A |
| 152 | A | O | −23.2 | −21.8 | −23.4 | 55 | A |
| 152 | A | CB | −23.1 | −24.7 | −24.9 | 54 | A |
| 153 | L | N | −25.3 | −22.6 | −24.0 | 51 | A |
| 153 | L | CA | −26.0 | −21.9 | −22.9 | 50 | A |
| 153 | L | C | −26.3 | −23.0 | −21.9 | 50 | A |
| 153 | L | O | −26.0 | −22.8 | −20.7 | 50 | A |
| 153 | L | CB | −27.3 | −21.4 | −23.5 | 52 | A |
| 153 | L | CG | −27.2 | −20.1 | −24.2 | 59 | A |
| 153 | L | CD1 | −28.6 | −19.5 | −24.7 | 60 | A |
| 153 | L | CD2 | −26.5 | −19.0 | −23.4 | 64 | A |
| 154 | V | N | −26.7 | −24.1 | −22.4 | 43 | A |
| 154 | V | CA | −27.0 | −25.3 | −21.5 | 43 | A |
| 154 | V | C | −25.7 | −26.2 | −21.6 | 43 | A |
| 154 | V | O | −25.2 | −26.5 | −22.6 | 42 | A |
| 154 | V | CB | −28.2 | −26.0 | −22.0 | 46 | A |
| 154 | V | CG1 | −28.4 | −27.3 | −21.1 | 45 | A |
| 154 | V | CG2 | −29.4 | −25.1 | −22.0 | 47 | A |
| 155 | L | N | −25.3 | −26.7 | −20.4 | 39 | A |
| 155 | L | CA | −24.2 | −27.6 | −20.3 | 37 | A |
| 155 | L | C | −24.3 | −28.8 | −21.3 | 38 | A |
| 155 | L | O | −25.4 | −29.4 | −21.4 | 36 | A |
| 155 | L | CB | −24.2 | −28.2 | −18.9 | 37 | A |
| 155 | L | CG | −23.0 | −29.1 | −18.6 | 38 | A |
| 155 | L | CD1 | −21.7 | −28.4 | −18.8 | 36 | A |
| 155 | L | CD2 | −23.1 | −29.6 | −17.1 | 37 | A |
| 156 | Q | N | −23.3 | −29.1 | −22.1 | 37 | A |
| 156 | Q | CA | −23.4 | −30.2 | −23.1 | 35 | A |
| 156 | Q | C | −22.5 | −31.3 | −22.6 | 40 | A |
| 156 | Q | O | −21.6 | −31.1 | −21.8 | 37 | A |
| 156 | Q | CB | −22.7 | −29.7 | −24.4 | 37 | A |
| 156 | Q | CG | −23.4 | −28.5 | −25.1 | 36 | A |
| 156 | Q | CD | −24.9 | −28.9 | −25.5 | 41 | A |
| 156 | Q | OE1 | −25.8 | −28.4 | −24.9 | 46 | A |
| 156 | Q | NE2 | −25.0 | −29.7 | −26.4 | 35 | A |
| 157 | Y | N | −22.8 | −32.5 | −23.1 | 38 | A |
| 157 | Y | CA | −21.9 | −33.6 | −22.7 | 39 | A |
| 157 | Y | C | −21.8 | −34.6 | −23.9 | 41 | A |
| 157 | Y | O | −22.6 | −34.5 | −24.8 | 39 | A |
| 157 | Y | CB | −22.4 | −34.4 | −21.5 | 39 | A |
| 157 | Y | CG | −23.7 | −35.2 | −21.7 | 42 | A |
| 157 | Y | CD1 | −23.6 | −36.5 | −22.0 | 44 | A |
| 157 | Y | CD2 | −24.9 | −34.6 | −21.7 | 43 | A |
| 157 | Y | CE1 | −24.7 | −37.3 | −22.2 | 43 | A |
| 157 | Y | CE2 | −26.1 | −35.4 | −21.9 | 43 | A |
| 157 | Y | CZ | −26.0 | −36.7 | −22.1 | 52 | A |
| 157 | Y | OH | −27.1 | −37.5 | −22.3 | 58 | A |
| 158 | L | N | −20.8 | −35.4 | −23.8 | 38 | A |
| 158 | L | CA | −20.5 | −36.3 | −24.9 | 36 | A |
| 158 | L | C | −19.6 | −37.4 | −24.5 | 39 | A |
| 158 | L | O | −18.6 | −37.2 | −23.8 | 39 | A |
| 158 | L | CB | −19.9 | −35.6 | −26.1 | 34 | A |
| 158 | L | CG | −19.3 | −36.3 | −27.3 | 36 | A |
| 158 | L | CD1 | −20.4 | −36.8 | −28.2 | 35 | A |
| 158 | L | CD2 | −18.3 | −35.4 | −28.0 | 34 | A |
| 159 | R | N | −19.9 | −38.7 | −24.9 | 37 | A |
| 159 | R | CA | −19.1 | −39.8 | −24.7 | 36 | A |
| 159 | R | C | −18.2 | −39.9 | −25.8 | 37 | A |
| 159 | R | O | −18.6 | −39.9 | −27.0 | 36 | A |
| 159 | R | CB | −20.0 | −41.1 | −24.7 | 34 | A |
| 159 | R | CG | −19.3 | −42.4 | −24.2 | 43 | A |
| 159 | R | CD | −20.0 | −43.7 | −24.8 | 49 | A |
| 159 | R | NE | −19.7 | −43.9 | −26.2 | 58 | A |
| 159 | R | CZ | −18.6 | −44.4 | −26.8 | 65 | A |
| 159 | R | NH1 | −17.5 | −44.7 | −26.1 | 48 | A |
| 159 | R | NH2 | −18.6 | −44.5 | −28.1 | 61 | A |
| 160 | V | N | −16.9 | −40.0 | −25.5 | 34 | A |
| 160 | V | CA | −15.8 | −40.1 | −26.5 | 32 | A |
| 160 | V | C | −15.0 | −41.3 | −26.2 | 34 | A |
| 160 | V | O | −14.6 | −41.6 | −25.1 | 36 | A |
| 160 | V | CB | −15.0 | −38.8 | −26.5 | 33 | A |
| 160 | V | CG1 | −15.7 | −37.6 | −27.1 | 33 | A |
| 160 | V | CG2 | −14.4 | −38.6 | −25.2 | 32 | A |
| 161 | P | N | −14.7 | −42.1 | −27.3 | 30 | A |
| 161 | P | CA | −13.9 | −43.3 | −27.2 | 30 | A |
| 161 | P | C | −12.4 | −43.0 | −27.2 | 33 | A |
| 161 | P | O | −12.0 | −42.0 | −27.9 | 34 | A |
| 161 | P | CB | −14.2 | −44.1 | −28.5 | 32 | A |
| 161 | P | CG | −14.6 | −43.1 | −29.4 | 36 | A |
| 161 | P | CD | −15.3 | −42.0 | −28.6 | 32 | A |
| 162 | L | N | −11.6 | −43.7 | −26.5 | 29 | A |
| 162 | L | CA | −10.2 | −43.5 | −26.4 | 29 | A |
| 162 | L | C | −9.7 | −44.0 | −27.8 | 33 | A |
| 162 | L | O | −10.1 | −45.0 | −28.4 | 33 | A |
| 162 | L | CB | −9.6 | −44.4 | −25.3 | 29 | A |
| 162 | L | CG | −8.1 | −44.4 | −25.1 | 32 | A |
| 162 | L | CD1 | −7.7 | −43.1 | −24.5 | 32 | A |
| 162 | L | CD2 | −7.8 | −45.5 | −24.1 | 33 | A |
| 163 | V | N | −8.7 | −43.3 | −28.3 | 32 | A |
| 163 | V | CA | −8.0 | −43.6 | −29.5 | 32 | A |
| 163 | V | C | −6.6 | −44.1 | −29.3 | 38 | A |
| 163 | V | O | −5.8 | −43.4 | −28.5 | 39 | A |
| 163 | V | CB | −8.0 | −42.3 | −30.4 | 35 | A |
| 163 | V | CG1 | −7.1 | −42.4 | −31.6 | 32 | A |
| 163 | V | CG2 | −9.5 | −42.1 | −30.9 | 36 | A |
| 164 | D | N | −6.2 | −45.1 | −30.0 | 36 | A |

TABLE 4-continued

Coordinates of Soaked Factor IXa-Compound A Complex

| | | | | | | |
|---|---|---|---|---|---|---|
| 164 | D | CA | -4.8 | -45.7 | -29.8 | 38 A |
| 164 | D | C | -3.8 | -44.7 | -30.1 | 43 A |
| 164 | D | O | -4.0 | -43.9 | -31.1 | 42 A |
| 164 | D | CB | -4.6 | -47.0 | -30.5 | 44 A |
| 164 | D | CG | -4.9 | -46.9 | -32.0 | 57 A |
| 164 | D | OD1 | -3.9 | -46.7 | -32.8 | 58 A |
| 164 | D | OD2 | -6.1 | -46.8 | -32.4 | 68 A |
| 165 | R | N | -2.7 | -44.7 | -29.4 | 39 A |
| 165 | R | CA | -1.7 | -43.8 | -29.6 | 40 A |
| 165 | R | C | -1.1 | -43.7 | -31.0 | 41 A |
| 165 | R | O | -0.8 | -42.7 | -31.6 | 40 A |
| 165 | R | CB | -0.5 | -44.0 | -28.6 | 40 A |
| 165 | R | CG | 0.8 | -43.4 | -29.0 | 45 A |
| 165 | R | CD | 1.8 | -43.3 | -27.9 | 50 A |
| 165 | R | NE | 1.7 | -41.9 | -27.4 | 61 A |
| 165 | R | CZ | 2.7 | -41.1 | -27.6 | 62 A |
| 165 | R | NH1 | 3.8 | -41.4 | -28.0 | 47 A |
| 165 | R | NH2 | 2.4 | -39.8 | -27.2 | 43 A |
| 166 | A | N | -0.9 | -44.9 | -31.7 | 38 A |
| 166 | A | CA | -0.4 | -44.9 | -33.0 | 38 A |
| 166 | A | C | -1.3 | -44.2 | -34.0 | 39 A |
| 166 | A | O | -0.9 | -43.4 | -34.8 | 40 A |
| 166 | A | CB | -0.1 | -46.4 | -33.5 | 39 A |
| 167 | T | N | -2.6 | -44.4 | -33.8 | 35 A |
| 167 | T | CA | -3.5 | -43.7 | -34.7 | 36 A |
| 167 | T | C | -3.5 | -42.2 | -34.4 | 46 A |
| 167 | T | O | -3.5 | -41.4 | -35.3 | 45 A |
| 167 | T | CB | -4.9 | -44.2 | -34.4 | 44 A |
| 167 | T | OG1 | -5.0 | -45.6 | -34.9 | 46 A |
| 167 | T | CG2 | -6.0 | -43.4 | -35.1 | 41 A |
| 168 | C | N | -3.3 | -41.9 | -33.1 | 44 A |
| 168 | C | CA | -3.3 | -40.5 | -32.8 | 44 A |
| 168 | C | C | -2.1 | -39.7 | -33.3 | 45 A |
| 168 | C | O | -2.2 | -38.6 | -33.8 | 43 A |
| 168 | C | CB | -3.3 | -40.2 | -31.3 | 47 A |
| 168 | C | SG | -3.7 | -38.5 | -31.0 | 54 A |
| 169 | L | N | -0.9 | -40.4 | -33.2 | 42 A |
| 169 | L | CA | 0.3 | -39.8 | -33.7 | 44 A |
| 169 | L | C | 0.3 | -39.6 | -35.2 | 47 A |
| 169 | L | O | 0.8 | -38.6 | -35.7 | 47 A |
| 169 | L | CB | 1.5 | -40.8 | -33.3 | 45 A |
| 169 | L | CG | 2.3 | -40.5 | -32.1 | 52 A |
| 169 | L | CD1 | 1.6 | -39.6 | -31.1 | 51 A |
| 169 | L | CD2 | 2.9 | -41.8 | -31.5 | 59 A |
| 170 | R | N | -0.3 | -40.5 | -35.9 | 44 A |
| 170 | R | CA | -0.4 | -40.4 | -37.4 | 45 A |
| 170 | R | C | -1.4 | -39.2 | -37.8 | 51 A |
| 170 | R | O | -1.3 | -38.8 | -38.9 | 51 A |
| 170 | R | CB | -1.0 | -41.6 | -38.1 | 40 A |
| 170 | R | CG | 0.0 | -42.7 | -38.2 | 44 A |
| 170 | R | CD | -0.5 | -43.9 | -39.0 | 45 A |
| 170 | R | NE | -1.8 | -44.4 | -38.6 | 52 A |
| 170 | R | CZ | -2.0 | -45.5 | -37.9 | 61 A |
| 170 | R | NH1 | -0.9 | -46.2 | -37.4 | 48 A |
| 170 | R | NH2 | -3.2 | -45.9 | -37.5 | 55 A |
| 171 | S | N | -2.2 | -38.8 | -36.9 | 45 A |
| 171 | S | CA | -3.2 | -37.8 | -37.1 | 43 A |
| 171 | S | C | -2.7 | -36.4 | -37.1 | 47 A |
| 171 | S | O | -3.4 | -35.4 | -37.5 | 45 A |
| 171 | S | CB | -4.4 | -38.0 | -36.1 | 44 A |
| 171 | S | OG | -4.1 | -37.2 | -34.9 | 41 A |
| 172 | T | N | -1.6 | -36.2 | -36.5 | 44 A |
| 172 | T | CA | -1.1 | -34.8 | -36.3 | 45 A |
| 172 | T | C | 0.3 | -34.5 | -36.6 | 52 A |
| 172 | T | O | 1.1 | -35.4 | -36.6 | 52 A |
| 172 | T | CB | -1.5 | -34.3 | -34.9 | 54 A |
| 172 | T | OG1 | -1.2 | -32.9 | -34.8 | 57 A |
| 172 | T | CG2 | -0.7 | -35.1 | -33.8 | 44 A |
| 173 | K | N | 0.6 | -33.3 | -36.7 | 52 A |
| 173 | K | CA | 2.0 | -32.8 | -36.9 | 55 A |
| 173 | K | C | 2.5 | -32.4 | -35.5 | 58 A |
| 173 | K | O | 3.8 | -32.6 | -35.2 | 58 A |
| 173 | K | CB | 2.1 | -31.6 | -37.8 | 60 A |
| 173 | K | CG | 1.9 | -30.3 | -37.0 | 92 A |
| 173 | K | CD | 1.8 | -29.1 | -38.0 | 0 A |
| 173 | K | CE | 1.8 | -27.8 | -37.2 | 0 A |
| 173 | K | NZ | 0.7 | -26.9 | -37.8 | 0 A |
| 174 | F | N | 1.6 | -31.9 | -34.6 | 50 A |
| 174 | F | CA | 2.0 | -31.5 | -33.3 | 47 A |
| 174 | F | C | 2.5 | -32.7 | -32.4 | 47 A |
| 174 | F | O | 2.2 | -33.8 | -32.7 | 49 A |
| 174 | F | CB | 0.8 | -30.9 | -32.6 | 48 A |
| 174 | F | CG | 0.5 | -29.5 | -33.1 | 50 A |
| 174 | F | CD1 | 1.3 | -28.4 | -32.8 | 54 A |
| 174 | F | CD2 | -0.6 | -29.3 | -33.9 | 50 A |
| 174 | F | CE1 | 1.0 | -27.2 | -33.3 | 55 A |
| 174 | F | CE2 | -0.9 | -28.1 | -34.5 | 55 A |
| 174 | F | CZ | -0.1 | -27.0 | -34.2 | 54 A |
| 175 | T | N | 3.3 | -32.4 | -31.5 | 42 A |
| 175 | T | CA | 3.9 | -33.5 | -30.6 | 41 A |
| 175 | T | C | 2.8 | -33.9 | -29.6 | 42 A |
| 175 | T | O | 2.1 | -33.1 | -29.0 | 41 A |
| 175 | T | CB | 5.1 | -33.1 | -29.9 | 49 A |
| 175 | T | OG1 | 6.0 | -32.5 | -30.8 | 56 A |
| 175 | T | CG2 | 5.8 | -34.3 | -29.2 | 46 A |
| 176 | I | N | 2.6 | -35.2 | -29.5 | 39 A |
| 176 | I | CA | 1.6 | -35.8 | -28.5 | 39 A |
| 176 | I | C | 2.5 | -36.2 | -27.5 | 40 A |
| 176 | I | O | 3.1 | -37.5 | -27.9 | 38 A |
| 176 | I | CB | 0.6 | -36.8 | -29.2 | 42 A |
| 176 | I | CG1 | -0.1 | -36.2 | -30.4 | 43 A |
| 176 | I | CG2 | -0.4 | -37.2 | -28.1 | 40 A |
| 176 | I | CD1 | -0.9 | -35.0 | -30.0 | 41 A |
| 177 | Y | N | 2.6 | -36.0 | -26.3 | 35 A |
| 177 | Y | CA | 3.5 | -36.6 | -25.3 | 36 A |
| 177 | Y | C | 2.7 | -37.8 | -24.7 | 36 A |
| 177 | Y | O | 1.5 | -38.0 | -24.9 | 36 A |
| 177 | Y | CB | 3.8 | -35.5 | -24.3 | 39 A |
| 177 | Y | CG | 4.7 | -34.4 | -24.9 | 42 A |
| 177 | Y | CD1 | 4.1 | -33.2 | -25.2 | 44 A |
| 177 | Y | CD2 | 6.0 | -34.6 | -25.2 | 43 A |
| 177 | Y | CE1 | 4.9 | -32.1 | -25.7 | 46 A |
| 177 | Y | CE2 | 6.8 | -33.6 | -25.8 | 44 A |
| 177 | Y | CZ | 6.2 | -32.3 | -26.0 | 55 A |
| 177 | Y | OH | 7.0 | -31.3 | -26.5 | 67 A |
| 178 | N | N | 3.5 | -38.7 | -24.0 | 31 A |
| 178 | N | CA | 2.9 | -39.9 | -23.5 | 31 A |
| 178 | N | C | 1.9 | -39.8 | -22.3 | 35 A |
| 178 | N | O | 1.1 | -40.7 | -22.0 | 37 A |
| 178 | N | CB | 4.1 | -40.8 | -23.0 | 32 A |
| 178 | N | CG | 4.8 | -41.4 | -24.2 | 47 A |
| 178 | N | OD1 | 4.2 | -42.2 | -24.9 | 42 A |
| 178 | N | ND2 | 6.0 | -40.9 | -24.5 | 41 A |
| 179 | N | N | 1.9 | -38.6 | -21.7 | 33 A |
| 179 | N | CA | 1.0 | -38.3 | -20.6 | 32 A |
| 179 | N | C | -0.2 | -37.4 | -21.1 | 36 A |
| 179 | N | O | -0.9 | -36.8 | -20.3 | 33 A |
| 179 | N | CB | 1.7 | -37.9 | -19.4 | 34 A |
| 179 | N | CG | 2.2 | -39.1 | -18.6 | 40 A |
| 179 | N | OD1 | 1.5 | -40.1 | -18.5 | 38 A |
| 179 | N | ND2 | 3.5 | -39.1 | -18.3 | 32 A |
| 180A | M | N | -0.4 | -37.5 | -22.4 | 31 A |
| 180B | M | N | -0.5 | -37.5 | -22.4 | 35 A |
| 180A | M | CA | -1.6 | -36.9 | -23.1 | 30 A |
| 180B | M | CA | -1.6 | -36.9 | -23.0 | 35 A |
| 180A | M | C | -2.2 | -38.1 | -23.8 | 33 A |
| 180B | M | C | -2.2 | -38.0 | -23.8 | 36 A |
| 180A | M | O | -1.6 | -39.1 | -24.0 | 32 A |
| 180B | M | O | -1.5 | -39.0 | -24.2 | 35 A |
| 180A | M | CB | -1.1 | -35.9 | -24.3 | 30 A |
| 180B | M | CB | -1.2 | -35.7 | -23.8 | 38 A |
| 180A | M | CG | -0.4 | -34.6 | -23.9 | 33 A |
| 180B | M | CG | -0.8 | -34.6 | -22.9 | 42 A |
| 180A | M | SD | 0.2 | -33.8 | -25.5 | 37 A |
| 180B | M | SD | -0.3 | -33.1 | -23.5 | 48 A |
| 180A | M | CE | 0.5 | -32.1 | -24.9 | 33 A |
| 180B | M | CE | -1.9 | -32.1 | -23.2 | 44 A |
| 181 | F | N | -3.5 | -38.0 | -24.0 | 32 A |
| 181 | F | CA | -4.2 | -39.1 | -24.8 | 30 A |
| 181 | F | C | -5.1 | -38.4 | -25.7 | 38 A |
| 181 | F | O | -5.3 | -37.2 | -25.7 | 34 A |
| 181 | F | CB | -4.9 | -40.0 | -23.8 | 30 A |
| 181 | F | CG | -6.1 | -39.4 | -23.1 | 29 A |
| 181 | F | CD1 | -7.4 | -39.6 | -23.6 | 30 A |
| 181 | F | CD2 | -6.0 | -38.9 | -21.8 | 25 A |
| 181 | F | CE1 | -8.5 | -39.1 | -22.9 | 29 A |

TABLE 4-continued

Coordinates of Soaked Factor IXa-Compound A Complex

| | | | | | | |
|---|---|---|---|---|---|---|
| 181 | F | CE2 | −7.1 | −38.5 | −21.1 | 28 | A |
| 181 | F | CZ | −8.3 | −38.5 | −21.6 | 29 | A |
| 182 | C | N | −5.6 | −39.2 | −26.7 | 38 | A |
| 182 | C | CA | −6.6 | −38.7 | −27.7 | 41 | A |
| 182 | C | C | −7.8 | −39.5 | −27.6 | 36 | A |
| 182 | C | O | −7.8 | −40.7 | −27.2 | 34 | A |
| 182 | C | CB | −6.0 | −39.0 | −29.1 | 45 | A |
| 182 | C | SG | −4.3 | −38.4 | −29.1 | 53 | A |
| 183 | A | N | −8.9 | −38.8 | −27.9 | 31 | A |
| 183 | A | CA | −10.2 | −39.4 | −27.8 | 31 | A |
| 183 | A | C | −11.1 | −38.7 | −28.8 | 34 | A |
| 183 | A | O | −10.9 | −37.5 | −29.2 | 34 | A |
| 183 | A | CB | −10.8 | −39.2 | −26.4 | 32 | A |
| 184 | G | N | −12.0 | −39.4 | −29.4 | 32 | A |
| 184 | G | CA | −12.9 | −38.9 | −30.4 | 33 | A |
| 184 | G | C | −13.2 | −39.9 | −31.4 | 38 | A |
| 184 | G | O | −12.9 | −41.1 | −31.3 | 37 | A |
| 184A | F | N | −13.9 | −39.4 | −32.5 | 35 | A |
| 184A | F | CA | −14.4 | −40.2 | −33.6 | 33 | A |
| 184A | F | C | −13.6 | −40.2 | −34.9 | 36 | A |
| 184A | F | O | −13.3 | −39.1 | −35.4 | 34 | A |
| 184A | F | CB | −15.8 | −39.9 | −33.8 | 35 | A |
| 184A | F | CG | −16.7 | −40.2 | −32.6 | 34 | A |
| 184A | F | CD1 | −16.9 | −39.3 | −31.7 | 37 | A |
| 184A | F | CD2 | −17.2 | −41.5 | −32.4 | 34 | A |
| 184A | F | CE1 | −17.6 | −39.5 | −30.5 | 37 | A |
| 184A | F | CE2 | −18.0 | −41.8 | −31.4 | 37 | A |
| 184A | F | CZ | −18.2 | −40.8 | −30.4 | 35 | A |
| 185 | H | N | −13.4 | −41.3 | −35.5 | 34 | A |
| 185 | H | CA | −12.8 | −41.8 | −36.8 | 34 | A |
| 185 | H | C | −13.2 | −40.5 | −37.9 | 38 | A |
| 185 | H | O | −12.3 | −39.9 | −38.6 | 39 | A |
| 185 | H | CB | −13.0 | −42.9 | −37.3 | 33 | A |
| 185 | H | CG | −12.2 | −43.3 | −38.5 | 35 | A |
| 185 | H | ND1 | −12.4 | −42.8 | −39.8 | 37 | A |
| 185 | H | CD2 | −11.1 | −44.0 | −38.6 | 35 | A |
| 185 | H | CE1 | −11.5 | −43.2 | −40.6 | 35 | A |
| 185 | H | NE2 | −10.7 | −44.0 | −40.0 | 36 | A |
| 186 | E | N | −14.5 | −40.3 | −37.9 | 34 | A |
| 186 | E | CA | −15.2 | −39.4 | −38.9 | 35 | A |
| 186 | E | C | −15.5 | −38.0 | −38.3 | 42 | A |
| 186 | E | O | −16.2 | −37.3 | −38.9 | 42 | A |
| 186 | E | CB | −16.5 | −40.1 | −39.3 | 35 | A |
| 186 | E | CG | −16.3 | −41.4 | −40.2 | 37 | A |
| 186 | E | CD | −15.5 | −41.1 | −41.4 | 51 | A |
| 186 | E | OE1 | −14.2 | −41.3 | −41.3 | 43 | A |
| 186 | E | OE2 | −16.1 | −40.6 | −42.4 | 55 | A |
| 187 | G | N | −14.9 | −37.7 | −37.1 | 40 | A |
| 187 | G | CA | −15.2 | −36.4 | −36.5 | 38 | A |
| 187 | G | C | −16.7 | −36.1 | −36.2 | 41 | A |
| 187 | G | O | −17.4 | −37.1 | −35.9 | 40 | A |
| 188 | G | N | −17.1 | −34.9 | −36.3 | 39 | A |
| 188 | G | CA | −18.5 | −34.6 | −36.0 | 38 | A |
| 188 | G | C | −18.9 | −34.4 | −34.5 | 43 | A |
| 188 | G | O | −19.9 | −33.8 | −34.2 | 44 | A |
| 188A | R | N | −18.1 | −35.0 | −33.6 | 38 | A |
| 188A | R | CA | −18.4 | −34.9 | −32.2 | 36 | A |
| 188A | R | C | −17.1 | −34.7 | −31.5 | 39 | A |
| 188A | R | O | −16.1 | −35.5 | −31.7 | 38 | A |
| 188A | R | CB | −19.1 | −36.1 | −31.6 | 39 | A |
| 188A | R | CG | −20.2 | −36.7 | −32.5 | 41 | A |
| 188A | R | CD | −21.0 | −37.8 | −31.8 | 51 | A |
| 188A | R | NE | −22.0 | −38.5 | −32.6 | 64 | A |
| 188A | R | CZ | −22.4 | −39.7 | −32.3 | 75 | A |
| 188A | R | NH1 | −22.0 | −40.3 | −31.2 | 54 | A |
| 188A | R | NH2 | −23.3 | −40.3 | −33.1 | 58 | A |
| 189 | D | N | −17.0 | −33.7 | −30.6 | 37 | A |
| 189 | D | CA | −15.7 | −33.5 | −30.0 | 36 | A |
| 189 | D | C | −15.9 | −32.4 | −28.9 | 41 | A |
| 189 | D | O | −16.9 | −31.7 | −28.9 | 41 | A |
| 189 | D | CB | −14.8 | −32.9 | −31.1 | 36 | A |
| 189 | D | CG | −13.3 | −33.0 | −30.8 | 42 | A |
| 189 | D | OD1 | −12.9 | −33.4 | −29.7 | 39 | A |
| 189 | D | OD2 | −12.5 | −32.4 | −31.7 | 38 | A |
| 190 | S | N | −14.9 | −32.2 | −28.1 | 39 | A |
| 190 | S | CA | −14.8 | −31.1 | −27.2 | 38 | A |
| 190 | S | C | −14.4 | −29.9 | −28.1 | 41 | A |
| 190 | S | O | −14.0 | −30.1 | −29.3 | 38 | A |
| 190 | S | CB | −13.6 | −31.4 | −26.3 | 36 | A |
| 190 | S | OG | −14.0 | −32.1 | −25.2 | 52 | A |
| 191 | C | N | −14.4 | −28.7 | −27.6 | 41 | A |
| 191 | C | CA | −14.0 | −27.5 | −28.4 | 40 | A |
| 191 | C | C | −13.7 | −26.4 | −27.5 | 42 | A |
| 191 | C | O | −13.7 | −26.4 | −26.3 | 41 | A |
| 191 | C | CB | −15.2 | −27.2 | −29.3 | 42 | A |
| 191 | C | SG | −14.8 | −26.1 | −30.8 | 46 | A |
| 192 | Q | N | −13.2 | −25.3 | −28.2 | 40 | A |
| 192 | Q | CA | −12.9 | −24.0 | −27.5 | 39 | A |
| 192 | Q | C | −13.9 | −23.7 | −26.4 | 37 | A |
| 192 | Q | O | −15.1 | −23.7 | −26.7 | 37 | A |
| 192 | Q | CB | −12.8 | −22.9 | −28.6 | 42 | A |
| 192 | Q | CG | −12.6 | −21.5 | −27.9 | 59 | A |
| 192 | Q | CD | −11.2 | −21.2 | −27.8 | 92 | A |
| 192 | Q | OE1 | −10.6 | −20.6 | −28.7 | 98 | A |
| 192 | Q | NE2 | −10.5 | −21.8 | −26.8 | 83 | A |
| 193 | G | N | −13.4 | −23.4 | −25.2 | 34 | A |
| 193 | G | CA | −14.3 | −23.0 | −24.2 | 34 | A |
| 193 | G | C | −14.5 | −24.2 | −23.2 | 39 | A |
| 193 | G | O | −14.9 | −24.1 | −22.1 | 37 | A |
| 194 | D | N | −14.3 | −25.5 | −23.7 | 37 | A |
| 194 | D | CA | −14.4 | −26.7 | −22.9 | 36 | A |
| 194 | D | C | −13.1 | −27.0 | −22.1 | 38 | A |
| 194 | D | O | −13.1 | −27.8 | −21.2 | 37 | A |
| 194 | D | CB | −14.8 | −27.9 | −23.7 | 35 | A |
| 194 | D | CG | −16.1 | −27.8 | −24.3 | 37 | A |
| 194 | D | OD1 | −17.1 | −27.4 | −23.6 | 36 | A |
| 194 | D | OD2 | −16.3 | −28.2 | −25.5 | 38 | A |
| 195 | S | N | −12.0 | −26.4 | −22.7 | 33 | A |
| 195 | S | CA | −10.7 | −26.7 | −22.1 | 33 | A |
| 195 | S | C | −10.7 | −26.6 | −20.6 | 36 | A |
| 195 | S | O | −11.4 | −25.7 | −20.1 | 34 | A |
| 195 | S | CB | −9.6 | −25.8 | −22.7 | 35 | A |
| 195 | S | OG | −9.7 | −25.8 | −24.1 | 48 | A |
| 196 | G | N | −9.9 | −27.4 | −19.9 | 31 | A |
| 196 | G | CA | −9.9 | −27.4 | −18.5 | 32 | A |
| 196 | G | C | −10.9 | −28.2 | −17.8 | 35 | A |
| 196 | G | O | −10.9 | −28.6 | −16.6 | 34 | A |
| 197 | G | N | −12.0 | −28.5 | −18.6 | 31 | A |
| 197 | G | CA | −13.1 | −29.3 | −18.1 | 30 | A |
| 197 | G | C | −12.8 | −30.8 | −18.0 | 34 | A |
| 197 | G | O | −11.6 | −31.3 | −18.3 | 32 | A |
| 198 | P | N | −13.7 | −31.6 | −17.5 | 30 | A |
| 198 | P | CA | −13.5 | −33.0 | −17.2 | 30 | A |
| 198 | P | C | −13.7 | −34.0 | −18.3 | 33 | A |
| 198 | P | O | −14.5 | −33.9 | −19.1 | 32 | A |
| 198 | P | CB | −14.5 | −33.3 | −16.1 | 31 | A |
| 198 | P | CG | −15.7 | −32.4 | −16.6 | 36 | A |
| 198 | P | CD | −15.0 | −31.1 | −17.0 | 31 | A |
| 199 | H | N | −12.8 | −35.0 | −18.2 | 29 | A |
| 199 | H | CA | −13.0 | −36.3 | −19.0 | 28 | A |
| 199 | H | C | −13.1 | −37.7 | −17.9 | 30 | A |
| 199 | H | O | −12.2 | −37.5 | −17.0 | 28 | A |
| 199 | H | CB | −11.8 | −36.6 | −19.9 | 29 | A |
| 199 | H | CG | −11.9 | −37.9 | −20.5 | 32 | A |
| 199 | H | ND1 | −11.6 | −39.1 | −19.8 | 32 | A |
| 199 | H | CD2 | −12.1 | −38.3 | −21.8 | 32 | A |
| 199 | H | CE1 | −11.6 | −40.1 | −20.7 | 32 | A |
| 199 | H | NE2 | −12.0 | −39.6 | −21.9 | 32 | A |
| 200 | V | N | −14.3 | −37.9 | −17.7 | 30 | A |
| 200 | V | CA | −14.5 | −38.8 | −16.6 | 32 | A |
| 200 | V | C | −14.9 | −40.2 | −17.1 | 38 | A |
| 200 | V | O | −15.5 | −40.3 | −18.2 | 36 | A |
| 200 | V | CB | −15.6 | −38.3 | −15.6 | 34 | A |
| 200 | V | CG1 | −15.3 | −36.8 | −15.1 | 32 | A |
| 200 | V | CG2 | −16.9 | −38.4 | −16.3 | 33 | A |
| 201 | T | N | −14.6 | −41.2 | −16.3 | 35 | A |
| 201 | T | CA | −14.9 | −42.6 | −16.6 | 33 | A |
| 201 | T | C | −15.8 | −43.1 | −15.5 | 35 | A |
| 201 | T | O | −15.5 | −43.0 | −14.4 | 35 | A |
| 201 | T | CB | −13.6 | −43.4 | −16.8 | 35 | A |
| 201 | T | OG1 | −12.8 | −42.9 | −17.8 | 31 | A |
| 201 | T | CG2 | −14.0 | −44.9 | −17.0 | 28 | A |
| 202 | E | N | −17.0 | −43.7 | −15.9 | 35 | A |
| 202 | E | CA | −17.9 | −44.2 | −14.9 | 37 | A |
| 202 | E | C | −17.5 | −45.6 | −14.6 | 42 | A |
| 202 | E | O | −17.4 | −46.5 | −15.4 | 40 | A |

TABLE 4-continued

Coordinates of Soaked Factor IXa-Compound A Complex

| | | | | | | |
|---|---|---|---|---|---|---|
| 202 | E | CB | −19.3 | −44.3 | −15.6 | 37 | A |
| 202 | E | CG | −19.9 | −42.9 | −15.9 | 52 | A |
| 202 | E | CD | −21.3 | −43.1 | −16.7 | 81 | A |
| 202 | E | OE1 | −21.5 | −44.1 | −17.4 | 81 | A |
| 202 | E | OE2 | −22.1 | −42.1 | −16.6 | 66 | A |
| 203 | V | N | −17.3 | −45.9 | −13.3 | 39 | A |
| 203 | V | CA | −16.9 | −47.2 | −12.8 | 39 | A |
| 203 | V | C | −18.0 | −47.7 | −11.9 | 48 | A |
| 203 | V | O | −18.2 | −47.2 | −10.8 | 46 | A |
| 203 | V | CB | −15.6 | −47.1 | −12.0 | 40 | A |
| 203 | V | CG1 | −15.2 | −48.5 | −11.5 | 41 | A |
| 203 | V | CG2 | −14.6 | −46.5 | −12.9 | 40 | A |
| 204 | E | N | −18.9 | −48.6 | −12.4 | 49 | A |
| 204 | E | CA | −20.0 | −49.1 | −11.7 | 50 | A |
| 204 | E | C | −20.8 | −48.0 | −11.1 | 53 | A |
| 204 | E | O | −21.1 | −48.0 | −9.9 | 53 | A |
| 204 | E | CB | −19.6 | −50.0 | −10.6 | 52 | A |
| 204 | E | CG | −18.9 | −51.3 | −11.1 | 69 | A |
| 204 | E | CD | −20.0 | −52.4 | −11.2 | 99 | A |
| 204 | E | OE1 | −20.0 | −53.3 | −10.3 | 0 | A |
| 204 | E | OE2 | −20.9 | −52.3 | −12.1 | 95 | A |
| 205 | G | N | −21.2 | −46.9 | −11.8 | 49 | A |
| 205 | G | CA | −22.0 | −45.9 | −11.3 | 48 | A |
| 205 | G | C | −21.3 | −44.8 | −10.5 | 49 | A |
| 205 | G | O | −21.9 | −43.8 | −10.0 | 49 | A |
| 206 | T | N | −19.9 | −44.8 | −10.4 | 42 | A |
| 206 | T | CA | −19.1 | −43.8 | −9.8 | 41 | A |
| 206 | T | C | −18.2 | −43.2 | −10.8 | 42 | A |
| 206 | T | O | −17.4 | −44.0 | −11.4 | 37 | A |
| 206 | T | CB | −18.4 | −44.3 | −8.5 | 43 | A |
| 206 | T | OG1 | −19.4 | −44.8 | −7.6 | 49 | A |
| 206 | T | CG2 | −17.6 | −43.3 | −7.8 | 40 | A |
| 207 | S | N | −18.2 | −41.9 | −11.0 | 37 | A |
| 207 | S | CA | −17.4 | −41.3 | −12.0 | 33 | A |
| 207 | S | C | −16.0 | −40.9 | −11.4 | 36 | A |
| 207 | S | O | −16.0 | −40.4 | −10.3 | 33 | A |
| 207 | S | CB | −18.0 | −40.1 | −12.6 | 33 | A |
| 207 | S | OG | −19.1 | −40.5 | −13.4 | 37 | A |
| 208 | F | N | −15.0 | −41.2 | −12.1 | 32 | A |
| 208 | F | CA | −13.6 | −40.8 | −11.7 | 31 | A |
| 208 | F | C | −13.0 | −39.9 | −12.8 | 33 | A |
| 208 | F | O | −13.3 | −40.1 | −14.0 | 31 | A |
| 208 | F | CB | −12.8 | −42.1 | −11.6 | 32 | A |
| 208 | F | CG | −13.0 | −42.9 | −10.4 | 32 | A |
| 208 | F | CD1 | −14.0 | −43.8 | −10.3 | 35 | A |
| 208 | F | CD2 | −12.2 | −42.7 | −9.3 | 32 | A |
| 208 | F | CE1 | −14.3 | −44.5 | −9.1 | 36 | A |
| 208 | F | CE2 | −12.4 | −43.4 | −8.1 | 36 | A |
| 208 | F | CZ | −13.4 | −44.3 | −8.0 | 33 | A |
| 209 | L | N | −12.2 | −39.0 | −12.4 | 30 | A |
| 209 | L | CA | −11.6 | −38.1 | −13.3 | 30 | A |
| 209 | L | C | −10.4 | −38.8 | −14.0 | 33 | A |
| 209 | L | O | −9.4 | −39.2 | −13.3 | 31 | A |
| 209 | L | CB | −11.0 | −36.9 | −12.6 | 27 | A |
| 209 | L | CG | −10.5 | −35.7 | −13.4 | 29 | A |
| 209 | L | CD1 | −11.7 | −35.1 | −14.2 | 27 | A |
| 209 | L | CD2 | −9.9 | −34.6 | −12.5 | 24 | A |
| 210 | T | N | −10.5 | −39.0 | −15.3 | 32 | A |
| 210 | T | CA | −9.5 | −39.7 | −16.1 | 31 | A |
| 210 | T | C | −8.6 | −38.7 | −17.0 | 32 | A |
| 210 | T | O | −7.5 | −39.0 | −17.4 | 32 | A |
| 210 | T | CB | −10.0 | −40.9 | −16.9 | 29 | A |
| 210 | T | OG1 | −11.3 | −40.6 | −17.5 | 29 | A |
| 210 | T | CG2 | −10.2 | −42.0 | −15.9 | 26 | A |
| 211 | G | N | −9.2 | −37.5 | −17.3 | 31 | A |
| 211 | G | CA | −8.5 | −36.6 | −18.1 | 30 | A |
| 211 | G | C | −8.9 | −35.1 | −17.9 | 34 | A |
| 211 | G | O | −9.9 | −34.8 | −17.4 | 31 | A |
| 212 | I | N | −8.0 | −34.2 | −18.4 | 31 | A |
| 212 | I | CA | −8.4 | −32.8 | −18.5 | 30 | A |
| 212 | I | C | −8.5 | −32.4 | −20.0 | 32 | A |
| 212 | I | O | −7.6 | −32.7 | −20.8 | 28 | A |
| 212 | I | CB | −7.3 | −31.9 | −17.8 | 33 | A |
| 212 | I | CG1 | −6.9 | −32.3 | −16.4 | 32 | A |
| 212 | I | CG2 | −7.9 | −30.4 | −17.8 | 32 | A |
| 212 | I | CD1 | −8.0 | −32.4 | −15.4 | 30 | A |
| 213 | I | N | −9.7 | −31.8 | −20.3 | 30 | A |
| 213 | I | CA | −9.8 | −31.4 | −21.7 | 31 | A |
| 213 | I | C | −8.7 | −30.4 | −22.0 | 35 | A |
| 213 | I | O | −8.5 | −29.4 | −21.2 | 33 | A |
| 213 | I | CB | −11.2 | −30.7 | −22.0 | 35 | A |
| 213 | I | CG1 | −12.3 | −31.8 | −21.5 | 34 | A |
| 213 | I | CG2 | −11.4 | −30.3 | −23.5 | 37 | A |
| 213 | I | CD1 | −13.7 | −31.2 | −21.5 | 35 | A |
| 214 | S | N | −7.9 | −30.6 | −23.0 | 32 | A |
| 214 | S | CA | −6.8 | −29.8 | −23.3 | 32 | A |
| 214 | S | C | −6.8 | −28.9 | −24.6 | 39 | A |
| 214 | S | O | −6.8 | −27.7 | −24.5 | 37 | A |
| 214 | S | CB | −5.5 | −30.5 | −23.1 | 32 | A |
| 214 | S | OG | −4.4 | −29.6 | −23.1 | 39 | A |
| 215 | W | N | −6.7 | −29.6 | −25.7 | 35 | A |
| 215 | W | CA | −6.7 | −28.9 | −27.0 | 35 | A |
| 215 | W | C | −7.0 | −29.8 | −28.2 | 40 | A |
| 215 | W | O | −7.2 | −31.0 | −28.0 | 36 | A |
| 215 | W | CB | −5.3 | −28.2 | −27.2 | 33 | A |
| 215 | W | CG | −4.2 | −29.3 | −27.3 | 34 | A |
| 215 | W | CD1 | −3.5 | −29.8 | −26.3 | 36 | A |
| 215 | W | CD2 | −3.6 | −29.9 | −28.5 | 35 | A |
| 215 | W | NE1 | −2.5 | −30.6 | −26.7 | 37 | A |
| 215 | W | CE2 | −2.5 | −30.7 | −28.1 | 39 | A |
| 215 | W | CE3 | −3.8 | −29.7 | −29.9 | 36 | A |
| 215 | W | CZ2 | −1.7 | −31.4 | −29.0 | 39 | A |
| 215 | W | CZ3 | −3.1 | −30.5 | −30.8 | 38 | A |
| 215 | W | CH2 | −2.0 | −31.3 | −30.3 | 39 | A |
| 216 | G | N | −7.0 | −29.3 | −29.4 | 38 | A |
| 216 | G | CA | −7.3 | −30.0 | −30.6 | 37 | A |
| 216 | G | C | −7.1 | −29.1 | −31.8 | 41 | A |
| 216 | G | O | −7.1 | −27.9 | −31.6 | 40 | A |
| 217 | E | N | −6.9 | −29.6 | −33.0 | 39 | A |
| 217 | E | CA | −6.7 | −28.7 | −34.2 | 39 | A |
| 217 | E | C | −8.1 | −28.5 | −34.7 | 41 | A |
| 217 | E | O | −8.8 | −29.4 | −35.3 | 40 | A |
| 217 | E | CB | −5.9 | −29.4 | −35.2 | 41 | A |
| 217 | E | CG | −4.5 | −29.7 | −34.7 | 44 | A |
| 217 | E | CD | −3.6 | −30.6 | −35.7 | 67 | A |
| 217 | E | OE1 | −3.1 | −31.7 | −35.3 | 50 | A |
| 217 | E | OE2 | −3.5 | −30.2 | −36.9 | 53 | A |
| 219 | E | N | −8.7 | −27.3 | −34.3 | 38 | A |
| 219 | E | CA | −10.1 | −27.0 | −34.5 | 40 | A |
| 219 | E | C | −10.9 | −28.1 | −33.8 | 45 | A |
| 219 | E | O | −10.4 | −28.7 | −32.8 | 46 | A |
| 219 | E | CB | −10.6 | −27.0 | −36.0 | 42 | A |
| 219 | E | CG | −9.7 | −26.2 | −36.9 | 57 | A |
| 219 | E | CD | −9.7 | −26.8 | −38.4 | 95 | A |
| 219 | E | OE1 | −9.0 | −27.8 | −38.6 | 0 | A |
| 219 | E | OE2 | −10.6 | −26.3 | −39.2 | 80 | A |
| 220 | C | N | −12.2 | −28.3 | −34.2 | 42 | A |
| 220 | C | CA | −13.0 | −29.2 | −33.4 | 42 | A |
| 220 | C | C | −13.8 | −30.1 | −34.4 | 45 | A |
| 220 | C | O | −14.2 | −29.6 | −35.5 | 41 | A |
| 220 | C | CB | −14.1 | −28.4 | −32.6 | 42 | A |
| 220 | C | SG | −13.3 | −27.1 | −31.7 | 47 | A |
| 221 | A | N | −13.9 | −31.3 | −34.0 | 40 | A |
| 221 | A | CA | −14.8 | −32.3 | −34.7 | 38 | A |
| 221 | A | C | −14.5 | −32.6 | −36.2 | 40 | A |
| 221 | A | O | −15.3 | −33.1 | −36.9 | 39 | A |
| 221 | A | CB | −16.2 | −31.9 | −34.6 | 38 | A |
| 221A | M | N | −13.2 | −32.3 | −36.6 | 39 | A |
| 221A | M | CA | −12.8 | −32.6 | −38.0 | 40 | A |
| 221A | M | C | −12.4 | −34.0 | −38.2 | 43 | A |
| 221A | M | O | −11.6 | −34.6 | −37.4 | 43 | A |
| 221A | M | CB | −11.5 | −31.8 | −38.3 | 43 | A |
| 221A | M | CG | −11.7 | −30.2 | −38.3 | 50 | A |
| 221A | M | SD | −13.2 | −29.6 | −39.2 | 57 | A |
| 221A | M | CE | −13.8 | −28.1 | −38.2 | 53 | A |
| 222 | K | N | −12.9 | −34.6 | −39.2 | 38 | A |
| 222 | K | CA | −12.5 | −36.0 | −39.6 | 37 | A |
| 222 | K | C | −11.0 | −36.1 | −39.7 | 41 | A |
| 222 | K | O | −10.4 | −35.3 | −40.3 | 42 | A |
| 222 | K | CB | −13.1 | −36.4 | −41.0 | 40 | A |
| 222 | K | CG | −12.4 | −37.6 | −41.6 | 36 | A |
| 222 | K | CD | −13.1 | −38.2 | −42.7 | 44 | A |
| 222 | K | CE | −12.3 | −39.4 | −43.3 | 40 | A |
| 222 | K | NZ | −13.2 | −40.5 | −43.9 | 61 | A |
| 223 | G | N | −10.4 | −37.1 | −39.0 | 37 | A |
| 223 | G | CA | −9.0 | −37.3 | −39.0 | 35 | A |

TABLE 4-continued

Coordinates of Soaked Factor IXa-Compound A Complex

| | | | | | | |
|---|---|---|---|---|---|---|
| 223 | G | C | −8.2 | −36.5 | −37.9 | 40 | A |
| 223 | G | O | −7.0 | −36.7 | −37.8 | 38 | A |
| 224 | K | N | −8.9 | −35.8 | −37.1 | 34 | A |
| 224 | K | CA | −8.3 | −35.1 | −35.9 | 34 | A |
| 224 | K | C | −9.0 | −35.6 | −34.7 | 39 | A |
| 224 | K | O | −10.2 | −36.0 | −34.8 | 40 | A |
| 224 | K | CB | −8.5 | −33.6 | −36.0 | 36 | A |
| 224 | K | CG | −7.8 | −32.9 | −37.3 | 38 | A |
| 224 | K | CD | −6.3 | −33.0 | −37.1 | 41 | A |
| 224 | K | CE | −5.5 | −32.7 | −38.4 | 54 | A |
| 224 | K | NZ | −4.1 | −32.9 | −38.2 | 49 | A |
| 225 | Y | N | −8.4 | −35.6 | −33.5 | 35 | A |
| 225 | Y | CA | −9.0 | −36.0 | −32.3 | 35 | A |
| 225 | Y | C | −8.8 | −35.0 | −31.2 | 37 | A |
| 225 | Y | O | −8.0 | −34.1 | −31.3 | 36 | A |
| 225 | Y | CB | −8.2 | −37.3 | −31.9 | 34 | A |
| 225 | Y | CG | −8.4 | −38.4 | −32.8 | 33 | A |
| 225 | Y | CD1 | −9.7 | −39.1 | −32.9 | 33 | A |
| 225 | Y | CD2 | −7.5 | −38.8 | −33.8 | 33 | A |
| 225 | Y | CE1 | −9.9 | −40.1 | −33.8 | 33 | A |
| 225 | Y | CE2 | −7.8 | −39.8 | −34.8 | 34 | A |
| 225 | Y | CZ | −9.0 | −40.4 | −34.7 | 36 | A |
| 225 | Y | OH | −9.3 | −41.5 | −35.6 | 38 | A |
| 226 | G | N | −9.6 | −35.1 | −30.1 | 35 | A |
| 226 | G | CA | −9.3 | −34.2 | −29.0 | 34 | A |
| 226 | G | C | −8.1 | −34.7 | −28.3 | 35 | A |
| 226 | G | O | −7.9 | −35.9 | −28.2 | 34 | A |
| 227 | I | N | −7.3 | −33.8 | −27.7 | 32 | A |
| 227 | I | CA | −6.1 | −34.2 | −26.9 | 30 | A |
| 227 | I | C | −6.4 | −33.8 | −25.5 | 35 | A |
| 227 | I | O | −7.0 | −32.7 | −25.2 | 34 | A |
| 227 | I | CB | −4.9 | −33.5 | −27.5 | 33 | A |
| 227 | I | CG1 | −4.8 | −33.6 | −29.0 | 33 | A |
| 227 | I | CG2 | −3.6 | −34.0 | −26.7 | 33 | A |
| 227 | I | CD1 | −4.5 | −35.0 | −29.6 | 35 | A |
| 228 | Y | N | −6.1 | −34.7 | −24.6 | 31 | A |
| 228 | Y | CA | −6.4 | −34.6 | −23.2 | 29 | A |
| 228 | Y | C | −5.2 | −34.9 | −22.4 | 32 | A |
| 228 | Y | O | −4.3 | −35.6 | −22.8 | 30 | A |
| 228 | Y | CB | −7.5 | −35.6 | −22.8 | 29 | A |
| 228 | Y | CG | −8.8 | −35.5 | −23.5 | 29 | A |
| 228 | Y | CD1 | −8.9 | −35.9 | −24.9 | 30 | A |
| 228 | Y | CD2 | −9.9 | −34.9 | −22.9 | 30 | A |
| 228 | Y | CE1 | −10.1 | −35.7 | −25.6 | 29 | A |
| 228 | Y | CE2 | −11.0 | −34.6 | −23.6 | 30 | A |
| 228 | Y | CZ | −11.2 | −35.0 | −24.9 | 38 | A |
| 228 | Y | OH | −12.4 | −34.7 | −25.6 | 34 | A |
| 229 | T | N | −5.1 | −34.2 | −21.2 | 30 | A |
| 229 | T | CA | −4.1 | −34.5 | −20.2 | 30 | A |
| 229 | T | C | −4.5 | −35.8 | −19.4 | 33 | A |
| 229 | T | O | −5.6 | −35.9 | −18.9 | 31 | A |
| 229 | T | CB | −4.0 | −33.3 | −19.3 | 35 | A |
| 229 | T | OG1 | −3.6 | −32.2 | −20.1 | 34 | A |
| 229 | T | CG2 | −2.9 | −33.5 | −18.1 | 33 | A |
| 230 | K | N | −3.5 | −36.7 | −19.2 | 31 | A |
| 230 | K | CA | −3.8 | −37.9 | −18.4 | 30 | A |
| 230 | K | C | −3.8 | −37.5 | −16.9 | 31 | A |
| 230 | K | O | −2.8 | −37.0 | −16.5 | 30 | A |
| 230 | K | CB | −2.8 | −39.0 | −18.7 | 30 | A |
| 230 | K | CG | −2.9 | −39.7 | −20.1 | 32 | A |
| 230 | K | CD | −1.9 | −40.9 | −20.1 | 34 | A |
| 230 | K | CE | −1.8 | −41.5 | −21.5 | 34 | A |
| 230 | K | NZ | −0.8 | −42.5 | −21.5 | 37 | A |
| 231 | V | N | −4.9 | −37.6 | −16.2 | 30 | A |
| 231 | V | CA | −4.9 | −37.2 | −14.8 | 29 | A |
| 231 | V | C | −4.0 | −38.2 | −14.0 | 34 | A |
| 231 | V | O | −3.5 | −37.8 | −13.0 | 33 | A |
| 231 | V | CB | −6.4 | −37.2 | −14.3 | 33 | A |
| 231 | V | CG1 | −6.4 | −37.1 | −12.8 | 34 | A |
| 231 | V | CG2 | −7.1 | −36.0 | −15.0 | 32 | A |
| 232 | S | N | −3.8 | −39.4 | −14.5 | 31 | A |
| 232 | S | CA | −3.0 | −40.4 | −13.8 | 31 | A |
| 232 | S | C | −1.6 | −39.9 | −13.5 | 34 | A |
| 232 | S | O | −1.0 | −40.2 | −12.4 | 34 | A |
| 232 | S | CB | −2.8 | −41.7 | −14.5 | 30 | A |
| 232 | S | OG | −2.1 | −41.5 | −15.8 | 34 | A |
| 233 | R | N | −1.1 | −39.1 | −14.4 | 30 | A |
| 233 | R | CA | 0.3 | −38.5 | −14.2 | 29 | A |
| 233 | R | C | 0.4 | −37.5 | −13.1 | 33 | A |
| 233 | R | O | 1.5 | −37.2 | −12.6 | 31 | A |
| 233 | R | CB | 0.6 | −37.8 | −15.6 | 27 | A |
| 233 | R | CG | 1.8 | −36.8 | −15.6 | 29 | A |
| 233 | R | CD | 3.2 | −37.5 | −15.2 | 29 | A |
| 233 | R | NE | 4.2 | −36.5 | −15.4 | 33 | A |
| 233 | R | CZ | 4.6 | −35.8 | −14.5 | 43 | A |
| 233 | R | NH1 | 3.9 | −35.5 | −13.4 | 32 | A |
| 233 | R | NH2 | 5.6 | −34.7 | −14.7 | 32 | A |
| 234 | Y | N | −0.7 | −37.0 | −12.6 | 29 | A |
| 234 | Y | CA | −0.7 | −35.9 | −11.6 | 29 | A |
| 234 | Y | C | −1.5 | −36.1 | −10.3 | 34 | A |
| 234 | Y | O | −1.6 | −35.2 | −9.5 | 33 | A |
| 234 | Y | CB | −1.4 | −34.6 | −12.3 | 29 | A |
| 234 | Y | CG | −0.6 | −34.2 | −13.6 | 28 | A |
| 234 | Y | CD1 | 0.6 | −33.5 | −13.4 | 30 | A |
| 234 | Y | CD2 | −1.0 | −34.5 | −14.8 | 28 | A |
| 234 | Y | CE1 | 1.4 | −33.2 | −14.5 | 35 | A |
| 234 | Y | CE2 | −0.3 | −34.1 | −16.0 | 28 | A |
| 234 | Y | CZ | 0.9 | −33.5 | −15.8 | 32 | A |
| 234 | Y | OH | 1.7 | −33.1 | −16.9 | 37 | A |
| 235 | V | N | −1.9 | −37.4 | −10.2 | 33 | A |
| 235 | V | CA | −2.7 | −37.7 | −8.9 | 35 | A |
| 235 | V | C | −2.0 | −37.3 | −7.6 | 38 | A |
| 235 | V | O | −2.6 | −36.7 | −6.8 | 39 | A |
| 235 | V | CB | −3.2 | −39.2 | −9.0 | 39 | A |
| 235 | V | CG1 | −3.9 | −39.5 | −7.7 | 41 | A |
| 235 | V | CG2 | −4.1 | −39.3 | −10.1 | 37 | A |
| 236 | N | N | −0.7 | −37.7 | −7.4 | 35 | A |
| 236 | N | CA | −0.0 | −37.4 | −6.1 | 36 | A |
| 236 | N | C | −0.1 | −35.9 | −5.9 | 39 | A |
| 236 | N | O | −0.4 | −35.4 | −4.8 | 37 | A |
| 236 | N | CB | 1.4 | −37.9 | −6.0 | 36 | A |
| 236 | N | CG | 2.3 | −37.3 | −4.8 | 62 | A |
| 236 | N | OD1 | 2.7 | −36.1 | −4.8 | 50 | A |
| 236 | N | ND2 | 2.7 | −38.2 | −3.9 | 50 | A |
| 237 | W | N | 0.3 | −35.1 | −7.0 | 34 | A |
| 237 | W | CA | 0.3 | −33.6 | −6.8 | 32 | A |
| 237 | W | C | −1.1 | −33.1 | −6.5 | 33 | A |
| 237 | W | O | −1.2 | −32.2 | −5.6 | 32 | A |
| 237 | W | CB | 0.8 | −33.0 | −8.2 | 31 | A |
| 237 | W | CG | 0.7 | −31.5 | −8.3 | 30 | A |
| 237 | W | CD1 | 1.6 | −30.6 | −7.8 | 33 | A |
| 237 | W | CD2 | −0.2 | −30.8 | −9.1 | 29 | A |
| 237 | W | NE1 | 1.2 | −29.3 | −8.2 | 32 | A |
| 237 | W | CE2 | 0.2 | −29.4 | −9.0 | 32 | A |
| 237 | W | CE3 | −1.2 | −31.2 | −9.9 | 30 | A |
| 237 | W | CZ2 | −0.5 | −28.4 | −9.7 | 31 | A |
| 237 | W | CZ3 | −2.0 | −30.2 | −10.6 | 31 | A |
| 237 | W | CH2 | −1.6 | −28.8 | −10.5 | 31 | A |
| 238 | I | N | −2.1 | −33.6 | −7.2 | 29 | A |
| 238 | I | CA | −3.5 | −33.1 | −6.9 | 30 | A |
| 238 | I | C | −3.9 | −33.3 | −5.4 | 36 | A |
| 238 | I | O | −4.3 | −32.4 | −4.7 | 33 | A |
| 238 | I | CB | −4.5 | −33.7 | −7.8 | 31 | A |
| 238 | I | CG1 | −4.3 | −33.3 | −9.3 | 31 | A |
| 238 | I | CG2 | −5.9 | −33.3 | −7.4 | 30 | A |
| 238 | I | CD1 | −5.2 | −34.1 | −10.3 | 32 | A |
| 239 | K | N | −3.7 | −34.6 | −4.9 | 32 | A |
| 239 | K | CA | −4.1 | −34.9 | −3.6 | 33 | A |
| 239 | K | C | −3.2 | −34.2 | −2.5 | 40 | A |
| 239 | K | O | −3.8 | −33.7 | −1.5 | 41 | A |
| 239 | K | CB | −4.0 | −36.4 | −3.4 | 35 | A |
| 239 | K | CG | −5.1 | −37.1 | −4.3 | 48 | A |
| 239 | K | CD | −5.4 | −38.5 | −3.9 | 52 | A |
| 239 | K | CE | −6.5 | −39.2 | −4.7 | 47 | A |
| 239 | K | NZ | −7.8 | −38.5 | −4.5 | 49 | A |
| 240 | E | N | −2.0 | −33.9 | −2.9 | 35 | A |
| 240 | E | CA | −1.1 | −33.2 | −2.0 | 34 | A |
| 240 | E | C | −1.5 | −31.7 | −1.9 | 42 | A |
| 240 | E | O | −1.6 | −31.2 | −0.8 | 41 | A |
| 240 | E | CB | 0.4 | −33.4 | −2.3 | 35 | A |
| 240 | E | CG | 1.3 | −32.3 | −1.8 | 42 | A |
| 240 | E | CD | 1.5 | −32.4 | −0.4 | 57 | A |
| 240 | E | OE1 | 1.2 | −33.4 | 0.2 | 61 | A |
| 240 | E | OE2 | 2.0 | −31.4 | 0.3 | 62 | A |
| 241 | K | N | −1.7 | −31.1 | −3.0 | 37 | A |
| 241 | K | CA | −2.0 | −29.6 | −3.0 | 37 | A |

TABLE 4-continued

Coordinates of Soaked Factor IXa-Compound A Complex

| | | | | | | |
|---|---|---|---|---|---|---|
| 241 | K | C | −3.4 | −29.3 | −2.5 | 39 | A |
| 241 | K | O | −3.6 | −28.2 | −2.0 | 38 | A |
| 241 | K | CB | −1.8 | −29.0 | −4.4 | 38 | A |
| 241 | K | CG | −0.4 | −29.0 | −4.9 | 47 | A |
| 241 | K | CD | 0.6 | −28.4 | −3.9 | 58 | A |
| 241 | K | CE | 2.0 | −29.0 | −4.1 | 75 | A |
| 241 | K | NZ | 3.1 | −28.0 | −4.2 | 78 | A |
| 242 | T | N | −4.3 | −30.2 | −2.6 | 37 | A |
| 242 | T | CA | −5.7 | −30.0 | −2.3 | 36 | A |
| 242 | T | C | −6.2 | −30.5 | −0.9 | 40 | A |
| 242 | T | O | −7.3 | −30.5 | −0.5 | 41 | A |
| 242 | T | CB | −6.7 | −30.5 | −3.3 | 35 | A |
| 242 | T | OG1 | −6.6 | −31.9 | −3.4 | 31 | A |
| 242 | T | CG2 | −6.4 | −29.8 | −4.7 | 32 | A |
| 243 | K | N | −5.2 | −31.1 | −0.2 | 41 | A |
| 243 | K | CA | −5.5 | −31.7 | 1.2 | 43 | A |
| 243 | K | C | −6.2 | −30.6 | 2.0 | 47 | A |
| 243 | K | O | −5.7 | −29.5 | 2.0 | 46 | A |
| 243 | K | CB | −4.1 | −32.0 | 1.9 | 47 | A |
| 243 | K | CG | −3.8 | −33.5 | 2.0 | 54 | A |
| 243 | K | CD | −2.3 | −33.7 | 2.0 | 54 | A |
| 243 | K | CE | −1.8 | −35.1 | 2.4 | 64 | A |
| 243 | K | NZ | −2.3 | −36.1 | 1.4 | 81 | A |
| 244 | L | N | −7.3 | −31.0 | 2.6 | 46 | A |
| 244 | L | CA | −8.0 | −30.0 | 3.4 | 49 | A |
| 244 | L | C | −7.7 | −30.1 | 4.9 | 57 | A |
| 244 | L | O | −7.7 | −31.2 | 5.5 | 59 | A |
| 244 | L | CB | −9.6 | −30.2 | 3.3 | 49 | A |
| 244 | L | CG | −10.2 | −29.6 | 2.0 | 52 | A |
| 244 | L | CD1 | −11.7 | −29.7 | 2.0 | 53 | A |
| 244 | L | CD2 | −9.7 | −28.3 | 1.8 | 54 | A |
| 87 | T | N | −7.8 | −63.2 | −7.0 | 74 | B |
| 87 | T | CA | −6.6 | −62.3 | −7.5 | 73 | B |
| 87 | T | C | −7.1 | −61.0 | −8.2 | 73 | B |
| 87 | T | O | −7.9 | −61.1 | −9.1 | 72 | B |
| 87 | T | CB | −5.6 | −63.1 | −8.3 | 77 | B |
| 87 | T | OG1 | −4.4 | −62.5 | −8.2 | 79 | B |
| 87 | T | CG2 | −6.1 | −63.1 | −9.8 | 74 | B |
| 88 | C | N | −6.4 | −59.9 | −7.8 | 68 | B |
| 88 | C | CA | −6.8 | −58.6 | −8.4 | 65 | B |
| 88 | C | C | −6.7 | −58.6 | −9.9 | 71 | B |
| 88 | C | O | −7.6 | −58.2 | −10.6 | 71 | B |
| 88 | C | CB | −6.0 | −57.5 | −7.9 | 63 | B |
| 88 | C | SG | −6.2 | −57.3 | −6.1 | 66 | B |
| 89 | N | N | −5.6 | −59.2 | −10.5 | 68 | B |
| 89 | N | CA | −5.4 | −59.3 | −11.9 | 69 | B |
| 89 | N | C | −6.4 | −60.2 | −12.7 | 72 | B |
| 89 | N | O | −6.3 | −60.4 | −13.8 | 71 | B |
| 89 | N | CB | −4.0 | −59.6 | −12.3 | 77 | B |
| 89 | N | CG | −3.5 | −60.9 | −11.6 | 0 | B |
| 89 | N | OD1 | −3.7 | −62.0 | −12.1 | 0 | B |
| 89 | N | ND2 | −2.9 | −60.8 | −10.4 | 0 | B |
| 90 | I | N | −7.5 | −60.6 | −11.9 | 68 | B |
| 90 | I | CA | −8.5 | −61.4 | −12.6 | 67 | B |
| 90 | I | C | −9.8 | −60.8 | −12.2 | 68 | B |
| 90 | I | O | −10.3 | −60.9 | −11.0 | 68 | B |
| 90 | I | CB | −8.4 | −62.9 | −12.1 | 72 | B |
| 90 | I | CG1 | −7.2 | −63.6 | −12.7 | 73 | B |
| 90 | I | CG2 | −9.7 | −63.7 | −12.6 | 72 | B |
| 90 | I | CD1 | −6.9 | −63.2 | −14.2 | 81 | B |
| 91 | K | N | −10.5 | −60.1 | −13.1 | 64 | B |
| 91 | K | CA | −11.7 | −59.4 | −12.8 | 62 | B |
| 91 | K | C | −11.7 | −58.4 | −11.6 | 61 | B |
| 91 | K | O | −12.6 | −58.3 | −10.9 | 60 | B |
| 91 | K | CB | −12.9 | −60.3 | −12.7 | 66 | B |
| 91 | K | CG | −13.6 | −60.6 | −14.0 | 92 | B |
| 91 | K | CD | −15.0 | −60.9 | −13.9 | 0 | B |
| 91 | K | CE | −15.8 | −59.6 | −13.6 | 0 | B |
| 91 | K | NZ | −16.9 | −59.8 | −12.6 | 0 | B |
| 92 | N | N | −10.5 | −57.8 | −11.4 | 55 | B |
| 92 | N | CA | −10.3 | −56.9 | −10.2 | 55 | B |
| 92 | N | C | −10.6 | −57.5 | −8.9 | 58 | B |
| 92 | N | O | −10.9 | −56.8 | −7.9 | 55 | B |
| 92 | N | CB | −11.1 | −55.6 | −10.5 | 49 | B |
| 92 | N | CG | −10.6 | −54.4 | −9.6 | 56 | B |
| 92 | N | OD1 | −11.4 | −53.7 | −9.0 | 46 | B |
| 92 | N | ND2 | −9.2 | −54.2 | −9.6 | 42 | B |
| 93 | G | N | −10.5 | −58.8 | −8.8 | 55 | B |
| 93 | G | CA | −10.8 | −59.6 | −7.6 | 55 | B |
| 93 | G | C | −12.2 | −59.4 | −7.1 | 60 | B |
| 93 | G | O | −12.5 | −59.4 | −6.0 | 60 | B |
| 94 | R | N | −13.1 | −59.2 | −8.1 | 58 | B |
| 94 | R | CA | −14.5 | −58.9 | −7.9 | 58 | B |
| 94 | R | C | −14.8 | −57.6 | −7.1 | 58 | B |
| 94 | R | O | −15.9 | −57.3 | −6.8 | 55 | B |
| 94 | R | CB | −15.2 | −60.1 | −7.2 | 64 | B |
| 94 | R | CG | −14.9 | −61.4 | −7.9 | 80 | B |
| 94 | R | CD | −15.6 | −61.5 | −9.2 | 98 | B |
| 94 | R | NE | −15.0 | −62.6 | −10.0 | 0 | B |
| 94 | R | CZ | −15.6 | −63.1 | −11.1 | 0 | B |
| 94 | R | NH1 | −16.8 | −62.7 | −11.5 | 0 | B |
| 94 | R | NH2 | −15.0 | −64.2 | −11.7 | 0 | B |
| 95 | C | N | −13.7 | −56.8 | −6.8 | 54 | B |
| 95 | C | CA | −13.8 | −55.6 | −6.1 | 54 | B |
| 95 | C | C | −14.4 | −54.5 | −7.0 | 56 | B |
| 95 | C | O | −14.0 | −54.4 | −8.1 | 56 | B |
| 95 | C | CB | −12.4 | −55.1 | −5.7 | 54 | B |
| 95 | C | SG | −11.5 | −56.7 | −4.6 | 58 | B |
| 96 | E | N | −15.4 | −53.8 | −6.5 | 52 | B |
| 96 | E | CA | −16.1 | −52.8 | −7.3 | 51 | B |
| 96 | E | C | −15.2 | −51.6 | −7.7 | 52 | B |
| 96 | E | O | −15.4 | −51.1 | −8.8 | 51 | B |
| 96 | E | CB | −17.3 | −52.3 | −6.6 | 52 | B |
| 96 | E | CG | −18.2 | −51.3 | −7.4 | 58 | B |
| 96 | E | CD | −19.3 | −50.7 | −6.5 | 67 | B |
| 96 | E | OE1 | −20.1 | −51.4 | −5.9 | 80 | B |
| 96 | E | OE2 | −19.4 | −49.5 | −6.5 | 66 | B |
| 97 | Q | N | −14.3 | −51.2 | −6.8 | 44 | B |
| 97 | Q | CA | −13.4 | −50.1 | −7.1 | 41 | B |
| 97 | Q | C | −12.0 | −50.6 | −7.0 | 43 | B |
| 97 | Q | O | −11.5 | −51.1 | −8.1 | 46 | B |
| 97 | Q | CB | −13.7 | −49.0 | −6.0 | 40 | B |
| 97 | Q | CG | −14.9 | −48.2 | −6.5 | 36 | B |
| 97 | Q | CD | −15.3 | −47.0 | −5.6 | 45 | B |
| 97 | Q | OE1 | −14.5 | −46.5 | −4.7 | 47 | B |
| 97 | Q | NE2 | −16.5 | −46.4 | −5.8 | 41 | B |
| 98 | F | N | −11.4 | −50.6 | −5.9 | 39 | B |
| 98 | F | CA | −10.0 | −51.0 | −5.8 | 41 | B |
| 98 | F | C | −9.7 | −52.4 | −5.1 | 55 | B |
| 98 | F | O | −10.5 | −52.9 | −4.3 | 53 | B |
| 98 | F | CB | −9.2 | −49.9 | −5.0 | 41 | B |
| 98 | F | CG | −9.6 | −48.5 | −5.4 | 42 | B |
| 98 | F | CD1 | −9.8 | −48.2 | −6.8 | 44 | B |
| 98 | F | CD2 | −9.8 | −47.5 | −4.5 | 44 | B |
| 98 | F | CE1 | −10.2 | −46.9 | −7.2 | 45 | B |
| 98 | F | CE2 | −10.1 | −46.2 | −4.7 | 47 | B |
| 98 | F | CZ | −10.3 | −45.9 | −6.2 | 44 | B |
| 99 | C | N | −8.6 | −53.0 | −5.5 | 56 | B |
| 99 | C | CA | −8.3 | −54.3 | −5.1 | 59 | B |
| 99 | C | C | −6.8 | −54.4 | −4.8 | 65 | B |
| 99 | C | O | −5.9 | −53.9 | −5.5 | 64 | B |
| 99 | C | CB | −8.5 | −55.3 | −6.2 | 60 | B |
| 99 | C | SG | −8.2 | −57.1 | −5.8 | 65 | B |
| 100 | K | N | −6.5 | −55.1 | −3.6 | 63 | B |
| 100 | K | CA | −5.1 | −55.3 | −3.2 | 64 | B |
| 100 | K | C | −5.0 | −56.8 | −2.8 | 68 | B |
| 100 | K | O | −5.8 | −57.4 | −2.2 | 66 | B |
| 100 | K | CB | −4.8 | −54.4 | −1.9 | 69 | B |
| 100 | K | CG | −3.6 | −53.6 | −2.0 | 94 | B |
| 100 | K | CD | −3.4 | −52.8 | −0.7 | 0 | B |
| 100 | K | CE | −3.8 | −51.3 | −0.8 | 0 | B |
| 100 | K | NZ | −3.5 | −50.5 | 0.4 | 0 | B |
| 101 | N | N | −3.9 | −57.4 | −3.4 | 65 | B |
| 101 | N | CA | −3.6 | −58.8 | −3.1 | 66 | B |
| 101 | N | C | −3.1 | −59.0 | −1.7 | 71 | B |
| 101 | N | O | −2.2 | −58.2 | −1.3 | 72 | B |
| 101 | N | CB | −2.6 | −59.3 | −4.1 | 64 | B |
| 101 | N | CG | −3.2 | −59.8 | −5.4 | 73 | B |
| 101 | N | OD1 | −4.4 | −60.1 | −5.5 | 62 | B |
| 101 | N | ND2 | −2.4 | −59.9 | −6.5 | 68 | B |
| 107 | V | N | −7.3 | −61.4 | −1.4 | 66 | B |
| 107 | V | CA | −7.8 | −60.2 | −2.0 | 67 | B |
| 107 | V | C | −8.5 | −59.3 | −1.0 | 70 | B |
| 107 | V | O | −9.6 | −59.7 | −0.5 | 72 | B |
| 107 | V | CB | −8.6 | −60.4 | −3.2 | 70 | B |
| 107 | V | CG1 | −9.8 | −59.4 | −3.3 | 69 | B |

TABLE 4-continued

Coordinates of Soaked Factor IXa-Compound A Complex

| | | | | | | |
|---|---|---|---|---|---|---|
| 107 | V | CG2 | −7.7 | −60.3 | −4.5 | 70 | B |
| 108 | V | N | −8.0 | −58.0 | −0.8 | 63 | B |
| 108 | V | CA | −8.7 | −57.0 | 0.0 | 61 | B |
| 108 | V | C | −9.3 | −55.9 | −0.9 | 65 | B |
| 108 | V | O | −8.5 | −55.2 | −1.6 | 66 | B |
| 108 | V | CB | −7.7 | −56.4 | 1.0 | 64 | B |
| 108 | V | CG1 | −8.4 | −55.4 | 1.9 | 63 | B |
| 108 | V | CG2 | −6.9 | −37.4 | 1.9 | 63 | B |
| 109 | C | N | −10.6 | −55.8 | −0.8 | 60 | B |
| 109 | C | CA | −11.3 | −54.8 | −1.6 | 58 | B |
| 109 | C | C | −11.3 | −53.4 | −0.9 | 63 | B |
| 109 | C | O | −11.4 | −53.4 | 0.3 | 63 | B |
| 109 | C | CB | −12.7 | −55.2 | −2.0 | 56 | B |
| 109 | C | SG | −12.8 | −56.6 | −3.2 | 59 | B |
| 110 | S | N | −11.2 | −52.3 | −1.6 | 58 | B |
| 110 | S | CA | −11.3 | −51.0 | −1.0 | 55 | B |
| 110 | S | C | −12.0 | −50.0 | −1.9 | 58 | B |
| 110 | S | O | −12.4 | −50.3 | −3.0 | 55 | B |
| 110 | S | CB | −10.0 | −50.5 | −0.5 | 55 | B |
| 110 | S | OG | −9.0 | −50.3 | −1.5 | 51 | B |
| 111 | C | N | −12.3 | −48.8 | −1.4 | 54 | B |
| 111 | C | CA | −13.1 | −47.8 | −2.0 | 54 | B |
| 111 | C | C | −12.5 | −46.4 | −1.9 | 51 | B |
| 111 | C | O | −11.6 | −46.2 | −1.1 | 47 | B |
| 111 | C | CB | −14.5 | −47.7 | −1.4 | 57 | B |
| 111 | C | SG | −15.5 | −49.2 | −1.3 | 62 | B |
| 112 | T | N | −13.0 | −45.5 | −2.7 | 46 | B |
| 112 | T | CA | −12.5 | −44.1 | −2.7 | 44 | B |
| 112 | T | C | −13.1 | −43.5 | −1.5 | 49 | B |
| 112 | T | O | −14.2 | −43.9 | −1.1 | 51 | B |
| 112 | T | CB | −12.7 | −43.4 | −4.0 | 44 | B |
| 112 | T | OG1 | −11.9 | −42.2 | −4.1 | 44 | B |
| 112 | T | CG2 | −14.2 | −43.0 | −4.2 | 34 | B |
| 113 | E | N | −12.5 | −42.4 | −1.1 | 45 | B |
| 113 | E | CA | −13.0 | −41.6 | 0.0 | 49 | B |
| 113 | E | C | −14.5 | −41.2 | −0.2 | 49 | B |
| 113 | E | O | −14.9 | −40.9 | −1.3 | 45 | B |
| 113 | E | CB | −12.2 | −40.3 | 0.1 | 48 | B |
| 113 | E | CG | −12.6 | −39.3 | 1.1 | 71 | B |
| 113 | E | CD | −11.6 | −39.3 | 2.3 | 0 | B |
| 113 | E | OE1 | −12.1 | −39.6 | 3.5 | 95 | B |
| 113 | E | OE2 | −10.4 | −39.0 | 2.1 | 0 | B |
| 114 | G | N | −15.2 | −41.3 | 0.9 | 47 | B |
| 114 | G | CA | −16.7 | −41.0 | 0.9 | 47 | B |
| 114 | G | C | −17.5 | −42.2 | 0.8 | 51 | B |
| 114 | G | O | −18.7 | −42.2 | 0.8 | 49 | B |
| 115 | Y | N | −16.8 | −43.3 | 0.6 | 48 | B |
| 115 | Y | CA | −17.4 | −44.6 | 0.3 | 49 | B |
| 115 | Y | C | −16.8 | −45.6 | 1.4 | 54 | B |
| 115 | Y | O | −15.7 | −45.4 | 1.9 | 53 | B |
| 115 | Y | CB | −17.0 | −45.2 | −1.1 | 50 | B |
| 115 | Y | CG | −17.7 | −44.4 | −2.2 | 49 | B |
| 115 | Y | CD1 | −19.0 | −44.8 | −2.6 | 50 | B |
| 115 | Y | CD2 | −17.2 | −43.3 | −2.7 | 48 | B |
| 115 | Y | CE1 | −19.7 | −44.1 | −3.6 | 51 | B |
| 115 | Y | CE2 | −17.8 | −42.5 | −3.7 | 47 | B |
| 115 | Y | CZ | −19.1 | −43.0 | −4.1 | 51 | B |
| 115 | Y | OH | −19.7 | −42.2 | −5.0 | 49 | B |
| 116 | R | N | −17.5 | −46.7 | 1.6 | 53 | B |
| 116 | R | CA | −17.1 | −47.7 | 2.6 | 53 | B |
| 116 | R | C | −17.4 | −49.1 | 2.0 | 56 | B |
| 116 | R | O | −18.3 | −49.3 | 1.2 | 54 | B |
| 116 | R | CB | −17.9 | −47.5 | 3.9 | 54 | B |
| 116 | R | CG | −19.4 | −47.8 | 3.7 | 68 | B |
| 116 | R | CD | −20.1 | −48.0 | 5.1 | 77 | B |
| 116 | R | NE | −21.4 | −47.5 | 5.0 | 76 | B |
| 116 | R | CZ | −21.8 | −46.4 | 5.7 | 91 | B |
| 116 | R | NH1 | −20.9 | −45.8 | 6.5 | 79 | B |
| 116 | R | NH2 | −23.1 | −46.0 | 5.6 | 79 | B |
| 117 | L | N | −16.5 | −50.1 | 2.3 | 57 | B |
| 117 | L | CA | −16.7 | −51.4 | 1.8 | 60 | B |
| 117 | L | C | −18.0 | −52.0 | 2.2 | 68 | B |
| 117 | L | O | −18.3 | −52.0 | 3.4 | 70 | B |
| 117 | L | CB | −15.5 | −52.3 | 2.1 | 60 | B |
| 117 | L | CG | −15.5 | −53.5 | 1.2 | 66 | B |
| 117 | L | CD1 | −15.4 | −53.2 | −0.2 | 66 | B |
| 117 | L | CD2 | −14.2 | −54.4 | 1.6 | 71 | B |
| 118 | A | N | −18.9 | −52.4 | 1.3 | 64 | B |
| 118 | A | CA | −20.2 | −53.0 | 1.7 | 65 | B |
| 118 | A | C | −20.1 | −54.3 | 2.5 | 75 | B |
| 118 | A | O | −19.0 | −54.9 | 2.7 | 72 | B |
| 118 | A | CB | −21.1 | −53.2 | 0.5 | 65 | B |
| 119 | E | N | −21.3 | −54.8 | 2.9 | 76 | B |
| 119 | E | CA | −21.3 | −56.0 | 3.7 | 77 | B |
| 119 | E | C | −20.6 | −57.2 | 3.0 | 77 | B |
| 119 | E | O | −19.7 | −57.8 | 3.5 | 75 | B |
| 119 | E | CB | −22.8 | −56.4 | 4.0 | 79 | B |
| 119 | E | CG | −23.3 | −55.6 | 5.2 | 98 | B |
| 119 | E | CD | −23.5 | −54.1 | 5.0 | 0 | B |
| 119 | E | OE1 | −23.8 | −53.7 | 3.8 | 0 | B |
| 119 | E | OE2 | −23.4 | −53.3 | 5.9 | 0 | B |
| 120 | N | N | −21.0 | −57.4 | 1.7 | 71 | B |
| 120 | N | CA | −20.4 | −58.4 | 0.9 | 69 | B |
| 120 | N | C | −18.9 | −58.3 | 0.7 | 70 | B |
| 120 | N | O | −18.4 | −59.1 | −0.0 | 68 | B |
| 120 | N | CB | −21.1 | −58.5 | −0.5 | 68 | B |
| 120 | N | CG | −20.8 | −57.3 | −1.4 | 84 | B |
| 120 | N | OD1 | −20.0 | −56.4 | −1.0 | 76 | B |
| 120 | N | ND2 | −21.3 | −57.3 | −2.6 | 66 | B |
| 121 | Q | N | −18.3 | −57.3 | 1.3 | 66 | B |
| 121 | Q | CA | −16.9 | −57.1 | 1.2 | 66 | B |
| 121 | Q | C | −16.3 | −56.8 | −0.2 | 70 | B |
| 121 | Q | O | −15.1 | −56.8 | −0.4 | 69 | B |
| 121 | Q | CB | −16.1 | −58.2 | 1.9 | 67 | B |
| 121 | Q | CG | −16.3 | −58.3 | 3.4 | 79 | B |
| 121 | Q | CD | −16.2 | −57.0 | 4.2 | 0 | B |
| 121 | Q | OE1 | −15.0 | −56.6 | 4.4 | 95 | B |
| 121 | Q | NE2 | −17.3 | −56.4 | 4.6 | 92 | B |
| 122 | K | N | −17.2 | −56.6 | −1.1 | 65 | B |
| 122 | K | CA | −16.8 | −56.3 | −2.5 | 66 | B |
| 122 | K | C | −17.3 | −55.0 | −3.0 | 70 | B |
| 122 | K | O | −16.5 | −54.1 | −3.4 | 70 | B |
| 122 | K | CB | −17.4 | −57.4 | −3.4 | 69 | B |
| 122 | K | CG | −16.9 | −58.8 | −3.1 | 77 | B |
| 122 | K | CD | −15.8 | −59.3 | −4.1 | 77 | B |
| 122 | K | CE | −14.9 | −60.3 | −3.4 | 82 | B |
| 122 | K | NZ | −13.6 | −59.8 | −2.9 | 81 | B |
| 123 | S | N | −18.6 | −54.7 | −2.9 | 65 | B |
| 123 | S | CA | −19.2 | −53.5 | −3.3 | 63 | B |
| 123 | S | C | −18.9 | −52.3 | −2.4 | 64 | B |
| 123 | S | O | −18.5 | −52.4 | −1.3 | 63 | B |
| 123 | S | CB | −20.7 | −53.8 | −3.4 | 63 | B |
| 123 | S | OG | −21.0 | −54.5 | −4.5 | 65 | B |
| 124 | C | N | −19.1 | −51.1 | −3.0 | 61 | B |
| 124 | C | CA | −18.8 | −49.8 | −2.4 | 60 | B |
| 124 | C | C | −20.1 | −49.1 | −2.2 | 61 | B |
| 124 | C | O | −21.0 | −49.1 | −3.1 | 63 | B |
| 124 | C | CB | −17.8 | −49.0 | −3.2 | 59 | B |
| 124 | C | SG | −16.1 | −49.6 | −3.2 | 63 | B |
| 125 | E | N | −20.2 | −48.4 | −1.1 | 55 | B |
| 125 | E | CA | −21.5 | −47.7 | −0.8 | 54 | B |
| 125 | E | C | −21.1 | −46.4 | −0.0 | 57 | B |
| 125 | E | O | −20.1 | −46.4 | 0.7 | 56 | B |
| 125 | E | CB | −22.4 | −48.5 | 0.1 | 56 | B |
| 125 | E | CG | −21.8 | −48.7 | 1.6 | 67 | B |
| 125 | E | CD | −22.8 | −49.3 | 2.5 | 0 | B |
| 125 | E | OE1 | −23.1 | −50.5 | 2.5 | 79 | B |
| 125 | E | OE2 | −23.4 | −48.5 | 3.4 | 0 | B |
| 126 | P | N | −21.9 | −45.4 | −0.2 | 54 | B |
| 126 | P | CA | −21.8 | −44.0 | 0.4 | 55 | B |
| 126 | P | C | −21.6 | −44.0 | 1.9 | 63 | B |
| 126 | P | O | −22.4 | −44.6 | 2.6 | 67 | B |
| 126 | P | CB | −23.1 | −43.3 | −0.0 | 56 | B |
| 126 | P | CG | −23.5 | −44.0 | −1.3 | 59 | B |
| 126 | P | CD | −23.0 | −45.5 | −1.1 | 54 | B |
| 127 | A | N | −20.6 | −43.3 | 2.4 | 59 | B |
| 127 | A | CA | −20.4 | −43.2 | 3.8 | 59 | B |
| 127 | A | C | −20.6 | −41.7 | 4.2 | 63 | B |
| 127 | A | O | −20.2 | −41.3 | 5.2 | 64 | B |
| 127 | A | CB | −19.0 | −43.6 | 4.2 | 59 | B |
| 128 | V | N | −21.2 | −41.0 | 3.2 | 57 | B |
| 128 | V | CA | −21.4 | −39.5 | 3.4 | 53 | B |
| 128 | V | C | −22.6 | −39.1 | 2.6 | 54 | B |
| 128 | V | O | −23.2 | −39.9 | 1.8 | 56 | B |
| 128 | V | CB | −20.2 | −38.7 | 3.1 | 56 | B |
| 128 | V | CG1 | −19.0 | −39.3 | 3.8 | 55 | B |

TABLE 4-continued

Coordinates of Soaked Factor IXa-Compound A Complex

| | | | | | | |
|---|---|---|---|---|---|---|
| 128 | V | CG2 | −20.0 | −38.7 | 1.6 | 55 | B |
| 129 | P | N | −23.1 | −37.9 | 2.9 | 48 | B |
| 129 | P | CA | −24.3 | −37.4 | 2.2 | 48 | B |
| 129 | P | C | −24.1 | −37.2 | 0.7 | 52 | B |
| 129 | P | O | −25.0 | −37.4 | −0.1 | 52 | B |
| 129 | P | CB | −24.6 | −36.1 | 2.8 | 50 | B |
| 129 | P | CG | −23.8 | −36.0 | 4.0 | 54 | B |
| 129 | P | CD | −22.6 | −36.9 | 3.9 | 48 | B |
| 130 | F | N | −23.0 | −36.6 | 0.3 | 49 | B |
| 130 | F | CA | −22.7 | −36.4 | −1.2 | 47 | B |
| 130 | F | C | −21.4 | −36.9 | −1.6 | 49 | B |
| 130 | F | O | −20.4 | −36.1 | −1.7 | 48 | B |
| 130 | F | CB | −22.9 | −34.9 | −1.5 | 47 | B |
| 130 | F | CG | −24.4 | −34.4 | −1.2 | 48 | B |
| 130 | F | CD1 | −24.7 | −33.8 | −0.0 | 49 | B |
| 130 | F | CD2 | −25.4 | −34.7 | −2.2 | 47 | B |
| 130 | F | CE1 | −26.0 | −33.5 | 0.3 | 49 | B |
| 130 | F | CE2 | −26.7 | −34.3 | −1.9 | 50 | B |
| 130 | F | CZ | −27.0 | −33.7 | −0.7 | 47 | B |
| 131 | P | N | −21.2 | −38.2 | −1.7 | 47 | B |
| 131 | P | CA | −19.9 | −38.8 | −2.1 | 45 | B |
| 131 | P | C | −19.5 | −38.4 | −3.5 | 44 | B |
| 131 | P | O | −20.4 | −38.2 | −4.4 | 43 | B |
| 131 | P | CB | −20.1 | −40.3 | −1.9 | 46 | B |
| 131 | P | CG | −21.5 | −40.5 | −2.2 | 50 | B |
| 131 | P | CD | −22.3 | −39.2 | −1.8 | 47 | B |
| 132 | C | N | −18.2 | −38.2 | −3.8 | 42 | B |
| 132 | C | CA | −17.8 | −37.8 | −5.1 | 40 | B |
| 132 | C | C | −18.3 | −38.7 | −6.2 | 44 | B |
| 132 | C | O | −18.6 | −39.9 | −5.9 | 44 | B |
| 132 | C | CB | −16.2 | −37.9 | −5.1 | 40 | B |
| 132 | C | SG | −15.5 | −39.6 | −4.9 | 44 | B |
| 133 | G | N | −18.4 | −38.2 | −7.4 | 38 | B |
| 133 | G | CA | −18.7 | −39.0 | −8.6 | 37 | B |
| 133 | G | C | −20.1 | −39.5 | −8.7 | 40 | B |
| 133 | G | O | −20.3 | −40.4 | −9.5 | 38 | B |
| 134 | R | N | −21.0 | −39.1 | −7.9 | 39 | B |
| 134 | R | CA | −22.4 | −39.7 | −8.1 | 39 | B |
| 134 | R | C | −23.4 | −36.6 | −8.4 | 41 | B |
| 134 | R | O | −23.4 | −37.6 | −7.9 | 42 | B |
| 134 | R | CB | −22.8 | −40.4 | −6.8 | 43 | B |
| 134 | R | CG | −22.0 | −41.6 | −6.5 | 65 | B |
| 134 | R | CD | −22.6 | −42.8 | −7.1 | 77 | B |
| 134 | R | NE | −22.2 | −44.1 | −6.5 | 94 | B |
| 134 | R | CZ | −22.9 | −44.7 | −5.5 | 0 | B |
| 134 | R | NH1 | −24.1 | −44.2 | −5.1 | 0 | B |
| 134 | R | NH2 | −22.4 | −45.8 | −5.0 | 0 | B |
| 135 | V | N | −24.3 | −39.0 | −9.3 | 38 | B |
| 135 | V | CA | −25.4 | −38.2 | −9.7 | 41 | B |
| 135 | V | C | −26.5 | −38.6 | −8.6 | 49 | B |
| 135 | V | O | −26.8 | −39.7 | −8.4 | 49 | B |
| 135 | V | CB | −25.8 | −38.6 | −11.1 | 45 | B |
| 135 | V | CG1 | −27.2 | −37.9 | −11.4 | 44 | B |
| 135 | V | CG2 | −24.8 | −38.1 | −12.1 | 44 | B |
| 136 | S | N | −27.0 | −37.5 | −8.0 | 48 | B |
| 136 | S | CA | −28.0 | −37.8 | −6.9 | 48 | B |
| 136 | S | C | −29.3 | −37.1 | −7.1 | 61 | B |
| 136 | S | O | −30.2 | −37.2 | −6.3 | 63 | B |
| 136 | S | CB | −27.4 | −37.5 | −5.5 | 46 | B |
| 136 | S | OG | −27.1 | −36.2 | −5.4 | 46 | B |
| 137 | V | N | −29.4 | −36.3 | −8.2 | 62 | B |
| 137 | V | CA | −30.6 | −35.6 | −8.6 | 64 | B |
| 137 | V | C | −31.4 | −36.5 | −9.5 | 75 | B |
| 137 | V | O | −30.8 | −37.2 | −10.3 | 75 | B |
| 137 | V | CB | −30.3 | −34.3 | −9.3 | 68 | B |
| 137 | V | CG1 | −31.5 | −33.7 | −9.9 | 68 | B |
| 137 | V | CG2 | −29.5 | −33.3 | −8.4 | 68 | B |
| 138 | S | N | −32.7 | −36.5 | −9.4 | 74 | B |
| 138 | S | CA | −33.5 | −37.3 | −10.3 | 75 | B |
| 138 | S | C | −33.2 | −37.0 | −11.7 | 80 | B |
| 138 | S | O | −33.0 | −35.9 | −12.1 | 79 | B |
| 138 | S | CB | −35.0 | −37.0 | −10.0 | 79 | B |
| 138 | S | OG | −35.8 | −37.8 | −10.9 | 89 | B |
| 139 | Q | N | −33.1 | −38.1 | −12.5 | 78 | B |
| 139 | Q | CA | −32.7 | −38.0 | −14.0 | 78 | B |
| 139 | Q | C | −33.9 | −38.2 | −14.9 | 83 | B |
| 139 | Q | O | −34.4 | −37.3 | −15.5 | 83 | B |
| 139 | Q | CB | −31.5 | −38.9 | −14.3 | 79 | B |
| 139 | Q | CG | −30.2 | −38.4 | −13.7 | 78 | B |
| 139 | Q | CD | −29.7 | −37.1 | −14.3 | 80 | B |
| 139 | Q | OE1 | −29.6 | −36.1 | −13.7 | 73 | B |
| 139 | Q | NE2 | −29.3 | −37.2 | −15.6 | 67 | B |
| 500 | X | CA | −27.9 | −20.4 | −14.5 | 94 | Q |
| 501 | X | C1 | 6.0 | −36.0 | −18.3 | 37 | Q |
| 501 | X | O1 | 5.1 | −36.9 | −18.2 | 36 | Q |
| 501 | X | O2 | 6.2 | −35.1 | −17.4 | 38 | Q |
| 501 | X | C2 | 6.7 | −35.8 | −19.7 | 38 | Q |
| 501 | X | C3 | 6.7 | −36.9 | −20.7 | 40 | Q |
| 501 | X | O7 | 7.5 | −38.0 | −20.2 | 38 | Q |
| 501 | X | C4 | 7.3 | −36.5 | −22.0 | 44 | Q |
| 501 | X | C5 | 7.3 | −37.5 | −23.1 | 44 | Q |
| 501 | X | O3 | 6.2 | −38.1 | −23.5 | 41 | Q |
| 501 | X | O4 | 8.4 | −37.8 | −23.6 | 52 | Q |
| 501 | X | C6 | 5.3 | −37.5 | −20.9 | 36 | Q |
| 501 | X | O5 | 5.3 | −38.8 | −20.6 | 40 | Q |
| 501 | X | O6 | 4.3 | −36.8 | −21.2 | 39 | Q |
| 502 | X | C1 | 9.3 | −41.0 | −18.6 | 52 | Q |
| 502 | X | O1 | 9.7 | −40.8 | −19.9 | 51 | Q |
| 502 | X | O2 | 10.0 | −40.5 | −17.7 | 57 | Q |
| 502 | X | C2 | 8.0 | −41.7 | −18.4 | 44 | Q |
| 502 | X | C3 | 6.8 | −41.3 | −19.3 | 43 | Q |
| 502 | X | O7 | 6.6 | −39.9 | −19.1 | 39 | Q |
| 502 | X | C4 | 5.6 | −42.1 | −19.0 | 41 | Q |
| 502 | X | C5 | 5.2 | −42.2 | −17.5 | 46 | Q |
| 502 | X | O3 | 4.7 | −41.1 | −16.9 | 46 | Q |
| 502 | X | O4 | 5.3 | −43.3 | −17.0 | 46 | Q |
| 502 | X | C6 | 7.1 | −41.3 | −20.8 | 47 | Q |
| 502 | X | O5 | 7.1 | −40.1 | −21.2 | 46 | Q |
| 502 | X | O6 | 7.4 | −42.4 | −21.4 | 49 | Q |
| 503 | X | C1 | 4.7 | −33.6 | −7.9 | 42 | Q |
| 503 | X | O1 | 5.3 | −32.9 | −8.8 | 40 | Q |
| 503 | X | O2 | 4.3 | −33.0 | −6.8 | 44 | Q |
| 503 | X | C2 | 4.3 | −35.0 | −8.2 | 37 | Q |
| 503 | X | C3 | 4.2 | −35.4 | −9.7 | 36 | Q |
| 503 | X | O7 | 3.3 | −34.5 | −10.3 | 32 | Q |
| 503 | X | C4 | 3.8 | −36.9 | −9.9 | 30 | Q |
| 503 | X | C5 | 2.3 | −37.1 | −9.5 | 34 | Q |
| 503 | X | O3 | 1.6 | −36.1 | −9.4 | 35 | Q |
| 503 | X | O4 | 2.0 | −38.3 | −9.3 | 38 | Q |
| 503 | X | C6 | 5.6 | −35.2 | −10.4 | 33 | Q |
| 503 | X | O5 | 5.6 | −34.3 | −11.4 | 35 | Q |
| 503 | X | O6 | 6 | −35.7 | −9.9 | 37 | Q |
| 1 | Z | N1 | −10.9 | −31.4 | −28.3 | 42 | S |
| 1 | Z | C2 | −10.8 | −30.4 | −29.1 | 41 | S |
| 1 | Z | N3 | −10.9 | −30.5 | −30.5 | 41 | S |
| 1 | Z | C4 | −10.5 | −29.0 | −28.6 | 41 | S |
| 1 | Z | C5 | −10.3 | −28.9 | −27.2 | 36 | S |
| 1 | Z | C6 | −10.1 | −27.6 | −26.6 | 39 | S |
| 1 | Z | C7 | −9.9 | −26.5 | −27.5 | 37 | S |
| 1 | Z | C8 | −10.0 | −26.5 | −28.9 | 42 | S |
| 1 | Z | C9 | −10.3 | −27.9 | −29.4 | 38 | S |
| 1 | Z | N14 | −9.9 | −25.6 | −29.8 | 47 | S |
| 1 | Z | C15 | −8.8 | −25.1 | −30.4 | 48 | S |
| 1 | Z | C16 | −9.2 | −24.2 | −31.4 | 51 | S |
| 1 | Z | C17 | −10.5 | −24.2 | −31.4 | 52 | S |
| 1 | Z | N18 | −11.0 | −25.1 | −30.4 | 48 | S |
| 1 | Z | C19 | −11.4 | −23.4 | −32.3 | 52 | S |
| 1 | Z | C23 | −7.4 | −25.5 | −30.0 | 50 | S |
| 1 | Z | N24 | −6.4 | −25.1 | −30.8 | 49 | S |
| 1 | Z | C25 | −5.1 | −25.5 | −30.7 | 44 | S |
| 1 | Z | O26 | −7.2 | −26.2 | −29.1 | 48 | S |
| 1 | Z | C27 | −4.4 | −26.1 | −31.8 | 44 | S |
| 1 | Z | C28 | −3.0 | −26.1 | −31.6 | 46 | S |
| 1 | Z | C29 | −2.5 | −26.4 | −30.3 | 49 | S |
| 1 | Z | C30 | −3.2 | −25.9 | −29.3 | 46 | S |
| 1 | Z | C31 | −4.5 | −25.5 | −29.5 | 47 | S |
| 1 | Z | N36 | −1.1 | −26.9 | −30.0 | 51 | S |
| 1 | Z | C37 | 0.0 | −26.0 | −30.1 | 58 | S |
| 1 | Z | C38 | 1.1 | −26.9 | −29.6 | 60 | S |
| 1 | Z | N39 | 0.6 | −28.1 | −29.3 | 57 | S |
| 1 | Z | C40 | −0.7 | −28.1 | −29.6 | 53 | S |
| 1 | Z | C41 | 0.3 | −24.7 | −30.4 | 64 | S |
| 1 | Z | C42 | 1.6 | −24.2 | −30.3 | 65 | S |
| 1 | Z | C43 | 2.6 | −25.0 | −29.9 | 64 | S |
| 1 | Z | C44 | 2.4 | −26.3 | −29.5 | 63 | S |
| 2 | O | O | −23.3 | −29.4 | −32.3 | 53 | W |

TABLE 4-continued

Coordinates of Soaked Factor IXa-Compound A Complex

| | | | | | | |
|---|---|---|---|---|---|---|
| 3 | O | O | -32.1 | -33.5 | -13.5 | 61 | W |
| 4 | O | O | -26.7 | -35.1 | -9.2 | 43 | W |
| 5 | O | O | -17.9 | -34.9 | -17.2 | 37 | W |
| 6 | O | O | -15.5 | -27.9 | -19.8 | 31 | W |
| 7 | O | O | -21.2 | -25.4 | -12.9 | 44 | W |
| 9 | O | O | -26.0 | -25.1 | -4.8 | 38 | W |
| 10 | O | O | 4.2 | -20.5 | -17.6 | 52 | W |
| 11 | O | O | 4.5 | -26.5 | -20.3 | 33 | W |
| 12 | O | O | -18.8 | -26.9 | 2.4 | 50 | W |
| 13 | O | O | -11.9 | -35.5 | -5.5 | 37 | W |
| 14 | O | O | -0.7 | -46.1 | -8.0 | 43 | W |
| 15 | O | O | -16.9 | -25.3 | -20.1 | 38 | W |
| 17 | O | O | -4.3 | -42.0 | -26.8 | 36 | W |
| 18 | O | O | -0.7 | -30.9 | -37.6 | 52 | W |
| 21 | O | O | -10.9 | -38.0 | -36.7 | 38 | W |
| 22 | O | O | -14.2 | -36.5 | -32.8 | 42 | W |
| 23 | O | O | -18.7 | -39.5 | -36.4 | 40 | W |
| 24 | O | O | -12.7 | -35.5 | -28.2 | 36 | W |
| 25 | O | O | -9.3 | -22.9 | -24.4 | 53 | W |
| 26 | O | O | -4.8 | -29.9 | -20.1 | 50 | W |
| 27 | O | O | -12.3 | -44.6 | -20.0 | 32 | W |
| 28 | O | O | -17.3 | -44.0 | -18.9 | 39 | W |
| 29 | O | O | -8.0 | -34.1 | -2.9 | 41 | W |
| 30 | O | O | -14.1 | -52.3 | -4.0 | 57 | W |
| 31 | O | O | -9.2 | -41.2 | -11.2 | 31 | W |
| 32 | O | O | -11.0 | -30.6 | -14.9 | 32 | W |
| 33 | O | O | -6.0 | -35.0 | -0.8 | 52 | W |
| 34 | O | O | -10.1 | -33.8 | -0.9 | 47 | W |
| 35 | O | O | -20.8 | -27.0 | -25.1 | 40 | W |
| 36 | O | O | -22.9 | -38.4 | -15.2 | 40 | W |
| 41 | O | O | -10.6 | -33.2 | -33.1 | 48 | W |
| 42 | O | O | -12.6 | -34.7 | -34.2 | 43 | W |
| 43 | O | O | -10.5 | -31.3 | -35.1 | 43 | W |
| 44 | O | O | -5.4 | -35.2 | -33.8 | 38 | W |
| 45 | O | O | -6.5 | -32.3 | -33.0 | 45 | W |
| 46 | O | O | -24.3 | -36.9 | -29.0 | 56 | W |
| 47 | O | O | -21.4 | -41.1 | -12.1 | 50 | W |
| 48 | O | O | -20.4 | -39.4 | -15.6 | 44 | W |
| 49 | O | O | -25.1 | -29.4 | -11.3 | 47 | W |
| 50 | O | O | -27.2 | -28.5 | -12.6 | 47 | W |
| 51 | O | O | -21.3 | -28.2 | -10.5 | 39 | W |
| 52 | O | O | -20.5 | -29.0 | 2.2 | 48 | W |
| 53 | O | O | -8.9 | -36.0 | -4.6 | 40 | W |
| 54 | O | O | -1.2 | -19.2 | -18.8 | 66 | W |
| 56 | O | O | 6.4 | -28.2 | -20.5 | 44 | W |
| 57 | O | O | -22.7 | -19.8 | -2.4 | 44 | W |
| 58 | O | O | -24.7 | -19.7 | -3.9 | 49 | W |
| 59 | O | O | 8.1 | -33.7 | -12.2 | 34 | W |
| 60 | O | O | 2.8 | -34.5 | -20.9 | 46 | W |
| 62 | O | O | -0.8 | -31.9 | -20.6 | 35 | W |
| 63 | O | O | -9.4 | -42.6 | -4.5 | 45 | W |
| 64 | O | O | -5.4 | -40.6 | -16.8 | 29 | W |
| 65 | O | O | -3.8 | -42.7 | -17.6 | 31 | W |
| 66 | O | O | -8.1 | -51.0 | -18.1 | 42 | W |
| 67 | O | O | -11.1 | -43.4 | -22.1 | 33 | W |
| 68 | O | O | -12.1 | -41.6 | -23.9 | 33 | W |
| 69 | O | O | -20.9 | -40.1 | -28.2 | 48 | W |
| 70 | O | O | -0.8 | -47.6 | -30.4 | 50 | W |
| 71 | O | O | -5.4 | -46.6 | -39.8 | 57 | W |
| 72 | O | O | -10.6 | -43.6 | -34.7 | 36 | W |
| 73 | O | O | -14.4 | -33.2 | -40.9 | 48 | W |
| 81 | O | O | -11.3 | -14.3 | -19.8 | 60 | W |
| 82 | O | O | 0.8 | -33.8 | -19.4 | 40 | W |
| 83 | O | O | -22.7 | -39.1 | -26.1 | 39 | W |
| 84 | O | O | -29.2 | -26.6 | -12.0 | 45 | W |
| 85 | O | O | -24.5 | -30.9 | -14.0 | 51 | W |
| 86 | O | O | -23.9 | -36.8 | -26.1 | 49 | W |
| 87 | O | O | -26.7 | -39.8 | -24.0 | 64 | W |
| 88 | O | O | -8.0 | -34.3 | -40.6 | 51 | W |
| 92 | O | O | -2.1 | -17.4 | -7.3 | 44 | W |
| 93 | O | O | -15.1 | -52.2 | -17.9 | 63 | W |
| 94 | O | O | 0.1 | -39.8 | -9.9 | 58 | W |
| 97 | O | O | -24.7 | -42.7 | -31.6 | 55 | W |
| 101 | O | O | -23.2 | -30.2 | -28.3 | 49 | W |
| 102 | O | O | -22.9 | -28.5 | -13.1 | 48 | W |
| 103 | O | O | -23.2 | -17.7 | -5.7 | 42 | W |
| 104 | O | O | -15.7 | -11.6 | -8.0 | 55 | W |
| 105 | O | O | -17.7 | -14.5 | -6.3 | 53 | W |
| 106 | O | O | -11.4 | -12.8 | -3.3 | 52 | W |
| 108 | O | O | 10.2 | -28.0 | -15.3 | 55 | W |
| 109 | O | O | 7.8 | -33.0 | -21.9 | 47 | W |
| 110 | O | O | 7.3 | -29.0 | -22.8 | 46 | W |
| 111 | O | O | -24.3 | -35.8 | -6.1 | 42 | W |
| 112 | O | O | -11.7 | -39.4 | -4.6 | 41 | W |
| 113 | O | O | -3.5 | -49.4 | -6.8 | 47 | W |
| 114 | O | O | -6.9 | -46.1 | -6.1 | 44 | W |
| 115 | O | O | -7.5 | -52.6 | -1.6 | 55 | W |
| 116 | O | O | -18.0 | -47.6 | -7.9 | 56 | W |
| 117 | O | O | -6.3 | -16.5 | -14.5 | 49 | W |
| 118 | O | O | -9.8 | -32.1 | -26.0 | 37 | W |
| 119 | O | O | 2.5 | -30.1 | -28.4 | 52 | W |
| 120 | O | O | -18.0 | -23.6 | -37.1 | 75 | W |
| 121 | O | O | -12.3 | -43.4 | -32.5 | 31 | W |
| 122 | O | O | -9.8 | -40.5 | -39.4 | 44 | W |
| 123 | O | O | -8.1 | -41.7 | -37.9 | 35 | W |
| 124 | O | O | -18.3 | -50.0 | -15.0 | 57 | W |
| 125 | O | O | -1.7 | -26.3 | -1.4 | 47 | W |
| 131 | O | O | -19.2 | -31.2 | 3.0 | 57 | W |
| 132 | O | O | -7.4 | -16.6 | -17.0 | 45 | W |
| 133 | O | O | -7.8 | -15.3 | -9.7 | 54 | W |
| 134 | O | O | 3.2 | -33.7 | -4.7 | 45 | W |
| 135 | O | O | 5.1 | -30.2 | -6.3 | 45 | W |
| 136 | O | O | 5.8 | -42.7 | -14.1 | 43 | W |
| 137 | O | O | 2.8 | -41.2 | -14.9 | 41 | W |
| 138 | O | O | 1.5 | -42.5 | -19.6 | 41 | W |
| 139 | O | O | 0.6 | -41.5 | -16.0 | 47 | W |
| 140 | O | O | -2.5 | -48.7 | -14.5 | 40 | W |
| 141 | O | O | -0.1 | -40.9 | -25.9 | 38 | W |
| 142 | O | O | -0.6 | -42.8 | -24.3 | 46 | W |
| 143 | O | O | -2.4 | -44.9 | -20.7 | 44 | W |
| 144 | O | O | 2.9 | -44.1 | -21.4 | 53 | W |
| 145 | O | O | -4.0 | -45.1 | -22.7 | 50 | W |
| 146 | O | O | -3.5 | -43.8 | -24.7 | 52 | W |
| 147 | O | O | -11.5 | -45.4 | -30.9 | 35 | W |
| 148 | O | O | -2.2 | -40.7 | -27.6 | 41 | W |
| 149 | O | O | -21.2 | -47.5 | -14.5 | 59 | W |
| 150 | O | O | -23.3 | -37.6 | -4.1 | 47 | W |
| 151 | O | O | -16.5 | -38.7 | -1.6 | 48 | W |
| 152 | O | O | -17.7 | -35.5 | -1.1 | 62 | W |

Example 16

Preparation of Factor IXa-Compound C Complex

Compound C

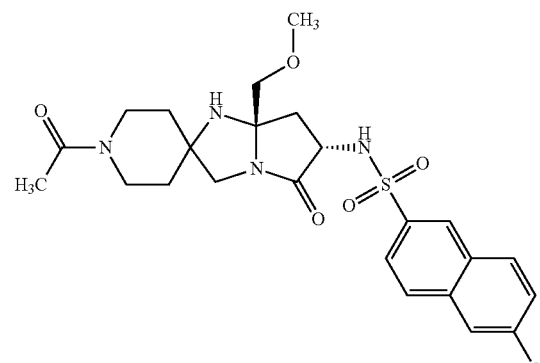

Figure 6:
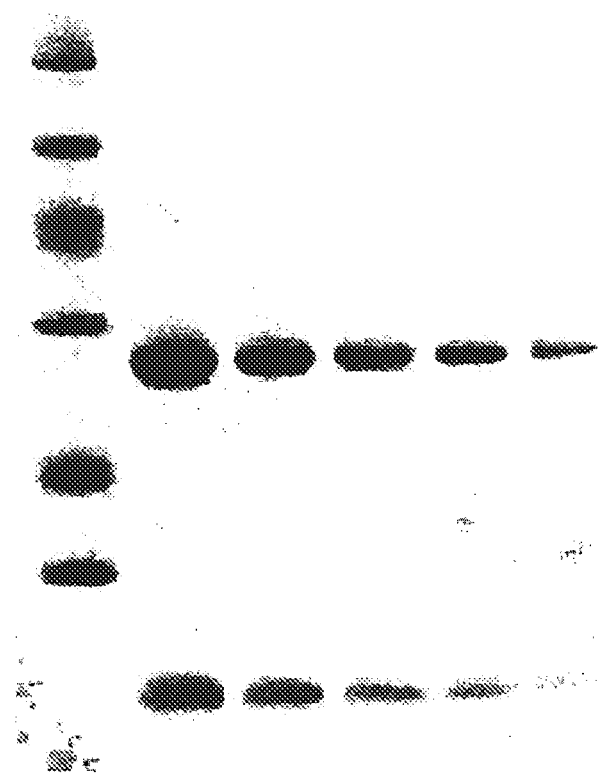
FIG. 6. SDS-PAGE gel analysis of human wild type factor IXa

Compound C was added to a final concentration of 1 mM into 22.5 μL of fIXa at 0.23 mg/mL. (6.4 μM). The final DMSO concentration was 1%. The complex was rotated on a nutator for 2-18 hours at 2° C. The sample was clarified by low speed centrifugation followed by a 52 fold concentration step using centrifugation with a 5000 Molecular Weight Cut Off Millipore Ultrafree micro concentrator to 10-12 mg/ml. Dynamic light scattering used to measure the aggregation state (D'Arcy, A., *Acta Cryst* D50:469-471 (1994)) of the concentrated fIXa-Compound C complex was consistent with a 33K MW protein which is a monodisperse monomer in solution. SDS PAGE analysis showed no visible signs of degradation four days post setup (FIG. 6). Dynamic light scattering and SDS PAGE results were consistent with a stable monodisperse fIXa complex suitable for crystallization screening.

Example 17

Crystallization of factor IXa-Compound C Complex

The factor IXa-Compound C complex from Example 16 was crystallized using a hanging-drop vapor diffusion method. The protein (0.5 µl; 10 mg/ml) in 25 mM Tris, pH 8.0, 0.15 M sodium chloride, 1% DMSO buffer was mixed with an equal volume of precipitant solution containing 14% PEG 6000 (v/v), 0.1 M citric acid, pH 5.67, placed on the underside of a siliconized Teflon coverslip and sealed in close proximity to 0.08 mL of the precipitant solution. Crystallization plates were incubated at 4° C.; orthorhombic crystals (0.01×0.05 mm) grew over 1-9 days. FIG. 7 shows a photomicrograph of the factor IXa-Compound C complex crystals grown for 8 days, at 70× magnification.

Example 18

Crystallographic Analysis of Factor IXa-Compound C Complex

Prior to data collection crystals were harvested and cryo-protected for 1-3 minutes in the crystallization solution containing 25% glycerol. The crystals were then frozen directly into liquid nitrogen. X-ray diffraction was collected using a Rigaku generator equipped with a Raxis 4 detector. Data were integrated and scaled using the HKL package.

| Data Collection Statistics | |
|---|---|
| Resolution | 35.0-2.3 Å |
| No. of collected reflections | 176165 |
| No. of unique reflections (F >= 0) | 22255 |
| R-sym | 7.8% |
| Percent of theoretical (I/s >= 1) | 97.7% |
| Unit Cell | a = 99.2 Å, b = 99.2 Å, c = 97.3 Å, α = β = γ = 90° |
| Space Group | P4$_3$2$_1$2 |
| Asymmetric unit | 1 molecule |

Example 19

Structure Determination of Factor IXa-Compound C Complex

The crystal structure was solved using Rigid Body refinement with the starting model 1RFN. Refinement was done using the program AUTOBUSTER (Global Phasing Limited.).

| | |
|---|---|
| Number of reflections | 20978 |
| Resolution limits | 15.2-2.30 Å |
| Completeness for range | 94.9% |
| FREE R TEST SET COUNT & SIZE | 1001 (4.8%) |
| Number of protein atoms | 2188 |
| Number of solvent atoms | 95 |
| R-factor | 0.203 |
| R-free | 0.253 |
| RMSD bond length | 0.010 Å |
| RMSD bond angles | 1.24° |

The following table contains one line for each atom in one Factor IXa monomer. The columns are: 1) residue number, 2) I-letter amino acid code, 3) atom name, 4) x-coordinate, 5) y-coordinate, 6) z-coordinate, 7) B-factor, 8) Chain ID. (Amino Acid Code X are Calcium or Citrate, Z is Compound C and O for water) The numbering scheme is based on chymotrypsin. Note: B fractors greater than 100 appear as 0 in column 7.

TABLE 5

Coordinates of Factor IXa co-crystal Compound C complex

| | | | | | | | |
|---|---|---|---|---|---|---|---|
| 16 | V | N | −18.4 | −27.1 | −26.8 | 33 | A |
| 16 | V | CA | −18.7 | −28.4 | −27.3 | 33 | A |
| 16 | V | C | −19.5 | −28.5 | −28.6 | 39 | A |
| 16 | V | O | −20.7 | −28.1 | −28.6 | 40 | A |
| 16 | V | CB | −19.3 | −29.3 | −26.2 | 35 | A |
| 16 | V | CG1 | −19.6 | −30.7 | −26.7 | 34 | A |
| 16 | V | CG2 | −18.5 | −29.3 | −24.9 | 34 | A |
| 17 | V | N | −18.9 | −29.0 | −29.6 | 37 | A |
| 17 | V | CA | −19.6 | −29.1 | −30.9 | 36 | A |
| 17 | V | C | −20.1 | −30.6 | −31.0 | 40 | A |
| 17 | V | O | −19.4 | −31.5 | −30.8 | 38 | A |
| 17 | V | CB | −18.6 | −28.9 | −32.1 | 39 | A |
| 17 | V | CG1 | −19.4 | −29.2 | −33.4 | 37 | A |
| 17 | V | CG2 | −18.1 | −27.4 | −32.1 | 39 | A |
| 18 | G | N | −21.4 | −30.7 | −31.4 | 40 | A |
| 18 | G | CA | −22.0 | −32.0 | −31.6 | 40 | A |
| 18 | G | C | −22.4 | −32.7 | −30.4 | 43 | A |
| 18 | G | O | −22.6 | −33.9 | −30.3 | 42 | A |
| 19 | G | N | −22.6 | −31.9 | −29.3 | 39 | A |
| 19 | G | CA | −23.0 | −32.4 | −28.0 | 39 | A |
| 19 | G | C | −24.5 | −32.3 | −27.7 | 43 | A |
| 19 | G | O | −25.4 | −32.1 | −28.6 | 43 | A |
| 20 | E | N | −24.9 | −32.4 | −26.4 | 39 | A |
| 20 | E | CA | −26.2 | −32.4 | −26.0 | 38 | A |
| 20 | E | C | −26.2 | −31.5 | −24.7 | 43 | A |
| 20 | E | O | −25.2 | −31.4 | −24.0 | 43 | A |
| 20 | E | CB | −26.6 | −33.8 | −25.4 | 40 | A |
| 20 | E | CG | −27.3 | −34.7 | −26.4 | 52 | A |
| 20 | E | CD | −27.4 | −36.1 | −25.8 | 81 | A |
| 20 | E | OE1 | −26.4 | −36.8 | −25.7 | 65 | A |
| 20 | E | OE2 | −28.6 | −36.4 | −25.5 | 80 | A |
| 21 | D | N | −27.4 | −31.0 | −24.4 | 41 | A |
| 21 | D | CA | −27.6 | −30.2 | −23.2 | 42 | A |
| 21 | D | C | −27.4 | −31.1 | −22.0 | 45 | A |
| 21 | D | O | −28.1 | −32.1 | −21.9 | 43 | A |
| 21 | D | CB | −29.0 | −29.6 | −23.2 | 44 | A |
| 21 | D | CG | −29.2 | −28.4 | −24.1 | 49 | A |
| 21 | D | OD1 | −30.2 | −27.7 | −23.9 | 53 | A |
| 21 | D | OD2 | −28.3 | −28.1 | −25.0 | 47 | A |
| 22 | A | N | −26.7 | −30.6 | −21.0 | 42 | A |
| 22 | A | CA | −26.6 | −31.4 | −19.7 | 42 | A |
| 22 | A | C | −27.9 | −31.1 | −19.0 | 45 | A |
| 22 | A | O | −28.5 | −30.0 | −19.2 | 43 | A |
| 22 | A | CB | −25.4 | −30.9 | −18.9 | 43 | A |
| 23 | K | N | −28.4 | −31.9 | −18.1 | 42 | A |
| 23 | K | CA | −29.5 | −31.7 | −17.2 | 42 | A |
| 23 | K | C | −28.9 | −31.0 | −16.0 | 47 | A |
| 23 | K | O | −27.8 | −31.2 | −15.6 | 46 | A |
| 23 | K | CB | −30.2 | −33.0 | −16.8 | 44 | A |
| 23 | K | CG | −31.2 | −33.5 | −17.8 | 54 | A |
| 23 | K | CD | −31.6 | −34.9 | −17.5 | 64 | A |
| 23 | K | CE | −32.5 | −35.5 | −18.5 | 77 | A |
| 23 | K | NZ | −32.6 | −37.0 | −18.3 | 85 | A |
| 24 | P | N | −29.7 | −30.2 | −15.2 | 42 | A |
| 24 | P | CA | −29.2 | −29.6 | −14.0 | 40 | A |
| 24 | P | C | −28.6 | −30.7 | −13.1 | 41 | A |

TABLE 5-continued

Coordinates of Factor IXa co-crystal Compound C complex

| | | | | | | |
|---|---|---|---|---|---|---|
| 24 | P | O | −29.1 | −31.8 | −13.0 | 39 A |
| 24 | P | CB | −30.4 | −29.0 | −13.3 | 41 A |
| 24 | P | CG | −31.3 | −28.7 | −14.4 | 45 A |
| 24 | P | CD | −31.1 | −29.7 | −15.5 | 42 A |
| 25 | G | N | −27.4 | −30.4 | −12.5 | 37 A |
| 25 | G | CA | −26.7 | −31.4 | −11.6 | 36 A |
| 25 | G | C | −26.2 | −32.7 | −12.3 | 37 A |
| 25 | G | O | −25.9 | −33.6 | −11.6 | 37 A |
| 26 | Q | N | −26.1 | −32.7 | −13.6 | 32 A |
| 26 | Q | CA | −25.6 | −33.8 | −14.3 | 33 A |
| 26 | Q | C | −24.1 | −33.9 | −14.3 | 37 A |
| 26 | Q | O | −23.5 | −35.0 | −14.3 | 36 A |
| 26 | Q | CB | −26.1 | −33.8 | −15.8 | 34 A |
| 26 | Q | CG | −25.8 | −35.1 | −16.5 | 31 A |
| 26 | Q | CD | −26.4 | −35.1 | −17.9 | 42 A |
| 26 | Q | OE1 | −27.3 | −34.4 | −18.3 | 39 A |
| 26 | Q | NE2 | −25.9 | −36.1 | −18.7 | 28 A |
| 27 | F | N | −23.4 | −32.7 | −14.2 | 32 A |
| 27 | F | CA | −21.9 | −32.6 | −14.2 | 30 A |
| 27 | F | C | −21.6 | −31.7 | −13.1 | 31 A |
| 27 | F | O | −21.0 | −30.6 | −13.3 | 30 A |
| 27 | F | CB | −21.3 | −32.2 | −15.5 | 30 A |
| 27 | F | CG | −21.6 | −33.1 | −16.6 | 31 A |
| 27 | F | CD1 | −22.8 | −32.9 | −17.4 | 32 A |
| 27 | F | CD2 | −20.9 | −34.3 | −16.8 | 33 A |
| 27 | F | CE1 | −23.2 | −33.8 | −18.3 | 33 A |
| 27 | F | CE2 | −21.2 | −35.2 | −17.8 | 36 A |
| 27 | F | CZ | −22.4 | −35.0 | −18.6 | 33 A |
| 28 | P | N | −21.9 | −32.0 | −11.8 | 28 A |
| 28 | P | CA | −21.8 | −31.1 | −10.7 | 27 A |
| 28 | P | C | −20.4 | −30.7 | −10.3 | 32 A |
| 28 | P | O | −20.2 | −29.7 | −9.6 | 32 A |
| 28 | P | CB | −22.5 | −31.9 | −9.6 | 27 A |
| 28 | P | CG | −22.4 | −33.4 | −10.0 | 32 A |
| 28 | P | CD | −22.2 | −33.4 | −11.5 | 28 A |
| 29 | W | N | −19.4 | −31.4 | −10.9 | 28 A |
| 29 | W | CA | −18.0 | −31.0 | −10.6 | 27 A |
| 29 | W | C | −17.5 | −29.9 | −11.6 | 27 A |
| 29 | W | O | −16.4 | −29.4 | −11.4 | 25 A |
| 29 | W | CB | −17.1 | −32.2 | −10.8 | 25 A |
| 29 | W | CG | −17.5 | −33.0 | −12.0 | 26 A |
| 29 | W | CD1 | −17.0 | −32.8 | −13.3 | 28 A |
| 29 | W | CD2 | −18.3 | −34.1 | −12.0 | 26 A |
| 29 | W | NE1 | −17.6 | −33.8 | −14.1 | 28 A |
| 29 | W | CE2 | −18.4 | −34.6 | −13.3 | 30 A |
| 29 | W | CE3 | −19.1 | −34.8 | −11.0 | 28 A |
| 29 | W | CZ2 | −19.2 | −35.7 | −13.7 | 29 A |
| 29 | W | CZ3 | −19.9 | −35.9 | −11.4 | 29 A |
| 29 | W | CH2 | −19.9 | −36.3 | −12.7 | 29 A |
| 30 | Q | N | −18.3 | −29.7 | −12.6 | 26 A |
| 30 | Q | CA | −18.0 | −28.7 | −13.7 | 28 A |
| 30 | Q | C | −18.0 | −27.3 | −13.2 | 34 A |
| 30 | Q | O | −18.9 | −26.9 | −12.4 | 36 A |
| 30 | Q | CB | −19.0 | −28.9 | −14.8 | 30 A |
| 30 | Q | CG | −18.8 | −27.8 | −16.0 | 27 A |
| 30 | Q | CD | −17.6 | −28.1 | −16.9 | 33 A |
| 30 | Q | OE1 | −16.8 | −27.1 | −17.2 | 30 A |
| 30 | Q | NE2 | −17.4 | −29.3 | −17.3 | 24 A |
| 31 | V | N | −17.0 | −26.5 | −13.6 | 30 A |
| 31 | V | CA | −17.0 | −25.0 | −13.3 | 28 A |
| 31 | V | C | −16.7 | −24.3 | −14.5 | 32 A |
| 31 | V | O | −16.1 | −24.8 | −15.5 | 28 A |
| 31 | V | CB | −16.2 | −24.6 | −12.0 | 29 A |
| 31 | V | CG1 | −16.6 | −25.4 | −10.8 | 29 A |
| 31 | V | CG2 | −14.7 | −24.7 | −12.3 | 28 A |
| 32 | V | N | −17.0 | −23.0 | −14.5 | 31 A |
| 32 | V | CA | −16.7 | −22.1 | −15.6 | 31 A |
| 32 | V | C | −15.9 | −21.0 | −15.1 | 35 A |
| 32 | V | O | −16.0 | −20.6 | −13.9 | 33 A |
| 32 | V | CB | −18.0 | −21.6 | −16.3 | 36 A |
| 32 | V | CG1 | −18.8 | −20.8 | −15.3 | 35 A |
| 32 | V | CG2 | −17.7 | −20.7 | −17.5 | 36 A |
| 33 | L | N | −14.9 | −20.5 | −15.9 | 34 A |
| 33 | L | CA | −14.0 | −19.5 | −15.4 | 33 A |
| 33 | L | C | −14.4 | −18.2 | −16.2 | 40 A |
| 33 | L | O | −14.6 | −18.2 | −17.4 | 39 A |
| 33 | L | CB | −12.6 | −19.8 | −15.7 | 32 A |
| 33 | L | CG | −12.0 | −21.1 | −15.2 | 35 A |
| 33 | L | CD1 | −10.5 | −21.0 | −15.3 | 34 A |
| 33 | L | CD2 | −12.5 | −21.5 | −13.8 | 33 A |
| 34 | N | N | −14.5 | −17.1 | −15.4 | 38 A |
| 34 | N | CA | −14.8 | −15.8 | −16.0 | 38 A |
| 34 | N | C | −13.7 | −14.8 | −15.6 | 47 A |
| 34 | N | O | −13.1 | −14.8 | −14.5 | 46 A |
| 34 | N | CB | −16.1 | −15.2 | −15.4 | 30 A |
| 34 | N | CG | −17.3 | −16.1 | −15.6 | 45 A |
| 34 | N | OD1 | −17.5 | −16.7 | −16.7 | 48 A |
| 34 | N | ND2 | −18.2 | −16.2 | −14.6 | 40 A |
| 35 | G | N | −13.3 | −14.0 | −16.6 | 48 A |
| 35 | G | CA | −12.3 | −12.9 | −16.5 | 50 A |
| 35 | G | C | −12.8 | −11.7 | −17.2 | 59 A |
| 35 | G | O | −14.0 | −11.3 | −17.0 | 59 A |
| 36 | K | N | −11.9 | −11.0 | −18.1 | 59 A |
| 36 | K | CA | −12.3 | −10.0 | −18.9 | 60 A |
| 36 | K | C | −13.4 | −10.6 | −19.9 | 63 A |
| 36 | K | O | −14.3 | −9.8 | −20.2 | 65 A |
| 36 | K | CB | −11.0 | −9.6 | −19.8 | 63 A |
| 36 | K | CG | −11.3 | −8.8 | −21.0 | 84 A |
| 36 | K | CD | −10.5 | −7.5 | −21.0 | 96 A |
| 36 | K | CE | −10.8 | −6.6 | −22.1 | 0 A |
| 36 | K | NZ | −9.8 | −6.6 | −23.1 | 0 A |
| 38 | V | N | −13.2 | −11.8 | −20.3 | 55 A |
| 38 | V | CA | −14.2 | −12.5 | −21.1 | 52 A |
| 38 | V | C | −14.8 | −13.6 | −20.1 | 50 A |
| 38 | V | O | −14.2 | −14.2 | −19.4 | 48 A |
| 38 | V | CB | −13.4 | −13.2 | −22.3 | 56 A |
| 38 | V | CG1 | −14.2 | −14.3 | −22.9 | 55 A |
| 38 | V | CG2 | −13.2 | −12.1 | −23.4 | 55 A |
| 39 | D | N | −16.1 | −13.6 | −20.2 | 44 A |
| 39 | D | CA | −16.9 | −14.6 | −19.4 | 43 A |
| 39 | D | C | −16.8 | −15.9 | −20.1 | 45 A |
| 39 | D | O | −16.7 | −16.0 | −21.3 | 43 A |
| 39 | D | CB | −18.3 | −14.2 | −19.2 | 45 A |
| 39 | D | CG | −18.4 | −13.2 | −18.0 | 64 A |
| 39 | D | OD1 | −17.5 | −12.4 | −17.8 | 66 A |
| 39 | D | OD2 | −19.4 | −13.4 | −17.2 | 80 A |
| 40 | A | N | −16.8 | −17.0 | −19.3 | 39 A |
| 40 | A | CA | −16.7 | −18.4 | −19.8 | 37 A |
| 40 | A | C | −15.6 | −18.6 | −20.8 | 38 A |
| 40 | A | O | −15.9 | −19.2 | −21.9 | 40 A |
| 40 | A | CB | −18.1 | −18.8 | −20.5 | 38 A |
| 41 | F | N | −14.4 | −18.2 | −20.5 | 33 A |
| 41 | F | CA | −13.3 | −18.3 | −21.4 | 32 A |
| 41 | F | C | −12.6 | −19.7 | −21.3 | 39 A |
| 41 | F | O | −11.9 | −20.1 | −22.2 | 40 A |
| 41 | F | CB | −12.2 | −17.2 | −21.2 | 32 A |
| 41 | F | CG | −11.5 | −17.3 | −19.9 | 32 A |
| 41 | F | CD1 | −12.0 | −16.7 | −18.7 | 34 A |
| 41 | F | CD2 | −10.3 | −17.9 | −19.8 | 31 A |
| 41 | F | CE1 | −11.4 | −16.8 | −17.5 | 33 A |
| 41 | F | CE2 | −9.6 | −18.0 | −18.6 | 32 A |
| 41 | F | CZ | −10.2 | −17.5 | −17.4 | 30 A |
| 42 | C | N | −12.9 | −20.4 | −20.2 | 35 A |
| 42 | C | CA | −12.3 | −21.7 | −20.0 | 36 A |
| 42 | C | C | −13.2 | −22.5 | −19.0 | 37 A |
| 42 | C | O | −14.0 | −21.9 | −18.3 | 35 A |
| 42 | C | CB | −10.9 | −21.6 | −19.3 | 38 A |
| 42 | C | SG | −9.5 | −21.6 | −20.5 | 43 A |
| 43 | G | N | −12.9 | −23.8 | −18.8 | 27 A |
| 43 | G | CA | −13.6 | −24.5 | −17.8 | 26 A |
| 43 | G | C | −12.6 | −24.9 | −16.7 | 27 A |
| 43 | G | O | −11.4 | −24.6 | −16.8 | 28 A |
| 44 | G | N | −13.1 | −25.7 | −15.7 | 22 A |
| 44 | G | CA | −12.3 | −26.2 | −14.6 | 21 A |
| 44 | G | C | −13.2 | −27.3 | −14.0 | 26 A |
| 44 | G | O | −14.4 | −27.5 | −14.4 | 24 A |
| 45 | S | N | −12.6 | −28.0 | −13.0 | 23 A |
| 45 | S | CA | −13.3 | −29.1 | −12.3 | 24 A |
| 45 | S | C | −13.0 | −28.9 | −10.8 | 28 A |
| 45 | S | O | −11.9 | −28.5 | −10.5 | 25 A |
| 45 | S | CB | −12.7 | −30.5 | −12.6 | 29 A |
| 45 | S | OG | −12.9 | −30.9 | −14.0 | 35 A |
| 46 | I | N | −14.0 | −29.3 | −10.0 | 27 A |
| 46 | I | CA | −13.9 | −29.2 | −8.5 | 25 A |
| 46 | I | C | −13.0 | −30.4 | −8.0 | 29 A |
| 46 | I | O | −13.4 | −31.5 | −8.1 | 28 A |

TABLE 5-continued

Coordinates of Factor IXa co-crystal Compound C complex

| | | | | | | |
|---|---|---|---|---|---|---|
| 46 | I | CB | −15.3 | −29.2 | −7.9 | 28 A |
| 46 | I | CG1 | −16.1 | −28.0 | −8.4 | 28 A |
| 46 | I | CG2 | −15.2 | −29.1 | −6.3 | 26 A |
| 46 | I | CD1 | −17.4 | −27.9 | −7.8 | 28 A |
| 47 | V | N | −11.9 | −30.1 | −7.4 | 25 A |
| 47 | V | CA | −11.1 | −31.1 | −6.7 | 25 A |
| 47 | V | C | −11.6 | −31.2 | −5.3 | 30 A |
| 47 | V | O | −11.9 | −32.3 | −4.8 | 31 A |
| 47 | V | CB | −9.6 | −30.7 | −6.7 | 26 A |
| 47 | V | CG1 | −8.8 | −31.7 | −5.9 | 25 A |
| 47 | V | CG2 | −9.0 | −30.6 | −8.1 | 24 A |
| 48 | N | N | −11.9 | −30.1 | −4.6 | 29 A |
| 48 | N | CA | −12.5 | −30.1 | −3.3 | 28 A |
| 48 | N | C | −13.2 | −28.7 | −3.1 | 34 A |
| 48 | N | O | −13.3 | −27.9 | −4.0 | 35 A |
| 48 | N | CB | −11.6 | −30.6 | −2.2 | 22 A |
| 48 | N | CG | −10.4 | −29.7 | −2.0 | 36 A |
| 48 | N | OD1 | −10.5 | −28.5 | −2.2 | 34 A |
| 48 | N | ND2 | −9.3 | −30.3 | −1.6 | 30 A |
| 49 | E | N | −13.7 | −28.5 | −1.9 | 32 A |
| 49 | E | CA | −14.4 | −27.2 | −1.6 | 32 A |
| 49 | E | C | −13.6 | −25.9 | −1.8 | 34 A |
| 49 | E | O | −14.2 | −24.8 | −2.0 | 31 A |
| 49 | E | CB | −14.9 | −27.2 | −0.1 | 33 A |
| 49 | E | CG | −15.8 | −28.4 | 0.3 | 56 A |
| 49 | E | CD | −15.0 | −29.7 | 0.9 | 87 A |
| 49 | E | OE1 | −15.2 | −30.0 | 2.1 | 88 A |
| 49 | E | OE2 | −14.3 | −30.4 | 0.1 | 53 A |
| 50 | K | N | −12.3 | −26.0 | −1.8 | 31 A |
| 50 | K | CA | −11.4 | −24.8 | −1.9 | 30 A |
| 50 | K | C | −10.6 | −24.8 | −3.2 | 33 A |
| 50 | K | O | −9.9 | −23.8 | −3.5 | 33 A |
| 50 | K | CB | −10.5 | −24.7 | −0.7 | 33 A |
| 50 | K | CG | −11.1 | −24.0 | 0.5 | 41 A |
| 50 | K | CD | −11.0 | −22.5 | 0.4 | 38 A |
| 50 | K | CE | −9.6 | −22.0 | 0.9 | 50 A |
| 50 | K | NZ | −9.5 | −20.5 | 0.9 | 60 A |
| 51 | W | N | −10.6 | −25.9 | −4.0 | 29 A |
| 51 | W | CA | −9.7 | −26.1 | −5.1 | 28 A |
| 51 | W | C | −10.3 | −26.5 | −6.4 | 29 A |
| 51 | W | O | −11.2 | −27.4 | −6.4 | 25 A |
| 51 | W | CB | −8.6 | −27.0 | −4.8 | 26 A |
| 51 | W | CG | −7.7 | −26.5 | −3.8 | 27 A |
| 51 | W | CD1 | −7.8 | −26.8 | −2.4 | 30 A |
| 51 | W | CD2 | −6.5 | −25.7 | −3.9 | 26 A |
| 51 | W | NE1 | −6.8 | −26.2 | −1.7 | 29 A |
| 51 | W | CE2 | −6.0 | −25.5 | −2.6 | 30 A |
| 51 | W | CE3 | −5.8 | −25.2 | −5.0 | 27 A |
| 51 | W | CZ2 | −4.8 | −24.7 | −2.4 | 28 A |
| 51 | W | CZ3 | −4.7 | −24.4 | −4.8 | 29 A |
| 51 | W | CH2 | −4.2 | −24.2 | −3.5 | 29 A |
| 52 | I | N | −9.9 | −25.9 | −7.5 | 27 A |
| 52 | I | CA | −10.3 | −26.1 | −8.9 | 26 A |
| 52 | I | C | −9.1 | −26.6 | −9.6 | 28 A |
| 52 | I | O | −8.0 | −26.0 | −9.4 | 29 A |
| 52 | I | CB | −10.9 | −24.8 | −9.6 | 28 A |
| 52 | I | CG1 | −12.0 | −24.2 | −8.8 | 28 A |
| 52 | I | CG2 | −11.3 | −25.1 | −11.0 | 25 A |
| 52 | I | CD1 | −13.2 | −25.2 | −8.6 | 26 A |
| 53 | V | N | −9.2 | −27.5 | −10.5 | 24 A |
| 53 | V | CA | −8.1 | −27.9 | −11.4 | 24 A |
| 53 | V | C | −8.5 | −27.4 | −12.8 | 29 A |
| 53 | V | O | −9.6 | −27.6 | −13.2 | 29 A |
| 53 | V | CB | −7.7 | −29.5 | −11.3 | 27 A |
| 53 | V | CG1 | −6.4 | −29.8 | −12.1 | 26 A |
| 53 | V | CG2 | −8.9 | −30.4 | −11.8 | 25 A |
| 54 | T | N | −7.5 | −26.9 | −13.5 | 25 A |
| 54 | T | CA | −7.8 | −26.4 | −14.8 | 23 A |
| 54 | T | C | −6.6 | −26.5 | −15.7 | 24 A |
| 54 | T | O | −5.6 | −27.2 | −15.3 | 22 A |
| 54 | T | CB | −8.3 | −24.9 | −14.7 | 26 A |
| 54 | T | OG1 | −8.8 | −24.4 | −16.0 | 29 A |
| 54 | T | CG2 | −7.2 | −24.0 | −14.2 | 26 A |
| 55 | A | N | −6.5 | −25.9 | −16.9 | 22 A |
| 55 | A | CA | −5.3 | −26.0 | −17.7 | 22 A |
| 55 | A | C | −4.5 | −24.7 | −17.4 | 28 A |
| 55 | A | O | −5.0 | −23.7 | −17.1 | 27 A |
| 55 | A | CB | −5.7 | −26.0 | −19.2 | 22 A |
| 56 | A | N | −3.2 | −24.9 | −17.4 | 27 A |
| 56 | A | CA | −2.3 | −23.8 | −17.1 | 26 A |
| 56 | A | C | −2.4 | −22.7 | −18.1 | 32 A |
| 56 | A | O | −2.3 | −21.5 | −17.8 | 32 A |
| 56 | A | CB | −0.8 | −24.3 | −16.9 | 26 A |
| 57 | H | N | −2.5 | −23.0 | −19.4 | 30 A |
| 57 | H | CA | −2.6 | −22.0 | −20.4 | 30 A |
| 57 | H | C | −3.8 | −21.1 | −20.3 | 37 A |
| 57 | H | O | −3.9 | −20.1 | −21.0 | 38 A |
| 57 | H | CB | −2.5 | −22.6 | −21.8 | 30 A |
| 57 | H | CG | −3.9 | −23.2 | −22.3 | 34 A |
| 57 | H | ND1 | −4.1 | −24.5 | −22.3 | 37 A |
| 57 | H | CD2 | −5.0 | −22.5 | −22.7 | 36 A |
| 57 | H | CE1 | −5.4 | −24.7 | −22.7 | 35 A |
| 57 | H | NE2 | −5.9 | −23.5 | −22.9 | 36 A |
| 58 | C | N | −4.7 | −21.4 | −19.4 | 35 A |
| 58 | C | CA | −5.9 | −20.6 | −19.2 | 36 A |
| 58 | C | C | −5.7 | −19.6 | −18.2 | 43 A |
| 58 | C | O | −6.5 | −18.7 | −18.0 | 43 A |
| 58 | C | CB | −7.1 | −21.5 | −18.6 | 37 A |
| 58 | C | SG | −7.9 | −22.6 | −19.8 | 43 A |
| 59 | V | N | −4.7 | −19.7 | −17.3 | 40 A |
| 59 | V | CA | −4.6 | −18.9 | −16.2 | 41 A |
| 59 | V | C | −3.2 | −18.3 | −16.0 | 56 A |
| 59 | V | O | −2.2 | −18.6 | −16.7 | 59 A |
| 59 | V | CB | −5.1 | −19.6 | −14.9 | 42 A |
| 59 | V | CG1 | −6.6 | −19.9 | −15.0 | 41 A |
| 59 | V | CG2 | −4.4 | −21.0 | −14.7 | 40 A |
| 60 | E | N | −3.1 | −17.3 | −15.1 | 59 A |
| 60 | E | CA | −1.8 | −16.6 | −14.9 | 62 A |
| 60 | E | C | −1.9 | −15.7 | −13.6 | 69 A |
| 60 | E | O | −2.7 | −14.7 | −13.6 | 66 A |
| 60 | E | CB | −1.3 | −15.9 | −16.1 | 63 A |
| 60 | E | CG | −2.0 | −14.6 | −16.3 | 72 A |
| 60 | E | CD | −1.7 | −14.0 | −17.7 | 88 A |
| 60 | E | OE1 | −0.5 | −13.9 | −18.0 | 61 A |
| 60 | E | OE2 | −2.7 | −13.8 | −18.5 | 90 A |
| 60A | T | N | −1.1 | −16.0 | −12.6 | 69 A |
| 60A | T | CA | −0.9 | −15.3 | −11.4 | 69 A |
| 60A | T | C | −0.8 | −13.8 | −11.8 | 75 A |
| 60A | T | O | 0.1 | −13.4 | −12.4 | 76 A |
| 60A | T | CB | 0.3 | −15.8 | −10.6 | 79 A |
| 60A | T | OG1 | 0.4 | −17.2 | −10.6 | 74 A |
| 60A | T | CG2 | 0.3 | −15.2 | −9.2 | 78 A |
| 61 | G | N | −1.9 | −13.0 | −11.4 | 71 A |
| 61 | G | CA | −1.9 | −11.6 | −11.7 | 70 A |
| 61 | G | C | −3.2 | −11.2 | −12.4 | 72 A |
| 61 | G | O | −3.8 | −10.1 | −12.1 | 74 A |
| 62 | V | N | −3.7 | −12.0 | −13.3 | 65 A |
| 62 | V | CA | −5.0 | −11.8 | −14.0 | 62 A |
| 62 | V | C | −6.1 | −12.3 | −13.1 | 60 A |
| 62 | V | O | −6.1 | −13.5 | −12.7 | 59 A |
| 62 | V | CB | −5.1 | −12.4 | −15.4 | 66 A |
| 62 | V | CG1 | −6.3 | −11.9 | −16.2 | 65 A |
| 62 | V | CG2 | −3.8 | −12.2 | −16.1 | 66 A |
| 63 | K | N | −7.0 | −11.4 | −12.6 | 52 A |
| 63 | K | CA | −8.1 | −11.7 | −11.7 | 49 A |
| 63 | K | C | −9.1 | −12.5 | −12.4 | 49 A |
| 63 | K | O | −9.6 | −12.1 | −13.5 | 49 A |
| 63 | K | CB | −8.7 | −10.4 | −11.1 | 52 A |
| 63 | K | CG | −8.2 | −10.1 | −9.7 | 82 A |
| 63 | K | CD | −6.7 | −10.2 | −9.5 | 98 A |
| 63 | K | CE | −6.3 | −9.4 | −8.3 | 0 A |
| 63 | K | NZ | −5.1 | −10.0 | −7.6 | 0 A |
| 64 | I | N | −9.6 | −13.6 | −11.8 | 43 A |
| 64 | I | CA | −10.6 | −14.4 | −12.4 | 41 A |
| 64 | I | C | −11.6 | −14.9 | −11.3 | 37 A |
| 64 | I | O | −11.2 | −15.0 | −10.2 | 33 A |
| 64 | I | CB | −10.1 | −15.6 | −13.2 | 45 A |
| 64 | I | CG1 | −9.3 | −16.5 | −12.3 | 45 A |
| 64 | I | CG2 | −9.2 | −15.1 | −14.4 | 47 A |
| 64 | I | CD1 | −8.5 | −17.5 | −13.0 | 50 A |
| 65 | T | N | −12.8 | −15.2 | −11.7 | 32 A |
| 65 | T | CA | −13.7 | −15.9 | −10.8 | 32 A |
| 65 | T | C | −14.1 | −17.2 | −11.4 | 36 A |
| 65 | T | O | −14.1 | −17.6 | −12.5 | 33 A |
| 65 | T | CB | −14.9 | −14.9 | −10.5 | 42 A |
| 65 | T | OG1 | −15.6 | −14.6 | −11.7 | 41 A |

TABLE 5-continued

Coordinates of Factor IXa co-crystal Compound C complex

| | | | | | | |
|---|---|---|---|---|---|---|
| 65 | T | CG2 | −14.5 | −13.6 | −9.8 | 40 A |
| 66 | V | N | −14.7 | −18.0 | −10.4 | 34 A |
| 66 | V | CA | −15.1 | −19.3 | −10.8 | 35 A |
| 66 | V | C | −16.6 | −19.4 | −10.4 | 36 A |
| 66 | V | O | −17.0 | −18.9 | −9.3 | 36 A |
| 66 | V | CB | −14.2 | −20.3 | −10.0 | 39 A |
| 66 | V | CG1 | −14.9 | −21.7 | −9.8 | 37 A |
| 66 | V | CG2 | −12.8 | −20.4 | −10.6 | 39 A |
| 67 | V | N | −17.4 | −20.1 | −11.2 | 31 A |
| 67 | V | CA | −18.7 | −20.4 | −10.9 | 30 A |
| 67 | V | C | −19.0 | −21.8 | −10.9 | 35 A |
| 67 | V | O | −19.0 | −22.5 | −12.0 | 36 A |
| 67 | V | CB | −19.7 | −19.6 | −11.8 | 32 A |
| 67 | V | CG1 | −21.2 | −19.8 | −11.3 | 31 A |
| 67 | V | CG2 | −19.3 | −18.1 | −12.0 | 31 A |
| 68 | A | N | −19.4 | −22.4 | −9.8 | 30 A |
| 68 | A | CA | −19.9 | −23.7 | −9.6 | 30 A |
| 68 | A | C | −21.4 | −23.8 | −9.7 | 39 A |
| 68 | A | O | −22.1 | −22.8 | −9.6 | 39 A |
| 68 | A | CB | −19.3 | −24.3 | −8.4 | 30 A |
| 69 | G | N | −22.0 | −25.0 | −9.8 | 37 A |
| 69 | G | CA | −23.4 | −25.2 | −9.9 | 36 A |
| 69 | G | C | −24.1 | −24.5 | −11.0 | 39 A |
| 69 | G | O | −25.3 | −24.2 | −10.8 | 38 A |
| 70 | E | N | −23.4 | −24.2 | −12.1 | 36 A |
| 70 | E | CA | −24.0 | −23.5 | −13.2 | 34 A |
| 70 | E | C | −24.6 | −24.4 | −14.2 | 41 A |
| 70 | E | O | −24.1 | −25.6 | −14.4 | 42 A |
| 70 | E | CB | −22.9 | −22.7 | −13.9 | 34 A |
| 70 | E | CG | −23.3 | −21.8 | −15.0 | 46 A |
| 70 | E | CD | −24.2 | −20.7 | −14.5 | 67 A |
| 70 | E | OE1 | −25.4 | −21.0 | −14.4 | 66 A |
| 70 | E | OE2 | −23.7 | −19.6 | −14.2 | 61 A |
| 71 | H | N | −25.7 | −24.0 | −14.9 | 40 A |
| 71 | H | CA | −26.4 | −24.8 | −15.9 | 41 A |
| 71 | H | C | −26.6 | −24.0 | −17.2 | 47 A |
| 71 | H | O | −25.9 | −24.2 | −18.2 | 47 A |
| 71 | H | CB | −27.7 | −25.3 | −15.3 | 43 A |
| 71 | H | CG | −28.6 | −26.0 | −16.3 | 47 A |
| 71 | H | ND1 | −28.3 | −27.3 | −16.7 | 50 A |
| 71 | H | CD2 | −29.7 | −25.6 | −17.0 | 50 A |
| 71 | H | CE1 | −29.2 | −27.7 | −17.6 | 50 A |
| 71 | H | NE2 | −30.0 | −26.7 | −17.9 | 50 A |
| 72 | N | N | −27.5 | −23.0 | −17.1 | 45 A |
| 72 | N | CA | −27.7 | −22.0 | −18.2 | 46 A |
| 72 | N | C | −27.0 | −20.7 | −17.8 | 52 A |
| 72 | N | O | −27.3 | −20.1 | −16.8 | 51 A |
| 72 | N | CB | −29.2 | −21.8 | −18.2 | 47 A |
| 72 | N | CG | −29.7 | −21.0 | −19.5 | 62 A |
| 72 | N | OD1 | −29.1 | −20.1 | −20.0 | 44 A |
| 72 | N | ND2 | −30.9 | −21.4 | −19.9 | 56 A |
| 73 | I | N | −25.9 | −20.3 | −18.6 | 53 A |
| 73 | I | CA | −25.1 | −19.2 | −18.2 | 55 A |
| 73 | I | C | −25.9 | −17.8 | −18.3 | 63 A |
| 73 | I | O | −25.3 | −16.8 | −17.8 | 62 A |
| 73 | I | CB | −23.7 | −19.1 | −18.8 | 57 A |
| 73 | I | CG1 | −23.7 | −19.4 | −20.3 | 58 A |
| 73 | I | CG2 | −22.7 | −20.0 | −18.2 | 54 A |
| 73 | I | CD1 | −22.5 | −18.9 | −21.1 | 66 A |
| 74 | E | N | −27.1 | −17.8 | −18.8 | 63 A |
| 74 | E | CA | −27.9 | −16.6 | −18.9 | 64 A |
| 74 | E | C | −29.2 | −16.8 | −18.2 | 68 A |
| 74 | E | O | −30.2 | −16.3 | −18.7 | 71 A |
| 74 | E | CB | −28.1 | −16.3 | −20.3 | 65 A |
| 74 | E | CG | −29.1 | −17.3 | −21.0 | 83 A |
| 74 | E | CD | −30.1 | −16.6 | −22.0 | 0 A |
| 74 | E | OE1 | −29.8 | −15.6 | −22.6 | 88 A |
| 74 | E | OE2 | −31.2 | −17.1 | −22.1 | 94 A |
| 75 | E | N | −29.3 | −17.4 | −17.0 | 63 A |
| 75 | E | CA | −30.6 | −17.5 | −16.3 | 62 A |
| 75 | E | C | −30.4 | −18.1 | −14.9 | 69 A |
| 75 | E | O | −30.5 | −19.3 | −14.7 | 72 A |
| 75 | E | CB | −31.6 | −18.4 | −17.2 | 64 A |
| 75 | E | CG | −32.9 | −18.6 | −16.5 | 78 A |
| 75 | E | CD | −33.6 | −19.9 | −17.0 | 0 A |
| 75 | E | OE1 | −33.8 | −20.0 | −18.2 | 0 A |
| 75 | E | OE2 | −34.1 | −20.7 | −16.1 | 0 A |
| 76 | T | N | −30.3 | −17.2 | −13.9 | 63 A |
| 76 | T | CA | −30.1 | −17.5 | −12.5 | 63 A |
| 76 | T | C | −31.0 | −18.7 | −12.1 | 65 A |
| 76 | T | O | −32.3 | −18.6 | −12.2 | 64 A |
| 76 | T | CB | −30.4 | −16.3 | −11.6 | 71 A |
| 76 | T | OG1 | −29.4 | −15.3 | −11.9 | 76 A |
| 76 | T | CG2 | −30.3 | −16.7 | −10.2 | 66 A |
| 77 | E | N | −30.4 | −19.8 | −11.7 | 61 A |
| 77 | E | CA | −31.2 | −21.0 | −11.3 | 60 A |
| 77 | E | C | −31.1 | −21.2 | −9.8 | 63 A |
| 77 | E | O | −31.8 | −22.2 | −9.3 | 61 A |
| 77 | E | CB | −30.7 | −22.2 | −12.1 | 62 A |
| 77 | E | CG | −31.4 | −22.4 | −13.4 | 76 A |
| 77 | E | CD | −30.5 | −22.8 | −14.6 | 88 A |
| 77 | E | OE1 | −29.4 | −22.3 | −14.6 | 61 A |
| 77 | E | OE2 | −31.0 | −23.5 | −15.5 | 81 A |
| 78 | H | N | −30.4 | −20.4 | −9.1 | 59 A |
| 78 | H | CA | −30.3 | −20.5 | −7.7 | 58 A |
| 78 | H | C | −29.4 | −21.6 | −7.1 | 57 A |
| 78 | H | O | −29.4 | −21.9 | −5.9 | 57 A |
| 78 | H | CB | −31.7 | −20.5 | −7.0 | 60 A |
| 78 | H | CG | −32.5 | −19.4 | −7.6 | 65 A |
| 78 | H | ND1 | −32.1 | −18.0 | −7.5 | 67 A |
| 78 | H | CD2 | −33.6 | −19.4 | −8.3 | 67 A |
| 78 | H | CE1 | −33.0 | −17.3 | −8.2 | 67 A |
| 78 | H | NE2 | −33.9 | −18.1 | −8.6 | 67 A |
| 79 | T | N | −28.6 | −22.3 | −8.0 | 48 A |
| 79 | T | CA | −27.7 | −23.3 | −7.7 | 46 A |
| 79 | T | C | −26.3 | −22.9 | −7.8 | 47 A |
| 79 | T | O | −25.4 | −23.6 | −7.4 | 46 A |
| 79 | T | CB | −28.0 | −24.5 | −8.6 | 43 A |
| 79 | T | OG1 | −27.8 | −24.1 | −10.0 | 43 A |
| 79 | T | CG2 | −29.4 | −25.0 | −8.5 | 37 A |
| 80 | E | N | −26.1 | −21.7 | −8.4 | 41 A |
| 80 | E | CA | −24.8 | −21.2 | −8.6 | 41 A |
| 80 | E | C | −24.0 | −20.7 | −7.4 | 43 A |
| 80 | E | O | −24.6 | −20.1 | −6.5 | 43 A |
| 80 | E | CB | −24.8 | −20.1 | −9.7 | 42 A |
| 80 | E | CG | −25.8 | −20.3 | −10.8 | 60 A |
| 80 | E | CD | −27.3 | −20.1 | −10.4 | 76 A |
| 80 | E | OE1 | −27.6 | −19.4 | −9.4 | 68 A |
| 80 | E | OE2 | −28.2 | −20.6 | −11.2 | 69 A |
| 81 | Q | N | −22.7 | −20.9 | −7.4 | 35 A |
| 81 | Q | CA | −21.8 | −20.4 | −6.4 | 33 A |
| 81 | Q | C | −20.6 | −19.8 | −7.0 | 38 A |
| 81 | Q | O | −19.8 | −20.5 | −7.6 | 40 A |
| 81 | Q | CB | −21.4 | −21.6 | −5.5 | 35 A |
| 81 | Q | CG | −22.5 | −22.1 | −4.7 | 29 A |
| 81 | Q | CD | −22.1 | −23.3 | −3.8 | 33 A |
| 81 | Q | OE1 | −21.1 | −23.3 | −3.2 | 31 A |
| 81 | Q | NE2 | −23.0 | −24.2 | −3.7 | 33 A |
| 82 | K | N | −20.5 | −18.5 | −6.8 | 37 A |
| 82 | K | CA | −19.3 | −17.8 | −7.4 | 35 A |
| 82 | K | C | −18.3 | −17.5 | −6.4 | 35 A |
| 82 | K | O | −18.5 | −17.3 | −5.2 | 33 A |
| 82 | K | CB | −19.8 | −16.5 | −8.1 | 36 A |
| 82 | K | CG | −18.7 | −15.5 | −8.5 | 47 A |
| 82 | K | CD | −19.2 | −14.4 | −9.4 | 55 A |
| 82 | K | CE | −19.3 | −13.1 | −8.6 | 56 A |
| 82 | K | NZ | −18.3 | −13.0 | −7.5 | 58 A |
| 83 | R | N | −17.0 | −17.6 | −6.8 | 33 A |
| 83 | R | CA | −15.9 | −17.4 | −5.9 | 31 A |
| 83 | R | C | −14.8 | −16.7 | −6.6 | 32 A |
| 83 | R | O | −14.6 | −16.8 | −7.8 | 31 A |
| 83 | R | CB | −15.3 | −18.7 | −5.3 | 28 A |
| 83 | R | CG | −16.3 | −19.5 | −4.5 | 35 A |
| 83 | R | CD | −16.6 | −18.9 | −3.2 | 30 A |
| 83 | R | NE | −17.5 | −19.8 | −2.4 | 28 A |
| 83 | R | CZ | −18.8 | −19.7 | −2.4 | 41 A |
| 83 | R | NH1 | −19.5 | −18.9 | −3.2 | 28 A |
| 83 | R | NH2 | −19.5 | −20.6 | −1.6 | 24 A |
| 84 | N | N | −13.9 | −16.0 | −5.8 | 29 A |
| 84 | N | CA | −12.8 | −15.4 | −6.4 | 29 A |
| 84 | N | C | −11.6 | −16.3 | −6.2 | 34 A |
| 84 | N | O | −11.5 | −17.0 | −5.2 | 31 A |
| 84 | N | CB | −12.5 | −14.0 | −5.7 | 30 A |
| 84 | N | CG | −13.5 | −13.0 | −5.9 | 52 A |
| 84 | N | OD1 | −14.4 | −13.1 | −6.7 | 50 A |
| 84 | N | ND2 | −13.5 | −12.0 | −5.0 | 40 A |

TABLE 5-continued

Coordinates of Factor IXa co-crystal Compound C complex

| | | | | | | |
|---|---|---|---|---|---|---|
| 85 | V | N | −10.7 | −16.3 | −7.2 | 33 A |
| 85 | V | CA | −9.5 | −17.1 | −7.1 | 31 A |
| 85 | V | C | −8.5 | −16.3 | −6.3 | 35 A |
| 85 | V | O | −8.1 | −15.2 | −6.7 | 37 A |
| 85 | V | CB | −9.0 | −17.4 | −8.6 | 31 A |
| 85 | V | CG1 | −7.6 | −18.0 | −8.5 | 29 A |
| 85 | V | CG2 | −10.0 | −18.3 | −9.3 | 30 A |
| 86 | I | N | −8.0 | −16.8 | −5.2 | 34 A |
| 86 | I | CA | −7.0 | −16.1 | −4.4 | 33 A |
| 86 | I | C | −5.6 | −16.6 | −4.6 | 41 A |
| 86 | I | O | −4.6 | −16.0 | −4.1 | 42 A |
| 86 | I | CB | −7.3 | −16.1 | −2.9 | 35 A |
| 86 | I | CG1 | −7.3 | −17.6 | −2.5 | 34 A |
| 86 | I | CG2 | −8.6 | −15.4 | −2.6 | 34 A |
| 86 | I | CD1 | −7.2 | −17.7 | −0.9 | 32 A |
| 87 | R | N | −5.5 | −17.6 | −5.4 | 39 A |
| 87 | R | CA | −4.1 | −18.3 | −5.7 | 38 A |
| 87 | R | C | −4.1 | −19.2 | −6.9 | 40 A |
| 87 | R | O | −5.1 | −20.0 | −7.1 | 37 A |
| 87 | R | CB | −3.6 | −18.9 | −4.4 | 36 A |
| 87 | R | CG | −2.3 | −19.5 | −4.5 | 42 A |
| 87 | R | CD | −1.8 | −19.9 | −3.1 | 48 A |
| 87 | R | NE | −0.6 | −20.7 | −3.0 | 58 A |
| 87 | R | CZ | −0.6 | −21.8 | −2.2 | 73 A |
| 87 | R | NH1 | −1.6 | −22.1 | −1.4 | 56 A |
| 87 | R | NH2 | 0.6 | −22.5 | −2.2 | 53 A |
| 88 | I | N | −3.1 | −19.1 | −7.7 | 38 A |
| 88 | I | CA | −3.0 | −19.9 | −8.9 | 36 A |
| 88 | I | C | −1.7 | −20.7 | −8.7 | 39 A |
| 88 | I | O | −0.7 | −20.2 | −8.4 | 39 A |
| 88 | I | CB | −3.0 | −19.1 | −10.2 | 38 A |
| 88 | I | CG1 | −4.4 | −18.4 | −10.3 | 37 A |
| 88 | I | CG2 | −2.9 | −20.0 | −11.4 | 38 A |
| 88 | I | CD1 | −4.5 | −17.3 | −11.3 | 29 A |
| 89 | I | N | −1.8 | −22.1 | −8.8 | 33 A |
| 89 | I | CA | −0.6 | −22.9 | −8.8 | 31 A |
| 89 | I | C | −0.5 | −23.7 | −10.1 | 31 A |
| 89 | I | O | −1.1 | −24.7 | −10.3 | 32 A |
| 89 | I | CB | −0.6 | −23.9 | −7.7 | 33 A |
| 89 | I | CG1 | −0.8 | −23.2 | −6.3 | 34 A |
| 89 | I | CG2 | 0.8 | −24.6 | −7.6 | 28 A |
| 89 | I | CD1 | −0.7 | −24.0 | −5.1 | 34 A |
| 90 | P | N | 0.3 | −23.2 | −11.1 | 29 A |
| 90 | P | CA | 0.6 | −23.9 | −12.3 | 33 A |
| 90 | P | C | 1.5 | −25.0 | −11.9 | 33 A |
| 90 | P | O | 2.3 | −24.8 | −11.0 | 34 A |
| 90 | P | CB | 1.4 | −22.9 | −13.2 | 31 A |
| 90 | P | CG | 1.1 | −21.6 | −12.6 | 36 A |
| 90 | P | CD | 0.9 | −21.8 | −11.1 | 32 A |
| 91 | H | N | 1.5 | −26.1 | −12.6 | 30 A |
| 91 | H | CA | 2.5 | −27.2 | −12.3 | 29 A |
| 91 | H | C | 3.9 | −26.5 | −12.5 | 34 A |
| 91 | H | O | 4.1 | −25.8 | −13.5 | 34 A |
| 91 | H | CB | 2.4 | −28.4 | −13.2 | 28 A |
| 91 | H | CG | 3.3 | −29.5 | −12.9 | 30 A |
| 91 | H | ND1 | 3.0 | −30.4 | −11.9 | 32 A |
| 91 | H | CD2 | 4.5 | −29.8 | −13.4 | 32 A |
| 91 | H | CE1 | 4.0 | −31.3 | −11.8 | 31 A |
| 91 | H | NE2 | 4.9 | −31.0 | −12.7 | 32 A |
| 92 | H | N | 4.9 | −26.8 | −11.6 | 30 A |
| 92 | H | CA | 6.2 | −26.3 | −11.7 | 29 A |
| 92 | H | C | 7.0 | −26.5 | −13.0 | 34 A |
| 92 | H | O | 8.0 | −25.8 | −13.3 | 34 A |
| 92 | H | CB | 7.1 | −26.7 | −10.5 | 31 A |
| 92 | H | CG | 7.3 | −28.2 | −10.4 | 35 A |
| 92 | H | ND1 | 8.3 | −28.8 | −11.1 | 38 A |
| 92 | H | CD2 | 6.6 | −29.2 | −9.9 | 38 A |
| 92 | H | CE1 | 8.3 | −30.1 | −10.9 | 36 A |
| 92 | H | NE2 | 7.2 | −30.4 | −10.1 | 37 A |
| 93 | N | N | 6.5 | −27.5 | −13.8 | 29 A |
| 93 | N | CA | 7.2 | −27.8 | −15.1 | 29 A |
| 93 | N | C | 6.5 | −27.1 | −16.2 | 34 A |
| 93 | N | O | 6.9 | −27.2 | −17.4 | 42 A |
| 93 | N | CB | 7.1 | −29.3 | −15.4 | 33 A |
| 93 | N | CG | 8.1 | −30.2 | −14.6 | 37 A |
| 93 | N | OD1 | 7.8 | −31.3 | −14.2 | 37 A |
| 93 | N | ND2 | 9.3 | −29.7 | −14.4 | 33 A |
| 94 | Y | N | 5.5 | −26.3 | −15.9 | 29 A |
| 94 | Y | CA | 4.8 | −25.5 | −16.9 | 28 A |
| 94 | Y | C | 5.7 | −24.3 | −17.2 | 38 A |
| 94 | Y | O | 6.1 | −23.5 | −16.4 | 38 A |
| 94 | Y | CB | 3.4 | −25.0 | −16.5 | 27 A |
| 94 | Y | CG | 2.7 | −24.3 | −17.6 | 27 A |
| 94 | Y | CD1 | 2.2 | −25.0 | −18.7 | 27 A |
| 94 | Y | CD2 | 2.5 | −22.9 | −17.5 | 27 A |
| 94 | Y | CE1 | 1.6 | −24.3 | −19.7 | 27 A |
| 94 | Y | CE2 | 1.9 | −22.2 | −18.6 | 26 A |
| 94 | Y | CZ | 1.5 | −23.0 | −19.7 | 32 A |
| 94 | Y | OH | 0.8 | −22.4 | −20.7 | 35 A |
| 95 | N | N | 5.9 | −24.0 | −18.5 | 40 A |
| 95 | N | CA | 6.6 | −22.8 | −19.0 | 40 A |
| 95 | N | C | 6.1 | −22.4 | −20.3 | 40 A |
| 95 | N | O | 6.4 | −22.9 | −21.3 | 39 A |
| 95 | N | CB | 8.1 | −23.1 | −19.1 | 45 A |
| 95 | N | CG | 8.9 | −21.9 | −19.3 | 56 A |
| 95 | N | OD1 | 8.5 | −21.0 | −20.1 | 50 A |
| 95 | N | ND2 | 10.0 | −21.8 | −18.6 | 50 A |
| 95A | A | N | 5.2 | −21.4 | −20.3 | 36 A |
| 95A | A | CA | 4.6 | −20.9 | −21.5 | 37 A |
| 95A | A | C | 5.5 | −20.4 | −22.6 | 44 A |
| 95A | A | O | 5.2 | −20.5 | −23.8 | 45 A |
| 95A | A | CB | 3.5 | −19.9 | −21.2 | 36 A |
| 95B | A | N | 6.7 | −19.9 | −22.2 | 43 A |
| 95B | A | CA | 7.6 | −19.4 | −23.2 | 43 A |
| 95B | A | C | 8.4 | −20.6 | −23.9 | 49 A |
| 95B | A | O | 9.0 | −20.3 | −24.9 | 51 A |
| 95B | A | CB | 8.6 | −18.5 | −22.6 | 44 A |
| 96 | I | N | 8.3 | −21.8 | −23.4 | 44 A |
| 96 | I | CA | 8.9 | −22.9 | −24.1 | 42 A |
| 96 | I | C | 7.8 | −23.7 | −24.8 | 46 A |
| 96 | I | O | 7.9 | −24.0 | −26.0 | 46 A |
| 96 | I | CB | 9.6 | −23.8 | −23.0 | 43 A |
| 96 | I | CG1 | 10.9 | −23.1 | −22.5 | 43 A |
| 96 | I | CG2 | 10.0 | −25.1 | −23.7 | 44 A |
| 96 | I | CD1 | 11.6 | −23.9 | −21.4 | 51 A |
| 97 | N | N | 6.8 | −23.9 | −24.1 | 42 A |
| 97 | N | CA | 5.6 | −24.6 | −24.7 | 39 A |
| 97 | N | C | 4.4 | −24.3 | −23.9 | 42 A |
| 97 | N | O | 4.2 | −24.8 | −22.8 | 44 A |
| 97 | N | CB | 5.9 | −26.1 | −24.8 | 34 A |
| 97 | N | CG | 4.9 | −26.8 | −25.6 | 51 A |
| 97 | N | OD1 | 3.7 | −26.3 | −25.8 | 38 A |
| 97 | N | ND2 | 5.3 | −27.8 | −26.3 | 47 A |
| 98 | K | N | 3.5 | −23.6 | −24.5 | 37 A |
| 98 | K | CA | 2.2 | −23.2 | −23.9 | 37 A |
| 98 | K | C | 1.2 | −24.3 | −23.9 | 39 A |
| 98 | K | O | 0.3 | −24.1 | −22.8 | 36 A |
| 98 | K | CB | 1.6 | −22.0 | −24.7 | 38 A |
| 98 | K | CG | 0.3 | −21.5 | −24.2 | 46 A |
| 98 | K | CD | −0.3 | −20.5 | −25.2 | 60 A |
| 98 | K | CE | −1.7 | −20.2 | −24.9 | 76 A |
| 98 | K | NZ | −1.9 | −19.2 | −23.8 | 87 A |
| 99 | Y | N | 1.4 | −25.4 | −24.3 | 35 A |
| 99 | Y | CA | 0.5 | −26.6 | −24.1 | 34 A |
| 99 | Y | C | 1.1 | −27.8 | −23.6 | 37 A |
| 99 | Y | O | 0.5 | −28.9 | −23.6 | 37 A |
| 99 | Y | CB | −0.2 | −26.8 | −25.5 | 35 A |
| 99 | Y | CG | −1.1 | −25.7 | −25.9 | 36 A |
| 99 | Y | CD1 | −2.3 | −25.5 | −25.2 | 36 A |
| 99 | Y | CD2 | −0.6 | −24.7 | −26.7 | 38 A |
| 99 | Y | CE1 | −3.1 | −24.4 | −25.5 | 37 A |
| 99 | Y | CE2 | −1.4 | −23.6 | −27.0 | 40 A |
| 99 | Y | CZ | −2.7 | −23.4 | −26.4 | 46 A |
| 99 | Y | OH | −3.4 | −22.3 | −26.7 | 48 A |
| 100 | N | N | 2.3 | −27.7 | −22.9 | 34 A |
| 100 | N | CA | 2.9 | −28.9 | −22.3 | 32 A |
| 100 | N | C | 2.9 | −28.6 | −20.8 | 34 A |
| 100 | N | O | 3.0 | −27.5 | −20.4 | 32 A |
| 100 | N | CB | 4.3 | −29.2 | −22.9 | 30 A |
| 100 | N | CG | 4.8 | −30.5 | −22.5 | 43 A |
| 100 | N | OD1 | 6.0 | −30.7 | −22.6 | 42 A |
| 100 | N | ND2 | 3.9 | −31.5 | −22.2 | 31 A |
| 101 | H | N | 2.7 | −29.7 | −20.0 | 30 A |
| 101 | H | CA | 2.6 | −29.6 | −18.6 | 29 A |
| 101 | H | C | 1.5 | −28.6 | −18.2 | 33 A |
| 101 | H | O | 1.6 | −27.9 | −17.3 | 34 A |

TABLE 5-continued

Coordinates of Factor IXa co-crystal Compound C complex

| | | | | | | |
|---|---|---|---|---|---|---|
| 101 | H | CB | 4.0 | −29.2 | −18.0 | 29 | A |
| 101 | H | CG | 5.1 | −30.2 | −18.2 | 32 | A |
| 101 | H | ND1 | 6.2 | −29.8 | −19.0 | 33 | A |
| 101 | H | CD2 | 5.2 | −31.5 | −17.9 | 32 | A |
| 101 | H | CE1 | 7.0 | −30.9 | −19.0 | 31 | A |
| 101 | H | NE2 | 6.4 | −31.9 | −18.4 | 31 | A |
| 102 | D | N | 0.4 | −28.8 | −19.0 | 30 | A |
| 102 | D | CA | −0.7 | −27.8 | −19.0 | 29 | A |
| 102 | D | C | −1.7 | −28.0 | −18.0 | 32 | A |
| 102 | D | O | −2.9 | −28.4 | −18.3 | 31 | A |
| 102 | D | CB | −1.2 | −27.8 | −20.5 | 30 | A |
| 102 | D | CG | −2.0 | −26.6 | −20.8 | 35 | A |
| 102 | D | OD1 | −2.0 | −25.6 | −20.0 | 34 | A |
| 102 | D | OD2 | −2.8 | −26.6 | −21.8 | 41 | A |
| 103 | I | N | −1.3 | −27.9 | −16.7 | 29 | A |
| 103 | I | CA | −2.3 | −28.1 | −15.6 | 28 | A |
| 103 | I | C | −2.0 | −27.1 | −14.5 | 29 | A |
| 103 | I | O | −0.9 | −26.7 | −14.3 | 27 | A |
| 103 | I | CB | −2.2 | −29.6 | −15.2 | 30 | A |
| 103 | I | CG1 | −3.4 | −30.0 | −14.2 | 29 | A |
| 103 | I | CG2 | −0.8 | −29.8 | −14.5 | 32 | A |
| 103 | I | CD1 | −3.5 | −31.4 | −14.0 | 27 | A |
| 104 | A | N | −3.0 | −26.6 | −13.8 | 24 | A |
| 104 | A | CA | −2.9 | −25.5 | −12.8 | 23 | A |
| 104 | A | C | −4.0 | −25.7 | −11.8 | 29 | A |
| 104 | A | O | −5.0 | −26.3 | −12.1 | 29 | A |
| 104 | A | CB | −3.0 | −24.1 | −13.4 | 22 | A |
| 105 | L | N | −3.8 | −25.3 | −10.6 | 28 | A |
| 105 | L | CA | −4.8 | −25.4 | −9.5 | 27 | A |
| 105 | L | C | −5.1 | −24.0 | −9.1 | 31 | A |
| 105 | L | O | −4.3 | −23.1 | −9.0 | 28 | A |
| 105 | L | CB | −4.1 | −26.2 | −8.3 | 27 | A |
| 105 | L | CG | −3.9 | −27.7 | −8.6 | 29 | A |
| 105 | L | CD1 | −2.9 | −28.2 | −7.5 | 26 | A |
| 105 | L | CD2 | −5.2 | −28.5 | −8.6 | 24 | A |
| 106 | L | N | −6.4 | −23.8 | −8.8 | 30 | A |
| 106 | L | CA | −7.0 | −22.5 | −8.3 | 28 | A |
| 106 | L | C | −7.5 | −22.6 | −6.9 | 31 | A |
| 106 | L | O | −8.4 | −23.4 | −6.7 | 27 | A |
| 106 | L | CB | −8.1 | −22.0 | −9.2 | 26 | A |
| 106 | L | CG | −7.9 | −22.2 | −10.8 | 30 | A |
| 106 | L | CD1 | −9.2 | −21.8 | −11.4 | 28 | A |
| 106 | L | CD2 | −6.7 | −21.4 | −11.3 | 28 | A |
| 107 | E | N | −7.1 | −21.7 | −6.1 | 30 | A |
| 107 | E | CA | −7.6 | −21.7 | −4.7 | 28 | A |
| 107 | E | C | −8.7 | −20.7 | −4.6 | 32 | A |
| 107 | E | O | −8.6 | −19.6 | −5.1 | 34 | A |
| 107 | E | CB | −6.5 | −21.4 | −3.6 | 29 | A |
| 107 | E | CG | −7.0 | −21.7 | −2.2 | 33 | A |
| 107 | E | CD | −5.9 | −21.3 | −1.2 | 44 | A |
| 107 | E | OE1 | −4.8 | −20.8 | −1.6 | 45 | A |
| 107 | E | OE2 | −6.1 | −21.6 | −0.0 | 47 | A |
| 108 | L | N | −9.8 | −21.1 | −4.0 | 30 | A |
| 108 | L | CA | −11.0 | −20.2 | −3.8 | 31 | A |
| 108 | L | C | −10.9 | −19.4 | −2.5 | 33 | A |
| 108 | L | O | −10.4 | −19.9 | −1.5 | 30 | A |
| 108 | L | CB | −12.3 | −21.2 | −3.7 | 31 | A |
| 106 | L | CG | −12.5 | −22.0 | −5.0 | 36 | A |
| 108 | L | CD1 | −13.9 | −22.6 | −4.9 | 35 | A |
| 108 | L | CD2 | −12.3 | −21.2 | −6.3 | 30 | A |
| 109 | D | N | −11.5 | −18.2 | −2.5 | 31 | A |
| 109 | D | CA | −11.5 | −17.3 | −1.3 | 30 | A |
| 109 | D | C | −12.3 | −17.9 | −0.2 | 35 | A |
| 109 | D | O | −11.9 | −17.8 | 1.0 | 35 | A |
| 109 | D | CB | −11.9 | −15.9 | −1.7 | 30 | A |
| 109 | D | CG | −13.3 | −15.8 | −2.2 | 42 | A |
| 109 | D | OD1 | −13.9 | −16.8 | −2.7 | 47 | A |
| 109 | D | OD2 | −13.9 | −14.7 | −2.2 | 39 | A |
| 110 | E | N | −13.4 | −18.5 | −0.5 | 34 | A |
| 110 | E | CA | −14.3 | −19.1 | 0.5 | 33 | A |
| 110 | E | C | −14.7 | −20.5 | −0.1 | 35 | A |
| 110 | E | O | −15.1 | −20.6 | −1.2 | 35 | A |
| 110 | E | CB | −15.6 | −18.3 | 0.7 | 30 | A |
| 110 | E | CG | −15.4 | −17.0 | 1.4 | 37 | A |
| 110 | E | CD | −14.7 | −17.1 | 2.8 | 43 | A |
| 110 | E | OE1 | −14.3 | −16.1 | 3.3 | 33 | A |
| 110 | E | OE2 | −14.7 | −18.2 | 3.4 | 36 | A |
| 111 | P | N | −14.8 | −21.5 | 0.8 | 29 | A |
| 111 | P | CA | −15.1 | −22.8 | 0.3 | 28 | A |
| 111 | P | C | −16.5 | −22.9 | −0.4 | 35 | A |
| 111 | P | O | −17.4 | −22.1 | −0.1 | 36 | A |
| 111 | P | CB | −15.2 | −23.7 | 1.6 | 29 | A |
| 111 | P | CG | −14.9 | −22.8 | 2.7 | 32 | A |
| 111 | P | CD | −14.6 | −21.5 | 2.3 | 29 | A |
| 112 | L | N | −16.7 | −23.8 | −1.3 | 32 | A |
| 112 | L | CA | −17.9 | −24.0 | −1.9 | 31 | A |
| 112 | L | C | −18.7 | −24.9 | −0.9 | 34 | A |
| 112 | L | O | −18.1 | −25.4 | 0.0 | 30 | A |
| 112 | L | CB | −17.7 | −24.9 | −3.2 | 31 | A |
| 112 | L | CG | −16.9 | −24.2 | −4.3 | 32 | A |
| 112 | L | CD1 | −16.6 | −25.3 | −5.4 | 30 | A |
| 112 | L | CD2 | −17.8 | −23.1 | −5.0 | 30 | A |
| 113 | V | N | −20.0 | −24.9 | −1.1 | 32 | A |
| 113 | V | CA | −20.9 | −25.7 | −0.2 | 30 | A |
| 113 | V | C | −21.3 | −26.9 | −1.1 | 34 | A |
| 113 | V | O | −21.9 | −26.7 | −2.1 | 32 | A |
| 113 | V | CB | −22.1 | −24.9 | 0.2 | 33 | A |
| 113 | V | CG1 | −23.0 | −25.8 | 1.0 | 32 | A |
| 113 | V | CG2 | −21.7 | −23.7 | 1.0 | 34 | A |
| 114 | L | N | −20.9 | −28.1 | −0.7 | 32 | A |
| 114 | L | CA | −21.3 | −29.3 | −1.4 | 32 | A |
| 114 | L | C | −22.7 | −29.6 | −1.4 | 39 | A |
| 114 | L | O | −23.3 | −29.5 | −0.3 | 39 | A |
| 114 | L | CB | −20.4 | −30.4 | −1.1 | 31 | A |
| 114 | L | CG | −18.9 | −30.2 | −1.0 | 33 | A |
| 114 | L | CD1 | −18.1 | −31.4 | −0.7 | 30 | A |
| 114 | L | CD2 | −18.4 | −29.6 | −2.3 | 34 | A |
| 115 | N | N | −23.3 | −29.9 | −2.5 | 37 | A |
| 115 | N | CA | −24.7 | −30.3 | −2.6 | 36 | A |
| 115 | N | C | −24.8 | −31.0 | −4.0 | 39 | A |
| 115 | N | O | −23.8 | −31.3 | −4.7 | 39 | A |
| 115 | N | CB | −25.6 | −29.0 | −2.5 | 34 | A |
| 115 | N | CG | −25.4 | −28.0 | −3.5 | 40 | A |
| 115 | N | OD1 | −25.0 | −28.3 | −4.7 | 39 | A |
| 115 | N | ND2 | −25.5 | −26.7 | −3.1 | 32 | A |
| 116 | S | N | −26.0 | −31.3 | −4.4 | 36 | A |
| 116 | S | CA | −26.3 | −32.0 | −5.7 | 35 | A |
| 116 | S | C | −25.8 | −31.2 | −6.9 | 38 | A |
| 116 | S | O | −25.7 | −31.8 | −8.0 | 36 | A |
| 116 | S | CB | −27.8 | −32.4 | −5.8 | 37 | A |
| 116 | S | OG | −28.1 | −33.4 | −4.9 | 39 | A |
| 117 | Y | N | −25.6 | −29.9 | −6.8 | 35 | A |
| 117 | Y | CA | −25.2 | −29.1 | −7.9 | 35 | A |
| 117 | Y | C | −23.7 | −28.8 | −7.8 | 35 | A |
| 117 | Y | O | −23.2 | −28.3 | −8.8 | 34 | A |
| 117 | Y | CB | −26.0 | −27.8 | −8.0 | 37 | A |
| 117 | Y | CG | −27.5 | −28.1 | −8.2 | 40 | A |
| 117 | Y | CD1 | −28.0 | −28.4 | −9.4 | 41 | A |
| 117 | Y | CD2 | −28.3 | −28.2 | −7.1 | 41 | A |
| 117 | Y | CE1 | −29.4 | −28.7 | −9.6 | 42 | A |
| 117 | Y | CE2 | −29.7 | −28.6 | −7.2 | 44 | A |
| 117 | Y | CZ | −30.2 | −28.8 | −8.5 | 47 | A |
| 117 | Y | OH | −31.5 | −29.1 | −8.6 | 49 | A |
| 118 | V | N | −23.1 | −29.1 | −6.7 | 28 | A |
| 118 | V | CA | −21.7 | −28.7 | −6.5 | 28 | A |
| 118 | V | C | −21.0 | −29.8 | −5.7 | 35 | A |
| 118 | V | O | −21.1 | −30.0 | −4.5 | 33 | A |
| 118 | V | CB | −21.7 | −27.3 | −5.7 | 30 | A |
| 118 | V | CG1 | −20.3 | −26.9 | −5.4 | 29 | A |
| 118 | V | CG2 | −22.4 | −26.3 | −6.6 | 30 | A |
| 119 | T | N | −20.4 | −30.7 | −6.5 | 36 | A |
| 119 | T | CA | −19.7 | −31.9 | −6.1 | 35 | A |
| 119 | T | C | −18.4 | −32.1 | −6.7 | 37 | A |
| 119 | T | O | −18.2 | −31.9 | −7.9 | 35 | A |
| 119 | T | CB | −20.7 | −33.1 | −6.4 | 38 | A |
| 119 | T | OG1 | −21.9 | −32.9 | −5.7 | 37 | A |
| 119 | T | CG2 | −20.1 | −34.5 | −6.1 | 30 | A |
| 120 | P | N | −17.4 | −32.6 | −5.9 | 33 | A |
| 120 | P | CA | −16.0 | −32.8 | −6.5 | 32 | A |
| 120 | P | C | −16.3 | −34.0 | −7.4 | 35 | A |
| 120 | P | O | −16.9 | −34.8 | −7.4 | 34 | A |
| 120 | P | CB | −15.2 | −33.1 | −5.3 | 33 | A |
| 120 | P | CG | −16.0 | −32.5 | −4.1 | 38 | A |
| 120 | P | CD | −17.4 | −32.8 | −4.5 | 34 | A |
| 121 | I | N | −15.0 | −34.0 | −8.3 | 29 | A |
| 121 | I | CA | −14.8 | −35.1 | −9.2 | 27 | A |

TABLE 5-continued

Coordinates of Factor IXa co-crystal Compound C complex

| | | | | | | |
|---|---|---|---|---|---|---|
| 121 | I | C | −13.9 | −36.0 | −8.4 | 32 A |
| 121 | I | O | −13.1 | −35.5 | −7.6 | 34 A |
| 121 | I | CB | −14.2 | −34.7 | −10.6 | 28 A |
| 121 | I | CG1 | −14.1 | −35.9 | −11.5 | 27 A |
| 121 | I | CG2 | −12.8 | −34.0 | −10.4 | 26 A |
| 121 | I | CD1 | −15.4 | −36.4 | −12.0 | 25 A |
| 122 | C | N | −13.9 | −37.3 | −8.6 | 30 A |
| 122 | C | CA | −13.0 | −38.2 | −7.9 | 30 A |
| 122 | C | C | −11.7 | −38.3 | −8.7 | 30 A |
| 122 | C | O | −11.7 | −38.1 | −9.9 | 29 A |
| 122 | C | CB | −13.6 | −39.7 | −7.7 | 32 A |
| 122 | C | SG | −15.2 | −39.8 | −7.1 | 37 A |
| 123 | I | N | −10.6 | −38.5 | −8.0 | 28 A |
| 123 | I | CA | −9.3 | −38.6 | −8.6 | 29 A |
| 123 | I | C | −8.6 | −39.8 | −8.0 | 35 A |
| 123 | I | O | −8.4 | −39.8 | −6.8 | 34 A |
| 123 | I | CB | −8.5 | −37.3 | −8.4 | 31 A |
| 123 | I | CG1 | −9.2 | −36.1 | −9.0 | 31 A |
| 123 | I | CG2 | −7.1 | −37.5 | −8.9 | 30 A |
| 123 | I | CD1 | −8.4 | −34.8 | −8.9 | 30 A |
| 124 | A | N | −8.4 | −40.8 | −8.8 | 32 A |
| 124 | A | CA | −7.7 | −42.1 | −8.3 | 30 A |
| 124 | A | C | −6.2 | −41.9 | −8.3 | 35 A |
| 124 | A | O | −5.7 | −40.8 | −8.6 | 36 A |
| 124 | A | CB | −8.1 | −43.2 | −9.2 | 30 A |
| 125 | D | N | −5.5 | −42.9 | −7.9 | 32 A |
| 125 | D | CA | −4.0 | −42.8 | −8.0 | 31 A |
| 125 | D | C | −3.6 | −42.9 | −9.4 | 31 A |
| 125 | D | O | −4.3 | −43.1 | −10.4 | 32 A |
| 125 | D | CB | −3.4 | −43.8 | −7.0 | 34 A |
| 125 | D | CG | −3.7 | −45.3 | −7.4 | 39 A |
| 125 | D | OD1 | −4.3 | −45.6 | −8.5 | 39 A |
| 125 | D | OD2 | −3.2 | −46.2 | −6.7 | 47 A |
| 126 | K | N | −2.3 | −42.8 | −9.7 | 29 A |
| 126 | K | CA | −1.7 | −42.8 | −11.0 | 28 A |
| 126 | K | C | −2.1 | −44.0 | −11.8 | 33 A |
| 126 | K | O | −2.5 | −43.9 | −13.0 | 32 A |
| 126 | K | CB | −0.2 | −42.7 | −10.8 | 31 A |
| 126 | K | CG | 0.7 | −42.9 | −12.0 | 34 A |
| 126 | K | CD | 2.1 | −42.5 | −11.7 | 32 A |
| 126 | K | CE | 3.0 | −43.0 | −12.8 | 36 A |
| 126 | K | NZ | 4.5 | −42.6 | −12.7 | 33 A |
| 127 | E | N | −2.0 | −45.1 | −11.2 | 31 A |
| 127 | E | CA | −2.2 | −46.4 | −11.8 | 31 A |
| 127 | E | C | −3.7 | −46.6 | −12.3 | 34 A |
| 127 | E | O | −3.9 | −47.0 | −13.4 | 33 A |
| 127 | E | CB | −1.8 | −47.5 | −10.8 | 33 A |
| 127 | E | CG | −2.5 | −48.9 | −11.3 | 47 A |
| 127 | E | CD | −2.2 | −50.0 | −10.3 | 66 A |
| 127 | E | OE1 | −1.9 | −51.1 | −10.8 | 44 A |
| 127 | E | OE2 | −2.4 | −49.8 | −9.0 | 53 A |
| 128 | Y | N | −4.6 | −46.3 | −11.4 | 29 A |
| 128 | Y | CA | −6.0 | −46.4 | −11.7 | 27 A |
| 128 | Y | C | −6.5 | −45.3 | −12.6 | 30 A |
| 128 | Y | O | −7.5 | −45.6 | −13.4 | 27 A |
| 128 | Y | CE | −6.9 | −46.5 | −10.5 | 27 A |
| 128 | Y | CG | −7.0 | −48.0 | −10.0 | 31 A |
| 128 | Y | CD1 | −6.2 | −48.5 | −9.1 | 33 A |
| 128 | Y | CD2 | −8.0 | −48.8 | −10.6 | 32 A |
| 128 | Y | CE1 | −6.3 | −49.8 | −8.7 | 35 A |
| 128 | Y | CE2 | −8.1 | −50.1 | −10.2 | 33 A |
| 128 | Y | CZ | −7.3 | −50.6 | −9.3 | 40 A |
| 128 | Y | OH | −7.4 | −51.9 | −8.9 | 43 A |
| 129 | T | N | −6.0 | −44.1 | −12.5 | 28 A |
| 129 | T | CA | −6.3 | −43.0 | −13.4 | 28 A |
| 129 | T | C | −6.0 | −43.5 | −14.9 | 29 A |
| 129 | T | O | −6.8 | −43.3 | −15.8 | 31 A |
| 129 | T | CB | −5.6 | −41.7 | −13.1 | 32 A |
| 129 | T | OG1 | −6.0 | −41.3 | −11.7 | 32 A |
| 129 | T | CG2 | −6.0 | −40.6 | −14.0 | 28 A |
| 129A | N | N | −4.9 | −44.1 | −15.0 | 26 A |
| 129A | N | CA | −4.4 | −44.7 | −16.3 | 27 A |
| 129A | N | C | −5.3 | −45.9 | −16.7 | 32 A |
| 129A | N | O | −5.6 | −46.0 | −17.9 | 32 A |
| 129A | N | CB | −2.9 | −45.0 | −16.2 | 29 A |
| 129A | N | CG | −2.4 | −45.4 | −17.5 | 48 A |
| 129A | N | OD1 | −2.5 | −44.7 | −18.6 | 36 A |
| 129A | N | ND2 | −1.7 | −46.5 | −17.6 | 36 A |
| 129B | I | N | −5.6 | −46.8 | −15.8 | 30 A |
| 129B | I | CA | −6.5 | −47.9 | −16.1 | 30 A |
| 129B | I | C | −7.8 | −47.3 | −16.6 | 34 A |
| 129B | I | O | −8.4 | −47.8 | −17.6 | 35 A |
| 129B | I | CB | −6.7 | −48.8 | −14.9 | 32 A |
| 129B | I | CG1 | −5.5 | −49.7 | −14.6 | 32 A |
| 129B | I | CG2 | −8.0 | −49.5 | −15.1 | 29 A |
| 129B | I | CD1 | −5.5 | −50.5 | −13.2 | 27 A |
| 130 | F | N | −8.4 | −46.3 | −15.9 | 29 A |
| 130 | F | CA | −9.7 | −45.7 | −16.3 | 27 A |
| 130 | F | C | −9.6 | −45.0 | −17.7 | 30 A |
| 130 | F | O | −10.5 | −45.1 | −18.5 | 29 A |
| 130 | F | CB | −10.3 | −44.8 | −15.2 | 29 A |
| 130 | F | CG | −10.4 | −45.5 | −13.9 | 32 A |
| 130 | F | CD1 | −10.7 | −46.9 | −13.8 | 35 A |
| 130 | F | CD2 | −10.5 | −44.7 | −12.7 | 35 A |
| 130 | F | CE1 | −11.0 | −47.4 | −12.5 | 36 A |
| 130 | F | CE2 | −10.7 | −45.3 | −11.4 | 37 A |
| 130 | F | CZ | −10.9 | −46.7 | −11.3 | 36 A |
| 131 | L | N | −8.5 | −44.2 | −17.9 | 27 A |
| 131 | L | CA | −8.4 | −43.6 | −19.3 | 27 A |
| 131 | L | C | −8.5 | −44.7 | −20.4 | 34 A |
| 131 | L | O | −9.2 | −44.5 | −21.4 | 35 A |
| 131 | L | CB | −7.1 | −42.9 | −19.4 | 26 A |
| 131 | L | CG | −6.9 | −42.2 | −20.7 | 30 A |
| 131 | L | CD1 | −5.4 | −41.8 | −21.0 | 27 A |
| 131 | L | CD2 | −7.9 | −41.0 | −20.9 | 30 A |
| 132 | K | N | −7.8 | −45.8 | −20.1 | 30 A |
| 132 | K | CA | −7.7 | −46.9 | −21.1 | 29 A |
| 132 | K | C | −9.0 | −47.7 | −21.4 | 32 A |
| 132 | K | O | −9.0 | −48.4 | −22.3 | 31 A |
| 132 | K | CB | −6.6 | −47.9 | −20.7 | 30 A |
| 132 | K | CG | −5.2 | −47.2 | −20.7 | 39 A |
| 132 | K | CD | −4.1 | −48.3 | −21.0 | 50 A |
| 132 | K | CE | −2.8 | −48.1 | −20.3 | 67 A |
| 132 | K | NZ | −1.9 | −49.2 | −20.4 | 81 A |
| 133 | F | N | −10.0 | −47.5 | −20.5 | 31 A |
| 133 | F | CA | −11.4 | −48.1 | −20.8 | 30 A |
| 133 | F | C | −11.8 | −47.5 | −22.1 | 38 A |
| 133 | F | O | −12.7 | −48.0 | −22.8 | 39 A |
| 133 | F | CB | −12.4 | −47.5 | −19.8 | 31 A |
| 133 | F | CG | −12.3 | −48.2 | −18.4 | 32 A |
| 133 | F | CD1 | −11.4 | −49.2 | −18.1 | 35 A |
| 133 | F | CD2 | −13.2 | −47.8 | −17.4 | 35 A |
| 133 | F | CE1 | −11.4 | −49.8 | −16.9 | 35 A |
| 133 | F | CE2 | −13.2 | −48.4 | −16.2 | 37 A |
| 133 | F | CZ | −12.2 | −49.4 | −15.9 | 34 A |
| 134 | G | N | −11.2 | −46.4 | −22.6 | 34 A |
| 134 | G | CA | −11.4 | −45.8 | −23.9 | 30 A |
| 134 | G | C | −12.6 | −44.9 | −24.1 | 32 A |
| 134 | G | O | −12.7 | −44.5 | −25.3 | 33 A |
| 135 | S | N | −13.4 | −44.3 | −23.1 | 28 A |
| 135 | S | CA | −14.5 | −43.8 | −23.4 | 28 A |
| 135 | S | C | −14.6 | −42.7 | −22.3 | 34 A |
| 135 | S | O | −14.7 | −43.1 | −21.1 | 34 A |
| 135 | S | CB | −15.8 | −44.6 | −23.4 | 34 A |
| 135 | S | OG | −17.0 | −43.8 | −23.7 | 43 A |
| 136 | G | N | −14.6 | −41.4 | −22.6 | 29 A |
| 136 | G | CA | −14.7 | −40.4 | −21.6 | 27 A |
| 136 | G | C | −15.8 | −39.4 | −21.9 | 31 A |
| 136 | G | O | −16.3 | −39.5 | −23.0 | 31 A |
| 137 | Y | N | −16.1 | −38.6 | −20.9 | 30 A |
| 137 | Y | CA | −17.1 | −37.5 | −21.1 | 31 A |
| 137 | Y | C | −16.4 | −36.2 | −20.9 | 34 A |
| 137 | Y | O | −15.7 | −36.0 | −19.9 | 34 A |
| 137 | Y | CB | −18.2 | −37.7 | −20.1 | 33 A |
| 137 | Y | CG | −19.3 | −38.7 | −20.5 | 38 A |
| 137 | Y | CD1 | −19.1 | −40.0 | −20.1 | 40 A |
| 137 | Y | CD2 | −20.3 | −38.3 | −21.3 | 41 A |
| 137 | Y | CE1 | −20.1 | −41.0 | −20.5 | 42 A |
| 137 | Y | CE2 | −21.2 | −39.3 | −21.7 | 42 A |
| 137 | Y | CZ | −21.1 | −40.6 | −21.3 | 51 A |
| 137 | Y | OH | −22.1 | −41.5 | −21.8 | 53 A |
| 138 | V | N | −16.6 | −35.2 | −21.8 | 27 A |
| 138 | V | CA | −16.1 | −33.9 | −21.8 | 26 A |
| 138 | V | C | −17.4 | −33.0 | −21.7 | 32 A |
| 138 | V | O | −18.5 | −33.5 | −22.0 | 30 A |
| 138 | V | CB | −15.2 | −33.5 | −23.0 | 29 A |

TABLE 5-continued

Coordinates of Factor IXa co-crystal Compound C complex

| | | | | | | |
|---|---|---|---|---|---|---|
| 138 | V | CG1 | −13.9 | −34.4 | −23.0 | 29 | A |
| 138 | V | CG2 | −16.0 | −33.6 | −24.3 | 28 | A |
| 139 | S | N | −17.3 | −31.9 | −21.1 | 30 | A |
| 139 | S | CA | −18.4 | −30.9 | −20.9 | 30 | A |
| 139 | S | C | −17.9 | −29.5 | −20.8 | 34 | A |
| 139 | S | O | −16.7 | −29.3 | −20.5 | 32 | A |
| 139 | S | CB | −19.2 | −31.3 | −19.6 | 31 | A |
| 139 | S | OG | −18.4 | −31.5 | −18.5 | 34 | A |
| 140 | G | N | −18.7 | −28.5 | −21.1 | 34 | A |
| 140 | G | CA | −18.3 | −27.1 | −20.9 | 34 | A |
| 140 | G | C | −19.3 | −26.2 | −21.6 | 37 | A |
| 140 | G | O | −20.2 | −26.5 | −22.3 | 37 | A |
| 141 | W | N | −19.0 | −24.9 | −21.5 | 34 | A |
| 141 | W | CA | −19.8 | −23.8 | −22.1 | 34 | A |
| 141 | W | C | −19.0 | −23.3 | −23.4 | 39 | A |
| 141 | W | O | −19.3 | −22.2 | −23.8 | 37 | A |
| 141 | W | CB | −20.1 | −22.7 | −21.2 | 31 | A |
| 141 | W | CG | −21.1 | −23.1 | −20.2 | 31 | A |
| 141 | W | CD1 | −22.5 | −23.0 | −20.3 | 35 | A |
| 141 | W | CD2 | −20.9 | −23.7 | −18.9 | 32 | A |
| 141 | W | NE1 | −23.1 | −23.4 | −19.2 | 35 | A |
| 141 | W | CE2 | −22.1 | −23.8 | −18.3 | 36 | A |
| 141 | W | CE3 | −19.7 | −24.0 | −18.2 | 33 | A |
| 141 | W | CZ2 | −22.3 | −24.4 | −17.0 | 35 | A |
| 141 | W | CZ3 | −19.9 | −24.5 | −16.9 | 33 | A |
| 141 | W | CH2 | −21.1 | −24.7 | −16.3 | 33 | A |
| 142 | G | N | −18.1 | −24.0 | −23.9 | 39 | A |
| 142 | G | CA | −17.4 | −23.7 | −25.1 | 38 | A |
| 142 | G | C | −18.3 | −23.5 | −26.3 | 43 | A |
| 142 | G | O | −19.5 | −23.7 | −26.2 | 43 | A |
| 143 | R | N | −17.7 | −23.0 | −27.4 | 42 | A |
| 143 | R | CA | −18.4 | −22.8 | −28.6 | 44 | A |
| 143 | R | C | −19.0 | −24.1 | −29.2 | 49 | A |
| 143 | R | O | −18.5 | −25.1 | −29.1 | 48 | A |
| 143 | R | CB | −17.4 | −22.3 | −29.6 | 48 | A |
| 143 | R | CG | −17.9 | −21.9 | −31.0 | 67 | A |
| 143 | R | CD | −16.7 | −21.2 | −31.8 | 81 | A |
| 143 | R | NE | −16.1 | −20.1 | −31.0 | 96 | A |
| 143 | R | CZ | −14.8 | −19.9 | −30.9 | 0 | A |
| 143 | R | NH1 | −14.0 | −20.7 | −31.6 | 91 | A |
| 143 | R | NH2 | −14.4 | −18.9 | −30.2 | 95 | A |
| 144 | V | N | −20.3 | −24.0 | −29.6 | 49 | A |
| 144 | V | CA | −21.0 | −25.1 | −30.2 | 51 | A |
| 144 | V | C | −20.9 | −25.1 | −31.7 | 60 | A |
| 144 | V | O | −21.3 | −26.1 | −32.3 | 57 | A |
| 144 | V | CB | −22.5 | −25.1 | −29.7 | 57 | A |
| 144 | V | CG1 | −22.6 | −25.5 | −28.3 | 57 | A |
| 144 | V | CG2 | −23.0 | −23.7 | −29.8 | 58 | A |
| 145 | F | N | −20.4 | −24.1 | −32.3 | 65 | A |
| 145 | F | CA | −20.2 | −24.0 | −33.8 | 68 | A |
| 145 | F | C | −18.8 | −23.5 | −34.2 | 74 | A |
| 145 | F | O | −18.0 | −23.1 | −33.4 | 74 | A |
| 145 | F | CB | −21.4 | −23.5 | −34.5 | 71 | A |
| 145 | F | CG | −22.3 | −24.5 | −35.1 | 75 | A |
| 145 | F | CD1 | −23.5 | −24.7 | −34.6 | 79 | A |
| 145 | F | CD2 | −21.8 | −25.5 | −36.0 | 79 | A |
| 145 | F | CE1 | −24.3 | −25.8 | −35.0 | 81 | A |
| 145 | F | CE2 | −22.6 | −26.5 | −36.5 | 83 | A |
| 145 | F | CZ | −23.8 | −26.7 | −36.0 | 81 | A |
| 149 | G | N | −17.9 | −19.3 | −34.0 | 70 | A |
| 149 | G | CA | −19.3 | −19.6 | −33.7 | 69 | A |
| 149 | G | C | −19.7 | −19.2 | −32.3 | 73 | A |
| 149 | G | O | −19.0 | −18.8 | −31.4 | 72 | A |
| 150 | R | N | −21.0 | −19.3 | −32.0 | 69 | A |
| 150 | R | CA | −21.7 | −18.9 | −30.8 | 70 | A |
| 150 | R | C | −21.2 | −19.8 | −29.6 | 70 | A |
| 150 | R | O | −21.2 | −21.1 | −29.7 | 68 | A |
| 150 | R | CB | −23.2 | −19.0 | −30.9 | 73 | A |
| 150 | R | CG | −23.9 | −20.3 | −30.5 | 86 | A |
| 150 | R | CD | −24.8 | −20.8 | −31.6 | 0 | A |
| 150 | R | NE | −25.9 | −21.7 | −31.1 | 0 | A |
| 150 | R | CZ | −26.2 | −22.9 | −31.6 | 0 | A |
| 150 | R | NH1 | −25.5 | −23.4 | −32.6 | 0 | A |
| 150 | R | NH2 | −27.2 | −23.6 | −31.1 | 0 | A |
| 151 | S | N | −20.9 | −19.2 | −28.4 | 61 | A |
| 151 | S | CA | −20.6 | −19.9 | −27.2 | 58 | A |
| 151 | S | C | −21.8 | −20.3 | −26.4 | 60 | A |
| 151 | S | O | −22.8 | −19.6 | −26.4 | 63 | A |
| 151 | S | CB | −19.7 | −19.0 | −26.3 | 59 | A |
| 151 | S | OG | −20.2 | −19.0 | −25.0 | 69 | A |
| 152 | A | N | −21.8 | −21.5 | −25.8 | 51 | A |
| 152 | A | CA | −23.0 | −22.1 | −25.2 | 48 | A |
| 152 | A | C | −23.7 | −21.4 | −24.0 | 50 | A |
| 152 | A | O | −23.1 | −20.7 | −23.2 | 50 | A |
| 152 | A | CB | −22.9 | −23.6 | −24.9 | 49 | A |
| 153 | L | N | −25.0 | −21.5 | −24.0 | 48 | A |
| 153 | L | CA | −25.8 | −20.9 | −22.9 | 48 | A |
| 153 | L | C | −26.0 | −22.0 | −21.9 | 46 | A |
| 153 | L | O | −25.7 | −21.8 | −20.7 | 48 | A |
| 153 | L | CB | −27.1 | −20.4 | −23.4 | 49 | A |
| 153 | L | CG | −27.1 | −19.3 | −24.4 | 55 | A |
| 153 | L | CD1 | −28.5 | −19.0 | −25.0 | 56 | A |
| 153 | L | CD2 | −26.5 | −18.0 | −23.9 | 57 | A |
| 154 | V | N | −26.5 | −23.2 | −22.3 | 38 | A |
| 154 | V | CA | −26.7 | −24.3 | −21.4 | 36 | A |
| 154 | V | C | −25.4 | −25.3 | −21.5 | 41 | A |
| 154 | V | O | −24.9 | −25.5 | −22.6 | 40 | A |
| 154 | V | CB | −27.9 | −25.2 | −21.8 | 37 | A |
| 154 | V | CG1 | −28.1 | −26.4 | −20.9 | 36 | A |
| 154 | V | CG2 | −29.1 | −24.3 | −21.9 | 36 | A |
| 155 | L | N | −25.0 | −25.7 | −20.4 | 36 | A |
| 155 | L | CA | −23.8 | −26.7 | −20.4 | 34 | A |
| 155 | L | C | −24.0 | −27.8 | −21.3 | 36 | A |
| 155 | L | O | −25.1 | −28.5 | −21.3 | 35 | A |
| 155 | L | CB | −23.7 | −27.2 | −19.0 | 33 | A |
| 155 | L | CG | −22.5 | −28.2 | −18.7 | 35 | A |
| 155 | L | CD1 | −21.2 | −27.5 | −18.9 | 33 | A |
| 155 | L | CD2 | −22.7 | −28.8 | −17.3 | 32 | A |
| 156 | Q | N | −23.0 | −28.1 | −22.1 | 33 | A |
| 156 | Q | CA | −23.0 | −29.2 | −23.1 | 33 | A |
| 156 | Q | C | −22.1 | −30.3 | −22.6 | 38 | A |
| 156 | Q | O | −21.1 | −30.1 | −21.9 | 37 | A |
| 156 | Q | CB | −22.4 | −28.7 | −24.5 | 34 | A |
| 156 | Q | CG | −23.1 | −27.5 | −25.1 | 42 | A |
| 156 | Q | CD | −24.5 | −27.9 | −25.5 | 39 | A |
| 156 | Q | OE1 | −25.5 | −27.6 | −24.8 | 35 | A |
| 156 | Q | NE2 | −24.6 | −28.7 | −26.5 | 26 | A |
| 157 | Y | N | −22.4 | −31.5 | −23.1 | 35 | A |
| 157 | Y | CA | −21.6 | −32.7 | −22.7 | 34 | A |
| 157 | Y | C | −21.5 | −33.6 | −23.9 | 37 | A |
| 157 | Y | O | −22.3 | −33.6 | −24.8 | 37 | A |
| 157 | Y | CB | −22.1 | −33.4 | −21.5 | 35 | A |
| 157 | Y | CG | −23.4 | −34.2 | −21.8 | 39 | A |
| 157 | Y | CD1 | −23.3 | −35.6 | −22.1 | 41 | A |
| 157 | Y | CD2 | −24.6 | −33.7 | −21.7 | 40 | A |
| 157 | Y | CE1 | −24.4 | −36.4 | −22.3 | 41 | A |
| 157 | Y | CE2 | −25.8 | −34.4 | −21.9 | 42 | A |
| 157 | Y | CZ | −25.6 | −35.8 | −22.2 | 51 | A |
| 157 | Y | OH | −26.8 | −36.5 | −22.3 | 57 | A |
| 158 | L | N | −20.4 | −34.3 | −24.0 | 33 | A |
| 158 | L | CA | −20.1 | −35.2 | −25.1 | 33 | A |
| 158 | L | C | −19.3 | −36.4 | −24.7 | 37 | A |
| 158 | L | O | −18.3 | −36.2 | −23.9 | 35 | A |
| 158 | L | CB | −19.5 | −34.4 | −26.2 | 31 | A |
| 158 | L | CG | −18.8 | −35.2 | −27.3 | 33 | A |
| 158 | L | CD1 | −19.9 | −35.7 | −28.3 | 33 | A |
| 158 | L | CD2 | −17.8 | −34.3 | −28.1 | 32 | A |
| 159 | R | N | −19.6 | −37.6 | −25.2 | 34 | A |
| 159 | R | CA | −18.8 | −38.8 | −25.0 | 33 | A |
| 159 | R | C | −17.8 | −38.9 | −26.1 | 31 | A |
| 159 | R | O | −18.1 | −38.8 | −27.3 | 26 | A |
| 159 | R | CB | −19.7 | −40.0 | −24.9 | 32 | A |
| 159 | R | CG | −18.9 | −41.3 | −24.5 | 38 | A |
| 159 | R | CD | −19.6 | −42.6 | −24.9 | 46 | A |
| 159 | R | NE | −19.4 | −42.8 | −26.4 | 54 | A |
| 159 | R | CZ | −18.4 | −43.3 | −27.0 | 57 | A |
| 159 | R | NH1 | −17.3 | −43.7 | −26.3 | 40 | A |
| 159 | R | NH2 | −18.4 | −43.5 | −28.3 | 47 | A |
| 160 | V | N | −16.5 | −39.0 | −25.8 | 28 | A |
| 160 | V | CA | −15.5 | −39.0 | −26.8 | 27 | A |
| 160 | V | C | −14.7 | −40.4 | −26.6 | 33 | A |
| 160 | V | O | −14.2 | −40.7 | −25.6 | 35 | A |
| 160 | V | CB | −14.5 | −37.7 | −26.7 | 29 | A |
| 160 | V | CG1 | −15.3 | −36.5 | −27.2 | 28 | A |
| 160 | V | CG2 | −14.0 | −37.5 | −25.4 | 28 | A |
| 161 | P | N | −14.4 | −41.0 | −27.8 | 29 | A |

TABLE 5-continued

Coordinates of Factor IXa co-crystal Compound C complex

| 161 | P | CA | −13.6 | −42.2 | −27.7 | 28 | A |
| 161 | P | C | −12.1 | −42.0 | −27.6 | 29 | A |
| 161 | P | O | −11.7 | −41.0 | −28.2 | 25 | A |
| 161 | P | CB | −14.0 | −43.0 | −29.0 | 30 | A |
| 161 | P | CG | −14.5 | −42.0 | −29.9 | 35 | A |
| 161 | P | CD | −15.1 | −40.9 | −29.1 | 30 | A |
| 162 | L | N | −11.3 | −42.8 | −27.0 | 28 | A |
| 162 | L | CA | −9.9 | −42.6 | −27.0 | 28 | A |
| 162 | L | C | −9.4 | −43.0 | −28.4 | 33 | A |
| 162 | L | O | −9.9 | −43.9 | −29.0 | 33 | A |
| 162 | L | CB | −9.3 | −43.5 | −26.0 | 27 | A |
| 162 | L | CG | −7.7 | −43.4 | −25.8 | 27 | A |
| 162 | L | CD1 | −7.4 | −42.0 | −25.2 | 24 | A |
| 162 | L | CD2 | −7.4 | −44.4 | −24.7 | 31 | A |
| 163 | V | N | −8.4 | −42.2 | −28.9 | 31 | A |
| 163 | V | CA | −7.8 | −42.5 | −30.1 | 29 | A |
| 163 | V | C | −6.4 | −42.9 | −29.8 | 35 | A |
| 163 | V | O | −5.7 | −42.3 | −29.0 | 36 | A |
| 163 | V | CB | −7.8 | −41.2 | −31.0 | 32 | A |
| 163 | V | CG1 | −7.0 | −41.4 | −32.3 | 30 | A |
| 163 | V | CG2 | −9.2 | −40.8 | −31.3 | 31 | A |
| 164 | D | N | −6.0 | −44.0 | −30.4 | 31 | A |
| 164 | D | CA | −4.6 | −44.6 | −30.2 | 29 | A |
| 164 | D | C | −3.6 | −43.6 | −30.6 | 33 | A |
| 164 | D | O | −3.7 | −42.8 | −31.5 | 29 | A |
| 164 | D | CB | −4.4 | −45.9 | −31.0 | 31 | A |
| 164 | D | CG | −4.5 | −45.7 | −32.5 | 47 | A |
| 164 | D | OD1 | −3.5 | −45.7 | −33.1 | 50 | A |
| 164 | D | OD2 | −5.7 | −45.5 | −32.9 | 58 | A |
| 165 | R | N | −2.5 | −43.6 | −29.9 | 30 | A |
| 165 | R | CA | −1.3 | −42.8 | −30.1 | 30 | A |
| 165 | R | C | −0.9 | −42.8 | −31.6 | 37 | A |
| 165 | R | O | −0.5 | −41.7 | −32.2 | 39 | A |
| 165 | R | CB | −0.2 | −43.1 | −29.2 | 26 | A |
| 165 | R | CG | 1.1 | −42.5 | −29.6 | 41 | A |
| 165 | R | CD | 2.2 | −42.6 | −28.4 | 42 | A |
| 165 | R | NE | 2.3 | −41.3 | −27.9 | 50 | A |
| 165 | R | CZ | 3.4 | −40.5 | −28.2 | 58 | A |
| 165 | R | NH1 | 4.4 | −40.9 | −28.8 | 65 | A |
| 165 | R | NH2 | 3.4 | −39.3 | −27.7 | 45 | A |
| 166 | A | N | −0.8 | −43.9 | −32.2 | 35 | A |
| 166 | A | CA | −0.3 | −44.0 | −33.6 | 34 | A |
| 166 | A | C | −1.2 | −43.2 | −34.6 | 40 | A |
| 166 | A | O | −0.7 | −42.2 | −35.2 | 39 | A |
| 166 | A | CB | −0.2 | −45.5 | −34.1 | 34 | A |
| 167 | T | N | −2.5 | −43.4 | −34.5 | 38 | A |
| 167 | T | CA | −3.4 | −42.7 | −35.3 | 39 | A |
| 167 | T | C | −3.3 | −41.2 | −35.0 | 43 | A |
| 167 | T | O | −3.4 | −40.3 | −35.9 | 43 | A |
| 167 | T | CB | −4.9 | −43.2 | −35.0 | 38 | A |
| 167 | T | OG1 | −4.9 | −44.5 | −35.5 | 36 | A |
| 167 | T | CG2 | −5.9 | −42.3 | −35.7 | 28 | A |
| 168 | C | N | −3.1 | −40.9 | −33.7 | 41 | A |
| 168 | C | CA | −3.1 | −39.5 | −33.2 | 42 | A |
| 168 | C | C | −1.8 | −38.8 | −33.7 | 39 | A |
| 168 | C | O | −1.9 | −37.7 | −34.2 | 35 | A |
| 168 | C | CB | −3.2 | −39.6 | −31.7 | 45 | A |
| 168 | C | SG | −2.7 | −38.1 | −30.8 | 52 | A |
| 169 | L | N | −0.7 | −39.5 | −33.6 | 34 | A |
| 169 | L | CA | 0.6 | −38.9 | −34.2 | 35 | A |
| 169 | L | C | 0.5 | −38.6 | −35.7 | 42 | A |
| 169 | L | O | 1.0 | −37.5 | −36.1 | 42 | A |
| 169 | L | CB | 1.8 | −39.8 | −33.9 | 35 | A |
| 169 | L | CG | 2.7 | −39.6 | −32.6 | 40 | A |
| 169 | L | CD1 | 2.0 | −39.2 | −31.3 | 38 | A |
| 169 | L | CD2 | 3.5 | −40.8 | −32.4 | 44 | A |
| 170 | R | N | −0.1 | −39.5 | −36.5 | 39 | A |
| 170 | R | CA | −0.2 | −39.2 | −37.9 | 39 | A |
| 170 | R | C | −1.2 | −38.1 | −38.3 | 44 | A |
| 170 | R | O | −1.3 | −37.6 | −39.4 | 45 | A |
| 170 | R | CB | −0.7 | −40.4 | −38.7 | 37 | A |
| 170 | R | CG | 0.3 | −41.6 | −38.6 | 40 | A |
| 170 | R | CD | −0.2 | −42.9 | −39.4 | 46 | A |
| 170 | R | NE | −1.6 | −43.3 | −39.0 | 52 | A |
| 170 | R | CZ | −1.7 | −44.5 | −38.3 | 60 | A |
| 170 | R | NH1 | −0.7 | −45.2 | −38.0 | 40 | A |
| 170 | R | NH2 | −3.0 | −44.9 | −38.0 | 51 | A |
| 171 | S | N | −2.0 | −37.7 | −37.3 | 39 | A |
| 171 | S | CA | −3.0 | −36.7 | −37.5 | 36 | A |
| 171 | S | C | −2.5 | −35.2 | −37.5 | 39 | A |
| 171 | S | O | −3.2 | −34.3 | −37.8 | 38 | A |
| 171 | S | CB | −4.2 | −36.8 | −36.5 | 38 | A |
| 171 | S | OG | −3.8 | −36.2 | −35.2 | 41 | A |
| 172 | T | N | −1.3 | −35.0 | −37.4 | 35 | A |
| 172 | T | CA | −0.8 | −33.7 | −36.6 | 36 | A |
| 172 | T | C | 0.7 | −33.6 | −36.9 | 41 | A |
| 172 | T | O | 1.4 | −34.6 | −36.9 | 41 | A |
| 172 | T | CB | −1.2 | −33.2 | −35.2 | 36 | A |
| 172 | T | OG1 | −0.8 | −31.9 | −35.0 | 39 | A |
| 172 | T | CG2 | −0.7 | −34.1 | −34.1 | 31 | A |
| 173 | K | N | 1.2 | −32.3 | −37.1 | 39 | A |
| 173 | K | CA | 2.6 | −32.1 | −37.3 | 39 | A |
| 173 | K | C | 3.2 | −31.6 | −36.0 | 41 | A |
| 173 | K | O | 4.4 | −31.6 | −35.8 | 40 | A |
| 173 | K | CB | 2.8 | −31.0 | −38.4 | 43 | A |
| 173 | K | CG | 2.0 | −29.7 | −38.1 | 70 | A |
| 173 | K | CD | 2.7 | −28.4 | −38.5 | 70 | A |
| 173 | K | CE | 2.5 | −27.3 | −37.4 | 67 | A |
| 173 | K | NZ | 1.8 | −26.1 | −38.0 | 77 | A |
| 174 | F | N | 2.3 | −31.2 | −35.0 | 38 | A |
| 174 | F | CA | 2.7 | −30.9 | −33.7 | 37 | A |
| 174 | F | C | 3.2 | −32.1 | −32.9 | 38 | A |
| 174 | F | O | 2.9 | −33.2 | −33.2 | 36 | A |
| 174 | F | CB | 1.6 | −30.3 | −32.9 | 38 | A |
| 174 | F | CG | 1.3 | −28.9 | −33.3 | 38 | A |
| 174 | F | CD1 | 2.1 | −27.8 | −33.0 | 41 | A |
| 174 | F | CD2 | 0.1 | −28.6 | −34.0 | 39 | A |
| 174 | F | CE1 | 1.8 | −26.5 | −33.4 | 41 | A |
| 174 | F | CE2 | −0.3 | −27.3 | −34.3 | 42 | A |
| 174 | F | CZ | 0.6 | −26.3 | −34.0 | 39 | A |
| 175 | T | N | 4.0 | −31.8 | −31.9 | 38 | A |
| 175 | T | CA | 4.5 | −32.9 | −31.0 | 37 | A |
| 175 | T | C | 3.5 | −33.3 | −29.9 | 38 | A |
| 175 | T | O | 3.2 | −32.4 | −29.2 | 40 | A |
| 175 | T | CB | 6.0 | −32.6 | −30.5 | 42 | A |
| 175 | T | OG1 | 6.9 | −32.6 | −31.6 | 52 | A |
| 175 | T | CG2 | 6.5 | −33.8 | −29.6 | 34 | A |
| 176 | I | N | 3.0 | −34.5 | −30.0 | 33 | A |
| 176 | I | CA | 2.1 | −35.0 | −28.9 | 34 | A |
| 176 | I | C | 2.9 | −35.8 | −27.9 | 36 | A |
| 176 | I | O | 3.5 | −36.8 | −28.3 | 33 | A |
| 176 | I | CB | 1.0 | −35.9 | −29.5 | 38 | A |
| 176 | I | CG1 | 0.3 | −35.2 | −30.7 | 38 | A |
| 176 | I | CG2 | −0.0 | −36.3 | −28.4 | 35 | A |
| 176 | I | CD1 | −0.2 | −33.8 | −30.4 | 45 | A |
| 177 | Y | N | 3.1 | −35.7 | −26.7 | 35 | A |
| 177 | Y | CA | 3.9 | −35.9 | −25.7 | 34 | A |
| 177 | Y | C | 3.2 | −37.1 | −25.1 | 35 | A |
| 177 | Y | O | 1.9 | −37.3 | −25.3 | 32 | A |
| 177 | Y | CB | 4.3 | −34.9 | −24.6 | 35 | A |
| 177 | Y | CG | 5.2 | −33.9 | −25.2 | 39 | A |
| 177 | Y | CD1 | 4.7 | −32.6 | −25.4 | 40 | A |
| 177 | Y | CD2 | 6.5 | −34.2 | −25.5 | 40 | A |
| 177 | Y | CE1 | 5.6 | −31.6 | −25.9 | 40 | A |
| 177 | Y | CE2 | 7.4 | −33.2 | −26.0 | 41 | A |
| 177 | Y | CZ | 6.9 | −31.9 | −26.3 | 54 | A |
| 177 | Y | OH | 7.8 | −31.0 | −26.8 | 58 | A |
| 178 | N | N | 3.9 | −38.0 | −24.5 | 31 | A |
| 178 | N | CA | 3.3 | −39.2 | −24.0 | 30 | A |
| 178 | N | C | 2.3 | −39.1 | −22.9 | 33 | A |
| 178 | N | O | 1.5 | −40.0 | −22.6 | 29 | A |
| 178 | N | CB | 4.3 | −40.2 | −23.5 | 29 | A |
| 178 | N | CG | 5.1 | −40.8 | −24.7 | 43 | A |
| 178 | N | OD1 | 4.7 | −41.7 | −25.4 | 37 | A |
| 178 | N | ND2 | 6.3 | −40.2 | −24.9 | 34 | A |
| 179 | N | N | 2.3 | −37.9 | −22.2 | 30 | A |
| 179 | N | CA | 1.4 | −37.6 | −21.1 | 29 | A |
| 179 | N | C | 0.2 | −36.7 | −21.5 | 34 | A |
| 179 | N | O | −0.4 | −36.1 | −20.7 | 31 | A |
| 179 | N | CB | 2.1 | −37.3 | −19.8 | 24 | A |
| 179 | N | CG | 2.6 | −38.6 | −19.1 | 36 | A |
| 179 | N | OD1 | 1.9 | −39.6 | −18.9 | 29 | A |
| 179 | N | ND2 | 3.9 | −38.5 | −18.8 | 21 | A |
| 180 | M | N | −0.1 | −36.7 | −22.8 | 32 | A |
| 180 | M | CA | −1.2 | −36.0 | −23.4 | 32 | A |
| 180 | M | C | −1.8 | −37.2 | −24.2 | 31 | A |

TABLE 5-continued

Coordinates of Factor IXa co-crystal Compound C complex

| | | | | | | |
|---|---|---|---|---|---|---|
| 180 | M | O | −1.2 | −38.2 | −24.5 | 30 | A |
| 180 | M | CB | −0.6 | −35.0 | −24.5 | 38 | A |
| 180 | M | CG | 0.0 | −33.7 | −24.0 | 45 | A |
| 180 | M | SD | 0.8 | −33.0 | −25.5 | 56 | A |
| 180 | M | CE | 0.8 | −31.2 | −25.1 | 53 | A |
| 181 | F | N | −3.1 | −37.1 | −24.4 | 28 | A |
| 181 | F | CA | −3.8 | −38.1 | −25.3 | 26 | A |
| 181 | F | C | −4.7 | −37.5 | −26.3 | 33 | A |
| 181 | F | O | −5.0 | −36.3 | −26.2 | 28 | A |
| 181 | F | CB | −4.5 | −39.2 | −24.4 | 25 | A |
| 181 | F | CG | −5.7 | −38.6 | −23.6 | 24 | A |
| 181 | F | CD1 | −7.0 | −38.6 | −24.1 | 25 | A |
| 181 | F | CD2 | −5.5 | −38.1 | −22.3 | 22 | A |
| 181 | F | CE1 | −8.1 | −38.2 | −23.3 | 24 | A |
| 181 | F | CE2 | −6.5 | −37.7 | −21.5 | 25 | A |
| 181 | F | CZ | −7.8 | −37.7 | −22.1 | 24 | A |
| 182 | C | N | −5.2 | −38.3 | −27.2 | 37 | A |
| 182 | C | CA | −6.1 | −37.8 | −28.3 | 39 | A |
| 182 | C | C | −7.5 | −38.4 | −28.1 | 35 | A |
| 182 | C | O | −7.6 | −39.6 | −27.8 | 34 | A |
| 182 | C | CB | −5.6 | −38.3 | −29.6 | 44 | A |
| 182 | C | SG | −4.4 | −37.2 | −30.4 | 50 | A |
| 183 | A | N | −8.5 | −37.7 | −28.3 | 28 | A |
| 183 | A | CA | −9.9 | −38.2 | −28.2 | 26 | A |
| 183 | A | C | −10.8 | −37.5 | −29.3 | 31 | A |
| 183 | A | O | −10.6 | −36.4 | −29.6 | 30 | A |
| 183 | A | CB | −10.5 | −38.1 | −26.8 | 25 | A |
| 184 | G | N | −11.7 | −38.3 | −29.8 | 29 | A |
| 184 | G | CA | −12.6 | −37.8 | −30.8 | 29 | A |
| 184 | G | C | −12.9 | −38.8 | −31.9 | 34 | A |
| 184 | G | O | −12.6 | −40.0 | −31.8 | 33 | A |
| 184A | F | N | −13.7 | −38.3 | −32.9 | 29 | A |
| 184A | F | CA | −14.2 | −39.2 | −33.9 | 26 | A |
| 184A | F | C | −13.5 | −39.1 | −35.2 | 31 | A |
| 184A | F | O | −13.1 | −38.0 | −35.7 | 30 | A |
| 184A | F | CB | −15.7 | −38.8 | −34.1 | 27 | A |
| 184A | F | CG | −16.5 | −39.1 | −32.9 | 30 | A |
| 184A | F | CD1 | −16.6 | −38.2 | −31.9 | 33 | A |
| 184A | F | CD2 | −17.1 | −40.4 | −32.7 | 31 | A |
| 184A | F | CE1 | −17.3 | −38.5 | −30.7 | 34 | A |
| 184A | F | CE2 | −17.9 | −40.7 | −31.6 | 33 | A |
| 184A | F | CZ | −18.0 | −39.8 | −30.6 | 31 | A |
| 185 | H | N | −13.3 | −40.3 | −35.8 | 28 | A |
| 185 | H | CA | −12.7 | −40.4 | −37.2 | 28 | A |
| 185 | H | C | −13.2 | −39.4 | −38.2 | 34 | A |
| 185 | H | O | −12.4 | −38.8 | −38.9 | 34 | A |
| 185 | H | CB | −12.9 | −41.8 | −37.7 | 26 | A |
| 185 | H | CG | −12.1 | −42.1 | −38.9 | 29 | A |
| 185 | H | ND1 | −12.4 | −41.6 | −40.2 | 31 | A |
| 185 | H | CD2 | −11.0 | −42.9 | −39.1 | 29 | A |
| 185 | H | CE1 | −11.6 | −42.1 | −41.1 | 29 | A |
| 185 | H | NE2 | −10.7 | −42.9 | −40.5 | 29 | A |
| 186 | E | N | −14.5 | −39.2 | −38.2 | 32 | A |
| 186 | E | CA | −15.1 | −38.3 | −39.2 | 32 | A |
| 186 | E | C | −15.4 | −36.9 | −38.6 | 38 | A |
| 186 | E | O | −16.2 | −36.1 | −39.3 | 37 | A |
| 186 | E | CB | −16.4 | −38.9 | −39.8 | 32 | A |
| 186 | E | CG | −16.2 | −40.1 | −40.6 | 33 | A |
| 186 | E | CD | −15.4 | −39.9 | −41.8 | 43 | A |
| 186 | E | OE1 | −14.2 | −40.1 | −41.8 | 42 | A |
| 186 | E | OE2 | −16.0 | −39.3 | −42.8 | 43 | A |
| 187 | G | N | −14.9 | −36.5 | −37.5 | 33 | A |
| 187 | G | CA | −15.2 | −35.2 | −36.8 | 32 | A |
| 187 | G | C | −16.6 | −35.0 | −36.5 | 38 | A |
| 187 | G | O | −17.3 | −36.0 | −36.1 | 39 | A |
| 188 | G | N | −17.1 | −33.8 | −36.5 | 34 | A |
| 188 | G | CA | −18.5 | −33.6 | −36.2 | 34 | A |
| 188 | G | C | −18.8 | −33.3 | −34.7 | 39 | A |
| 188 | G | O | −19.8 | −32.7 | −34.3 | 40 | A |
| 188A | R | N | −18.0 | −34.0 | −33.9 | 36 | A |
| 188A | R | CA | −18.2 | −33.9 | −32.4 | 36 | A |
| 188A | R | C | −16.9 | −33.7 | −31.7 | 36 | A |
| 188A | R | O | −15.9 | −34.5 | −31.9 | 37 | A |
| 188A | R | CB | −18.8 | −35.3 | −31.9 | 35 | A |
| 188A | R | CG | −20.2 | −35.5 | −32.5 | 42 | A |
| 188A | R | CD | −20.7 | −36.8 | −31.9 | 53 | A |
| 188A | R | NE | −21.8 | −37.4 | −32.6 | 56 | A |
| 188A | R | CZ | −22.2 | −38.7 | −32.4 | 70 | A |
| 188A | R | NH1 | −21.7 | −39.5 | −31.5 | 50 | A |
| 188A | R | NH2 | −23.2 | −39.2 | −33.1 | 57 | A |
| 189 | D | N | −16.8 | −32.6 | −31.0 | 34 | A |
| 189 | D | CA | −15.5 | −32.3 | −30.4 | 34 | A |
| 189 | D | C | −15.7 | −31.2 | −29.3 | 42 | A |
| 189 | D | O | −16.7 | −30.5 | −29.2 | 44 | A |
| 189 | D | CB | −14.6 | −31.7 | −31.5 | 37 | A |
| 189 | D | CG | −13.1 | −31.8 | −31.2 | 46 | A |
| 189 | D | OD1 | −12.8 | −32.2 | −30.0 | 44 | A |
| 189 | D | OD2 | −12.4 | −31.4 | −32.0 | 41 | A |
| 190 | S | N | −14.6 | −31.0 | −28.5 | 39 | A |
| 190 | S | CA | −14.5 | −30.0 | −27.5 | 37 | A |
| 190 | S | C | −14.1 | −28.7 | −28.4 | 42 | A |
| 190 | S | O | −13.7 | −28.9 | −29.5 | 39 | A |
| 190 | S | CB | −13.3 | −30.2 | −26.6 | 34 | A |
| 190 | S | OG | −13.7 | −31.1 | −25.6 | 36 | A |
| 191 | C | N | −14.4 | −27.5 | −27.9 | 41 | A |
| 191 | C | CA | −14.1 | −26.3 | −28.7 | 42 | A |
| 191 | C | C | −13.6 | −25.2 | −27.8 | 42 | A |
| 191 | C | O | −13.4 | −25.4 | −26.6 | 42 | A |
| 191 | C | CB | −15.3 | −25.9 | −29.5 | 46 | A |
| 191 | C | SG | −15.0 | −24.9 | −31.0 | 50 | A |
| 192 | Q | N | −13.3 | −24.1 | −28.4 | 39 | A |
| 192 | Q | CA | −12.8 | −22.9 | −27.7 | 38 | A |
| 192 | Q | C | −13.7 | −22.6 | −26.6 | 39 | A |
| 192 | Q | O | −14.9 | −22.5 | −26.7 | 41 | A |
| 192 | Q | CB | −12.8 | −21.7 | −28.7 | 41 | A |
| 192 | Q | CG | −12.1 | −20.5 | −28.1 | 65 | A |
| 192 | Q | CD | −11.0 | −19.9 | −29.0 | 98 | A |
| 192 | Q | OE1 | −11.2 | −19.1 | −29.9 | 97 | A |
| 192 | Q | NE2 | −9.8 | −20.5 | −28.9 | 88 | A |
| 193 | G | N | −13.2 | −22.4 | −25.4 | 34 | A |
| 193 | G | CA | −14.0 | −22.1 | −24.2 | 33 | A |
| 193 | G | C | −14.2 | −23.3 | −23.3 | 37 | A |
| 193 | G | O | −14.8 | −23.1 | −22.3 | 38 | A |
| 194 | D | N | −13.8 | −24.4 | −23.8 | 34 | A |
| 194 | D | CA | −13.9 | −25.7 | −23.1 | 33 | A |
| 194 | D | C | −12.6 | −26.1 | −22.4 | 34 | A |
| 194 | D | O | −12.6 | −26.9 | −21.4 | 32 | A |
| 194 | D | CB | −14.3 | −26.9 | −24.1 | 34 | A |
| 194 | D | CG | −15.7 | −26.8 | −24.6 | 37 | A |
| 194 | D | OD1 | −16.6 | −26.5 | −23.7 | 35 | A |
| 194 | D | OD2 | −16.0 | −27.0 | −25.8 | 41 | A |
| 195 | S | N | −11.5 | −25.6 | −22.9 | 30 | A |
| 195 | S | CA | −10.2 | −25.8 | −22.3 | 31 | A |
| 195 | S | C | −10.2 | −25.7 | −20.9 | 31 | A |
| 195 | S | O | −10.8 | −24.8 | −20.3 | 31 | A |
| 195 | S | CB | −9.1 | −24.9 | −22.9 | 33 | A |
| 195 | S | OG | −8.9 | −25.2 | −24.3 | 47 | A |
| 196 | G | N | −9.4 | −26.5 | −20.2 | 25 | A |
| 196 | G | CA | −9.3 | −26.5 | −18.8 | 24 | A |
| 196 | G | C | −10.3 | −27.4 | −18.1 | 29 | A |
| 196 | G | O | −10.2 | −27.8 | −17.0 | 29 | A |
| 197 | G | N | −11.4 | −27.6 | −18.8 | 26 | A |
| 197 | G | CA | −12.5 | −28.4 | −18.4 | 25 | A |
| 197 | G | C | −12.2 | −29.9 | −18.3 | 31 | A |
| 197 | G | O | −11.1 | −30.3 | −18.6 | 28 | A |
| 198 | P | N | −13.2 | −30.6 | −17.7 | 31 | A |
| 198 | P | CA | −13.0 | −32.1 | −17.4 | 30 | A |
| 198 | P | C | −13.2 | −33.1 | −18.5 | 31 | A |
| 198 | P | O | −14.1 | −33.0 | −19.3 | 28 | A |
| 198 | P | CB | −14.0 | −32.4 | −16.3 | 31 | A |
| 198 | P | CG | −15.2 | −31.5 | −16.7 | 35 | A |
| 198 | P | CD | −14.5 | −30.2 | −17.2 | 32 | A |
| 199 | H | N | −12.3 | −34.1 | −18.5 | 28 | A |
| 199 | H | CA | −12.5 | −35.4 | −19.3 | 26 | A |
| 199 | H | C | −12.6 | −36.4 | −18.2 | 29 | A |
| 199 | H | O | −11.7 | −36.6 | −17.4 | 26 | A |
| 199 | H | CB | −11.4 | −35.6 | −20.3 | 26 | A |
| 199 | H | CG | −11.4 | −37.0 | −21.0 | 29 | A |
| 199 | H | ND1 | −11.1 | −38.1 | −20.3 | 30 | A |
| 199 | H | CD2 | −11.8 | −37.3 | −22.2 | 31 | A |
| 199 | H | CE1 | −11.2 | −39.1 | −21.2 | 30 | A |
| 199 | H | NE2 | −11.6 | −38.6 | −22.4 | 31 | A |
| 200 | V | N | −13.8 | −37.0 | −18.0 | 28 | A |
| 200 | V | CA | −14.1 | −38.0 | −17.0 | 28 | A |
| 200 | V | C | −14.4 | −39.4 | −17.5 | 32 | A |
| 200 | V | O | −15.0 | −39.5 | −18.5 | 28 | A |

TABLE 5-continued

Coordinates of Factor IXa co-crystal Compound C complex

| | | | | | | |
|---|---|---|---|---|---|---|
| 200 | V | CB | −15.2 | −37.5 | −16.0 | 29 A |
| 200 | V | CG1 | −14.9 | −36.1 | −15.4 | 29 A |
| 200 | V | CG2 | −16.6 | −37.6 | −16.6 | 28 A |
| 201 | T | N | −14.1 | −40.3 | −16.6 | 30 A |
| 201 | T | CA | −14.5 | −41.7 | −16.9 | 30 A |
| 201 | T | C | −15.4 | −42.2 | −15.8 | 33 A |
| 201 | T | O | −15.2 | −42.1 | −14.6 | 34 A |
| 201 | T | CB | −13.2 | −42.6 | −17.1 | 36 A |
| 201 | T | OG1 | −12.4 | −42.0 | −18.1 | 34 A |
| 201 | T | CG2 | −13.5 | −44.0 | −17.4 | 32 A |
| 202 | E | N | −16.6 | −42.8 | −16.2 | 29 A |
| 202 | E | CA | −17.5 | −43.4 | −15.3 | 30 A |
| 202 | E | C | −17.1 | −44.8 | −15.0 | 40 A |
| 202 | E | O | −17.0 | −45.7 | −15.9 | 38 A |
| 202 | E | CB | −18.9 | −43.4 | −15.9 | 30 A |
| 202 | E | CG | −19.4 | −42.1 | −16.3 | 45 A |
| 202 | E | CD | −20.8 | −42.2 | −16.9 | 70 A |
| 202 | E | OE1 | −21.1 | −43.1 | −17.7 | 59 A |
| 202 | E | OE2 | −21.6 | −41.3 | −16.7 | 66 A |
| 203 | V | N | −16.9 | −45.0 | −13.7 | 39 A |
| 203 | V | CA | −16.5 | −46.4 | −13.2 | 39 A |
| 203 | V | C | −17.6 | −46.9 | −12.3 | 44 A |
| 203 | V | O | −17.6 | −46.7 | −11.1 | 45 A |
| 203 | V | CB | −15.2 | −46.3 | −12.5 | 44 A |
| 203 | V | CG1 | −14.7 | −47.6 | −11.9 | 44 A |
| 203 | V | CG2 | −14.1 | −45.6 | −13.3 | 43 A |
| 204 | E | N | −18.6 | −47.5 | −13.0 | 42 A |
| 204 | E | CA | −19.7 | −48.1 | −12.2 | 42 A |
| 204 | E | C | −20.5 | −47.0 | −11.5 | 47 A |
| 204 | E | O | −20.7 | −47.1 | −10.3 | 46 A |
| 204 | E | CB | −19.2 | −49.1 | −11.2 | 43 A |
| 204 | E | CG | −18.9 | −50.4 | −11.9 | 60 A |
| 204 | E | CD | −19.9 | −51.5 | −11.5 | 93 A |
| 204 | E | OE1 | −19.8 | −52.1 | −10.4 | 93 A |
| 204 | E | OE2 | −21.0 | −51.6 | −12.2 | 89 A |
| 205 | G | N | −20.9 | −45.9 | −12.2 | 43 A |
| 205 | G | CA | −21.6 | −44.9 | −11.6 | 43 A |
| 205 | G | C | −20.8 | −43.8 | −10.8 | 44 A |
| 205 | G | O | −21.4 | −42.8 | −10.3 | 46 A |
| 206 | T | N | −19.5 | −44.0 | −10.7 | 37 A |
| 206 | T | CA | −18.7 | −43.0 | −10.1 | 35 A |
| 206 | T | C | −17.7 | −42.4 | −11.2 | 38 A |
| 206 | T | O | −17.0 | −43.2 | −11.8 | 38 A |
| 206 | T | CB | −17.9 | −43.5 | −8.9 | 34 A |
| 206 | T | OG1 | −18.8 | −44.2 | −8.0 | 38 A |
| 206 | T | CG2 | −17.3 | −42.4 | −8.1 | 38 A |
| 207 | S | N | −17.8 | −41.1 | −11.3 | 33 A |
| 207 | S | CA | −16.9 | −40.4 | −12.3 | 31 A |
| 207 | S | C | −15.5 | −40.1 | −11.7 | 33 A |
| 207 | S | O | −15.4 | −39.7 | −10.6 | 31 A |
| 207 | S | CB | −17.6 | −39.2 | −12.9 | 30 A |
| 207 | S | OG | −18.7 | −39.6 | −13.7 | 30 A |
| 208 | F | N | −14.5 | −40.4 | −12.5 | 28 A |
| 208 | F | CA | −13.1 | −40.1 | −12.1 | 25 A |
| 208 | F | C | −12.5 | −39.2 | −13.1 | 28 A |
| 208 | F | O | −12.9 | −39.3 | −14.3 | 26 A |
| 208 | F | CB | −12.3 | −41.4 | −12.0 | 25 A |
| 208 | F | CG | −12.6 | −42.2 | −10.7 | 26 A |
| 208 | F | CD1 | −13.6 | −43.1 | −10.7 | 27 A |
| 208 | F | CD2 | −11.7 | −42.1 | −9.6 | 27 A |
| 208 | F | CE1 | −13.9 | −43.8 | −9.6 | 28 A |
| 208 | F | CE2 | −12.0 | −42.8 | −8.5 | 29 A |
| 208 | F | CZ | −13.1 | −43.6 | −8.4 | 27 A |
| 209 | L | N | −11.7 | −38.3 | −12.7 | 28 A |
| 209 | L | CA | −11.0 | −37.3 | −13.6 | 27 A |
| 209 | L | C | −9.9 | −38.0 | −14.3 | 30 A |
| 209 | L | O | −8.9 | −38.5 | −13.6 | 27 A |
| 209 | L | CB | −10.5 | −36.2 | −12.8 | 27 A |
| 209 | L | CG | −10.0 | −35.0 | −13.6 | 30 A |
| 209 | L | CD1 | −11.1 | −34.4 | −14.4 | 28 A |
| 209 | L | CD2 | −9.3 | −33.9 | −12.7 | 32 A |
| 210 | T | N | −10.0 | −38.2 | −15.6 | 28 A |
| 210 | T | CA | −9.0 | −38.8 | −16.5 | 27 A |
| 210 | T | C | −8.1 | −37.9 | −17.3 | 32 A |
| 210 | T | O | −7.0 | −38.2 | −17.7 | 34 A |
| 210 | T | CB | −9.5 | −40.1 | −17.2 | 28 A |
| 210 | T | OG1 | −10.7 | −39.8 | −17.8 | 24 A |
| 210 | T | CG2 | −9.8 | −41.2 | −16.1 | 27 A |
| 211 | G | N | −8.6 | −36.7 | −17.7 | 29 A |
| 211 | G | CA | −7.9 | −35.7 | −18.5 | 28 A |
| 211 | G | C | −8.4 | −34.3 | −18.3 | 29 A |
| 211 | G | O | −9.5 | −34.0 | −17.8 | 28 A |
| 212 | I | N | −7.6 | −33.4 | −18.8 | 25 A |
| 212 | I | CA | −7.9 | −32.0 | −18.9 | 24 A |
| 212 | I | C | −8.1 | −31.6 | −20.3 | 29 A |
| 212 | I | O | −7.2 | −31.9 | −21.1 | 27 A |
| 212 | I | CB | −6.9 | −31.0 | −18.2 | 25 A |
| 212 | I | CG1 | −6.4 | −31.5 | −16.8 | 24 A |
| 212 | I | CG2 | −7.3 | −29.6 | −18.2 | 23 A |
| 212 | I | CD1 | −7.5 | −31.5 | −15.7 | 29 A |
| 213 | I | N | −9.2 | −31.0 | −20.7 | 28 A |
| 213 | I | CA | −9.4 | −30.5 | −22.1 | 27 A |
| 213 | I | C | −8.3 | −29.5 | −22.4 | 33 A |
| 213 | I | O | −8.2 | −28.5 | −21.7 | 32 A |
| 213 | I | CB | −10.8 | −29.9 | −22.3 | 29 A |
| 213 | I | CG1 | −11.9 | −30.8 | −21.8 | 28 A |
| 213 | I | CG2 | −11.0 | −29.4 | −23.7 | 30 A |
| 213 | I | CD1 | −13.3 | −30.3 | −21.8 | 27 A |
| 214 | S | N | −7.5 | −29.8 | −23.4 | 28 A |
| 214 | S | CA | −6.3 | −28.9 | −23.7 | 28 A |
| 214 | S | C | −6.5 | −28.1 | −25.0 | 35 A |
| 214 | S | O | −6.6 | −26.9 | −24.9 | 34 A |
| 214 | S | CB | −5.0 | −29.7 | −23.7 | 31 A |
| 214 | S | OG | −3.9 | −28.8 | −23.5 | 41 A |
| 215 | W | N | −6.3 | −28.7 | −26.1 | 30 A |
| 215 | W | CA | −6.3 | −28.0 | −27.4 | 31 A |
| 215 | W | C | −6.6 | −28.8 | −28.6 | 36 A |
| 215 | W | O | −6.6 | −30.0 | −28.5 | 35 A |
| 215 | W | CB | −4.9 | −27.3 | −27.6 | 30 A |
| 215 | W | CG | −3.8 | −28.3 | −27.7 | 30 A |
| 215 | W | CD1 | −3.1 | −28.8 | −26.7 | 32 A |
| 215 | W | CD2 | −3.2 | −28.7 | −28.9 | 30 A |
| 215 | W | NE1 | −2.1 | −29.6 | −27.2 | 31 A |
| 215 | W | CE2 | −2.1 | −29.6 | −28.6 | 33 A |
| 215 | W | CE3 | −3.4 | −28.6 | −30.3 | 31 A |
| 215 | W | CZ2 | −1.3 | −30.2 | −29.5 | 33 A |
| 215 | W | CZ3 | −2.6 | −29.2 | −31.2 | 32 A |
| 215 | W | CH2 | −1.5 | −29.9 | −30.8 | 33 A |
| 216 | G | N | −6.8 | −28.1 | −29.7 | 33 A |
| 216 | G | CA | −7.1 | −28.7 | −31.0 | 33 A |
| 216 | G | C | −6.6 | −27.8 | −32.1 | 39 A |
| 216 | G | O | −6.2 | −26.6 | −31.9 | 38 A |
| 217 | E | N | −6.6 | −28.3 | −33.3 | 40 A |
| 217 | E | CA | −6.2 | −27.4 | −34.5 | 42 A |
| 217 | E | C | −7.4 | −26.9 | −35.1 | 53 A |
| 217 | E | O | −7.5 | −25.8 | −35.5 | 58 A |
| 217 | E | CB | −5.3 | −28.1 | −35.5 | 43 A |
| 217 | E | CG | −3.9 | −28.4 | −35.0 | 46 A |
| 217 | E | CD | −3.1 | −29.3 | −35.8 | 75 A |
| 217 | E | OE1 | −2.9 | −30.5 | −35.4 | 65 A |
| 217 | E | OE2 | −2.6 | −28.9 | −36.9 | 71 A |
| 219 | E | N | −8.5 | −27.7 | −34.9 | 51 A |
| 219 | E | CA | −9.8 | −27.2 | −35.4 | 53 A |
| 219 | E | C | −10.8 | −27.8 | −34.4 | 56 A |
| 219 | E | O | −10.4 | −28.4 | −33.4 | 57 A |
| 219 | E | CB | −10.1 | −27.8 | −36.8 | 55 A |
| 219 | E | CG | −9.3 | −27.2 | −37.9 | 69 A |
| 219 | E | CD | −9.9 | −25.9 | −38.5 | 97 A |
| 219 | E | OE1 | −10.5 | −25.2 | −37.7 | 0 A |
| 219 | E | OE2 | −9.7 | −25.6 | −39.7 | 91 A |
| 220 | C | N | −12.1 | −27.5 | −34.6 | 49 A |
| 220 | C | CA | −13.1 | −28.1 | −33.7 | 47 A |
| 220 | C | C | −13.8 | −29.0 | −34.8 | 44 A |
| 220 | C | O | −14.2 | −28.5 | −35.9 | 42 A |
| 220 | C | CB | −14.2 | −27.1 | −33.2 | 48 A |
| 220 | C | SG | −13.6 | −25.9 | −32.0 | 54 A |
| 221 | A | N | −13.9 | −30.3 | −34.4 | 37 A |
| 221 | A | CA | −14.8 | −31.2 | −35.1 | 35 A |
| 221 | A | C | −14.5 | −31.5 | −36.6 | 42 A |
| 221 | A | O | −15.4 | −31.8 | −37.3 | 42 A |
| 221 | A | CB | −16.2 | −30.9 | −34.9 | 34 A |
| 221A | M | N | −13.2 | −31.4 | −37.0 | 41 A |
| 221A | M | CA | −12.8 | −31.6 | −38.4 | 43 A |
| 221A | M | C | −12.3 | −33.0 | −38.6 | 42 A |
| 221A | M | O | −11.4 | −33.5 | −37.9 | 43 A |
| 221A | M | CB | −11.7 | −30.6 | −38.9 | 48 A |

TABLE 5-continued

Coordinates of Factor IXa co-crystal Compound C complex

| | | | | | | |
|---|---|---|---|---|---|---|
| 221A | M | CG | −12.2 | −29.1 | −38.8 | 56 A |
| 221A | M | SD | −13.5 | −28.6 | −40.0 | 64 A |
| 221A | M | CE | −14.8 | −28.2 | −38.7 | 61 A |
| 222 | K | N | −12.9 | −33.7 | −39.6 | 35 A |
| 222 | K | CA | −12.4 | −35.0 | −40.0 | 34 A |
| 222 | K | C | −10.9 | −35.1 | −40.1 | 38 A |
| 222 | K | O | −10.3 | −34.3 | −40.8 | 40 A |
| 222 | K | CB | −13.1 | −35.4 | −41.3 | 35 A |
| 222 | K | CG | −12.4 | −36.6 | −41.9 | 42 A |
| 222 | K | CD | −13.0 | −37.2 | −43.2 | 50 A |
| 222 | K | CE | −12.4 | −38.6 | −43.4 | 49 A |
| 222 | K | NZ | −12.9 | −39.3 | −44.5 | 60 A |
| 223 | G | N | −10.3 | −36.0 | −39.4 | 33 A |
| 223 | G | CA | −8.8 | −36.1 | −39.5 | 32 A |
| 223 | G | C | −8.1 | −35.4 | −38.4 | 36 A |
| 223 | G | O | −6.9 | −35.7 | −38.2 | 36 A |
| 224 | K | N | −8.7 | −34.6 | −37.6 | 34 A |
| 224 | K | CA | −8.1 | −33.9 | −36.5 | 33 A |
| 224 | K | C | −8.8 | −34.4 | −35.2 | 35 A |
| 224 | K | O | −10.0 | −34.8 | −35.2 | 34 A |
| 224 | K | CB | −8.4 | −32.4 | −36.7 | 33 A |
| 224 | K | CG | −7.5 | −31.9 | −37.8 | 32 A |
| 224 | K | CD | −6.1 | −32.1 | −37.5 | 40 A |
| 224 | K | CE | −5.2 | −31.4 | −38.5 | 43 A |
| 224 | K | NZ | −3.8 | −31.6 | −38.0 | 53 A |
| 225 | Y | N | −8.1 | −34.4 | −34.1 | 32 A |
| 225 | Y | CA | −8.6 | −34.8 | −32.8 | 32 A |
| 225 | Y | C | −8.4 | −33.8 | −31.7 | 35 A |
| 225 | Y | O | −7.6 | −32.9 | −31.8 | 36 A |
| 225 | Y | CB | −7.9 | −36.2 | −32.4 | 31 A |
| 225 | Y | CG | −8.2 | −37.3 | −33.3 | 28 A |
| 225 | Y | CD1 | −9.4 | −37.9 | −33.3 | 28 A |
| 225 | Y | CD2 | −7.2 | −37.6 | −34.3 | 28 A |
| 225 | Y | CE1 | −9.7 | −38.9 | −34.3 | 25 A |
| 225 | Y | CE2 | −7.6 | −38.7 | −35.3 | 27 A |
| 225 | Y | CZ | −8.8 | −39.3 | −35.2 | 33 A |
| 225 | Y | OH | −9.1 | −40.4 | −36.0 | 30 A |
| 226 | G | N | −9.1 | −34.0 | −30.6 | 31 A |
| 226 | G | CA | −8.9 | −33.1 | −29.4 | 31 A |
| 226 | G | C | −7.7 | −33.7 | −28.7 | 32 A |
| 226 | G | O | −7.4 | −34.9 | −28.7 | 32 A |
| 227 | I | N | −6.8 | −32.8 | −28.2 | 25 A |
| 227 | I | CA | −5.6 | −33.1 | −27.4 | 23 A |
| 227 | I | C | −5.9 | −32.8 | −25.9 | 28 A |
| 227 | I | O | −6.4 | −31.8 | −25.6 | 25 A |
| 227 | I | CB | −4.4 | −32.4 | −28.0 | 25 A |
| 227 | I | CG1 | −4.3 | −32.5 | −29.5 | 25 A |
| 227 | I | CG2 | −3.1 | −32.9 | −27.3 | 24 A |
| 227 | I | CD1 | −3.9 | −34.0 | −29.9 | 25 A |
| 228 | Y | N | −5.6 | −33.8 | −25.0 | 25 A |
| 228 | Y | CA | −5.9 | −33.7 | −23.6 | 24 A |
| 228 | Y | C | −4.7 | −34.0 | −22.8 | 29 A |
| 228 | Y | O | −3.9 | −34.8 | −23.2 | 31 A |
| 228 | Y | CB | −7.1 | −34.7 | −23.2 | 25 A |
| 228 | Y | CG | −8.4 | −34.5 | −23.9 | 26 A |
| 228 | Y | CD1 | −8.5 | −34.9 | −25.3 | 27 A |
| 228 | Y | CD2 | −9.4 | −33.9 | −23.3 | 24 A |
| 228 | Y | CE1 | −9.7 | −34.6 | −26.0 | 26 A |
| 228 | Y | CE2 | −10.6 | −33.6 | −24.0 | 27 A |
| 228 | Y | CZ | −10.7 | −34.0 | −25.4 | 31 A |
| 228 | Y | OH | −11.9 | −33.8 | −26.1 | 28 A |
| 229 | T | N | −4.6 | −33.4 | −21.6 | 25 A |
| 229 | T | CA | −3.6 | −33.7 | −20.6 | 24 A |
| 229 | T | C | −4.0 | −34.9 | −19.8 | 28 A |
| 229 | T | O | −5.2 | −35.0 | −19.4 | 24 A |
| 229 | T | CB | −3.4 | −32.5 | −19.7 | 30 A |
| 229 | T | OG1 | −2.9 | −31.4 | −20.6 | 33 A |
| 229 | T | CG2 | −2.4 | −32.8 | −18.6 | 25 A |
| 230 | K | N | −3.1 | −35.8 | −19.6 | 28 A |
| 230 | K | CA | −3.3 | −37.0 | −18.8 | 27 A |
| 230 | K | C | −3.2 | −36.7 | −17.3 | 29 A |
| 230 | K | O | −2.2 | −36.2 | −16.9 | 26 A |
| 230 | K | CB | −2.2 | −38.1 | −19.2 | 28 A |
| 230 | K | CG | −2.6 | −39.0 | −20.4 | 27 A |
| 230 | K | CD | −1.6 | −40.1 | −20.5 | 27 A |
| 230 | K | CE | −1.5 | −40.6 | −21.9 | 22 A |
| 230 | K | NZ | −0.6 | −41.8 | −22.1 | 28 A |
| 231 | V | N | −4.3 | −36.8 | −16.6 | 27 A |
| 231 | V | CA | −4.3 | −36.5 | −15.2 | 26 A |
| 231 | V | C | −3.4 | −37.4 | −14.4 | 28 A |
| 231 | V | O | −2.9 | −37.1 | −13.4 | 27 A |
| 231 | V | CB | −5.8 | −36.5 | −14.7 | 29 A |
| 231 | V | CG1 | −5.9 | −36.6 | −13.2 | 28 A |
| 231 | V | CG2 | −6.5 | −35.1 | −15.1 | 27 A |
| 232 | S | N | −3.3 | −38.7 | −14.8 | 27 A |
| 232 | S | CA | −2.5 | −39.7 | −14.1 | 27 A |
| 232 | S | C | −1.1 | −39.2 | −13.8 | 30 A |
| 232 | S | O | −0.5 | −39.6 | −12.8 | 28 A |
| 232 | S | CB | −2.4 | −41.0 | −15.0 | 29 A |
| 232 | S | OG | −1.7 | −40.8 | −16.2 | 27 A |
| 233 | R | N | −0.6 | −38.4 | −14.7 | 28 A |
| 233 | R | CA | 0.8 | −37.8 | −14.6 | 24 A |
| 233 | R | C | 0.9 | −36.8 | −13.4 | 25 A |
| 233 | R | O | 2.0 | −36.5 | −13.0 | 24 A |
| 233 | R | CB | 1.1 | −37.2 | −16.0 | 21 A |
| 233 | R | CG | 2.2 | −36.2 | −16.0 | 27 A |
| 233 | R | CD | 3.6 | −36.8 | −15.7 | 26 A |
| 233 | R | NE | 4.7 | −35.9 | −15.8 | 29 A |
| 233 | R | CZ | 5.0 | −35.0 | −14.9 | 36 A |
| 233 | R | NH1 | 4.4 | −35.0 | −13.8 | 25 A |
| 233 | R | NH2 | 6.0 | −34.1 | −15.1 | 24 A |
| 234 | Y | N | −0.2 | −36.3 | −13.0 | 21 A |
| 234 | Y | CA | −0.3 | −35.2 | −12.0 | 22 A |
| 234 | Y | C | −1.0 | −35.5 | −10.7 | 26 A |
| 234 | Y | O | −1.2 | −34.6 | −9.9 | 25 A |
| 234 | Y | CB | −0.9 | −34.0 | −12.6 | 22 A |
| 234 | Y | CG | −0.1 | −33.5 | −13.8 | 23 A |
| 234 | Y | CD1 | 1.2 | −32.9 | −13.7 | 26 A |
| 234 | Y | CD2 | −0.5 | −33.7 | −15.1 | 22 A |
| 234 | Y | CE1 | 1.9 | −32.5 | −14.8 | 24 A |
| 234 | Y | CE2 | 0.2 | −33.4 | −16.2 | 23 A |
| 234 | Y | CZ | 1.4 | −32.8 | −16.1 | 29 A |
| 234 | Y | OH | 2.2 | −32.5 | −17.2 | 30 A |
| 235 | V | N | −1.4 | −36.8 | −10.5 | 24 A |
| 235 | V | CA | −2.1 | −37.2 | −9.3 | 26 A |
| 235 | V | C | −1.5 | −36.8 | −8.0 | 30 A |
| 235 | V | O | −2.1 | −36.2 | −7.1 | 31 A |
| 235 | V | CB | −2.7 | −38.6 | −9.4 | 31 A |
| 235 | V | CG1 | −3.3 | −39.0 | −8.0 | 34 A |
| 235 | V | CG2 | −3.8 | −38.7 | −10.4 | 28 A |
| 236 | N | N | −0.2 | −37.1 | −7.8 | 30 A |
| 236 | N | CA | 0.5 | −36.8 | −6.5 | 30 A |
| 236 | N | C | 0.5 | −35.3 | −6.3 | 34 A |
| 236 | N | O | 0.3 | −34.8 | −5.2 | 33 A |
| 236 | N | CB | 2.0 | −37.3 | −6.5 | 31 A |
| 236 | N | CG | 2.8 | −36.9 | −5.3 | 53 A |
| 236 | N | OD1 | 3.1 | −35.7 | −5.0 | 39 A |
| 236 | N | ND2 | 3.1 | −37.8 | −4.3 | 38 A |
| 237 | W | N | 0.8 | −34.5 | −7.3 | 32 A |
| 237 | W | CA | 0.9 | −33.1 | −7.2 | 30 A |
| 237 | W | C | −0.5 | −32.5 | −6.8 | 32 A |
| 237 | W | O | −0.5 | −31.6 | −5.9 | 32 A |
| 237 | W | CB | 1.4 | −32.5 | −8.5 | 26 A |
| 237 | W | CG | 1.3 | −30.9 | −8.6 | 26 A |
| 237 | W | CD1 | 2.2 | −30.0 | −8.1 | 29 A |
| 237 | W | CD2 | 0.3 | −30.2 | −9.3 | 25 A |
| 237 | W | NE1 | 1.9 | −28.8 | −8.5 | 28 A |
| 237 | W | CE2 | 0.7 | −28.8 | −9.3 | 28 A |
| 237 | W | CE3 | −0.7 | −30.5 | −10.2 | 27 A |
| 237 | W | CZ2 | 0.0 | −27.8 | −9.9 | 27 A |
| 237 | W | CZ3 | −1.5 | −29.5 | −10.8 | 27 A |
| 237 | W | CH2 | −1.0 | −28.2 | −10.7 | 27 A |
| 238 | I | N | −1.5 | −32.9 | −7.5 | 29 A |
| 238 | I | CA | −2.9 | −32.5 | −7.2 | 28 A |
| 238 | I | C | −3.3 | −32.7 | −5.7 | 32 A |
| 238 | I | O | −3.7 | −31.8 | −5.0 | 33 A |
| 238 | I | CB | −4.0 | −33.1 | −8.1 | 30 A |
| 238 | I | CG1 | −3.8 | −32.6 | −9.5 | 30 A |
| 238 | I | CG2 | −5.4 | −32.8 | −7.6 | 27 A |
| 238 | I | CD1 | −4.6 | −33.4 | −10.5 | 22 A |
| 239 | K | N | −3.2 | −33.9 | −5.3 | 29 A |
| 239 | K | CA | −3.5 | −34.4 | −3.9 | 28 A |
| 239 | K | C | −2.7 | −33.6 | −2.8 | 35 A |
| 239 | K | O | −3.2 | −33.1 | −1.8 | 37 A |
| 239 | K | CB | −3.3 | −35.9 | −3.7 | 27 A |
| 239 | K | CG | −4.6 | −36.5 | −4.2 | 40 A |

TABLE 5-continued

Coordinates of Factor IXa co-crystal Compound C complex

| | | | | | | |
|---|---|---|---|---|---|---|
| 239 | K | CD | −4.5 | −37.9 | −4.8 | 56 | A |
| 239 | K | CE | −5.8 | −38.5 | −5.3 | 63 | A |
| 239 | K | NZ | −7.0 | −37.9 | −4.7 | 52 | A |
| 240 | E | N | −1.4 | −33.4 | −3.1 | 29 | A |
| 240 | E | CA | −0.5 | −32.6 | −2.3 | 28 | A |
| 240 | E | C | −0.9 | −31.2 | −2.1 | 35 | A |
| 240 | E | O | −1.1 | −30.7 | −1.0 | 36 | A |
| 240 | E | CB | 0.9 | −32.7 | −2.8 | 28 | A |
| 240 | E | CG | 2.0 | −31.8 | −2.0 | 29 | A |
| 240 | E | CD | 1.9 | −32.1 | −0.5 | 53 | A |
| 240 | E | OE1 | 1.4 | −33.1 | −0.1 | 51 | A |
| 240 | E | OE2 | 2.4 | −31.2 | 0.2 | 47 | A |
| 241 | K | N | −1.1 | −30.5 | −3.2 | 31 | A |
| 241 | K | CA | −1.4 | −29.1 | −3.2 | 30 | A |
| 241 | K | C | −2.8 | −28.8 | −2.7 | 35 | A |
| 241 | K | O | −3.0 | −27.6 | −2.2 | 35 | A |
| 241 | K | CB | −1.2 | −28.4 | −4.6 | 33 | A |
| 241 | K | CG | 0.1 | −28.6 | −5.2 | 34 | A |
| 241 | K | CD | 1.3 | −28.1 | −4.3 | 31 | A |
| 241 | K | CE | 2.5 | −27.9 | −5.2 | 50 | A |
| 241 | K | NZ | 3.8 | −27.7 | −4.3 | 51 | A |
| 242 | T | N | −3.7 | −29.6 | −2.9 | 31 | A |
| 242 | T | CA | −5.1 | −29.3 | −2.6 | 31 | A |
| 242 | T | C | −5.5 | −29.8 | −1.2 | 38 | A |
| 242 | T | O | −6.7 | −29.8 | −0.8 | 39 | A |
| 242 | T | CB | −6.1 | −29.8 | −3.6 | 28 | A |
| 242 | T | OG1 | −6.0 | −31.1 | −3.6 | 25 | A |
| 242 | T | CG2 | −5.7 | −29.3 | −5.0 | 23 | A |
| 243 | K | N | −4.5 | −30.4 | −0.5 | 39 | A |
| 243 | K | CA | −4.7 | −31.0 | 0.9 | 41 | A |
| 243 | K | C | −5.5 | −29.9 | 1.8 | 44 | A |
| 243 | K | O | −5.0 | −28.8 | 1.9 | 42 | A |
| 243 | K | CB | −3.3 | −31.3 | 1.5 | 45 | A |
| 243 | K | CG | −3.3 | −32.5 | 2.4 | 60 | A |
| 243 | K | CD | −2.8 | −33.7 | 1.7 | 61 | A |
| 243 | K | CE | −1.4 | −34.2 | 2.2 | 58 | A |
| 243 | K | NZ | −1.3 | −35.6 | 2.3 | 59 | A |
| 244 | L | N | −6.6 | −30.3 | 2.4 | 44 | A |
| 244 | L | CA | −7.4 | −29.4 | 3.2 | 44 | A |
| 244 | L | C | −6.9 | −29.5 | 4.7 | 52 | A |
| 244 | L | O | −6.9 | −30.6 | 5.3 | 53 | A |
| 244 | L | CB | −8.9 | −29.6 | 3.1 | 43 | A |
| 244 | L | CG | −9.4 | −29.1 | 1.8 | 45 | A |
| 244 | L | CD1 | −10.9 | −29.3 | 1.7 | 45 | A |
| 244 | L | CD2 | −9.1 | −27.7 | 1.7 | 46 | A |
| 86 | M | N | −10.0 | −63.4 | −7.0 | 87 | B |
| 86 | M | CA | −8.9 | −64.1 | −6.5 | 87 | B |
| 86 | M | C | −7.6 | −63.3 | −6.8 | 85 | B |
| 86 | M | O | −6.7 | −63.2 | −5.9 | 84 | B |
| 86 | M | CB | −8.7 | −65.5 | −7.0 | 91 | B |
| 86 | M | CG | −9.0 | −65.7 | −8.5 | 97 | B |
| 86 | M | SD | −9.2 | −67.4 | −9.0 | 0 | B |
| 86 | M | CE | −11.1 | −67.6 | −8.8 | 0 | B |
| 87 | T | N | −7.5 | −62.7 | −7.9 | 76 | B |
| 87 | T | CA | −6.4 | −61.8 | −8.3 | 73 | B |
| 87 | T | C | −6.8 | −60.5 | −8.9 | 71 | B |
| 87 | T | O | −7.9 | −60.4 | −9.6 | 69 | B |
| 87 | T | CB | −5.3 | −62.5 | −9.0 | 78 | B |
| 87 | T | OG1 | −4.3 | −61.5 | −9.3 | 80 | B |
| 87 | T | CG2 | −5.8 | −63.0 | −10.4 | 73 | B |
| 88 | C | N | −6.0 | −59.4 | −8.7 | 64 | B |
| 88 | C | CA | −6.4 | −58.1 | −9.2 | 60 | B |
| 88 | C | C | −6.3 | −58.0 | −10.7 | 67 | B |
| 88 | C | O | −7.2 | −57.4 | −11.4 | 66 | B |
| 88 | C | CB | −5.6 | −57.0 | −8.6 | 57 | B |
| 88 | C | SG | −5.9 | −56.8 | −6.8 | 59 | B |
| 89 | N | N | −5.3 | −58.6 | −11.3 | 65 | B |
| 89 | N | CA | −5.1 | −58.7 | −12.8 | 65 | B |
| 89 | N | C | −6.2 | −59.6 | −13.4 | 69 | B |
| 89 | N | O | −6.0 | −59.9 | −14.6 | 70 | B |
| 89 | N | CB | −3.7 | −59.1 | −13.2 | 68 | B |
| 89 | N | CG | −3.2 | −60.4 | −12.5 | 0 | B |
| 89 | N | OD1 | −3.5 | −61.6 | −12.9 | 0 | B |
| 89 | N | ND2 | −2.5 | −60.2 | −11.4 | 0 | B |
| 90 | I | N | −7.2 | −60.0 | −12.7 | 65 | B |
| 90 | I | CA | −8.3 | −60.7 | −13.3 | 65 | B |
| 90 | I | C | −9.6 | −60.0 | −12.8 | 68 | B |
| 90 | I | O | −10.0 | −60.1 | −11.7 | 68 | B |
| 90 | I | CB | −8.4 | −62.2 | −12.9 | 70 | B |
| 90 | I | CG1 | −8.5 | −62.5 | −11.4 | 70 | B |
| 90 | I | CG2 | −7.2 | −63.0 | −13.5 | 70 | B |
| 90 | I | CD1 | −9.9 | −62.7 | −10.8 | 75 | B |
| 91 | K | N | −10.3 | −59.3 | −13.8 | 62 | B |
| 91 | K | CA | −11.5 | −58.6 | −13.5 | 60 | B |
| 91 | K | C | −11.4 | −57.7 | −12.2 | 61 | B |
| 91 | K | O | −12.4 | −57.5 | −11.5 | 60 | B |
| 91 | K | CB | −12.7 | −59.6 | −13.4 | 62 | B |
| 91 | K | CG | −13.3 | −59.9 | −14.7 | 81 | B |
| 91 | K | CD | −14.7 | −60.4 | −14.6 | 0 | B |
| 91 | K | CE | −15.7 | −59.3 | −14.2 | 0 | B |
| 91 | K | NZ | −16.6 | −59.7 | −13.0 | 0 | B |
| 92 | N | N | −10.2 | −57.1 | −12.0 | 57 | B |
| 92 | N | CA | −10.0 | −56.2 | −10.9 | 56 | B |
| 92 | N | C | −10.2 | −56.8 | −9.5 | 58 | B |
| 92 | N | O | −10.4 | −56.1 | −8.5 | 56 | B |
| 92 | N | CB | −10.8 | −54.9 | −11.1 | 53 | B |
| 92 | N | CG | −10.2 | −53.7 | −10.2 | 56 | B |
| 92 | N | OD1 | −11.0 | −53.0 | −9.5 | 42 | B |
| 92 | N | ND2 | −8.9 | −53.6 | −10.2 | 41 | B |
| 93 | G | N | −10.0 | −58.1 | −9.4 | 55 | B |
| 93 | G | CA | −10.2 | −58.9 | −8.2 | 54 | B |
| 93 | G | C | −11.7 | −58.8 | −7.8 | 57 | B |
| 93 | G | O | −12.0 | −58.9 | −6.6 | 56 | B |
| 94 | R | N | −12.5 | −58.4 | −8.7 | 52 | B |
| 94 | R | CA | −14.0 | −58.3 | −8.5 | 52 | B |
| 94 | R | C | −14.3 | −56.9 | −7.8 | 54 | B |
| 94 | R | O | −15.5 | −56.6 | −7.5 | 53 | B |
| 94 | R | CB | −14.5 | −59.4 | −7.7 | 54 | B |
| 94 | R | CG | −15.4 | −60.3 | −8.5 | 76 | B |
| 94 | R | CD | −14.9 | −60.6 | −9.9 | 96 | B |
| 94 | R | NE | −14.5 | −62.0 | −10.1 | 0 | B |
| 94 | R | CZ | −15.0 | −62.7 | −11.1 | 0 | B |
| 94 | R | NH1 | −15.9 | −62.2 | −11.9 | 0 | B |
| 94 | R | NH2 | −14.7 | −64.0 | −11.2 | 0 | B |
| 95 | C | N | −13.3 | −56.2 | −7.5 | 51 | B |
| 95 | C | CA | −13.4 | −54.9 | −6.7 | 51 | B |
| 95 | C | C | −14.1 | −53.8 | −7.6 | 53 | B |
| 95 | C | O | −13.6 | −53.5 | −8.7 | 53 | B |
| 95 | C | CB | −12.1 | −54.4 | −6.2 | 51 | B |
| 95 | C | SG | −11.2 | −55.5 | −5.2 | 56 | B |
| 96 | E | N | −15.1 | −53.2 | −7.1 | 47 | B |
| 96 | E | CA | −15.8 | −52.1 | −7.8 | 45 | B |
| 96 | E | C | −14.9 | −51.0 | −8.2 | 47 | B |
| 96 | E | O | −15.0 | −50.5 | −9.3 | 44 | B |
| 96 | E | CB | −17.0 | −51.6 | −6.9 | 45 | B |
| 96 | E | CG | −17.8 | −50.6 | −7.7 | 49 | B |
| 96 | E | CD | −18.8 | −49.9 | −6.7 | 59 | B |
| 96 | E | OE1 | −19.4 | −50.6 | −5.9 | 60 | B |
| 96 | E | OE2 | −19.0 | −48.7 | −6.8 | 48 | B |
| 97 | Q | N | −14.0 | −50.6 | −7.3 | 40 | B |
| 97 | Q | CA | −13.0 | −49.5 | −7.6 | 35 | B |
| 97 | Q | C | −11.6 | −50.0 | −7.6 | 38 | B |
| 97 | Q | O | −11.1 | −50.3 | −8.7 | 38 | B |
| 97 | Q | CB | −13.2 | −48.4 | −6.4 | 34 | B |
| 97 | Q | CG | −14.4 | −47.5 | −6.9 | 29 | B |
| 97 | Q | CD | −14.6 | −46.3 | −6.0 | 35 | B |
| 97 | Q | OE1 | −13.7 | −46.1 | −5.2 | 43 | B |
| 97 | Q | NE2 | −15.8 | −45.7 | −6.0 | 25 | B |
| 98 | F | N | −10.9 | −50.0 | −6.5 | 35 | B |
| 98 | F | CA | −9.5 | −50.4 | −6.3 | 36 | B |
| 98 | F | C | −9.3 | −51.8 | −5.8 | 47 | B |
| 98 | F | O | −10.0 | −52.3 | −4.9 | 48 | B |
| 98 | F | CB | −8.8 | −49.3 | −5.5 | 38 | B |
| 98 | F | CG | −9.1 | −47.9 | −5.9 | 39 | B |
| 98 | F | CD1 | −9.4 | −47.6 | −7.2 | 41 | B |
| 98 | F | CD2 | −9.2 | −46.9 | −5.0 | 40 | B |
| 98 | F | CE1 | −9.8 | −46.4 | −7.6 | 40 | B |
| 98 | F | CE2 | −9.5 | −45.6 | −5.4 | 43 | B |
| 98 | F | CZ | −9.8 | −45.4 | −6.7 | 40 | B |
| 99 | C | N | −8.2 | −52.4 | −6.2 | 47 | B |
| 99 | C | CA | −7.9 | −53.8 | −5.9 | 50 | B |
| 99 | C | C | −6.4 | −53.9 | −5.5 | 55 | B |
| 99 | C | O | −5.5 | −53.4 | −6.2 | 53 | B |
| 99 | C | CB | −8.2 | −54.7 | −7.0 | 53 | B |
| 99 | C | SG | −7.9 | −56.5 | −6.7 | 59 | B |
| 100 | K | N | −6.1 | −54.5 | −4.4 | 55 | B |

TABLE 5-continued

Coordinates of Factor IXa co-crystal Compound C complex

| | | | | | | |
|---|---|---|---|---|---|---|
| 100 | K | CA | −4.8 | −54.8 | −3.9 | 56 | B |
| 100 | K | C | −4.7 | −56.3 | −3.5 | 62 | B |
| 100 | K | O | −5.6 | −56.8 | −2.9 | 62 | B |
| 100 | K | CB | −4.5 | −53.9 | −2.7 | 58 | B |
| 100 | K | CG | −3.1 | −53.9 | −2.2 | 79 | B |
| 100 | K | CD | −3.0 | −53.3 | −0.8 | 0 | B |
| 100 | K | CE | −3.4 | −51.8 | −0.7 | 0 | B |
| 100 | K | NZ | −3.1 | −51.2 | 0.6 | 0 | B |
| 101 | N | N | −3.5 | −56.9 | −3.8 | 60 | B |
| 101 | N | CA | −3.2 | −58.3 | −3.5 | 59 | B |
| 101 | N | C | −2.7 | −58.5 | −2.1 | 59 | B |
| 101 | N | O | −1.9 | −57.8 | −1.6 | 57 | B |
| 101 | N | CB | −2.2 | −58.9 | −4.5 | 60 | B |
| 101 | N | CG | −2.8 | −59.1 | −5.9 | 67 | B |
| 101 | N | OD1 | −4.0 | −59.5 | −6.0 | 69 | B |
| 101 | N | ND2 | −2.0 | −58.9 | −6.9 | 51 | B |
| 107 | V | N | −7.2 | −61.1 | −2.1 | 59 | B |
| 107 | V | CA | −7.5 | −59.8 | −2.7 | 58 | B |
| 107 | V | C | −8.2 | −58.8 | −1.7 | 63 | B |
| 107 | V | O | −9.3 | −59.2 | −1.2 | 63 | B |
| 107 | V | CB | −8.2 | −59.9 | −4.0 | 60 | B |
| 107 | V | CG1 | −9.4 | −58.9 | −4.2 | 59 | B |
| 107 | V | CG2 | −7.2 | −59.8 | −5.2 | 59 | B |
| 108 | V | N | −7.7 | −57.6 | −1.5 | 59 | B |
| 108 | V | CA | −8.3 | −56.6 | −0.7 | 58 | B |
| 108 | V | C | −8.9 | −55.5 | −1.6 | 61 | B |
| 108 | V | O | −8.2 | −54.9 | −2.4 | 61 | B |
| 108 | V | CB | −7.4 | −56.0 | 0.4 | 61 | B |
| 108 | V | CG1 | −8.2 | −55.0 | 1.3 | 60 | B |
| 108 | V | CG2 | −6.7 | −57.0 | 1.2 | 61 | B |
| 109 | C | N | −10.2 | −55.2 | −1.5 | 55 | B |
| 109 | C | CA | −10.8 | −54.1 | −2.3 | 52 | B |
| 109 | C | C | −10.8 | −52.8 | −1.5 | 55 | B |
| 109 | C | O | −10.8 | −52.9 | −0.2 | 55 | B |
| 109 | C | CB | −12.3 | −54.5 | −2.6 | 52 | B |
| 109 | C | SG | −12.4 | −55.9 | −3.7 | 56 | B |
| 110 | S | N | −10.7 | −51.7 | −2.2 | 49 | B |
| 110 | S | CA | −10.7 | −50.4 | −1.6 | 47 | B |
| 110 | S | C | −11.5 | −49.3 | −2.4 | 50 | B |
| 110 | S | O | −11.9 | −49.6 | −3.5 | 48 | B |
| 110 | S | CB | −9.3 | −49.9 | −1.2 | 47 | B |
| 110 | S | OG | −8.4 | −50.1 | −2.2 | 55 | B |
| 111 | C | N | −11.8 | −48.2 | −1.8 | 49 | B |
| 111 | C | CA | −12.6 | −47.1 | −2.5 | 48 | B |
| 111 | C | C | −12.0 | −45.8 | −2.3 | 48 | B |
| 111 | C | O | −11.0 | −45.6 | −1.5 | 46 | B |
| 111 | C | CB | −14.0 | −47.0 | −1.8 | 49 | B |
| 111 | C | SG | −14.9 | −48.6 | −1.7 | 55 | B |
| 112 | T | N | −12.4 | −44.9 | −3.2 | 42 | B |
| 112 | T | CA | −11.9 | −43.5 | −3.1 | 42 | B |
| 112 | T | C | −12.5 | −42.8 | −1.9 | 44 | B |
| 112 | T | O | −13.5 | −43.3 | −1.3 | 43 | B |
| 112 | T | CB | −12.2 | −42.7 | −4.4 | 43 | B |
| 112 | T | OG1 | −11.5 | −41.5 | −4.5 | 42 | B |
| 112 | T | CG2 | −13.7 | −42.4 | −4.6 | 40 | B |
| 113 | E | N | −11.9 | −41.7 | −1.4 | 42 | B |
| 113 | E | CA | −12.4 | −40.9 | −0.3 | 42 | B |
| 113 | E | C | −13.9 | −40.5 | −0.4 | 43 | B |
| 113 | E | O | −14.3 | −40.3 | −1.5 | 45 | B |
| 113 | E | CB | −11.5 | −39.6 | −0.1 | 44 | B |
| 113 | E | CG | −12.0 | −38.6 | 0.9 | 58 | B |
| 113 | E | CD | −11.7 | −39.1 | 2.4 | 91 | B |
| 113 | E | OE1 | −12.6 | −38.9 | 3.2 | 73 | B |
| 113 | E | OE2 | −10.6 | −39.6 | 2.7 | 87 | B |
| 114 | G | N | −14.6 | −40.6 | 0.7 | 36 | B |
| 114 | G | CA | −16.0 | −40.3 | 0.7 | 35 | B |
| 114 | G | C | −16.8 | −41.6 | 0.4 | 40 | B |
| 114 | G | O | −18.1 | −41.6 | 0.4 | 39 | B |
| 115 | Y | N | −16.1 | −42.7 | 0.2 | 37 | B |
| 115 | Y | CA | −16.8 | −44.0 | −0.0 | 39 | B |
| 115 | Y | C | −16.2 | −45.0 | 1.0 | 45 | B |
| 115 | Y | O | −15.1 | −44.9 | 1.5 | 42 | B |
| 115 | Y | CB | −16.6 | −44.5 | −1.4 | 40 | B |
| 115 | Y | CG | −17.3 | −43.7 | −2.5 | 40 | B |
| 115 | Y | CD1 | −18.6 | −44.1 | −2.9 | 40 | B |
| 115 | Y | CD2 | −16.7 | −42.6 | −3.1 | 40 | B |
| 115 | Y | CE1 | −19.2 | −43.3 | −3.9 | 39 | B |
| 115 | Y | CE2 | −17.4 | −41.8 | −4.0 | 40 | B |
| 115 | Y | CZ | −18.6 | −42.2 | −4.4 | 38 | B |
| 115 | Y | OH | −19.3 | −41.4 | −5.3 | 37 | B |
| 116 | R | N | −17.1 | −45.9 | 1.3 | 45 | B |
| 116 | R | CA | −16.7 | −47.0 | 2.2 | 46 | B |
| 116 | R | C | −17.0 | −48.4 | 1.5 | 49 | B |
| 116 | R | O | −17.8 | −48.5 | 0.6 | 47 | B |
| 116 | R | CB | −17.4 | −46.9 | 3.6 | 50 | B |
| 116 | R | CG | −18.9 | −47.3 | 3.5 | 60 | B |
| 116 | R | CD | −19.5 | −47.2 | 4.9 | 69 | B |
| 116 | R | NE | −20.9 | −46.9 | 4.8 | 69 | B |
| 116 | R | CZ | −21.5 | −45.8 | 5.4 | 77 | B |
| 116 | R | NH1 | −20.8 | −45.0 | 6.1 | 52 | B |
| 116 | R | NH2 | −22.8 | −45.7 | 5.2 | 69 | B |
| 117 | L | N | −16.2 | −49.3 | 1.9 | 48 | B |
| 117 | L | CA | −16.4 | −50.7 | 1.3 | 49 | B |
| 117 | L | C | −17.7 | −51.2 | 1.8 | 56 | B |
| 117 | L | O | −18.0 | −51.1 | 3.0 | 55 | B |
| 117 | L | CB | −15.2 | −51.6 | 1.7 | 48 | B |
| 117 | L | CG | −15.0 | −52.8 | 0.8 | 52 | B |
| 117 | L | CD1 | −14.8 | −52.4 | −0.7 | 51 | B |
| 117 | L | CD2 | −13.8 | −53.6 | 1.3 | 52 | B |
| 118 | A | N | −18.6 | −51.7 | 1.0 | 55 | B |
| 118 | A | CA | −19.9 | −52.2 | 1.4 | 55 | B |
| 118 | A | C | −19.7 | −53.6 | 2.1 | 64 | B |
| 118 | A | O | −18.6 | −54.1 | 2.3 | 63 | B |
| 118 | A | CB | −20.8 | −52.4 | 0.2 | 54 | B |
| 119 | E | N | −20.8 | −54.2 | 2.5 | 65 | B |
| 119 | E | CA | −20.8 | −55.5 | 3.2 | 65 | B |
| 119 | E | C | −20.1 | −56.7 | 2.5 | 65 | B |
| 119 | E | O | −19.4 | −57.4 | 3.1 | 65 | B |
| 119 | E | CB | −22.2 | −55.9 | 3.6 | 67 | B |
| 119 | E | CG | −22.8 | −55.1 | 4.8 | 88 | B |
| 119 | E | CD | −23.1 | −53.6 | 4.5 | 0 | B |
| 119 | E | OE1 | −23.6 | −53.4 | 3.3 | 0 | B |
| 119 | E | OE2 | −23.0 | −52.8 | 5.4 | 0 | B |
| 120 | N | N | −20.3 | −56.8 | 1.1 | 60 | B |
| 120 | N | CA | −19.7 | −57.8 | 0.3 | 58 | B |
| 120 | N | C | −18.2 | −57.6 | 0.2 | 61 | B |
| 120 | N | O | −17.5 | −58.5 | −0.3 | 59 | B |
| 120 | N | CB | −20.3 | −57.9 | −1.0 | 58 | B |
| 120 | N | CG | −20.2 | −56.6 | −1.9 | 73 | B |
| 120 | N | OD1 | −19.4 | −55.7 | −1.5 | 59 | B |
| 120 | N | ND2 | −20.9 | −56.5 | −3.0 | 57 | B |
| 121 | Q | N | −17.7 | −56.5 | 0.7 | 58 | B |
| 121 | Q | CA | −16.2 | −56.2 | 0.7 | 58 | B |
| 121 | Q | C | −15.7 | −56.0 | −0.8 | 62 | B |
| 121 | Q | O | −14.5 | −56.1 | −1.0 | 62 | B |
| 121 | Q | CB | −15.4 | −57.4 | 1.3 | 59 | B |
| 121 | Q | CG | −15.8 | −57.6 | 2.8 | 64 | B |
| 121 | Q | CD | −15.6 | −56.4 | 3.6 | 84 | B |
| 121 | Q | OE1 | −14.5 | −56.1 | 4.1 | 80 | B |
| 121 | Q | NE2 | −16.7 | −55.7 | 3.9 | 73 | B |
| 122 | K | N | −16.6 | −55.8 | −1.7 | 57 | B |
| 122 | K | CA | −16.2 | −55.6 | −3.1 | 57 | B |
| 122 | K | C | −16.8 | −54.3 | −3.6 | 59 | B |
| 122 | K | O | −16.1 | −53.5 | −4.3 | 59 | B |
| 122 | K | CB | −16.8 | −56.8 | −4.0 | 59 | B |
| 122 | K | CG | −16.3 | −58.2 | −3.6 | 71 | B |
| 122 | K | CD | −15.3 | −58.7 | −4.7 | 74 | B |
| 122 | K | CE | −14.4 | −59.8 | −4.1 | 80 | B |
| 122 | K | NZ | −13.1 | −59.3 | −3.8 | 84 | B |
| 123 | S | N | −18.1 | −54.0 | −3.3 | 53 | B |
| 123 | S | CA | −18.8 | −52.8 | −3.7 | 51 | B |
| 123 | S | C | −18.4 | −51.6 | −2.8 | 54 | B |
| 123 | S | O | −17.9 | −51.8 | −1.7 | 54 | B |
| 123 | S | CB | −20.3 | −53.1 | −3.6 | 52 | B |
| 123 | S | OG | −20.6 | −53.8 | −4.8 | 62 | B |
| 124 | C | N | −18.7 | −50.4 | −3.4 | 52 | B |
| 124 | C | CA | −18.3 | −49.2 | −2.6 | 51 | B |
| 124 | C | C | −19.6 | −48.4 | −2.4 | 53 | B |
| 124 | C | O | −20.5 | −48.4 | −3.2 | 53 | B |
| 124 | C | CB | −17.4 | −48.3 | −3.5 | 51 | B |
| 124 | C | SG | −15.7 | −48.9 | −3.4 | 54 | B |
| 125 | E | N | −19.7 | −47.8 | −1.2 | 50 | B |
| 125 | E | CA | −20.9 | −47.1 | −0.9 | 50 | B |
| 125 | E | C | −20.6 | −45.7 | −0.2 | 50 | B |
| 125 | E | O | −19.5 | −45.5 | 0.4 | 49 | B |
| 125 | E | CB | −21.8 | −47.9 | 0.1 | 52 | B |

TABLE 5-continued

Coordinates of Factor IXa co-crystal Compound C complex

| | | | | | | |
|---|---|---|---|---|---|---|
| 125 | E | CG | −21.1 | −48.4 | 1.4 | 62 | B |
| 125 | E | CD | −22.1 | −49.0 | 2.4 | 91 | B |
| 125 | E | OE1 | −22.1 | −50.2 | 2.6 | 75 | B |
| 125 | E | OE2 | −22.8 | −48.2 | 3.1 | 98 | B |
| 126 | P | N | −21.5 | −44.7 | −0.4 | 43 | B |
| 126 | P | CA | −21.3 | −43.4 | 0.2 | 44 | B |
| 126 | P | C | −21.0 | −43.4 | 1.7 | 52 | B |
| 126 | P | O | −21.6 | −44.1 | 2.5 | 55 | B |
| 126 | P | CB | −22.6 | −42.7 | −0.1 | 45 | B |
| 126 | P | CG | −22.9 | −43.3 | −1.5 | 48 | B |
| 126 | P | CD | −22.5 | −44.7 | −1.4 | 43 | B |
| 127 | A | N | −20.0 | −42.7 | 2.2 | 50 | B |
| 127 | A | CA | −19.6 | −42.5 | 3.6 | 50 | B |
| 127 | A | C | −19.8 | −41.1 | 4.0 | 56 | B |
| 127 | A | O | −19.5 | −40.7 | 5.1 | 55 | B |
| 127 | A | CB | −18.2 | −42.9 | 3.8 | 50 | B |
| 128 | V | N | −20.4 | −40.3 | 3.1 | 51 | B |
| 128 | V | CA | −20.6 | −38.8 | 3.2 | 48 | B |
| 128 | V | C | −21.8 | −38.5 | 2.5 | 48 | B |
| 128 | V | O | −22.4 | −39.3 | 1.7 | 49 | B |
| 128 | V | CB | −19.3 | −38.0 | 2.8 | 51 | B |
| 128 | V | CG1 | −18.1 | −38.4 | 3.6 | 49 | B |
| 128 | V | CG2 | −19.0 | −38.2 | 1.3 | 51 | B |
| 129 | P | N | −22.3 | −37.3 | 2.7 | 44 | B |
| 129 | P | CA | −23.6 | −36.9 | 2.1 | 43 | B |
| 129 | P | C | −23.5 | −36.6 | 0.6 | 46 | B |
| 129 | P | O | −24.4 | −36.8 | −0.2 | 47 | B |
| 129 | P | CB | −24.0 | −35.6 | 2.8 | 44 | B |
| 129 | P | CG | −23.1 | −35.5 | 4.0 | 49 | B |
| 129 | P | CD | −22.0 | −36.4 | 3.9 | 45 | B |
| 130 | F | N | −22.4 | −36.0 | 0.2 | 43 | B |
| 130 | F | CA | −22.1 | −35.7 | −1.2 | 39 | B |
| 130 | F | C | −20.8 | −36.2 | −1.7 | 44 | B |
| 130 | F | O | −19.9 | −35.3 | −2.0 | 44 | B |
| 130 | F | CB | −22.3 | −34.2 | −1.5 | 38 | B |
| 130 | F | CG | −23.7 | −33.7 | −1.1 | 37 | B |
| 130 | F | CD1 | −24.0 | −33.2 | 0.1 | 38 | B |
| 130 | F | CD2 | −24.7 | −34.0 | −2.0 | 37 | B |
| 130 | F | CE1 | −25.3 | −32.8 | 0.5 | 38 | B |
| 130 | F | CE2 | −26.0 | −33.6 | −1.7 | 38 | B |
| 130 | F | CZ | −26.3 | −33.0 | −0.4 | 35 | B |
| 131 | P | N | −20.6 | −37.5 | −1.8 | 41 | B |
| 131 | P | CA | −19.3 | −38.1 | −2.3 | 40 | B |
| 131 | P | C | −19.0 | −37.7 | −3.8 | 39 | B |
| 131 | P | O | −19.9 | −37.5 | −4.6 | 34 | B |
| 131 | P | CB | −19.6 | −39.6 | −2.2 | 42 | B |
| 131 | P | CG | −21.1 | −39.8 | −2.4 | 46 | B |
| 131 | P | CD | −21.7 | −38.5 | −1.8 | 43 | B |
| 132 | C | N | −17.7 | −37.6 | −4.0 | 36 | B |
| 132 | C | CA | −17.2 | −37.2 | −5.3 | 34 | B |
| 132 | C | C | −17.8 | −38.1 | −6.5 | 40 | B |
| 132 | C | O | −18.1 | −39.3 | −6.3 | 39 | B |
| 132 | C | CB | −15.7 | −37.2 | −5.3 | 34 | B |
| 132 | C | SG | −15.0 | −39.0 | −5.2 | 39 | B |
| 133 | G | N | −17.8 | −37.5 | −7.6 | 37 | B |
| 133 | G | CA | −18.1 | −38.1 | −8.9 | 36 | B |
| 133 | G | C | −19.5 | −38.8 | −9.0 | 40 | B |
| 133 | G | O | −19.7 | −39.6 | −9.8 | 38 | B |
| 134 | R | N | −20.4 | −38.4 | −8.1 | 40 | B |
| 134 | R | CA | −21.8 | −38.9 | −8.2 | 40 | B |
| 134 | R | C | −22.8 | −37.9 | −8.5 | 41 | B |
| 134 | R | O | −22.8 | −36.8 | −8.0 | 39 | B |
| 134 | R | CB | −22.2 | −39.7 | −7.0 | 44 | B |
| 134 | R | CG | −21.6 | −41.1 | −6.9 | 64 | B |
| 134 | R | CD | −22.6 | −42.3 | −7.0 | 74 | B |
| 134 | R | NE | −22.1 | −43.6 | −6.6 | 89 | B |
| 134 | R | CZ | −22.5 | −44.3 | −5.6 | 0 | B |
| 134 | R | NH1 | −23.6 | −43.8 | −4.9 | 0 | B |
| 134 | R | NH2 | −22.0 | −45.4 | −5.3 | 99 | B |
| 135 | V | N | −23.8 | −38.3 | −9.4 | 39 | B |
| 135 | V | CA | −24.9 | −37.4 | −9.8 | 40 | B |
| 135 | V | C | −26.0 | −37.7 | −8.7 | 46 | B |
| 135 | V | O | −26.5 | −38.8 | −8.7 | 48 | B |
| 135 | V | CB | −25.4 | −37.8 | −11.2 | 42 | B |
| 135 | V | CG1 | −26.7 | −37.1 | −11.4 | 41 | B |
| 135 | V | CG2 | −24.4 | −37.3 | −12.2 | 41 | B |
| 136 | S | N | −26.3 | −36.7 | −7.9 | 43 | B |
| 136 | S | CA | −27.3 | −37.0 | −6.8 | 43 | B |
| 136 | S | C | −28.6 | −36.3 | −7.0 | 51 | B |
| 136 | S | O | −29.5 | −36.3 | −6.2 | 51 | B |
| 136 | S | CB | −26.7 | −36.6 | −5.5 | 42 | B |
| 136 | S | OG | −26.6 | −35.2 | −5.4 | 46 | B |
| 137 | V | N | −28.7 | −35.6 | −8.2 | 53 | B |
| 137 | V | CA | −29.9 | −34.8 | −8.5 | 56 | B |
| 137 | V | C | −30.8 | −35.8 | −9.4 | 66 | B |
| 137 | V | O | −30.2 | −36.6 | −10.1 | 67 | B |
| 137 | V | CB | −29.5 | −33.6 | −9.3 | 61 | B |
| 137 | V | CG1 | −30.4 | −33.4 | −10.6 | 62 | B |
| 137 | V | CG2 | −29.6 | −32.3 | −8.5 | 61 | B |
| 138 | S | N | −32.1 | −35.7 | −9.3 | 65 | B |
| 138 | S | CA | −32.9 | −36.5 | −10.2 | 66 | B |
| 138 | S | C | −32.7 | −36.2 | −11.6 | 71 | B |
| 138 | S | O | −32.5 | −35.1 | −12.0 | 70 | B |
| 138 | S | CB | −34.4 | −36.2 | −9.9 | 70 | B |
| 138 | S | OG | −35.2 | −36.9 | −10.8 | 79 | B |
| 139 | Q | N | −32.6 | −37.3 | −12.4 | 69 | B |
| 139 | Q | CA | −32.3 | −37.2 | −13.9 | 70 | B |
| 139 | Q | C | −33.4 | −37.7 | −14.7 | 77 | B |
| 139 | Q | O | −34.0 | −36.9 | −15.5 | 78 | B |
| 139 | Q | CB | −31.0 | −37.9 | −14.2 | 71 | B |
| 139 | Q | CG | −29.8 | −37.4 | −13.5 | 79 | B |
| 139 | Q | CD | −29.1 | −36.2 | −14.2 | 77 | B |
| 139 | Q | OE1 | −29.0 | −35.1 | −13.6 | 62 | B |
| 139 | Q | NE2 | −28.8 | −36.4 | −15.4 | 61 | B |
| 500 | X | CA | −27.6 | −20.2 | −14.3 | 87 | Q |
| 501 | X | C1 | 6.5 | −35.4 | −18.6 | 34 | Q |
| 501 | X | O1 | 5.6 | −36.4 | −18.6 | 35 | Q |
| 501 | X | O2 | 6.6 | −34.5 | −17.8 | 36 | Q |
| 501 | X | C2 | 7.2 | −35.3 | −20.1 | 29 | Q |
| 501 | X | C3 | 7.1 | −36.4 | −21.2 | 31 | Q |
| 501 | X | O7 | 7.9 | −37.5 | −20.6 | 26 | Q |
| 501 | X | C4 | 7.8 | −36.0 | −22.5 | 37 | Q |
| 501 | X | C5 | 7.9 | −37.0 | −23.6 | 42 | Q |
| 501 | X | O3 | 6.8 | −37.6 | −24.1 | 40 | Q |
| 501 | X | O4 | 9.0 | −37.5 | −23.9 | 50 | Q |
| 501 | X | C6 | 5.7 | −37.0 | −21.4 | 29 | Q |
| 501 | X | O5 | 5.7 | −38.3 | −21.1 | 29 | Q |
| 501 | X | O6 | 4.7 | −36.2 | −21.7 | 31 | Q |
| 502 | X | C1 | 9.7 | −40.4 | −19.1 | 44 | Q |
| 502 | X | O1 | 10.1 | −40.2 | −20.3 | 46 | Q |
| 502 | X | O2 | 10.3 | −39.8 | −18.1 | 51 | Q |
| 502 | X | C2 | 8.5 | −41.0 | −18.9 | 36 | Q |
| 502 | X | C3 | 7.3 | −40.7 | −19.8 | 38 | Q |
| 502 | X | O7 | 7.1 | −39.3 | −19.5 | 35 | Q |
| 502 | X | C4 | 6.0 | −41.4 | −19.4 | 34 | Q |
| 502 | X | C5 | 5.7 | −41.5 | −18.0 | 39 | Q |
| 502 | X | O3 | 5.2 | −40.4 | −17.4 | 38 | Q |
| 502 | X | O4 | 5.7 | −42.6 | −17.5 | 41 | Q |
| 502 | X | C6 | 7.6 | −40.7 | −21.3 | 38 | Q |
| 502 | X | O5 | 7.6 | −39.4 | −21.7 | 37 | Q |
| 502 | X | O6 | 7.8 | −41.7 | −21.9 | 40 | Q |
| 503 | X | C1 | 5.2 | −33.0 | −8.3 | 36 | Q |
| 503 | X | O1 | 5.9 | −32.3 | −9.2 | 39 | Q |
| 503 | X | O2 | 4.8 | −32.3 | −7.2 | 40 | Q |
| 503 | X | C2 | 4.8 | −34.4 | −8.6 | 34 | Q |
| 503 | X | C3 | 4.8 | −34.8 | −10.1 | 32 | Q |
| 503 | X | O7 | 3.7 | −34.0 | −10.6 | 34 | Q |
| 503 | X | C4 | 4.3 | −36.2 | −10.2 | 30 | Q |
| 503 | X | C5 | 2.9 | −36.5 | −9.8 | 32 | Q |
| 503 | X | O3 | 2.2 | −35.4 | −9.6 | 34 | Q |
| 503 | X | O4 | 2.5 | −37.6 | −9.6 | 32 | Q |
| 503 | X | C6 | 6.1 | −34.6 | −10.8 | 31 | Q |
| 503 | X | O5 | 6.1 | −33.8 | −11.9 | 35 | Q |
| 503 | X | O6 | 7.1 | −35.2 | −10.4 | 31 | Q |
| 1 | Z | C1 | −9.9 | −25.0 | −28.8 | 36 | S |
| 1 | Z | C2 | −9.8 | −26.0 | −27.9 | 39 | S |
| 1 | Z | C3 | −10.0 | −27.4 | −28.3 | 38 | S |
| 1 | Z | C4 | −10.3 | −27.7 | −29.6 | 34 | S |
| 1 | Z | C5 | −10.4 | −26.7 | −30.6 | 32 | S |
| 1 | Z | C6 | −10.2 | −25.4 | −30.2 | 39 | S |
| 1 | Z | C10 | −9.8 | −28.4 | −27.3 | 35 | S |
| 1 | Z | C11 | −9.9 | −29.7 | −27.8 | 35 | S |
| 1 | Z | C12 | −10.3 | −30.0 | −29.1 | 35 | S |
| 1 | Z | C13 | −10.5 | −29.0 | −30.0 | 33 | S |
| 1 | Z | CL17 | −9.6 | −31.0 | −26.6 | 36 | S |
| 1 | Z | S18 | −10.3 | −24.1 | −31.4 | 46 | S |

TABLE 5-continued

Coordinates of Factor IXa co-crystal Compound C complex

| | | | | | | |
|---|---|---|---|---|---|---|
| 1 | Z | O19 | −11.3 | −23.1 | −31.0 | 49 S |
| 1 | Z | O20 | −10.3 | −24.7 | −32.7 | 44 S |
| 1 | Z | N21 | −8.9 | −23.2 | −31.3 | 46 S |
| 1 | Z | C22 | −7.6 | −23.8 | −31.6 | 49 S |
| 1 | Z | C23 | −6.7 | −23.0 | −32.6 | 52 S |
| 1 | Z | C24 | −5.6 | −22.4 | −31.7 | 55 S |
| 1 | Z | N25 | −5.7 | −23.1 | −30.5 | 49 S |
| 1 | Z | C26 | −6.8 | −23.9 | −30.4 | 48 S |
| 1 | Z | C29 | −5.8 | −20.9 | −31.4 | 66 S |
| 1 | Z | O30 | −5.7 | −20.1 | −32.6 | 77 S |
| 1 | Z | C33 | −5.8 | −18.7 | −32.4 | 81 S |
| 1 | Z | N37 | −4.2 | −22.8 | −32.1 | 53 S |
| 1 | Z | C38 | −3.5 | −23.3 | −30.9 | 47 S |
| 1 | Z | C39 | −4.5 | −23.0 | −29.7 | 49 S |
| 1 | Z | O42 | −7.0 | −24.7 | −29.4 | 46 S |
| 1 | Z | C43 | −2.2 | −22.6 | −30.7 | 43 S |
| 1 | Z | C44 | −1.0 | −23.2 | −31.5 | 41 S |
| 1 | Z | N45 | −1.0 | −24.6 | −31.2 | 45 S |
| 1 | Z | C46 | −2.2 | −25.4 | −31.6 | 40 S |
| 1 | Z | C47 | −3.4 | −24.8 | −30.8 | 40 S |
| 1 | Z | C56 | 0.0 | −25.3 | −30.5 | 44 S |
| 1 | Z | C57 | −0.2 | −26.8 | −30.2 | 39 S |
| 1 | Z | O61 | 1.0 | −24.7 | −30.1 | 49 S |
| 2 | O | O | −22.8 | −28.3 | −32.6 | 50 W |
| 4 | O | O | −26.0 | −34.3 | −9.3 | 36 W |
| 5 | O | O | −17.4 | −33.9 | −17.6 | 36 W |
| 6 | O | O | −15.1 | −27.2 | −20.1 | 32 W |
| 7 | O | O | −20.7 | −24.5 | −13.2 | 37 W |
| 9 | O | O | −25.4 | −24.4 | −4.8 | 34 W |
| 10 | O | O | 4.5 | −19.8 | −18.0 | 46 W |
| 11 | O | O | 5.0 | −25.8 | −20.5 | 26 W |
| 12 | O | O | −18.1 | −26.3 | 2.4 | 36 W |
| 13 | O | O | −11.3 | −34.9 | −5.8 | 32 W |
| 14 | O | O | −0.3 | −45.7 | −8.7 | 44 W |
| 15 | O | O | −16.4 | −24.4 | −20.2 | 39 W |
| 16 | O | O | −26.8 | −23.6 | −26.0 | 49 W |
| 17 | O | O | −4.0 | −40.9 | −27.2 | 28 W |
| 18 | O | O | −0.6 | −30.3 | −38.1 | 41 W |
| 19 | O | O | 2.9 | −29.3 | −28.4 | 41 W |
| 20 | O | O | 2.8 | −35.8 | −34.3 | 49 W |
| 21 | O | O | −10.9 | −37.0 | −36.8 | 36 W |
| 22 | O | O | −14.0 | −35.3 | −33.1 | 39 W |
| 23 | O | O | −18.6 | −38.3 | −36.6 | 40 W |
| 24 | O | O | −12.4 | −34.4 | −28.3 | 29 W |
| 26 | O | O | −4.3 | −29.2 | −20.3 | 30 W |
| 27 | O | O | −12.0 | −43.7 | −20.2 | 30 W |
| 28 | O | O | −16.8 | −42.9 | −19.2 | 32 W |
| 29 | O | O | −7.2 | −33.6 | −3.1 | 35 W |
| 30 | O | O | −13.8 | −51.6 | −4.5 | 46 W |
| 31 | O | O | −8.7 | −40.3 | −11.5 | 26 W |
| 32 | O | O | −10.6 | −29.9 | −15.0 | 29 W |
| 33 | O | O | −5.7 | −34.3 | −1.2 | 43 W |
| 34 | O | O | −9.6 | −33.1 | −1.0 | 47 W |
| 35 | O | O | −20.4 | −26.0 | −25.2 | 38 W |
| 36 | O | O | −22.5 | −37.5 | −15.4 | 42 W |
| 41 | O | O | −10.1 | −31.4 | −33.2 | 44 W |
| 44 | O | O | −5.3 | −34.1 | −34.3 | 36 W |
| 45 | O | O | −4.9 | −31.7 | −33.3 | 49 W |
| 47 | O | O | −21.0 | −40.3 | −12.4 | 41 W |
| 48 | O | O | −20.1 | −38.4 | −15.9 | 40 W |
| 49 | O | O | −24.5 | −28.7 | −11.2 | 43 W |
| 50 | O | O | −26.7 | −27.7 | −12.6 | 43 W |
| 51 | O | O | −20.7 | −27.3 | −10.5 | 25 W |
| 53 | O | O | −8.5 | −35.2 | −4.9 | 39 W |
| 56 | O | O | 7.3 | −27.6 | −20.7 | 46 W |
| 57 | O | O | −22.0 | −18.9 | −2.4 | 29 W |
| 58 | O | O | −24.2 | −19.0 | −3.8 | 36 W |
| 59 | O | O | 8.7 | −33.2 | −12.6 | 30 W |
| 60 | O | O | 3.4 | −34.0 | −21.3 | 40 W |
| 62 | O | O | −0.2 | −31.1 | −20.9 | 29 W |
| 63 | O | O | −8.9 | −42.1 | −5.0 | 38 W |
| 64 | O | O | −5.1 | −39.9 | −17.1 | 22 W |
| 65 | O | O | −3.4 | −41.9 | −18.0 | 28 W |
| 66 | O | O | −8.0 | −50.3 | −18.6 | 37 W |
| 67 | O | O | −10.6 | −42.5 | −22.7 | 29 W |
| 68 | O | O | −11.5 | −40.6 | −24.2 | 26 W |
| 69 | O | O | −20.7 | −39.2 | −28.7 | 43 W |
| 70 | O | O | −0.8 | −46.8 | −30.8 | 41 W |
| 71 | O | O | −5.2 | −46.1 | −40.2 | 50 W |
| 72 | O | O | −10.3 | −42.6 | −35.0 | 34 W |
| 82 | O | O | 1.3 | −33.2 | −19.7 | 35 W |
| 83 | O | O | −22.2 | −38.1 | −26.4 | 40 W |
| 86 | O | O | −23.8 | −35.8 | −26.3 | 45 W |
| 88 | O | O | −8.0 | −33.0 | −41.6 | 49 W |
| 92 | O | O | −1.2 | −16.7 | −7.4 | 39 W |
| 93 | O | O | −14.6 | −51.1 | −18.6 | 49 W |
| 97 | O | O | −24.1 | −41.5 | −31.4 | 46 W |
| 101 | O | O | −32.0 | −32.4 | −13.3 | 50 W |
| 102 | O | O | −22.4 | −27.5 | −13.5 | 40 W |
| 103 | O | O | −5.5 | −15.6 | −14.7 | 43 W |
| 104 | O | O | −17.1 | −14.0 | −5.9 | 45 W |
| 105 | O | O | −11.0 | −12.7 | −8.3 | 53 W |
| 106 | O | O | −11.0 | −38.6 | −4.8 | 41 W |
| 107 | O | O | −6.4 | −45.5 | −6.7 | 37 W |
| 108 | O | O | −2.0 | −47.9 | −15.2 | 33 W |
| 109 | O | O | −12.2 | −42.4 | −33.0 | 26 W |
| 110 | O | O | −11.4 | −44.4 | −31.2 | 31 W |
| 111 | O | O | −0.1 | −42.2 | −24.8 | 37 W |
| 112 | O | O | 1.9 | −42.0 | −20.0 | 34 W |
| 113 | O | O | −3.8 | −44.4 | −23.1 | 50 W |
| 114 | O | O | 0.2 | −40.2 | −26.3 | 35 W |
| 115 | O | O | −2.0 | −40.0 | −28.2 | 34 W |
| 116 | O | O | −2.9 | −42.6 | −25.6 | 37 W |
| 117 | O | O | −23.0 | −35.9 | −29.1 | 44 W |
| 118 | O | O | −16.7 | −46.6 | −18.1 | 48 W |
| 121 | O | O | −23.0 | −29.1 | −28.3 | 44 W |
| 122 | O | O | −28.8 | −25.9 | −11.9 | 46 W |
| 123 | O | O | −24.1 | −29.8 | −14.1 | 51 W |
| 124 | O | O | 3.9 | −31.3 | −4.8 | 79 W |
| 125 | O | O | 3.8 | −26.4 | −8.6 | 42 W |
| 126 | O | O | −19.9 | −28.4 | 2.0 | 51 W |
| 127 | O | O | 0.9 | −40.8 | −16.7 | 38 W |
| 128 | O | O | −7.9 | −40.5 | −38.5 | 31 W |
| 129 | O | O | −9.7 | −39.5 | −39.7 | 39 W |
| 130 | O | O | −5.0 | −39.8 | −38.5 | 46 W |
| 131 | O | O | −20.1 | −43.8 | −30.9 | 45 W |
| 132 | O | O | −16.2 | −45.9 | −29.5 | 35 W |
| 133 | O | O | −15.1 | −45.4 | −27.0 | 41 W |

Example 20

Generation of Soaked Factor IXa-Compound D Complex Crystals

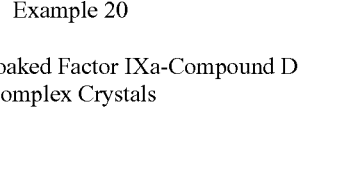

Compound D

A factor IXa-Compound C crystal as described in example 16 was transferred to a 1 µl hanging drop containing 1 mM Compound D, 1% DMSO, 14% PEG 6000 (v/v), 0.1 M citric acid, pH 5.67 solution. The drop was subsequently incubated at 4° C. for 1-20 days.

Example 21

Crystallographic Analysis of Soaked Factor IXa-Compound D Complex Crystals

Prior to data collection, crystals were harvested and cryo-protected for 5 seconds in the crystallization solution containing 25% glycerol. The crystals were then frozen directly into liquid nitrogen. X-ray diffraction was collected using a Rigaku generator equipped with a Raxis 4++ detector. Data were integrated and scaled using the HKL package.

| Data Collection Statistics | |
|---|---|
| Resolution | 25.0-2.5 Å |
| No. of collected reflections | 129130 |
| No. of unique reflections (F >= 0) | 18101 |
| R-sym | 7.6% |
| Percent of theoretical (I/s >= 1) | 97.4% |
| Unit Cell | a = 100.5 Å, b = 100.5 Å, c = 98.4 Å, α = β = γ = 90° |
| Space Group | P4₃2₁2 |
| Asymmetric unit | 1 molecule |

Example 22

Structure Determination of Soaked Factor IXa-Compound D Crystals

The crystal structure was solved using Rigid Body refinement with the starting model 1RFN. Refinement was done using the program AUTOBUSTER (Global Phasing Limited.).

| | |
|---|---|
| Number of reflections | 17512 |
| Resolution limits | 16.5-2.50 Å |
| Completeness for range | 97.45% |
| FREE R TEST SET COUNT & SIZE | 835 (4.8%) |
| Number of protein atoms | 2196 |
| Number of solvent atoms | 85 |
| R-factor | 0.19.9 |
| R-free | 0.24.0 |
| RMSD bond length | 0.010 Å |
| RMSD bond angles | 1.26° |

The following table contains one line for each atom in one Factor IXa monomer. The columns are: 1) residue number, 2) 1-letter amino acid code, 3) atom name, 4) x-coordinate, 5) y-coordinate, 6) z-coordinate, 7) B-factor, 8) Chain ID. (Amino Acid Code X are Calcium or Citrate, Z is Compound D and O for water) The numbering scheme is based on chymotrypsin. Note: B tractors greater than 100 appear as 0 in column 7.

TABLE 6

Coordinates of Factor IXa-Compound D complex

| 16 | V | N | −18.7 | −28.3 | −26.7 | 41 | A |
|---|---|---|---|---|---|---|---|
| 16 | V | CA | −18.9 | −29.7 | −27.2 | 40 | A |
| 16 | V | C | −19.7 | −29.7 | −28.5 | 45 | A |
| 16 | V | O | −20.8 | −29.2 | −28.5 | 45 | A |
| 16 | V | CB | −19.5 | −30.6 | −26.1 | 44 | A |
| 16 | V | CG1 | −19.9 | −32.0 | −26.7 | 44 | A |
| 16 | V | CG2 | −18.7 | −30.7 | −24.9 | 44 | A |
| 17 | V | N | −19.0 | −30.2 | −29.6 | 44 | A |
| 17 | V | CA | −19.7 | −30.3 | −30.9 | 44 | A |
| 17 | V | C | −20.3 | −31.7 | −31.0 | 50 | A |
| 17 | V | O | −19.7 | −32.7 | −30.6 | 49 | A |
| 17 | V | CB | −18.6 | −30.1 | −32.0 | 48 | A |
| 17 | V | CG1 | −19.3 | −30.5 | −33.4 | 45 | A |
| 17 | V | CG2 | −18.1 | −28.7 | −32.0 | 47 | A |
| 18 | G | N | −21.6 | −31.7 | −31.4 | 46 | A |
| 18 | G | CA | −22.3 | −32.9 | −31.6 | 45 | A |
| 18 | G | C | −22.6 | −33.8 | −30.4 | 49 | A |
| 18 | G | O | −22.8 | −35.0 | −30.5 | 47 | A |

TABLE 6-continued

Coordinates of Factor IXa-Compound D complex

| 19 | G | N | −22.8 | −33.1 | −29.3 | 47 | A |
|---|---|---|---|---|---|---|---|
| 19 | G | CA | −23.2 | −33.7 | −28.0 | 47 | A |
| 19 | G | C | −24.6 | −33.5 | −27.7 | 51 | A |
| 19 | G | O | −25.5 | −33.3 | −28.6 | 51 | A |
| 20 | E | N | −25.0 | −33.6 | −26.4 | 46 | A |
| 20 | E | CA | −26.3 | −33.5 | −25.9 | 45 | A |
| 20 | E | C | −26.5 | −32.6 | −24.7 | 48 | A |
| 20 | E | O | −25.5 | −32.5 | −23.9 | 46 | A |
| 20 | E | CB | −26.9 | −34.9 | −25.6 | 46 | A |
| 20 | E | CG | −27.6 | −35.6 | −26.8 | 59 | A |
| 20 | E | CD | −27.5 | −37.1 | −26.7 | 90 | A |
| 20 | E | OE1 | −27.4 | −37.6 | −25.5 | 76 | A |
| 20 | E | OE2 | −27.7 | −37.8 | −27.7 | 95 | A |
| 21 | D | N | −27.6 | −32.1 | −24.5 | 48 | A |
| 21 | D | CA | −27.9 | −31.3 | −23.3 | 48 | A |
| 21 | D | C | −27.8 | −32.2 | −22.1 | 52 | A |
| 21 | D | O | −28.4 | −33.3 | −22.2 | 52 | A |
| 21 | D | CB | −29.4 | −30.8 | −23.4 | 49 | A |
| 21 | D | CG | −29.6 | −29.6 | −24.3 | 57 | A |
| 21 | D | OD1 | −30.6 | −28.9 | −24.2 | 61 | A |
| 21 | D | OD2 | −28.7 | −29.2 | −25.0 | 57 | A |
| 22 | A | N | −27.2 | −31.8 | −21.1 | 47 | A |
| 22 | A | CA | −27.2 | −32.6 | −19.9 | 47 | A |
| 22 | A | C | −28.5 | −32.2 | −19.1 | 51 | A |
| 22 | A | O | −29.0 | −31.1 | −19.4 | 52 | A |
| 22 | A | CB | −26.0 | −32.3 | −19.0 | 47 | A |
| 23 | K | N | −29.0 | −33.1 | −18.3 | 45 | A |
| 23 | K | CA | −30.1 | −32.7 | −17.4 | 46 | A |
| 23 | K | C | −29.6 | −32.1 | −16.1 | 54 | A |
| 23 | K | O | −28.4 | −32.3 | −15.8 | 54 | A |
| 23 | K | CB | −31.0 | −34.0 | −17.0 | 46 | A |
| 23 | K | CG | −31.6 | −34.7 | −18.2 | 54 | A |
| 23 | K | CD | −31.8 | −36.2 | −17.9 | 66 | A |
| 23 | K | CE | −32.9 | −36.8 | −18.8 | 73 | A |
| 23 | K | NZ | −33.3 | −38.1 | −18.3 | 81 | A |
| 24 | P | N | −30.4 | −31.4 | −15.4 | 50 | A |
| 24 | P | CA | −29.9 | −30.9 | −14.1 | 49 | A |
| 24 | P | C | −29.3 | −32.0 | −13.2 | 53 | A |
| 24 | P | O | −30.0 | −33.0 | −13.0 | 54 | A |
| 24 | P | CB | −31.1 | −30.2 | −13.5 | 49 | A |
| 24 | P | CG | −31.9 | −29.7 | −14.6 | 54 | A |
| 24 | P | CD | −31.6 | −30.7 | −15.8 | 51 | A |
| 25 | G | N | −28.2 | −31.7 | −12.6 | 48 | A |
| 25 | G | CA | −27.5 | −32.6 | −11.6 | 46 | A |
| 25 | G | C | −26.9 | −33.8 | −12.3 | 47 | A |
| 25 | G | O | −26.4 | −34.7 | −11.6 | 45 | A |
| 26 | Q | N | −26.8 | −33.8 | −13.7 | 42 | A |
| 26 | Q | CA | −26.2 | −34.9 | −14.4 | 42 | A |
| 26 | Q | C | −24.7 | −35.0 | −14.3 | 47 | A |
| 26 | Q | O | −24.1 | −36.1 | −14.3 | 48 | A |
| 26 | Q | CB | −26.7 | −35.0 | −15.8 | 42 | A |
| 26 | Q | CG | −26.5 | −36.3 | −16.4 | 36 | A |
| 26 | Q | CD | −26.9 | −36.3 | −17.9 | 54 | A |
| 26 | Q | OE1 | −27.6 | −35.5 | −18.3 | 46 | A |
| 26 | Q | NE2 | −26.4 | −37.3 | −18.7 | 49 | A |
| 27 | F | N | −24.0 | −33.9 | −14.2 | 41 | A |
| 27 | F | CA | −22.6 | −33.8 | −14.0 | 39 | A |
| 27 | F | C | −22.3 | −32.8 | −12.9 | 40 | A |
| 27 | F | O | −21.6 | −31.7 | −13.2 | 40 | A |
| 27 | F | CB | −21.9 | −33.4 | −15.4 | 40 | A |
| 27 | F | CG | −22.3 | −34.3 | −16.5 | 40 | A |
| 27 | F | CD1 | −23.4 | −34.1 | −17.3 | 41 | A |
| 27 | F | CD2 | −21.5 | −35.5 | −16.7 | 41 | A |
| 27 | F | CE1 | −23.8 | −34.9 | −18.3 | 41 | A |
| 27 | F | CE2 | −21.9 | −36.3 | −17.7 | 43 | A |
| 27 | F | CZ | −23.0 | −36.1 | −18.5 | 40 | A |
| 28 | P | N | −22.7 | −33.1 | −11.7 | 36 | A |
| 28 | P | CA | −22.5 | −32.2 | −10.5 | 36 | A |
| 28 | P | C | −21.1 | −31.8 | −10.2 | 42 | A |
| 28 | P | O | −20.9 | −31.0 | −9.2 | 42 | A |
| 28 | P | CB | −23.3 | −33.0 | −9.4 | 37 | A |
| 28 | P | CG | −23.1 | −34.4 | −9.9 | 41 | A |
| 28 | P | CD | −23.1 | −34.4 | −11.4 | 37 | A |
| 29 | W | N | −20.1 | −32.4 | −10.8 | 37 | A |
| 29 | W | CA | −18.7 | −32.1 | −10.5 | 34 | A |
| 29 | W | C | −18.1 | −31.1 | −11.5 | 36 | A |
| 29 | W | O | −17.1 | −30.5 | −11.2 | 36 | A |
| 29 | W | CB | −17.8 | −33.4 | −10.6 | 32 | A |

TABLE 6-continued

Coordinates of Factor IXa-Compound D complex

| | | | | | | |
|---|---|---|---|---|---|---|
| 29 | W | CG | −18.2 | −34.2 | −11.8 | 33 | A |
| 29 | W | CD1 | −17.8 | −33.9 | −13.1 | 36 | A |
| 29 | W | CD2 | −19.0 | −35.3 | −11.8 | 33 | A |
| 29 | W | NE1 | −18.3 | −34.9 | −13.9 | 36 | A |
| 29 | W | CE2 | −19.1 | −35.7 | −13.1 | 38 | A |
| 29 | W | CE3 | −19.7 | −36.0 | −10.8 | 35 | A |
| 29 | W | CZ2 | −19.7 | −36.8 | −13.5 | 38 | A |
| 29 | W | CZ3 | −20.5 | −37.1 | −11.2 | 37 | A |
| 29 | W | CH2 | −20.5 | −37.5 | −12.6 | 38 | A |
| 30 | Q | N | −18.9 | −30.8 | −12.5 | 32 | A |
| 30 | Q | CA | −18.5 | −29.8 | −13.5 | 33 | A |
| 30 | Q | C | −18.7 | −28.3 | −13.0 | 39 | A |
| 30 | Q | O | −19.7 | −28.0 | −12.4 | 40 | A |
| 30 | Q | CB | −19.5 | −29.9 | −14.7 | 34 | A |
| 30 | Q | CG | −19.3 | −28.9 | −15.8 | 33 | A |
| 30 | Q | CD | −18.2 | −29.1 | −16.7 | 45 | A |
| 30 | Q | OE1 | −17.4 | −28.2 | −17.0 | 44 | A |
| 30 | Q | NE2 | −18.2 | −30.3 | −17.3 | 37 | A |
| 31 | V | N | −17.7 | −27.5 | −13.3 | 34 | A |
| 31 | V | CA | −17.8 | −26.1 | −13.0 | 33 | A |
| 31 | V | C | −17.4 | −25.3 | −14.3 | 39 | A |
| 31 | V | O | −16.8 | −25.8 | −15.3 | 40 | A |
| 31 | V | CB | −16.9 | −25.7 | −11.8 | 35 | A |
| 31 | V | CG1 | −17.2 | −26.6 | −10.6 | 33 | A |
| 31 | V | CG2 | −15.5 | −25.6 | −12.1 | 34 | A |
| 32 | V | N | −17.8 | −24.0 | −14.4 | 38 | A |
| 32 | V | CA | −17.4 | −23.1 | −15.5 | 37 | A |
| 32 | V | C | −16.6 | −22.0 | −14.9 | 38 | A |
| 32 | V | O | −16.7 | −21.6 | −13.8 | 37 | A |
| 32 | V | CB | −18.7 | −22.6 | −16.3 | 40 | A |
| 32 | V | CG1 | −19.6 | −21.7 | −15.4 | 39 | A |
| 32 | V | CG2 | −18.2 | −21.8 | −17.5 | 39 | A |
| 33 | L | N | −15.5 | −21.6 | −15.7 | 37 | A |
| 33 | L | CA | −14.7 | −20.5 | −15.3 | 37 | A |
| 33 | L | C | −15.1 | −19.3 | −16.1 | 45 | A |
| 33 | L | O | −15.5 | −19.4 | −17.3 | 45 | A |
| 33 | L | CB | −13.2 | −20.8 | −15.5 | 36 | A |
| 33 | L | CG | −12.6 | −22.2 | −15.0 | 39 | A |
| 33 | L | CD1 | −11.1 | −22.2 | −15.1 | 37 | A |
| 33 | L | CD2 | −13.1 | −22.5 | −13.6 | 37 | A |
| 34 | N | N | −15.1 | −18.1 | −15.4 | 44 | A |
| 34 | N | CA | −15.4 | −16.8 | −16.0 | 45 | A |
| 34 | N | C | −14.3 | −15.8 | −15.7 | 52 | A |
| 34 | N | O | −13.8 | −15.3 | −14.6 | 53 | A |
| 34 | N | CB | −16.7 | −16.2 | −15.3 | 41 | A |
| 34 | N | CG | −17.9 | −17.0 | −15.6 | 59 | A |
| 34 | N | OD1 | −18.3 | −17.4 | −16.7 | 38 | A |
| 34 | N | ND2 | −18.6 | −17.3 | −14.5 | 58 | A |
| 35 | G | N | −13.8 | −15.1 | −16.7 | 51 | A |
| 35 | G | CA | −12.8 | −14.1 | −16.6 | 53 | A |
| 35 | G | C | −13.2 | −12.8 | −17.4 | 62 | A |
| 35 | G | O | −14.3 | −12.3 | −17.3 | 60 | A |
| 36 | K | N | −12.2 | −12.4 | −18.3 | 64 | A |
| 36 | K | CA | −12.6 | −11.2 | −19.1 | 65 | A |
| 36 | K | C | −13.7 | −11.6 | −20.0 | 69 | A |
| 36 | K | O | −14.6 | −10.8 | −20.4 | 71 | A |
| 36 | K | CB | −11.4 | −10.8 | −20.0 | 70 | A |
| 36 | K | CG | −10.1 | −11.8 | −19.9 | 89 | A |
| 36 | K | CD | −9.1 | −11.5 | −20.9 | 99 | A |
| 36 | K | CE | −7.9 | −10.8 | −20.4 | 0 | A |
| 36 | K | NZ | −6.9 | −10.3 | −21.4 | 0 | A |
| 38 | V | N | −13.8 | −12.9 | −20.3 | 64 | A |
| 38 | V | CA | −14.8 | −13.6 | −21.1 | 61 | A |
| 38 | V | C | −15.5 | −14.6 | −20.2 | 61 | A |
| 38 | V | O | −14.8 | −15.2 | −19.4 | 61 | A |
| 38 | V | CB | −14.2 | −14.2 | −22.3 | 64 | A |
| 38 | V | CG1 | −15.2 | −15.3 | −22.8 | 65 | A |
| 38 | V | CG2 | −14.0 | −13.2 | −23.4 | 64 | A |
| 39 | D | N | −16.8 | −14.7 | −20.2 | 54 | A |
| 39 | D | CA | −17.4 | −15.7 | −19.4 | 53 | A |
| 39 | D | C | −17.4 | −17.1 | −20.1 | 54 | A |
| 39 | D | O | −17.2 | −17.1 | −21.3 | 52 | A |
| 39 | D | CB | −18.9 | −15.2 | −19.1 | 55 | A |
| 39 | D | CG | −18.9 | −14.2 | −17.9 | 69 | A |
| 39 | D | OD1 | −17.9 | −13.5 | −17.7 | 70 | A |
| 39 | D | OD2 | −19.9 | −14.2 | −17.2 | 77 | A |
| 40 | A | N | −17.4 | −18.1 | −19.3 | 49 | A |
| 40 | A | CA | −17.4 | −19.5 | −19.7 | 47 | A |
| 40 | A | C | −16.2 | −19.7 | −20.7 | 47 | A |
| 40 | A | O | −16.4 | −20.3 | −21.8 | 46 | A |
| 40 | A | CB | −18.7 | −19.9 | −20.3 | 48 | A |
| 41 | F | N | −15.0 | −19.3 | −20.4 | 41 | A |
| 41 | F | CA | −13.9 | −19.5 | −21.3 | 39 | A |
| 41 | F | C | −13.3 | −20.9 | −21.2 | 44 | A |
| 41 | F | O | −12.6 | −21.3 | −22.1 | 45 | A |
| 41 | F | CB | −12.9 | −18.4 | −21.2 | 39 | A |
| 41 | F | CG | −12.1 | −18.4 | −19.9 | 38 | A |
| 41 | F | CD1 | −12.7 | −17.9 | −18.7 | 38 | A |
| 41 | F | CD2 | −10.9 | −18.9 | −19.8 | 39 | A |
| 41 | F | CE1 | −12.0 | −17.9 | −17.5 | 38 | A |
| 41 | F | CE2 | −10.2 | −19.0 | −18.6 | 41 | A |
| 41 | F | CZ | −10.8 | −18.4 | −17.4 | 38 | A |
| 42 | C | N | −13.5 | −21.6 | −20.1 | 40 | A |
| 42 | C | CA | −12.9 | −22.9 | −19.8 | 40 | A |
| 42 | C | C | −13.8 | −23.6 | −18.8 | 41 | A |
| 42 | C | O | −14.6 | −22.9 | −18.2 | 40 | A |
| 42 | C | CB | −11.5 | −22.7 | −19.2 | 41 | A |
| 42 | C | SG | −10.1 | −22.7 | −20.4 | 47 | A |
| 43 | G | N | −13.6 | −24.9 | −18.5 | 35 | A |
| 43 | G | CA | −14.3 | −25.6 | −17.5 | 32 | A |
| 43 | G | C | −13.4 | −26.1 | −16.4 | 35 | A |
| 43 | G | O | −12.2 | −25.8 | −16.4 | 35 | A |
| 44 | G | N | −13.9 | −26.9 | −15.5 | 29 | A |
| 44 | G | CA | −13.1 | −27.4 | −14.4 | 27 | A |
| 44 | G | C | −13.9 | −28.5 | −13.7 | 32 | A |
| 44 | G | O | −15.1 | −28.7 | −14.1 | 30 | A |
| 45 | S | N | −13.3 | −29.2 | −12.7 | 29 | A |
| 45 | S | CA | −14.0 | −30.2 | −12.0 | 30 | A |
| 45 | S | C | −13.7 | −30.0 | −10.5 | 35 | A |
| 45 | S | O | −12.7 | −29.5 | −10.1 | 35 | A |
| 45 | S | CB | −13.4 | −31.6 | −12.3 | 32 | A |
| 45 | S | OG | −13.6 | −31.9 | −13.7 | 44 | A |
| 46 | I | N | −14.8 | −30.3 | −9.7 | 33 | A |
| 46 | I | CA | −14.7 | −30.2 | −8.3 | 33 | A |
| 46 | I | C | −13.8 | −31.4 | −7.7 | 38 | A |
| 46 | I | O | −14.2 | −32.6 | −7.9 | 35 | A |
| 46 | I | CB | −16.1 | −30.2 | −7.6 | 36 | A |
| 46 | I | CG1 | −16.9 | −29.0 | −8.1 | 35 | A |
| 46 | I | CG2 | −16.0 | −30.2 | −6.1 | 34 | A |
| 46 | I | CD1 | −18.3 | −29.1 | −7.7 | 33 | A |
| 47 | V | N | −12.7 | −31.1 | −7.0 | 34 | A |
| 47 | V | CA | −11.9 | −32.1 | −6.4 | 34 | A |
| 47 | V | C | −12.5 | −32.3 | −4.9 | 40 | A |
| 47 | V | O | −12.8 | −33.4 | −4.5 | 40 | A |
| 47 | V | CB | −10.4 | −31.6 | −6.3 | 35 | A |
| 47 | V | CG1 | −9.6 | −32.6 | −5.4 | 34 | A |
| 47 | V | CG2 | −9.8 | −31.5 | −7.7 | 34 | A |
| 48 | N | N | −12.8 | −31.2 | −4.3 | 38 | A |
| 48 | N | CA | −13.4 | −31.1 | −3.0 | 38 | A |
| 48 | N | C | −14.1 | −29.8 | −2.8 | 41 | A |
| 48 | N | O | −14.1 | −29.0 | −3.8 | 39 | A |
| 48 | N | CB | −12.5 | −31.5 | −1.8 | 36 | A |
| 48 | N | CG | −11.4 | −30.6 | −1.6 | 42 | A |
| 48 | N | OD1 | −11.5 | −29.4 | −1.7 | 34 | A |
| 48 | N | ND2 | −10.2 | −31.2 | −1.2 | 40 | A |
| 49 | E | N | −14.6 | −29.4 | −1.6 | 39 | A |
| 49 | E | CA | −15.3 | −28.2 | −1.5 | 39 | A |
| 49 | E | C | −14.5 | −26.9 | −1.6 | 41 | A |
| 49 | E | O | −15.1 | −25.8 | −1.9 | 39 | A |
| 49 | E | CB | −16.1 | −28.2 | −0.2 | 40 | A |
| 49 | E | CG | −15.3 | −27.8 | 1.0 | 60 | A |
| 49 | E | CD | −15.6 | −28.7 | 2.2 | 86 | A |
| 49 | E | OE1 | −15.8 | −29.9 | 2.0 | 84 | A |
| 49 | E | OE2 | −15.5 | −28.2 | 3.3 | 67 | A |
| 50 | K | N | −13.2 | −27.0 | −1.5 | 36 | A |
| 50 | K | CA | −12.3 | −25.8 | −1.6 | 35 | A |
| 50 | K | C | −11.4 | −25.8 | −2.9 | 39 | A |
| 50 | K | O | −10.7 | −24.8 | −3.1 | 39 | A |
| 50 | K | CB | −11.4 | −25.7 | −0.4 | 37 | A |
| 50 | K | CG | −12.0 | −25.0 | 0.8 | 53 | A |
| 50 | K | CD | −12.0 | −23.4 | 0.6 | 50 | A |
| 50 | K | CE | −10.8 | −22.8 | 1.1 | 47 | A |
| 50 | K | NZ | −10.7 | −21.3 | 0.8 | 55 | A |
| 51 | W | N | −11.5 | −26.9 | −3.7 | 34 | A |
| 51 | W | CA | −10.6 | −27.0 | −4.8 | 34 | A |
| 51 | W | C | −11.2 | −27.5 | −6.1 | 37 | A |

TABLE 6-continued

Coordinates of Factor IXa-Compound D complex

| | | | | | | |
|---|---|---|---|---|---|---|
| 51 | W | O | −12.0 | −28.4 | −6.1 | 35 | A |
| 51 | W | CB | −9.4 | −28.0 | −4.4 | 32 | A |
| 51 | W | CG | −8.4 | −27.4 | −3.4 | 33 | A |
| 51 | W | CD1 | −8.5 | −27.6 | −2.0 | 36 | A |
| 51 | W | CD2 | −7.3 | −26.6 | −3.6 | 32 | A |
| 51 | W | NE1 | −7.5 | −26.9 | −1.4 | 34 | A |
| 51 | W | CE2 | −6.7 | −26.3 | −2.3 | 36 | A |
| 51 | W | CE3 | −6.6 | −26.2 | −4.8 | 33 | A |
| 51 | W | CZ2 | −5.5 | −25.6 | −2.2 | 35 | A |
| 51 | W | CZ3 | −5.4 | −25.4 | −4.6 | 35 | A |
| 51 | W | CH2 | −4.9 | −25.1 | −3.3 | 35 | A |
| 52 | I | N | −10.7 | −26.9 | −7.2 | 35 | A |
| 52 | I | CA | −11.1 | −27.2 | −8.5 | 35 | A |
| 52 | I | C | −9.9 | −27.6 | −9.3 | 37 | A |
| 52 | I | O | −8.8 | −27.0 | −9.1 | 34 | A |
| 52 | I | CB | −11.8 | −25.9 | −9.2 | 37 | A |
| 52 | I | CG1 | −13.0 | −25.4 | −8.4 | 35 | A |
| 52 | I | CG2 | −12.0 | −26.1 | −10.7 | 34 | A |
| 52 | I | CD1 | −14.0 | −26.4 | −8.2 | 39 | A |
| 53 | V | N | −10.0 | −28.6 | −10.2 | 32 | A |
| 53 | V | CA | −8.9 | −28.9 | −11.1 | 30 | A |
| 53 | V | C | −9.2 | −28.5 | −12.5 | 34 | A |
| 53 | V | O | −10.4 | −28.7 | −13.0 | 34 | A |
| 53 | V | CB | −8.4 | −30.4 | −11.0 | 35 | A |
| 53 | V | CG1 | −7.1 | −30.6 | −11.8 | 35 | A |
| 53 | V | CG2 | −9.5 | −31.4 | −11.4 | 34 | A |
| 54 | T | N | −8.3 | −27.9 | −13.2 | 30 | A |
| 54 | T | CA | −8.5 | −27.4 | −14.5 | 29 | A |
| 54 | T | C | −7.2 | −27.6 | −15.4 | 33 | A |
| 54 | T | O | −6.3 | −28.2 | −14.9 | 31 | A |
| 54 | T | CB | −9.0 | −26.0 | −14.4 | 30 | A |
| 54 | T | OG1 | −9.4 | −25.5 | −15.7 | 37 | A |
| 54 | T | CG2 | −7.8 | −25.1 | −13.8 | 24 | A |
| 55 | A | N | −7.2 | −27.0 | −16.6 | 30 | A |
| 55 | A | CA | −6.1 | −27.0 | −17.5 | 30 | A |
| 55 | A | C | −5.3 | −25.7 | −17.1 | 37 | A |
| 55 | A | O | −5.8 | −24.7 | −16.8 | 38 | A |
| 55 | A | CB | −6.5 | −26.9 | −19.0 | 30 | A |
| 56 | A | N | −3.9 | −25.8 | −17.2 | 31 | A |
| 56 | A | CA | −3.1 | −24.7 | −16.8 | 30 | A |
| 56 | A | C | −3.1 | −23.6 | −17.9 | 40 | A |
| 56 | A | O | −3.0 | −22.4 | −17.5 | 41 | A |
| 56 | A | CB | −1.7 | −25.3 | −16.6 | 29 | A |
| 57 | H | N | −3.4 | −23.9 | −19.1 | 37 | A |
| 57 | H | CA | −3.4 | −22.9 | −20.1 | 35 | A |
| 57 | H | C | −4.6 | −22.0 | −19.9 | 42 | A |
| 57 | H | O | −4.8 | −20.9 | −20.5 | 43 | A |
| 57 | H | CB | −3.3 | −23.4 | −21.6 | 34 | A |
| 57 | H | CG | −4.6 | −24.0 | −22.1 | 37 | A |
| 57 | H | ND1 | −4.9 | −25.4 | −22.1 | 38 | A |
| 57 | H | CD2 | −5.8 | −23.4 | −22.6 | 37 | A |
| 57 | H | CE1 | −6.1 | −25.6 | −22.6 | 37 | A |
| 57 | H | NE2 | −6.7 | −24.4 | −22.9 | 37 | A |
| 58 | C | N | −5.5 | −22.4 | −19.1 | 41 | A |
| 58 | C | CA | −6.7 | −21.6 | −18.8 | 42 | A |
| 58 | C | C | −6.5 | −20.5 | −17.8 | 48 | A |
| 58 | C | O | −7.3 | −19.6 | −17.6 | 50 | A |
| 58 | C | CB | −7.9 | −22.5 | −18.3 | 42 | A |
| 58 | C | SG | −8.5 | −23.6 | −19.5 | 47 | A |
| 59 | V | N | −5.4 | −20.6 | −17.0 | 42 | A |
| 59 | V | CA | −5.2 | −19.8 | −15.9 | 43 | A |
| 59 | V | C | −3.9 | −19.1 | −15.8 | 57 | A |
| 59 | V | O | −3.0 | −19.3 | −16.5 | 57 | A |
| 59 | V | CB | −5.6 | −20.6 | −14.6 | 45 | A |
| 59 | V | CG1 | −7.1 | −20.7 | −14.6 | 44 | A |
| 59 | V | CG2 | −5.0 | −22.0 | −14.5 | 43 | A |
| 60 | E | N | −3.8 | −18.1 | −14.8 | 63 | A |
| 60 | E | CA | −2.6 | −17.3 | −14.7 | 67 | A |
| 60 | E | C | −2.7 | −16.3 | −13.5 | 74 | A |
| 60 | E | O | −3.7 | −15.5 | −13.4 | 75 | A |
| 60 | E | CB | −2.3 | −16.6 | −16.0 | 69 | A |
| 60 | E | CG | −3.0 | −15.3 | −16.2 | 78 | A |
| 60 | E | CD | −2.7 | −17.6 | −17.5 | 0 | A |
| 60 | E | OE1 | −1.5 | −14.3 | −17.7 | 0 | A |
| 60 | E | OE2 | −3.6 | −14.5 | −18.3 | 86 | A |
| 62 | V | N | −4.4 | −13.2 | −13.0 | 61 | A |
| 62 | V | CA | −5.7 | −12.9 | −13.6 | 60 | A |
| 62 | V | C | −6.9 | −13.4 | −12.9 | 63 | A |
| 62 | V | O | −6.9 | −14.6 | −12.5 | 66 | A |
| 62 | V | CB | −5.6 | −13.3 | −15.1 | 64 | A |
| 62 | V | CG1 | −7.0 | −12.9 | −15.8 | 63 | A |
| 62 | V | CG2 | −4.5 | −12.6 | −15.8 | 64 | A |
| 63 | K | N | −7.8 | −12.5 | −12.6 | 59 | A |
| 63 | K | CA | −9.0 | −12.8 | −11.7 | 57 | A |
| 63 | K | C | −10.0 | −13.7 | −12.4 | 58 | A |
| 63 | K | O | −10.6 | −13.3 | −13.4 | 57 | A |
| 63 | K | CB | −9.6 | −11.5 | −11.3 | 59 | A |
| 63 | K | CG | −10.1 | −11.4 | −9.9 | 78 | A |
| 63 | K | CD | −11.3 | −10.5 | −9.7 | 88 | A |
| 63 | K | CE | −12.6 | −11.1 | −10.2 | 86 | A |
| 63 | K | NZ | −13.6 | −11.3 | −9.1 | 86 | A |
| 64 | I | N | −10.3 | −14.8 | −11.7 | 52 | A |
| 64 | I | CA | −11.2 | −15.8 | −12.2 | 50 | A |
| 64 | I | C | −12.3 | −16.1 | −11.1 | 45 | A |
| 64 | I | O | −12.1 | −16.1 | −10.0 | 41 | A |
| 64 | I | CB | −10.4 | −17.2 | −12.5 | 54 | A |
| 64 | I | CG1 | −9.5 | −17.0 | −13.7 | 55 | A |
| 64 | I | CG2 | −11.3 | −18.3 | −12.6 | 54 | A |
| 64 | I | CD1 | −10.3 | −16.4 | −14.9 | 64 | A |
| 65 | T | N | −13.5 | −16.4 | −11.6 | 43 | A |
| 65 | T | CA | −14.5 | −16.9 | −10.7 | 42 | A |
| 65 | T | C | −15.0 | −18.2 | −11.2 | 44 | A |
| 65 | T | O | −15.0 | −18.5 | −12.4 | 44 | A |
| 65 | T | CB | −15.7 | −15.9 | −10.5 | 49 | A |
| 65 | T | OG1 | −16.4 | −15.7 | −11.7 | 50 | A |
| 65 | T | CG2 | −15.1 | −14.6 | −10.0 | 51 | A |
| 66 | V | N | −15.3 | −19.1 | −10.3 | 39 | A |
| 66 | V | CA | −15.8 | −20.5 | −10.7 | 39 | A |
| 66 | V | C | −17.3 | −20.6 | −10.4 | 43 | A |
| 66 | V | O | −17.8 | −20.1 | −9.3 | 41 | A |
| 66 | V | CB | −15.0 | −21.5 | −9.8 | 42 | A |
| 66 | V | CG1 | −15.8 | −22.8 | −9.7 | 41 | A |
| 66 | V | CG2 | −13.6 | −21.7 | −10.4 | 41 | A |
| 67 | V | N | −18.0 | −21.3 | −11.2 | 39 | A |
| 67 | V | CA | −19.5 | −21.5 | −11.0 | 38 | A |
| 67 | V | C | −19.8 | −23.0 | −11.0 | 40 | A |
| 67 | V | O | −19.8 | −23.6 | −12.0 | 39 | A |
| 67 | V | CB | −20.4 | −20.5 | −11.9 | 41 | A |
| 67 | V | CG1 | −21.9 | −20.7 | −11.5 | 41 | A |
| 67 | V | CG2 | −20.0 | −19.1 | −11.8 | 40 | A |
| 68 | A | N | −20.1 | −23.5 | −9.8 | 37 | A |
| 68 | A | CA | −20.6 | −24.8 | −9.6 | 37 | A |
| 68 | A | C | −22.2 | −24.8 | −9.6 | 47 | A |
| 68 | A | O | −22.8 | −23.8 | −9.5 | 48 | A |
| 68 | A | CB | −20.1 | −25.4 | −8.3 | 37 | A |
| 69 | G | N | −22.8 | −26.0 | −9.8 | 44 | A |
| 69 | G | CA | −24.3 | −26.1 | −9.9 | 44 | A |
| 69 | G | C | −24.9 | −25.4 | −11.1 | 48 | A |
| 69 | G | O | −26.1 | −25.2 | −11.2 | 48 | A |
| 70 | E | N | −24.1 | −25.1 | −12.1 | 43 | A |
| 70 | E | CA | −24.5 | −24.4 | −13.4 | 42 | A |
| 70 | E | C | −25.1 | −25.5 | −14.3 | 51 | A |
| 70 | E | O | −24.7 | −26.7 | −14.4 | 51 | A |
| 70 | E | CB | −23.4 | −23.7 | −14.0 | 43 | A |
| 70 | E | CG | −23.9 | −22.8 | −15.1 | 53 | A |
| 70 | E | CD | −25.0 | −21.8 | −14.6 | 74 | A |
| 70 | E | OE1 | −26.1 | −22.3 | −14.5 | 91 | A |
| 70 | E | OE2 | −24.7 | −20.7 | −14.3 | 57 | A |
| 71 | H | N | −26.2 | −25.1 | −15.1 | 50 | A |
| 71 | H | CA | −26.9 | −25.9 | −16.1 | 51 | A |
| 71 | H | C | −27.1 | −25.0 | −17.3 | 57 | A |
| 71 | H | O | −26.4 | −25.1 | −18.3 | 58 | A |
| 71 | H | CB | −28.2 | −26.4 | −15.5 | 52 | A |
| 71 | H | CG | −29.0 | −27.1 | −16.5 | 57 | A |
| 71 | H | ND1 | −28.8 | −28.5 | −16.8 | 59 | A |
| 71 | H | CD2 | −30.2 | −26.8 | −17.2 | 59 | A |
| 71 | H | CE1 | −29.7 | −28.9 | −17.7 | 58 | A |
| 71 | H | NE2 | −30.5 | −27.9 | −17.9 | 58 | A |
| 72 | N | N | −28.0 | −24.1 | −17.2 | 55 | A |
| 72 | N | CA | −28.3 | −23.1 | −18.2 | 55 | A |
| 72 | N | C | −27.5 | −21.8 | −17.8 | 61 | A |
| 72 | N | O | −27.9 | −21.2 | −16.8 | 60 | A |
| 72 | N | CB | −29.8 | −22.8 | −18.4 | 53 | A |
| 72 | N | CG | −30.1 | −22.1 | −19.7 | 66 | A |
| 72 | N | OD1 | −29.4 | −21.1 | −20.1 | 54 | A |
| 72 | N | ND2 | −31.1 | −22.5 | −20.4 | 56 | A |

TABLE 6-continued

Coordinates of Factor IXa-Compound D complex

| | | | | | | |
|---|---|---|---|---|---|---|
| 73 | I | N | −26.5 | −21.5 | −18.5 | 63 | A |
| 73 | I | CA | −25.8 | −20.2 | −18.1 | 65 | A |
| 73 | I | C | −26.5 | −18.9 | −18.3 | 74 | A |
| 73 | I | O | −26.2 | −17.9 | −17.6 | 76 | A |
| 73 | I | CB | −24.3 | −20.2 | −18.6 | 68 | A |
| 73 | I | CG1 | −24.2 | −20.5 | −20.1 | 69 | A |
| 73 | I | CG2 | −23.4 | −21.2 | −17.9 | 68 | A |
| 73 | I | CD1 | −22.8 | −20.4 | −20.7 | 77 | A |
| 74 | E | N | −27.6 | −18.9 | −19.1 | 72 | A |
| 74 | E | CA | −28.4 | −17.7 | −19.2 | 72 | A |
| 74 | E | C | −29.7 | −17.8 | −18.5 | 76 | A |
| 74 | E | O | −30.7 | −17.3 | −18.9 | 76 | A |
| 74 | E | CB | −28.7 | −17.4 | −20.7 | 74 | A |
| 74 | E | CG | −27.4 | −17.0 | −21.5 | 89 | A |
| 74 | E | CD | −27.6 | −16.0 | −22.7 | 0 | A |
| 74 | E | OE1 | −28.7 | −16.1 | −23.3 | 0 | A |
| 74 | E | OE2 | −26.7 | −15.2 | −22.9 | 0 | A |
| 75 | E | N | −29.7 | −18.4 | −17.3 | 72 | A |
| 75 | E | CA | −30.9 | −18.6 | −16.6 | 71 | A |
| 75 | E | C | −30.7 | −19.0 | −15.1 | 73 | A |
| 75 | E | O | −30.2 | −20.1 | −14.9 | 73 | A |
| 75 | E | CB | −31.8 | −19.6 | −17.3 | 72 | A |
| 75 | E | CG | −33.3 | −19.3 | −17.2 | 89 | A |
| 75 | E | CD | −34.1 | −20.6 | −17.6 | 0 | A |
| 75 | E | OE1 | −34.5 | −20.6 | −18.7 | 0 | A |
| 75 | E | OE2 | −34.2 | −21.5 | −16.7 | 0 | A |
| 76 | T | N | −31.1 | −18.2 | −14.2 | 68 | A |
| 76 | T | CA | −31.0 | −18.6 | −12.7 | 66 | A |
| 76 | T | C | −31.8 | −19.8 | −12.4 | 68 | A |
| 76 | T | O | −33.0 | −19.7 | −12.7 | 69 | A |
| 76 | T | CB | −31.3 | −17.4 | −11.9 | 73 | A |
| 76 | T | OG1 | −30.3 | −16.4 | −12.1 | 77 | A |
| 76 | T | CG2 | −31.3 | −17.8 | −10.4 | 65 | A |
| 77 | E | N | −31.2 | −20.8 | −11.9 | 61 | A |
| 77 | E | CA | −32.0 | −22.1 | −11.5 | 59 | A |
| 77 | E | C | −31.9 | −22.3 | −10.0 | 60 | A |
| 77 | E | O | −32.5 | −23.2 | −9.5 | 58 | A |
| 77 | E | CB | −31.3 | −23.3 | −12.2 | 60 | A |
| 77 | E | CG | −31.9 | −23.5 | −13.6 | 67 | A |
| 77 | E | CD | −30.8 | −23.9 | −14.7 | 81 | A |
| 77 | E | OE1 | −29.7 | −23.3 | −14.7 | 69 | A |
| 77 | E | OE2 | −31.1 | −24.8 | −15.5 | 66 | A |
| 78 | H | N | −31.2 | −21.4 | −9.3 | 56 | A |
| 78 | H | CA | −31.1 | −21.5 | −7.9 | 57 | A |
| 78 | H | C | −30.3 | −22.7 | −7.3 | 57 | A |
| 78 | H | O | −30.4 | −23.0 | −6.2 | 57 | A |
| 78 | H | CB | −32.6 | −21.5 | −7.3 | 60 | A |
| 78 | H | CG | −33.4 | −20.4 | −7.8 | 65 | A |
| 78 | H | ND1 | −33.1 | −19.0 | −7.4 | 67 | A |
| 78 | H | CD2 | −34.3 | −20.3 | −8.8 | 67 | A |
| 78 | H | CE1 | −33.9 | −18.2 | −8.2 | 67 | A |
| 78 | H | NE2 | −34.6 | −19.0 | −9.0 | 67 | A |
| 79 | T | N | −29.5 | −23.2 | −8.2 | 50 | A |
| 79 | T | CA | −28.6 | −24.3 | −7.8 | 47 | A |
| 79 | T | C | −27.1 | −23.9 | −7.9 | 44 | A |
| 79 | T | O | −26.3 | −24.6 | −7.2 | 41 | A |
| 79 | T | CB | −28.8 | −25.6 | −8.7 | 51 | A |
| 79 | T | OG1 | −29.1 | −25.2 | −10.0 | 49 | A |
| 79 | T | CG2 | −30.0 | −26.4 | −8.1 | 48 | A |
| 80 | E | N | −26.8 | −22.8 | −8.5 | 38 | A |
| 80 | E | CA | −25.5 | −22.3 | −8.7 | 38 | A |
| 80 | E | C | −24.8 | −21.8 | −7.4 | 44 | A |
| 80 | E | O | −25.5 | −21.2 | −6.5 | 46 | A |
| 80 | E | CB | −25.5 | −21.1 | −9.7 | 39 | A |
| 80 | E | CG | −26.4 | −21.4 | −10.9 | 52 | A |
| 80 | E | CD | −27.9 | −21.1 | −10.7 | 73 | A |
| 80 | E | OE1 | −28.3 | −20.7 | −9.6 | 70 | A |
| 80 | E | OE2 | −28.7 | −21.3 | −11.7 | 70 | A |
| 81 | Q | N | −23.5 | −21.9 | −7.5 | 39 | A |
| 81 | Q | CA | −22.6 | −21.4 | −6.4 | 37 | A |
| 81 | Q | C | −21.4 | −20.8 | −7.0 | 42 | A |
| 81 | Q | O | −20.6 | −21.5 | −7.7 | 40 | A |
| 81 | Q | CB | −22.3 | −22.6 | −5.5 | 38 | A |
| 81 | Q | CG | −23.4 | −23.2 | −4.7 | 31 | A |
| 81 | Q | CD | −22.9 | −24.3 | −3.7 | 42 | A |
| 81 | Q | OE1 | −21.9 | −24.1 | −3.1 | 33 | A |
| 81 | Q | NE2 | −23.8 | −25.3 | −3.5 | 35 | A |
| 82 | K | N | −21.2 | −19.5 | −6.8 | 40 | A |
| 82 | K | CA | −20.1 | −18.8 | −7.3 | 38 | A |
| 82 | K | C | −19.0 | −18.5 | −6.3 | 44 | A |
| 82 | K | O | −19.3 | −18.4 | −5.1 | 43 | A |
| 82 | K | CB | −20.5 | −17.5 | −8.0 | 38 | A |
| 82 | K | CG | −19.5 | −16.9 | −8.9 | 48 | A |
| 82 | K | CD | −20.1 | −15.6 | −9.6 | 65 | A |
| 82 | K | CE | −20.0 | −14.4 | −8.7 | 75 | A |
| 82 | K | NZ | −20.4 | −13.2 | −9.5 | 85 | A |
| 83 | R | N | −17.8 | −18.6 | −6.7 | 40 | A |
| 83 | R | CA | −16.7 | −18.4 | −5.7 | 39 | A |
| 83 | R | C | −15.6 | −17.6 | −6.5 | 43 | A |
| 83 | R | O | −15.5 | −17.7 | −7.7 | 43 | A |
| 83 | R | CB | −16.2 | −19.7 | −5.2 | 37 | A |
| 83 | R | CG | −17.3 | −20.5 | −4.4 | 33 | A |
| 83 | R | CD | −17.6 | −19.7 | −3.1 | 35 | A |
| 83 | R | NE | −18.4 | −20.6 | −2.2 | 35 | A |
| 83 | R | CZ | −19.7 | −20.7 | −2.3 | 47 | A |
| 83 | R | NH1 | −20.4 | −19.9 | −3.2 | 29 | A |
| 83 | R | NH2 | −20.4 | −21.5 | −1.6 | 38 | A |
| 84 | N | N | −14.8 | −16.9 | −5.7 | 38 | A |
| 84 | N | CA | −13.6 | −16.3 | −6.3 | 38 | A |
| 84 | N | C | −12.5 | −17.3 | −6.1 | 43 | A |
| 84 | N | O | −12.4 | −17.9 | −5.0 | 44 | A |
| 84 | N | CB | −13.2 | −15.0 | −5.6 | 38 | A |
| 84 | N | CG | −14.2 | −13.9 | −5.8 | 59 | A |
| 84 | N | OD1 | −15.1 | −14.0 | −6.6 | 51 | A |
| 84 | N | ND2 | −14.0 | −12.8 | −5.1 | 53 | A |
| 85 | V | N | −11.5 | −17.3 | −7.0 | 39 | A |
| 85 | V | CA | −10.3 | −18.1 | −6.9 | 39 | A |
| 85 | V | C | −9.3 | −17.3 | −6.1 | 44 | A |
| 85 | V | O | −9.1 | −16.1 | −6.4 | 45 | A |
| 85 | V | CB | −9.9 | −18.5 | −8.3 | 40 | A |
| 85 | V | CG1 | −8.5 | −18.9 | −8.3 | 39 | A |
| 85 | V | CG2 | −10.8 | −19.5 | −9.0 | 39 | A |
| 86 | I | N | −8.8 | −17.8 | −5.0 | 41 | A |
| 86 | I | CA | −7.8 | −17.1 | −4.2 | 41 | A |
| 86 | I | C | −6.4 | −17.6 | −4.4 | 46 | A |
| 86 | I | O | −5.4 | −17.1 | −3.8 | 46 | A |
| 86 | I | CB | −8.2 | −17.1 | −2.7 | 43 | A |
| 86 | I | CG1 | −8.2 | −18.5 | −2.2 | 42 | A |
| 86 | I | CG2 | −9.5 | −16.4 | −2.4 | 41 | A |
| 86 | I | CD1 | −8.0 | −18.6 | −0.7 | 36 | A |
| 87 | R | N | −6.2 | −18.7 | −5.1 | 43 | A |
| 87 | R | CA | −4.9 | −19.3 | −5.3 | 43 | A |
| 87 | R | C | −5.0 | −20.2 | −6.6 | 47 | A |
| 87 | R | O | −5.9 | −21.0 | −6.7 | 47 | A |
| 87 | R | CB | −4.5 | −20.1 | −4.1 | 40 | A |
| 87 | R | CG | −3.0 | −20.6 | −4.1 | 47 | A |
| 87 | R | CD | −2.5 | −20.7 | −2.7 | 62 | A |
| 87 | R | NE | −1.8 | −21.9 | −2.5 | 88 | A |
| 87 | R | CZ | −2.2 | −22.9 | −1.6 | 0 | A |
| 87 | R | NH1 | −3.3 | −22.8 | −1.0 | 88 | A |
| 87 | R | NH2 | −1.4 | −24.0 | −1.5 | 0 | A |
| 88 | I | N | −4.0 | −20.0 | −7.5 | 42 | A |
| 88 | I | CA | −3.9 | −20.7 | −8.7 | 39 | A |
| 88 | I | C | −2.6 | −21.5 | −8.6 | 41 | A |
| 88 | I | O | −1.5 | −21.0 | −8.5 | 40 | A |
| 88 | I | CB | −3.8 | −19.8 | −9.9 | 41 | A |
| 88 | I | CG1 | −5.0 | −18.9 | −10.0 | 41 | A |
| 88 | I | CG2 | −3.6 | −20.7 | −11.2 | 40 | A |
| 88 | I | CD1 | −5.2 | −18.2 | −11.4 | 36 | A |
| 89 | I | N | −2.7 | −22.9 | −8.6 | 35 | A |
| 89 | I | CA | −1.4 | −23.7 | −8.6 | 34 | A |
| 89 | I | C | −1.3 | −24.5 | −9.9 | 38 | A |
| 89 | I | O | −1.7 | −25.6 | −10.0 | 36 | A |
| 89 | I | CB | −1.4 | −24.6 | −7.4 | 36 | A |
| 89 | I | CG1 | −1.7 | −23.9 | −6.1 | 36 | A |
| 89 | I | CG2 | 0.0 | −25.3 | −7.4 | 32 | A |
| 89 | I | CD1 | −1.7 | −24.8 | −4.9 | 35 | A |
| 90 | P | N | −0.6 | −23.9 | −10.9 | 34 | A |
| 90 | P | CA | −0.3 | −24.7 | −12.1 | 33 | A |
| 90 | P | C | 0.8 | −25.8 | −11.7 | 37 | A |
| 90 | P | O | 1.6 | −25.6 | −10.8 | 35 | A |
| 90 | P | CB | 0.4 | −23.7 | −13.0 | 34 | A |
| 90 | P | CG | 0.9 | −22.6 | −12.2 | 38 | A |
| 90 | P | CD | 0.2 | −22.7 | −10.8 | 35 | A |
| 91 | H | N | 0.7 | −27.0 | −12.4 | 34 | A |
| 91 | H | CA | 1.7 | −28.0 | −12.0 | 32 | A |

TABLE 6-continued

Coordinates of Factor IXa-Compound D complex

| 91 | H | C | 3.2 | -27.4 | -12.2 | 35 | A |
| 91 | H | O | 3.4 | -26.6 | -13.1 | 34 | A |
| 91 | H | CB | 1.6 | -29.3 | -12.9 | 32 | A |
| 91 | H | CG | 2.6 | -30.4 | -12.6 | 35 | A |
| 91 | H | ND1 | 2.4 | -31.4 | -11.6 | 37 | A |
| 91 | H | CD2 | 3.8 | -30.6 | -13.1 | 36 | A |
| 91 | H | CE1 | 3.4 | -32.2 | -11.6 | 36 | A |
| 91 | H | NE2 | 4.3 | -31.7 | -12.5 | 36 | A |
| 92 | H | N | 4.1 | -27.8 | -11.3 | 32 | A |
| 92 | H | CA | 5.4 | -27.2 | -11.4 | 33 | A |
| 92 | H | C | 6.2 | -27.4 | -12.8 | 38 | A |
| 92 | H | O | 7.0 | -26.6 | -13.1 | 40 | A |
| 92 | H | CB | 6.3 | -27.6 | -10.3 | 35 | A |
| 92 | H | CG | 6.6 | -29.1 | -10.2 | 41 | A |
| 92 | H | ND1 | 7.8 | -29.6 | -10.7 | 44 | A |
| 92 | H | CD2 | 5.8 | -30.1 | -9.8 | 44 | A |
| 92 | H | CE1 | 7.7 | -30.9 | -10.5 | 44 | A |
| 92 | H | NE2 | 6.6 | -31.2 | -10.0 | 44 | A |
| 93 | N | N | 5.8 | -28.5 | -13.5 | 33 | A |
| 93 | N | CA | 6.4 | -28.8 | -14.8 | 33 | A |
| 93 | N | C | 5.7 | -28.0 | -15.9 | 39 | A |
| 93 | N | O | 6.0 | -28.1 | -17.0 | 34 | A |
| 93 | N | CB | 6.4 | -30.3 | -15.1 | 32 | A |
| 93 | N | CG | 7.3 | -31.1 | -14.2 | 44 | A |
| 93 | N | OD1 | 7.0 | -32.3 | -13.9 | 46 | A |
| 93 | N | ND2 | 8.5 | -30.6 | -14.0 | 33 | A |
| 94 | Y | N | 4.7 | -27.2 | -15.5 | 37 | A |
| 94 | Y | CA | 4.1 | -26.4 | -16.6 | 37 | A |
| 94 | Y | C | 4.8 | -25.1 | -16.9 | 44 | A |
| 94 | Y | O | 5.2 | -24.3 | -16.0 | 43 | A |
| 94 | Y | CB | 2.6 | -26.1 | -16.2 | 35 | A |
| 94 | Y | CG | 1.9 | -25.3 | -17.3 | 33 | A |
| 94 | Y | CD1 | 1.4 | -25.9 | -18.4 | 34 | A |
| 94 | Y | CD2 | 1.9 | -23.9 | -17.3 | 31 | A |
| 94 | Y | CE1 | 0.8 | -25.2 | -19.4 | 34 | A |
| 94 | Y | CE2 | 1.2 | -23.1 | -18.3 | 29 | A |
| 94 | Y | CZ | 0.7 | -23.9 | -19.4 | 37 | A |
| 94 | Y | OH | 0.0 | -23.3 | -20.4 | 40 | A |
| 95 | N | N | 5.1 | -24.9 | -18.2 | 43 | A |
| 95 | N | CA | 5.8 | -23.6 | -18.6 | 44 | A |
| 95 | N | C | 5.2 | -23.2 | -20.0 | 46 | A |
| 95 | N | O | 5.6 | -23.9 | -21.0 | 45 | A |
| 95 | N | CB | 7.3 | -23.8 | -18.7 | 42 | A |
| 95 | N | CG | 8.0 | -22.6 | -19.1 | 63 | A |
| 95 | N | OD1 | 7.5 | -21.7 | -19.7 | 59 | A |
| 95 | N | ND2 | 9.3 | -22.6 | -18.9 | 51 | A |
| 95A | A | N | 4.3 | -22.3 | -20.0 | 43 | A |
| 95A | A | CA | 3.7 | -21.8 | -21.3 | 45 | A |
| 95A | A | C | 4.7 | -21.3 | -22.4 | 54 | A |
| 95A | A | O | 4.5 | -21.5 | -23.6 | 55 | A |
| 95A | A | CB | 2.6 | -20.8 | -21.1 | 46 | A |
| 95B | A | N | 5.8 | -20.7 | -21.9 | 52 | A |
| 95B | A | CA | 6.8 | -20.2 | -22.8 | 53 | A |
| 95B | A | C | 7.5 | -21.3 | -23.7 | 56 | A |
| 95B | A | O | 8.0 | -21.1 | -24.7 | 58 | A |
| 95B | A | CB | 7.9 | -19.5 | -22.0 | 54 | A |
| 96 | I | N | 7.4 | -22.6 | -23.1 | 50 | A |
| 96 | I | CA | 8.1 | -23.7 | -23.8 | 49 | A |
| 96 | I | C | 7.0 | -24.5 | -24.6 | 56 | A |
| 96 | I | O | 7.3 | -24.8 | -25.8 | 58 | A |
| 96 | I | CB | 8.7 | -24.6 | -22.8 | 50 | A |
| 96 | I | CG1 | 9.4 | -23.7 | -21.8 | 50 | A |
| 96 | I | CG2 | 9.5 | -25.7 | -23.4 | 48 | A |
| 96 | I | CD1 | 10.7 | -24.3 | -21.2 | 38 | A |
| 97 | N | N | 5.9 | -24.8 | -24.0 | 49 | A |
| 97 | N | CA | 4.8 | -25.6 | -24.6 | 45 | A |
| 97 | N | C | 3.5 | -25.3 | -23.8 | 48 | A |
| 97 | N | O | 3.4 | -25.6 | -22.6 | 49 | A |
| 97 | N | CB | 5.1 | -27.0 | -24.7 | 36 | A |
| 97 | N | CG | 4.0 | -27.8 | -25.4 | 54 | A |
| 97 | N | OD1 | 2.8 | -27.5 | -25.4 | 47 | A |
| 97 | N | ND2 | 4.4 | -28.9 | -26.1 | 46 | A |
| 98 | K | N | 2.6 | -24.6 | -24.5 | 41 | A |
| 98 | K | CA | 1.4 | -24.1 | -23.8 | 41 | A |
| 98 | K | C | 0.5 | -25.2 | -23.3 | 43 | A |
| 98 | K | O | -0.4 | -25.0 | -22.4 | 39 | A |
| 98 | K | CB | 0.7 | -23.1 | -24.7 | 44 | A |
| 98 | K | CG | -0.8 | -22.9 | -24.4 | 72 | A |
| 98 | K | CD | -1.3 | -21.7 | -25.2 | 89 | A |
| 98 | K | CE | -2.3 | -20.9 | -24.3 | 0 | A |
| 98 | K | NZ | -1.7 | -20.5 | -23.0 | 0 | A |
| 99 | Y | N | 0.7 | -26.4 | -23.9 | 36 | A |
| 99 | Y | CA | -0.2 | -27.6 | -23.7 | 38 | A |
| 99 | Y | C | 0.3 | -28.8 | -23.2 | 41 | A |
| 99 | Y | O | -0.3 | -29.8 | -23.1 | 42 | A |
| 99 | Y | CB | -1.0 | -27.9 | -25.0 | 41 | A |
| 99 | Y | CG | -1.9 | -26.7 | -25.5 | 44 | A |
| 99 | Y | CD1 | -2.9 | -26.3 | -24.7 | 45 | A |
| 99 | Y | CD2 | -1.5 | -26.0 | -26.6 | 47 | A |
| 99 | Y | CE1 | -3.7 | -25.2 | -25.1 | 43 | A |
| 99 | Y | CE2 | -2.3 | -24.9 | -27.1 | 50 | A |
| 99 | Y | CZ | -3.4 | -24.5 | -26.3 | 55 | A |
| 99 | Y | OH | -4.1 | -23.5 | -26.6 | 58 | A |
| 100 | N | N | 1.6 | -28.8 | -22.7 | 37 | A |
| 100 | N | CA | 2.2 | -30.0 | -22.1 | 36 | A |
| 100 | N | C | 2.1 | -29.7 | -20.6 | 38 | A |
| 100 | N | O | 2.2 | -28.5 | -20.1 | 35 | A |
| 100 | N | CB | 3.7 | -30.1 | -22.5 | 28 | A |
| 100 | N | CG | 4.3 | -31.4 | -22.1 | 39 | A |
| 100 | N | OD1 | 5.5 | -31.6 | -22.2 | 47 | A |
| 100 | N | ND2 | 3.5 | -32.4 | -21.8 | 26 | A |
| 101 | H | N | 2.0 | -30.8 | -19.8 | 36 | A |
| 101 | H | CA | 1.8 | -30.7 | -18.3 | 34 | A |
| 101 | H | C | 0.7 | -29.7 | -18.0 | 36 | A |
| 101 | H | O | 0.7 | -28.9 | -17.1 | 35 | A |
| 101 | H | CB | 3.1 | -30.3 | -17.6 | 34 | A |
| 101 | H | CG | 4.2 | -31.2 | -17.8 | 36 | A |
| 101 | H | ND1 | 5.4 | -30.8 | -18.5 | 36 | A |
| 101 | H | CD2 | 4.5 | -32.5 | -17.4 | 36 | A |
| 101 | H | CE1 | 6.2 | -31.8 | -18.5 | 35 | A |
| 101 | H | NE2 | 5.7 | -32.8 | -17.8 | 36 | A |
| 102 | D | N | -0.4 | -29.8 | -18.8 | 32 | A |
| 102 | D | CA | -1.5 | -28.9 | -18.8 | 32 | A |
| 102 | D | C | -2.5 | -29.3 | -17.7 | 37 | A |
| 102 | D | O | -3.6 | -29.8 | -18.0 | 35 | A |
| 102 | D | CB | -2.2 | -29.0 | -20.2 | 33 | A |
| 102 | D | CG | -2.9 | -27.7 | -20.4 | 37 | A |
| 102 | D | OD1 | -2.8 | -26.8 | -19.6 | 36 | A |
| 102 | D | OD2 | -3.7 | -27.7 | -21.4 | 45 | A |
| 103 | I | N | -2.2 | -28.9 | -16.5 | 34 | A |
| 103 | I | CA | -3.1 | -29.1 | -15.3 | 32 | A |
| 103 | I | C | -2.8 | -28.0 | -14.3 | 35 | A |
| 103 | I | O | -1.6 | -27.7 | -14.1 | 35 | A |
| 103 | I | CB | -3.0 | -30.6 | -14.8 | 32 | A |
| 103 | I | CG1 | -4.1 | -30.9 | -13.9 | 30 | A |
| 103 | I | CG2 | -1.5 | -30.9 | -14.1 | 28 | A |
| 103 | I | CD1 | -4.1 | -32.3 | -13.5 | 28 | A |
| 104 | A | N | -3.8 | -27.5 | -13.6 | 28 | A |
| 104 | A | CA | -3.7 | -26.6 | -12.6 | 27 | A |
| 104 | A | C | -4.8 | -26.8 | -11.5 | 36 | A |
| 104 | A | O | -5.9 | -27.3 | -11.8 | 35 | A |
| 104 | A | CB | -3.8 | -25.1 | -13.2 | 27 | A |
| 105 | L | N | -4.6 | -26.3 | -10.3 | 34 | A |
| 105 | L | CA | -5.5 | -26.4 | -9.2 | 32 | A |
| 105 | L | C | -6.0 | -25.0 | -8.9 | 39 | A |
| 105 | L | O | -5.2 | -24.1 | -8.9 | 38 | A |
| 105 | L | CB | -4.9 | -27.1 | -8.0 | 30 | A |
| 105 | L | CG | -4.5 | -28.5 | -8.1 | 32 | A |
| 105 | L | CD1 | -3.7 | -29.1 | -7.0 | 31 | A |
| 105 | L | CD2 | -5.7 | -29.4 | -8.4 | 31 | A |
| 106 | L | N | -7.3 | -24.8 | -8.5 | 37 | A |
| 106 | L | CA | -7.8 | -23.5 | -8.1 | 36 | A |
| 106 | L | C | -8.4 | -23.6 | -6.7 | 41 | A |
| 106 | L | O | -9.2 | -24.5 | -6.4 | 41 | A |
| 106 | L | CB | -8.9 | -23.0 | -9.0 | 35 | A |
| 106 | L | CG | -8.7 | -23.1 | -10.5 | 38 | A |
| 106 | L | CD1 | -10.0 | -22.6 | -11.2 | 37 | A |
| 106 | L | CD2 | -7.5 | -22.4 | -11.0 | 35 | A |
| 107 | E | N | -7.9 | -22.7 | -5.8 | 40 | A |
| 107 | E | CA | -8.5 | -22.7 | -4.4 | 38 | A |
| 107 | E | C | -9.6 | -21.6 | -4.3 | 40 | A |
| 107 | E | O | -9.5 | -20.5 | -4.8 | 39 | A |
| 107 | E | CB | -7.4 | -22.3 | -3.4 | 39 | A |
| 107 | E | CG | -7.9 | -22.4 | -1.9 | 41 | A |
| 107 | E | CD | -6.8 | -22.2 | -0.9 | 52 | A |
| 107 | E | OE1 | -5.7 | -21.7 | -1.3 | 61 | A |

TABLE 6-continued

Coordinates of Factor IXa-Compound D complex

| 107 | E | OE2 | −6.9 | −22.7 | 0.2 | 46 | A |
|---|---|---|---|---|---|---|---|
| 108 | L | N | −10.8 | −22.1 | −3.3 | 38 | A |
| 108 | L | CA | −11.9 | −21.2 | −3.7 | 37 | A |
| 108 | L | C | −11.9 | −20.4 | −2.4 | 40 | A |
| 108 | L | O | −11.4 | −20.9 | −1.4 | 41 | A |
| 108 | L | CB | −13.2 | −22.1 | −3.7 | 36 | A |
| 108 | L | CG | −13.4 | −23.0 | −4.9 | 38 | A |
| 108 | L | CD1 | −14.6 | −23.8 | −5.0 | 37 | A |
| 108 | L | CD2 | −13.1 | −22.3 | −6.2 | 37 | A |
| 109 | D | N | −12.3 | −19.1 | −2.4 | 35 | A |
| 109 | D | CA | −12.2 | −18.2 | −1.2 | 36 | A |
| 109 | D | C | −13.1 | −18.7 | −0.1 | 43 | A |
| 109 | D | O | −12.8 | −18.5 | 1.1 | 45 | A |
| 109 | D | CB | −12.7 | −16.8 | −1.5 | 37 | A |
| 109 | D | CG | −14.1 | −16.8 | −2.2 | 46 | A |
| 109 | D | OD1 | −14.6 | −17.8 | −2.5 | 49 | A |
| 109 | D | OD2 | −14.6 | −15.6 | −2.4 | 45 | A |
| 110 | E | N | −14.2 | −19.4 | −0.5 | 39 | A |
| 110 | E | CA | −15.1 | −19.9 | 0.5 | 39 | A |
| 110 | E | C | −15.6 | −21.3 | −0.0 | 42 | A |
| 110 | E | O | −15.9 | −21.5 | −1.2 | 43 | A |
| 110 | E | CB | −16.3 | −19.0 | 0.6 | 40 | A |
| 110 | E | CG | −16.7 | −18.6 | 2.0 | 47 | A |
| 110 | E | CD | −15.6 | −18.0 | 2.9 | 56 | A |
| 110 | E | OE1 | −15.3 | −16.8 | 2.8 | 42 | A |
| 110 | E | OE2 | −15.2 | −18.7 | 3.8 | 40 | A |
| 111 | P | N | −15.7 | −22.3 | 0.9 | 36 | A |
| 111 | P | CA | −16.1 | −23.6 | 0.5 | 35 | A |
| 111 | P | C | −17.4 | −23.7 | −0.3 | 41 | A |
| 111 | P | O | −18.3 | −22.9 | −0.1 | 41 | A |
| 111 | P | CB | −16.4 | −24.4 | 1.8 | 36 | A |
| 111 | P | CG | −15.6 | −23.6 | 2.8 | 39 | A |
| 111 | P | CD | −15.6 | −22.1 | 2.3 | 35 | A |
| 112 | L | N | −17.6 | −24.7 | −1.2 | 38 | A |
| 112 | L | CA | −18.8 | −25.0 | −1.9 | 37 | A |
| 112 | L | C | −19.6 | −25.8 | −0.8 | 40 | A |
| 112 | L | O | −19.0 | −26.4 | 0.1 | 37 | A |
| 112 | L | CB | −18.6 | −25.8 | −3.1 | 36 | A |
| 112 | L | CG | −17.9 | −25.1 | −4.3 | 40 | A |
| 112 | L | CD1 | −17.2 | −26.1 | −5.2 | 40 | A |
| 112 | L | CD2 | −18.8 | −24.1 | −5.0 | 39 | A |
| 113 | V | N | −20.9 | −25.8 | −1.0 | 37 | A |
| 113 | V | CA | −21.8 | −26.6 | −0.2 | 37 | A |
| 113 | V | C | −22.2 | −27.8 | −1.0 | 44 | A |
| 113 | V | O | −22.9 | −27.6 | −2.0 | 45 | A |
| 113 | V | CB | −22.9 | −25.7 | 0.4 | 38 | A |
| 113 | V | CG1 | −23.9 | −26.6 | 1.1 | 35 | A |
| 113 | V | CG2 | −22.4 | −24.7 | 1.5 | 38 | A |
| 114 | L | N | −21.8 | −29.0 | −0.6 | 40 | A |
| 114 | L | CA | −22.1 | −30.2 | −1.4 | 41 | A |
| 114 | L | C | −23.6 | −30.6 | −1.3 | 48 | A |
| 114 | L | O | −24.2 | −30.7 | −0.2 | 50 | A |
| 114 | L | CB | −21.2 | −31.4 | −1.0 | 39 | A |
| 114 | L | CG | −19.7 | −31.2 | −1.1 | 41 | A |
| 114 | L | CD1 | −19.0 | −32.4 | −0.7 | 39 | A |
| 114 | L | CD2 | −19.3 | −30.7 | −2.4 | 42 | A |
| 115 | N | N | −24.2 | −30.8 | −2.5 | 46 | A |
| 115 | N | CA | −25.5 | −31.2 | −2.6 | 46 | A |
| 115 | N | C | −25.7 | −32.0 | −3.9 | 50 | A |
| 115 | N | O | −24.7 | −32.4 | −4.5 | 51 | A |
| 115 | N | CB | −26.5 | −30.0 | −2.5 | 37 | A |
| 115 | N | CG | −26.2 | −29.0 | −3.7 | 59 | A |
| 115 | N | OD1 | −26.0 | −29.4 | −4.8 | 59 | A |
| 115 | N | ND2 | −26.3 | −27.7 | −3.4 | 46 | A |
| 116 | S | N | −26.9 | −32.2 | −4.4 | 46 | A |
| 116 | S | CA | −27.1 | −33.0 | −5.6 | 45 | A |
| 116 | S | C | −26.7 | −32.3 | −6.9 | 47 | A |
| 116 | S | O | −26.5 | −33.0 | −7.9 | 47 | A |
| 116 | S | CB | −28.6 | −33.4 | −5.7 | 44 | A |
| 116 | S | OG | −28.8 | −34.4 | −4.8 | 51 | A |
| 117 | Y | N | −26.4 | −31.0 | −6.8 | 41 | A |
| 117 | Y | CA | −26.0 | −30.2 | −8.0 | 42 | A |
| 117 | Y | C | −24.5 | −29.8 | −7.9 | 42 | A |
| 117 | Y | O | −24.0 | −29.3 | −8.9 | 42 | A |
| 117 | Y | CB | −26.9 | −29.0 | −8.2 | 45 | A |
| 117 | Y | CG | −28.3 | −29.3 | −8.2 | 50 | A |
| 117 | Y | CD1 | −29.0 | −29.6 | −9.4 | 52 | A |
| 117 | Y | CD2 | −29.1 | −29.3 | −7.0 | 52 | A |
| 117 | Y | CE1 | −30.3 | −29.9 | −9.4 | 55 | A |
| 117 | Y | CE2 | −30.5 | −29.6 | −7.0 | 53 | A |
| 117 | Y | CZ | −31.1 | −29.9 | −8.3 | 59 | A |
| 117 | Y | OH | −32.4 | −30.2 | −8.3 | 60 | A |
| 118 | V | N | −23.9 | −30.1 | −6.8 | 37 | A |
| 118 | V | CA | −22.5 | −29.7 | −6.5 | 36 | A |
| 118 | V | C | −21.9 | −30.9 | −5.8 | 43 | A |
| 118 | V | O | −22.1 | −31.0 | −4.5 | 44 | A |
| 118 | V | CB | −22.4 | −28.4 | −5.7 | 39 | A |
| 118 | V | CG1 | −21.0 | −28.0 | −5.5 | 37 | A |
| 118 | V | CG2 | −23.2 | −27.3 | −6.4 | 40 | A |
| 119 | T | N | −21.2 | −31.8 | −6.5 | 41 | A |
| 119 | T | CA | −20.7 | −33.0 | −5.9 | 40 | A |
| 119 | T | C | −19.3 | −33.2 | −6.5 | 40 | A |
| 119 | T | O | −19.1 | −32.9 | −7.7 | 39 | A |
| 119 | T | CB | −21.6 | −34.2 | −6.3 | 40 | A |
| 119 | T | OG1 | −22.9 | −34.0 | −5.7 | 40 | A |
| 119 | T | CG2 | −21.1 | −35.5 | −5.9 | 33 | A |
| 120 | P | N | −18.3 | −33.7 | −5.9 | 37 | A |
| 120 | P | CA | −17.0 | −33.8 | −6.3 | 34 | A |
| 120 | P | C | −16.9 | −35.1 | −7.3 | 39 | A |
| 120 | P | O | −17.8 | −35.9 | −7.2 | 39 | A |
| 120 | P | CB | −16.0 | −34.0 | −5.2 | 34 | A |
| 120 | P | CG | −16.8 | −33.6 | −3.9 | 38 | A |
| 120 | P | CD | −18.2 | −33.9 | −4.2 | 36 | A |
| 121 | I | N | −15.9 | −35.1 | −8.1 | 33 | A |
| 121 | I | CA | −15.6 | −36.2 | −9.0 | 31 | A |
| 121 | I | C | −14.6 | −37.1 | −8.1 | 37 | A |
| 121 | I | O | −13.8 | −36.6 | −7.3 | 36 | A |
| 121 | I | CB | −14.8 | −35.7 | −10.3 | 33 | A |
| 121 | I | CG1 | −14.7 | −36.8 | −11.3 | 31 | A |
| 121 | I | CG2 | −13.5 | −35.0 | −10.0 | 29 | A |
| 121 | I | CD1 | −16.0 | −37.5 | −11.7 | 34 | A |
| 122 | C | N | −14.7 | −38.4 | −8.3 | 35 | A |
| 122 | C | CA | −13.8 | −39.3 | −7.6 | 36 | A |
| 122 | C | C | −12.5 | −39.3 | −8.4 | 38 | A |
| 122 | C | O | −12.5 | −39.1 | −9.6 | 39 | A |
| 122 | C | CB | −14.3 | −40.7 | −7.5 | 38 | A |
| 122 | C | SG | −16.0 | −40.9 | −6.8 | 43 | A |
| 123 | I | N | −11.4 | −39.5 | −7.7 | 35 | A |
| 123 | I | CA | −10.1 | −39.6 | −8.3 | 34 | A |
| 123 | I | C | −9.4 | −40.8 | −7.6 | 41 | A |
| 123 | I | O | −9.1 | −40.7 | −6.4 | 39 | A |
| 123 | I | CB | −9.2 | −38.3 | −8.1 | 35 | A |
| 123 | I | CG1 | −10.0 | −37.1 | −8.6 | 35 | A |
| 123 | I | CG2 | −7.8 | −38.5 | −8.7 | 35 | A |
| 123 | I | CD1 | −9.1 | −35.7 | −8.5 | 30 | A |
| 124 | A | N | −9.1 | −41.8 | −8.4 | 39 | A |
| 124 | A | CA | −8.4 | −43.0 | −7.9 | 35 | A |
| 124 | A | C | −6.9 | −42.8 | −7.8 | 41 | A |
| 124 | A | O | −6.5 | −41.7 | −8.0 | 42 | A |
| 124 | A | CB | −8.8 | −44.2 | −8.7 | 35 | A |
| 125 | D | N | −6.2 | −43.8 | −7.4 | 37 | A |
| 125 | D | CA | −4.8 | −43.8 | −7.4 | 35 | A |
| 125 | D | C | −4.2 | −43.9 | −8.8 | 36 | A |
| 125 | D | O | −5.0 | −44.1 | −9.8 | 37 | A |
| 125 | D | CB | −4.2 | −44.9 | −6.4 | 36 | A |
| 125 | D | CG | −4.1 | −46.3 | −7.0 | 49 | A |
| 125 | D | OD1 | −4.6 | −46.5 | −8.2 | 49 | A |
| 125 | D | OD2 | −3.7 | −47.2 | −6.4 | 57 | A |
| 126 | K | N | −2.9 | −43.7 | −9.0 | 31 | A |
| 126 | K | CA | −2.3 | −43.7 | −10.3 | 30 | A |
| 126 | K | C | −2.7 | −44.9 | −11.2 | 38 | A |
| 126 | K | O | −3.0 | −44.8 | −12.4 | 37 | A |
| 126 | K | CB | −0.8 | −43.6 | −10.1 | 32 | A |
| 126 | K | CG | 0.1 | −43.7 | −11.4 | 40 | A |
| 126 | K | CD | 1.5 | −43.2 | −11.2 | 42 | A |
| 126 | K | CE | 2.4 | −43.7 | −12.3 | 41 | A |
| 126 | K | NZ | 3.9 | −43.3 | −12.0 | 45 | A |
| 127 | E | N | −2.5 | −46.1 | −10.6 | 36 | A |
| 127 | E | CA | −2.8 | −47.3 | −11.3 | 35 | A |
| 127 | E | C | −4.2 | −47.5 | −11.7 | 40 | A |
| 127 | E | O | −4.4 | −48.0 | −12.8 | 45 | A |
| 127 | E | CB | −2.4 | −48.5 | −10.3 | 37 | A |
| 127 | E | CG | −2.9 | −49.8 | −10.8 | 51 | A |
| 127 | E | CD | −2.6 | −51.0 | −9.8 | 74 | A |
| 127 | E | OE1 | −2.4 | −52.1 | −10.3 | 70 | A |
| 127 | E | OE2 | −2.5 | −50.8 | −8.6 | 73 | A |

TABLE 6-continued

Coordinates of Factor IXa-Compound D complex

| | | | | | | |
|---|---|---|---|---|---|---|
| 128 | Y | N | −5.1 | −47.2 | −10.9 | 37 | A |
| 128 | Y | CA | −6.5 | −47.4 | −11.2 | 35 | A |
| 128 | Y | C | −7.1 | −46.3 | −12.1 | 38 | A |
| 128 | Y | O | −8.0 | −46.6 | −12.9 | 39 | A |
| 128 | Y | CB | −7.4 | −47.5 | −10.0 | 36 | A |
| 128 | Y | CG | −7.6 | −48.9 | −9.5 | 39 | A |
| 128 | Y | CD1 | −6.7 | −49.4 | −8.5 | 41 | A |
| 128 | Y | CD2 | −8.5 | −49.7 | −10.1 | 40 | A |
| 128 | Y | CE1 | −6.8 | −50.7 | −8.1 | 43 | A |
| 128 | Y | CE2 | −8.6 | −51.1 | −9.7 | 42 | A |
| 128 | Y | CZ | −7.7 | −51.6 | −8.7 | 48 | A |
| 128 | Y | OH | −7.8 | −52.9 | −8.4 | 46 | A |
| 129 | T | N | −6.5 | −45.1 | −12.0 | 35 | A |
| 129 | T | CA | −7.0 | −44.0 | −12.9 | 34 | A |
| 129 | T | C | −6.6 | −44.5 | −14.3 | 38 | A |
| 129 | T | O | −7.4 | −44.4 | −15.3 | 39 | A |
| 129 | T | CB | −6.2 | −42.7 | −12.5 | 37 | A |
| 129 | T | OG1 | −6.8 | −42.3 | −11.2 | 38 | A |
| 129 | T | CG2 | −6.5 | −41.6 | −13.5 | 30 | A |
| 129A | N | N | −5.3 | −45.0 | −14.5 | 33 | A |
| 129A | N | CA | −4.9 | −45.5 | −15.7 | 34 | A |
| 129A | N | C | −5.7 | −46.7 | −16.3 | 40 | A |
| 129A | N | O | −6.1 | −46.8 | −17.5 | 41 | A |
| 129A | N | CB | −3.4 | −45.9 | −15.6 | 35 | A |
| 129A | N | CG | −2.9 | −46.4 | −17.0 | 46 | A |
| 129A | N | OD1 | −3.1 | −45.8 | −18.0 | 40 | A |
| 129A | N | ND2 | −2.2 | −47.5 | −17.0 | 37 | A |
| 129B | I | N | −6.0 | −47.7 | −15.4 | 35 | A |
| 129B | I | CA | −6.9 | −48.8 | −15.7 | 34 | A |
| 129B | I | C | −8.2 | −48.3 | −16.2 | 39 | A |
| 129B | I | O | −8.7 | −48.8 | −17.3 | 41 | A |
| 129B | I | CB | −7.0 | −49.8 | −14.5 | 37 | A |
| 129B | I | CG1 | −5.7 | −50.6 | −14.2 | 35 | A |
| 129B | I | CG2 | −8.3 | −50.7 | −14.6 | 34 | A |
| 129B | I | CD1 | −5.6 | −51.2 | −12.8 | 32 | A |
| 130 | F | N | −8.9 | −47.4 | −15.5 | 35 | A |
| 130 | F | CA | −10.1 | −46.8 | −15.9 | 35 | A |
| 130 | F | C | −10.1 | −46.1 | −17.3 | 37 | A |
| 130 | F | O | −10.9 | −46.3 | −18.1 | 38 | A |
| 130 | F | CB | −10.6 | −45.8 | −14.8 | 37 | A |
| 130 | F | CG | −10.9 | −46.4 | −13.5 | 40 | A |
| 130 | F | CD1 | −11.2 | −47.8 | −13.4 | 43 | A |
| 130 | F | CD2 | −10.9 | −45.7 | −12.3 | 42 | A |
| 130 | F | CE1 | −11.5 | −48.4 | −12.1 | 43 | A |
| 130 | F | CE2 | −11.2 | −46.3 | −11.1 | 45 | A |
| 130 | F | CZ | −11.5 | −47.6 | −11.0 | 42 | A |
| 131 | L | N | −9.0 | −45.3 | −17.5 | 33 | A |
| 131 | L | CA | −8.9 | −44.7 | −18.8 | 32 | A |
| 131 | L | C | −8.9 | −45.8 | −19.9 | 39 | A |
| 131 | L | O | −9.5 | −45.6 | −21.0 | 38 | A |
| 131 | L | CB | −7.5 | −44.0 | −18.9 | 31 | A |
| 131 | L | CG | −7.2 | −43.3 | −20.2 | 33 | A |
| 131 | L | CD1 | −5.8 | −42.8 | −20.1 | 33 | A |
| 131 | L | CD2 | −8.2 | −42.1 | −20.5 | 33 | A |
| 132 | K | N | −8.2 | −46.9 | −19.6 | 36 | A |
| 132 | K | CA | −8.1 | −48.0 | −20.6 | 36 | A |
| 132 | K | C | −9.4 | −48.8 | −20.8 | 39 | A |
| 132 | K | O | −9.5 | −49.6 | −21.8 | 37 | A |
| 132 | K | CB | −6.9 | −48.9 | −20.3 | 38 | A |
| 132 | K | CG | −5.6 | −48.2 | −20.3 | 39 | A |
| 132 | K | CD | −4.5 | −49.1 | −20.6 | 44 | A |
| 132 | K | CE | −3.5 | −49.4 | −19.5 | 62 | A |
| 132 | K | NZ | −2.1 | −49.6 | −19.9 | 73 | A |
| 133 | F | N | −10.5 | −48.6 | −20.1 | 35 | A |
| 133 | F | CA | −11.8 | −49.1 | −20.3 | 35 | A |
| 133 | F | C | −12.2 | −48.6 | −21.7 | 42 | A |
| 133 | F | O | −13.1 | −49.1 | −22.4 | 44 | A |
| 133 | F | CB | −12.8 | −48.7 | −19.3 | 36 | A |
| 133 | F | CG | −12.7 | −49.4 | −18.0 | 38 | A |
| 133 | F | CD1 | −11.8 | −50.3 | −17.8 | 42 | A |
| 133 | F | CD2 | −13.6 | −49.0 | −16.9 | 40 | A |
| 133 | F | CE1 | −11.6 | −51.0 | −16.5 | 41 | A |
| 133 | F | CE2 | −13.4 | −49.7 | −15.7 | 42 | A |
| 133 | F | CZ | −12.4 | −50.6 | −15.5 | 39 | A |
| 134 | G | N | −11.6 | −47.5 | −22.1 | 39 | A |
| 134 | G | CA | −11.7 | −46.9 | −23.4 | 38 | A |
| 134 | G | C | −12.9 | −46.1 | −23.8 | 41 | A |
| 134 | G | O | −13.2 | −45.9 | −25.0 | 41 | A |
| 135 | S | N | −13.7 | −45.6 | −22.8 | 39 | A |
| 135 | S | CA | −14.9 | −44.8 | −23.1 | 39 | A |
| 135 | S | C | −15.1 | −43.8 | −21.9 | 42 | A |
| 135 | S | O | −15.3 | −44.3 | −20.8 | 42 | A |
| 135 | S | CB | −16.1 | −45.7 | −23.2 | 40 | A |
| 135 | S | OG | −17.1 | −45.1 | −24.0 | 53 | A |
| 136 | G | N | −15.1 | −42.5 | −22.2 | 37 | A |
| 136 | G | CA | −15.3 | −41.5 | −21.2 | 37 | A |
| 136 | G | C | −16.4 | −40.5 | −21.6 | 42 | A |
| 136 | G | O | −16.8 | −40.5 | −22.8 | 42 | A |
| 137 | Y | N | −16.8 | −39.7 | −20.9 | 41 | A |
| 137 | Y | CA | −17.7 | −38.7 | −20.9 | 42 | A |
| 137 | Y | C | −17.0 | −37.3 | −20.7 | 44 | A |
| 137 | Y | O | −16.3 | −37.1 | −19.7 | 43 | A |
| 137 | Y | CB | −18.9 | −38.7 | −20.0 | 46 | A |
| 137 | Y | CG | −19.8 | −39.8 | −20.2 | 53 | A |
| 137 | Y | CD1 | −19.5 | −41.1 | −19.8 | 56 | A |
| 137 | Y | CD2 | −21.0 | −39.6 | −20.9 | 56 | A |
| 137 | Y | CE1 | −20.4 | −42.2 | −20.1 | 57 | A |
| 137 | Y | CE2 | −21.9 | −40.6 | −21.2 | 58 | A |
| 137 | Y | CZ | −21.5 | −41.9 | −20.8 | 69 | A |
| 137 | Y | OH | −22.4 | −43.0 | −21.1 | 75 | A |
| 138 | V | N | −17.2 | −36.5 | −21.7 | 36 | A |
| 138 | V | CA | −16.7 | −35.1 | −21.6 | 33 | A |
| 138 | V | C | −17.9 | −34.2 | −21.5 | 38 | A |
| 138 | V | O | −19.0 | −34.6 | −22.0 | 38 | A |
| 138 | V | CB | −15.7 | −34.8 | −22.8 | 34 | A |
| 138 | V | CG1 | −14.4 | −35.6 | −22.7 | 33 | A |
| 138 | V | CG2 | −16.3 | −35.0 | −24.2 | 33 | A |
| 139 | S | N | −17.7 | −33.0 | −21.0 | 35 | A |
| 139 | S | CA | −18.8 | −32.0 | −20.9 | 34 | A |
| 139 | S | C | −18.2 | −30.6 | −20.8 | 40 | A |
| 139 | S | O | −17.1 | −30.3 | −20.4 | 37 | A |
| 139 | S | CB | −19.7 | −32.3 | −19.6 | 36 | A |
| 139 | S | OG | −18.9 | −32.6 | −18.5 | 38 | A |
| 140 | G | N | −19.1 | −29.6 | −21.1 | 39 | A |
| 140 | G | CA | −18.7 | −28.2 | −21.1 | 40 | A |
| 140 | G | C | −19.7 | −27.3 | −21.8 | 48 | A |
| 140 | G | O | −20.6 | −27.7 | −22.5 | 48 | A |
| 141 | W | N | −19.4 | −26.0 | −21.7 | 44 | A |
| 141 | W | CA | −20.2 | −25.0 | −22.4 | 42 | A |
| 141 | W | C | −19.4 | −24.4 | −23.5 | 45 | A |
| 141 | W | O | −19.6 | −23.2 | −23.8 | 46 | A |
| 141 | W | CB | −20.6 | −23.9 | −21.4 | 39 | A |
| 141 | W | CG | −21.6 | −24.3 | −20.3 | 39 | A |
| 141 | W | CD1 | −23.0 | −24.1 | −20.5 | 42 | A |
| 141 | W | CD2 | −21.4 | −24.8 | −19.0 | 39 | A |
| 141 | W | NE1 | −23.6 | −24.5 | −19.3 | 41 | A |
| 141 | W | CE2 | −22.7 | −25.0 | −18.4 | 42 | A |
| 141 | W | CE3 | −20.2 | −25.2 | −18.3 | 41 | A |
| 141 | W | CZ2 | −22.8 | −25.5 | −17.1 | 42 | A |
| 141 | W | CZ3 | −20.4 | −25.7 | −17.0 | 42 | A |
| 141 | W | CH2 | −21.7 | −25.8 | −16.5 | 42 | A |
| 142 | G | N | −18.5 | −25.1 | −24.1 | 43 | A |
| 142 | G | CA | −17.7 | −24.7 | −25.2 | 42 | A |
| 142 | G | C | −18.5 | −24.5 | −26.5 | 46 | A |
| 142 | G | O | −19.7 | −24.8 | −26.5 | 41 | A |
| 143 | R | N | −17.8 | −24.2 | −27.6 | 46 | A |
| 143 | R | CA | −18.5 | −24.1 | −28.9 | 48 | A |
| 143 | R | C | −19.2 | −25.4 | −29.3 | 54 | A |
| 143 | R | O | −18.6 | −26.5 | −29.1 | 53 | A |
| 143 | R | CB | −17.7 | −23.6 | −30.1 | 46 | A |
| 143 | R | CG | −16.5 | −22.7 | −29.8 | 52 | A |
| 143 | R | CD | −15.8 | −22.4 | −31.0 | 56 | A |
| 143 | R | NE | −15.6 | −20.9 | −31.1 | 69 | A |
| 143 | R | CZ | −14.5 | −20.3 | −31.2 | 80 | A |
| 143 | R | NH1 | −13.4 | −21.0 | −31.3 | 77 | A |
| 143 | R | NH2 | −14.4 | −19.0 | −31.2 | 67 | A |
| 144 | V | N | −20.4 | −25.3 | −29.9 | 51 | A |
| 144 | V | CA | −21.1 | −26.4 | −30.4 | 52 | A |
| 144 | V | C | −20.9 | −26.6 | −31.9 | 59 | A |
| 144 | V | O | −21.5 | −27.5 | −32.5 | 57 | A |
| 144 | V | CB | −22.6 | −26.4 | −30.0 | 55 | A |
| 144 | V | CG1 | −22.7 | −26.4 | −28.5 | 53 | A |
| 144 | V | CG2 | −23.3 | −25.2 | −30.6 | 55 | A |
| 145 | F | N | −20.0 | −25.8 | −32.5 | 61 | A |
| 145 | F | CA | −19.6 | −25.8 | −33.9 | 63 | A |
| 145 | F | C | −18.2 | −25.3 | −34.0 | 71 | A |

TABLE 6-continued

Coordinates of Factor IXa-Compound D complex

| | | | | | | |
|---|---|---|---|---|---|---|
| 145 | F | O | −17.8 | −24.3 | −33.3 | 71 | A |
| 145 | F | CB | −20.6 | −25.0 | −34.8 | 64 | A |
| 145 | F | CG | −22.0 | −25.5 | −34.9 | 64 | A |
| 145 | F | CD1 | −23.1 | −24.9 | −34.3 | 67 | A |
| 145 | F | CD2 | −22.2 | −26.7 | −35.5 | 66 | A |
| 145 | F | CE1 | −24.4 | −25.4 | −34.3 | 67 | A |
| 145 | F | CE2 | −23.5 | −27.3 | −35.6 | 68 | A |
| 145 | F | CZ | −24.6 | −26.7 | −35.0 | 66 | A |
| 147 | H | N | −17.4 | −25.9 | −34.9 | 72 | A |
| 147 | H | CA | −15.9 | −25.5 | −35.0 | 74 | A |
| 147 | H | C | −15.6 | −24.0 | −34.8 | 81 | A |
| 147 | H | O | −14.7 | −23.7 | −33.9 | 81 | A |
| 147 | H | CB | −15.3 | −26.1 | −36.3 | 76 | A |
| 147 | H | CG | −13.9 | −25.5 | −36.5 | 80 | A |
| 147 | H | ND1 | −13.1 | −25.2 | −35.5 | 83 | A |
| 147 | H | CD2 | −13.2 | −25.3 | −37.7 | 83 | A |
| 147 | H | CE1 | −11.9 | −24.7 | −36.0 | 83 | A |
| 147 | H | NE2 | −12.0 | −24.8 | −37.3 | 83 | A |
| 148 | K | N | −16.2 | −23.1 | −35.5 | 77 | A |
| 148 | K | CA | −16.0 | −21.7 | −35.4 | 77 | A |
| 148 | K | C | −17.3 | −21.0 | −35.0 | 78 | A |
| 148 | K | O | −17.4 | −19.8 | −35.3 | 77 | A |
| 148 | K | CB | −15.3 | −21.1 | −36.6 | 79 | A |
| 148 | K | CG | −13.8 | −21.0 | −36.6 | 86 | A |
| 148 | K | CD | −13.2 | −21.2 | −38.0 | 0 | A |
| 148 | K | CE | −13.1 | −19.8 | −38.7 | 0 | A |
| 148 | K | NZ | −11.7 | −19.3 | −38.8 | 0 | A |
| 149 | G | N | −18.2 | −21.7 | −34.4 | 72 | A |
| 149 | G | CA | −19.5 | −21.2 | −34.0 | 71 | A |
| 149 | G | C | −19.8 | −20.8 | −32.6 | 73 | A |
| 149 | G | O | −18.9 | −20.5 | −31.8 | 72 | A |
| 150 | R | N | −21.1 | −20.8 | −32.3 | 69 | A |
| 150 | R | CA | −21.6 | −20.4 | −31.0 | 68 | A |
| 150 | R | C | −21.3 | −21.4 | −29.8 | 65 | A |
| 150 | R | O | −21.3 | −22.6 | −30.0 | 63 | A |
| 150 | R | CB | −23.1 | −20.2 | −31.1 | 70 | A |
| 150 | R | CG | −23.9 | −21.5 | −30.7 | 85 | A |
| 150 | R | CD | −25.1 | −21.8 | −31.7 | 95 | A |
| 150 | R | NE | −26.1 | −22.6 | −31.0 | 0 | A |
| 150 | R | CZ | −26.8 | −23.6 | −31.6 | 0 | A |
| 150 | R | NH1 | −26.5 | −23.9 | −32.9 | 0 | A |
| 150 | R | NH2 | −27.7 | −24.3 | −30.9 | 0 | A |
| 151 | S | N | −21.2 | −20.8 | −28.7 | 60 | A |
| 151 | S | CA | −21.0 | −21.6 | −27.4 | 59 | A |
| 151 | S | C | −22.3 | −22.0 | −26.9 | 63 | A |
| 151 | S | O | −23.3 | −21.8 | −27.6 | 66 | A |
| 151 | S | CB | −20.3 | −20.7 | −26.4 | 63 | A |
| 151 | S | OG | −19.0 | −20.4 | −26.9 | 75 | A |
| 152 | A | N | −22.4 | −22.8 | −25.8 | 55 | A |
| 152 | A | CA | −23.6 | −23.3 | −25.4 | 53 | A |
| 152 | A | C | −24.2 | −22.6 | −24.2 | 59 | A |
| 152 | A | O | −23.5 | −22.0 | −23.4 | 62 | A |
| 152 | A | CB | −23.8 | −24.8 | −25.1 | 53 | A |
| 153 | L | N | −25.5 | −22.7 | −24.1 | 55 | A |
| 153 | L | CA | −26.2 | −22.1 | −22.9 | 54 | A |
| 153 | L | C | −26.5 | −23.3 | −21.9 | 55 | A |
| 153 | L | O | −26.2 | −23.1 | −20.8 | 56 | A |
| 153 | L | CB | −27.5 | −21.4 | −23.4 | 55 | A |
| 153 | L | CG | −27.2 | −20.2 | −24.2 | 60 | A |
| 153 | L | CD1 | −28.5 | −19.5 | −24.7 | 60 | A |
| 153 | L | CD2 | −26.2 | −19.2 | −23.6 | 62 | A |
| 154 | V | N | −26.9 | −24.4 | −22.4 | 48 | A |
| 154 | V | CA | −27.1 | −25.6 | −21.6 | 46 | A |
| 154 | V | C | −25.8 | −26.5 | −21.6 | 49 | A |
| 154 | V | O | −25.2 | −26.7 | −22.7 | 47 | A |
| 154 | V | CB | −28.3 | −26.4 | −22.1 | 48 | A |
| 154 | V | CG1 | −28.5 | −27.7 | −21.2 | 47 | A |
| 154 | V | CG2 | −29.6 | −25.6 | −22.0 | 48 | A |
| 155 | L | N | −25.5 | −27.0 | −20.5 | 42 | A |
| 155 | L | CA | −24.3 | −27.8 | −20.4 | 39 | A |
| 155 | L | C | −24.4 | −29.0 | −21.4 | 42 | A |
| 155 | L | O | −25.5 | −29.6 | −21.5 | 43 | A |
| 155 | L | CB | −24.1 | −28.4 | −19.0 | 38 | A |
| 155 | L | CG | −23.0 | −29.4 | −18.8 | 39 | A |
| 155 | L | CD1 | −21.7 | −28.7 | −19.2 | 38 | A |
| 155 | L | CD2 | −23.0 | −29.8 | −17.3 | 38 | A |
| 156 | Q | N | −23.4 | −29.2 | −22.2 | 39 | A |
| 156 | Q | CA | −23.4 | −30.3 | −23.2 | 39 | A |
| 156 | Q | C | −22.5 | −31.5 | −22.7 | 41 | A |
| 156 | Q | O | −21.5 | −31.4 | −22.0 | 38 | A |
| 156 | Q | CB | −22.7 | −29.8 | −24.5 | 40 | A |
| 156 | Q | CG | −23.4 | −28.7 | −25.2 | 45 | A |
| 156 | Q | CD | −24.8 | −29.1 | −25.6 | 58 | A |
| 156 | Q | OE1 | −25.8 | −28.8 | −25.0 | 58 | A |
| 156 | Q | NE2 | −24.9 | −29.9 | −26.7 | 40 | A |
| 157 | Y | N | −22.9 | −32.7 | −23.1 | 41 | A |
| 157 | Y | CA | −22.1 | −33.9 | −22.8 | 41 | A |
| 157 | Y | C | −21.9 | −34.8 | −24.0 | 44 | A |
| 157 | Y | O | −22.7 | −34.7 | −24.9 | 43 | A |
| 157 | Y | CB | −22.6 | −34.7 | −21.6 | 41 | A |
| 157 | Y | CG | −23.8 | −35.5 | −21.9 | 42 | A |
| 157 | Y | CD1 | −23.7 | −36.9 | −22.0 | 44 | A |
| 157 | Y | CD2 | −25.1 | −35.0 | −21.9 | 42 | A |
| 157 | Y | CE1 | −24.8 | −37.7 | −22.2 | 43 | A |
| 157 | Y | CE2 | −26.2 | −35.7 | −22.1 | 43 | A |
| 157 | Y | CZ | −26.1 | −37.1 | −22.3 | 52 | A |
| 157 | Y | OH | −27.2 | −37.9 | −22.5 | 54 | A |
| 158 | L | N | −20.9 | −35.6 | −24.0 | 40 | A |
| 158 | L | CA | −20.6 | −36.5 | −25.1 | 38 | A |
| 158 | L | C | −19.7 | −37.6 | −24.6 | 40 | A |
| 158 | L | O | −18.7 | −37.4 | −23.9 | 41 | A |
| 158 | L | CB | −19.8 | −35.7 | −26.2 | 37 | A |
| 158 | L | CG | −19.2 | −36.4 | −27.4 | 38 | A |
| 158 | L | CD1 | −20.2 | −36.9 | −28.3 | 37 | A |
| 158 | L | CD2 | −18.3 | −35.3 | −27.2 | 35 | A |
| 159 | R | N | −20.1 | −38.8 | −25.1 | 37 | A |
| 159 | R | CA | −19.2 | −40.0 | −24.8 | 37 | A |
| 159 | R | C | −18.2 | −40.1 | −26.0 | 39 | A |
| 159 | R | O | −18.6 | −40.1 | −27.2 | 38 | A |
| 159 | R | CB | −20.1 | −41.3 | −24.8 | 37 | A |
| 159 | R | CG | −19.4 | −42.5 | −24.2 | 44 | A |
| 159 | R | CD | −20.0 | −43.8 | −24.7 | 61 | A |
| 159 | R | NE | −20.0 | −43.9 | −26.1 | 78 | A |
| 159 | R | CZ | −19.0 | −44.3 | −26.9 | 82 | A |
| 159 | R | NH1 | −17.8 | −44.7 | −26.3 | 57 | A |
| 159 | R | NH2 | −19.1 | −44.3 | −28.2 | 61 | A |
| 160 | V | N | −16.9 | −40.2 | −25.7 | 35 | A |
| 160 | V | CA | −15.9 | −40.3 | −26.7 | 33 | A |
| 160 | V | C | −15.0 | −41.5 | −26.4 | 37 | A |
| 160 | V | O | −14.6 | −41.8 | −25.3 | 36 | A |
| 160 | V | CB | −15.0 | −39.0 | −26.8 | 37 | A |
| 160 | V | CG1 | −15.7 | −37.8 | −27.3 | 36 | A |
| 160 | V | CG2 | −14.3 | −38.7 | −25.4 | 36 | A |
| 161 | P | N | −14.7 | −42.2 | −27.5 | 34 | A |
| 161 | P | CA | −13.8 | −43.4 | −27.4 | 32 | A |
| 161 | P | C | −12.4 | −43.1 | −27.4 | 35 | A |
| 161 | P | O | −11.9 | −42.1 | −27.9 | 35 | A |
| 161 | P | CB | −14.2 | −44.2 | −28.6 | 33 | A |
| 161 | P | CG | −14.7 | −43.3 | −29.6 | 39 | A |
| 161 | P | CD | −15.3 | −42.2 | −28.8 | 36 | A |
| 162 | L | N | −11.6 | −43.9 | −26.6 | 32 | A |
| 162 | L | CA | −10.2 | −43.7 | −26.6 | 32 | A |
| 162 | L | C | −9.6 | −44.2 | −28.0 | 37 | A |
| 162 | L | O | −10.0 | −45.2 | −28.6 | 36 | A |
| 162 | L | CB | −9.6 | −44.6 | −25.5 | 31 | A |
| 162 | L | CG | −8.1 | −44.5 | −25.1 | 33 | A |
| 162 | L | CD1 | −7.8 | −43.0 | −24.6 | 32 | A |
| 162 | L | CD2 | −7.8 | −45.5 | −24.1 | 31 | A |
| 163 | V | N | −8.6 | −43.4 | −28.5 | 34 | A |
| 163 | V | CA | −7.9 | −43.7 | −29.7 | 32 | A |
| 163 | V | C | −6.5 | −44.2 | −29.4 | 36 | A |
| 163 | V | O | −5.8 | −43.7 | −28.6 | 35 | A |
| 163 | V | CB | −7.9 | −42.4 | −30.6 | 33 | A |
| 163 | V | CG1 | −7.0 | −42.5 | −31.8 | 31 | A |
| 163 | V | CG2 | −9.3 | −42.1 | −31.1 | 33 | A |
| 164 | D | N | −6.1 | −45.3 | −30.1 | 35 | A |
| 164 | D | CA | −4.7 | −45.8 | −29.8 | 36 | A |
| 164 | D | C | −3.7 | −44.8 | −30.2 | 42 | A |
| 164 | D | O | −3.9 | −44.0 | −31.0 | 42 | A |
| 164 | D | CB | −4.4 | −47.1 | −30.7 | 41 | A |
| 164 | D | CG | −4.7 | −46.9 | −32.1 | 61 | A |
| 164 | D | OD1 | −3.8 | −46.9 | −33.0 | 60 | A |
| 164 | D | OD2 | −5.9 | −47.0 | −32.5 | 74 | A |
| 165 | R | N | −2.6 | −44.9 | −29.5 | 40 | A |
| 165 | R | CA | −1.5 | −43.9 | −29.6 | 40 | A |
| 165 | R | C | −1.0 | −43.8 | −31.1 | 46 | A |

TABLE 6-continued

Coordinates of Factor IXa-Compound D complex

| | | | | | | |
|---|---|---|---|---|---|---|
| 165 | R | O | −0.9 | −42.7 | −31.6 | 48 | A |
| 165 | R | CB | −0.4 | −44.2 | −28.7 | 38 | A |
| 165 | R | CG | 0.7 | −43.2 | −28.8 | 44 | A |
| 165 | R | CD | 1.8 | −43.4 | −27.7 | 37 | A |
| 165 | R | NE | 2.2 | −42.0 | −27.4 | 42 | A |
| 165 | R | CZ | 3.4 | −41.5 | −27.7 | 61 | A |
| 165 | R | NH1 | 4.3 | −42.2 | −28.3 | 77 | A |
| 165 | R | NH2 | 3.6 | −40.2 | −27.4 | 44 | A |
| 166 | A | N | −0.8 | −45.0 | −31.7 | 42 | A |
| 166 | A | CA | −0.3 | −45.0 | −33.1 | 40 | A |
| 166 | A | C | −1.2 | −44.2 | −34.1 | 44 | A |
| 166 | A | O | −0.7 | −43.4 | −34.9 | 46 | A |
| 166 | A | CB | −0.2 | −46.5 | −33.5 | 40 | A |
| 167 | T | N | −2.5 | −44.4 | −34.0 | 39 | A |
| 167 | T | CA | −3.5 | −43.7 | −34.8 | 40 | A |
| 167 | T | C | −3.5 | −42.2 | −34.5 | 51 | A |
| 167 | T | O | −3.6 | −41.3 | −35.4 | 54 | A |
| 167 | T | CB | −4.9 | −44.2 | −34.5 | 41 | A |
| 167 | T | OG1 | −5.0 | −45.6 | −35.0 | 38 | A |
| 167 | T | CG2 | −6.0 | −43.4 | −35.2 | 34 | A |
| 168 | C | N | −3.3 | −41.9 | −33.2 | 47 | A |
| 168 | C | CA | −3.3 | −40.5 | −32.7 | 49 | A |
| 168 | C | C | −2.0 | −39.8 | −33.2 | 46 | A |
| 168 | C | O | −2.0 | −38.7 | −33.7 | 41 | A |
| 168 | C | CB | −3.3 | −40.6 | −31.2 | 51 | A |
| 168 | C | SG | −3.1 | −39.1 | −30.2 | 57 | A |
| 169 | L | N | −0.9 | −40.5 | −33.1 | 42 | A |
| 169 | L | CA | 0.4 | −40.0 | −33.6 | 41 | A |
| 169 | L | C | 0.3 | −39.6 | −35.1 | 45 | A |
| 169 | L | O | 0.8 | −38.6 | −35.5 | 45 | A |
| 169 | L | CB | 1.5 | −41.0 | −33.3 | 41 | A |
| 169 | L | CG | 2.4 | −40.6 | −32.1 | 45 | A |
| 169 | L | CD1 | 1.7 | −39.9 | −31.0 | 43 | A |
| 169 | L | CD2 | 3.3 | −41.7 | −31.6 | 45 | A |
| 170 | R | N | −0.3 | −40.5 | −35.9 | 43 | A |
| 170 | R | CA | −0.4 | −40.3 | −37.3 | 43 | A |
| 170 | R | C | −1.3 | −39.1 | −37.6 | 46 | A |
| 170 | R | O | −1.5 | −38.7 | −38.8 | 48 | A |
| 170 | R | CB | −1.0 | −41.5 | −38.1 | 38 | A |
| 170 | R | CG | −0.1 | −42.7 | −38.1 | 47 | A |
| 170 | R | CD | −0.6 | −43.9 | −39.0 | 52 | A |
| 170 | R | NE | −1.9 | −44.4 | −38.7 | 54 | A |
| 170 | R | CZ | −2.1 | −45.5 | −37.9 | 66 | A |
| 170 | R | NH1 | −1.1 | −46.1 | −37.4 | 36 | A |
| 170 | R | NH2 | −3.3 | −45.9 | −37.7 | 42 | A |
| 171 | S | N | −2.1 | −38.6 | −36.6 | 41 | A |
| 171 | S | CA | −3.1 | −37.6 | −36.9 | 40 | A |
| 171 | S | C | −2.6 | −36.2 | −36.9 | 43 | A |
| 171 | S | O | −3.4 | −35.2 | −37.2 | 42 | A |
| 171 | S | CB | −4.3 | −37.8 | −36.0 | 39 | A |
| 171 | S | OG | −4.1 | −37.3 | −34.7 | 37 | A |
| 172 | T | N | −1.4 | −36.0 | −36.5 | 40 | A |
| 172 | T | CA | −1.0 | −34.6 | −36.2 | 39 | A |
| 172 | T | C | 0.5 | −34.5 | −36.4 | 46 | A |
| 172 | T | O | 1.3 | −35.5 | −36.4 | 45 | A |
| 172 | T | CB | −1.4 | −34.2 | −34.8 | 45 | A |
| 172 | T | OG1 | −1.1 | −32.8 | −34.6 | 46 | A |
| 172 | T | CG2 | −0.7 | −35.0 | −33.7 | 40 | A |
| 173 | K | N | 1.0 | −33.2 | −36.7 | 46 | A |
| 173 | K | CA | 2.4 | −32.9 | −36.9 | 46 | A |
| 173 | K | C | 2.9 | −32.5 | −35.5 | 47 | A |
| 173 | K | O | 4.1 | −32.4 | −35.3 | 46 | A |
| 173 | K | CB | 2.5 | −31.8 | −37.9 | 49 | A |
| 173 | K | CG | 2.0 | −30.4 | −37.4 | 71 | A |
| 173 | K | CD | 3.0 | −29.3 | −37.8 | 86 | A |
| 173 | K | CE | 2.5 | −27.9 | −37.3 | 91 | A |
| 173 | K | NZ | 1.1 | −27.7 | −37.6 | 0 | A |
| 174 | F | N | 1.9 | −32.2 | −34.6 | 44 | A |
| 174 | F | CA | 2.2 | −31.8 | −33.3 | 41 | A |
| 174 | F | C | 2.7 | −33.0 | −32.5 | 43 | A |
| 174 | F | O | 2.5 | −34.1 | −32.9 | 41 | A |
| 174 | F | CB | 1.0 | −31.1 | −32.6 | 42 | A |
| 174 | F | CG | 0.7 | −29.8 | −33.3 | 44 | A |
| 174 | F | CD1 | 1.6 | −28.7 | −33.3 | 50 | A |
| 174 | F | CD2 | −0.5 | −29.7 | −34.0 | 46 | A |
| 174 | F | CE1 | 1.3 | −27.5 | −33.9 | 50 | A |
| 174 | F | CE2 | −0.8 | −28.5 | −34.7 | 51 | A |
| 174 | F | CZ | 0.1 | −27.4 | −34.6 | 49 | A |
| 175 | T | N | 3.3 | −32.7 | −31.3 | 42 | A |
| 175 | T | CA | 3.8 | −33.7 | −30.4 | 41 | A |
| 175 | T | C | 2.8 | −34.1 | −29.3 | 41 | A |
| 175 | T | O | 2.3 | −33.3 | −28.6 | 40 | A |
| 175 | T | CB | 5.2 | −33.3 | −29.9 | 48 | A |
| 175 | T | OG1 | 6.0 | −33.0 | −31.0 | 53 | A |
| 175 | T | CG2 | 5.8 | −34.3 | −29.0 | 42 | A |
| 176 | I | N | 2.5 | −35.4 | −29.3 | 37 | A |
| 176 | I | CA | 1.6 | −36.0 | −28.3 | 35 | A |
| 176 | I | C | 2.5 | −36.7 | −27.4 | 39 | A |
| 176 | I | O | 3.2 | −37.7 | −27.8 | 36 | A |
| 176 | I | CB | 0.5 | −36.9 | −29.0 | 36 | A |
| 176 | I | CG1 | −0.2 | −36.2 | −30.1 | 36 | A |
| 176 | I | CG2 | −0.6 | −37.3 | −26.0 | 34 | A |
| 176 | I | CD1 | −0.6 | −34.7 | −29.7 | 42 | A |
| 177 | Y | N | 2.7 | −36.3 | −26.2 | 37 | A |
| 177 | Y | CA | 3.6 | −36.9 | −25.2 | 35 | A |
| 177 | Y | C | 2.8 | −38.0 | −24.6 | 37 | A |
| 177 | Y | O | 1.6 | −38.1 | −24.7 | 37 | A |
| 177 | Y | CB | 4.0 | −35.9 | −24.2 | 35 | A |
| 177 | Y | CG | 4.9 | −34.9 | −24.8 | 35 | A |
| 177 | Y | CD1 | 4.4 | −33.6 | −25.0 | 35 | A |
| 177 | Y | CD2 | 6.2 | −35.1 | −25.2 | 35 | A |
| 177 | Y | CE1 | 5.2 | −32.6 | −25.5 | 37 | A |
| 177 | Y | CE2 | 7.0 | −34.2 | −25.7 | 36 | A |
| 177 | Y | CZ | 6.5 | −32.9 | −25.9 | 50 | A |
| 177 | Y | OH | 7.3 | −31.9 | −26.4 | 58 | A |
| 178 | N | N | 3.5 | −38.9 | −23.9 | 35 | A |
| 178 | N | CA | 2.9 | −40.1 | −23.3 | 34 | A |
| 178 | N | C | 1.8 | −40.0 | −22.3 | 34 | A |
| 178 | N | O | 1.0 | −40.9 | −22.1 | 30 | A |
| 178 | N | CB | 4.0 | −41.1 | −22.9 | 36 | A |
| 178 | N | CG | 4.8 | −41.6 | −24.0 | 48 | A |
| 178 | N | OD1 | 4.4 | −42.2 | −24.9 | 43 | A |
| 176 | N | ND2 | 6.1 | −41.1 | −24.1 | 40 | A |
| 179 | N | N | 1.9 | −38.8 | −21.6 | 31 | A |
| 179 | N | CA | 0.8 | −38.6 | −20.6 | 32 | A |
| 179 | N | C | −0.3 | −37.6 | −21.1 | 36 | A |
| 179 | N | O | −0.9 | −36.9 | −20.3 | 34 | A |
| 179 | N | CB | 1.4 | −38.1 | −19.2 | 36 | A |
| 179 | N | CG | 2.1 | −39.3 | −18.5 | 40 | A |
| 179 | N | OD1 | 1.5 | −40.3 | −18.3 | 39 | A |
| 179 | N | ND2 | 3.4 | −39.1 | −18.2 | 33 | A |
| 180 | M | N | −0.5 | −37.7 | −22.4 | 34 | A |
| 180 | M | CA | −1.6 | −37.0 | −23.1 | 34 | A |
| 180 | M | C | −2.2 | −38.3 | −23.8 | 37 | A |
| 180 | M | O | −1.6 | −39.3 | −24.0 | 37 | A |
| 180 | M | CB | −1.1 | −36.1 | −24.1 | 37 | A |
| 180 | M | CG | −0.6 | −34.7 | −23.6 | 42 | A |
| 180 | M | SD | 0.1 | −33.9 | −25.0 | 49 | A |
| 180 | M | CE | 0.6 | −32.4 | −24.3 | 45 | A |
| 181 | F | N | −3.5 | −38.2 | −24.1 | 33 | A |
| 181 | F | CA | −4.2 | −39.2 | −24.9 | 30 | A |
| 181 | F | C | −5.1 | −38.5 | −25.8 | 36 | A |
| 181 | F | O | −5.4 | −37.3 | −25.7 | 34 | A |
| 181 | F | CB | −4.9 | −40.2 | −23.9 | 30 | A |
| 181 | F | CG | −6.1 | −39.6 | −23.2 | 30 | A |
| 181 | F | CD1 | −7.4 | −39.6 | −23.7 | 31 | A |
| 181 | F | CD2 | −6.0 | −39.1 | −21.9 | 30 | A |
| 181 | F | CE1 | −8.6 | −39.2 | −23.0 | 31 | A |
| 181 | F | CE2 | −7.1 | −38.7 | −21.1 | 32 | A |
| 181 | F | CZ | −6.4 | −38.7 | −21.7 | 30 | A |
| 182 | C | N | −5.6 | −39.3 | −26.8 | 39 | A |
| 182 | C | CA | −6.4 | −38.9 | −27.9 | 43 | A |
| 182 | C | C | −7.8 | −39.5 | −27.6 | 41 | A |
| 182 | C | O | −7.8 | −40.7 | −27.2 | 41 | A |
| 182 | C | CB | −5.9 | −39.5 | −29.2 | 49 | A |
| 182 | C | SG | −5.0 | −38.3 | −30.1 | 56 | A |
| 183 | A | N | −8.9 | −38.7 | −27.9 | 34 | A |
| 183 | A | CA | −10.2 | −39.4 | −27.8 | 32 | A |
| 183 | A | C | −11.0 | −38.7 | −28.8 | 37 | A |
| 183 | A | O | −10.7 | −37.6 | −29.2 | 35 | A |
| 183 | A | CB | −10.7 | −39.4 | −26.3 | 32 | A |
| 184 | G | N | −12.1 | −39.4 | −29.3 | 38 | A |
| 184 | G | CA | −12.9 | −38.9 | −30.4 | 38 | A |
| 184 | G | C | −13.3 | −40.0 | −31.4 | 43 | A |
| 184 | G | O | −12.9 | −41.1 | −31.3 | 42 | A |
| 184A | F | N | −14.0 | −39.5 | −32.5 | 38 | A |

TABLE 6-continued

Coordinates of Factor IXa-Compound D complex

| | | | | | | |
|---|---|---|---|---|---|---|
| 184A | F | CA | −14.4 | −40.4 | −33.6 | 36 A |
| 184A | F | C | −13.5 | −40.3 | −34.9 | 42 A |
| 184A | F | O | −13.1 | −39.2 | −35.3 | 42 A |
| 184A | F | CB | −15.8 | −40.1 | −33.9 | 37 A |
| 184A | F | CG | −16.8 | −40.4 | −32.8 | 37 A |
| 184A | F | CD1 | −17.1 | −39.4 | −31.9 | 39 A |
| 184A | F | CD2 | −17.2 | −41.7 | −32.5 | 36 A |
| 184A | F | CE1 | −17.9 | −39.7 | −30.8 | 40 A |
| 184A | F | CE2 | −18.0 | −42.0 | −31.5 | 38 A |
| 184A | F | CZ | −18.3 | −41.0 | −30.6 | 37 A |
| 185 | H | N | −13.4 | −41.4 | −35.6 | 39 A |
| 185 | H | CA | −12.7 | −41.6 | −36.9 | 36 A |
| 185 | H | C | −13.2 | −40.6 | −37.9 | 41 A |
| 185 | H | O | −12.4 | −40.0 | −38.6 | 42 A |
| 185 | H | CB | −12.8 | −43.0 | −37.4 | 34 A |
| 185 | H | CG | −12.0 | −43.3 | −38.6 | 35 A |
| 185 | H | ND1 | −12.3 | −42.8 | −39.9 | 36 A |
| 185 | H | CD2 | −10.9 | −44.1 | −38.8 | 32 A |
| 185 | H | CE1 | −11.4 | −43.2 | −40.7 | 33 A |
| 185 | H | NE2 | −10.6 | −44.0 | −40.1 | 32 A |
| 186 | E | N | −14.5 | −40.4 | −38.0 | 39 A |
| 186 | E | CA | −15.1 | −39.5 | −38.9 | 39 A |
| 186 | E | C | −15.4 | −38.1 | −38.4 | 45 A |
| 186 | E | O | −16.1 | −37.3 | −39.1 | 45 A |
| 186 | E | CB | −16.3 | −40.2 | −39.5 | 40 A |
| 186 | E | CG | −16.1 | −41.5 | −40.3 | 41 A |
| 186 | E | CD | −15.3 | −41.2 | −41.5 | 55 A |
| 186 | E | OE1 | −14.0 | −41.3 | −41.5 | 42 A |
| 186 | E | OE2 | −15.9 | −40.8 | −42.6 | 53 A |
| 187 | G | N | −14.9 | −37.7 | −37.3 | 41 A |
| 187 | G | CA | −15.2 | −36.4 | −36.7 | 41 A |
| 187 | G | C | −16.7 | −36.3 | −36.4 | 45 A |
| 187 | G | O | −17.4 | −37.3 | −36.0 | 45 A |
| 188 | G | N | −17.2 | −35.1 | −36.4 | 41 A |
| 188 | G | CA | −18.6 | −34.8 | −36.1 | 40 A |
| 188 | G | C | −18.9 | −34.5 | −34.7 | 45 A |
| 188 | G | O | −19.0 | −33.8 | −34.4 | 46 A |
| 188A | R | N | −18.3 | −35.2 | −33.8 | 41 A |
| 188A | R | CA | −18.6 | −35.1 | −32.3 | 41 A |
| 188A | R | C | −17.2 | −34.9 | −31.7 | 45 A |
| 188A | R | O | −16.3 | −35.7 | −32.0 | 45 A |
| 188A | R | CB | −19.2 | −36.4 | −31.8 | 41 A |
| 188A | R | CG | −20.4 | −36.9 | −32.6 | 47 A |
| 188A | R | CD | −21.3 | −37.9 | −31.8 | 55 A |
| 188A | R | NE | −22.2 | −38.6 | −32.6 | 63 A |
| 188A | R | CZ | −22.5 | −39.9 | −32.5 | 79 A |
| 188A | R | NH1 | −22.0 | −40.7 | −31.5 | 47 A |
| 188A | R | NH2 | −23.3 | −40.5 | −33.4 | 81 A |
| 189 | D | N | −17.1 | −33.9 | −30.8 | 42 A |
| 189 | D | CA | −15.8 | −33.6 | −30.2 | 41 A |
| 189 | D | C | −15.9 | −32.6 | −29.1 | 45 A |
| 189 | D | O | −16.9 | −31.9 | −28.9 | 44 A |
| 189 | D | CB | −14.9 | −33.1 | −31.3 | 42 A |
| 189 | D | CG | −13.4 | −33.1 | −31.0 | 46 A |
| 189 | D | OD1 | −13.0 | −33.6 | −29.9 | 41 A |
| 189 | D | OD2 | −12.6 | −32.6 | −31.8 | 48 A |
| 190 | S | N | −14.7 | −32.3 | −28.5 | 43 A |
| 190 | S | CA | −14.5 | −31.2 | −27.5 | 42 A |
| 190 | S | C | −14.2 | −30.0 | −28.3 | 46 A |
| 190 | S | O | −13.9 | −30.1 | −29.5 | 43 A |
| 190 | S | CB | −13.3 | −31.6 | −26.7 | 43 A |
| 190 | S | OG | −13.8 | −31.9 | −25.4 | 57 A |
| 191 | C | N | −14.2 | −28.8 | −27.7 | 46 A |
| 191 | C | CA | −14.0 | −27.6 | −28.4 | 48 A |
| 191 | C | C | −13.5 | −26.5 | −27.5 | 49 A |
| 191 | C | O | −13.6 | −26.7 | −26.2 | 47 A |
| 191 | C | CB | −15.2 | −27.2 | −29.2 | 52 A |
| 191 | C | SG | −15.0 | −26.2 | −30.8 | 59 A |
| 192 | Q | N | −13.1 | −25.4 | −28.0 | 46 A |
| 192 | Q | CA | −12.8 | −24.2 | −27.2 | 46 A |
| 192 | Q | C | −13.9 | −23.8 | −26.3 | 44 A |
| 192 | Q | O | −15.0 | −23.7 | −26.7 | 42 A |
| 192 | Q | CB | −12.4 | −23.0 | −28.1 | 47 A |
| 192 | Q | CG | −11.6 | −22.0 | −27.5 | 57 A |
| 192 | Q | CD | −11.6 | −20.7 | −28.3 | 78 A |
| 192 | Q | OE1 | −12.2 | −20.6 | −29.3 | 67 A |
| 192 | Q | NE2 | −11.0 | −19.6 | −27.7 | 89 A |
| 193 | G | N | −13.6 | −23.5 | −25.0 | 38 A |
| 193 | G | CA | −14.5 | −23.3 | −24.0 | 37 A |
| 193 | G | C | −14.7 | −24.5 | −23.1 | 43 A |
| 193 | G | O | −15.2 | −24.3 | −21.9 | 44 A |
| 194 | D | N | −14.3 | −25.7 | −23.6 | 38 A |
| 194 | D | CA | −14.4 | −26.9 | −22.8 | 37 A |
| 194 | D | C | −13.1 | −27.3 | −22.1 | 38 A |
| 194 | D | O | −13.2 | −28.0 | −21.1 | 38 A |
| 194 | D | CB | −14.8 | −28.1 | −23.6 | 37 A |
| 194 | D | CG | −16.1 | −27.9 | −24.4 | 41 A |
| 194 | D | OD1 | −17.0 | −27.3 | −23.8 | 42 A |
| 194 | D | OD2 | −16.2 | −28.3 | −25.6 | 42 A |
| 195 | S | N | −12.0 | −26.8 | −22.6 | 33 A |
| 195 | S | CA | −10.7 | −27.1 | −22.0 | 33 A |
| 195 | S | C | −10.7 | −26.8 | −20.5 | 35 A |
| 195 | S | O | −11.4 | −25.9 | −20.0 | 34 A |
| 195 | S | CB | −9.6 | −26.3 | −22.6 | 36 A |
| 195 | S | OG | −9.5 | −26.7 | −23.9 | 46 A |
| 196 | G | N | −9.9 | −27.7 | −19.7 | 30 A |
| 196 | G | CA | −9.9 | −27.6 | −18.3 | 30 A |
| 196 | G | C | −11.1 | −28.4 | −17.7 | 35 A |
| 196 | G | O | −11.0 | −28.8 | −16.5 | 37 A |
| 197 | G | N | −12.1 | −28.8 | −18.5 | 32 A |
| 197 | G | CA | −13.2 | −29.6 | −18.0 | 33 A |
| 197 | G | C | −12.9 | −31.1 | −17.9 | 40 A |
| 197 | G | O | −11.8 | −31.5 | −18.2 | 39 A |
| 198 | P | N | −13.8 | −31.8 | −17.4 | 36 A |
| 198 | P | CA | −13.5 | −33.2 | −17.1 | 35 A |
| 198 | P | C | −13.7 | −34.3 | −18.3 | 37 A |
| 198 | P | O | −14.6 | −34.2 | −19.1 | 34 A |
| 198 | P | CB | −14.6 | −33.6 | −16.1 | 37 A |
| 198 | P | CG | −15.8 | −32.8 | −16.5 | 41 A |
| 198 | P | CD | −15.2 | −31.5 | −16.9 | 37 A |
| 199 | H | N | −12.9 | −35.3 | −18.2 | 35 A |
| 199 | H | CA | −13.1 | −36.5 | −19.0 | 34 A |
| 199 | H | C | −13.3 | −37.6 | −17.9 | 34 A |
| 199 | H | O | −12.4 | −37.8 | −17.1 | 31 A |
| 199 | H | CB | −11.9 | −36.8 | −19.9 | 34 A |
| 199 | H | CG | −12.0 | −38.1 | −20.6 | 36 A |
| 199 | H | ND1 | −11.6 | −39.3 | −20.0 | 36 A |
| 199 | H | CD2 | −12.4 | −38.4 | −21.8 | 37 A |
| 199 | H | CE1 | −11.7 | −40.3 | −20.9 | 36 A |
| 199 | H | NE2 | −12.2 | −39.8 | −22.0 | 37 A |
| 200 | V | N | −14.4 | −38.2 | −17.8 | 32 A |
| 200 | V | CA | −14.7 | −39.1 | −16.7 | 33 A |
| 200 | V | C | −15.1 | −40.5 | −17.2 | 37 A |
| 200 | V | O | −15.7 | −40.7 | −18.2 | 36 A |
| 200 | V | CB | −15.7 | −38.6 | −15.7 | 37 A |
| 200 | V | CG1 | −15.5 | −37.2 | −15.3 | 35 A |
| 200 | V | CG2 | −17.2 | −38.8 | −16.2 | 37 A |
| 201 | T | N | −14.7 | −41.5 | −16.4 | 34 A |
| 201 | T | CA | −15.0 | −42.9 | −16.7 | 34 A |
| 201 | T | C | −16.0 | −43.5 | −15.6 | 39 A |
| 201 | T | O | −15.7 | −43.4 | −14.4 | 37 A |
| 201 | T | CB | −13.7 | −43.7 | −16.8 | 37 A |
| 201 | T | OG1 | −12.8 | −43.1 | −17.8 | 32 A |
| 201 | T | CG2 | −13.9 | −45.2 | −17.0 | 26 A |
| 202 | E | N | −17.2 | −44.0 | −16.0 | 38 A |
| 202 | E | CA | −18.1 | −44.5 | −15.1 | 39 A |
| 202 | E | C | −17.7 | −46.0 | −14.7 | 44 A |
| 202 | E | O | −17.7 | −46.8 | −15.6 | 45 A |
| 202 | E | CB | −19.5 | −44.5 | −15.6 | 40 A |
| 202 | E | CG | −20.1 | −43.1 | −15.9 | 60 A |
| 202 | E | CD | −21.5 | −43.2 | −16.6 | 81 A |
| 202 | E | OE1 | −21.8 | −44.3 | −17.1 | 62 A |
| 202 | E | OE2 | −22.2 | −42.2 | −16.6 | 76 A |
| 203 | V | N | −17.4 | −46.2 | −13.5 | 38 A |
| 203 | V | CA | −17.0 | −47.5 | −13.0 | 37 A |
| 203 | V | C | −18.2 | −48.1 | −12.1 | 44 A |
| 203 | V | O | −18.2 | −47.7 | −10.9 | 44 A |
| 203 | V | CB | −15.7 | −47.4 | −12.2 | 40 A |
| 203 | V | CG1 | −15.2 | −48.7 | −11.7 | 40 A |
| 203 | V | CG2 | −14.7 | −46.6 | −13.0 | 40 A |
| 204 | E | N | −19.0 | −48.9 | −12.6 | 45 A |
| 204 | E | CA | −20.1 | −49.4 | −11.8 | 46 A |
| 204 | E | C | −21.0 | −48.3 | −11.2 | 51 A |
| 204 | E | O | −21.3 | −48.4 | −10.0 | 50 A |
| 204 | E | CB | −19.6 | −50.4 | −10.8 | 48 A |
| 204 | E | CG | −18.8 | −51.6 | −11.3 | 65 A |

TABLE 6-continued

Coordinates of Factor IXa-Compound D complex

| | | | | | | |
|---|---|---|---|---|---|---|
| 204 | E | CD | −19.7 | −52.8 | −11.4 | 0 | A |
| 204 | E | OE1 | −19.4 | −53.8 | −10.7 | 0 | A |
| 204 | E | OE2 | −20.7 | −52.7 | −12.1 | 0 | A |
| 205 | G | N | −21.3 | −47.3 | −11.9 | 48 | A |
| 205 | G | CA | −22.1 | −46.3 | −11.2 | 48 | A |
| 205 | G | C | −21.4 | −45.1 | −10.6 | 52 | A |
| 205 | G | O | −22.0 | −44.1 | −10.2 | 53 | A |
| 206 | T | N | −20.1 | −45.2 | −10.4 | 46 | A |
| 206 | T | CA | −19.3 | −44.1 | −9.8 | 45 | A |
| 206 | T | C | −18.3 | −43.6 | −10.9 | 44 | A |
| 206 | T | O | −17.5 | −44.3 | −11.5 | 43 | A |
| 206 | T | CB | −18.5 | −44.6 | −8.6 | 47 | A |
| 206 | T | OG1 | −19.4 | −45.2 | −7.7 | 54 | A |
| 206 | T | CG2 | −17.9 | −43.4 | −7.9 | 42 | A |
| 207 | S | N | −18.4 | −42.3 | −11.1 | 39 | A |
| 207 | S | CA | −17.5 | −41.7 | −12.1 | 36 | A |
| 207 | S | C | −16.2 | −41.2 | −11.5 | 38 | A |
| 207 | S | O | −16.2 | −40.7 | −10.4 | 35 | A |
| 207 | S | CB | −18.3 | −40.4 | −12.7 | 39 | A |
| 207 | S | OG | −19.4 | −40.8 | −13.5 | 41 | A |
| 208 | F | N | −15.1 | −41.5 | −12.2 | 35 | A |
| 208 | F | CA | −13.8 | −41.1 | −11.7 | 34 | A |
| 208 | F | C | −13.2 | −40.2 | −12.8 | 34 | A |
| 208 | F | O | −13.5 | −40.4 | −14.0 | 31 | A |
| 208 | F | CB | −12.9 | −42.4 | −11.5 | 35 | A |
| 208 | F | CG | −13.2 | −43.1 | −10.3 | 36 | A |
| 208 | F | CD1 | −14.2 | −44.1 | −10.3 | 38 | A |
| 208 | F | CD2 | −12.4 | −43.0 | −9.2 | 38 | A |
| 208 | F | CE1 | −14.4 | −44.8 | −9.2 | 39 | A |
| 208 | F | CE2 | −12.7 | −43.7 | −8.0 | 40 | A |
| 208 | F | CZ | −13.7 | −44.6 | −8.0 | 38 | A |
| 209 | L | N | −12.3 | −39.3 | −12.4 | 30 | A |
| 209 | L | CA | −11.7 | −38.4 | −13.4 | 31 | A |
| 209 | L | C | −10.5 | −39.2 | −14.0 | 37 | A |
| 209 | L | O | −9.6 | −39.6 | −13.3 | 34 | A |
| 209 | L | CB | −11.2 | −37.2 | −12.6 | 29 | A |
| 209 | L | CG | −10.7 | −35.9 | −13.4 | 29 | A |
| 209 | L | CD1 | −11.8 | −35.3 | −14.1 | 26 | A |
| 209 | L | CD2 | −9.9 | −34.9 | −12.5 | 23 | A |
| 210 | T | N | −10.6 | −39.3 | −15.4 | 34 | A |
| 210 | T | CA | −9.5 | −40.0 | −16.2 | 32 | A |
| 210 | T | C | −8.7 | −39.0 | −17.0 | 37 | A |
| 210 | T | O | −7.5 | −39.3 | −17.3 | 37 | A |
| 210 | T | CB | −10.0 | −41.2 | −16.9 | 29 | A |
| 210 | T | OG1 | −11.2 | −41.0 | −17.6 | 29 | A |
| 210 | T | CG2 | −10.4 | −42.3 | −15.9 | 24 | A |
| 211 | G | N | −9.2 | −37.8 | −17.3 | 31 | A |
| 211 | G | CA | −8.5 | −36.8 | −18.1 | 29 | A |
| 211 | G | C | −9.0 | −35.4 | −17.9 | 33 | A |
| 211 | G | O | −10.1 | −35.1 | −17.4 | 32 | A |
| 212 | I | N | −8.2 | −34.4 | −18.3 | 32 | A |
| 212 | I | CA | −8.5 | −33.0 | −18.4 | 32 | A |
| 212 | I | C | −8.6 | −32.7 | −19.9 | 36 | A |
| 212 | I | O | −7.8 | −33.2 | −20.6 | 36 | A |
| 212 | I | CB | −7.3 | −32.1 | −17.7 | 33 | A |
| 212 | I | CG1 | −6.9 | −32.6 | −16.4 | 32 | A |
| 212 | I | CG2 | −7.7 | −30.7 | −17.7 | 32 | A |
| 212 | I | CD1 | −8.0 | −32.7 | −15.3 | 37 | A |
| 213 | I | N | −9.7 | −32.0 | −20.3 | 33 | A |
| 213 | I | CA | −9.9 | −31.7 | −21.6 | 32 | A |
| 213 | I | C | −8.8 | −30.6 | −21.9 | 38 | A |
| 213 | I | O | −8.7 | −29.6 | −21.2 | 38 | A |
| 213 | I | CB | −11.3 | −31.0 | −21.9 | 35 | A |
| 213 | I | CG1 | −12.4 | −32.0 | −21.5 | 34 | A |
| 213 | I | CG2 | −11.4 | −30.5 | −23.4 | 35 | A |
| 213 | I | CD1 | −13.8 | −31.4 | −21.6 | 33 | A |
| 214 | S | N | −7.9 | −30.9 | −22.9 | 37 | A |
| 214 | S | CA | −6.8 | −30.0 | −23.1 | 37 | A |
| 214 | S | C | −6.9 | −29.2 | −24.4 | 40 | A |
| 214 | S | O | −7.2 | −28.0 | −24.3 | 38 | A |
| 214 | S | CB | −5.5 | −30.8 | −23.0 | 39 | A |
| 214 | S | OG | −4.4 | −29.9 | −23.1 | 51 | A |
| 215 | W | N | −6.6 | −29.7 | −25.5 | 40 | A |
| 215 | W | CA | −6.6 | −29.0 | −26.8 | 40 | A |
| 215 | W | C | −6.9 | −29.8 | −28.0 | 44 | A |
| 215 | W | O | −7.2 | −31.0 | −27.9 | 43 | A |
| 215 | W | CB | −5.2 | −28.3 | −27.0 | 38 | A |
| 215 | W | CG | −4.1 | −29.3 | −27.1 | 39 | A |
| 215 | W | CD1 | −3.5 | −30.0 | −26.1 | 42 | A |
| 215 | W | CD2 | −3.4 | −29.8 | −28.3 | 39 | A |
| 215 | W | NE1 | −2.6 | −30.9 | −26.5 | 43 | A |
| 215 | W | CE2 | −2.5 | −30.7 | −27.9 | 44 | A |
| 215 | W | CE3 | −3.6 | −29.5 | −29.7 | 41 | A |
| 215 | W | CZ2 | −1.7 | −31.4 | −28.8 | 43 | A |
| 215 | W | CZ3 | −2.8 | −30.1 | −30.6 | 42 | A |
| 215 | W | CH2 | −1.8 | −31.1 | −30.2 | 43 | A |
| 216 | G | N | −6.7 | −29.3 | −29.2 | 44 | A |
| 216 | G | CA | −6.9 | −30.0 | −30.4 | 44 | A |
| 216 | G | C | −6.8 | −29.0 | −31.6 | 51 | A |
| 216 | G | O | −6.7 | −27.8 | −31.4 | 51 | A |
| 217 | E | N | −6.7 | −29.5 | −32.8 | 48 | A |
| 217 | E | CA | −6.6 | −28.6 | −34.0 | 46 | A |
| 217 | E | C | −8.0 | −28.3 | −34.3 | 58 | A |
| 217 | E | O | −8.7 | −27.8 | −33.4 | 61 | A |
| 217 | E | CB | −5.8 | −29.2 | −35.1 | 46 | A |
| 217 | E | CG | −4.4 | −29.4 | −34.7 | 44 | A |
| 217 | E | CD | −3.6 | −30.3 | −35.7 | 72 | A |
| 217 | E | OE1 | −3.3 | −31.5 | −35.4 | 71 | A |
| 217 | E | OE2 | −3.2 | −29.7 | −36.7 | 68 | A |
| 219 | E | N | −8.6 | −28.6 | −35.4 | 58 | A |
| 219 | E | CA | −10.0 | −28.2 | −35.5 | 60 | A |
| 219 | E | C | −11.1 | −29.1 | −35.0 | 65 | A |
| 219 | E | O | −11.1 | −30.3 | −35.2 | 67 | A |
| 219 | E | CB | −10.4 | −27.5 | −36.8 | 62 | A |
| 219 | E | CG | −10.1 | −28.3 | −38.1 | 83 | A |
| 219 | E | CD | −10.9 | −27.8 | −39.2 | 0 | A |
| 219 | E | OE1 | −12.1 | −28.3 | −39.4 | 0 | A |
| 219 | E | OE2 | −10.5 | −26.8 | −39.9 | 0 | A |
| 220 | C | N | −12.0 | −28.5 | −34.2 | 56 | A |
| 220 | C | CA | −13.1 | −29.2 | −33.5 | 54 | A |
| 220 | C | C | −13.8 | −30.1 | −34.5 | 51 | A |
| 220 | C | O | −14.3 | −29.6 | −35.6 | 48 | A |
| 220 | C | CB | −14.1 | −28.3 | −32.9 | 55 | A |
| 220 | C | SG | −13.4 | −27.1 | −31.7 | 60 | A |
| 221 | A | N | −14.0 | −31.4 | −34.2 | 45 | A |
| 221 | A | CA | −14.8 | −32.3 | −34.9 | 43 | A |
| 221 | A | C | −14.4 | −32.6 | −36.4 | 47 | A |
| 221 | A | O | −15.3 | −33.1 | −37.1 | 46 | A |
| 221 | A | CB | −16.2 | −32.0 | −34.7 | 43 | A |
| 221A | M | N | −13.2 | −32.3 | −36.8 | 43 | A |
| 221A | M | CA | −12.8 | −32.7 | −38.2 | 44 | A |
| 221A | M | C | −12.4 | −34.1 | −38.3 | 46 | A |
| 221A | M | O | −11.5 | −34.6 | −37.6 | 47 | A |
| 221A | M | CB | −11.6 | −31.8 | −38.5 | 48 | A |
| 221A | M | CG | −11.3 | −31.7 | −40.0 | 54 | A |
| 221A | M | SD | −9.8 | −30.6 | −40.5 | 62 | A |
| 221A | M | CE | −8.4 | −31.9 | −40.7 | 59 | A |
| 222 | K | N | −12.8 | −34.8 | −39.4 | 39 | A |
| 222 | K | CA | −12.4 | −36.1 | −39.7 | 38 | A |
| 222 | K | C | −10.9 | −36.1 | −39.8 | 42 | A |
| 222 | K | O | −10.3 | −35.5 | −40.5 | 44 | A |
| 222 | K | CB | −13.0 | −36.5 | −41.1 | 40 | A |
| 222 | K | CG | −12.3 | −37.7 | −41.8 | 33 | A |
| 222 | K | CD | −13.3 | −38.3 | −42.9 | 35 | A |
| 222 | K | CE | −12.7 | −39.5 | −43.7 | 28 | A |
| 222 | K | NZ | −11.8 | −40.4 | −42.9 | 45 | A |
| 223 | G | N | −10.3 | −37.1 | −39.1 | 36 | A |
| 223 | G | CA | −8.9 | −37.3 | −39.1 | 34 | A |
| 223 | G | C | −8.2 | −36.6 | −38.0 | 40 | A |
| 223 | G | O | −7.0 | −36.8 | −37.7 | 41 | A |
| 224 | K | N | −8.9 | −35.7 | −37.3 | 37 | A |
| 224 | K | CA | −8.3 | −35.0 | −36.1 | 36 | A |
| 224 | K | C | −9.0 | −35.5 | −34.8 | 39 | A |
| 224 | K | O | −10.1 | −35.9 | −34.9 | 39 | A |
| 224 | K | CB | −8.5 | −33.5 | −36.3 | 38 | A |
| 224 | K | CG | −7.7 | −32.9 | −37.3 | 30 | A |
| 224 | K | CD | −6.2 | −32.9 | −37.0 | 39 | A |
| 224 | K | CE | −5.3 | −32.8 | −38.2 | 54 | A |
| 224 | K | NZ | −3.8 | −32.8 | −37.8 | 72 | A |
| 225 | Y | N | −8.3 | −35.5 | −33.7 | 35 | A |
| 225 | Y | CA | −8.9 | −35.9 | −32.4 | 33 | A |
| 225 | Y | C | −8.7 | −34.9 | −31.3 | 36 | A |
| 225 | Y | O | −7.8 | −34.1 | −31.4 | 38 | A |
| 225 | Y | CB | −8.2 | −37.3 | −32.0 | 32 | A |
| 225 | Y | CG | −8.5 | −38.4 | −32.9 | 32 | A |
| 225 | Y | CD1 | −9.7 | −39.0 | −33.0 | 32 | A |

TABLE 6-continued

Coordinates of Factor IXa-Compound D complex

| | | | | | | |
|---|---|---|---|---|---|---|
| 225 | Y | CD2 | −7.5 | −38.8 | −33.9 | 33 A |
| 225 | Y | CE1 | −10.0 | −40.1 | −33.9 | 31 A |
| 225 | Y | CE2 | −7.7 | −39.8 | −34.8 | 33 A |
| 225 | Y | CZ | −9.0 | −40.5 | −34.8 | 38 A |
| 225 | Y | OH | −9.3 | −41.5 | −35.7 | 36 A |
| 226 | G | N | −9.5 | −35.0 | −30.3 | 33 A |
| 226 | G | CA | −9.3 | −34.2 | −29.1 | 32 A |
| 226 | G | C | −8.1 | −34.8 | −28.3 | 34 A |
| 226 | G | O | −7.9 | −36.0 | −28.3 | 31 A |
| 227 | I | N | −7.3 | −33.9 | −27.7 | 33 A |
| 227 | I | CA | −6.1 | −34.3 | −26.9 | 33 A |
| 227 | I | C | −6.4 | −33.9 | −25.4 | 36 A |
| 227 | I | O | −7.0 | −32.8 | −25.2 | 34 A |
| 227 | I | CB | −4.8 | −33.5 | −27.3 | 37 A |
| 227 | I | CG1 | −4.7 | −33.5 | −28.8 | 37 A |
| 227 | I | CG2 | −3.6 | −34.2 | −26.7 | 35 A |
| 227 | I | CD1 | −4.9 | −34.8 | −29.5 | 38 A |
| 228 | Y | N | −6.1 | −34.9 | −24.6 | 33 A |
| 228 | Y | CA | −6.4 | −34.8 | −23.1 | 30 A |
| 228 | Y | C | −5.2 | −35.0 | −22.3 | 31 A |
| 228 | Y | O | −4.2 | −35.6 | −22.8 | 30 A |
| 228 | Y | CB | −7.5 | −35.8 | −22.8 | 30 A |
| 228 | Y | CG | −8.8 | −35.6 | −23.5 | 29 A |
| 228 | Y | CD1 | −8.9 | −36.0 | −24.9 | 29 A |
| 228 | Y | CD2 | −9.9 | −35.1 | −22.9 | 29 A |
| 228 | Y | CE1 | −10.1 | −35.8 | −25.6 | 29 A |
| 228 | Y | CE2 | −11.1 | −34.9 | −23.6 | 30 A |
| 228 | Y | CZ | −11.2 | −35.2 | −24.9 | 37 A |
| 228 | Y | OH | −12.4 | −35.0 | −25.6 | 36 A |
| 229 | T | N | −5.2 | −34.5 | −21.1 | 28 A |
| 229 | T | CA | −4.1 | −34.8 | −20.1 | 28 A |
| 229 | T | C | −4.5 | −36.0 | −19.4 | 31 A |
| 229 | T | O | −5.7 | −36.2 | −18.9 | 29 A |
| 229 | T | CB | −4.0 | −33.6 | −19.2 | 33 A |
| 229 | T | OG1 | −3.7 | −32.4 | −19.9 | 39 A |
| 229 | T | CG2 | −2.9 | −33.8 | −18.1 | 26 A |
| 230 | K | N | −3.5 | −36.9 | −19.2 | 28 A |
| 230 | K | CA | −3.8 | −38.1 | −18.4 | 27 A |
| 230 | K | C | −3.7 | −37.7 | −16.9 | 31 A |
| 230 | K | O | −2.7 | −37.1 | −16.4 | 31 A |
| 230 | K | CB | −2.7 | −39.1 | −18.6 | 28 A |
| 230 | K | CG | −3.0 | −39.9 | −19.9 | 30 A |
| 230 | K | CD | −2.1 | −41.1 | −20.0 | 25 A |
| 230 | K | CE | −1.9 | −41.6 | −21.4 | 26 A |
| 230 | K | NZ | −1.0 | −42.8 | −21.4 | 33 A |
| 231 | V | N | −4.8 | −37.9 | −16.2 | 27 A |
| 231 | V | CA | −4.9 | −37.5 | −14.8 | 27 A |
| 231 | V | C | −4.1 | −38.4 | −13.9 | 33 A |
| 231 | V | O | −3.6 | −38.0 | −12.9 | 33 A |
| 231 | V | CB | −6.4 | −37.4 | −14.4 | 30 A |
| 231 | V | CG1 | −6.6 | −37.6 | −12.9 | 28 A |
| 231 | V | CG2 | −7.1 | −36.2 | −14.9 | 29 A |
| 232 | S | N | −3.9 | −39.7 | −14.3 | 31 A |
| 232 | S | CA | −3.1 | −40.6 | −13.6 | 32 A |
| 232 | S | C | −1.7 | −40.1 | −13.3 | 35 A |
| 232 | S | O | −1.1 | −40.5 | −12.3 | 36 A |
| 232 | S | CB | −3.0 | −42.0 | −14.3 | 38 A |
| 232 | S | OG | −2.5 | −41.8 | −15.6 | 42 A |
| 233 | R | N | −1.2 | −39.3 | −14.2 | 30 A |
| 233 | R | CA | 0.1 | −38.8 | −14.1 | 28 A |
| 233 | R | C | 0.3 | −37.8 | −13.0 | 33 A |
| 233 | R | O | 1.4 | −37.4 | −12.6 | 33 A |
| 233 | R | CB | 0.5 | −38.1 | −15.5 | 26 A |
| 233 | R | CG | 1.6 | −37.1 | −15.5 | 33 A |
| 233 | R | CD | 3.0 | −37.7 | −15.3 | 27 A |
| 233 | R | NE | 4.0 | −36.7 | −15.4 | 31 A |
| 233 | R | CZ | 4.3 | −35.8 | −14.4 | 45 A |
| 233 | R | NH1 | 3.7 | −35.9 | −13.3 | 31 A |
| 233 | R | NH2 | 5.3 | −34.9 | −14.6 | 31 A |
| 234 | Y | N | −0.9 | −37.3 | −12.5 | 30 A |
| 234 | Y | CA | −0.9 | −36.2 | −11.5 | 29 A |
| 234 | Y | C | −1.7 | −36.4 | −10.3 | 38 A |
| 234 | Y | O | −1.8 | −35.5 | −9.4 | 36 A |
| 234 | Y | CB | −1.5 | −34.9 | −12.2 | 29 A |
| 234 | Y | CG | −0.8 | −34.5 | −13.4 | 27 A |
| 234 | Y | CD1 | 0.4 | −33.8 | −13.3 | 28 A |
| 234 | Y | CD2 | −1.2 | −34.9 | −14.7 | 28 A |
| 234 | Y | CE1 | 1.1 | −33.5 | −14.5 | 30 A |
| 234 | Y | CE2 | −0.5 | −34.5 | −15.8 | 29 A |
| 234 | Y | CZ | 0.7 | −33.8 | −15.7 | 34 A |
| 234 | Y | OH | 1.4 | −33.5 | −16.8 | 35 A |
| 235 | V | N | −2.1 | −37.6 | −10.1 | 37 A |
| 235 | V | CA | −2.9 | −38.1 | −8.9 | 36 A |
| 235 | V | C | −2.3 | −37.7 | −7.6 | 41 A |
| 235 | V | O | −3.0 | −37.2 | −6.7 | 43 A |
| 235 | V | CB | −3.4 | −39.5 | −9.0 | 39 A |
| 235 | V | CG1 | −4.1 | −40.0 | −7.7 | 41 A |
| 235 | V | CG2 | −4.5 | −39.6 | −10.1 | 38 A |
| 236 | N | N | −1.0 | −38.0 | −7.4 | 38 A |
| 236 | N | CA | −0.4 | −37.7 | −6.1 | 37 A |
| 236 | N | C | −0.4 | −36.2 | −5.8 | 41 A |
| 236 | N | O | −0.7 | −35.8 | −4.7 | 43 A |
| 236 | N | CB | 1.0 | −38.2 | −6.0 | 40 A |
| 236 | N | CG | 1.1 | −39.8 | −6.1 | 78 A |
| 236 | N | OD1 | 0.0 | −40.4 | −5.9 | 57 A |
| 236 | N | ND2 | 2.2 | −40.3 | −6.6 | 86 A |
| 237 | W | N | 0.0 | −35.4 | −6.8 | 37 A |
| 237 | W | CA | 0.1 | −34.0 | −6.8 | 34 A |
| 237 | W | C | −1.3 | −33.3 | −6.4 | 38 A |
| 237 | W | O | −1.4 | −32.4 | −5.6 | 38 A |
| 237 | W | CB | 0.6 | −33.4 | −8.1 | 31 A |
| 237 | W | CG | 0.6 | −31.9 | −8.2 | 32 A |
| 237 | W | CD1 | 1.4 | −31.0 | −7.6 | 35 A |
| 237 | W | CD2 | −0.3 | −31.1 | −9.0 | 31 A |
| 237 | W | NE1 | 1.1 | −29.7 | −8.0 | 34 A |
| 237 | W | CE2 | −0.0 | −29.8 | −8.9 | 34 A |
| 237 | W | CE3 | −1.4 | −31.5 | −9.8 | 31 A |
| 237 | W | CZ2 | −0.7 | −28.8 | −9.5 | 34 A |
| 237 | W | CZ3 | −2.1 | −30.5 | −10.5 | 33 A |
| 237 | W | CH2 | −1.8 | −29.1 | −10.3 | 34 A |
| 238 | I | N | −2.4 | −33.8 | −7.1 | 32 A |
| 238 | I | CA | −3.7 | −33.3 | −6.8 | 32 A |
| 238 | I | C | −4.1 | −33.6 | −5.3 | 37 A |
| 238 | I | O | −4.6 | −32.7 | −4.6 | 35 A |
| 238 | I | CB | −4.8 | −33.9 | −7.7 | 34 A |
| 238 | I | CG1 | −4.5 | −33.7 | −9.2 | 32 A |
| 238 | I | CG2 | −6.2 | −33.5 | −7.3 | 32 A |
| 238 | I | CD1 | −5.4 | −34.5 | −10.2 | 28 A |
| 239 | K | N | −4.0 | −34.8 | −4.9 | 32 A |
| 239 | K | CA | −4.3 | −35.3 | −3.6 | 31 A |
| 239 | K | C | −3.6 | −34.5 | −2.5 | 41 A |
| 239 | K | O | −4.1 | −34.2 | −1.4 | 44 A |
| 239 | K | CB | −4.0 | −36.8 | −3.4 | 32 A |
| 239 | K | CG | −5.3 | −37.7 | −3.5 | 45 A |
| 239 | K | CD | −5.5 | −38.4 | −4.8 | 52 A |
| 239 | K | CE | −6.5 | −39.6 | −4.8 | 53 A |
| 239 | K | NZ | −7.9 | −39.1 | −4.5 | 56 A |
| 240 | E | N | −2.3 | −34.3 | −2.8 | 37 A |
| 240 | E | CA | −1.5 | −33.6 | −1.8 | 37 A |
| 240 | E | C | −1.8 | −32.1 | −1.8 | 46 A |
| 240 | E | O | −2.0 | −31.5 | −0.7 | 49 A |
| 240 | E | CB | −0.0 | −33.8 | −2.1 | 38 A |
| 240 | E | CG | 0.8 | −32.6 | −1.9 | 49 A |
| 240 | E | CD | 1.4 | −32.6 | −0.5 | 87 A |
| 240 | E | OE1 | 1.0 | −33.6 | 0.3 | 84 A |
| 240 | E | OE2 | 2.1 | −31.7 | −0.1 | 90 A |
| 241 | K | N | −1.9 | −31.4 | −2.9 | 41 A |
| 241 | K | CA | −2.2 | −30.0 | −2.8 | 38 A |
| 241 | K | C | −3.6 | −29.7 | −2.3 | 39 A |
| 241 | K | O | −3.9 | −28.6 | −1.9 | 39 A |
| 241 | K | CB | −1.9 | −29.3 | −4.2 | 38 A |
| 241 | K | CG | −0.4 | −29.2 | −4.5 | 47 A |
| 241 | K | CD | 0.4 | −28.6 | −3.3 | 51 A |
| 241 | K | CE | 1.8 | −29.1 | −3.3 | 66 A |
| 241 | K | NZ | 2.8 | −28.2 | −3.9 | 70 A |
| 242 | T | N | −4.5 | −30.6 | −2.4 | 35 A |
| 242 | T | CA | −6.0 | −30.4 | −2.1 | 34 A |
| 242 | T | C | −6.4 | −30.9 | −0.7 | 42 A |
| 242 | T | O | −7.6 | −30.9 | −0.4 | 39 A |
| 242 | T | CB | −6.9 | −30.9 | −3.2 | 33 A |
| 242 | T | OG1 | −6.8 | −33.3 | −3.3 | 32 A |
| 242 | T | CG2 | −6.6 | −30.2 | −4.6 | 24 A |
| 243 | K | N | −5.5 | −31.5 | 0.0 | 43 A |
| 243 | K | CA | −5.7 | −32.1 | 1.3 | 44 A |
| 243 | K | C | −6.4 | −31.1 | 2.2 | 48 A |
| 243 | K | O | −5.9 | −30.0 | 2.4 | 45 A |

TABLE 6-continued

Coordinates of Factor IXa-Compound D complex

| | | | | | | |
|---|---|---|---|---|---|---|
| 243 | K | CB | −4.3 | −32.4 | 2.0 | 49 | A |
| 243 | K | CG | −4.0 | −33.8 | 2.2 | 58 | A |
| 243 | K | CD | −2.5 | −34.0 | 2.2 | 62 | A |
| 243 | K | CE | −2.0 | −35.5 | 2.5 | 77 | A |
| 243 | K | NZ | −2.1 | −36.4 | 1.4 | 82 | A |
| 244 | L | N | −7.6 | −31.4 | 2.7 | 47 | A |
| 244 | L | CA | −8.4 | −30.5 | 3.5 | 48 | A |
| 244 | L | C | −8.0 | −30.4 | 5.0 | 55 | A |
| 244 | L | O | −7.8 | −31.5 | 5.6 | 56 | A |
| 244 | L | CB | −9.9 | −30.8 | 3.4 | 46 | A |
| 244 | L | CG | −10.6 | −30.2 | 2.1 | 47 | A |
| 244 | L | CD1 | −12.1 | −30.2 | 2.2 | 47 | A |
| 244 | L | CD2 | −10.1 | −28.8 | 1.9 | 42 | A |
| 86 | M | N | −10.4 | −64.4 | −5.6 | 86 | B |
| 86 | M | CA | −9.2 | −65.1 | −5.8 | 86 | B |
| 86 | M | C | −8.0 | −64.3 | −6.1 | 86 | B |
| 86 | M | O | −7.1 | −64.2 | −5.2 | 85 | B |
| 86 | M | CB | −9.4 | −66.2 | −6.8 | 89 | B |
| 86 | M | CG | −10.0 | −67.5 | −6.2 | 94 | B |
| 86 | M | SD | −9.2 | −69.0 | −6.7 | 0 | B |
| 86 | M | CE | −7.8 | −69.1 | −5.3 | 97 | B |
| 87 | T | N | −7.9 | −63.7 | −7.2 | 79 | B |
| 87 | T | CA | −6.7 | −62.8 | −7.6 | 77 | B |
| 87 | T | C | −7.2 | −61.5 | −8.3 | 74 | B |
| 87 | T | O | −8.1 | −61.5 | −9.1 | 73 | B |
| 87 | T | CB | −5.7 | −63.6 | −8.5 | 83 | B |
| 87 | T | OG1 | −4.4 | −62.9 | −8.4 | 82 | B |
| 87 | T | CG2 | −6.1 | −63.7 | −9.9 | 80 | B |
| 88 | C | N | −6.6 | −60.4 | −7.9 | 68 | B |
| 88 | C | CA | −6.9 | −59.1 | −8.5 | 66 | B |
| 88 | C | C | −6.8 | −59.0 | −10.0 | 72 | B |
| 88 | C | O | −7.7 | −58.4 | −10.6 | 71 | B |
| 88 | C | CB | −6.1 | −58.0 | −7.9 | 65 | B |
| 88 | C | SG | −6.4 | −57.7 | −6.1 | 67 | B |
| 89 | N | N | −5.8 | −59.7 | −10.5 | 69 | B |
| 89 | N | CA | −5.5 | −59.7 | −12.0 | 70 | B |
| 89 | N | C | −6.5 | −60.6 | −12.7 | 74 | B |
| 89 | N | O | −6.1 | −61.0 | −13.9 | 75 | B |
| 89 | N | CB | −4.0 | −60.0 | −12.3 | 77 | B |
| 89 | N | CG | −3.5 | −61.1 | −11.4 | 0 | B |
| 89 | N | OD1 | −3.9 | −62.3 | −11.5 | 0 | B |
| 89 | N | ND2 | −2.5 | −60.8 | −10.6 | 0 | B |
| 90 | I | N | −7.6 | −60.9 | −12.1 | 71 | B |
| 90 | I | CA | −8.7 | −61.6 | −12.8 | 70 | B |
| 90 | I | C | −10.0 | −61.1 | −12.3 | 73 | B |
| 90 | I | O | −10.4 | −61.3 | −11.2 | 73 | B |
| 90 | I | CB | −8.6 | −63.2 | −12.5 | 74 | B |
| 90 | I | CG1 | −7.3 | −63.8 | −12.8 | 74 | B |
| 90 | I | CG2 | −9.8 | −63.9 | −13.2 | 74 | B |
| 90 | I | CD1 | −7.0 | −63.7 | −14.3 | 81 | B |
| 91 | K | N | −10.7 | −60.3 | −13.2 | 70 | B |
| 91 | K | CA | −11.9 | −59.6 | −12.8 | 69 | B |
| 91 | K | C | −11.9 | −58.7 | −11.6 | 72 | B |
| 91 | K | O | −12.8 | −58.5 | −10.9 | 70 | B |
| 91 | K | CB | −13.0 | −60.7 | −12.6 | 72 | B |
| 91 | K | CG | −13.6 | −61.2 | −13.9 | 96 | B |
| 91 | K | CD | −14.9 | −60.6 | −14.2 | 0 | B |
| 91 | K | CE | −15.3 | −59.5 | −13.2 | 0 | B |
| 91 | K | NZ | −16.5 | −59.7 | −12.5 | 0 | B |
| 92 | N | N | −10.7 | −58.2 | −11.3 | 67 | B |
| 92 | N | CA | −10.5 | −57.2 | −10.2 | 66 | B |
| 92 | N | C | −10.7 | −57.9 | −8.9 | 69 | B |
| 92 | N | O | −11.0 | −57.2 | −7.9 | 67 | B |
| 92 | N | CB | −11.3 | −56.0 | −10.4 | 64 | B |
| 92 | N | CG | −10.9 | −54.8 | −9.6 | 58 | B |
| 92 | N | OD1 | −11.6 | −54.1 | −8.9 | 50 | B |
| 92 | N | ND2 | −9.6 | −54.5 | −9.6 | 41 | B |
| 93 | G | N | −10.6 | −59.2 | −8.8 | 65 | B |
| 93 | G | CA | −10.9 | −59.9 | −7.5 | 65 | B |
| 93 | G | C | −12.4 | −59.8 | −7.2 | 68 | B |
| 93 | G | O | −12.8 | −59.9 | −6.0 | 69 | B |
| 94 | R | N | −13.2 | −59.5 | −8.2 | 64 | B |
| 94 | R | CA | −14.7 | −59.3 | −8.0 | 64 | B |
| 94 | R | C | −15.0 | −58.0 | −7.3 | 64 | B |
| 94 | R | O | −16.1 | −57.7 | −7.0 | 60 | B |
| 94 | R | CB | −15.3 | −60.5 | −7.2 | 70 | B |
| 94 | R | CG | −15.9 | −61.6 | −8.0 | 87 | B |
| 94 | R | CD | −15.5 | −61.4 | −9.5 | 0 | B |
| 94 | R | NE | −15.0 | −62.7 | −10.1 | 0 | B |
| 94 | R | CZ | −15.3 | −63.2 | −11.2 | 0 | B |
| 94 | R | NH1 | −16.3 | −62.7 | −11.9 | 0 | B |
| 94 | R | NH2 | −14.8 | −64.3 | −11.7 | 0 | B |
| 95 | C | N | −13.9 | −57.3 | −6.9 | 60 | B |
| 95 | C | CA | −14.0 | −56.0 | −6.2 | 59 | B |
| 95 | C | C | −14.6 | −54.9 | −7.1 | 58 | B |
| 95 | C | O | −14.1 | −54.6 | −8.2 | 56 | B |
| 95 | C | CB | −12.6 | −55.5 | −5.8 | 60 | B |
| 95 | C | SG | −11.7 | −56.6 | −4.6 | 64 | B |
| 96 | E | N | −15.7 | −54.3 | −6.6 | 54 | B |
| 96 | E | CA | −16.4 | −53.2 | −7.3 | 53 | B |
| 96 | E | C | −15.4 | −52.0 | −7.7 | 56 | B |
| 96 | E | O | −15.6 | −51.4 | −8.8 | 56 | B |
| 96 | E | CB | −17.6 | −52.7 | −6.6 | 53 | B |
| 96 | E | CG | −18.4 | −51.7 | −7.4 | 54 | B |
| 96 | E | CD | −19.5 | −51.1 | −6.6 | 71 | B |
| 96 | E | OE1 | −20.2 | −51.8 | −5.8 | 68 | B |
| 96 | E | OE2 | −19.7 | −49.8 | −6.8 | 78 | B |
| 97 | Q | N | −14.5 | −51.6 | −6.8 | 48 | B |
| 97 | Q | CA | −13.6 | −50.5 | −7.0 | 46 | B |
| 97 | Q | C | −12.1 | −51.0 | −7.0 | 50 | B |
| 97 | Q | O | −11.6 | −51.4 | −8.1 | 51 | B |
| 97 | Q | CB | −13.8 | −49.4 | −6.1 | 46 | B |
| 97 | Q | CG | −15.0 | −48.5 | −6.5 | 34 | B |
| 97 | Q | CD | −15.4 | −47.4 | −5.6 | 54 | B |
| 97 | Q | OE1 | −14.6 | −46.9 | −4.7 | 52 | B |
| 97 | Q | NE2 | −16.6 | −46.9 | −5.8 | 35 | B |
| 98 | F | N | −11.5 | −51.0 | −5.9 | 46 | B |
| 98 | F | CA | −10.1 | −51.4 | −5.8 | 47 | B |
| 98 | F | C | −9.9 | −52.8 | −5.1 | 57 | B |
| 98 | F | O | −10.6 | −53.2 | −4.2 | 57 | B |
| 98 | F | CB | −9.3 | −50.3 | −5.2 | 48 | B |
| 98 | F | CG | −9.8 | −48.9 | −5.5 | 47 | B |
| 98 | F | CD1 | −9.9 | −48.4 | −6.8 | 48 | B |
| 98 | F | CD2 | −10.1 | −48.0 | −4.4 | 48 | B |
| 98 | F | CE1 | −10.4 | −47.1 | −7.1 | 48 | B |
| 98 | F | CE2 | −10.5 | −46.7 | −4.7 | 50 | B |
| 98 | F | CZ | −10.7 | −46.3 | −6.0 | 47 | B |
| 99 | C | N | −8.8 | −53.4 | −5.6 | 58 | B |
| 99 | C | CA | −8.4 | −54.7 | −5.1 | 60 | B |
| 99 | C | C | −6.9 | −54.9 | −4.8 | 65 | B |
| 99 | C | O | −6.1 | −54.5 | −5.6 | 66 | B |
| 99 | C | CB | −8.8 | −55.7 | −6.2 | 62 | B |
| 99 | C | SG | −8.4 | −57.5 | −6.0 | 67 | B |
| 100 | K | N | −6.6 | −55.4 | −3.6 | 63 | B |
| 100 | K | CA | −5.2 | −55.6 | −3.2 | 63 | B |
| 100 | K | C | −5.0 | −57.1 | −3.0 | 69 | B |
| 100 | K | O | −5.8 | −57.8 | −2.3 | 67 | B |
| 100 | K | CB | −5.0 | −54.9 | −1.8 | 66 | B |
| 100 | K | CG | −3.7 | −54.1 | −1.8 | 89 | B |
| 100 | K | CD | −2.9 | −54.4 | −0.5 | 0 | B |
| 100 | K | CE | −3.5 | −53.7 | 0.8 | 0 | B |
| 100 | K | NZ | −2.6 | −53.6 | 1.9 | 0 | B |
| 101 | N | N | −3.9 | −57.7 | −3.6 | 67 | B |
| 101 | N | CA | −3.6 | −59.1 | −3.4 | 68 | B |
| 101 | N | C | −3.0 | −59.5 | −2.1 | 74 | B |
| 101 | N | O | −2.4 | −58.6 | −1.4 | 75 | B |
| 101 | N | CB | −2.8 | −59.7 | −4.6 | 64 | B |
| 101 | N | CG | −3.7 | −60.2 | −5.7 | 85 | B |
| 101 | N | OD1 | −4.8 | −60.6 | −5.5 | 74 | B |
| 101 | N | ND2 | −3.1 | −60.3 | −7.0 | 80 | B |
| 107 | V | N | −7.5 | −61.9 | −1.4 | 65 | B |
| 107 | V | CA | −7.9 | −60.6 | −2.0 | 66 | B |
| 107 | V | C | −8.7 | −59.7 | −1.0 | 73 | B |
| 107 | V | O | −9.6 | −60.1 | −0.4 | 74 | B |
| 107 | V | CB | −8.8 | −60.9 | −3.3 | 68 | B |
| 107 | V | CG1 | −10.0 | −59.9 | −3.3 | 67 | B |
| 107 | V | CG2 | −7.9 | −60.8 | −4.5 | 68 | B |
| 108 | V | N | −8.2 | −58.4 | −0.9 | 68 | B |
| 108 | V | CA | −8.9 | −57.5 | −0.1 | 66 | B |
| 108 | V | C | −9.5 | −56.4 | −1.0 | 70 | B |
| 108 | V | O | −8.8 | −55.7 | −1.7 | 70 | B |
| 108 | V | CB | −8.0 | −56.8 | 1.0 | 69 | B |
| 108 | V | CG1 | −8.7 | −55.7 | 1.7 | 67 | B |
| 108 | V | CG2 | −7.5 | −57.9 | 2.0 | 68 | B |
| 109 | C | N | −10.8 | −56.1 | −0.8 | 65 | B |
| 109 | C | CA | −11.5 | −55.0 | −1.6 | 63 | B |

TABLE 6-continued

Coordinates of Factor IXa-Compound D complex

| | | | | | | |
|---|---|---|---|---|---|---|
| 109 | C | C | −11.5 | −53.7 | −0.8 | 67 B |
| 109 | C | O | −11.5 | −53.7 | 0.4 | 67 B |
| 109 | C | CB | −12.9 | −55.4 | −2.0 | 61 B |
| 109 | C | SG | −13.0 | −56.9 | −3.1 | 64 B |
| 110 | S | N | −11.4 | −52.6 | −1.6 | 62 B |
| 110 | S | CA | −11.4 | −51.2 | −1.1 | 59 B |
| 110 | S | C | −12.3 | −50.3 | −1.9 | 63 B |
| 110 | S | O | −12.8 | −50.8 | −3.0 | 63 B |
| 110 | S | CB | −10.0 | −50.6 | −1.0 | 61 B |
| 110 | S | OG | −9.1 | −51.5 | −1.6 | 74 B |
| 111 | C | N | −12.5 | −49.1 | −1.5 | 60 B |
| 111 | C | CA | −13.4 | −48.2 | −2.1 | 59 B |
| 111 | C | C | −12.8 | −46.8 | −2.0 | 56 B |
| 111 | C | O | −11.9 | −46.6 | −1.2 | 54 B |
| 111 | C | CB | −14.7 | −48.1 | −1.3 | 61 B |
| 111 | C | SG | −15.8 | −49.5 | −1.2 | 66 B |
| 112 | T | N | −13.3 | −45.9 | −2.8 | 51 B |
| 112 | T | CA | −12.8 | −44.5 | −2.8 | 49 B |
| 112 | T | C | −13.4 | −43.8 | −1.6 | 52 B |
| 112 | T | O | −14.5 | −44.2 | −1.2 | 54 B |
| 112 | T | CB | −13.0 | −43.8 | −4.1 | 46 B |
| 112 | T | OG1 | −12.2 | −42.6 | −4.1 | 53 B |
| 112 | T | CG2 | −14.5 | −43.4 | −4.2 | 34 B |
| 113 | E | N | −12.8 | −42.8 | −1.1 | 49 B |
| 113 | E | CA | −13.3 | −42.0 | 0.0 | 50 B |
| 113 | E | C | −14.7 | −41.5 | −0.2 | 55 B |
| 113 | E | O | −15.1 | −41.0 | −1.3 | 55 B |
| 113 | E | CB | −12.4 | −40.8 | 0.2 | 52 B |
| 113 | E | CG | −12.9 | −39.7 | 1.2 | 71 B |
| 113 | E | CD | −11.9 | −39.4 | 2.3 | 0 B |
| 113 | E | OE1 | −12.1 | −40.0 | 3.4 | 0 B |
| 113 | E | OE2 | −11.0 | −38.6 | 2.1 | 0 B |
| 114 | G | N | −15.5 | −41.6 | 0.9 | 50 B |
| 114 | G | CA | −17.0 | −41.3 | 0.9 | 48 B |
| 114 | G | C | −17.8 | −42.5 | 0.7 | 52 B |
| 114 | G | O | −19.0 | −42.5 | 0.6 | 51 B |
| 115 | Y | N | −17.0 | −43.7 | 0.6 | 48 B |
| 115 | Y | CA | −17.7 | −45.0 | 0.3 | 48 B |
| 115 | Y | C | −17.1 | −46.0 | 1.4 | 57 B |
| 115 | Y | O | −16.0 | −45.9 | 1.8 | 57 B |
| 115 | Y | CB | −17.4 | −45.5 | −1.0 | 48 B |
| 115 | Y | CG | −18.0 | −44.8 | −2.2 | 47 B |
| 115 | Y | CD1 | −19.2 | −45.2 | −2.7 | 48 B |
| 115 | Y | CD2 | −17.5 | −43.6 | −2.7 | 47 B |
| 115 | Y | CE1 | −19.9 | −44.5 | −3.7 | 49 B |
| 115 | Y | CE2 | −18.1 | −42.9 | −3.7 | 47 B |
| 115 | Y | CZ | −19.3 | −43.4 | −4.2 | 51 B |
| 115 | Y | OH | −19.9 | −42.7 | −5.2 | 50 B |
| 116 | R | N | −18.0 | −47.0 | 1.7 | 54 B |
| 116 | R | CA | −17.6 | −48.0 | 2.6 | 54 B |
| 116 | R | C | −17.9 | −49.3 | 1.9 | 56 B |
| 116 | R | O | −18.8 | −49.4 | 1.1 | 55 B |
| 116 | R | CB | −18.4 | −47.9 | 3.9 | 55 B |
| 116 | R | CG | −19.8 | −48.6 | 3.8 | 65 B |
| 116 | R | CD | −20.5 | −48.6 | 5.1 | 68 B |
| 116 | R | NE | −21.7 | −47.8 | 5.2 | 64 B |
| 116 | R | CZ | −21.8 | −46.7 | 5.9 | 82 B |
| 116 | R | NH1 | −20.7 | −46.3 | 6.7 | 57 B |
| 116 | R | NH2 | −22.9 | −46.0 | 5.9 | 77 B |
| 117 | L | N | −17.1 | −50.3 | 2.3 | 56 B |
| 117 | L | CA | −17.3 | −51.7 | 1.7 | 58 B |
| 117 | L | C | −18.6 | −52.3 | 2.1 | 67 B |
| 117 | L | O | −19.1 | −52.2 | 3.3 | 68 B |
| 117 | L | CB | −16.1 | −52.6 | 2.2 | 57 B |
| 117 | L | CG | −15.7 | −53.8 | 1.4 | 61 B |
| 117 | L | CD1 | −15.4 | −53.4 | −0.1 | 61 B |
| 117 | L | CD2 | −14.5 | −54.4 | 2.0 | 60 B |
| 118 | A | N | −19.3 | −52.8 | 1.2 | 68 B |
| 118 | A | CA | −20.7 | −53.4 | 1.4 | 69 B |
| 118 | A | C | −20.6 | −54.6 | 2.3 | 81 B |
| 118 | A | O | −19.5 | −55.0 | 2.8 | 82 B |
| 118 | A | CB | −21.4 | −53.8 | 0.2 | 70 B |
| 119 | E | N | −21.7 | −55.2 | 2.6 | 81 B |
| 119 | E | CA | −21.7 | −56.4 | 3.5 | 82 B |
| 119 | E | C | −21.1 | −57.6 | 2.8 | 82 B |
| 119 | E | O | −20.4 | −58.4 | 3.4 | 81 B |
| 119 | E | CB | −23.1 | −56.7 | 4.0 | 84 B |
| 119 | E | CG | −23.6 | −55.8 | 5.2 | 0 B |
| 119 | E | CD | −23.8 | −54.3 | 4.7 | 0 B |
| 119 | E | OE1 | −24.1 | −54.1 | 3.5 | 0 B |
| 119 | E | OE2 | −23.7 | −53.4 | 5.5 | 0 B |
| 120 | N | N | −21.3 | −57.6 | 1.5 | 75 B |
| 120 | N | CA | −20.7 | −58.7 | 0.7 | 73 B |
| 120 | N | C | −19.2 | −58.7 | 0.6 | 75 B |
| 120 | N | O | −18.6 | −59.6 | 0.1 | 75 B |
| 120 | N | CB | −21.4 | −58.8 | −0.7 | 72 B |
| 120 | N | CG | −21.0 | −57.6 | −1.6 | 80 B |
| 120 | N | OD1 | −20.0 | −56.9 | −1.3 | 74 B |
| 120 | N | ND2 | −21.7 | −57.4 | −2.6 | 63 B |
| 121 | Q | N | −18.6 | −57.6 | 1.1 | 71 B |
| 121 | Q | CA | −17.2 | −57.5 | 1.1 | 71 B |
| 121 | Q | C | −16.6 | −57.2 | −0.3 | 73 B |
| 121 | Q | O | −15.3 | −57.1 | −0.5 | 72 B |
| 121 | Q | CB | −16.5 | −58.7 | 1.8 | 71 B |
| 121 | Q | CG | −16.5 | −58.8 | 3.3 | 78 B |
| 121 | Q | CD | −16.6 | −57.4 | 4.0 | 0 B |
| 121 | Q | OE1 | −15.6 | −56.8 | 4.3 | 96 B |
| 121 | Q | NE2 | −17.8 | −57.0 | 4.4 | 0 B |
| 122 | K | N | −17.4 | −57.0 | −1.3 | 67 B |
| 122 | K | CA | −17.0 | −56.7 | −2.7 | 67 B |
| 122 | K | C | −17.5 | −55.3 | −3.1 | 72 B |
| 122 | K | O | −16.7 | −54.4 | −3.5 | 72 B |
| 122 | K | CB | −17.4 | −57.8 | −3.7 | 69 B |
| 122 | K | CG | −17.2 | −59.3 | −3.3 | 75 B |
| 122 | K | CD | −15.9 | −59.8 | −3.9 | 78 B |
| 122 | K | CE | −14.8 | −59.7 | −2.9 | 83 B |
| 122 | K | NZ | −13.7 | −60.6 | −3.0 | 77 B |
| 123 | S | N | −18.8 | −55.1 | −3.0 | 66 B |
| 123 | S | CA | −19.5 | −53.9 | −3.3 | 64 B |
| 123 | S | C | −19.1 | −52.7 | −2.5 | 68 B |
| 123 | S | O | −18.6 | −52.8 | −1.4 | 68 B |
| 123 | S | CB | −21.0 | −54.1 | −3.4 | 65 B |
| 123 | S | OG | −21.3 | −54.8 | −4.6 | 70 B |
| 124 | C | N | −19.4 | −51.5 | −3.0 | 64 B |
| 124 | C | CA | −19.1 | −50.3 | −2.3 | 63 B |
| 124 | C | C | −20.4 | −49.4 | −2.1 | 66 B |
| 124 | C | O | −21.2 | −49.4 | −3.0 | 64 B |
| 124 | C | CB | −18.1 | −49.4 | −3.2 | 63 B |
| 124 | C | SG | −16.4 | −49.9 | −3.1 | 67 B |
| 125 | E | N | −20.4 | −48.8 | −1.0 | 61 B |
| 125 | E | CA | −21.6 | −48.0 | −0.7 | 62 B |
| 125 | E | C | −21.3 | −46.7 | −0.0 | 63 B |
| 125 | E | O | −20.2 | −46.6 | 0.6 | 63 B |
| 125 | E | CB | −22.6 | −48.8 | 0.2 | 64 B |
| 125 | E | CG | −21.9 | −49.5 | 1.4 | 82 B |
| 125 | E | CD | −23.0 | −50.0 | 2.4 | 0 B |
| 125 | E | OE1 | −23.8 | −50.9 | 2.0 | 83 B |
| 125 | E | OE2 | −23.0 | −49.5 | 3.5 | 93 B |
| 126 | P | N | −22.1 | −45.7 | −0.2 | 57 B |
| 126 | P | CA | −22.0 | −44.3 | 0.3 | 57 B |
| 126 | P | C | −21.9 | −44.3 | 1.9 | 63 B |
| 126 | P | O | −22.7 | −44.9 | 2.5 | 67 B |
| 126 | P | CB | −23.3 | −43.6 | −0.1 | 58 B |
| 126 | P | CG | −23.7 | −44.4 | −1.4 | 62 B |
| 126 | P | CD | −23.3 | −45.8 | −1.2 | 58 B |
| 127 | A | N | −20.9 | −43.7 | 2.4 | 58 B |
| 127 | A | CA | −20.7 | −43.5 | 3.8 | 58 B |
| 127 | A | C | −20.8 | −42.0 | 4.1 | 63 B |
| 127 | A | O | −20.4 | −41.6 | 5.2 | 64 B |
| 127 | A | CB | −19.2 | −44.0 | 4.2 | 58 B |
| 128 | V | N | −21.4 | −41.3 | 3.2 | 55 B |
| 128 | V | CA | −21.6 | −39.9 | 3.4 | 52 B |
| 128 | V | C | −22.8 | −39.4 | 2.6 | 54 B |
| 128 | V | O | −23.4 | −40.1 | 1.7 | 54 B |
| 128 | V | CB | −20.4 | −39.1 | 3.0 | 55 B |
| 128 | V | CG1 | −19.2 | −39.5 | 3.8 | 54 B |
| 128 | V | CG2 | −20.2 | −39.1 | 1.5 | 54 B |
| 129 | P | N | −23.3 | −38.2 | 2.9 | 50 B |
| 129 | P | CA | −24.5 | −37.8 | 2.2 | 50 B |
| 129 | P | C | −24.3 | −37.6 | 0.7 | 55 B |
| 129 | P | O | −25.2 | −38.1 | −0.1 | 55 B |
| 129 | P | CB | −24.9 | −36.5 | 2.9 | 51 B |
| 129 | P | CG | −24.2 | −36.5 | 4.2 | 55 B |
| 129 | P | CD | −23.0 | −37.3 | 4.0 | 51 B |
| 130 | F | N | −23.2 | −36.9 | 0.3 | 51 B |
| 130 | F | CA | −23.0 | −36.7 | −1.1 | 49 B |

TABLE 6-continued

Coordinates of Factor IXa-Compound D complex

| | | | | | | |
|---|---|---|---|---|---|---|
| 130 | F | C | −21.6 | −37.2 | −1.5 | 50 | B |
| 130 | F | O | −20.7 | −36.4 | −1.7 | 51 | B |
| 130 | F | CB | −23.1 | −35.2 | −1.4 | 49 | B |
| 130 | F | CG | −24.5 | −34.7 | −1.1 | 49 | B |
| 130 | F | CD1 | −24.8 | −34.2 | 0.2 | 50 | B |
| 130 | F | CD2 | −25.6 | −34.9 | −2.0 | 48 | B |
| 130 | F | CE1 | −26.1 | −33.7 | 0.5 | 48 | B |
| 130 | F | CE2 | −26.9 | −34.5 | −1.7 | 49 | B |
| 130 | F | CZ | −27.1 | −33.9 | −0.4 | 46 | B |
| 131 | P | N | −21.4 | −38.5 | −1.6 | 44 | B |
| 131 | P | CA | −20.2 | −39.1 | −2.0 | 42 | B |
| 131 | P | C | −19.8 | −38.7 | −3.5 | 42 | B |
| 131 | P | O | −20.6 | −38.5 | −4.3 | 39 | B |
| 131 | P | CB | −20.5 | −40.6 | −2.0 | 43 | B |
| 131 | P | CG | −22.0 | −40.7 | −2.3 | 47 | B |
| 131 | P | CD | −22.6 | −39.4 | −1.8 | 44 | B |
| 132 | C | N | −18.5 | −38.6 | −3.7 | 39 | B |
| 132 | C | CA | −18.0 | −38.2 | −5.1 | 40 | B |
| 132 | C | C | −18.5 | −39.1 | −6.2 | 46 | B |
| 132 | C | O | −18.6 | −40.3 | −6.0 | 46 | B |
| 132 | C | CB | −16.4 | −38.3 | −5.1 | 40 | B |
| 132 | C | SG | −15.8 | −40.0 | −5.0 | 44 | B |
| 133 | G | N | −18.6 | −38.5 | −7.4 | 44 | B |
| 133 | G | CA | −19.0 | −39.3 | −8.6 | 43 | B |
| 133 | G | C | −20.3 | −40.0 | −8.7 | 49 | B |
| 133 | G | O | −20.5 | −40.9 | −9.5 | 49 | B |
| 134 | R | N | −21.3 | −39.5 | −7.9 | 48 | B |
| 134 | R | CA | −22.6 | −40.1 | −7.9 | 47 | B |
| 134 | R | C | −23.6 | −39.0 | −8.4 | 46 | B |
| 134 | R | O | −23.6 | −37.9 | −7.9 | 44 | B |
| 134 | R | CB | −23.1 | −40.5 | −6.5 | 50 | B |
| 134 | R | CG | −22.6 | −41.9 | −6.1 | 70 | B |
| 134 | R | CD | −22.4 | −42.8 | −7.3 | 76 | B |
| 134 | R | NE | −22.0 | −44.2 | −6.8 | 92 | B |
| 134 | R | CZ | −22.7 | −45.0 | −6.2 | 0 | B |
| 134 | R | NH1 | −24.0 | −44.7 | −5.9 | 0 | B |
| 134 | R | NH2 | −22.3 | −46.2 | −5.9 | 0 | B |
| 135 | V | N | −24.5 | −39.3 | −9.3 | 45 | B |
| 135 | V | CA | −25.6 | −38.4 | −9.7 | 44 | B |
| 135 | V | C | −26.7 | −38.8 | −8.7 | 53 | B |
| 135 | V | O | −27.1 | −40.0 | −8.6 | 52 | B |
| 135 | V | CB | −26.0 | −38.7 | −11.2 | 45 | B |
| 135 | V | CG1 | −27.3 | −38.0 | −11.5 | 43 | B |
| 135 | V | CG2 | −24.9 | −38.2 | −12.1 | 45 | B |
| 136 | S | N | −27.2 | −37.8 | −8.0 | 52 | B |
| 136 | S | CA | −28.2 | −38.1 | −7.0 | 53 | B |
| 136 | S | C | −29.5 | −37.3 | −7.2 | 63 | B |
| 136 | S | O | −30.4 | −37.3 | −6.3 | 63 | B |
| 136 | S | CB | −27.6 | −37.7 | −5.6 | 52 | B |
| 136 | S | OG | −27.4 | −36.3 | −5.5 | 54 | B |
| 137 | V | N | −29.6 | −36.7 | −8.3 | 63 | B |
| 137 | V | CA | −30.9 | −35.9 | −8.7 | 64 | B |
| 137 | V | C | −31.6 | −36.8 | −9.7 | 75 | B |
| 137 | V | O | −30.9 | −37.3 | −10.7 | 76 | B |
| 137 | V | CB | −30.5 | −34.5 | −9.2 | 66 | B |
| 137 | V | CG1 | −31.5 | −34.0 | −10.2 | 65 | B |
| 137 | V | CG2 | −30.3 | −33.6 | −8.1 | 66 | B |
| 138 | S | N | −32.9 | −36.9 | −9.6 | 74 | B |
| 138 | S | CA | −33.7 | −37.7 | −10.6 | 74 | B |
| 138 | S | C | −33.4 | −37.3 | −12.0 | 79 | B |
| 138 | S | O | −33.3 | −36.1 | −12.4 | 78 | B |
| 138 | S | CB | −35.2 | −37.5 | −10.2 | 78 | B |
| 138 | S | OG | −35.9 | −38.6 | −10.8 | 86 | B |
| 139 | Q | N | −33.3 | −38.3 | −12.9 | 77 | B |
| 139 | Q | CA | −33.0 | −38.1 | −14.3 | 76 | B |
| 139 | Q | C | −34.2 | −38.4 | −15.2 | 82 | B |
| 139 | Q | O | −35.1 | −37.6 | −15.5 | 82 | B |
| 139 | Q | CB | −31.8 | −38.9 | −14.8 | 76 | B |
| 139 | Q | CG | −30.5 | −38.6 | −14.0 | 74 | B |
| 139 | Q | CD | −29.9 | −37.3 | −14.5 | 76 | B |
| 139 | Q | OE1 | −29.8 | −36.3 | −13.8 | 72 | B |
| 139 | Q | NE2 | −29.6 | −37.2 | −15.8 | 58 | B |
| 500 | X | CA | −28.2 | −21.4 | −14.1 | 0 | B |
| 501 | X | C1 | 6.0 | −36.1 | −18.2 | 42 | Q |
| 501 | X | O1 | 5.3 | −37.2 | −18.0 | 40 | Q |
| 501 | X | O2 | 6.0 | −35.2 | −17.3 | 44 | Q |
| 501 | X | C2 | 6.6 | −35.9 | −19.6 | 39 | Q |
| 501 | X | C3 | 6.6 | −37.1 | −20.6 | 36 | Q |
| 501 | X | O7 | 7.4 | −38.2 | −20.0 | 32 | Q |
| 501 | X | C4 | 7.2 | −36.7 | −21.9 | 37 | Q |
| 501 | X | C5 | 7.3 | −37.8 | −23.0 | 41 | Q |
| 501 | X | O3 | 6.2 | −38.4 | −23.4 | 40 | Q |
| 501 | X | O4 | 8.5 | −38.2 | −23.3 | 46 | Q |
| 501 | X | C6 | 5.2 | −37.8 | −23.0 | 34 | Q |
| 501 | X | O5 | 5.4 | −39.0 | −20.5 | 37 | Q |
| 501 | X | O6 | 4.3 | −37.1 | −21.2 | 35 | Q |
| 502 | X | C1 | 9.2 | −41.4 | −18.4 | 51 | Q |
| 502 | X | O1 | 9.6 | −41.2 | −19.6 | 55 | Q |
| 502 | X | O2 | 9.8 | −40.9 | −17.4 | 56 | Q |
| 502 | X | C2 | 7.8 | −42.0 | −18.3 | 44 | Q |
| 502 | X | C3 | 6.7 | −41.4 | −19.2 | 43 | Q |
| 502 | X | O7 | 6.7 | −40.0 | −19.0 | 36 | Q |
| 502 | X | C4 | 5.4 | −42.0 | −19.0 | 47 | Q |
| 502 | X | C5 | 5.0 | −42.3 | −17.6 | 51 | Q |
| 502 | X | O3 | 4.5 | −41.3 | −16.9 | 54 | Q |
| 502 | X | O4 | 5.3 | −43.4 | −17.2 | 49 | Q |
| 502 | X | C6 | 7.1 | −41.4 | −20.7 | 45 | Q |
| 502 | X | O5 | 7.2 | −40.2 | −21.1 | 47 | Q |
| 502 | X | O6 | 7.4 | −42.5 | −21.2 | 46 | Q |
| 503 | X | C1 | 4.6 | −33.7 | −7.7 | 42 | Q |
| 503 | X | O1 | 5.1 | −33.0 | −8.6 | 39 | Q |
| 503 | X | O2 | 4.5 | −33.3 | −6.4 | 46 | Q |
| 503 | X | C2 | 4.1 | −35.1 | −8.1 | 41 | Q |
| 503 | X | C3 | 4.1 | −35.5 | −9.6 | 43 | Q |
| 503 | X | O7 | 3.1 | −34.6 | −10.2 | 41 | Q |
| 503 | X | C4 | 3.7 | −36.9 | −9.8 | 41 | Q |
| 503 | X | C5 | 2.3 | −37.3 | −9.3 | 41 | Q |
| 503 | X | O3 | 1.4 | −36.4 | −9.1 | 45 | Q |
| 503 | X | O4 | 2.1 | −38.5 | −9.2 | 38 | Q |
| 503 | X | C6 | 5.6 | −35.2 | −10.3 | 42 | Q |
| 503 | X | O5 | 5.5 | −34.5 | −11.3 | 43 | Q |
| 503 | X | O6 | 6.5 | −35.8 | −9.7 | 42 | Q |
| 1 | Z | C1 | −8.6 | −21.0 | −23.7 | 67 | S |
| 1 | Z | C2 | −8.3 | −20.2 | −22.6 | 67 | S |
| 1 | Z | C3 | −7.1 | −19.6 | −22.5 | 69 | S |
| 1 | Z | C4 | −6.1 | −19.7 | −23.5 | 72 | S |
| 1 | Z | C5 | −6.4 | −20.5 | −24.6 | 75 | S |
| 1 | Z | C6 | −7.7 | −21.1 | −24.7 | 74 | S |
| 1 | Z | C12 | −8.0 | −22.0 | −25.9 | 76 | S |
| 1 | Z | N13 | −7.8 | −21.5 | −27.3 | 75 | S |
| 1 | Z | N14 | −8.3 | −22.7 | −28.0 | 73 | S |
| 1 | Z | C15 | −8.6 | −23.7 | −27.1 | 73 | S |
| 1 | Z | C16 | −8.4 | −23.2 | −25.8 | 74 | S |
| 1 | Z | O17 | −8.7 | −23.9 | −24.6 | 69 | S |
| 1 | Z | C18 | −9.0 | −25.0 | −27.5 | 68 | S |
| 1 | Z | N19 | −9.2 | −25.6 | −28.7 | 65 | S |
| 1 | Z | C20 | −9.7 | −26.9 | −28.5 | 57 | S |
| 1 | Z | C21 | −9.7 | −27.1 | −27.1 | 59 | S |
| 1 | Z | N22 | −9.3 | −25.9 | −26.5 | 63 | S |
| 1 | Z | C23 | −10.0 | −27.8 | −29.4 | 51 | S |
| 1 | Z | C24 | −10.4 | −29.1 | −28.9 | 55 | S |
| 1 | Z | C25 | −10.4 | −29.3 | −27.5 | 56 | S |
| 1 | Z | C26 | −10.1 | −28.3 | −26.6 | 56 | S |
| 1 | Z | C30 | −10.7 | −30.1 | −29.8 | 58 | S |
| 1 | Z | N31 | −10.2 | −30.0 | −31.1 | 65 | S |
| 1 | Z | N32 | −11.2 | −31.3 | −29.4 | 57 | S |
| 2 | O | O | −23.4 | −29.6 | −32.4 | 60 | W |
| 4 | O | O | −26.7 | −35.4 | −9.1 | 37 | W |
| 5 | O | O | −18.1 | −35.1 | −17.2 | 42 | W |
| 6 | O | O | −15.6 | −28.2 | −19.8 | 30 | W |
| 7 | O | O | −21.4 | −25.7 | −13.1 | 43 | W |
| 9 | O | O | −26.4 | −25.6 | −5.0 | 40 | W |
| 10 | O | O | 4.0 | −20.6 | −17.9 | 51 | W |
| 11 | O | O | 4.2 | −26.6 | −20.4 | 33 | W |
| 12 | O | O | −19.0 | −27.4 | 2.7 | 39 | W |
| 13 | O | O | −11.9 | −35.9 | −5.6 | 34 | W |
| 14 | O | O | −1.0 | −46.6 | −7.8 | 47 | W |
| 15 | O | O | −17.1 | −25.6 | −20.0 | 38 | W |
| 16 | O | O | −27.1 | −25.4 | −26.6 | 64 | W |
| 17 | O | O | −4.3 | −42.0 | −27.0 | 38 | W |
| 18 | O | O | −4.6 | −31.4 | −37.7 | 52 | W |
| 20 | O | O | 2.3 | −36.9 | −33.9 | 58 | W |
| 21 | O | O | −11.1 | −38.0 | −36.6 | 41 | W |
| 22 | O | O | −13.9 | −36.7 | −33.0 | 35 | W |
| 23 | O | O | −18.7 | −39.5 | −36.5 | 48 | W |
| 24 | O | O | −12.7 | −35.7 | −28.1 | 36 | W |

TABLE 6-continued

Coordinates of Factor IXa-Compound D complex

| | | | | | | | |
|---|---|---|---|---|---|---|---|
| 27 | O | O | −12.6 | −44.8 | −20.3 | 38 | W |
| 28 | O | O | −17.6 | −44.2 | −19.1 | 34 | W |
| 29 | O | O | −8.0 | −34.6 | −2.7 | 44 | W |
| 30 | O | O | −14.5 | −52.8 | −4.2 | 61 | W |
| 31 | O | O | −9.4 | −41.4 | −11.1 | 27 | W |
| 32 | O | O | −11.2 | −31.0 | −14.8 | 31 | W |
| 33 | O | O | −6.4 | −35.5 | −0.6 | 52 | W |
| 34 | O | O | −10.2 | −34.2 | −0.8 | 47 | W |
| 35 | O | O | −20.6 | −27.0 | −25.3 | 35 | W |
| 36 | O | O | −23.2 | −38.7 | −15.4 | 48 | W |
| 41 | O | O | −10.0 | −32.3 | −33.3 | 53 | W |
| 42 | O | O | −12.6 | −35.0 | −34.4 | 46 | W |
| 44 | O | O | −5.4 | −35.2 | −33.8 | 37 | W |
| 45 | O | O | −4.7 | −32.7 | −32.9 | 46 | W |
| 46 | O | O | −24.2 | −36.9 | −29.0 | 56 | W |
| 47 | O | O | −21.6 | −41.6 | −12.2 | 46 | W |
| 48 | O | O | −20.7 | −39.5 | −15.8 | 46 | W |
| 49 | O | O | −25.1 | −29.7 | −11.3 | 46 | W |
| 51 | O | O | −21.4 | −28.3 | −10.5 | 45 | W |
| 52 | O | O | −20.7 | −29.2 | 2.1 | 49 | W |
| 53 | O | O | −9.3 | −36.5 | −4.7 | 39 | W |
| 57 | O | O | −1.0 | −18.9 | −18.3 | 67 | W |
| 55 | O | O | −5.5 | −15.3 | −8.1 | 54 | W |
| 57 | O | O | −23.0 | −20.0 | −2.3 | 40 | W |
| 58 | O | O | −25.1 | −19.9 | −3.9 | 45 | W |
| 59 | O | O | 8.2 | −33.8 | −12.0 | 27 | W |
| 60 | O | O | 3.0 | −34.7 | −20.9 | 34 | W |
| 62 | O | O | −0.7 | −32.1 | −20.4 | 37 | W |
| 63 | O | O | −9.4 | −43.1 | −4.4 | 42 | W |
| 64 | O | O | −5.4 | −41.0 | −16.6 | 35 | W |
| 65 | O | O | −3.8 | −42.9 | −17.5 | 35 | W |
| 66 | O | O | −8.0 | −51.4 | −18.2 | 45 | W |
| 67 | O | O | −11.1 | −43.7 | −22.3 | 39 | W |
| 68 | O | O | −12.1 | −41.9 | −23.9 | 32 | W |
| 69 | O | O | −20.9 | −40.3 | −28.3 | 56 | W |
| 70 | O | O | −0.8 | −47.8 | −30.7 | 60 | W |
| 71 | O | O | −5.0 | −46.8 | −39.8 | 53 | W |
| 72 | O | O | −10.3 | −43.6 | −34.7 | 33 | W |
| 81 | O | O | −10.4 | −14.8 | −19.9 | 64 | W |
| 82 | O | O | 0.6 | −34.1 | −19.3 | 44 | W |
| 83 | O | O | −22.9 | −39.2 | −26.1 | 41 | W |
| 84 | O | O | −29.7 | −26.7 | −12.3 | 54 | W |
| 85 | O | O | −24.7 | −31.1 | −13.9 | 54 | W |
| 86 | O | O | −24.1 | −37.0 | −26.3 | 49 | W |
| 87 | O | O | −27.2 | −40.0 | −24.6 | 72 | W |
| 89 | O | O | −24.0 | −36.6 | −33.5 | 57 | W |
| 90 | O | O | −21.3 | −39.6 | −36.0 | 73 | W |
| 91 | O | O | −12.8 | −45.6 | 1.9 | 57 | W |
| 92 | O | O | −2.1 | −17.5 | −6.9 | 41 | W |
| 93 | O | O | −15.0 | −52.4 | −18.1 | 54 | W |
| 94 | O | O | −0.1 | −40.1 | −9.6 | 49 | W |
| 95 | O | O | −19.9 | −45.0 | −30.7 | 46 | W |
| 96 | O | O | −24.4 | −39.0 | −30.2 | 75 | W |
| 97 | O | O | −24.5 | −42.9 | −31.5 | 63 | W |
| 101 | O | O | −9.9 | −32.0 | −26.2 | 36 | W |
| 102 | O | O | −20.6 | −18.5 | −16.8 | 51 | W |
| 103 | O | O | −3.9 | −49.8 | −6.7 | 56 | W |
| 104 | O | O | −4.9 | −54.4 | −9.3 | 59 | W |
| 105 | O | O | −11.3 | −45.5 | −31.0 | 35 | W |
| 106 | O | O | 8.0 | −33.3 | −21.7 | 42 | W |
| 107 | O | O | −14.7 | −33.4 | −41.1 | 54 | W |
| 108 | O | O | −23.1 | −30.3 | −28.6 | 48 | W |
| 109 | O | O | −23.1 | −28.5 | −13.2 | 48 | W |
| 110 | O | O | −2.2 | −49.1 | −14.7 | 47 | W |
| 111 | O | O | −12.3 | −43.6 | −32.7 | 33 | W |

Example 23

Factor IXa and Xa Protease Assays

The following factor IXa and Xa assays were performed to determine that ability of various compounds to inhibit factor IXa and factor Xa protease activity.

Factor IXa Functional Assay Protocol:
Buffer:
50 mM Tris pH 8.0
5 mM $CaCl_2.2H_2O$
100 mM NaCl
15% vol/vol Ethylene Glycol
Enzyme:
Human plasma factor IXa. (American Diagnostica Inc. product)
Enzyme is diluted 1:800 in buffer to achieve 0.0057 μg/ml working stock for use in assay. Mixed by inversion.
Substrate:
Spectrozyme factor IXa Fluorogenic substrate (American Diagnostica Inc.; Stamford, Conn.): Methylsulfonyl-D-cyclohexylglycyl-glycyl-arginine-paranitroanilide monoacetate salt. The substrate (10 umoles lyophilized) was reconstituted with 1 ml water to give a 10 mM stock. The substrate was then further diluted to 300 μm in buffer for use in assay and mixed by inversion.
Procedure in 384 Well Plate:
Added 10 μl vehicle or compound
Added 10 μl Factor IXa enzyme.
Added 10 μl Fluorogenic substrate.
Incubated reaction at room temperature for 2 h.
Quenched with 5 ul 50% acetic acid.
Read Fluorescence—Absorbance 360 nm; Emission 440 nm
Factor Xa Functional Assay Protocol:
Buffer:
20 mM Tris pH 8.0
2.5 mM $CaCl_2.2H_2O$
200 mM NaCl
Enzyme:
Human plasma factor Xa. (American Diagnostica Inc.; see supra)
Resuspended enyme in water to 80 ug/ml.
Enzyme was diluted to 0.133 μg/ml in buffer. Mixed by inversion.
Substrate:
Spectrozyme factor IXa Fluorogenic substrate (American Diagnostica Inc.)
Reconstituted with 1 ml water to give a 10 mM stock. The substrate was then further diluted to 300 μM in buffer for use in assay. Mixed by inversion.
Procedure in 384 Well Plate:
Added 10 μl vehicle or compound
Added 10 μl Factor Xa enzyme.
Added 10 μl Fluorogenic substrate.
Incubated reaction at room temperature for 2 h.
Quenched with 5 μl 50% acetic acid.
Read Fluorescence Absorbance 360 nm; Emission 440 nm

Example 24

Cloning of Recombinant Human Factor IX(R318A)

The mutant rFIXa(R318A) was made starting with the wt-pENTR/SD/D-TOPO vector as the template and a modification of the QuickChange protocol (Wang W, Malcolm B A. Methods Mol Biol. 182:37-43 (2002) using the following complementary primers:

(SEQ ID NO: 16)
1) R318A(+): CCACAAAGGGGCATCAGCTTTAGTTCTTC (SEQ ID NO: 17)
2) R318A(−): GAAGAACTAAAGCTGATGCCCCTTTGTGG

After the sequence was confirmed, the expression vector was made by the Gateway LR reaction between the pENTR/

SD/D-TOPO shuttle and the pDest 14™ E. coli expression vector (Invitrogen, Carlsbad, Calif.).

Example 25

Expression of Recombinant Human Factor IX(R318A)

A colony from freshly transformed cells was grown in 10 ml terrific broth with 100 µg/ml ampicillin for 3 hours at 37° C. The 10 ml of culture was then used to initiate a 1.0 L culture with the same medium, and it was grown to an OD of approximately 1.0 at 37° C. and stored at 4° C. overnight for inoculation of a 10 L tank (terrific broth containing 100 µg/ml ampicillin). The 10 L culture was grown to an OD of 0.8-1.0 at 37° C., and was induced with 0.5 mM IPTG. The cells were harvested by centrifugation at 5000 g after 4-6 hours and stored at −20° C.

Example 26

Purification of Recombinant Human Factor IX(R318A)

The purification and refolding of fIX was performed essentially as described by Hopfner at al. (supra). The pellet from the 6 L fermentation was re-suspended in 150 ml of 50 mM Tris pH 7.3 and lysed by 2 passes through a micro-fluidizer. DNA was digested by the addition of 2 mM $MgCl_2$ and 1000 U Benzonase and incubated at room temperature for 30 minutes. The mixture was made with 2% Triton X-100, 0.5 M NaCl and 20 mM EDTA and was incubated for an additional 30 minutes. Inclusion bodies were isolated by centrifugation at 25,000 g for 30 minutes. The inclusion bodies were solubilized in 6 M guanidine HCl, 100 mM Tris-HCl, 20 mM EDTA, 150 mM oxidized glutathione/15 mM reduced glutathione, pH 8.2 at a concentration of 5.0 mg/ml and incubated for 3 hours at room temperature. After adjusting the pH to 5.0 the protein was dialyzed, at 4° C., against several changes of 6 M guanidine HCl, 100 mM Tris-HCl, 20 mM EDTA, pH 5.0. The dialyzed protein was recovered and refolding was initiated by diluting 100-fold into 50 mM Tris, 0.5 M arginine, 1 mM EDTA, 20 mM $CaCl_2$, 0.5 mM cysteine, pH 8.5 and incubated with gentle stirring for at least 3 days at 4° C.

The refolding solution was concentrated to a minimum volume using an Amicon pellicon device fitted with a 10 k filter, clarified by centrifugation at 5000 g for 15 minutes and dialyzed overnight against several changes of 50 mM Tris-HCl pH 8.0, 0.05 M NaCl. The dialyzed protein was applied to a 10 ml Q-Sepharose FF column equilibrated with 50 mM Tris-HCl pH 8.0, 50 mM NaCl and the refolded rFIX was eluted with a 50-500 mM NaCl gradient. The protein containing fractions were pooled, adjusted to 1 mg/ml, and stored at −80° C.

Example 27

Activation and Preparation of Factor IXa(R318A) Complexes (General)

Aliquots of purified fIX were defrosted as needed and were activated by incubating overnight at 37° C. with 20 µg/ml of Russell's Viper venom (RVV) (Sigma V2501). The activated protein was desalted into 50 mM Tris-HCl pH 8.0, 50 mM NaCl, using a HiPrep desalting column, and applied to a HiTrap 5 ml QHP column. The flow-through containing the purified fIXa was collected, concentrated to and applied to a Superdex 8-200 column equilibrated with 25 mM Tris-HCl pH 8.0, 0.15 M NaCl. The monomer fractions were pooled and inhibitor was added to 100 µM. The protein was concentrated to 10 mg/ml (330 µM) and additional inhibitor was added to 660-1000 µM.

Following activation, the activation polypeptide was removed to create two separate polypeptides: DVTCNIKN-GRCEQFCKNSADNKVVCSCTEGYRLAENQKSCEPA-VPFPCGRVSVSQTEKLTR (SEQ ID NO: 13); and VVGGEDAKPGQFPWQVVLNGKVDAFCGGSI-VNEKWIVTAAHCVETGVKITVVAGEHNIEETEHT-EQKRN VIRIIPHHNYNAAINKYNHDIALLELDE-PLVLNSYVTPICIADKEYTNIFLKFGSGYVEGWGRV-FEKGA SALVLQYLRVPLVDRATCLRETKFTIYN-NMFCAGFFIEGGRDSCQGDSGGPHVTEVEGTSF-LTGIISWGE ECAMKGKYGIYTKVSRYVNWIKEKT-KLT (SEQ ID NO: 18); which were joined by disulfide bridges. The alanine in bold face indicates the mutation site. This activated dimeric molecule is factor IXa(R318A) and was used for further crystallization studies.

Preparation of Specific Factor IXa R318A-Compound A Complex

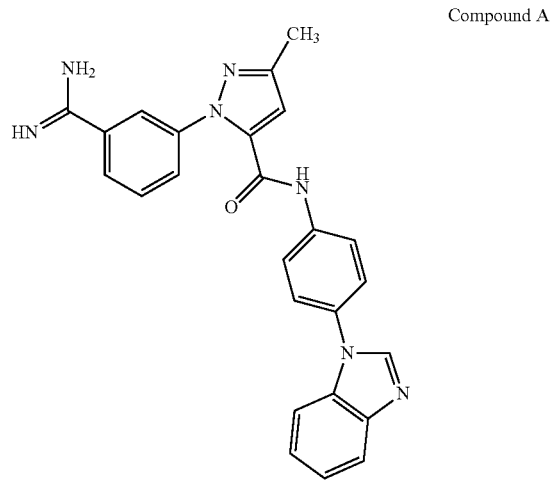 [SMILES: Cc1cc(C(=O)Nc2ccc(-n3cnc4ccccc43)cc2)n(-c2cccc(C(=N)N)c2)n1]

Compound A

Compound A was added to a final concentration of 1 mM into 22.5 µL of fIXa R318A mutant at 023 mg/ml. (6.4 µM). The final DMSO concentration was 1%. The complex was rotated on a nutator for 2-18 hours at 2° C. The sample was clarified by low speed centrifugation followed by a 52 fold concentration step using centrifugation with a 5000 Molecular Weight Cut Off Millipore Ultrafree micro concentrator (Millipore, Billerica, Mass.) to 10-12 mg/ml. Dynamic light scattering was used to measure the aggregation state of the concentrated fIXa R318A-Compound A complex. A single component was observed-consistent with a monodisperse monomer (33000 MW) in solution. SDS PAGE analysis showed no visible signs of degradation four days post setup. Dynamic light scattering and SDS PAGE results were consistent with a stable monodisperse fIXa complex suitable for crystallization screening.

The fIXaR318A mutant can also be used for forming complexes with Compounds B-D using methods described herein and exemplified for Compound A.

Example 28

Crystallization of Factor IXa R318A-Compound A Complex

The factor IXa R318A-Compound A complex from Example 5 was crystallized using a hanging-drop vapor diffusion method. The protein (0.5 µl; 6 mg/ml) in 25 mM Tris, pH 8.0, 0.15 M sodium chloride, buffer was mixed with an equal volume of precipitant solution containing 20% PEG 6000 (v/v), 0.1 M citric acid, pH 5.9 placed on the underside of a siliconized Teflon coverslip and sealed in close proximity to 0.08 mL of the precipitant solution. Crystallization plates were incubated at 4° C.; orthorhombic crystals (0.01×0.05 mm) grew over 1-30 days.

Factor IXaR318A-Compound B-D complexes can also be crystallized using methods described herein and exemplified for Compound A.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

---

We claim:
1. A method for determining the structure of a complex comprising a compound and a peptide bound to factor IXa protein, wherein said factor IXa is selected from the group consisting of SEQ ID NO: 14 and 18, said peptide comprises SEQ ID NO: 13 and said compound is selected from the group consisting of:

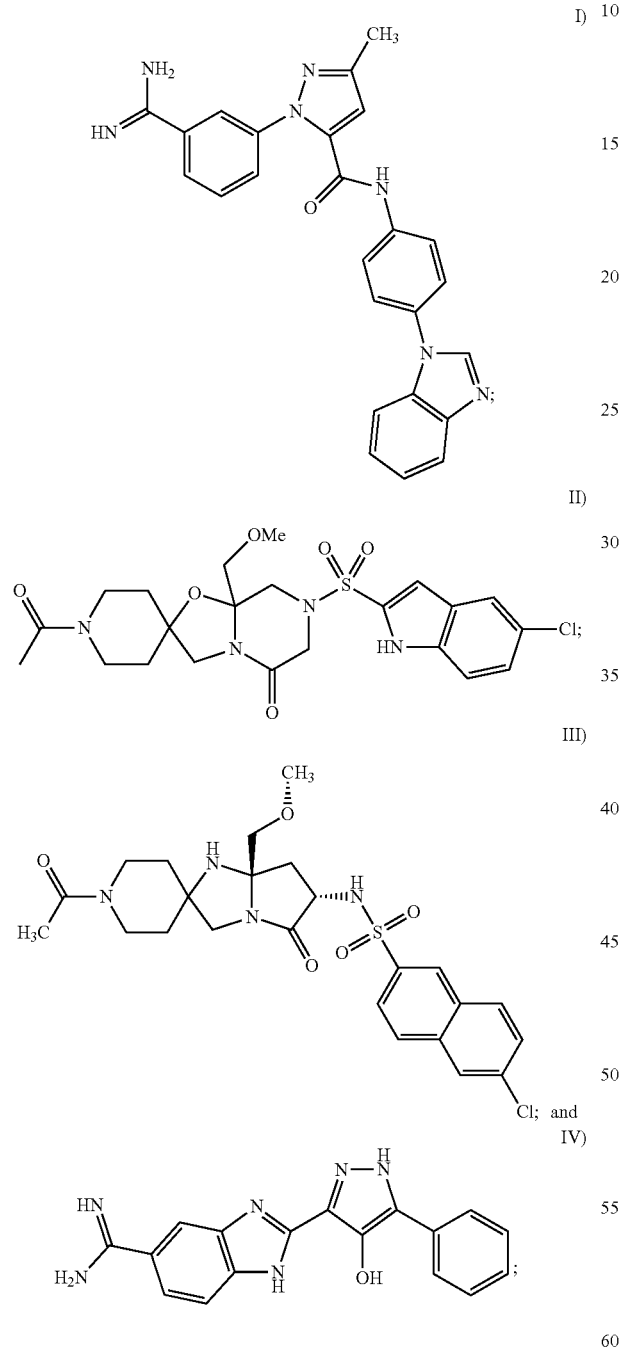

said method comprising: (a) mixing the factor IXa protein with the compound; (b) crystallizing said factor IXa protein-compound complex; and (c) determining the three-dimensional structure of the complex which results in atomic coordinate data of any one of Tables 2-6 optionally varied by a root mean square deviation of conserved residue backbone atoms or of alpha carbon atoms of less than about 1.5 Å when superimposed on backbone atoms described in Table 2, 3, 4, 5 or 6, and wherein the resultant crystal of part (b) forms in one of in the following crystalline space groups and unit cell parameters:

(i) space group $P2_12_12_1$ having unit cell dimensions a=48.1 Å, b=69.8 Å, c=92.1 Å and $\alpha=\beta=\gamma=90°$ or space group $P4_32_12$ having unit cell dimensions a=100.4 Å, b=100.4 Å, c=97.3 Å and $\alpha=\beta=\gamma=90°$;

(ii) space group $P4_32_12$ having unit cell dimensions a=100.6 Å, b=100.6 Å, c=98.1 Å and $\alpha=\beta=\gamma=90°$;

(iii) space group $P4_32_12$ having unit cell dimensions a=99.2 Å, b=99.2 Å, c=97.3 Å and $\alpha=\beta=\gamma=90°$; and (iv) space group $P4_32_12$ having unit cell dimensions a=100.5 Å, b=100.5 Å, c=98.4 Å and $\alpha=\beta=\gamma=90°$.

2. A method for determining the structure of a complex comprising a first compound and a peptide bound to factor IXa protein and a second compound, wherein said factor IXa is selected from the group consisting of SEQ ID NO: 14 and 18, said peptide comprises SEQ ID NO: 13 and said first compound is selected from the group consisting of:

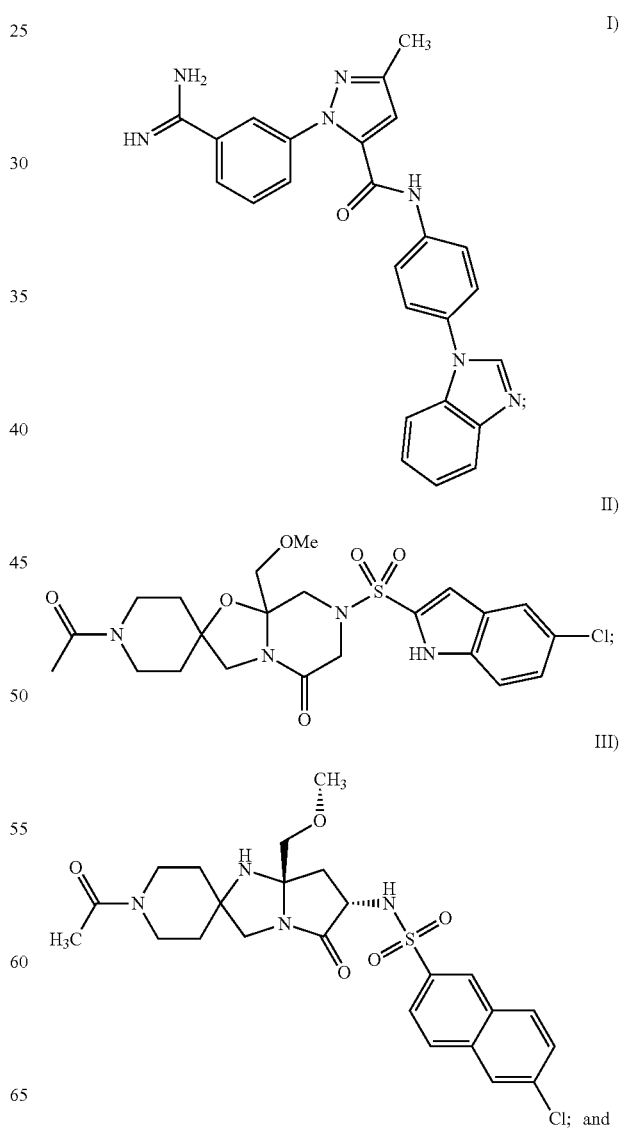

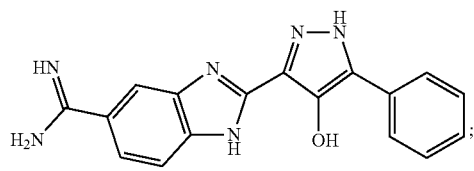

and wherein said second compound bound to said factor IXa protein is complexed with said first compound, said method comprising; (a) providing a crystal of factor IXa protein complexed with the first compound and the peptide, wherein said crystal forms in one of in the following crystalline space groups and unit cell parameters:

(i) space group P2$_1$2$_1$2$_1$ having unit cell dimensions a=48.1 Å, b=69.8 Å, c=92.1 Å and α=β=γ=90° or space group P4$_3$2$_1$2 having unit cell dimensions a=100.4 Å, b=100.4 Å, c=97.3 Å and α=β=γ=90°;

(ii) space group P4$_3$2$_1$2 having unit cell dimensions a=100.6 Å, b=100.6 Å, c=98.1 Å and α=β=γ=90°;

(iii) space group P4$_3$2$_1$2 having unit cell dimensions a=99.2 Å, b=99.2 Å, c=97.3 Å and α=β=γ=90°; and (iv) space group P4$_3$2$_1$2 having unit cell dimensions a=100.5 Å, b=100.5 Å, c=98.4 Å and α=β=γ=90°;

(b) soaking the crystal with a second compound to form a complex between said factor IXa protein and said second compound; and (c) determining the structure of the complex to determine the three-dimensional structure which results in atomic coordinate which varies by a root mean square deviation of conserved residue backbone atoms or of alpha carbon atoms of less than about 1.5 Å when superimposed on backbone atoms described in Table 2, 3, 4, 5 or 6.

3. A method for identifying a substance which inhibits blood clotting or binds to factor IXa comprising (a) providing a crystal of factor IXa protein complexed with a first compound and a peptide, wherein said factor IXa is selected from the group consisting of SEQ ID NO: 14 and 18, said peptide comprises SEQ ID NO: 13 and said first compound is selected from the group consisting of:

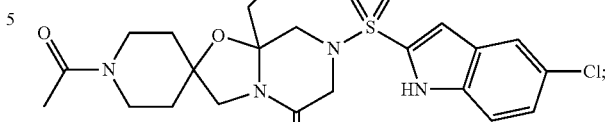

and said crystal forms in one of in the following crystalline space groups and unit cell parameters:

(i) space group P2$_1$2$_1$2$_1$ having unit cell dimensions a=48.1 Å, b=69.8 Å, c=92.1 Å and α=β=γ=90° or space group P4$_3$2$_1$2 having unit cell dimensions a=100.4 Å, b=100.4 Å, c=97.3 Å and α=β=γ=90°;

(ii) space group P4$_3$2$_1$2 having unit cell dimensions a=100.6 Å, b=100.6 Å, c=98.1 Å and α=β=γ=90°;

(iii) space group P4$_3$2$_1$2 having unit cell dimensions a=99.2 Å, b=99.2 Å, c=97.3 Å and α=β=γ=90°; and (iv) space group P4$_3$2$_1$2 having unit cell dimensions a=100.5 Å, b=100.5 Å, c=98.4 Å and α=β=γ=90°;

(b) soaking the crystal comprising the first compound with a second substance to form a complex between said factor IXa protein and said second substance; and ((c) determining the structure of the complex to determine the three-dimensional structure which results in atomic coordinate which varies by a root mean square deviation of conserved residue backbone atoms or of alpha carbon atoms of less than about 1.5 Å when superimposed on backbone atoms described in Table 2, 3, 4, 5 or 6; and, wherein if second said substance is observed to complex with factor IXa, optionally determining if the second substance selectively inhibits factor IXa proteolytic activity but not factor Xa proteolytic activity; wherein the second substance is identified as a blot clotting inhibitor or factor IXa binder if said complex and/or selective inhibition is observed.

4. The method of claim 3 wherein said proteolytic activity is determined by measuring proteolysis of Methylsulfonyl-D-cyclohexylglycyl-glycyl-arginine-paranitroanilide.

5. A method for identifying a substance which binds to factor IXa or inhibits blood clotting comprising:

(a) employing on a computer the structural coordinates of a complex comprising: a compound selected from the group consisting of I-IV, a peptide (SEQ ID NO: 13) and factor IXa (SEQ ID NO: 14 or 18) as set forth in any of Tables 2-6 and having a root-mean square deviation of less than 1.5 Å from the backbone atoms or alpha carbon atoms thereof, to generate three-dimensional models thereof in silico;

(b) utilizing the model(s) as generated in step (a) to analyze the interaction(s) of a candidate substance with the serine protease domain of factor IXa by computational docking means to determine the potential binding of said substance to factor IXa; and (c) optionally, synthesizing said candidate substance and/or determining if said candidate substance binds to factor IXa or inhibits factor IXa proteolytic activity in vitro;

And wherein compounds I-IV are:

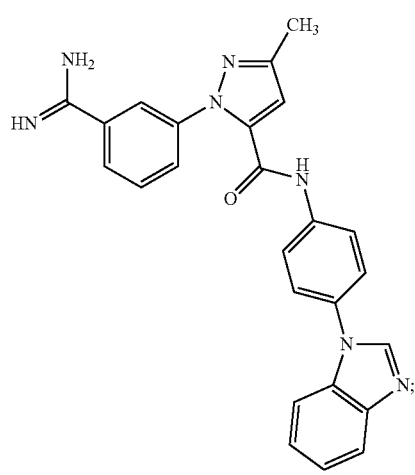

I)

-continued

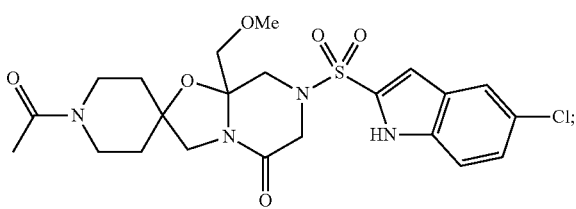

II)

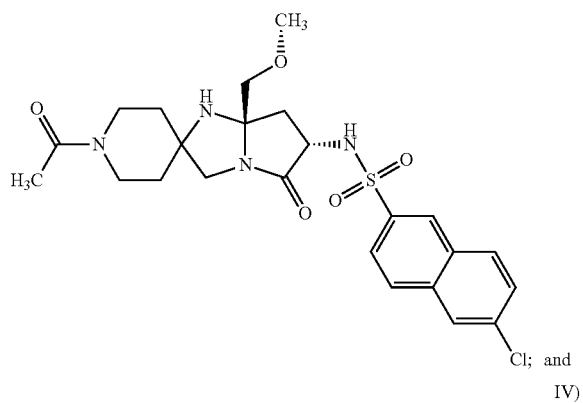

III)

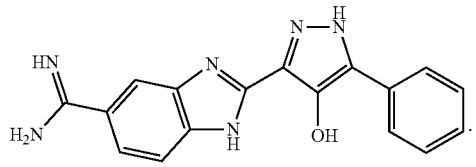

IV)

* * * * *

SEQUENCE LISTING

```
<160> NUMBER OF SEQ ID NOS: 19

<210> SEQ ID NO 1
<211> LENGTH: 415
<212> TYPE: PRT
<213> ORGANISM: Homo sapiens

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
```

```
                        260                 265                 270
Leu Glu Leu Asp Glu Pro Leu Val Leu Asn Ser Tyr Val Thr Pro Ile
                    275                 280                 285

Cys Ile Ala Asp Lys Glu Tyr Thr Asn Ile Phe Leu Lys Phe Gly Ser
                290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
                355                 360                 365

His Val Thr Glu Val Glu Gly Thr Ser Phe Leu Thr Gly Ile Ile Ser
                370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                    405                 410                 415

<210> SEQ ID NO 2
<211> LENGTH: 145
<212> TYPE: PRT
<213> ORGANISM: Homo sapiens

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
                100                 105                 110

Glu Gly Tyr Arg Leu Ala Glu Asn Gln Lys Ser Cys Glu Pro Ala Val
            115                 120                 125

Pro Phe Pro Cys Gly Arg Val Ser Val Ser Gln Thr Ser Lys Leu Thr
        130                 135                 140

Arg
145

<210> SEQ ID NO 3
<211> LENGTH: 233
<212> TYPE: PRT
<213> ORGANISM: Homo sapiens

<400> SEQUENCE: 3

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
                20                  25                  30
```

-continued

```
Glu Lys Trp Ile Val Thr Ala Ala His Cys Val Glu Thr Gly Val Lys
         35                  40                  45
Ile Thr Val Val Ala Gly Glu His Asn Ile Glu Glu Thr Glu His Thr
 50                  55                  60
Glu Gln Lys Arg Asn Val Ile Arg Ile Ile Pro His His Asn Tyr Asn
 65                  70                  75                  80
Ala Ala Ile Asn Lys Tyr Asn His Asp Ile Ala Leu Leu Glu Leu Asp
                 85                  90                  95
Glu Pro Leu Val Leu Asn Ser Tyr Val Thr Pro Ile Cys Ile Ala Asp
            100                 105                 110
Lys Glu Tyr Thr Asn Ile Phe Leu Lys Phe Gly Ser Gly Tyr Val Ser
            115                 120                 125
Gly Trp Gly Arg Val Phe His Lys Gly Arg Ser Ala Leu Val Leu Gln
        130                 135                 140
Tyr Leu Arg Val Pro Leu Val Asp Arg Ala Thr Cys Leu Arg Ser Thr
145                 150                 155                 160
Lys Phe Thr Ile Tyr Asn Asn Met Phe Cys Ala Gly Phe His Glu Gly
                165                 170                 175
Gly Arg Asp Ser Cys Gln Gly Asp Ser Gly Gly Pro His Val Thr Glu
            180                 185                 190
Val Glu Gly Thr Ser Phe Leu Thr Gly Ile Ile Ser Trp Gly Glu Glu
            195                 200                 205
Cys Ala Met Lys Gly Lys Tyr Gly Ile Tyr Thr Lys Val Ser Arg Tyr
        210                 215                 220
Val Asn Trp Ile Lys Glu Lys Thr Lys
225                 230

<210> SEQ ID NO 4
<211> LENGTH: 331
<212> TYPE: PRT
<213> ORGANISM: Homo sapiens

<400> SEQUENCE: 4

Asp Val Thr Cys Asn Ile Lys Asn Gly Arg Cys Glu Gln Phe Cys Lys
 1               5                  10                  15
Asn Ser Ala Asp Asn Lys Val Val Cys Ser Cys Thr Glu Gly Tyr Arg
             20                  25                  30
Leu Ala Glu Asn Gln Lys Ser Cys Glu Pro Ala Val Pro Phe Pro Cys
         35                  40                  45
Gly Arg Val Ser Val Ser Gln Thr Ser Lys Leu Thr Arg Ala Glu Thr
     50                  55                  60
Val Phe Pro Asp Val Asp Tyr Val Asn Ser Thr Glu Ala Glu Thr Ile
 65                  70                  75                  80
Leu Asp Asn Ile Thr Gln Ser Thr Gln Ser Phe Asn Asp Phe Thr Arg
                 85                  90                  95
Val Val Gly Gly Glu Asp Ala Lys Pro Gly Gln Phe Pro Trp Gln Val
            100                 105                 110
Val Leu Asn Gly Lys Val Asp Ala Phe Cys Gly Gly Ser Ile Val Asn
            115                 120                 125
Glu Lys Trp Ile Val Thr Ala Ala His Cys Val Glu Thr Gly Val Lys
        130                 135                 140
Ile Thr Val Val Ala Gly Glu His Asn Ile Glu Glu Thr Glu His Thr
145                 150                 155                 160
Glu Gln Lys Arg Asn Val Ile Arg Ile Ile Pro His His Asn Tyr Asn
                165                 170                 175
```

```
Ala Ala Ile Asn Lys Tyr Asn His Asp Ile Ala Leu Leu Glu Leu Asp
            180                 185                 190

Glu Pro Leu Val Leu Asn Ser Tyr Val Thr Pro Ile Cys Ile Ala Asp
        195                 200                 205

Lys Glu Tyr Thr Asn Ile Phe Leu Lys Phe Gly Ser Gly Tyr Val Ser
    210                 215                 220

Gly Trp Gly Arg Val Phe His Lys Gly Arg Ser Ala Leu Val Leu Gln
225                 230                 235                 240

Tyr Leu Arg Val Pro Leu Val Asp Arg Ala Thr Cys Leu Arg Ser Thr
                245                 250                 255

Lys Phe Thr Ile Tyr Asn Asn Met Phe Cys Ala Gly Phe His Glu Gly
            260                 265                 270

Gly Arg Asp Ser Cys Gln Gly Asp Ser Gly Gly Pro His Val Thr Glu
        275                 280                 285

Val Glu Gly Thr Ser Phe Leu Thr Gly Ile Ile Ser Trp Gly Glu Glu
    290                 295                 300

Cys Ala Met Lys Gly Lys Tyr Gly Ile Tyr Thr Lys Val Ser Arg Tyr
305                 310                 315                 320

Val Asn Trp Ile Lys Glu Lys Thr Lys Leu Thr
                325                 330

<210> SEQ ID NO 5
<211> LENGTH: 61
<212> TYPE: PRT
<213> ORGANISM: Homo sapiens

<400> SEQUENCE: 5

Asp Val Thr Cys Asn Ile Lys Asn Gly Arg Cys Glu Gln Phe Cys Lys
1               5                   10                  15

Asn Ser Ala Asp Asn Lys Val Val Cys Ser Cys Thr Glu Gly Tyr Arg
            20                  25                  30

Leu Ala Glu Asn Gln Lys Ser Cys Glu Pro Ala Val Pro Phe Pro Cys
        35                  40                  45

Gly Arg Val Ser Val Ser Gln Thr Ser Lys Leu Thr Arg
    50                  55                  60

<210> SEQ ID NO 6
<211> LENGTH: 5
<212> TYPE: PRT
<213> ORGANISM: Artificial Sequence
<220> FEATURE:
<223> OTHER INFORMATION: enterokinase cleavage site

<400> SEQUENCE: 6

Asp Asp Asp Asp Lys
1               5

<210> SEQ ID NO 7
<211> LENGTH: 4
<212> TYPE: PRT
<213> ORGANISM: Artificial Sequence
<220> FEATURE:
<223> OTHER INFORMATION: factor Xa cleavage site

<400> SEQUENCE: 7

Ile Asp Gly Arg
1

<210> SEQ ID NO 8
<211> LENGTH: 6
```

```
<212> TYPE: PRT
<213> ORGANISM: Artificial Sequence
<220> FEATURE:
<223> OTHER INFORMATION: thrombin cleavage site

<400> SEQUENCE: 8

Leu Val Pro Arg Gly Ser
1               5

<210> SEQ ID NO 9
<211> LENGTH: 8
<212> TYPE: PRT
<213> ORGANISM: Artificial Sequence
<220> FEATURE:
<223> OTHER INFORMATION: Prescission cleavage site

<400> SEQUENCE: 9

Leu Glu Val Leu Phe Gln Gly Pro
1               5

<210> SEQ ID NO 10
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 10

Glu Asn Leu Tyr Phe Gln Gly
1               5

<210> SEQ ID NO 11
<211> LENGTH: 7
<212> TYPE: PRT
<213> ORGANISM: Artificial Sequence
<220> FEATURE:
<223> OTHER INFORMATION: 3C protease cleavage site

<400> SEQUENCE: 11

Glu Thr Leu Phe Gln Gly Pro
1               5

<210> SEQ ID NO 12
<211> LENGTH: 5
<212> TYPE: PRT
<213> ORGANISM: Artificial Sequence
<220> FEATURE:
<223> OTHER INFORMATION: sortase A cleavage site

<400> SEQUENCE: 12

Leu Pro Glu Thr Gly
1               5

<210> SEQ ID NO 13
<211> LENGTH: 61
<212> TYPE: PRT
<213> ORGANISM: Homo sapiens

<400> SEQUENCE: 13

Asp Val Thr Cys Asn Ile Lys Asn Gly Arg Cys Glu Gln Phe Cys Lys
1               5                   10                  15

Asn Ser Ala Asp Asn Lys Val Val Cys Ser Cys Thr Glu Gly Tyr Arg
            20                  25                  30

Leu Ala Glu Asn Gln Lys Ser Cys Glu Pro Ala Val Pro Phe Pro Cys
        35                  40                  45

Gly Arg Val Ser Val Ser Gln Thr Ser Lys Leu Thr Arg
```

-continued

```
                50                  55                  60
```

<210> SEQ ID NO 14
<211> LENGTH: 235
<212> TYPE: PRT
<213> ORGANISM: Homo sapiens

<400> SEQUENCE: 14

```
Val Val Gly Gly Glu Asp Ala Lys Pro Gly Gln Phe Pro Trp Gln Val
1               5                  10                  15

Val Leu Asn Gly Lys Val Asp Ala Phe Cys Gly Gly Ser Ile Val Asn
                20                  25                  30

Glu Lys Trp Ile Val Thr Ala Ala His Cys Val Glu Thr Gly Val Lys
            35                  40                  45

Ile Thr Val Val Ala Gly Glu His Asn Ile Glu Thr Glu His
        50                  55                  60

Glu Gln Lys Arg Asn Val Ile Arg Ile Pro His His Asn Tyr Asn
65                  70                  75                  80

Ala Ala Ile Asn Lys Tyr Asn His Asp Ile Ala Leu Leu Glu Leu Asp
                85                  90                  95

Glu Pro Leu Val Leu Asn Ser Tyr Val Thr Pro Ile Cys Ile Ala Asp
                100                 105                 110

Lys Glu Tyr Thr Asn Ile Phe Leu Lys Phe Gly Ser Gly Tyr Val Ser
            115                 120                 125

Gly Trp Gly Arg Val Phe His Lys Gly Arg Ser Ala Leu Val Leu Gln
130                 135                 140

Tyr Leu Arg Val Pro Leu Val Asp Arg Ala Thr Cys Leu Arg Ser Thr
145                 150                 155                 160

Lys Phe Thr Ile Tyr Asn Asn Met Phe Cys Ala Gly Phe His Glu Gly
                165                 170                 175

Gly Arg Asp Ser Cys Gln Gly Asp Ser Gly Gly Pro His Val Thr Glu
            180                 185                 190

Val Glu Gly Thr Ser Phe Leu Thr Gly Ile Ile Ser Trp Gly Glu Glu
        195                 200                 205

Cys Ala Met Lys Gly Lys Tyr Gly Ile Tyr Thr Lys Val Ser Arg Tyr
210                 215                 220

Val Asn Trp Ile Lys Glu Lys Thr Lys Leu Thr
225                 230                 235
```

<210> SEQ ID NO 15
<211> LENGTH: 461
<212> TYPE: PRT
<213> ORGANISM: Homo sapiens

<400> SEQUENCE: 15

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95
```

```
Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Val Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 16
<211> LENGTH: 29
<212> TYPE: DNA
<213> ORGANISM: Artificial Sequence
<220> FEATURE:
<223> OTHER INFORMATION: R318A(+) primer

<400> SEQUENCE: 16
```

-continued

```
ccacaaaggg gcatcagctt tagttcttc                                              29
```

<210> SEQ ID NO 17
<211> LENGTH: 29
<212> TYPE: DNA
<213> ORGANISM: Artificial Sequence
<220> FEATURE:
<223> OTHER INFORMATION: R318A(-) primer

<400> SEQUENCE: 17

```
gaagaactaa agctgatgcc cctttgtgg                                              29
```

<210> SEQ ID NO 18
<211> LENGTH: 235
<212> TYPE: PRT
<213> ORGANISM: Homo sapiens

<400> SEQUENCE: 18

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Gly Val Lys
        35                  40                  45

Ile Thr Val Val Ala Gly Glu His Asn Ile Glu Glu Thr Glu His Thr
    50                  55                  60

Glu Gln Lys Arg Asn Val Ile Arg Ile Ile Pro His His Asn Tyr Asn
65                  70                  75                  80

Ala Ala Ile Asn Lys Tyr Asn His Asp Ile Ala Leu Leu Glu Leu Asp
                85                  90                  95

Glu Pro Leu Val Leu Asn Ser Tyr Val Thr Pro Ile Cys Ile Ala Asp
            100                 105                 110

Lys Glu Tyr Thr Asn Ile Phe Leu Lys Phe Gly Ser Gly Tyr Val Ser
        115                 120                 125

Gly Trp Gly Arg Val Phe His Lys Gly Ala Ser Ala Leu Val Leu Gln
    130                 135                 140

Tyr Leu Arg Val Pro Leu Val Asp Arg Ala Thr Cys Leu Arg Ser Thr
145                 150                 155                 160

Lys Phe Thr Ile Tyr Asn Asn Met Phe Cys Ala Gly Phe His Glu Gly
                165                 170                 175

Gly Arg Asp Ser Cys Gln Gly Asp Ser Gly Gly Pro His Val Thr Glu
            180                 185                 190

Val Glu Gly Thr Ser Phe Leu Thr Gly Ile Ile Ser Trp Gly Glu Glu
        195                 200                 205

Cys Ala Met Lys Gly Lys Tyr Gly Ile Tyr Thr Lys Val Ser Arg Tyr
    210                 215                 220

Val Asn Trp Ile Lys Glu Lys Thr Lys Leu Thr
225                 230                 235

<210> SEQ ID NO 19
<211> LENGTH: 7
<212> TYPE: DNA
<213> ORGANISM: Artificial Sequence
<220> FEATURE:
<223> OTHER INFORMATION: Sequence added to human Factor IX

<400> SEQUENCE: 19

```
caccatg                                                                       7
```